US006288213B1

(12) United States Patent
Stahl et al.

(10) Patent No.: US 6,288,213 B1
(45) Date of Patent: Sep. 11, 2001

(54) FATTY ACID TRANSPORT PROTEINS

(75) Inventors: Andreas Stahl, Allston; David J. Hirsch; Harvey F. Lodish, both of Brookline; Ruth E. Gimeno, Wellesley; Louis A. Tartaglia, Newton, all of MA (US)

(73) Assignee: Whitehead Institute for Biochemical Research, Cambridge, MA (US)

( * ) Notice: Subject to any disclaimer, the term of this patent is extended or adjusted under 35 U.S.C. 154(b) by 0 days.

(21) Appl. No.: 09/232,200

(22) Filed: Jan. 14, 1999

Related U.S. Application Data

(60) Provisional application No. 60/071,374, filed on Jan. 15, 1998, provisional application No. 60/093,491, filed on Jul. 20, 1998, and provisional application No. 60/110,941, filed on Dec. 4, 1998.

(51) Int. Cl.[7] .......................... C07K 14/47; C12N 15/12; C12N 15/62

(52) U.S. Cl. ........................ 530/350; 435/69.1; 435/71.1; 435/71.2; 435/252.3; 435/320.1; 435/471; 435/69.7

(58) Field of Search ........................... 530/350; 435/69.1, 435/71.1, 71.2, 252.3, 320.1, 325, 471, 69.7

(56) References Cited

U.S. PATENT DOCUMENTS 4,935,450 6/1990 Cone, Jr. .............................. 514/728

FOREIGN PATENT DOCUMENTS

WO 00/26245 5/2000 (WO) ............................ C07K/14/00

OTHER PUBLICATIONS

Database on DenEmbl, Kamijo et al. "Homo sapien mRNA for very–long–chain fatty acid synthetase", Accession No. D88308, Nov. 1197.*

Database on PIR–60, Schaffer etal. "Expression cloning and characterization of a novel adipocyte long chain fatty acid transport precursor", Accession No. A55093, Jan. 1995.*

Cunningham et al. Science, vol. 244, pp. 1081–1085, Jun. 1989.*

Rieger et al. Glossary of Genetics and Cytogenetics, Spring-Verlag, Berlin Heidleberg, New York, p. 17, 1976.*

Abumrad, N., et al., "Membrane Proteins Implicated in Long–Chain Fatty Acid Uptake by Mammalian Cells: CD36, FATP and FABPm," *Biochimica et Biophysica Acta* 1441: 4–13 (1999).

Berk, P.D.,and Stump D.D., "Mechanisms of Cellular Uptake of Long–Chain Free Fatty Acids," *Molecular and Cellular Biochem.* 192:17–31 (1999).

Berk, P.D., et al., "Characterization of Membrane Transport Processes: Lessons from the Study of BSP, Bilirubin, and Fatty Acid Uptake," *Seminars In Liver Disease* 16(2):107–120 (1996).

Boisclair, Y.R., et al., "Three Clustered Sp1 Sites Are Required for Efficient Transcription of the TATA–Less Promoter of the Gene for Insulin–Like Growth Factor–binding Protein–2 from the Rat," *American Society Biochem.* 268(33):24892–24901 (1993).

De Simone, V.,and Cortese, R., "Transcription Factors and Liver–Specific Genes," *Biochimica et Biophysica Acta* 1132:119–126 (1992).

Fitscher, B.A., et al., "Protein–Mediated Facilitated Uptake Processes for Fatty Acids, Bilirubin, and Other Amphipathic Compounds (43987)," *Proc Soc Exp Biol Med* 212:15–23 (1996).

Frohnert, B.I., et al., "Identification of a Functional Peroxisome Proliferator–Responsive Element in the Murine Fatty Acid Transport Protein Gene," *J. of Biological Chem.* 274(7):3970–3977 (1999).

Glatz, J.F.C., et al., "Molecular Mechanism of Cellular Uptake and Intracellular Translocation of Fatty Acids," *Prostaglandins, Leukotrienes and Essential Fatty Acids* 57(1):3–9 (1997).

Göttlicher, M., et al., "Fatty Acids Activate a Chimera of the Clofibric Acid–Activated Receptor and the Glucocorticoid Receptor," *Proc. Natl. Acad. Sci. USA* 89:4653–4657 (1992).

Grimaldi, P.A., et al., "Long Chain Fatty Acids as Modulators of Gene Transcription in Preadipose Cells," *Molecular and Cellular Biochem.* 192:63–68 (1999).

Hamilton, J.A., "Fatty Acid Transport: Difficult or Easy?," *J. Lipid Res.* 39:467–481 (1998).

Hanson, R.W. "Regulation of Phosphoenolpyruvate Carboxykinase (GTP) Gene Expression" *Annu. Rev. Biochem.* 66:581–611 (1997).

Heinemeyer, T., et al., "Databases on Transcriptional Regulation: TRANSFAC, TRRD and COMPEL," *Nucleic Acids Res.* 26(1):362–367 (1998).

(List continued on next page.)

*Primary Examiner*—Gary L. Kunz
*Assistant Examiner*—Fozia Hamud
(74) *Attorney, Agent, or Firm*—Hamilton, Brook, Smith & Reynolds, P.C.

(57) ABSTRACT

A family of fatty acid transport proteins (FATPs) mediate transport of long chain fatty acids (LCFAs) across cell membranes into cells. These proteins exhibit different expression patterns among the organs of mammals. Nucleic acids encoding FATPs of this family, vectors comprising these nucleic acids, as well as the production of FATP proteins in host cells are described. Also described are methods to test FATPs for fatty acid transport function, and methods to identify inhibitors or enhancers of transport function. The altering of LCFA uptake by administering to the mammal an inhibitor or enhancer of FATP transport function of a FATP in the small intestine can decrease or increase calories available as fats, and can decrease or increase circulating fatty acids. The organ specificity of FATP distribution can be exploited in methods to direct drugs, diagnostic indicators and so forth to an organ such as the heart.

14 Claims, 169 Drawing Sheets

OTHER PUBLICATIONS

Heinemeyer[1], T. et al., "Expanding the TRANSFAC Database Towards an Expert System of Regulatory Molecular Mechanisms," *Nucleic Acids Res.* 27(1):318–322 (1999).

Hua[1], X., et al., "Synergistic Cooperation of TFE3 and Smad Proteins in TGF–β–Induced Transcription of the Plasminogen Activator Inhibitor–1 Gene," *Genes & Development* 12: 3084–3095 (1998).

Lai, E., "Regulation of Hepatic Gene Expression and Development," *Seminars in Liver Disease* 12(3):246–251 (1992).

Lee, Y.H., et al., "A Novel cis–Acting Element Controlling the Rat CYP2D5 Gene and Requiring Cooperativity between C/EBPβ and SP1 Factor," *Molecular and Cellular Biology,* 14(2):1383–1394 (1994).

Martin, G., et al., "Coordinate Regulation of the Expression of the Fatty Acid Transport Protein and Acyl–CoA Synthetase Genes by PPARα and PPARγ Activators," *J. Biological Chem.* 272(45):28210–28217 (1997).

Memon, R.A., et al., "Regulation of Putative Fatty Acid Transporters and Acyl–CoA Synthetase in Liver and Adipose Tissue in ob/ob Mice," *Diabetes* 48:121–127 (1999).

Motojima, K., et al., "Expression of Putative Fatty Acid Transporter Genes Are Regulated by Peroxisome Proliferator–Activated Receptor α and γ Activators in a Tissue– and Inducer–Specific Manner," *J. Biol. Chem.* 273(27):16710–16714 (1998).

Rodenburg, R.J.T., et al., "A Functional Sp1 Binding Site Is Essential for the Activity of the Adult Liver–Specific Human Insulin–Like Growth Factor II Promoter," *Molecular Endocrinology* 11:237–250 (1997).

Rongnoparut, P., et al., "Isolation and Characterization of the Transcriptionally Regulated Mouse Liver (B–type) Phosphofructokinase Gene and Its Promoter," *J. Biological Chem.* 266(13):8086–8091 (1991).

Ryu, S., et al., "The Transcriptional Cofactor Complex CRSP is Required for Activity of the Enhancer–Binding Protein Sp1," *Nature* 397:446–450 (1999).

Schaffer, J.E.,and Lodish, H.F., "Molecular Mechanism of Long–Chain Fatty Acid Uptake," *TCM* 5(6):218–224 (1995).

Schoonjans, K., et al., "The Peroxisome Proliferator Activated Receptors (PPARs) and Their Effects on Lipid Metabolism and Adipocyte Differentiation," *Biochem. Biophys. Acta* 1302:93–109 (1996).

Sorensen, P.,and Wintersberger, E., "Sp1 and NF–Y Are Necessary and Sufficient for Growth–Dependent Regulation of the Hamster Thymidine Kinase Promoter*," *J. Biological Chem.* 274(43):30943–30949 (1999).

Stremmel, W., "Mechanism of Hepatic Fatty Acid Uptake," *J. Hepatology* 9:374–382 (1989).

Strausberg, R.; Data Submission; nc84e10.s1 NCI_CGAP_GC1 Homo sapiens cDNA clone Image:797514, Home sapiens (human); EMBL Accession No. Aa581592; (1997).

Hillier, L. et. al.; Data Submission; zu10c02.r1 Soares testis NHT Homo sapiens cDNA clone 731426 5', Homo sapiens(human);EMBL Accession No. AA469992; (1997).

Strausberg, R.; Data Submission; no82f09.s1 NCI_CGAP_AA1 Homo sapiens cDNA clone Image:1113353 similar to TR:G563829 G563829 Fatty Acid Transport Protein, Homo sapiens(human); EMBL Accession No. Aa614135; (1997).

Hillier, L., et al.; Data Submission; zc44h06.r1 /Soares senescent fibroblasts NbHSF Homo spiens cDNA clone 325211 5' similar to PIR:A55093 A55093 fatty acid transport protein precursor—mouse, Homo sapiens(human); EMBL Accession No. W48808; (1996).

Strausberg, R.; Data Submission; nn89d05.s1 NCI_CGAP_Br2 Homo sapiens cDNA clone Image:1098345 similar to TR:G563829 G563829 Fatty Acid Transport Protein, Homo sapiens(human); EMBL Accession No. AA614445; (1997).

Strausberg, R.; Data Submission; ne19b11.s1 NCI_CGAP_Co3 Homo sapiens cDNA clone Image:881661, Homo sapiens(human); EMBL Accession No. AA470762; (1997).

Uchiyama, A. et al., "Molecular Cloning of cDNA Encoding Rat Very Long–chain Acyl–CoA Synthetase," *J. Biol. Chem. 271(48)*:30360–30365 (1996).

Stuhlsatz–Krouper, S.M. et al., "Substitution of Alanine for Serine 250 in the Murine Fatty Acid Transport Protein Inhibits Long Chain Fatty Acid Transport," *J. Biol. Chem. 273(44)*:28642–28650 (1998).

Watkins, P.A. et al., "Disruption of the *Saccharomyces cerevisiae* FAT1 Gene Decreases Very Long–chain Fatty Acyl–CoA Synthetase Activity and Elevates Intracellular Very Long–chain Fatty Acid Concentrations," *J. Biol. Chem. 273(29)*:18210–18219 (1998).

Hirsch, D. et al., "A family of fatty acid transporters conserved from mycobacterium to man," *Proc. Natl. Acad. Sci. 95:*8625–8629 (1998).

Berger, J. et al., "A Novel Relative of the Very–Long–Chain Acyl–CoA Synthetase and Fatty Acid Transporter Protein Genes with a Distinct Expression Pattern," *Biochem. Biophys. Res. Commun. 247:*255–260 (1998).

Hui, T.Y. et al., "Characterization of the Murine Fatty Acid Transport Protein Gene and Its Insulin Response Sequence," *J. Biol. Chem. 273(42)*:27420–27429 (1998).

Færgeman, N.J. et al., "Disruption of the *Saccharomyces cerevisiae* Homologue to the Murine Fatty Acid Transport Protein Impairs Uptake and Growth on Long–chain Fatty Acids," *J. Biol. Chem. 272(13)*:8531–8538 (1997).

Schaap, F.G. et al., "Molecular cloning of fatty acid–transport protein cDNA from rat," *Biochem. Biohphys. Acta 1354:*29–34 (1997).

Schaffer, J.E. and Lodish, H.F., "Expression Cloning and Characterization of a Novel Adipocyte Long Chain Fatty Acid Transport Protein," *Cell (79)*:427–436 (1994).

Bonaldo, M.F. et al.; Data Submission; *Rattus norvegicus* cDNA clone; *Rattus norvegicus;* GenBank Accession No. AA817672; (1996).

Schaap, F.G. et al.; Data Submission; *Rattus norvegicus* fatty acid transport protein mRNA, complete cds.; *Rattus norvegicus;* GenBank Accession No. U89529; (1997).

Lee, N.H. et al.; Data Submission; Normalized rat heart, Bento Soares Rattus sp. cDNA clone; Rattus sp.; GenBank Accession No. AA799326; (1998).

Hui, T.Y. et al.; Data Submission; *Mus musculus* fatty acid transport protein (FATP) gene, exons 1–3; *Mus musculus;* GenBank Accession No. AF023256; (1997).

Schaffer, J.E. and Lodish, H.F.; Data Submission; *Mus musculus* fatty acid transport protein (FATP) mRNA, complete cds.; *Mus musculus;* GenBank Accession No. U15976; (1994).

Stahl, A. et al.; Data Submission; *Mus musculus* fatty acid transport protein 5 mRNA, complete cds.; *Mus musculus;* GenBank Accession No. AF072760; (1998).

Stahl, A. et al.; Data Submission; *Mus musculus* fatty acid transport protein 4 mRNA, partial cds.; *Mus musculus;* GenBank Accession No. AF072759; (1998).

Stahl, A. et al.; Data Submission; *Mus musculus* fatty acid transport protein 3 mRNA, partial cds.; *Mus musculus;* GenBank Accession No. AF072758; (1998).

Stahl, A. et al.; Data Submission; *Mus musculus* fatty acid transport protein 2 mRNA, complete cds.; *Mus musculus;* GenBank Accession No. AF072757; (1998).

Hui, T.Y. et al.; Data Submission; *Mus musculus* fatty acid transport protein (FATP) gene, exons 1–3; *Mus musculus;* GenBank Accession No. AF023256; (1997).

Hui, T.Y. et al.; Data Submission; *Mus musculus* fatty acid transport protein (FATP) gene, exons 4–7; *Mus musculus;* GenBank Accession No. AF023257; (1997).

Hui, T.Y. et al.; Data Submission; *Mus musculus* fatty acid transport protein (FATP) gene, exons 8–13 and complete cds.; *Mus musculus;* GenBank Accession No. AF023258; (1997).

Kamijo, K.; Data Submission; Homo sapiens mRNA for very–long–chain acyl–CoA synthetase, complete cds.; Homo sapiens (human); EMBL Accession No. D88308; (1996).

Harmon, C.M. et al., "Labelling of an 88 kDa adipocyte membrane protein by sulpho–N–succinimidyl long–chain fatty acids: inhibition of fatty acid transport," *Biochemical Society Transactions 20*(*4*):811–813 (1992).

Schaffer, J.E. et al., "Cloning and Structure–Function Analysis of Human Heart Fatty Acid Transport Protein," *Circulation 96*(*8*):2031 (1997).

Ghosh, B. et al., "Molecular cloning and sequencing of human palmitoyl–CoA ligase and its tissue specific expression," *Mol. Cell. Biochem. 151:*77–81 (1995).

Fitscher, B.A. et al., "Tissue distribution and cDNA cloning of a human fatty acid transport protein (hsFATP4)," *Biochmica et Biophysica Acta 1443:*381–385 (1998).

* cited by examiner

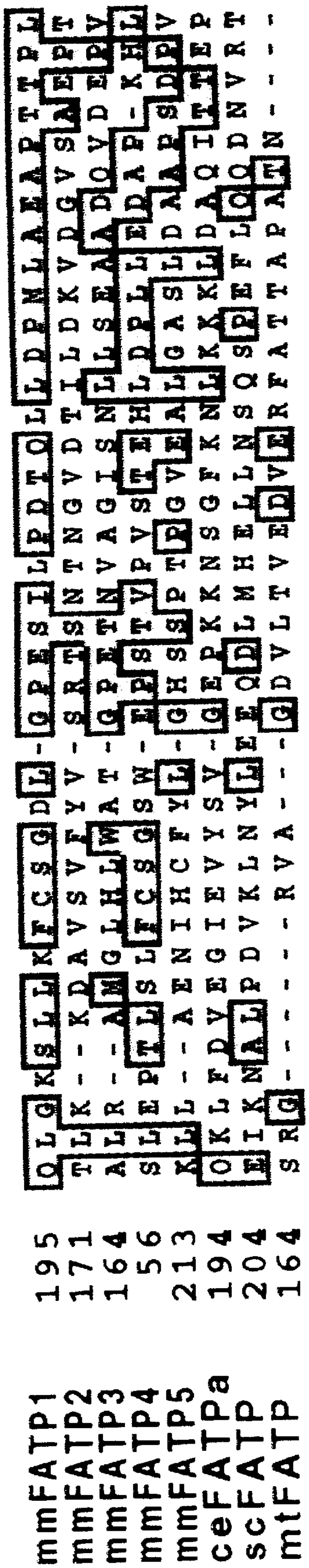

FIG. 1G

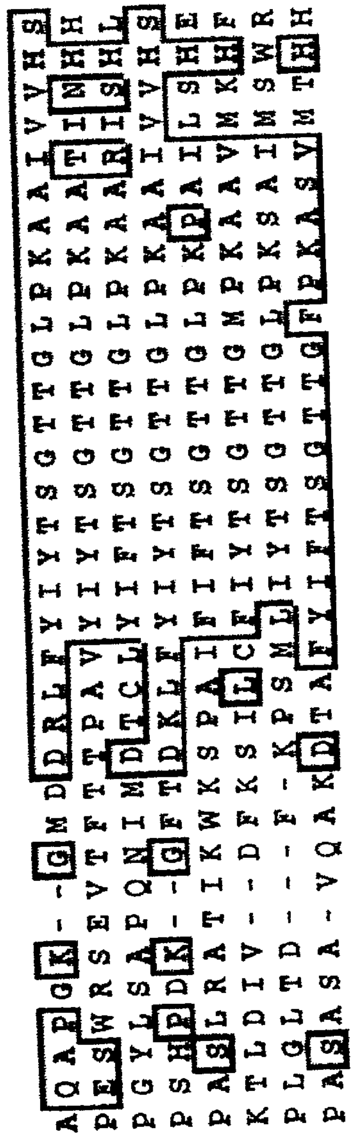

FIG. 1H

| | | | | | |
|---|---|---|---|---|---|
| mmFATP1 | 195 | QLGKSLLKFCSGDL- | -QPESILPDTQ | LLPDPMLAEAPTPL |
| mmFATP2 | 171 | TLK--KDAVSVFYV- | -SRTSNTNGVDT | ILDKVDGVSLAEPT |
| mmFATP3 | 164 | ALR--AMGLHLWAT- | -QPETNVAGIS | NLSEAADQVDEPV |
| mmFATP4 | 56 | SLEPTLSLFCSGW- | -EPSTYPVSTEHL | DPLLEDAP-KHL |
| mmFATP5 | 213 | KLL--AENIHCFYL- | -GHSSPTRGVEAL | GASLDAAPSDPV |
| ceFATPa | 194 | QKLFDYEGIEVYSV- | -GEPKKNSGFKNL | KKLDAQITEP |
| scFATP | 204 | EIKNALPDVKLNYLE | EQDLMHELLNSQS | PEFLQQDNVRT |
| mtFATP | 164 | SRG---------- | -GDVLTVEDVE | RFATTAPATN |

| | |
|---|---|
| AQAPGK--GMDDRLFYIYTSGTTGLPKAAIVVHS |
| PESWRSEVTFTPAVYIYTSGTTGLPKAATINHH |
| PGYLSAPQNIMDTCLYIFTSGTTGLPKAARISHL |
| PSHPDK--GFTDKLFYIYTSGTTGLPKAAIVVHS |
| PAGLRATIKWKSPAIFIFTSGTTGLPKPAILSHE |
| KTLDIV-DFKSILCFIYTSGTTGMPKAAVMKHF |
| PLGLTD--F-KPSMLIYTSGTTGLPKSAIMSWR |
| PASASA-VQAKDTAFYIFTSGTTGFPKASVMTHH |

```
mmFATP1  336  Y I G E I C R Y L L R Q P V R D V E Q R H R V R L A V G N G L R P A
mmFATP2  311  Y I G E L L R Y L C N T P Q K P N D R D H K V K K A L G N G L R G D
mmFATP3  304  Y I G E L C R Y L V N Q P P S K A E F D H K V R L A V G S G L R P D
mmFATP4  196  Y I G E L C R Y L L N Q P P R E A E S R H K V R M A L G N G L R Q S
mmFATP5  353  Y V G E I L R Y L C N V P E Q P E D K I H T V R L A M G T G L R A N
ceFATPa  335  Y I G E I C R Y L L A Q P V V E E E S R H R M R L L V G N G L R A E
scFATP   344  Y V G E V C R Y L L H T P I S K Y E K M H K V K V A Y G N G L R P D
mtFATP   295  Y I G E I C R Y L L N Q P A K P T D R A H Q V R V I C G N G L R P E
```

```
I W E E F T Q R F G V P Q I G E F Y G A T E C N C S I A N M D Q K - - - V G S
V W R E F I K R F G D I H V Y E F Y A S T E G N I G F V N Y P R K - - - I G A
T W E R F L R R F G P L Q I L E T Y G M T E G N V A T F N Y T G R - - - Q G A
I W T D F S S R F H I P Q V A E F Y G A T E C N C S L G N F D S R - - - V G A
V W K N F Q Q R F G P I R I W E F Y G S T E G N V G L M N Y V G H - - - C G A
I W Q P F V D R F R V - R I G E L Y G S T E G T S S L V N I D G H - - - V G A
I W Q D F R K R F N I E V I G E F Y A A T E A P F A T T T F Q K G D F G I G A
I W D E F T T R F G V A R V C E F Y A A S E G N S A F I N I F N V - - - P R T
```

```
                10        20        30        40        50        60        70        80        90
246 FIFTSGTTGLPKPAILSHERVIQVSNVLSFCGCR--ADDVVYDVLPLYHTIGLVLGFLGCLQVGATCVLAPKFSASRFWAECRQHGVTVI mmFATP1
265 YIYTSGTTGNPKPAVIKHFRYFWI-AMGAGKAFGINKSDVVYITMPMYHSAAGIMGIGSLIAFGSTAVIRKKFSASNFWKDCVKYNVTAT mmFATP5
249 -IYTSGTTGLPKSAIMSWRKSSVGCQVFG-HVLHMTNESTVFTAMPLFHSTAALLGACAILSHGGCLALSHKFSASTFWKQVYLTGATHI ceFATPa
256 YIYTSGTTGLPKAAIVVHSRYYRI-AAFGHHSYSMRAADVLYDCLPLYHSAGNIMGVGQCVIYGLTVVLRKKFSASRFWDDCVKYNCTVV scFATP
205 YIFTSGTTGFPKASVMTHHRWLRALAVFGGMGLRLKGSDTLYSCLPLYHNNALTVAVSSVINSGATLALGKSFSASRFWDEVIANRATAF mtFATP

               100       110       120       130       140       150       160       170       180
335 QYIGEICRYLLRQPVRDVEQRHRVRLAVGNGLRPAIWEEFTQRFGVPQIGEFYGATEC---NCSIANMDGKVGSCGFNSRILTHV---YP mmFATP1
353 LYVGEILRYLCNVPEQPEDKIHTVRLAMGTGLRANVWKNFQQRFGPIRIWEFYGSTEG---NVGLMNY---VGHCGAVGRTSCILRMLTP mmFATP5
338 QYIGEICRYLLAANPCPEEKQHNVRLMWGNGLRGQIWKEFVGRFGIKKIGELYGSTEG---NSNIVNVDNHVGACGFMP-IYPHIGSLYP ceFATPa
345 QYVGEVCRYLLHTPISKYEKMHKVKVAYGNGLRPDIWQDFRKRFNIEVIGEFYAATEAPFATTTFQKGDFGIGACRNYGTIIQWF-LSFQ scFATP
295 VYIGEICRYLLNQPAKPTDRAHQVRVICGNGLRPEIWDEFTTRFGVARVCEFYAASEG---NSAFINI---F----NVPRTAGVSPM--P mtFATP

               190       200       210       220       230       240       250       260       270
419 IRLVKVNEDTMEPL-RDSEGLCIPCQPGEPGLLVGQIN-QQDPLRRFDGYV-SDSATNKKIAHSVFRKGDSAYLSGDVLVMDELGYMYFR mmFATP1
437 FELVQFDIETAEPL-RDKQGFCIPVEPGKPGLLLTKVR-KNQP---FLGYRGSQAESNRKLVANVRRVGDLYFNTGDVLTLDQEGFFYFQ mmFATP5
424 VRLIKVDRATGELE-RDKNGLCVPCVPGETGEMVGVIK-EKDILLKFEGYV-SEGDTAKKIYRDVFKHGDKVFASGDILHWDDLGYLYFV ceFATPa
434 QTLVRMDPNDDSVIYRNSKGFCEVAPVGEPGEMLMRIFFPKKPETSFQGYLGNAKETKSKVVRDVFRRGDAWYRCGDLLKADEYGLWYFL scFATP
373 LAFVEYDLDTGDPL-RDASGRVRRVPDGEPGLLLSRVN-RLQP---FDGYTDP-VASEKKLVRNAFRDGDCWFNTGDVMSPQGMGHAAFV mtFATP

               280       290       300       310       320       330       340       350       360
506 DRSGDTFRWRGENVSTTEVEAVLSRLLGQT--DVAVYGVAVPGVEGKAGMAAIADPHS--QLDP--NSMYQELQK-VLASYARPIFLR mmFATP1
522 DRLGDTFRWKGENVSTGEVECVLSSLDFLE--EVNVYGVPVPGCEGKVGMAAVKLAPGK-TFDG--KKLYQHVRS-WLPAYATPHFIR mmFATP5
511 DRCGDTFRWKGENVSTTEVEGILQPVMDVE--DATVYGVTVGKMEGRAGMAGIVVKDGT-DVEKFIADITSRLTE-NLASYAIPVFIR ceFATPa
524 DRMGDTFRWKSENVSTTEVEDQLTASNKEQYAQVLVVGIKVPKYEGRAGFAVIKLTDNSLDITAKTKLLNDSLSRLNLPSYAMPLFVR scFATP
457 DRLGDTFRWKGENVATTQVEAALASDQTVE--ECTVYGVQIPRTGGRAGMAAITLRAGA-EFDG--QALARTVYG-HLPGYALPLFVR mtFATP
```

FIG. 6

| | mmFATP1 | mmFATP2 | mmFATP3 | mmFATP4 | mmFATP5 | rnFATP1 | rnVLACS | ceFATPa | ceFATPb | scFATP | mtFATP |
|---|---|---|---|---|---|---|---|---|---|---|---|
| mmFATP1 | 100.0 | | | | | | | | | | |
| mmFATP2 | 50.1 | 100.0 | | | | | | | | | |
| mmFATP3 | 51.8 | 53.3 | 100.0 | | | | | | | | |
| mmFATP4 | 72.6 | 48.4 | 51.7 | 100.0 | | | | | | | |
| mmFATP5 | 50.2 | 54.0 | 54.4 | 50.8 | 100.0 | | | | | | |
| rnFATP1 | 97.5 | 49.7 | 51.6 | 71.4 | 50.4 | 100.0 | | | | | |
| rnVLACS | 50.7 | 95.2 | 53.0 | 50.9 | 53.6 | 50.3 | 100.0 | | | | |
| ceFATPa | 54.1 | 48.6 | 47.2 | 53.6 | 47.0 | 53.9 | 49.1 | 100.0 | | | |
| ceFATPb | 55.7 | 48.8 | 46.8 | 54.2 | 47.3 | 54.9 | 49.0 | 60.3 | 100.0 | | |
| scFATP | 45.5 | 43.2 | 42.3 | 47.0 | 42.7 | 45.5 | 43.9 | 45.3 | 43.1 | 100.0 | |
| mtFATP | 47.5 | 47.8 | 43.9 | 48.2 | 47.2 | 47.1 | 48.3 | 44.9 | 44.5 | 42.3 | 100.0 |

FIG. 7 mmFATP3 DNA sequence

```
ACGACTCACTATAGGGCACAGCCTATGACGTCGCATGCAC 40
GCGTAAGCTTGGGCCCCTCGAGGGATCCTCTAGAGCGGCC 80
GCCGACCCCGAAAGCTCTCAGAGCCCGGTGCAGTCTGCCT 120
GCCGTCTCGCGTACCTGCCCCCGCAGCAGCCCACACACAC 160
CTTCCTCATCCACCCCGCGCAGCGCTTTAGCTACGCCGAG 200
GCTGAGCGCGACAGCAACCCGCATTGCTCGCCCTTTCTGC 240
GCGCACGGGGCTGCACCCGCGGCCGCCCAGCCTCGGGCAG 280
GCGCAGCACTGAGCAAGCCGCACCGTGCCGCCCTCCGGCT 320
GCAGATGCCGCTGCTAGAGGCACGACCGCGCCCCCTCTGG 360
CACCCGCCGCCGACCGTGCCGCTGCTCCTCCCAGCGGCCC 400
```

FIG. 8A

GGATTTCCTTTGGATTTGGTTGGCACTGGCCAAAGCTGGC 440
CTGCGCACGGCCTTTGTGCCCACCGCTTTACGCCGAGGAC 480
CCCTGCTGCACTGCCTCGCAGCTGCGGTGCGAGTGCCGCT 520
CGTGCTGGCCACAGAGTTCCTGGAGTCCCTGGAGCCGGAC 560
CTGCCGGCCTTCAGAGCCATGGGGCTCCACCTATGGGCGA 600
CGGGCCCTGAAACTAATGTAGCTGCAATCAGCAATTTGCT 640
ATCGGAAGCAGCAGACCAAGTGGATGAGCCAGTGCCGGGG 680
TACCTCTCTGCCCCCCAGAACATAATGGACACCTGCCTGT 720
ACATCTTCACCTCTGGCACTACTGGCCTGCCCAAGGCTGC 760
TCGAATCAGTCATCTGAAGGTTCTACAGTGCCAGGGATTC 800
TACCATCTGTGTGCAGTCCACCAGGAGGACGTGATCTACC 840
TCGCACTCCCACTGTACCACATGTCTGGCTCCCTTCTGGG 880
CATTGTGGCCTGCTTGGGCATTGGGGCCACCGTGGTGCTG 920
AAACCCAAGTTCTCAGCTAGCCAGTTCTGGGACGATTGCC 960
AGAAACACAGGGTGACAGTGTTCCAGTACATTGGGGAGTT 1000
GTGCCGATACCTCGTCAACCAGCCCCCGAGCAAGGCAGAG 1040
TTTGACCATAAGGTGCGCTTGGCAGTGGGCAGTGGGTTGC 1080
GCCCAGACACCTGGGAGCGTTTCCTGCGGCGATTTGGACC 1120
TCTGCAGATACTGGAGACGTATGGCATGACAGAGGGCAAC 1160
GTAGCTACGTTCAATTACACAGGACGGCAGGGTGCAGTGG 1200
GGCGAGCTTCCTGGCTTTACAAGCACATCTTCCCCTTCTC 1240
CTTGATTCGATACGATGTCATGACAGGGGAGCCTATTCGG 1280
AATGCCCAGGGGCACTGCATGACCACATCTCCAGGTGAGC 1320
CAGGCCTACTGGTGGCCCCAGTGAGCCAGCAGTCCCCCTT 1360
CCTGGGCTATGCTGGGGCTCCGGAGCTGGCCAAGGACAAG 1400
CTGCTGAAGGATGTCTTCTGGTCTGGGGACGTTTTCTTCA 1440
ATACTGGGGACCTCTTGGTCTGTGATGAGCAAGGCTTTCT 1480
TCACTTCCACGATCGTACTGGAGACACCATCAGGTGGAAG 1520
GGAGAGAATGTGGCCACAACTGAAGTGGCTGAGGTCTTGG 1560
AGACCCTGGACTTCCTTCAGGAGGTGAACATCTATGGAGT 1600
CACGGTGCCAGGCCACGAAGGCAGGGCAGGCATGGCGGCC 1640
TTGGCTCTGCGGCCCCCGCAGGCTCTGAACCTGGTGCAGC 1680
TCTACAGCCATGTTTCTGAGAACTTGCCACCGTATGCCCG 1720
ACCTCGGTTTCTCAGGCTCCAGGAATCTTTGGCCACTACT 1760
GAGACCTTCAAACAGCAGAAGGTTAGGATGGCCAATGAGG 1800
GCTTTGACCCCAGTGTACTGTCTGACCCACTCTATGTTCT 1840
GGACCAAGATATAGGGGCCTACCTGCCCCTCACACCTGCC 1880
CGGTACAGTGCCCTCCTGTCTGGAGACCTTCGAATCTGAA 1920
ACCTTCCACTTGAGGGAGGGGCTCGGAGGGTACAGGCCAC 1960
CATGGCTGCACCAGGGAGGGTTTTCGGGTATCTTTTGTAT 2000
ATGGAGTCATTATTTTGTAATAAACAGCTGGAGCTTAAAA 2040
AAAAAAAAAAAAAAAAAAAAAAAAAAAAAAAAAAAAAAAA 2080
AAAAAAA 2087

FIG. 8B mmFATP3 protein sequence

AADPESSESGCSLAWRLAYLAREQPTHTFLIHGAQRFSYAEAERESNRIA 50
RAFLRARGWTGGRRGSGRGSTEEGARVAPPAGDAAARGTTAPPLAPGATV 100
ALLLPAGPDFLWIWFGLAKAGLRTAFVPTALRRGPLLHCLRSCGASALVL 150
ATEFLESLEPDLPALRAMGLHLWATGPETNVAGISNLLSEAADQVDEPVP 200
GYLSAPQNIMDTCLYIFTSGTTGLPKAARISHLKVLQCQGFYHLCGVHQE 250
DVIYLALPLYHMSGSLLGIVGCLGIGATVVLKPKFSASQFWDDCQKHRVT 300
VFQYIGELCRYLVNQPPSKAEFDHKVRLAVGSGLRPDIWERFLRRFGPLQ 350
ILETYGMTEGNVATFNYTGRQGAVGRASWLYKHIFPFSLIRYDVMTGEPI 400
RNAQGHCMTTSPGEPGLLVAPVSQQSPFLGYAGAPELAKDKLLKDVFWSG 450
DVFFNTGDLLVCDEQGFLHFHDRTGDTIRWKGENVATTEVAEVLETLDFL 500
QEVNIYGVTVPGHEGRAGMAALALRPPQALNLVQLYSHVSENLPPYARPR 550
FLRLQESLATTETFKQQKVRMANEGFDPSVLSDPLYVLDQDIGAYLPLTP 600
ARYSALLSGDLRI 613

FIG. 9 mmFATP4 DNA sequence

CCCACGCGTCCGCCCACGCGTCCGGCATGGCCAAGCTGGG 40
CGTGGAGGCGGCTCTCATCAACACCAACCTTAGGCGGGAT 80
GCCCTGCGCCACTGTCTTGACACCTCAAAGGCACGAGCTC 120
TCATCTTTGGCAGTGAGATGGCCTCAGCTATCTGTGAGAT 160
CCATGCTAGCCTGGAGCCCACACTCAGCCTCTTCTGCTCT 200
GGATCCTGGGAGCCCAGCACAGTGCCCGTCAGCACAGAGC 240
ATCTGGACCCTCTTCTGGAAGATGCCCCGAAGCACCTGCC 280
CAGTCACCCAGACAAGGGTTTTACAGATAAGCTCTTCTAC 320
ATCTACACATCGGGCACCACGGGGCTACCCAAAGCTGCCA 360
TTGTGGTGCACAGCACGTATTATCGTATGGCTTCCCTGGT 400
GTACTATGGATTCCGCATGCGGCCTGATGACATTGTCTAT 440
GACTGCCTCCCCCTCTACCACTCAAGCAGGAAACATCGTG 480
GGGATTGGCAGTGCTTACTCCACGGCATGACTGTGGTGAT 520
CCGGAAGAAGTTCTCAGCCTCCCGGTTCTGGGATGATTGT 560
ATCAAGTACAACTGCACAGTGGTACAGTACATTGGCGAGC 600
TCTGCCGCTACCTCCTGAACCAGCCACCCCGTGAGGCTGA 640
GTCTCGGCACAAGGTGCGCATGGCACTGGGCAACGGTCTC 680
CGGCAGTCCATCTGGACCGACTTCTCCAGCCGTTTCCACA 720

FIG. 10A

TCCCCCAGGTGGCTGAGTTCTATGGGGCCACTGAATGCAA 760
CTGTAGCCTGGGCAACTTTGACAGCCGGGTGGGGGCCTGT 800
GGCTTCAATAGCCGCATCCTGTCCTTTGTGTACCCTATCC 840
GTTTGGTACGTGTCAATGAGGATACCATGGAACTGATCCG 880
GGGACCCGATGGAGTCTGCATTCCCTGTCAACCAGGTCAG 920
CCAGGCCAGCTGGTGGGTCGCATCATCCAGCAGGACCCTC 960
TGCGCCGTTTCGACGGGTACCTCAACCAGGGTGCCAACAA 1000
CAAGAAGATTGCTAATGATGTCTTCAAGAAGGGGGACCAA 1040
GCCTACCTCACTGGTGACGTCCTGGTGATGGATGAGCTGG 1080
GTTACCTGTACTTCCGAGATCGCACTGGGGACACGTTCCG 1120
CTGGAAAGGGGAGAATGTATCTACCACTGAGGTGGAGGGC 1160
ACACTCAGCCGCCTGCTTCATATGGCAGATGTGGCAGTTT 1200
ATGGTGTTGAGGTGCCAGGAACTGAAGGCCGAGCAGGAAT 1240
GGCTGCCGTTGCAAGTCCCATCAGCAACTGTGACCTGGAG 1280
AGCTTTGCACAGACCTTGAAAAAGGAGCTGCCTCTGTATG 1320
CCCGCCCCATCTTCCTGCGCTTCTTGCCTGAGCTGCACAA 1360
GACAGGGACCTTCAAGTTCCAGAAGACAGAGTTGCGGAAG 1400
GAGGCCTTTGACCCATCTGTTGTGAAAGACCCGCTGTTCT 1440
ATCTGGATGCTCGGAAGGGCTGCTACGTTGCACTGGACCA 1480
GGAGGCCTATACCCGCATCCAGGCAGGCGAGGAGAAGCTG 1520
TGATTTCCCCCTACATCCCTCTGAGGGCCAGAAGATGCTG 1560
GATTCAGAGCCCTAGCGTCCACCCCAGAGGGTCCTGGGCA 1600
ATGCCAGACCAAAGCTAGCAGGGCCCGCACCTCCGCCCCT 1640
AGGTGCTGATCTCCCCTCTCCCAAACTGCCAAGTGACTCA 1680
CTGCCGCTTCCCCGACCCTCCAGAGGCTTTCTGTGAAAGT 1720
CTCATCCAAGCTGTGTCTTCTGGTCCAGGCGTGGCCCCTG 1760
GCCCCAGGGTTTCTGATAGGCTCCTTTAGGATGGTATCTT 1800
GGGTCCAGCGGGCCAGGGTGTGGGAGAGGAGTCACTAAGA 1840
TCCCTCCAATCAGAAGGGAGCTTACAAAGGAACCAAGGCA 1880
AAGCCTGTAGACTCAGGAAGCTAAGTGGCCAGAGACTATA 1920
GTGGCCAGTCATCCCATGTCCACAGAGGATCTTGGTCCAG 1960
AGCTGCCAAAGTGTCACCTCTCCCTGCCTGCACCTCTGGG 2000
GAAAAGAGGACAGCATGTGGCCACTGGGCACCTGTCTCAA 2040
GAAGTCAGGATCACACACTCAGTCCTTGTTTCTCCAGGTT 2080
CCCTTGTTCTTGTCTCGGGGAGGGAGGGACGAGTGTCCTG 2120
TCTGTCCTTCCTGCCTGTCTGTGAGTCTGTGTTGCTTCTC 2160
CATCTGTCCTAGCCTGAGTGTGGGTGGAACAGGCATGAGG 2200
AGAGTGTGGCTCAGGGGCCAATAAACTCTGCCTTGACTCC 2240
TCTTAAAAAAAAAAAAAAAAAAAAAAAAAAAAAAAAAAAA 2280
AAAAAAAAAAAAAAAAAAAAA 2301

FIG. 10B mmFATP4 protein sequence

```
HASAHASGMAKLGVEAALINTNLRRDALRHCLDISKARAL  40
IFGSEMASAICEIHASLEPTLSLFCSGSWEPSIVPVSTEH  80
LDPLLEDAPKHLPSHPDKGFTDKLFYIYTSGTTGLPKAAI  120
VVHSRYYRMASLVYYGFRMRPDDIVYDCLPLYHSSRKHRG  160
DWQCLLHGMTVVIRKKFSASRFWDDCIKYNCTVVQYIGEL  200
CRYLLNQPPREAESRHKVRMALGNGLRQSIWIDFSSRFHI  240
PQVAEFYGATECNCSLGNFDSRVGACGFNSRILSFVYPIR  280
LVRVNEDTMELIRGPDGVCIPCQPGQPGQLVGRIIQQDPL  320
RRFDGYLNQGANNKKIANDVFKKGDQAYLTGDVLVMDELG  360
YLYFRDRTGDTFRWKGENVSTTEVEGTLSRLLHMADVAVY  400
GVEVPGTEGRAGMAAVASPISNCDLESFAQTLKKELPLYA  440
RPIFLRFLPELHKTGTFKFQKTELRKEGFDPSVVKDPLFY  480
LDARKGCYVALDQEAYTRIQAGEEKL                506
```

FIG. 11 mmFATP5 DNA sequence

```
CACTCATCAGAGCTAAGAGAGACTACACGCTCTCATCTAC  40
TTCAGAAAGAGCCAATGCCATGGGTATTTGGAAGAAACTA  80
ACCTTACTGCTGTTGCTGCTTCTGCTGGTTGGCCTGGGGC  120
AGCCCCCATGGCCAGCAGCTATGGCTCTGGCCCTGCGTTG  160
GTTCCTGGGAGACCCCACATGCCTTGTGCTGCTTGGCTTG  200
GCATTGCTGGGCAGACCCTGGATCAGCTCCTGGATGCCCC  240
ACTGGCTGAGCCTGGTAGGAGCAGCTCTTACCTTATTCCT  280
ATTGCCTCTACAGCCACCCCCAGGGCTACGCTGGCTGCAT  320
AAAGATGTGGCTTTCACCTTCAAGATGCTTTTCTATGGCC  360
TAAAGTTCAGGCGACGCCTTAACAAACATCCTCCAGAGAC  400
CTTTGTGGATGCTTTAGAGCGGCAAGCACTGGCATGGCCT  440
GACCGGGTGGCCCTTGGTGTGTACTGGGTCTGAGGGCTCCT  480
CAATCACAAATAGCCAGCTGGATGCCAGGTCCTGTCAGGC  520
AGCATGGGTCCTGAAAGCAAAGCTGAAGGATGCCGTAATC  560
CAGAACACAAGAGATGCTGCTGCTATCTTAGTTCTCCCGT  600
CCAAGACCATTTCTGCTTTGAGTGTGTTTCTGGGGTTGGC  640
CAAGTTGGGCTGCCCTGTGGCCTGGATCAATCCACACAGC  680
CGAGGGATGCCCTTGCTACACTCTGTACGGAGCTCTGGGG  720
CCAGTGTGCTGATTGTGGATCCAGACCTCCAGGAGAACCT  760
GGAAGAAGTCCTTCCCAAGCTGCTAGCTGAGAACATTCAC  800
```

FIG. 12A

TGCTTCTACCTTGGCCACAGCTCACCCACCCCGGCAGTAG 840
AGGCTCTGGCAGCTTCCCTGGATGCTGCACCTTCTGACCC 880
AGTACCTGCCAGCCTTCGAGCTACGATTAAGTGGAAATCT 920
CCTGCCATATTCATCTTTACTTCAGGCACCACTGGACTCC 960
CAAAGCCAGCCATCTTATCACATGAGCGGGTCATACAAGT 1000
GAGCAACGTGCTGTCCTTCTGTGGATGCAGAGCTGATGAT 1040
GTGGTCTATGACGTCCTACCTCTGTACCATACGATAGGGC 1080
TTGTCCTTGGATTCCTTGGCTGCTTACAAGTTGGAGCCAC 1120
CTGTGTCCTGGCCCCCAAGTTCTCTGCCTCCCGATTCTGG 1160
GCTGAGTGCCGGCAGCATGGCGTAACAGTGATCTTGTATG 1200
TGGGTGAAATCCTGCGGTACTTGTGTAACGTCCCTGAGCA 1240
ACCAGAAGACAAGATACATACAGTGCGCTTGGCCATGGGA 1280
ACTGGACTTCGGGCAAATGTGTGGAAAAACTTCCAGCAAC 1320
GCTTTGGTCCCATTCGGATCTGGGAATTCTACGGATCCAC 1360
AGAGGGCAATGTGGGCTTAATGAACTATGTGGGCCACTGC 1400
GGGGCTGTGGGAAGGACCAGCTGCATCCTTCGAATGCTGA 1440
CTCCCTTTGAGCTTGTACAGTTCGACATAGAGACAGCAGA 1480
GCCTCTGAGGGACAAACAGGGTTTTTGCATTCCTGTGGAG 1520
CCAGGAAAGCCAGGACTTCTTTTGACCAAGGTTCGAAAGA 1560
ACCAACCCTTCCTGGGCTACCGTGGTTCCCAGGCCGAGTC 1600
CAATCGGAAACTTGTTGCCGAATGTACGACGCGTAGGAGAC 1640
CTGTACTTCAACACTGGGCACGTGCTGACCTTGGACCAGG 1680
AAGGCTTCTTCTACTTTCAAGACCGCCTTGGTCACACCTT 1720
CCGGTGGAAGGGCGAAAACGTATCTACTGGAGAGGTGGAG 1760
TGTGTTTTGTCTAGCCTAGACTTCCTAGAGGAAGTCAATG 1800
TCTATGGTGTGCCCTGTGCCAGGGTGTGAGGGTAAGGTTGG 1840
CATGGCTGCTGTGAAACTGGCTCCTGGCAAGACTTTTGAT 1880
GGGCAGAAGCTATACCAGCATGTCCGCTCCTGGCTCCCTG 1920
CCTATGCCACACCTCATTTCATCCGTATCCAGGATTCCCT 1960
GGAGATCACAAACACCTACAAGCTGGTAAAGTCACGGCTG 2000
GTGCGTGAGGGTTTTGATGTGGGGATCATTGCTGACCCCC 2040
TCTACATACTGGACAACAAGGCCCAGACCTTCCGGAGTCT 2080
GATGCCAGATGTGTACCAGGCTGTGTGTGAAGGAACCTGG 2120
AATCTCTGACCACCTAGCCAACTGGAAGGCAATCCAAAAG 2160
TGTAGAGATTGACACTAGTCAGCTTCACAAAGTTGTCCGG 2200
GTTCCAGATGCCCATGGCCCAGTAGTACTTAGAGAATAAA 2240
CTTGAATGTGTATACAAAAAAAAAAAAAAAAAAAAAA 2277

FIG. 12B mmFATP5 protein sequence

MALALRWFLGDPTCLVLLGLALLGRPWISSWMPHWLSLVG 40
AALTLFLLPLQPPPGLRWLHKDVAFTFKMLFYGLKFRRRL 80
NKHPPEIFVDALERQALAWPDRVALVCIGSEGSSTTNSQL 120
DARSCQAAWVLKAKLKDAVIQNTRDAAAILVLPSKTISAL 160
SVFLGLAKLGCPVAWINPHSRGMPLLHSVRSSGASVLIVD 200
PDLQENLEEVLPKLLAENIHCFYLGHSSPTPGVEALGASL 240
DAAPSDPVPASLRATIKWKSPAIFIFTSGTTGLPKPAILS 280
HERVIQVSNVLSFCGCRADDVVYDVLPLYHTTGLVLGFLG 320
CLQVGATCVLAPKFSASRFWAECRQHGVTVILYVGEILRY 360
LCNVPEQPEDKIHTVRLAMGTGLRANVWKNFQQRFGPIRI 400
WEFYGSTEGNVGLMNYVGHCGAVGRTSCILRMLTPFELVQ 440
FDIETAEPLRDKQGFCIPVEPGKPGLLLTKVRKNQPFLGY 480
RGSQAESNRKLVANVRRVGDLYFNTGDVLTLDQEGFFYFQ 520
DRLGDTFRWKGENVSTGEVECVLSSLDFLEEVNVYGVPVP 560
GCEGKVGMAAVKLAPGKTFDGQKLYQHVRSWLPAYATPHF 600
IRIQDSLETTNTYKLVKSRLVREGFDVGIIADPLYILDNK 640
AQTFRSLMPDVYQAVCEGTWNL 662

FIG. 13 hsFATP2 DNA sequence

ATGGGATTGACTCTTTCCTGGACAAAGTGGATGAAGTATC 40
AACTGAACCTATCCCAGAGTCATGGAGGTCTGAAGTCACT 80
TTTTCCACTCCTGCCTTATACATTTATACTTCTGGAACCA 120
CAGGTCTTCCAAAAGCAGCCATGATCACTCATCAGCGCAT 160
ATGGTATGGAACTGGCCTCACTTTTGTAAGCGGATTGAAG 200
GCAGATGATGTCATCTATATCACTCTGCCCTTTTACCACA 240
GTGCTGCACTACTGATTGGCATTCACGGATGTATTGTGGC 280
TGGTGCTACTCTTGCCTTGCGGACTAAATTTTCAGCCAGC 320
CAGTTTTGGGATGACTGCAGAAAATACAACGTCACTGTCA 360
TTCAGTATATCGGTGAACTGCTTCGGTATTTATGCAACTC 400
ACCACAGAAACCAAATGACCGTGATCATAAAGTGAGACTG 440
GCACTGGGAAATGGCTTACGAGGAGATGTGTGGAGACAAT 480
TTGTCAAGAGATTTGGGGACATATGCATCTATGAGTTCTA 520
TGCTGCCACTGAAGGCAATATTGGATTTATGAATTATGCG 560
AGAAAAGTTGGTGCTGTTGGAAGAGTAAACTACCTACAGA 600
AAAAAATCATAACTTATGACCTGATTAAATATGATGTGGA 640
GAAAGATGAACCTGTCCGTGATGAAAATGGATATTGCGTC 680
AGAGTTCCCAAAGGTGAAGTTGGACTTCTGGTTTGCAAAA 720
TCACACAACTTACACCATTTAATGGCTATGCTGGAGCAAA 760
GGCTCAGACAGAGAAGAAAAAACTGAGAGATGTCTTTAAG 800

FIG. 14A

AAAGGAGACCTCTATTTCAACAGTGGAGATCTCTTAATGG 840
TTGACCATGAAAATTTCATCTATTTCCACGACAGAGTTGG 880
AGATACATTCCGGTGGAAAGGGGAAAATGTGGCCACCACT 920
GAAGTTGCTGATATAGTTGGACTGGTTGATTTTTTTCCAA 960
GGAAGTAAAATGTTTATGGCAGTGCATGGCCAAGATNAT 1000
GGAGGTTCGAATTGGCATGGCNTTCCNTTCAAAATGGAAA 1040
GAAAACCATGGAATTTGATGGAAAGAAATTTTTTCAGNAC 1080
ATTGCTGATAACCNACCTAGTTATGCAAGGCCCCGGTTTT 1120
NTAAGAANACAGGACACCATTGAGATCACTGGAATTTTTA 1160
AACACCGCAAAATGACCTTTGGTGGAGGAGGGCTTTAACC 1200
CNGCTGTCATCAAAGATGCCTTGTATTTTCTTGGATGACA 1240
CAGCAAAAATGTATGTGCCTATGACTGAGGACATNTATAA 1280
TGCCATAAGTGNTAAAACCCTGAAATTNTGAATATTCCCA 1320
GGAGGATAATTCAACATTTCCAGAAAGAAACTGAATGGAC 1360
AGCCACTTGATATAATCCAACTTTAATTTGATTGAAGATT 1400
GTGAGGAAATTTTGTAGGAAATTTGCATACCCGTAAAGGG 1440
AGACTTTTTTAAATAACAGTTGAGTCTTTGCAAGTAAAAA 1480
GATTTAGAGATTATTATTTTTCAGTGTGCACCTACTGTTT 1520
GTATTTGCAAACTGAGCTTGTTGGAGGGAAGGCATTATTT 1560
TTTAAAATACTTAGTAAATTAAAGAACACCAACATGTGAA 1600
AAAAAAAAAAAAAAAAAAAAAA 1622

FIG. 14B hsFATP2 protein sequence

YTYTSGTTGLPKAAMTTHQRIWYGTGLTFVSGLKADDVIY 40
TTLPFYHSAALLIGTHGCIVAGATLALRTKFSASQFWDDC 80
RKYNVTVIQYIGELLRYLCNSPQKPNDRDHKVRLALGNGL 120
RGDVWRQFVKRFGDICIYEFYAATEGNIGFMNYARKVGAV 160
GRVNYLQKKIITYDLIKYDVEKDEPVRDENGYCVRVPKGE 200
VGLLVCKITQLTPFNGYAGAKAQTEKKKLRDVFKKGDLYF 240
NSGDLLMVDHENFIYFHDRVGDTFRWKGENVATTEVADIV 280
GLVDFF 286

FIG. 15 hsFATP3 DNA sequence

CAATTCGGGACCCCCAGGGGCACTGTATGGCCACATCTCC 40
AGGTGAGCCAGGGGAAGTTGCTAAAGGATGTCTTCCGGCC 80
TGGGGATGTTTTCTTCAACACTGGGGACCTGCTGGTCTGC 120
GATGACCAAGGTTTTCTCCGCTTCCATGATCGTACTGGAG 160

FIG. 16A

ACACCTTCAGGTGGAAAGGGGAGAATGTGGCCACAACCGA 200
GGTGGCAGAGGTCTTCGAGGCCCTAGATTTTCTTCAGGAG 240
GTGAACGTCTATGGAGTCACTGTGCCAGGGCATGAAGGCA 280
GGCCTGGAATGGCAGCCCTAGTTCTGCGTCCCCCCCACGC 320
TTTGGACCTTATGCAGCTCTACACCCACGTGTCTGAGAAC 360
TTGCCACCTTATGCCCGGCCCCGATTCCTCAGGCTCCAGG 400
AGTCTTTGGCCACCACAGAGACCTTCAAACAGCAGAAAGT 440
TCGGATGGCAAATGAGGGCTTCGACCCCAGCACCCTGTCT 480
GACCCACTGTACGTTCTGGACCAGGCTGTAGGTGCCTACC 520
TGCCCCTCACAACTGCCCGGTACAGCGCCCTCCTGGCAGG 560
AAACCTTCGAATCTGAGAACTTCCACACCTGAGGCACCTG 600
AGAGAGGAACTCTGTGCGGTGCGGGCCGTTGCAGGTGTAC 640
TGGCTGTCAGGGATCTTTTTCTATACCAGAACTGCGGTCA 680
CTATTTTGTAATAAATGTGGCTGGAGCTGATCCAGCTGTC 720
TCTGACCTACAAAAAAAAAAAAAAAAAAAAAAA 753

FIG. 16B hsFATP3 protein sequence

QFGTPRGTVWPHLQVSQGKLLKDVFRPGDVFFNIGDLLVC 40
DDQGFLRFHDRTGDTFRWKGENVATTEVAEVFEALDFLQE 80
VNVYGVTVPGHEGRAGMAALVLRPPHALDLMQLYTHVSEN 120
LPPYARPRFLRLQESLATTETFKQQKVRMANEGFDPSTLS 160
DPLYVLDQAVGAYLPLTTARYSALLAGNLRI 191

FIG. 17 hsFATP4 DNA sequence

TCAAGTACAACTGCACGATTGTCATANCATTGGTGAACTG 40
TGCCGNTACCTCCTGAACCAGCCACCGCGGGAGGCAGAAA 80
ACCAGCACCAGGTTCGCATGGCACTAGGCAATGGCCTCCG 120
GCAGTCCATCTGGACCAACTTTTCCAGCCGCTTCCACATA 160
CCCCAGGTGGCTGAGTTYTACGGGGCCACAGAGTGCAACT 200
GTAGCCTGGGCAACTTCGACAGCCAGGTGGGGGCCTGTGG 240
TTTCAATAGCCGCATCCTGTCCTTCGTGTACCCCATCCGG 280
TTGGTACGTGTCAACGAGGACACCATGGAGCTGATCCGGG 320
GGCCCGACGGCGTCTGCATTCCCTGCCAGCCAGGTGAGCC 360
GGGCCAGCTGGTGGCCGCATCATCCAGAAAGACCCCCTG 400
CGCCGCTTCGATGGCTACCTCAACCAGGGCGCCAACAACA 440
AGAAGATTGCCAAGGATGTCTTCAAGAAGGGGGACCAGGC 480
CTACCTTACTGGTGATGTGCTGGTGATGGACGAGCTGGGC 520

FIG. 18A

TACCTGTACTTCCGAGACCGCACTGGGGACACGTTCCGCT 560
GGAAAGGTGAGAACGTGTCCACCACCGAGGTGGAAGGCAC 600
ACTCAGCCGCCTGCTGGACATGGCTGACGTGGCCGTGTAT 640
GGTGTCGAGGTGCCAGGAACCGAGGGCCGGGCCGGAATGG 680
CTGCTGTGGCCAGCCCCACTGGCAACTGTGACCTGGGAGC 720
GCTTTGCTCAGGTC 734

FIG. 18B hsFATP4 protein sequence

IGELCRYLLNQPPREAENQHQVRMALGNGLRQSIWINFSS 40
RFHIPQVAEFYGATECNCSLGNFDSQVGACGFNSRILSFV 80
YPIRLVRVNEDTMELIRGPDGVCIPCQPGEPGQLVGRIIQ 120
KDPLRRFDGYLNQGANNKKIAKDVFKKGDQAYLTGDVLVM 160
DELGYLYFRDRTGDTFRWKGENVSTTEVEGTLSRLLDMAD 200
VAVYGVEVPGTEG 213

FIG. 19 hsFATP5 DNA sequence

CNTGCCTCTTGTACCACGTGATGGCACTTTGTCGTTGGGA 40
TCCTCGGCTGCTTAGATCTCGGAGCCACCTGTGTTCTGGC 80
CCCCAAGTTCTCTACTTCCTGCTTCTGGGATGACTGTCGG 120
CAGCATGGCGTGACAGTGATCCTGTATGTGGGCGAGCTCC 160
TGCGNTACTTGTGTAACATTCCCCAGCAACCAGAGGACCG 200
GACACATACAGTCCGCCTGGCAATGGGCAATGGACTACGG 240
GCTGATGTGTGGGGAGACCTTCCAGCAGCGTTTCGGTCCT 280
ATTTCGGATCTNGGGAAGTCTTACGGGCTYCCACAGAAGG 320
GCAACATGGGGCTTTAGTTCAACTATTGTTGGGGGCGCTG 360
CGGGGSCCTGGRGGCAAAGATGGAGCTTGCCTCCTCCGAA 400
TGCTGTCCCCCTTTGAGCTGGTGCAGTTCGACATGGAGGC 440
GGCGGAGCCTGTGAGGGACAATCAGGGCTTCTGCATCCCT 480
GTAGGGCTAGGGGAGCCGGGGCTGCTGTTGACCAAGGTGG 520
TAAGCCAGCAACCCTTCGTGGGCTACCGCGCCCCCCGAGA 560
GCTGTCGGAACGGAAGCTGGTGCCGCAACGTGCGCAATCG 600
GGCGACGTTTACTACAACACCGGGGACGTACTGGCCATGG 640
ACCGCCGAAGGCTTCCTCTACTTCCGCGACCGACTCGGGA 680
CACCTTCCGATGGAAGGGCGAGAACGTGTCCACGCACGAG 720
GTGGAGGGCGTGTTGTCGCAGGTGGACTTCTTGCAACAGG 760
TTAACGTGTATGGCGTGTGCGTGCCAGGTTGTGAGGGTAA 800
GGTGGGCATGGCTGCTGTGGCATTAGCCCCCGGCCAGACT 840

FIG. 20A

TTCGACGGGGAGAAGTTGTACCAGCACGTTCGCGCTTGGC 880
TCCCTGCCTACGCTACCCCCCATTTCATCCGCATCCAGGA 920
CGCCATGGAGGTCACCAGCACGTTCAAACTGATGAAGACC 960
CGGTTGGTGCCGTGAGGGCTTCAATGTGGGATCGTGGTTG 1000
ACCCTCTGTTTGTACTGGACAACCGGGCCCAGTCCTTCCG 1040
GCCCCTGACGGCAGAAATGTACCAGGCTGTGTGTGAGGGA 1080
ACCTGGAGGCTCTGATCACCTGGCCAACCCACTGGGGTAG 1120
GGATCAAAGCCAGCCACCCCCACCCCAACACACTCGGTGT 1160
CCCTTTCATCCTGGGCCTGTGTGAATCCCAGCCTGGCCAT 1200
ACCCTCAACCTCAGTGGCTGGAAATGACAGTGGGCCCTG 1240
TAGCAGTGGCAGAATAAACTCAGMTGYGTTCACAGAAA 1278

FIG. 20B hsFATP5 protein sequence

EGQHGALVQLLLGALRGPGGKDGACLLRMLSPFELVQFDM 40
EAAEPVRDNQGFCIPVGLGEPGLLLTKVVSQQPFVGYRGP 80
RELSERKLVRNVRQSGDVYYNTGDVLAMDREGFLYFRDRL 120
GDTFRWKGENVSTHEVEGVLSQVDFLQQVNVYGVCVPGCE 160
GKVGMAAVALAPGQTFDGEKLYQHVRAWLPAYATPHFIR 199

FIG. 21 hsFATP6 DNA sequence

CGCTTGTGTGTTAAAGAAGAAATTTTCAGCAAGCCAGTTT 40
TGGAGTGACTGCAAGAAGTATGATGTGACTGTGTTTCAGT 80
ATATTGGAGAACTTTGTCGCTACCTTTGCAAACAATCTAA 120
GAGAGAAGGAGAAAAGGATCATAAGGTGCGTTTGGCAATT 160
GGAAATGGCATACGGAGTGATGTATGGAGAGAATTTTTAG 200
ACAGATTTGGAAATATAAAGGTGTGTGAACTTTATGCAGC 240
TACCGAATCAAGCATATCTTTCATGAACTACACTGGGAGA 280
ATTGGAGCAATTGGGAGAACAAATTTGTTTTACAAACTTC 320
TTTCCACTTTTGACTTAATAAAGTATGACTTTCAGAAAGA 360
TGAACCCATGAGAAATGAGCAGGGTTGGGTATTCATGAGA 400
AAAAGGAGACCTGGACTTCTCATTTCTCGAGTGAATGCAA 440
AAAATCCCTTCTTTGGCTATGCTGGGCCTTATAAGCACAC 480
AAAAGACAAATTGCTTTGTGATGTTTTTAAGAAGGGAGAT 520
GTTTACCTTAATACTGGAGACTTAATAGTCCAGGATCAGG 560
ACAATTTCCTTTATTTTTGGGACCGTACTGGAGACACTTT 600
CAGATGGAAAGGAGAAAATGTCGCAACCACTGAGGTTGCT 640
GATGTTATTGGAATGTTGGATTTCATACAGGAAGCAAACG 680
TCTATGGTGTGGCTATATCAGGTTATGAAGGAAGAGCAGG 720

FIG. 22A

AATGGCTTCTATTATTTTAAAACCAAATACATCTTTAGAT 760
TTGGAAAAAGTTTATGAACAAGTTGTAACATTTCTACCAG 800
CTTATGCTTGTCCACGATTTTTAAGAATTCAGGAAAAAAT 840
GGAAGCAACAGGAACATTCAAACTATTGAAGCATCAGTTG 880
GTGGAAGATGGATTTAATCCACTGAAAATTTCTGAACCAC 920
TTTACTTCATGGATAACTTGAAAAAGTCTTATGTTCTACT 960
GACCAGGGAACTTTATGATCAAATAATGTTAGGGGAAATA 1000
AAACTTTAAGATTTTTATATCTAGAACTTTCATATGCTTT 1040
CTTAGGAACAGTGAGAGCGGGGTATATGATTCTTTATGAA 1080
ATGGGGAAAGGGAGCTAACATTAATTATGCATGTACTATA 1120
TTTCCTTAATATGAGAGATAATTTTTTAATTGCATAAGAA 1160
TTTTAATTTCTTTTAATTGATATAAACAGAGTTGATTATT 1200
CTTTTTATCTATTTGGAGATTCAGTGCATAACTAAGTATT 1240
TTCCTTAATACTAAAGATTTTAAATAATAAATAGTGGCTA 1280
GCGGTTTGGACAATCACTAAAAATGTACTTTCTAATAAGT 1320
AAAATTTCTAATTTTGAATAAAAGATTAAATTTTACTGAA 1360
A 1361

FIG. 22B hsFATP6 protein sequence

ACVLKKKFSASQFWSDCKKYDVIVFQYIGELCRYLCKQSKREGEKDHKVR 50
LAIGNGIRSDVWREFLDRFGNIKVCELYAATESSISFMNYTGRIGAIGRT 100
NLFYKLLSIFDLIKYDFQKDEPMRNEQGWVFMRKRRPGLLISRVNAKNPF 150
FGYAGPYKHIKDKLLCDVFKKGDVYLNTGDLIVQDQDNFLYFWDRIGDTF 200
RWKGENVATTEVADVIGMLDFIQEANVYGVAISGYEGRAGMASIILKPNT 250
SLDLEKVYEQVVTFLPAYACPRFLRIQEKMEATGTFKLLKHQLVEDGFNP 300
LKISEPLYFMDNLKKSYVLLTRELYDQIMLGEIKL 335

FIG. 23 mtFATP DNA sequence

TAGTCGATAACGTCAAGGACGCTCTGCGGGCCTGCGCACC 40
TTCCTGAGGTTGGTCGACAACCAATTCGACATTTCGCAAA 80
CGAATCGAGGGCTTACGTGTCCGATTACTACGGCGGCGCA 120
CACACAACGGTCAGGCTGATCGACCTGGCAACTCGGATGC 160
CGCGAGTGTTGGCGGACACGCCGGTGATTGTGCGTGGGGC 200
AATGACCGGGCTGCTGGCCCGGCCGAATTCCAAGGCGTCG 240
ATCGGCACGGTGTTCCAGGACCGGGCCGCTCGCTACGGTG 280
ACCGAGTCTTCCTGAAATTCGGCGATCAGCAGCTGACCTA 320
CCGCGACGCTAACGCCACCGCCAACCGGTACGCCGCGGTG 360

FIG. 24A

TTGGCCGCCCGCGGCGTCGGCCCCGGCGACGTCGTTGGCA 400
TCATGTTGCGTAACTCACCCAGCACAGTCTTGGCGATGCT 440
GGCCACGGTCAAGTGCGGCGCTATCGCCGGCATGCTCAAC 480
TACCACCAGCGCGGCGAGGTGTTGGCGCACAGCCTGGGTC 520
TGCTGGACGCGAAGGTACTGATCGCAGAGTCCGACTTGGT 560
CAGCGCCGTCGCCGAATGCGGCGCCTCGCGCGGCCGGGTA 600
GCGGGCGACGTGCTGACCGTCGAGGACGTGGAGCGATTCG 640
CCACAACGGCGCCCGCCACCAACCCGGCGTCGGCGTCGGC 680
GGTGCAAGCCAAAGACACCGCGTTCTACATCTTCACCTCG 720
GGCACCACCGGATTTCCCAAGGCCAGTGTCATGACGCATC 760
ATCGGTGGCTGCGGCGGCTGGCCGTCTTCGGAGGGATGGG 800
GCTGCGGCTGAAGGGTTCCGACACGCTCTACAGCTGCCTG 840
CCGCTGTACCACAACAACGCGTTAACGGTCGCGGTGTCGT 880
CGGTGATCAATTCTGGGGCGACCCTGGCGCTGGGTAAGTC 920
GTTTTCGGCGTCGCGGTTCTGGCATCAGGTGATTGCCAAC 960
CGGCCGACGCGGTTCGTCTACATCGGCGAAATCTGCCGTT 1000
ATCTGCTCAACCAGCCGGCCAAGCCGACCGACCGTGCCCA 1040
CCAGGTGCGGGTGATCTGCGGTAACGGCTGCGGCCCGGAG 1080
ATCTGGGATCAGTTCACCACCCGCTTCGGGGTCGCGCGGG 1120
TGTGCGAGTTCTACGCCGCCAGCGAAGGCAACTCGGCCTT 1160
TATCAACATCTTCAACGTGCCCAGGACCGCCCGGGTATCG 1200
CCGATGCCGCTTGCCTTTGTGGAATACGACCTGGACACCG 1240
GCGATCCGCTGCGGGATGCGAGCGGGCGAGTGCGTCGGGT 1280
ACCCGACGGTGAACCCGGCCTGTTGCTTAGCCGGGTCAAC 1320
CGGCTGCAGCCGTTCGACGGCTACACCGACCCGGTTGCCA 1360
GCGAAAAGAAGTTGGTGCGCAACGCTTTTCGAGATGGCGA 1400
CTGTTGGTTCAACACCGGTGACGTGATGAGCCCGCAGGGC 1440
ATGGGCCATGCCGCCTTCGTCGATCGGCTGGGCGACACCT 1480
TCCGCTGGAAGGCGCGAGAATGTCGCCACCACTCAGGTCGA 1520
AGCGGCACTGGCCTCCGACCAGACCGTCGAGGAGTGCACG 1560
GTCTACGGCGTCCAGATTCCGCGCACCGGCGCGGCGCCCG 1600
GAATGGCCGCGATCACACTGCGCGCTGGCGCCGAATTCGA 1640
CGGCCAGGCGCTGGCCCGAACGGTTTACGGTCACTTGCCC 1680
GGCTATGCACTTCCGCTCTTTGTTCGGGTAGTCGGGTCGC 1720
TGGCGCACACCACGACGTTCAAGAGTCGCAAGGTGGAGTT 1760
GCGCAACCAGGCCTATGGCGCCGACATCGAGGATCCGCTG 1800
TACGTACTGGCCGGCCCGGACGAAGGATATGTGCCGTACT 1840
ACGCCGAATACCCTGACGAGGTTTCGCTCGGAAGGCGACC 1880
GCAGGGCTAGCGGATTCCGGCGCAGTCTCGATACCCGCA 1920
CTGGACGCTCGACGGTAACCAGGCACTATGGATGCGTGCG 1960
TTCAACACCGCCGGCCTCAGCCCGGTCGTTCAACACCGCCG 2000
GCGTTAG 2007

FIG. 24B mtFATP protein sequence msdyyggahttvrlidlatrmprvladtpvivrgamtgll 40
arpnskasigtvfqdraarygdrvflkfgdqgltyrdana 80
tanryaavlaargvgpgdvvgimlrnspstvlamlatvkc 120
gaiagmlnyhqrgevlahslglldakvliaesdlvsavae 160
cgasrgrvagdvltvedverfattapatrpasasavqakd 200
tafyiftsgttgfpkasvmthhrwlralavfggmglrlkg 240
sdtlysclplyhnnaltvavssvinsgatlalgksfsasr 280
fwdevianratafvyigeicryllnqpakptdrahqvrvi 320
cgnglrpeiwdefttrfgvarvcefyaasegnsafinifn 360
vprtagvspmplafveydldtgdplrdasgrvrrvpdgep 400
glllsrvnrlqpfdgytdpvasekklvrnafrdgdcwfnt 440
gdvmspqgmghaafvdrlgdtfrwkgenvattqveaalas 480
dqtveectvygvqiprtggragmaaitlragaefdgqala 520
rtvyghlpgyalplfvrvvgslahtttfksrkvelrnqay 560
gadiedplyvlagpdegyvpyyaeypeevslgrrpqg 597

FIG. 25 hsFATP1

1 tcg acc cac ggc gtc cgg gac ccc aaa gca gaa gcc cgc aca gta ggc aca gcg cac cca
61 aga agg gtc cag gag tct gca gaa aca gaa agg tcc ccg gcc tca gcc tcc tag tcc ctg
121 cct gcc tcc tgc ctg agc ttc tgg gag act gaa ggc acg gct tgc agc ttc agg atg cgg
M R
181 gct ccg ggt gcg ggc gcg gcc tcg gtg gtc tcg ctg gcg ctg ttg tgg ctg ctg ggg ctg
A P G A G A A S V V S L A L L W L L G L
241 ccg tgg acc tgg agc gcg gca gcg gcg ctc ggc gtg tac gtg ggc agc ggc ggc tgg cgc
P W T W S A A A A L G V Y V G S G G W R
301 ttc ctg cgc atc gtc tgc aag acc gcg agg cga gac ctc ttc ggt ctc tct gtg ctg atc
F L R I V C K T A R R D L F G L S V L I
361 cgc gtg cgc ctg gag ctg cgg cgg cac cag cgt gcc ggc cac acc atc ccg cgc atc ttt
R V R L E L R R H Q R A G H T I P R I F
421 cag gcg gta gtg cag cga cag ccc gag cgc ctg gcg ctg gtg gat gcc ggg acc ggc gag
Q A V V Q R Q P E R L A L V D A G T G E
481 tgc tgg acc ttt gcg cag ctg gac gcc tac tcc aat gcg gta gcc aac ctc ttc cgc cag
C W T F A Q L D A Y S N A V A N L F R Q
541 ctg ggc ttc gcg ccg ggc gac gtg gtg gcc atc ttc ctg gag ggc cgg ccg gag ttc gtg
L G F A P G D V V A I F L E G R P E F V
601 ggg ctg tgg ctg ggc ctg gcc aag gcg ggc atg gag gcc gcg ctg ctc aac gtg aac ctg
G L W L G L A K A G M E A A L L N V N L

FIG. 26A

```
661   cgg cgc gag ccc ctg gcc ttc tgc ctg ggc acc tcg ggc gct aag gcc ctg atc ttt gga
       R   R   E   P   L   A   F   C   L   G   T   S   G   A   K   A   L   I   F   G
721   gga gaa atg gtg gcg gcg gtg gcc gaa gtg agc ggg cat ctg ggg aaa agt ttg atc aag
       G   E   M   V   A   A   V   A   E   V   S   G   H   L   G   K   S   L   I   K
781   ttc tgc tct gga gac ttg ggg ccc gag ggc atc ttg ccg gac acc cac ctc ctg gac ccg
       F   C   S   G   D   L   G   P   E   G   I   L   P   D   T   H   L   L   D   P
841   ctg ctg aag gag gcc tct act gcc ccc ttg gca cag atc ccc agc aag ggc atg gac gat
       L   L   K   E   A   S   T   A   P   L   A   Q   I   P   S   K   G   M   D   D
901   cgt ctt ttc tac atc tac acg tcg ggg acc acc ggg ctg ccc aag gct gcc att gtc gtg
       R   L   F   Y   I   Y   T   S   G   T   T   G   L   P   K   A   A   I   V   V
961   cac agc agg tac tac cgc atg gca gcc ttc ggc cac cac gcc tac cgc atg cag gcg gct
       H   S   R   Y   Y   R   M   A   A   F   G   H   H   A   Y   R   M   Q   A   A
1021  gac gtg ctc tat gac tgc ctg ccc ctg tac cac tcg gca gga aac atc atc ggc gtg ggg
       D   V   L   Y   D   C   L   P   L   Y   H   S   A   G   N   I   I   G   V   G
1081  cag tgt ctc atc tat ggg ctg aca gtc gtc ctc cgc aag aaa ttc tcg gcc agc cgc ttc
       Q   C   L   I   Y   G   L   T   V   V   L   R   K   K   F   S   A   S   R   F
1141  tgg gac gac tgc atc aag tac aac tgc acg gtg gtt cag tac atc ggg gag atc tgc cgc
       W   D   D   C   I   K   Y   N   C   T   V   V   Q   Y   I   G   E   I   C   R
1201  tac ctg ctg aag cag ccg gtg cgc gag gcg gag agg cga cac cgc gtg cgc ctg gcg gtg
       Y   L   L   K   Q   P   V   R   E   A   E   R   R   H   R   V   R   L   A   V
```

FIG. 26B

```
1261  ggg aac ggg ctg cgt cct gcc atc tgg gag gag ttc acg gag cgc ttc ggc gta cgc caa
      G   N   G   L   R   P   A   I   W   E   E   F   T   E   R   F   G   V   R   Q
1321  atc ggg gag ttc tac ggc gcc acc gag tgc aac tgc agc att gcc aac atg gac ggc aag
      I   G   E   F   Y   G   A   T   E   C   N   C   S   I   A   N   M   D   G   K
1381  gtc ggc tcc tgt ggt ttc aac agc cgc atc ctg ccc cac gtg tac ccc atc cgg ctg gtg
      V   G   S   C   G   F   N   S   R   I   L   P   H   V   Y   P   I   R   L   V
1441  aag gtc aat gag gac aca atg gag ctg ctg cgg gat gcc cag ggc ctc tgc atc ccc tgc
      K   V   N   E   D   T   M   E   L   L   R   D   A   Q   G   L   C   I   P   C
1501  cag gcc ggg gag cct ggc ctc ctt gtg ggt cag atc aac caa cag gac ccg ctg cgc cgc
      Q   A   G   E   P   G   L   L   V   G   Q   I   N   Q   Q   D   P   L   R   R
1561  ttc gat ggc tat gtc agc gag agc gcc acc agc aag aag atc gcc cac agc gtc ttc agc
      F   D   G   Y   V   S   E   S   A   T   S   K   K   I   A   H   S   V   F   S
1621  aag ggc gac agc gcc tac ctc tca ggt gac gtg cta gtg atg gat gag ctg ggc tac atg
      K   G   D   S   A   Y   L   S   G   D   V   L   V   M   D   E   L   G   Y   M
1681  tac ttc cgg gac cgt agc ggg gac acc ttc cgc tgg cga ggg gag aac gtc tcc acc acc
      Y   F   R   D   R   S   G   D   T   F   R   W   R   G   E   N   V   S   T   T
1741  gag gtg gag ggc gtg ctg agc cgc ctg ctg ggc cag aca gac gtg gcc gtc tat ggg gtg
      E   V   E   G   V   L   S   R   L   L   G   Q   T   D   V   A   V   Y   G   V
1801  gct gtt cca gga gtg gag ggt aag gca ggg atg gcg gcc gtc gca gac ccc cac agc ctg
      A   V   P   G   V   E   G   K   A   G   M   A   A   V   A   D   P   H   S   L
1861  ctg gac ccc aac gcg ata tac cag gag ctg cag aag gtg ctg gca ccc tat gcc cgg ccc
      L   D   P   N   A   I   Y   Q   E   L   Q   K   V   L   A   P   Y   A   R   P
```

FIG. 26C

```
1921  atc ttc ctg cgc ctc ctg ccc cag gtg gac acc aca ggc acc ttc aag atc cag aag acg
      I   F   L   R   L   L   P   Q   V   D   T   T   G   T   F   K   I   Q   K   T
1981  agg ctg cag cga gag ggc ttt gac cca cgc cag acc tca gac cgg ctc ttc ttc ctg gac
      R   L   Q   R   E   G   F   D   P   R   Q   T   S   D   R   L   F   F   L   D
2041  ctg aag cag ggc cac tac ctg ccc tta aat gag gca gtc tac act cgc atc tgc tcg ggc
      L   K   Q   G   H   Y   L   P   L   N   E   A   V   Y   T   R   I   C   S   G
2101  gcc ttc gcc ctc tga agc tgt tcc tct act ggc cac aaa ctc tgg gcc tgg tgg gag agg
      A   F   A   L   *
2161  cca gct tga gcc aga cag cgc tgc cca ggg gtg gcc gcc tag tac aca ccc acc tgg ccg
2221  agc tgt acc tgg cac ggc cca tcc tgg act gag aaa ctg gaa cct cag agg aac ccg tgc
2281  ctc tct gct gcc ttg gtg ccc ctg tgt ctg cct cct ctc cct gct ttt cag cct ctg tct
2341  cct tcc atc cct gtc cct gtc tgg cct taa ctc ttc cct ctc ttt ctt ttc ttt ctt tct
2401  ttc ttt ttt ttt aag ata gag tct cac tct gct gcc cgg gct aga gtg cag tgg tgg gat
2461  ctc ggc tca ctg caa cct ctg cct cct ggg gtt caa gtg atc ctc cca cct cag cct cct
```

FIG. 26D 2521 gag tag ctg gga tta cag gca ccc gcc acc acg tcc agc taa ttt tta tat ttt tag tag
2581 aga cgg ggt ttc acc atg ttg gtc agg ctg gtc ttg aac tcc tga cct cag gtg atc cgc
2641 tgg cct cgg cct ccc aga gtg ctg gga tta tag gcg tga gcc tct ggc ccg gcc ttt cct
2701 ttt tcc tct cct ctc ctg ccg aga gtg gaa cac acg tgt cct ggg agc tgc atc ttg tgt
2761 agg gtc cag ctg ctt ttg ggg act gca gga atc atc tcc cct ggg ccc tgg act cgg act
2821 ggg gcc tcc cca cct ccc tct cgg ctg tgc ctt acg gag ccc caa tcc agg cct cct gtg
2881 gct gtt ggg ttc cag atg ctg cag ctc cat gtg act tcc aag cag gcc ctc cgc cct ccc
2941 tgc tga atg gag gag ccg ggg gtc ccc cag gcc aac tgg aaa atc tcc cag gct agg cca
3001 att gcc ttt tgc act tcc ccg ttc ctg tca cat ttc ccc agc ccc acc ttc ccc tcc tga
3061 tgc cct gaa agc ttc cgg aat tga ctg tga cca ctt gga tgt cac cac tgt cag ccc ctg
3121 cct tga tgt ccc cat tta gcc atc tcc atg gag ctc ctg ctg gag ggc cct gaa ccc tgc
3181 act gcg tgg ctg ccc agc cag ctg cct cct gtc ctg gga gga ggc ctc ctg ggt gtc ctc
3241 atc tgg tgt gtc tac tgg agg gtc cca cag gag agg cag cag agg ggt cag ggg agg tct
3301 cct gcc ggg ggt tgg cct ctc aag cct cag ggg ttc tag cct gtt gaa tat acc cca cct
3361 ggt ggg tgg ccc ctc cga tgt ccc cac tga tgg ctc tga cac cgt gtt ggt ggc gat gtc
3421 cca gac aat ccc acc agg acg gcc cag aca tcc cta ctg gct tcg ctg gtg gct cat ctc
3481 gaa cat cca cgc cag cct ttc tgg ggc cgg cca ccc agg ccg cct gtc cgt ctg tcc tcc
3541 ctc cag cag cac ccc ctg gcc cct gga gtg gtg ggg cca tgg caa gag aca ccg tgg cgt
3601 ctc atg tga act ttc ctg ggc act gtg gtt tta ttt cct aat tga ttt aag aaa taa acc
3661 tga aga ccg tct ggt gaa aaa aaa aaa aaa aaa agg gcg gcc gc

FIG. 26E hsFATP4

```
1    cga ccc acg cgt ccg ggc ggg cgg ggc cgg gcg gcg ggc ggg gct ggc ggg gcg gcc ggg
61   cca tgc agg gcg cag agc cgg cta aac cct gct gag acc cgg ctc cgt gcg tcc agg ggc
121  ggc taa tgc ccc tca cgc tgt cta cgc tgc tgc aac cgg gcc gca tct gga cgg ggc gcc
181  gcg cgg cgg agc cga cgc cgg gcc aca atg ctg ctt gga gcc tct ctg gtg ggg gtg ctg
                                         M   L   L   G   A   S   L   V   G   V   L
241  ctg ttc tcc aag ctg gtg ctg aaa ctg ccc tgg acc cag gtg gga ttc tcc ctg ttg ttc
     L   F   S   K   L   V   L   K   L   P   W   T   Q   V   G   F   S   L   L   F
301  ctc tac ttg gga tct ggc ggc tgg cgc ttc atc cgg gtc ttc atc aag acc atc agg cgc
     L   Y   L   G   S   G   G   W   R   F   I   R   V   F   I   K   T   I   R   R
361  gat atc ttt ggc ggc ctg gtc ctc ctg aag gtg aag gca aag gtg cga cag tgc ctg cag
     D   I   F   G   G   L   V   L   L   K   V   K   A   K   V   R   Q   C   L   Q
421  gag cgg cgg aca gtg ccc att ttg ttt gcc tct acc gtt cgg cgc cac ccc gac aag acg
     E   R   R   T   V   P   I   L   F   A   S   T   V   R   R   H   P   D   K   T
481  gcc ctg atc ttc gag ggc aca gat acc cac tgg acc ttc cgc cag ctg gat gag tac tca
     A   L   I   F   E   G   T   D   T   H   W   T   F   R   Q   L   D   E   Y   S
541  agc agt gta gcc aac ttc ctg cag gcc cgg ggc ctg gcc tcg ggc gat gtg gct gcc atc
     S   S   V   A   N   F   L   Q   A   R   G   L   A   S   G   D   V   A   A   I
601  ttc atg gag aac cgc aat gag ttc gtg ggc cta tgg ctg ggc atg gcc aag ctc ggt gtg
     F   M   E   N   R   N   E   F   V   G   L   W   L   G   M   A   K   L   G   V
```

FIG. 27A

```
661   gag gca gcc ctc atc aac acc aac ctg cgg cgg gat gct ctg ctc cac tgc ctc acc acc
      E   A   A   L   I   N   T   N   L   R   R   D   A   L   L   H   C   L   T   T
721   tcg cgc gca cgg gcc ctt gtc ttt ggc agc gaa atg gcc tca gcc atc tgt gag gtc cat
      S   R   A   R   A   L   V   F   G   S   E   M   A   S   A   I   C   E   V   H
781   gcc agc ctg gac ccc tcg ctc agc ctc ttc tgc tct ggc tcc tgg gag ccc ggt gcg gtg
      A   S   L   D   P   S   L   S   L   F   C   S   G   S   W   E   P   G   A   V
841   cct cca agc aca gaa cac ctg gac cct ctg ctg aaa gat gct ccc aag cac ctt ccc agt
      P   P   S   T   E   H   L   D   P   L   L   K   D   A   P   K   H   L   P   S
901   tgc cct gac aag ggc ttc aca gat aaa ctg ttc tac atc tac aca tcc ggc acc aca ggg
      C   P   D   K   G   F   T   D   K   L   F   Y   I   Y   T   S   G   T   T   G
961   ctg ccc aag gcc gcc atc gtg gtg cac agc agg tat tac cgc atg gct gcc ctg gtg tac
      L   P   K   A   A   I   V   V   H   S   R   Y   Y   R   M   A   A   L   V   Y
1021  tat gga ttc cgc atg cgg ccc aac gac atc gtc tat gac tgc ctc ccc ctc tac cac tca
      Y   G   F   R   M   R   P   N   D   I   V   Y   D   C   L   P   L   Y   H   S
1081  gca gga aac atc gtg gga atc ggc cag tgc ctg ctg cat ggc atg acg gtg gtg att cgg
      A   G   N   I   V   G   I   G   Q   C   L   L   H   G   M   T   V   V   I   R
1141  aag aag ttc tca gcc tcc cgg ttc tgg gac gat tgt atc aag tac aac tgc acg att gtg
      K   K   F   S   A   S   R   F   W   D   D   C   I   K   Y   N   C   T   I   V
1201  cag tac att ggt gaa ctg tgc cgc tac ctc ctg aac cag cca ccg cgg gag gca gaa aac
      Q   Y   I   G   E   L   C   R   Y   L   L   N   Q   P   P   R   E   A   E   N
```

FIG. 27B

```
1261  cag cac cag gtt cgc atg gca cta ggc aat ggc ctc cgg cag tcc atc tgg acc aac ttt
      Q   H   Q   V   R   M   A   L   G   N   G   L   R   Q   S   I   W   T   N   F
1321  tcc agc cgc ttc cac ata ccc cag gtg gct gag ttc tac ggg gcc aca gag tgc aac tgt
      S   S   R   F   H   I   P   Q   V   A   E   F   Y   G   A   T   E   C   N   C
1381  agc ctg ggc aac ttc gac agc cag gtg ggg gcc tgt ggt ttc aat agc cgc atc ctg tcc
      S   L   G   N   F   D   S   Q   V   G   A   C   G   F   N   S   R   I   L   S
1441  ttc gtg tac ccc atc cgg ttg gta cgt gtc aac gag gac acc atg gag ctg atc cgg ggg
      F   V   Y   P   I   R   L   V   R   V   N   E   D   T   M   E   L   I   R   G
1501  ccc gac ggc gtc tgc att ccc tgc cag cca ggt gag ccg ggc cag ctg gtg ggc cgc atc
      P   D   G   V   C   I   P   C   Q   P   G   E   P   G   Q   L   V   G   R   I
1561  atc cag aaa gac ccc ctg cgc cgc ttc gat ggc tac ctc aac cag ggc gcc aac aac aag
      I   Q   K   D   P   L   R   R   F   D   G   Y   L   N   Q   G   A   N   N   K
1621  aag att gcc aag gat gtc ttc aag aag ggg gac cag gcc tac ctt act ggt gat gtg ctg
      K   I   A   K   D   V   F   K   K   G   D   Q   A   Y   L   T   G   D   V   L
1681  gtg atg gac gag ctg ggc tac ctg tac ttc cga gac cgc act ggg gac acg ttc cgc tgg
      V   M   D   E   L   G   Y   L   Y   F   R   D   R   T   G   D   T   F   R   W
1741  aaa ggt gag aac gtg tcc acc acc gag gtg gaa ggc aca ctc agc cgc ctg ctg gac atg
      K   G   E   N   V   S   T   T   E   V   E   G   T   L   S   R   L   L   D   M
1801  gct gac gtg gcc gtg tat ggt gtc gag gtg cca gga acc gag ggc cgg gcc gga atg gct
      A   D   V   A   V   Y   G   V   E   V   P   G   T   E   G   R   A   G   M   A
1861  gct gtg gcc agc ccc act ggc aac tgt gac ctg gag cgc ttt gct cag gtc ttg gag aag
      A   V   A   S   P   T   G   N   C   D   L   E   R   F   A   Q   V   L   E   K
```

FIG. 27C

```
1921  gaa ctg ccc ctg tat gcg cgc ccc atc ttc ctg cgc ctc ctg cct gag ctg cac aaa aca
      E   L   P   L   Y   A   R   P   I   F   L   R   L   L   P   E   L   H   K   T
1981  gga acc tac aag ttc cag aag aca gag cta cgg aag gag ggc ttt gac ccg gct att gtg
      G   T   Y   K   F   Q   K   T   E   L   R   K   E   G   F   D   P   A   I   V
2041  aaa gac ccg ctg ttc tat cta gat gcc cag aag ggc cgc tac gtc ccg ctg gac caa gag
      K   D   P   L   F   Y   L   D   A   Q   K   G   R   Y   V   P   L   D   Q   E
2101  gcc tac agc cgc atc cag gca ggc gag gag aag ctg tga ttc ccc cca tcc ctc tga ggg
      A   Y   S   R   I   Q   A   G   E   E   K   L   *
2161  ccg gcg gat gct gga tcc gga gcc cca ggt tcc gcc cca gag cgg tcc tgg aca agg cca
2221  gac caa agc aag cag ggc ctg gca cct cca tcc tga ggt gct gcc cct cca tcc aaa act
2281  gcc aag tga ctc att gcc ttc cca acc ctt cca gag gct ttc tgt gaa agt ctc atg tcc
2341  aag ttc cgt ctt ctg ggc tgg gca ggc cct ctg gtt ccc agg ctg aga ctg acg ggt ttt
2401  ctc agg atg atg tct tgg gtg agg gta ggg aga gga caa ggg gtc acc gag ccc ttc cca
2461  gag agc agg gag ctt ata aat gga acc aga gca gaa gtc ccc aga ctc agg aag tca aca
2521  gag tgg gca ggg aca gtg gta gca tcc atc tgg tgg cca aag aga atc gta gcc cca gag
2581  ctg ccc aag ttc act ggg ctc cac ccc cac ctc cag gag ggg agg aga gga cct gac atc
2641  tgt agg tgg ccc ctg atg ccc cat cta cag cag gag gtc agg acc acg ccc ctg gcc tct
2701  ccc cac tcc ccc atc ctc ctc cct ggg tgg ctg cct gat tat ccc tca ggc agg gcc tct
2761  cag tcc ttg tgg gtc tgt gtc acc tcc atc tca gtc ttg gcc tgg cta tga ggg gag gag
2821  gaa tgg gag agg ggg ctc agg ggc caa taa act ctg cct tga gtc ctc cta aaa aaa aaa
2881  aaa aaa aaa aaa aaa aaa aaa aaa aaa ggg cgg ccg c
```

FIG. 27D

Protein Sequence 646 a.a. MRAPGAGAASVV....VYTRICSGAFAL
646 Amino Acids MW: 71062 Dalton

| | | n | n% | MW | MW% |
|---|---|---|---|---|---|
| A ala | Alanine | 64 | 9.9 | 4546 | 6.4 |
| C cys | cysteine | 15 | 2.3 | 1545 | 2.2 |
| D asp | aspartic acid | 30 | 4.6 | 3450 | 4.9 |
| E glu | glutamic acid | 31 | 4.8 | 4000 | 5.6 |
| F phe | phenylalanine | 29 | 4.5 | 4264 | 6.0 |
| G gly | glycine | 63 | 9.8 | 3592 | 5.1 |
| H his | histidine | 13 | 2.0 | 1781 | 2.5 |
| I ile | isoleucine | 29 | 4.5 | 3279 | 4.6 |
| K lys | lysine | 22 | 3.4 | 2818 | 4.0 |
| L leu | leucine | 77 | 11.9 | 8707 | 12.3 |
| M met | methionine | 11 | 1.7 | 1441 | 2.0 |
| N asn | asparagine | 15 | 2.3 | 1710 | 2.4 |
| P pro | proline | 29 | 4.5 | 2814 | 4.0 |
| Q gln | glutamine | 25 | 3.9 | 3201 | 4.5 |
| R arg | arginine | 49 | 7.6 | 7648 | 10.8 |
| S ser | serine | 33 | 5.1 | 2872 | 4.0 |
| T thr | threonine | 27 | 4.2 | 2728 | 3.8 |
| V val | valine | 51 | 7.9 | 5052 | 7.1 |
| W trp | tryptophan | 9 | 1.4 | 1674 | 2.4 |
| X ukw | unknown | -- | -- | | |
| Y tyr | tyrosine | 24 | 3.7 | 3913 | 5.5 |
| Z --- STOP | | | | | |

FIG. 28B hsFATP4.pep -> KD Hydrophobicity <11/1>

Protein sequence 643 a.a. MLLGASLVGVLL ... AYSRIQAGEEKL hs FATP4. pep-> A.A. Usage Protein Sequence 643 a.a. MLLGASLVGVLL...AYSRIQAGEEKL
643 Amino Acids MW: 72018 Dalton

| | | n | n% | MW | MW% |
|---|---|---|---|---|---|
| A ala | alanine | 46 | 7.2 | 3267 | 4.5 |
| C cys | cysteine | 16 | 2.5 | 1648 | 2.3 |
| D asp | aspartic acid | 33 | 5.1 | 3795 | 5.3 |
| E glu | glutamic acid | 33 | 5.1 | 4258 | 5.9 |
| F phe | phenylalanine | 34 | 5.3 | 5000 | 6.9 |
| G gly | glycine | 54 | 8.4 | 3079 | 4.3 |
| H his | histidine | 12 | 1.9 | 1644 | 2.3 |
| I ile | isoleucine | 30 | 4.7 | 3392 | 4.7 |
| K lys | lysine | 31 | 4.8 | 3970 | 5.5 |
| L leu | leucine | 76 | 11.8 | 8594 | 11.9 |
| M met | methionine | 12 | 1.9 | 1572 | 2.2 |
| N asn | asparagine | 21 | 3.3 | 2394 | 3.3 |
| P pro | proline | 31 | 4.8 | 3008 | 4.2 |
| Q gln | glutamine | 23 | 3.6 | 2945 | 4.1 |
| R arg | arginine | 45 | 7.0 | 7024 | 9.8 |
| S ser | serine | 35 | 5.4 | 3046 | 4.2 |
| T thr | threonine | 32 | 5.0 | 3233 | 4.5 |
| V val | valine | 46 | 7.2 | 4557 | 6.3 |
| W trp | tryptophan | 8 | 1.2 | 1488 | 2.1 |
| X ukw | unknown | -- | -- | | |
| Y tyr | tyrosine | 25 | 3.9 | 4076 | 5.7 |
| Z --- STOP | | | | | |

FIG. 29B

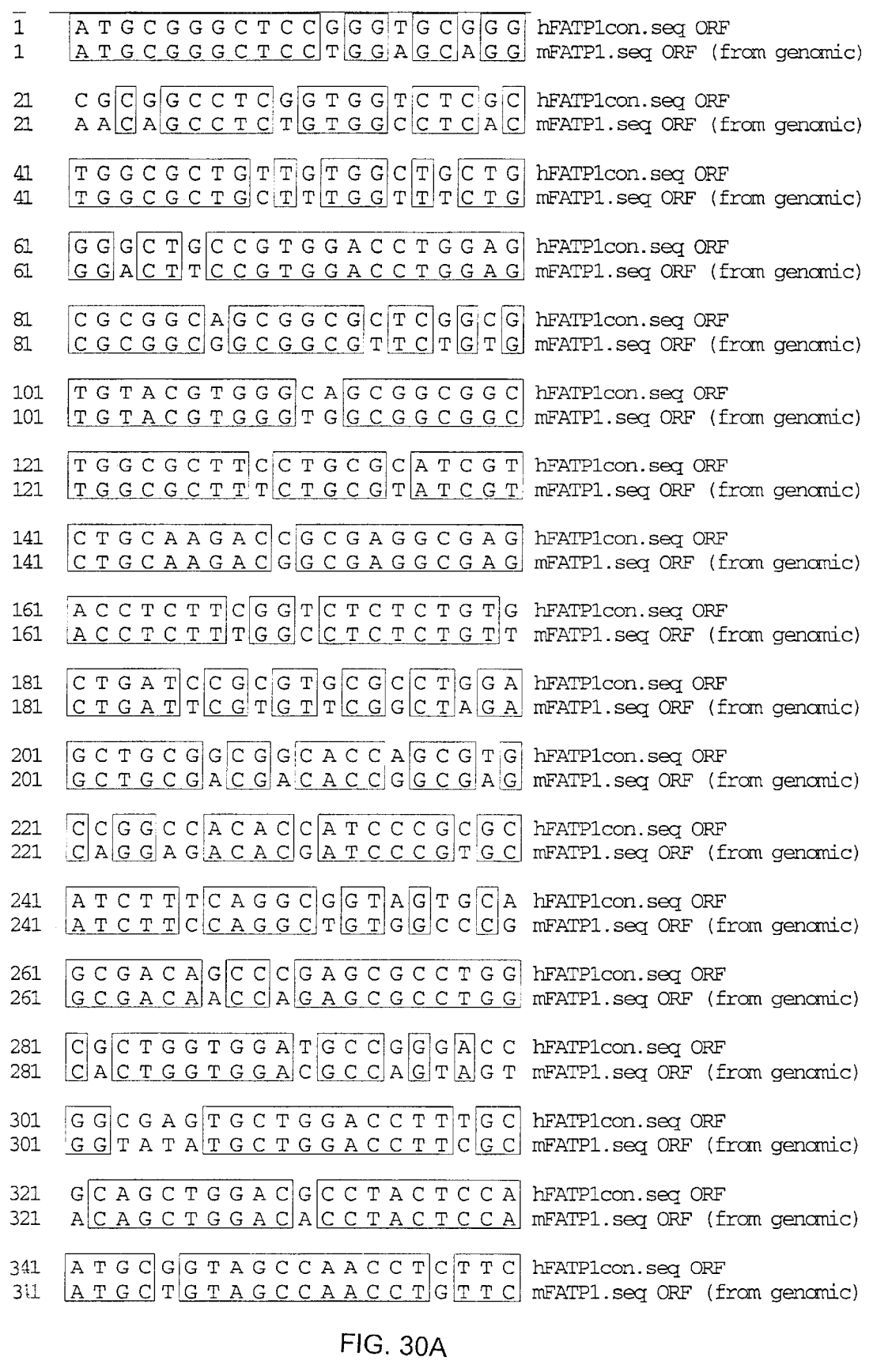

```
1    A T G C G G G C T C C G G G T G C G G G  hFATP1con.seq ORF
1    A T G C G G G C T C C T G G A G C A G G  mFATP1.seq ORF (from genomic)

21   C G C G G C C T C G G T G G T C T C G C  hFATP1con.seq ORF
21   A A C A G C C T C T G T G G C C T C A C  mFATP1.seq ORF (from genomic)

41   T G G C G C T G T T G T G G C T G C T G  hFATP1con.seq ORF
41   T G G C G C T G C T T T G G T T T C T G  mFATP1.seq ORF (from genomic)

61   G G G C T G C C G T G G A C C T G G A G  hFATP1con.seq ORF
61   G G A C T T C C G T G G A C C T G G A G  mFATP1.seq ORF (from genomic)

81   C G C G G C A G C G G C G C T C G G C G  hFATP1con.seq ORF
81   C G C G G C G G C G G C G T T C T G T G  mFATP1.seq ORF (from genomic)

101  T G T A C G T G G G C A G C G G C G G C  hFATP1con.seq ORF
101  T G T A C G T G G G T G G C G G C G G C  mFATP1.seq ORF (from genomic)

121  T G G C G C T T C C T G C G C A T C G T  hFATP1con.seq ORF
121  T G G C G C T T T C T G C G T A T C G T  mFATP1.seq ORF (from genomic)

141  C T G C A A G A C C G C G A G G C G A G  hFATP1con.seq ORF
141  C T G C A A G A C G G C G A G G C G A G  mFATP1.seq ORF (from genomic)

161  A C C T C T T C G G T C T C T C T G T G  hFATP1con.seq ORF
161  A C C T C T T T G G C C T C T C T G T T  mFATP1.seq ORF (from genomic)

181  C T G A T C C G C G T G C G C C T G G A  hFATP1con.seq ORF
181  C T G A T T C G T G T T C G G C T A G A  mFATP1.seq ORF (from genomic)

201  G C T G C G G C G G C A C C A G C G T G  hFATP1con.seq ORF
201  G C T G C G A C G A C A C C G G C G A G  mFATP1.seq ORF (from genomic)

221  C C G G C C A C A C C A T C C C G C G C  hFATP1con.seq ORF
221  C A G G A G A C A C G A T C C C G T G C  mFATP1.seq ORF (from genomic)

241  A T C T T T C A G G C G G T A G T G C A  hFATP1con.seq ORF
241  A T C T T C C A G G C T G T G G C C C G  mFATP1.seq ORF (from genomic)

261  G C G A C A G C C C G A G C G C C T G G  hFATP1con.seq ORF
261  G C G A C A A C C A G A G C G C C T G G  mFATP1.seq ORF (from genomic)

281  C G C T G G T G G A T G C C G G G A C C  hFATP1con.seq ORF
281  C A C T G G T G G A C G C C A G T A G T  mFATP1.seq ORF (from genomic)

301  G G C G A G T G C T G G A C C T T T G C  hFATP1con.seq ORF
301  G G T A T A T G C T G G A C C T T C G C  mFATP1.seq ORF (from genomic)

321  G C A G C T G G A C G C C T A C T C C A  hFATP1con.seq ORF
321  A C A G C T G G A C A C C T A C T C C A  mFATP1.seq ORF (from genomic)

341  A T G C G G T A G C C A A C C T C T T C  hFATP1con.seq ORF
341  A T G C T G T A G C C A A C C T G T T C  mFATP1.seq ORF (from genomic)
```

FIG. 30A

```
361 C G C C A G C T G G G C T T C G C G C C hFATP1con.seq ORF
361 C G C C A G C T G G G C T T T G C A C C mFATP1.seq ORF (from genomic)

381 G G G C G A C G T G G T G G C C A T C T hFATP1con.seq ORF
381 A G G C G A T G T G G T G G C T G T G T mFATP1.seq ORF (from genomic)

401 T C C T G G A G G G C C G G C C G G A G hFATP1con.seq ORF
401 T C C T G G A G G G C C G G C C G G A G mFATP1.seq ORF (from genomic)

421 T T C G T G G G G C T G T G G C T G G G hFATP1con.seq ORF
421 T T C G T G G G A C T G T G G C T G G G mFATP1.seq ORF (from genomic)

441 C C T G G C C A A G G C G G G C A T G G hFATP1con.seq ORF
441 C C T G G C C A A G G C C G G T G T G G mFATP1.seq ORF (from genomic)

461 A G G C C G C G C T G C T C A A C G T G hFATP1con.seq ORF
461 T G G C T G C T C T T C T C A A T G T C mFATP1.seq ORF (from genomic)

481 A A C C T G C G G C G C G A G C C C C T hFATP1con.seq ORF
481 A A C C T G A G G C G G G A G C C C C T mFATP1.seq ORF (from genomic)

501 G G C C T T C T G C C T G G G C A C C T hFATP1con.seq ORF
501 G G C C T T C T G C C T G G G C A C A T mFATP1.seq ORF (from genomic)

521 C G G G C G C T A A G G C C C T G A T C hFATP1con.seq ORF
521 C A G C T G C C A A G G C C C T C A T T mFATP1.seq ORF (from genomic)

541 T T T G G A G G A G A A A T G G T G G C hFATP1con.seq ORF
541 T A T G G C G G G G A G A T G G C A G C mFATP1.seq ORF (from genomic)

561 G G C G G T G G C C G A A G T G A G C G hFATP1con.seq ORF
561 G G C G G T G G C G G A G G T G A G C G mFATP1.seq ORF (from genomic)

581 G G C A T C T G G G G A A A A G T T T G hFATP1con.seq ORF
581 A G C A G C T G G G G A A G A G C C T C mFATP1.seq ORF (from genomic)

601 A T C A A G T T C T G C T C T G G A G A hFATP1con.seq ORF
601 C T C A A G T T C T G C T C T G G A G A mFATP1.seq ORF (from genomic)

621 C T T G G G G C C C G A G G G C A T C T hFATP1con.seq ORF
621 T C T G G G G C C T G A G A G C A T C C mFATP1.seq ORF (from genomic)

641 T G C C G G A C A C C C A C C T C C T G hFATP1con.seq ORF
641 T G C C T G A C A C G C A G C T C C T G mFATP1.seq ORF (from genomic)

661 G A C C C G C T G C T G A A G G A G G C hFATP1con.seq ORF
661 G A C C C C A T G C T T G C T G A G G C mFATP1.seq ORF (from genomic)

681 C T C T A C T G C C C C C T T G G C A C hFATP1con.seq ORF
681 G C C C A C C A C A C C C C T G G C A C mFATP1.seq ORF (from genomic)

701 A G A T C C C C A G C A A G G G C A T G hFATP1con.seq ORF
701 A A G C C C C A G G C A A G G G C A T G mFATP1.seq ORF (from genomic)
```

FIG. 30B

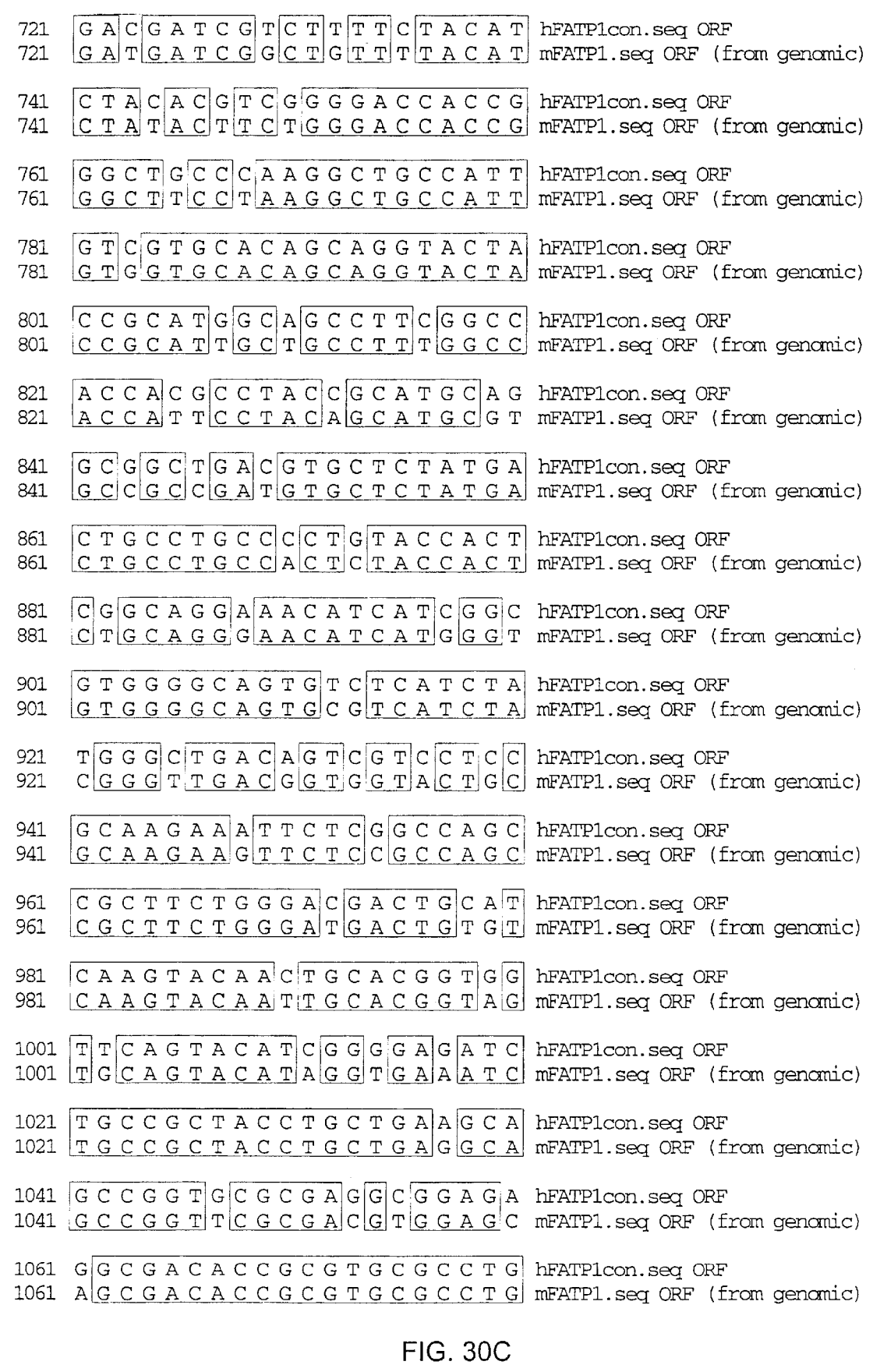

```
721  G A C G A T C G T C T T T T C T A C A T  hFATP1con.seq ORF
721  G A T G A T C G G C T G T T T T A C A T  mFATP1.seq ORF (from genomic)

741  C T A C A C G T C G G G G A C C A C C G  hFATP1con.seq ORF
741  C T A T A C T T C T G G G A C C A C C G  mFATP1.seq ORF (from genomic)

761  G G C T G C C C A A G G C T G C C A T T  hFATP1con.seq ORF
761  G G C T T C C T A A G G C T G C C A T T  mFATP1.seq ORF (from genomic)

781  G T C G T G C A C A G C A G G T A C T A  hFATP1con.seq ORF
781  G T G G T G C A C A G C A G G T A C T A  mFATP1.seq ORF (from genomic)

801  C C G C A T G G C A G C C T T C G G C C  hFATP1con.seq ORF
801  C C G C A T T G C T G C C T T T G G C C  mFATP1.seq ORF (from genomic)

821  A C C A C G C C T A C C G C A T G C A G  hFATP1con.seq ORF
821  A C C A T T C C T A C A G C A T G C G T  mFATP1.seq ORF (from genomic)

841  G C G G C T G A C G T G C T C T A T G A  hFATP1con.seq ORF
841  G C C G C C G A T G T G C T C T A T G A  mFATP1.seq ORF (from genomic)

861  C T G C C T G C C C C T G T A C C A C T  hFATP1con.seq ORF
861  C T G C C T G C C A C T C T A C C A C T  mFATP1.seq ORF (from genomic)

881  C G G C A G G A A A C A T C A T C G G C  hFATP1con.seq ORF
881  C T G C A G G G A A C A T C A T G G G T  mFATP1.seq ORF (from genomic)

901  G T G G G G C A G T G T C T C A T C T A  hFATP1con.seq ORF
901  G T G G G G C A G T G C G T C A T C T A  mFATP1.seq ORF (from genomic)

921  T G G G C T G A C A G T C G T C C T C C  hFATP1con.seq ORF
921  C G G G T T G A C G G T G G T A C T G C  mFATP1.seq ORF (from genomic)

941  G C A A G A A A T T C T C G G C C A G C  hFATP1con.seq ORF
941  G C A A G A A G T T C T C C G C C A G C  mFATP1.seq ORF (from genomic)

961  C G C T T C T G G G A C G A C T G C A T  hFATP1con.seq ORF
961  C G C T T C T G G G A T G A C T G T G T  mFATP1.seq ORF (from genomic)

981  C A A G T A C A A C T G C A C G G T G G  hFATP1con.seq ORF
981  C A A G T A C A A T T G C A C G G T A G  mFATP1.seq ORF (from genomic)

1001 T T C A G T A C A T C G G G G A G A T C  hFATP1con.seq ORF
1001 T G C A G T A C A T A G G T G A A A T C  mFATP1.seq ORF (from genomic)

1021 T G C C G C T A C C T G C T G A A G C A  hFATP1con.seq ORF
1021 T G C C G C T A C C T G C T G A G G C A  mFATP1.seq ORF (from genomic)

1041 G C C G G T G C G C G A G G C G G A G A  hFATP1con.seq ORF
1041 G C C G G T T C G C G A C G T G G A G C  mFATP1.seq ORF (from genomic)

1061 G G C G A C A C C G C G T G C G C C T G  hFATP1con.seq ORF
1061 A G C G A C A C C G C G T G C G C C T G  mFATP1.seq ORF (from genomic)
```

FIG. 30C

```
1081 GCGGTGGGGAACGGGCTGCG hFATP1con.seq ORF
1081 GCCGTGGGTAATGGGCTGCG mFATP1.seq ORF (from genomic)

1101 TCCTGCCATCTGGGAGGAGT hFATP1con.seq ORF
1101 GCCAGCCATCTGGGAGGAGT mFATP1.seq ORF (from genomic)

1121 TCACGGAGCGCTTCGGCGTA hFATP1con.seq ORF
1121 TCACGCAGCGCTTCGGTGTG mFATP1.seq ORF (from genomic)

1141 CGCCAAATCGGGGAGTTCTA hFATP1con.seq ORF
1141 CCACAGATCGGCGAGTTCTA mFATP1.seq ORF (from genomic)

1161 CGGCGCCACCGAGTGCAACT hFATP1con.seq ORF
1161 CGGCGCTACCGAGTGCAACT mFATP1.seq ORF (from genomic)

1181 GCAGCATTGCCAACATGGAC hFATP1con.seq ORF
1181 GCAGCATTGCCAACATGGAC mFATP1.seq ORF (from genomic)

1201 GGCAAGGTCGGCTCCTGTGG hFATP1con.seq ORF
1201 GGCAAGGTCGGCTCCTGCGG mFATP1.seq ORF (from genomic)

1221 TTTCAACAGCCGCATCCTGC hFATP1con.seq ORF
1221 CTTCAACAGCCGTATCCTCA mFATP1.seq ORF (from genomic)

1241 CCCACGTGTACCCCATCCGG hFATP1con.seq ORF
1241 CGCATGTGTACCCCATCCGT mFATP1.seq ORF (from genomic)

1261 CTGGTGAAGGTCAATGAGGA hFATP1con.seq ORF
1261 CTGGTCAAGGTCAATGAGGA mFATP1.seq ORF (from genomic)

1281 CACAATGGAGCTGCTGCGGG hFATP1con.seq ORF
1281 CACGATGGAGCCACTGCGGG mFATP1.seq ORF (from genomic)

1301 ATGCCCAGGGCCTCTGCATC hFATP1con.seq ORF
1301 ACTCCGAGGGCCTCTGCATC mFATP1.seq ORF (from genomic)

1321 CCCTGCCAGGCCGGGGAGCC hFATP1con.seq ORF
1321 CCGTGCCAGCCCGGGGAACC mFATP1.seq ORF (from genomic)

1341 TGGCCTCCTTGTGGGTCAGA hFATP1con.seq ORF
1341 CGGCCTTCTCGTGGGCCAGA mFATP1.seq ORF (from genomic)

1361 TCAACCAACAGGACCCGCTG hFATP1con.seq ORF
1361 TCAACCAGCAGGACCCTCTG mFATP1.seq ORF (from genomic)

1381 CGCCGCTTCGATGGCTATGT hFATP1con.seq ORF
1381 CGGCGTTTCGATGGTTATGT mFATP1.seq ORF (from genomic)

1401 CAGCGAGAGCGCCACCAGCA hFATP1con.seq ORF
1401 TAGTGACAGTGCCACCAACA mFATP1.seq ORF (from genomic)

1421 AGAAGATCGCCCACAGCGTC hFATP1con.seq ORF
1421 AGAAGATTGCCCACAGCGTT mFATP1.seq ORF (from genomic)
```

FIG. 30D

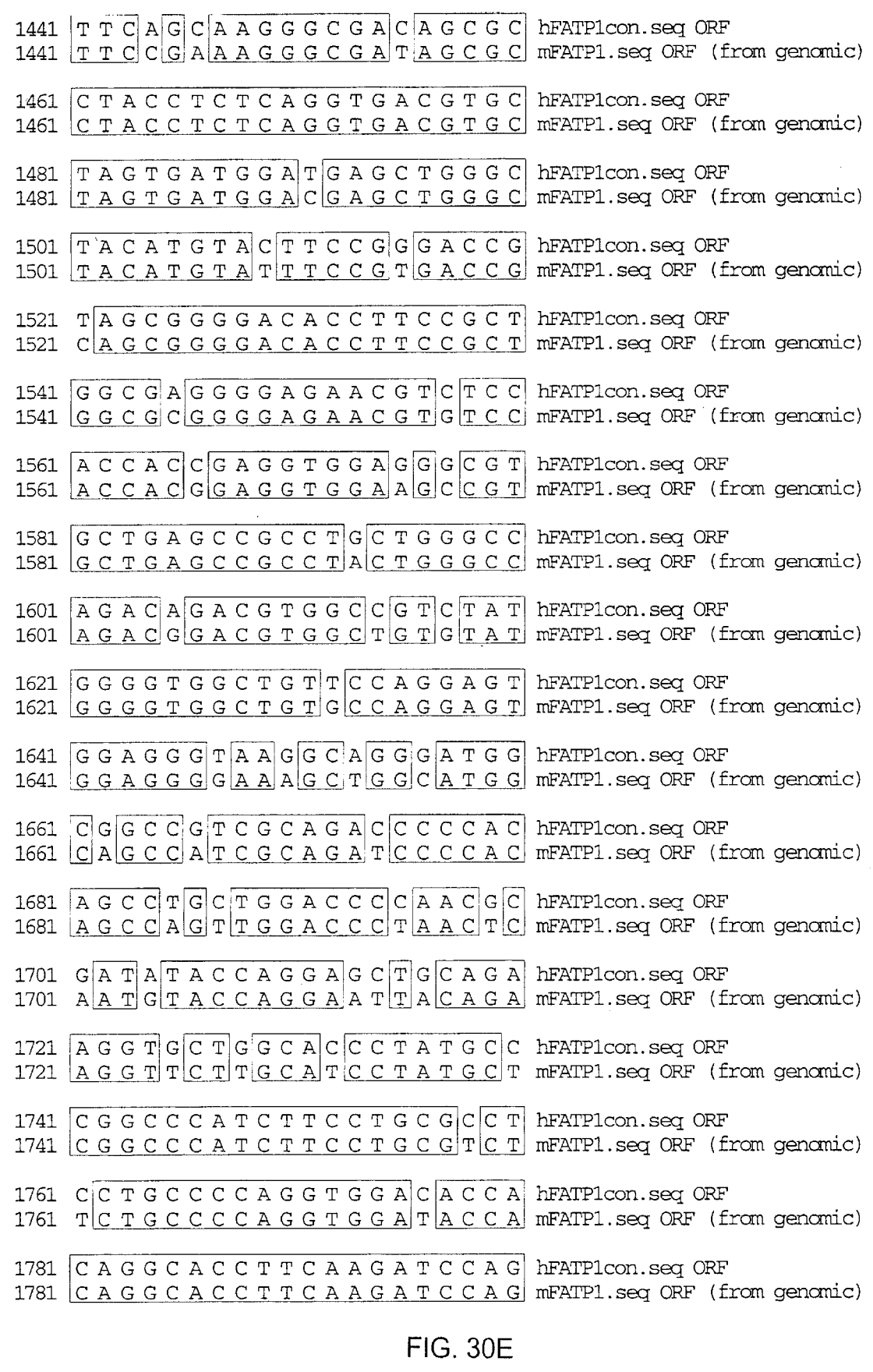

1441 T T C A G C A A G G G C G A C A G C G C hFATP1con.seq ORF
1441 T T C C G A A A G G G C G A T A G C G C mFATP1.seq ORF (from genomic)

1461 C T A C C T C T C A G G T G A C G T G C hFATP1con.seq ORF
1461 C T A C C T C T C A G G T G A C G T G C mFATP1.seq ORF (from genomic)

1481 T A G T G A T G G A T G A G C T G G G C hFATP1con.seq ORF
1481 T A G T G A T G G A C G A G C T G G G C mFATP1.seq ORF (from genomic)

1501 T A C A T G T A C T T C C G G G A C C G hFATP1con.seq ORF
1501 T A C A T G T A T T T C C G T G A C C G mFATP1.seq ORF (from genomic)

1521 T A G C G G G G A C A C C T T C C G C T hFATP1con.seq ORF
1521 C A G C G G G G A C A C C T T C C G C T mFATP1.seq ORF (from genomic)

1541 G G C G A G G G G A G A A C G T C T C C hFATP1con.seq ORF
1541 G G C G C G G G G A G A A C G T G T C C mFATP1.seq ORF (from genomic)

1561 A C C A C C G A G G T G G A G G G C G T hFATP1con.seq ORF
1561 A C C A C G G A G G T G G A A G C C G T mFATP1.seq ORF (from genomic)

1581 G C T G A G C C G C C T G C T G G G C C hFATP1con.seq ORF
1581 G C T G A G C C G C C T A C T G G G C C mFATP1.seq ORF (from genomic)

1601 A G A C A G A C G T G G C C G T C T A T hFATP1con.seq ORF
1601 A G A C G G A C G T G G C T G T G T A T mFATP1.seq ORF (from genomic)

1621 G G G G T G G C T G T T C C A G G A G T hFATP1con.seq ORF
1621 G G G G T G G C T G T G C C A G G A G T mFATP1.seq ORF (from genomic)

1641 G G A G G G T A A G G C A G G G A T G G hFATP1con.seq ORF
1641 G G A G G G G A A A G C T G G C A T G G mFATP1.seq ORF (from genomic)

1661 C G G C C G T C G C A G A C C C C C A C hFATP1con.seq ORF
1661 C A G C C A T C G C A G A T C C C C A C mFATP1.seq ORF (from genomic)

1681 A G C C T G C T G G A C C C C A A C G C hFATP1con.seq ORF
1681 A G C C A G T T G G A C C C T A A C T C mFATP1.seq ORF (from genomic)

1701 G A T A T A C C A G G A G C T G C A G A hFATP1con.seq ORF
1701 A A T G T A C C A G G A A T T A C A G A mFATP1.seq ORF (from genomic)

1721 A G G T G C T G G C A C C C T A T G C C hFATP1con.seq ORF
1721 A G G T T C T T G C A T C C T A T G C T mFATP1.seq ORF (from genomic)

1741 C G G C C C A T C T T C C T G C G C C T hFATP1con.seq ORF
1741 C G G C C C A T C T T C C T G C G T C T mFATP1.seq ORF (from genomic)

1761 C C T G C C C C A G G T G G A C A C C A hFATP1con.seq ORF
1761 T C T G C C C C A G G T G G A T A C C A mFATP1.seq ORF (from genomic)

1781 C A G G C A C C T T C A A G A T C C A G hFATP1con.seq ORF
1781 C A G G C A C C T T C A A G A T C C A G mFATP1.seq ORF (from genomic)

FIG. 30E

```
1801  A A G A C G A G G C T G C A G C G A G A  hFATP1con.seq ORF
1801  A A G A C C C G G C T G C A G C G T G A  mFATP1.seq ORF (from genomic)

1821  G G G C T T T G A C C C A C G C C A G A  hFATP1con.seq ORF
1821  A G G C T T T G A C C C C C G T C A G A  mFATP1.seq ORF (from genomic)

1841  C C T C A G A C C G G C T C T T C T T C  hFATP1con.seq ORF
1841  C C T C A G A C A G G C T C T T C T T T  mFATP1.seq ORF (from genomic)

1861  C T G G A C C T G A A G C A G G G C C A  hFATP1con.seq ORF
1861  C T A G A C C T G A A G C A G G G A C G  mFATP1.seq ORF (from genomic)

1881  C T A C C T G C C C T T A A A T G A G G  hFATP1con.seq ORF
1881  C T A T G T A C C C C T G G A T G A G A  mFATP1.seq ORF (from genomic)

1901  C A G T C T A C A C T C G C A T C T G C  hFATP1con.seq ORF
1901  G A G T C C A T G C C C G C A T T T G T  mFATP1.seq ORF (from genomic)

1921  T C G G G C G C C T T C G C C C T C T G  hFATP1con.seq ORF
1921  G C A G G C G A C T T C T C A C T C      mFATP1.seq ORF (from genomic)

1941  A                                        hFATP1con.seq ORF
1938                                           mFATP1.seq ORF (from genomic)
```

Decoration 'Decoration #2': Box residues that match the consensus named 'Consensus #1' exactly.

FIG. 30F

1 CTGTTCTCCAAGCTGGTGCTGAAACTGCCC hsFATP4
1 CTTGGGTCCAAGCTAGTGCTGAAGCTGCCC mmFATP4

31 TGGACCCAGGTGGGATTCTCCCTGTTGTTC hsFATP4
31 TGGACCCAGGTGGGATTCTCCCTGTTGCTC mmFATP4

61 CTCTACTTGGGATCTGGCGGCTGGCGCTTC hsFATP4
61 CTGTACTTGGGGTCTGGTGGCTGGCGTTTC mmFATP4

91 ATCCGGGTCTTCATCAAGACCATCAGGCGC hsFATP4
91 ATCCGGGTCTTCATCAAGACGGTCAGGAGA mmFATP4

121 GATATCTTTGGCGGCCTGGTCCTCCTGAAG hsFATP4
121 GATATCTTTGGTGGCATGGTGCTCCTGAAG mmFATP4

151 GTGAAGGCAAAGGTGCGACAGTGCCTGCAG hsFATP4
151 GTGAAGACCAAGGTGCGACGGTACCTTCAG mmFATP4

181 GAGCGGCGGACAGTGCCCATTTTGTTTGCC hsFATP4
181 GAGCGGAAGACGGTGCCCCTGCTGTTTGCT mmFATP4

FIG. 31A

| | | |
|---|---|---|
| 211 | T C T A C C G T T C G G C G C C A C C C C G A C A A G A C G | hsFATP4 |
| 211 | T C A A T G G T A C A G C G C C A C C C G G A C A A G A C A | mmFATP4 |
| 241 | G C C C T G A T C T T C G A G G G C A C A G A T A C C C A C | hsFATP4 |
| 241 | G C C C T G A T T T T C G A G G G C A C A G A C A C T C A C | mmFATP4 |
| 271 | T G G A C C T T C C G C C A G C T G G A T G A G T A C T C A | hsFATP4 |
| 271 | T G G A C C T T C C G C C A G C T G G A T G A G T A C T C C | mmFATP4 |
| 301 | A G C A G T G T A G C C A A C T T C C T G C A G G C C C G G | hsFATP4 |
| 301 | A G T A G T G T G G C C A A C T T C C T G C A G G C C C G G | mmFATP4 |
| 331 | G G C C T G G C C T C G G G C G A T G T G G C T G C C A T C | hsFATP4 |
| 331 | G G C C T G G C C T C A G G C A A T G T A G T T G C C C T C | mmFATP4 |
| 361 | T T C A T G G A G A A C C G C A A T G A G T T C G T G G G C | hsFATP4 |
| 361 | T T T A T G G A A A A C C G C A A T G A G T T T G T G G G T | mmFATP4 |
| 391 | C T A T G G C T G G G C A T G G C C A A G C T C G G T G T G | hsFATP4 |
| 391 | C T G T G G C T A G G C A T G G C C A A G C T G G G C G T G | mmFATP4 |

FIG. 31B

| | | |
|---|---|---|
| 421 | G A G G C A G C C C T C A T C A A C A C C A A C C T G C G G | hsFATP4 |
| 421 | G A G G C G G C T C T C A T C A A C A C C A A C C T T A G G | mmFATP4 |
| 451 | C G G G A T G C T C T G C T C C A C T G C C T C A C C A C C | hsFATP4 |
| 451 | C G G G A T G C C C T G C G C C A C T G T C T T G A C A C C | mmFATP4 |
| 481 | T C G C G C G C A C G G G C C C T T G T C T T T G G C A G C | hsFATP4 |
| 481 | T C A A A G G C A C G A G C T C T C A T C T T T G G C A G T | mmFATP4 |
| 511 | G A A A T G G C C T C A G C C A T C T G T G A G G T C C A T | hsFATP4 |
| 511 | G A G A T G G C C T C A G C T A T C T G T G A G A T C C A T | mmFATP4 |
| 541 | G C C A G C C T G G A C C C C T C G C T C A G C C T C T T C | hsFATP4 |
| 541 | G C T A G C C T G G A G C C C A C A C T C A G C C T C T T C | mmFATP4 |
| 571 | T G C T C T G G C T C C T G G G A G C C C G G T G C G G T G | hsFATP4 |
| 571 | T G C T C T G G A T C C T G G G A G C C C A G C A C A G T G | mmFATP4 |
| 601 | C C T C C A A G C A C A G A A C A C C T G G A C C C T C T G | hsFATP4 |
| 601 | C C C G T C A G C A C A G A G C A T C T G G A C C C T C T T | mmFATP4 |

FIG. 31C

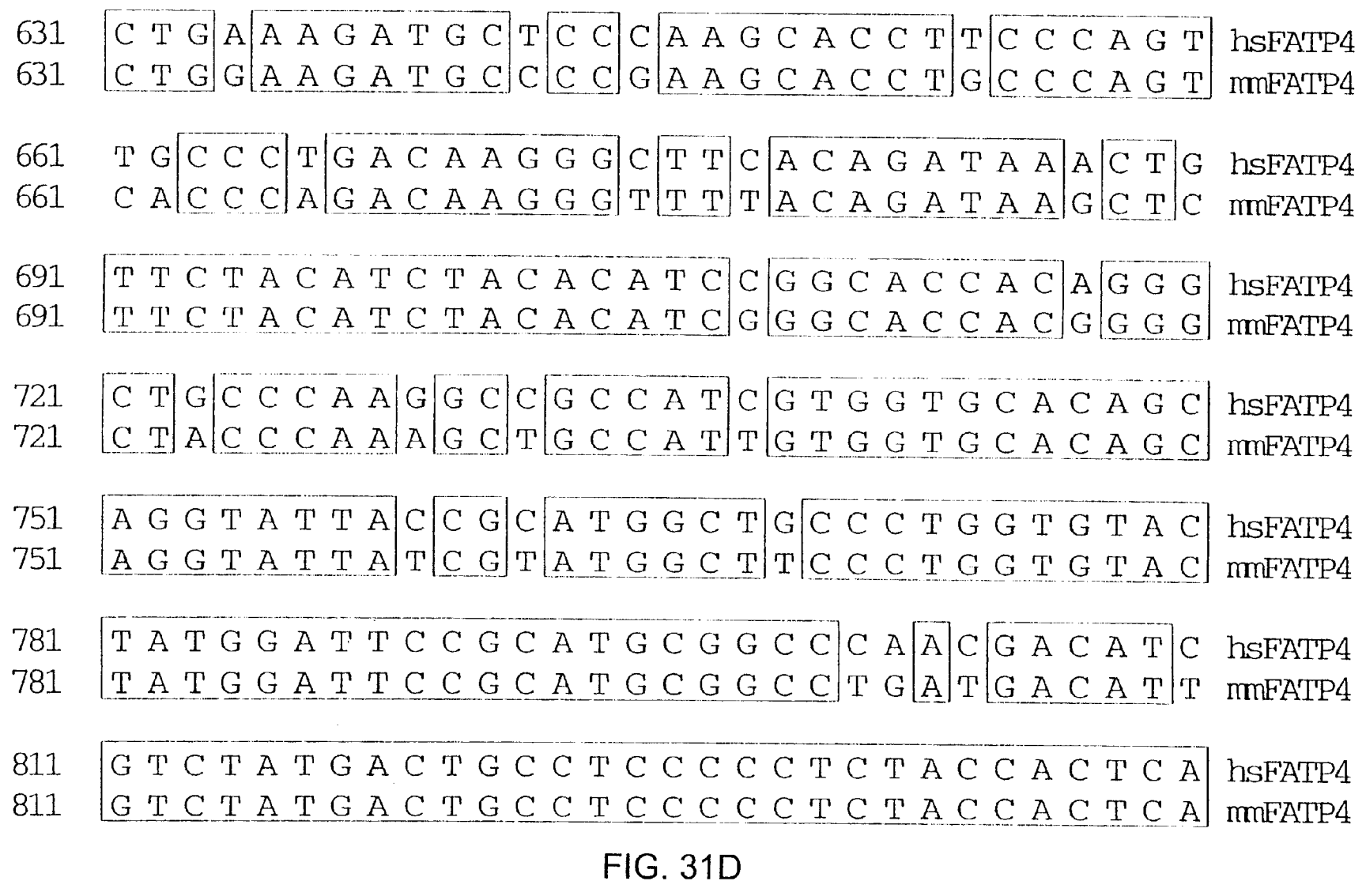

```
631  CTGAAAGATGCTCCCAAGCACCTTCCCAGT  hsFATP4
631  CTGGAAGATGCCCCGAAGCACCTGCCCAGT  mmFATP4

661  TGCCCTGACAAGGGCTTCACAGATAAACTG  hsFATP4
661  CACCCAGACAAGGGTTTTACAGATAAGCTC  mmFATP4

691  TTCTACATCTACACATCCGGCACCACAGGG  hsFATP4
691  TTCTACATCTACACATCGGGCACCACGGGG  mmFATP4

721  CTGCCCAAGGCCGCCATCGTGGTGCACAGC  hsFATP4
721  CTACCCAAAGCTGCCATTGTGGTGCACAGC  mmFATP4

751  AGGTATTACCGCATGGCTGCCCTGGTGTAC  hsFATP4
751  AGGTATTATCGTATGGCTTCCCTGGTGTAC  mmFATP4

781  TATGGATTCCGCATGCGGCCCAACGACATC  hsFATP4
781  TATGGATTCCGCATGCGGCCTGATGACATT  mmFATP4

811  GTCTATGACTGCCTCCCCCTCTACCACTCA  hsFATP4
811  GTCTATGACTGCCTCCCCCTCTACCACTCA  mmFATP4
```

FIG. 31D

```
841  - G C A G G A A A C A T C G T G G G A A T C G G C C A G T G  hsFATP4
841  A G C A G G A A A C A T C G T G G G G A T T G G C - A G T G  mmFATP4

870  C C T G C T G C A T G G C A T G A C G G T G G T G A T T C G  hsFATP4
870  C T T A C T C C A C G G C A T G A C T G T G G T G A T C C G  mmFATP4

900  G A A G A A G T T C T C A G C C T C C C G G T T C T G G G A  hsFATP4
900  G A A G A A G T T C T C A G C C T C C C G G T T C T G G G A  mmFATP4

930  C G A T T G T A T C A A G T A C A A C T G C A C G A T T G T  hsFATP4
930  T G A T T G T A T C A A G T A C A A C T G C A C A G T G G T  mmFATP4

960  G C A G T A C A T T G G T G A A C T G T G C C G C T A C C T  hsFATP4
960  A C A G T A C A T T G G C G A G C T C T G C C G C T A C C T  mmFATP4

990  C C T G A A C C A G C C A C C G C G G G A G G C A G A A A A  hsFATP4
990  C C T G A A C C A G C C A C C C C G T G A G G C T G A G T C  mmFATP4

1020 C C A G C A C C A G G T T C G C A T G G C A C T A G G C A A  hsFATP4
1020 T C G G C A C A A G G T G C G C A T G G C A C T G G G C A A  mmFATP4
```

FIG. 31E

| | | |
|---|---|---|
| 1050 | T G G C C T C C G G C A G T C C A T C T G G A C C A A C T T | hsFATP4 |
| 1050 | C G G T C T C C G G C A G T C C A T C T G G A C C G A C T T | mmFATP4 |
| 1080 | T T C C A G C C G C T T C C A C A T A C C C C A G G T G G C | hsFATP4 |
| 1080 | C T C C A G C C G T T T C C A C A T C C C C C A G G T G G C | mmFATP4 |
| 1110 | T G A G T T C T A C G G G G C C A C A G A G T G C A A C T G | hsFATP4 |
| 1110 | T G A G T T C T A T G G G G C C A C T G A A T G C A A C T G | mmFATP4 |
| 1140 | T A G C C T G G G C A A C T T C G A C A G C C A G G T G G G | hsFATP4 |
| 1140 | T A G C C T G G G C A A C T T T G A C A G C C G G G T G G G | mmFATP4 |
| 1170 | G G C C T G T G G T T T C A A T A G C C G C A T C C T G T C | hsFATP4 |
| 1170 | G G C C T G T G G C T T C A A T A G C C G C A T C C T G T C | mmFATP4 |
| 1200 | C T T C G T G T A C C C C A T C C G G T T G G T A C G T G T | hsFATP4 |
| 1200 | C T T T G T G T A C C C T A T C C G T T T G G T A C G T G T | mmFATP4 |
| 1230 | C A A C G A G G A C A C C A T G G A G C T G A T C C G G G G | hsFATP4 |
| 1230 | C A A T G A G G A T A C C A T G G A A C T G A T C C G G G G | mmFATP4 |

FIG. 31F

```
1260  GCCCGACGGCGTCTGCATTCCCTGCCAGCC  hsFATP4
1260  ACCCGATGGAGTCTGCATTCCCTGTCAACC  mmFATP4

1290  AGGTGAGCCGGGCCAGCTGGTGGGCCGCAT  hsFATP4
1290  AGGTCAGCCAGGCCAGCTGGTGGGTCGCAT  mmFATP4

1320  CATCCAGAAAGACCCCCTGCGCCGCTTCGA  hsFATP4
1320  CATCCAGCAGGACCCTCTGCGCCGTTTCGA  mmFATP4

1350  TGGCTACCTCAACCAGGGCGCCAACAACAA  hsFATP4
1350  CGGGTACCTCAACCAGGGTGCCAACAACAA  mmFATP4

1380  GAAGATTGCCAAGGATGTCTTCAAGAAGGG  hsFATP4
1380  GAAGATTGCTAATGATGTCTTCAAGAAGGG  mmFATP4

1410  GGACCAGGCCTACCTTACTGGTGATGTGCT  hsFATP4
1410  GGACCAAGCCTACCTCACTGGTGACGTCCT  mmFATP4

1440  GGTGATGGACGAGCTGGGCTACCTGTACTT  hsFATP4
1440  GGTGATGGATGAGCTGGGTTACCTGTACTT  mmFATP4
```

FIG. 31G

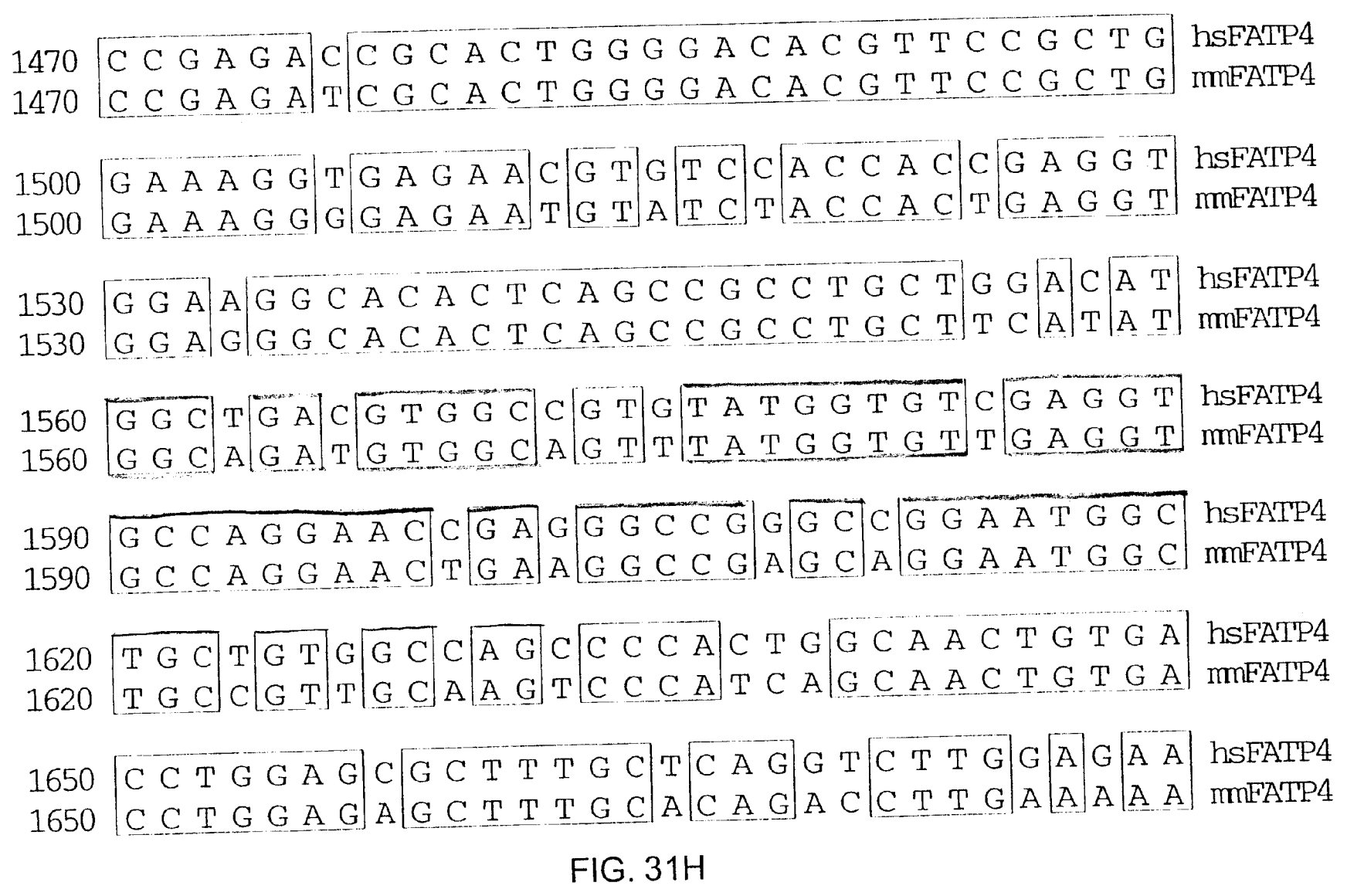

| | | |
|---|---|---|
| 1470 | C C G A G A C C G C A C T G G G G A C A C G T T C C G C T G | hsFATP4 |
| 1470 | C C G A G A T C G C A C T G G G G A C A C G T T C C G C T G | mmFATP4 |
| 1500 | G A A A G G T G A G A A C G T G T C C A C C A C C G A G G T | hsFATP4 |
| 1500 | G A A A G G G G A G A A T G T A T C T A C C A C T G A G G T | mmFATP4 |
| 1530 | G G A A G G C A C A C T C A G C C G C C T G C T G G A C A T | hsFATP4 |
| 1530 | G G A G G G C A C A C T C A G C C G C C T G C T T C A T A T | mmFATP4 |
| 1560 | G G C T G A C G T G G C C G T G T A T G G T G T C G A G G T | hsFATP4 |
| 1560 | G G C A G A T G T G G C A G T T T A T G G T G T T G A G G T | mmFATP4 |
| 1590 | G C C A G G A A C C G A G G G C C G G G C C G G A A T G G C | hsFATP4 |
| 1590 | G C C A G G A A C T G A A G G C C G A G C A G G A A T G G C | mmFATP4 |
| 1620 | T G C T G T G G C C A G C C C C A C T G G C A A C T G T G A | hsFATP4 |
| 1620 | T G C C G T T G C A A G T C C C A T C A G C A A C T G T G A | mmFATP4 |
| 1650 | C C T G G A G C G C T T T G C T C A G G T C T T G G A G A A | hsFATP4 |
| 1650 | C C T G G A G A G C T T T G C A C A G A C C T T G A A A A A | mmFATP4 |

FIG. 31H

```
1680 G G A A C T G C C C C T G T A T G C G C G C C C C A T C T T hsFATP4
1680 G G A G C T G C C T C T G T A T G C C C G C C C C A T C T T mmFATP4

1710 C C T G C G C C T C C T G C C T G A G C T G C A C A A A A C hsFATP4
1710 C C T G C G C T T C T T G C C T G A G C T G C A C A A G A C mmFATP4

1740 A G G A A C C T A C A A G T T C C A G A A G A C A G A G C T hsFATP4
1740 A G G G A C C T T C A A G T T C C A G A A G A C A G A G T T mmFATP4

1770 A C G G A A G G A G G G C T T T G A C C C G G C T A T T G T hsFATP4
1770 G C G G A A G G A G G G C T T T G A C C C A T C T G T T G T mmFATP4

1800 G A A A G A C C C G C T G T T C T A T C T A G A T G C C C A hsFATP4
1800 G A A A G A C C C G C T G T T C T A T C T G G A T G C T C G mmFATP4

1830 G A A G G G C C G C T A C G T C C C G C T G G A C C A A G A hsFATP4
1830 G A A G G G C T G C T A C G T T G C A C T G G A C C A G G A mmFATP4

1860 G G C C T A C A G C C G C A T C C A G G C A G G C G A G G A hsFATP4
1860 G G C C T A T A C C C G C A T C C A G G C A G G C G A G G A mmFATP4

1890 G A A G C T G hsFATP4
1890 G A A G C T G mmFATP4
```

FIG. 31I

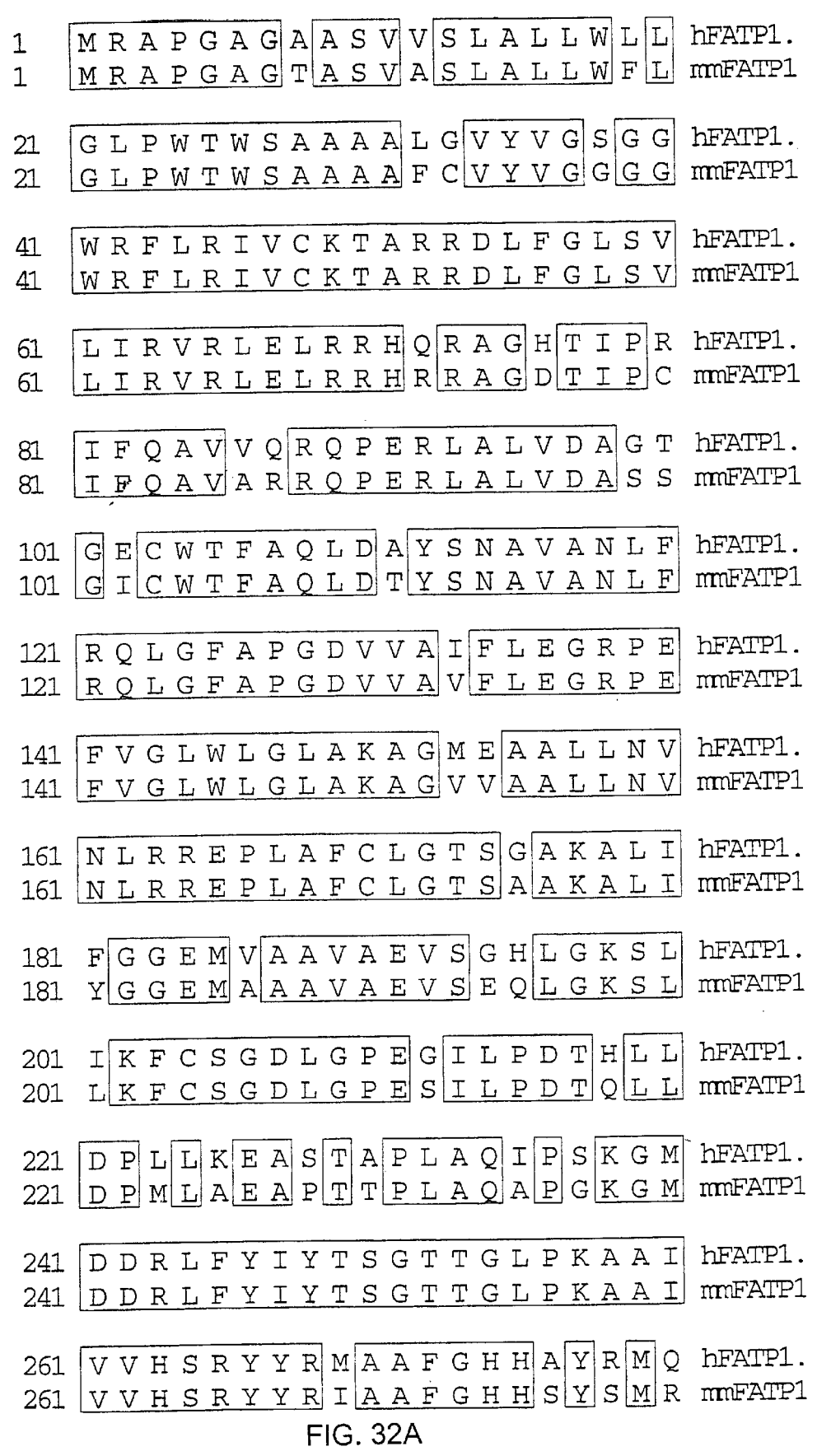

1 M R A P G A G A A S V V S L A L L W L L hFATP1.
1 M R A P G A G T A S V A S L A L L W F L mmFATP1

21 G L P W T W S A A A A L G V Y V G S G G hFATP1.
21 G L P W T W S A A A A F C V Y V G G G G mmFATP1

41 W R F L R I V C K T A R R D L F G L S V hFATP1.
41 W R F L R I V C K T A R R D L F G L S V mmFATP1

61 L I R V R L E L R R H Q R A G H T I P R hFATP1.
61 L I R V R L E L R R H R R A G D T I P C mmFATP1

81 I F Q A V V Q R Q P E R L A L V D A G T hFATP1.
81 I F Q A V A R R Q P E R L A L V D A S S mmFATP1

101 G E C W T F A Q L D A Y S N A V A N L F hFATP1.
101 G I C W T F A Q L D T Y S N A V A N L F mmFATP1

121 R Q L G F A P G D V V A I F L E G R P E hFATP1.
121 R Q L G F A P G D V V A V F L E G R P E mmFATP1

141 F V G L W L G L A K A G M E A A L L N V hFATP1.
141 F V G L W L G L A K A G V V A A L L N V mmFATP1

161 N L R R E P L A F C L G T S G A K A L I hFATP1.
161 N L R R E P L A F C L G T S A A K A L I mmFATP1

181 F G G E M V A A V A E V S G H L G K S L hFATP1.
181 Y G G E M A A A V A E V S E Q L G K S L mmFATP1

201 I K F C S G D L G P E G I L P D T H L L hFATP1.
201 L K F C S G D L G P E S I L P D T Q L L mmFATP1

221 D P L L K E A S T A P L A Q I P S K G M hFATP1.
221 D P M L A E A P T T P L A Q A P G K G M mmFATP1

241 D D R L F Y I Y T S G T T G L P K A A I hFATP1.
241 D D R L F Y I Y T S G T T G L P K A A I mmFATP1

261 V V H S R Y Y R M A A F G H H A Y R M Q hFATP1.
261 V V H S R Y Y R I A A F G H H S Y S M R mmFATP1

FIG. 32A

| | | |
|---|---|---|
| 281 | A A D V L Y D C L P L Y H S A G N I I G | hFATP1. |
| 281 | A A D V L Y D C L P L Y H S A G N I M G | mmFATP1 |
| 301 | V G Q C L I Y G L T V V L R K K F S A S | hFATP1. |
| 301 | V G Q C V I Y G L T V V L R K K F S A S | mmFATP1 |
| 321 | R F W D D C I K Y N C T V V Q Y I G E I | hFATP1. |
| 321 | R F W D D C V K Y N C T V V Q Y I G E I | mmFATP1 |
| 341 | C R Y L L K Q P V R E A E R R H R V R L | hFATP1. |
| 341 | C R Y L L R Q P V R D V E Q R H R V R L | mmFATP1 |
| 361 | A V G N G L R P A I W E E F T E R F G V | hFATP1. |
| 361 | A V G N G L R P A I W E E F T Q R F G V | mmFATP1 |
| 381 | R Q I G E F Y G A T E C N C S I A N M D | hFATP1. |
| 381 | P Q I G E F Y G A T E C N C S I A N M D | mmFATP1 |
| 401 | G K V G S C G F N S R I L P H V Y P I R | hFATP1. |
| 401 | G K V G S C G F N S R I L T H V Y P I R | mmFATP1 |
| 421 | L V K V N E D T M E L L R D A Q G L C I | hFATP1. |
| 421 | L V K V N E D T M E P L R D S E G L C I | mmFATP1 |
| 441 | P C Q A G E P G L L V G Q I N Q Q D P L | hFATP1. |
| 441 | P C Q P G E P G L L V G Q I N Q Q D P L | mmFATP1 |
| 461 | R R F D G Y V S E S A T S K K I A H S V | hFATP1. |
| 461 | R R F D G Y V S D S A T N K K I A H S V | mmFATP1 |
| 481 | F S K G D S A Y L S G D V L V M D E L G | hFATP1. |
| 481 | F R K G D S A Y L S G D V L V M D E L G | mmFATP1 |
| 501 | Y M Y F R D R S G D T F R W R G E N V S | hFATP1. |
| 501 | Y M Y F R D R S G D T F R W R G E N V S | mmFATP1 |
| 521 | T T E V E G V L S R L L G Q T D V A V Y | hFATP1. |
| 521 | T T E V E A V L S R L L G Q T D V A V Y | mmFATP1 |
| 541 | G V A V P G V E G K A G M A A V A D P H | hFATP1. |
| 541 | G V A V P G V E G K A G M A A I A D P H | mmFATP1 |

FIG. 32B

```
561  S L L D P N A I Y Q E L Q K V L A P Y A  hFATP1.
561  S Q L D P N S M Y Q E L Q K V L A S Y A  mmFATP1

581  R P I F L R L L P Q V D T T G T F K I Q  hFATP1.
581  R P I F L R L L P Q V D T T G T F K I Q  mmFATP1

601  K T R L Q R E G F D P R Q T S D R L F F  hFATP1.
601  K T R L Q R E G F D P R Q T S D R L F F  mmFATP1

621  L D L K Q G H Y L P L N E A V Y T R I C  hFATP1.
621  L D L K Q G R Y V P L D E R V H A R I C  mmFATP1

641  S G A F A L                              hFATP1.
641  A G D F S L                              mmFATP1
```

FIG. 32C

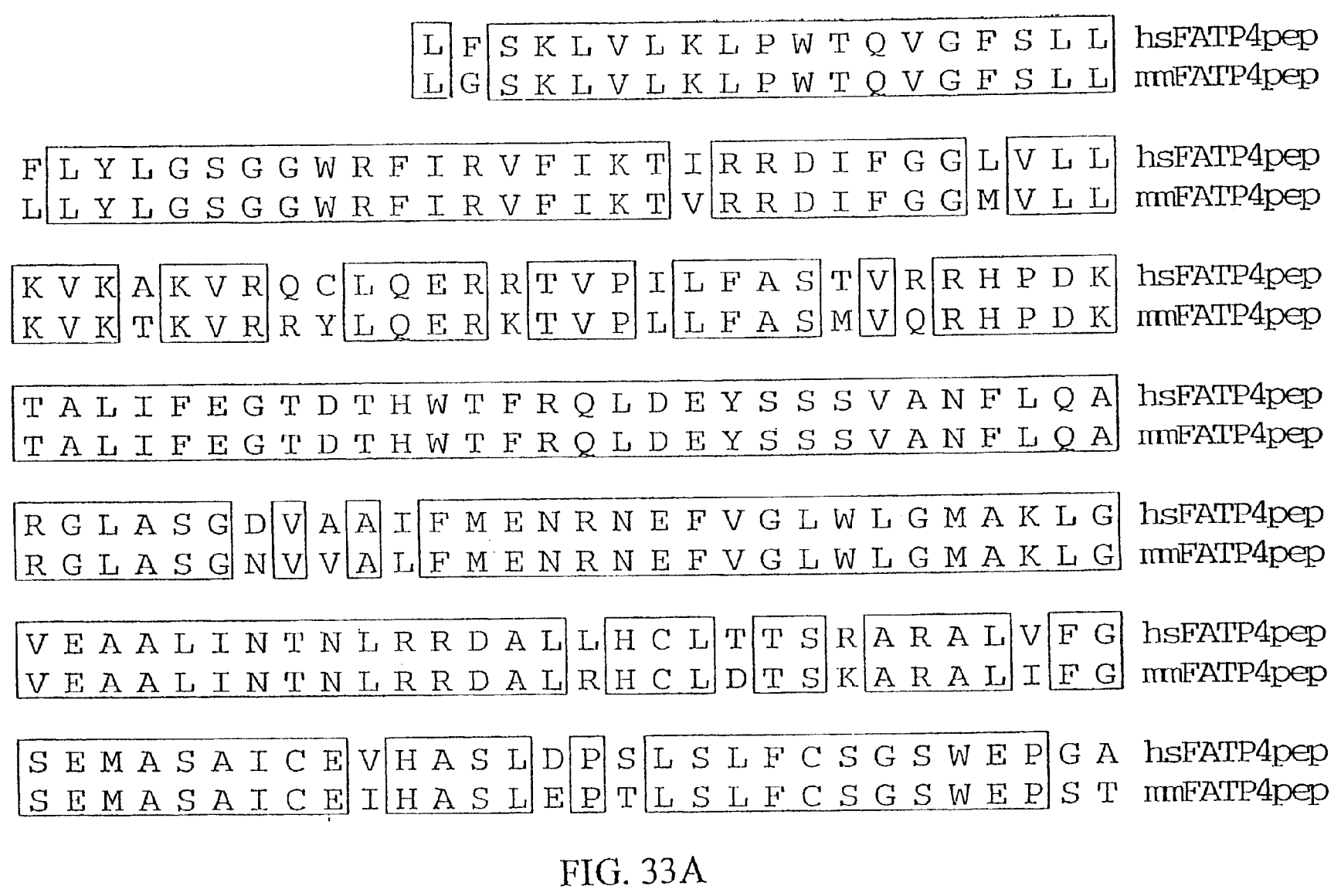

```
                  LFSKLVLKLPWTQVGFSLL hsFATP4pep
                  LGSKLVLKLPWTQVGFSLL mmFATP4pep

FLYLGSGGWRFIRVFIKTIRRDIFGGLVLL hsFATP4pep
LLYLGSGGWRFIRVFIKTVRRDIFGGMVLL mmFATP4pep

KVKAKVRQCLQERRTVPILFASTVRRHPDK hsFATP4pep
KVKTKVRRYLQERKTVPLLFASMVQRHPDK mmFATP4pep

TALIFEGTDTHWTFRQLDEYSSSVANFLQA hsFATP4pep
TALIFEGTDTHWTFRQLDEYSSSVANFLQA mmFATP4pep

RGLASGDVAAIFMENRNEFVGLWLGMAKLG hsFATP4pep
RGLASGNVVALFMENRNEFVGLWLGMAKLG mmFATP4pep

VEAALINTNLRRDALLHCLTTSRARALVFG hsFATP4pep
VEAALINTNLRRDALRHCLDTSKARALIFG mmFATP4pep

SEMASAICEVHASLDPSLSLFCSGSWEPGA hsFATP4pep
SEMASAICEIHASLEPTLSLFCSGSWEPST mmFATP4pep
```

FIG. 33A

```
V P P S T E H L D P L L K D A P K H L P S C P D K G F T D K  hsFATP4pep
V P V S T E H L D P L L E D A P K H L P S H P D K G F T D K  mmFATP4pep

L F Y I Y T S G T T G L P K A A I V V H S R Y Y R M A A L V  hsFATP4pep
L F Y I Y T S G T T G L P K A A I V V H S R Y Y R M A S L V  mmFATP4pep

Y Y G F R M R P N D I V Y D C L P L Y H S A G N I V G I G Q  hsFATP4pep
Y Y G F R M R P D D I V Y D C L P L Y H S S R K H R G D W Q  mmFATP4pep

C L L H G M T V V I R K K F S A S R F W D D C I K Y N C T I  hsFATP4pep
C L L H G M T V V I R K K F S A S R F W D D C I K Y N C T V  mmFATP4pep

V Q Y I G E L C R Y L L N Q P P R E A E N Q H Q V R M A L G  hsFATP4pep
V Q Y I G E L C R Y L L N Q P P R E A E S R H K V R M A L G  mmFATP4pep

N G L R Q S I W T N F S S R F H I P Q V A E F Y G A T E C N  hsFATP4pep
N G L R Q S I W T D F S S R F H I P Q V A E F Y G A T E C N  mmFATP4pep

C S L G N F D S Q V G A C G F N S R I L S F V Y P I R L V R  hsFATP4pep
C S L G N F D S R V G A C G F N S R I L S F V Y P I R L V R  mmFATP4pep
```

FIG. 33B

```
VNEDTMELIRGPDGVCIPCQPGEPGQLVGR hsFATP4pep
VNEDTMELIRGPDGVCIPCQPGQPGQLVGR mmFATP4pep

IIQKDPLRRFDGYLNQGANNKKIAKDVFKK hsFATP4pep
IIQQDPLRRFDGYLNQGANNKKIANDVFKK mmFATP4pep

GDQAYLTGDVLVMDELGYLYFRDRTGDTFR hsFATP4pep
GDQAYLTGDVLVMDELGYLYFRDRTGDTFR mmFATP4pep

WKGENVSTTEVEGTLSRLLDMADVAVYGVE hsFATP4pep
WKGENVSTTEVEGTLSRLLHMADVAVYGVE mmFATP4pep

VPGTEGRAGMAAVASPTGNCDLERFAQVLE hsFATP4pep
VPGTEGRAGMAAVASPISNCDLESFAQTLK mmFATP4pep

KELPLYARPIFLRLLPELHKTGTYKFQKTE hsFATP4pep
KELPLYARPIFLRFLPELHKTGTFKFQKTE mmFATP4pep

LRKEGFDPAIVKDPLFYLDAQKGRYVPLDQ hsFATP4pep
LRKEGFDPSVVKDPLFYLDARKGCYVALDQ mmFATP4pep

EAYSRIQAGEEKL hsFATP4pep
EAYTRIQAGEEKL mmFATP4pep
```

FIG. 33C hsFATP6

```
1     aac ggc aag taa gcg caa cgc aat taa tgt gag tag ctc act cat tag gca ccc cag gct
61    tta cac ttt atg ctt ccg ggc tcg tat gtt gtg tgg aat tgt gag cgg ata cca att tca
121   cac agg aac cag cta tga cat gat tac gaa ttt aat acg act cac tat agg gaa ttt ggc
181   cct cga ggc caa gaa ttc ggc acg agg ggt gct gag ccc ctg cgc ggt ttc tgg tgc gta
241   gag act gta aat cgc tgc gct tct cag tca tca tca tcc cag ctt ttc ccg gct cga att
301   cag cct cca act caa gct cgc ggg aaa gac tac ctg aga gga gaa aag ctt ctg tcc ctg
361   gac ctt ctt ctg agg gtg gag tcg gag gct ccc tgc ttt cca gcc gcc cag tga ccc aag
421   ctt aat ctt cag cac cac ttg ggg cga cct ttt cgg tgc aaa cct acg att ctg ttt ctc
481   agg att cct ccc cat ccc gct tcg ccc cgg aaa agc tga caa gaa ctt cag gtg taa gcc
541   ctg agt agt gag gat ctg cgg tct ccg tgg aga gct gtg cct gga aga gaa gga cgc tgg
601   tgg ggg ctg aga tca gag ctg tct tct ggc cca gtt gcc ccc atg ctt ctg tca tgg cta
                                                           M   L   L   S   W   L
661   aca gtt cta ggg gct gga atg gtc gtc ctg cac ttc ttg cag aaa ctc ctg ttc cct tac
      T   V   L   G   A   G   M   V   V   L   H   F   L   Q   K   L   L   F   P   Y
721   ttt tgg gat gac ttc tgg ttc gtg ttg aag gtg gtg ctc att ata att cgg ctg aag aag
      F   W   D   D   F   W   F   V   L   K   V   V   L   I   I   I   R   L   K   K
781   tat gaa aag aga ggg gag ctg gtg act gtg ctg gat aaa ttc ttg agt cat gcc aaa aga
      Y   E   K   R   G   E   L   V   T   V   L   D   K   F   L   S   H   A   K   R
```

FIG. 34A 841 caa cct cgg aaa cct ttc atc atc tat gag gga gac atc tac acc tat cag gat gta gac
Q P R K P F I I Y E G D I Y T Y Q D V D
901 aaa agg agc agc aga gtg gcc cat gtc ttc ctg aac cat tcc tct ctg aaa aag ggg gac
K R S S R V A H V F L N H S S L K K G D
961 acg gtg gct ctg ctg atg agc aat gag ccg gac ttc gtt cac gtg tgg ttc ggc ctc gcc
T V A L L M S N E P D F V H V W F G L A
1021 aag ctg ggc tgc gtg gtg gcc ttt ctc aac acc aac att cgc tcc aac tcc ctc ctg aat
K L G C V V A F L N T N I R S N S L L N
1081 tgc atc cgc gcc tgt ggg ccc aga gcc cta gtg gtg ggc gca gat ttg ctt gga acg gta
C I R A C G P R A L V V G A D L L G T V 1141 gaa gaa atc ctt cca agc ctc tca gaa aat atc agt gtt tgg ggg atg aaa gat tct gtt
E E I L P S L S E N I S V W G M K D S V
1201 cca caa ggt gta att tca ctc aaa gaa aaa ctg agc acc tca cct gat gag ccc gtg cca
P Q G V I S L K E K L S T S P D E P V P
1261 cgc agc cac cat gtt gtc tca ctc ctc aag tct act tgt ctt tac att ttt acc tct gga
R S H H V V S L L K S T C L Y I F T S G
1321 aca aca ggt cta cca aaa gca gct gtg att agt cag ctg cag gtt tta agg ggt tct gct
T T G L P K A A V I S Q L Q V L R G S A
1381 gtc ctg tgg gct ttt ggt tgt act gct cat gac att gtt tat ata acc ctt cct ctg tat
V L W A F G C T A H D I V Y I T L P L Y

FIG. 34B

```
1441   cat agt tca gca gct atc ctg gga att tct gga tgt gtt gag ttg ggt gcc act tgt gtg
       H   S   S   A   A   I   L   G   I   S   G   C   V   E   L   G   A   T   C   V
1501   tta aag aag aaa ttt tca gca agc cag ttt tgg agt gac tgc aag aag tat gat gtg act
       L   K   K   K   F   S   A   S   Q   F   W   S   D   C   K   K   Y   D   V   T
1561   gtg ttt cag tat att gga gaa ctt tgt cgc tac ctt tgc aaa caa tct aag aga gaa gga
       V   F   Q   Y   I   G   E   L   C   R   Y   L   C   K   Q   S   K   R   E   G
1621   gaa aag gat cat aag gtg cgt ttg gca att gga aat ggc ata cgg agt gat gta tgg aga
       E   K   D   H   K   V   R   L   A   I   G   N   G   I   R   S   D   V   W   R
1681   gaa ttt tta gac aga ttt gga aat ata aag gtg tgt gaa ctt tat gca gct acc gaa tca
       E   F   L   D   R   F   G   N   I   K   V   C   E   L   Y   A   A   T   E   S
1741   agc ata tct ttc atg aac tac act ggg aga att gga gca att ggg aga aca aat ttg ttt
       S   I   S   F   M   N   Y   T   G   R   I   G   A   I   G   R   T   N   L   F
1801   tac aaa ctt ctt tcc act ttt gac tta ata aag tat gac ttt cag aaa gat gaa ccc atg
       Y   K   L   L   S   T   F   D   L   I   K   Y   D   F   Q   K   D   E   P   M
1861   aga aat gag cag ggt tgg tgt att cat gtg aaa aaa gga gaa cct gga ctt ctc att tct
       R   N   E   Q   G   W   C   I   H   V   K   K   G   E   P   G   L   L   I   S
1921   cga gtg aat gca aaa aat ccc ttc ttt ggc tat gct ggg cct tat aag cac aca aaa gac
       R   V   N   A   K   N   P   F   F   G   Y   A   G   P   Y   K   H   T   K   D
1981   aaa ttg ctt tgt gat gtt ttt aag aag gga gat gtt tac ctt aat act gga gac tta ata
       K   L   L   C   D   V   F   K   K   G   D   V   Y   L   N   T   G   D   L   I
2041   gtc cag gat cag gac aat ttc ctt tat ttt tgg gac cgt act gga gac act ttc aga tgg
       V   Q   D   Q   D   N   F   L   Y   F   W   D   R   T   G   D   T   F   R   W
2101   aaa gga gaa aat gtc gca acc act gag gtt gct gat gtt att gga atg ttg gat ttc ata
```

FIG. 34C

```
         K   G   E   N   V   A   T   T   E   V   A   D   V   I   G   M   L   D   F   I
2161    cag gaa gca aac gtc tat ggt gtg gct ata tca ggt tat gaa gga aga gca gga atg gct
         Q   E   A   N   V   Y   G   V   A   I   S   G   Y   E   G   R   A   G   M   A
2221    tct att att tta aaa cca aat aca tct tta gat ttg gaa aaa gtt tat gaa caa gtt gta
         S   I   I   L   K   P   N   T   S   L   D   L   E   K   V   Y   E   Q   V   V
2281    aca ttt cta cca gct tat gct tgt cca cga ttt tta aga att cag gaa aaa atg gaa gca
         T   F   L   P   A   Y   A   C   P   R   F   L   R   I   Q   E   K   M   E   A
2341    aca gga aca ttc aaa cta ttg aag cat cag ttg gtg gaa gat gga ttt aat cca ctg aaa
         T   G   T   F   K   L   L   K   H   Q   L   V   E   D   G   F   N   P   L   K
2401    att tct gaa cca ctt tac ttc atg gat aac ttg aaa aag tct tat gtt cta ctg acc agg
         I   S   E   P   L   Y   F   M   D   N   L   K   K   S   Y   V   L   L   T   R
2461    gaa ctt tat gat caa ata atg tta ggg gaa ata aaa ctt taa gat ttt tat atc tag aac
         E   L   Y   D   Q   I   M   L   G   E   I   K   L   *
2521    ttt cat atg ctt tct tag gaa gag tga gag ggg ggt ata tga ttc ttt atg aaa tgg gga
2581    aag gga gct aac att aat tat gca tgt act ata ttt cct taa tat gag aga taa ttt ttt
2641    aat tgc ata aga att tta att tct ttt aat tga tat aaa cat tag ttg att att ctt ttt
2701    atc tat ttg gag att cag tgc ata act aag tat ttt cct taa tac taa aga ttt taa ata
2761    ata aat agt ggc tag cgg ttt gga caa tca cta aaa atg tac ttt cta ata agt aaa att
2821    tct aat ttt gaa taa aag att aaa ttt tac tga aaa aaa aaa aaa aaa aaa aaa ttg gcg
2881    gcc gc
```

FIG. 34D

Protein Sequence 619 a.a. MLLSWLTVLGAG....LYDQIMLGEIKL
619 Amino Acids MW: 70066 Dalton

| | | n | n% | MW | MW% |
|---|---|---|---|---|---|
| A ala | alanine | 33 | 5.3 | 2344 | 3.3 |
| C cys | cysteine | 14 | 2.3 | 1442 | 2.1 |
| D asp | aspartic acid | 34 | 5.5 | 3910 | 5.6 |
| E glu | glutamic acid | 31 | 5.0 | 4000 | 5.7 |
| F phe | phenylalanine | 34 | 5.5 | 5000 | 7.1 |
| G gly | glycine | 44 | 7.1 | 2508 | 3.6 |
| H his | histidine | 13 | 2.1 | 1781 | 2.5 |
| I ile | isoleucine | 37 | 6.0 | 4184 | 6.0 |
| K lys | lysine | 48 | 7.8 | 6148 | 8.8 |
| L leu | leucine | 75 | 12.1 | 8481 | 12.1 |
| M met | methionine | 11 | 1.8 | 1441 | 2.1 |
| N asn | asparagine | 21 | 3.4 | 2394 | 3.4 |
| P pro | proline | 21 | 3.4 | 2038 | 2.9 |
| Q gln | glutamine | 18 | 2.9 | 2305 | 3.3 |
| R arg | arginine | 27 | 4.4 | 4214 | 6.0 |
| S ser | serine | 40 | 6.5 | 3481 | 5.0 |
| T thr | threonine | 30 | 4.8 | 3031 | 4.3 |
| V val | valine | 51 | 8.2 | 5052 | 7.2 |
| W trp | tryptophan | 11 | 1.8 | 2046 | 2.9 |
| X ukw | unknown | -- | -- | | |
| Y tyr | tyrosine | 26 | 4.2 | 4239 | 6.1 |
| Z --- STOP | | | | | |

FIG. 35B hsFATP6 full-length protein

```
1   M R A P - - G A G A A S V V S L A L L W   hsFATP1pep
1   L - - - - - - - - - - - - - - F S K L -   hsFATP4pep
1   M L L S W L T V L G A G M V V L H F L Q   hsFATP6pep

19  L L G L P W T W S A A A A L G V Y V G S   hsFATP1pep
6   V L K L P W T Q V G F S L L F L Y L G S   hsFATP4pep
21  K L L F P Y F W D D F - - - - - - - - -   hsFATP6pep

39  G G W R F L R I V C K T A R R D L F G L   hsFATP1pep
26  G G W R F I R V F I K T I R R D I F G G   hsFATP4pep
32  - - W F V L K V - - - - - - - - - - - -   hsFATP6pep

59  S V L I R V R L E L R R H Q R A G H T I   hsFATP1pep
46  L V L L K V K A K V R Q C L Q E R R T V   hsFATP4pep
38  - V L I I I R L K K Y E K R G E L V T V   hsFATP6pep

79  P R I F Q A V V Q R Q P E R L A L V D A   hsFATP1pep
66  P I L F A S T V R R H P D K T A L I F E   hsFATP4pep
57  L D K F L S H A K R Q P R K P F I I Y E   hsFATP6pep
```

FIG. 36A

```
99   G T G E C W T F A Q L D A Y S N A V A N  hsFATP1pep
86   G T D T H W T F R Q L D E Y S S S V A N  hsFATP4pep
77   G - - D I Y T Y Q D V D K R S S R V A H  hsFATP6pep

119  - L F R Q L G F A P G D V V A I F L E G  hsFATP1pep
106  - F L Q A R G L A S G D V A A I F M E N  hsFATP4pep
95   V F L N H S S L K K G D T V A L L M S N  hsFATP6pep

138  R P E F V G L W L G L A K A G M E A A L  hsFATP1pep
125  R N E F V G L W L G M A K L G V E A A L  hsFATP4pep
115  E P D F V H V W F G L A K L G C V V A F  hsFATP6pep

158  L N V N L R R E P L A F C L G T S G A K  hsFATP1pep
145  I N T N L R R D A L L H C L T T S R A R  hsFATP4pep
135  L N T N I R S N S L L N C I R A C G P R  hsFATP6pep

178  A L I F G G E M V A A V A E V S G H L G  hsFATP1pep
165  A L V F G S E M A S A I C E V H A S L D  hsFATP4pep
155  A L V V G A D L L G T V E E I L P S L S  hsFATP6pep
```

FIG. 36B

```
198 K S L I K F C S G D L G P E G I L P D T hsFATP1pep
185 P S L S L F C S G S W E P G A V P P S T hsFATP4pep
175 E N I S V W G M K D S V P Q G V I S - - hsFATP6pep

218 H L L D P L L K E A S T A P L A Q I P S hsFATP1pep
205 E H L D P L L K D A P K - H L P S C P D hsFATP4pep
193 - - L K E K L S T S P D E P V P R S H H hsFATP6pep

238 K G - - M D D R L F Y I Y T S G T T G L hsFATP1pep
224 K G - - F T D K L F Y I Y T S G T T G L hsFATP4pep
211 V V S L L K S T C L Y I F T S G T T G L hsFATP6pep

256 P K A A I V V H S R Y Y R M A A F G H H hsFATP1pep
242 P K A A I V V H S R Y Y R M A A L V Y Y hsFATP4pep
231 P K A A V I S Q L Q V L R G S A - V L W hsFATP6pep

276 A Y R M Q A A D V L Y D C L P L Y H S A hsFATP1pep
262 G F R M R P N D I V Y D C L P L Y H S A hsFATP4pep
250 A F G C T A H D I V Y I T L P L Y H S S hsFATP6pep
```

FIG. 36C

```
296 GNIIGVGQCLIYGLTVVLRK hsFATP1pep
282 GNIVGIGQCLLHGMTVVIRK hsFATP4pep
270 AAILGISGCVELGATCVLKK hsFATP6pep

316 KFSASRFWDDCIKYNCTVVQ hsFATP1pep
302 KFSASRFWDDCIKYNCTIVQ hsFATP4pep
290 KFSASQFWSDCKKYDVTVFQ hsFATP6pep

336 YIGEICRYLLKQPVREAERR hsFATP1pep
322 YIGELCRYLLNQPPREAENQ hsFATP4pep
310 YIGELCRYLCKQSKREGEKD hsFATP6pep

356 HRVRLAVGNGLRPAIWEEFT hsFATP1pep
342 HQVRMALGNGLRQSIWTNFS hsFATP4pep
330 HKVRLAIGNGIRSDVWREFL hsFATP6pep

376 ERFGVRQIGEFYGATECNCS hsFATP1pep
362 SRFHIPQVAEFYGATECNCS hsFATP4pep
350 DRFGNIKVCELYAATESSIS hsFATP6pep
```

FIG. 36D

```
396 I A N M D G K V G S C G F N S R I L P H hsFATP1pep
382 L G N F D S Q V G A C G F N S R I L S F hsFATP4pep
370 F M N Y T G R I G A I G R T N L F Y K L hsFATP6pep

416 V Y P I R L V K V N E D T M E L L R D A hsFATP1pep
402 V Y P I R L V R V N E D T M E L I R G P hsFATP4pep
390 L S T F D L I K Y D F Q K D E P M R N E hsFATP6pep

436 Q G L C I P C Q A G E P G L L V G Q I N hsFATP1pep
422 D G V C I P C Q P G E P G Q L V G R I I hsFATP4pep
410 Q G W C I H V K K G E P G L L I S R V N hsFATP6pep

456 Q Q D P L R R F D G Y V S E S A T S K - hsFATP1pep
442 Q K D P L R R F D G Y L N Q G A N N K - hsFATP4pep
430 A K N P - - - F F G Y A G P Y K H T K D hsFATP6pep

475 K I A H S V F S K G D S A Y L - S G D V hsFATP1pep
461 K I A K D V F K K G D Q A Y L - T G D V hsFATP4pep
447 K L L C D V F K K G D - V Y L N T G D L hsFATP6pep
```

FIG. 36E

```
494 LVMDELGYMYFRDRSGDTFR hsFATP1pep
480 LVMDELGYLYFRDRTGDTFR hsFATP4pep
466 IVQDQDNFLYFWDRTGDTFR hsFATP6pep

514 WRGENVSTTEVEGVLSRLLG hsFATP1pep
500 WKGENVSTTEVEGTLSRLLD hsFATP4pep
486 WKGENVATTEVADVIGMLDF hsFATP6pep

534 QTDVAVYGVAVPGVEGKAGM hsFATP1pep
520 MADVAVYGVEVPGTEGRAGM hsFATP4pep
506 IQEANVYGVAISGYEGRAGM hsFATP6pep

554 AAVA-DPHSLLDPNAIYQEL hsFATP1pep
540 AAVA-SPTGNCDLERFAQVL hsFATP4pep
526 ASIILKPNTSLDLEKVYEQV hsFATP6pep

573 QKVLAPYARPIFLRLLPQVD hsFATP1pep
559 EKELPLYARPIFLRLLPELH hsFATP4pep
546 VTFLPAYACPRFLRIQEKME hsFATP6pep
```

FIG. 36F

```
593 T T G T F K I Q K T R L Q R E G F D P R hsFATP1pep
579 K T G T Y K F Q K T E L R K E G F D P A hsFATP4pep
566 A T G T F K L L K H Q L V E D G F N P L hsFATP6pep

613 Q T S D R L F F L D L K Q G H Y L P L N hsFATP1pep
599 I V K D P L F Y L D A Q K G R Y V P L D hsFATP4pep
586 K I S E P L Y F M D N L K K S Y V L L T hsFATP6pep

633 E A V Y T R I C S G A F A L hsFATP1pep
619 Q E A Y S R I Q A G E E K L hsFATP4pep
606 R E L Y D Q I M L G E I K L hsFATP6pep
```

FIG. 36G

```
hsFATP4_   1  MLL-GASLVGVLLFSKL-VLKLPWTQVGFSLLF  31
mmFATP4_   1  MLL-GASLVGVLLFSKL-VLKLPWTQVGFSLLX  31
hsFATP1_   1  MRAPGAGAASVVSLALLWLLGLPWTWSAAAALG  33

hsFATP4_  32  LYLGSGGWRFIRVFIKTIRRDIFGGLVLLKVKA  64
mmFATP4_  32  LYLGSGGWRFIRVFIKTVRRDIFGGMVLLKVKT  64
hsFATP1_  34  VYVGSGGWRFLRIVCKTARRDLFGLSVLIRVRL  66

hsFATP4_  65  KVRQCLQERRTVPILFASTVRRHPDKTALIFEG  97
mmFATP4_  65  KVRRYLQERKTVPLLFASMVQRHPDKTALIFEG  97
hsFATP1_  67  ELRRHQRAGHTIPRIFQAVVQRQPERLALVDAG  99

hsFATP4_  98  TDTHWTFRQLDEYSSSVANFLQARGLASGDVAA  130
mmFATP4_  98  TDTHWTFRQLDEYSSSVANFLQARGLASGNVVA  130
hsFATP1_ 100  TGECWTFAQLDAYSNAVANLFRQLGFAPGDVVA  132

hsFATP4_ 131  IFMENRNEFVGLWLGMAKLGVEAALINTNLRRD  163
mmFATP4_ 131  LFMENRNEFVGLWXGMAKLGVEAALINTNLRRD  163
hsFATP1_ 133  IFLEGRPEFVGLWLGLAKAGMEAALLNVNLRRE  165

hsFATP4_ 164  ALLHCLTTSRARALVFGSEMASAICEVHASLDP  196
mmFATP4_ 164  ALRHCLDTSKARALIFGSEMASAICEIHASLEP  196
hsFATP1_ 166  PLAFCLGTSGAKALIFGGEMVAAVAEVSGHLGK  198

hsFATP4_ 197  SLSLFCSGSWEPGAVPPSTEHLDPLLKDAP-KH  228
mmFATP4_ 197  TLSLFCSGSWEPSTVPVSTEHLDPLLEDAP-KH  228
hsFATP1_ 199  SLIKFCSGDLGPEGILPDTHLLDPLLKEASTAP  231
```

FIG. 39A

```
hsFATP4_ 229  LPSCPDKGFTDKLFYIYTSGTTGLPKAAIVVHS  261
mmFATP4_ 229  LPSHPDKGFTDKLFYIYTSGTTGLPKAAIVVHS  261
hsFATP1_ 232  LAQIPSKGMDDRLFYIYTSGTTGLPKAAIVVHS  264

hsFATP4_ 262  RYYRMAALVYYGFRMRPNDIVYDCLPLYHSAGN  294
mmFATP4_ 262  RYYRMASLVYYGFRMRPDDIVYDCLPLYHSSRK  294
hsFATP1_ 265  RYYRMAAFGHHAYRMQAADVLYDCLPLYHSAGN  297

hsFATP4_ 295  IVGIGQCLLHGMTVVIRKKFSASRFWDDCIKYN  327
mmFATP4_ 295  HRGDWQCLLHGMTVVIRKKFSASRFWDDCIKYN  327
hsFATP1_ 298  IIGVGQCLIYGLTVVLRKKFSASRFWDDCIKYN  330

hsFATP4_ 328  CTIVQYIGELCRYLLNQPPREAENQHQVRMALG  360
mmFATP4_ 328  CTVVQYIGELCRYLLNQPPREAESRHKVRMALG  360
hsFATP1_ 331  CTVVQYIGEICRYLLKQPVREAERRHRVRLAVG  363

hsFATP4_ 361  NGLRQSIWTNFSSRFHIPQVAEFYGATECNCSL  393
mmFATP4_ 361  NGLRQSIWTDFSSRFHIPQVAEFYGATECNCSL  393
hsFATP1_ 364  NGLRPAIWEEFTERFGVRQIGEFYGATECNCSI  396

hsFATP4_ 394  GNFDSQVGACGFNSRILSFVYPIRLVRVNEDTM  426
mmFATP4_ 394  GNFDSRVGACGFNSRILSFVYPIRLVRVNEDTM  426
hsFATP1_ 397  ANMDGKVGSCGFNSRILPHVYPIRLVKVNEDTM  429
```

FIG. 39B

```
hsFATP4_ 427  ELIRGPDGVCIPCQPGEPGQLVGRIIQKDPLRR  459
mmFATP4_ 427  ELIRGPDGVCIPCQPGQPGQLVGRIIQQDPLRR  459
hsFATP1_ 430  ELLRDAQGLCIPCQAGEPGLLVGQINQQDPLRR  462

hsFATP4_ 460  FDGYLNQGANNKKIAKDVFKKGDQAYLTGDVLV  492
mmFATP4_ 460  FDGYLNQGANNKKIANDVFKKGDQAYLTGDVLV  492
hsFATP1_ 463  FDGYVSESATSKKIAHSVFSKGDSAYLSGDVLV  495

hsFATP4_ 493  MDELGYLYFRDRTGDTFRWKGENVSTTEVEGTL  525
mmFATP4_ 493  MDELGYLYFRDRTGDTFRWKGENVSTTEVEGTL  525
hsFATP1_ 496  MDELGYMYFRDRSGDTFRWRGENVSTTEVEGVL  528

hsFATP4_ 526  SRLLDMADVAVYGVEVPGTEGRAGMAAVASPTG  558
mmFATP4_ 526  SRLLHMADVAVYGVEVPGTEGRAGMAAVASPIS  558
hsFATP1_ 529  SRLLGQTDVAVYGVAVPGVEGKAGMAAVADPHS  561

hsFATP4_ 559  NCDLERFAQVLEKELPLYARPIFLRLLPELHKT  591
mmFATP4_ 559  NCDLESFAQTLKKELPLYARPIFLRFLPELHKT  591
hsFATP1_ 562  LLDPNAIYQELQKVLAPYARPIFLRLLPQVDTT  594

hsFATP4_ 592  GTYKFQKTELRKEGFDPAIVKDPLFYLDAQKGR  624
mmFATP4_ 592  GTFKFQKTELRKEGFDPSVVKDPLFYLDARKGC  624
hsFATP1_ 595  GTFKIQKTRLQREGFDPRQTSDRLFFLDLKQGH  627

hsFATP4_ 625  YVPLDQEAYSRIQAGEEKL  643
mmFATP4_ 625  YVALDQEAYTRIQAGEEKL  643
hsFATP1_ 628  YLPLNEAVYTRICSGAFAL  646
```

FIG. 39C mmFATP4 DNA sequence

ATGCTGCTTGGAGCCTCTCTGGTGGGGGCGCTACTGTTCTCCAAGC
TAGTGCTGAAGCTGCCCTGGACCCAGGTGGGATTCTCCCTGTTGCT
CCTGTACTTGGGGTCTGGTGGCTGGCGTTTCATCCGGGTCTTCATC
AAGACGGTCAGGAGAGATATCTTTGGTGGCATGGTGCTCCTGAAGG
TGAAGACCAAGGTGCGACGGTACCTTCAGGAGCGGAAGACGGTGCC
CCTGCTGTTTGCTTCAATGGTACAGCGCCACCCGGACAAGACAGCC
CTGATTTTCGAGGGCACAGACACTCACTGGACCTTCCGCCAGCTGG
ATGAGTACTCCAGTAGTGTGGCCAACTTCCTGCAGGCCCGGGGCCT
GGCCTCAGGCAATGTAGTTGCCCTCTTTATGGAAAACCGCAATGAG
TTTGTGGGTCTGTGGCTAGGCATGGCCAAGCTGGGCGTGGAGGCGG
CTCTCATCAACACCAACCTTAGGCGGATGCCCTGCGCCACTGTCT
TGACACCTCAAAGGCACGAGCTCTCATCTTTGGCAGTGAGATGGCC
TCAGCTATCTGTGAGATCCATGCTAGCCTGGAGCCCACACTCAGCC
TCTTCTGCTCTGGATCCTGGGAGCCCAGCACAGTGCCCGTCAGCAC
AGAGCATCTGGACCCTCTTCTGGAAGATGCCCCGAAGCACCTGCCC
AGTCACCCAGACAAGGGTTTACAGATAAGCTCTTCTACATCTACA
CATCGGGCACCACGGGGCTACCCAAAGCTGCCATTGTGGTGCACAG
CAGGTATTATCGTATGGCTTCCCTGGTGTACTATGGATTCCGCATG
CGGCCTGATGACATTGTCTATGACTGCCTCCCCCTCTACCACTCAA
GCAGGAAACATCGTGGGGATTGGCAGTGCTTACTCCACGGCATGAC
TGTGGTGATCCGGAAGAAGTTCTCAGCCTCCCGGTTCTGGGATGAT
TGTATCAAGTACAACTGCACAGTGGTACAGTACATTGGCGAGCTCT
GCCGCTACCTCCTGAACCAGCCACCCCGTGAGGCTGAGTCTCGGCA
CAAGGTGCGCATGGCACTGGGCAACGGTCTCCGGCAGTCCATCTGG
ACCGACTTCTCCAGCCGTTTCCACATCCCCCAGGTGGCTGAGTTCT
ATGGGGCCACTGAATGCAACTGTAGCCTGGGCAACTTTGACAGCCG
GGTGGGGGCCTGTGGCTTCAATAGCCGCATCCTGTCCTTTGTGTAC
CCTATCCGTTTGGTACGTGTCAATGAGGATACCATGGAACTGATCC
GGGGACCCGATGGAGTCTGCATTCCCTGTCAACCAGGTCAGCCAGG
CCAGCTGGTGGGTCGCATCATCCAGCAGGACCCTCTGCGCCGTTTC

FIG. 43A

GACGGGTACCTCAACCAGGGTGCCAACAACAAGAAGATTGCTAATG
ATGTCTTCAAGAAGGGGGACCAAGCCTACCTCACTGGTGACGTCCT
GGTGATGGATGAGCTGGGTTACCTGTACTTCCGAGATCGCACTGGG
GACACGTTCCGCTGGAAAGGGGAGAATGTATCTACCACTGAGGTGG
AGGGCACACTCAGCCGCCTGCTTCATATGGCAGATGTGGCAGTTTA
TGGTGTTGAGGTGCCAGGAACTGAAGGCCGAGCAGGAATGGCTGCC
GTTGCAAGTCCCATCAGCAACTGTGACCTGGAGAGCTTTGCACAGA
CCTTGAAAAAGGAGCTGCCTCTGTATGCCCGCCCCATCTTCCTGCG
CTTCTTGCCTGAGCTGCACAAGACAGGGACCTTCAAGTTCCAGAAG
ACAGAGTTGCGGAAGGAGGGCTTTGACCCATCTGTTGTGAAAGACC
CGCTGTTCTATCTGGATGCTCGGAAGGGCTGCTACGTTGCACTGGA
CCAGGAGGCCTATACCCGCATCCAGGCAGGCGAGGAGAAGCTGTGA
TTTCCCCCTACATCCCTCTGAGGGCCAGAAGATGCTGGATTCAGAG
CCCTAGCGTCCACCCCAGAGGGTCCTGGGCAATGCCAGACCAAAGC
TAGCAGGGCCCGCACCTCCGCCCCTAGGTGCTGATCTCCCCTCTCC
CAAACTGCCAAGTGACTCACTGCCGCTTCCCCGACCCTCCAGAGGC
TTTCTGTGAAAGTCTCATCCAAGCTGTGTCTTCTGGTCCAGGCGTG
GCCCCTGGCCCCAGGGTTTCTGATAGGCTCCTTTAGGATGGTATCT
TGGGTCCAGCGGGCCAGGGTGTGGGAGAGGAGTCACTAAGATCCCT
CCAATCAGAAGGGAGCTTACAAAGGAACCAAGGCAAAGCCTGTAGA
CTCAGGAAGCTAAGTGGCCAGAGACTATAGTGGCCAGTCATCCCAT
GTCCACAGAGGATCTTGGTCCAGAGCTGCCAAAGTGTCACCTCTCC
CTGCCTGCACCTCTGGGGAAAAGAGGACAGCATGTGGCCACTGGGC
ACCTGTCTCAAGAAGTCAGGATCACACACTCAGTCCTTGTTTCTCC
AGGTTCCCTTGTTCTTGTCTCGGGGAGGGAGGGACGAGTGTCCTGT
CTGTCCTTCCTGCCTGTCTGTGAGTCTGTGTTGCTTCTCCATCTGT
CCTAGCCTGAGTGTGGGTGGAACAGGCATGAGGAGAGTGTGGCTCA
GGGGCCAATAAACTCTGCCTTGACTCCTCTTAAAAAAAAAAAAAAA
AAAAAAAAAAAAAAAAAAAAAAAAAAAAAAAAAAAAAAAAA

FIG. 43B mmFATP4 protein sequence

MLLGASLVGALLFSKLVLKLPWTQVGFSLLLLYLGSGGWRFIRVFI
KTVRRDIFGGMVLLKVKTKVRRYLQERKTVPLLFASMVQRHPDKTA
LIFEGTDTHWTFRQLDEYSSSVANFLQARGLASGNVVALFMENRNE
FVGLWLGMAKLGVEAALINTNLRRDALRHCLDTSKARALIFGSEMA
SAICEIHASLEPTLSLFCSGSWEPSTVPVSTEHLDPLLEDAPKHLP
SHPDKGFTDKLFYIYTSGTTGLPKAAIVVHSRYYRMASLVYYGFRM
RPDDIVYDCLPLYHSSRKHRGDWQCLLHGMTVVIRKKFSASRFWDD
CIKYNCTVVQYIGELCRYLLNQPPREAESRHKVRMALGNGLRQSIW
TDFSSRFHIPQVAEFYGATECNCSLGNFDSRVGACGFNSRILSFVY
PIRLVRVNEDTMELIRGPDGVCIPCQPGQPGQLVGRIIQQDPLRRF
DGYLNQGANNKKIANDVFKKGDQAYLTGDVLVMDELGYLYFRDRTG
DTFRWKGENVSTTEVEGTLSRLLHMADVAVYGVEVPGTEGRAGMAA
VASPISNCDLESFAQTLKKELPLYARPIFLRFLPELHKTGTFKFQK
TELRKEGFDPSVVKDPLFYLDARKGCYVALDQEAYTRIQAGEEKL

FIG. 43C hsFATP1 full length DNA

```
          10        20        30        40
TCGACCCACGGCGTCCGGGACCCCAAAGCAGAAGCCCGCA 40
CAGTAGGCACAGCGCACCCAAGAAGGGTCCAGGAGTCTGC 80
AGAAACAGAAAGGTCCCCGGCCTCAGCCTCCTAGTCCCTG 120
CCTGCCTCCTGCCTGAGCTTCTGGGAGACTGAAGGCACGG 160
CTTGCAGCTTCAGGATGCGGGCTCCGGGTGCGGGCGCGGC 200
         210       220       230       240
CTCGGTGGTCTCGCTGGCGCTGTTGTGGCTGCTGGGGCTG 240
CCGTGGACCTGGAGCGCGGCAGCGGCGCTCGGCGTGTACG 280
TGGGCAGCGGCGGCTGGCGCTTCCTGCGCATCGTCTGCAA 320
GACCGCGAGGCGAGACCTCTTCGGTCTCTCTGTGCTGATC 360
CGCGTGCGCCTGGAGCTGCGGCGGCACCAGCGTGCCGGCC 400
         410       420       430       440
ACACCATCCCGCGCATCTTTCAGGCGGTAGTGCAGCGACA 440
GCCCGAGCGCCTGGCGCTGGTGGATGCCGGGACCGGCGAG 480
TGCTGGACCTTTGCGCAGCTGGACGCCTACTCCAATGCGG 520
TAGCCAACCTCTTCCGCCAGCTGGGCTTCGCGCCGGGCGA 560
CGTGGTGGCCATCTTCCTGGAGGGCCGGCCGGAGTTCGTG 600
         610       620       630       640
GGGCTGTGGCTGGGCCTGGCCAAGGCGGGCATGGAGGCCG 640
CGCTGCTCAACGTGAACCTGCGGCGCGAGCCCCTGGCCTT 680
CTGCCTGGGCACCTCGGGCGCTAAGGCCCTGATCTTTGGA 720
GGAGAAATGGTGGCGGCGGTGGCCGAAGTGAGCGGGCATC 760
TGGGGAAAAGTTTGATCAAGTTCTGCTCTGGAGACTTGGG 800
         810       820       830       840
GCCCGAGGGCATCTTGCCGGACACCCACCTCCTGGACCCG 840
CTGCTGAAGGAGGCCTCTACTGCCCCCTTGGCACAGATCC 880
CCAGCAAGGGCATGGACGATCGTCTTTTCTACATCTACAC 920
GTCGGGGACCACCGGGCTGCCCAAGGCTGCCATTGTCGTG 960
CACAGCAGGTACTACCGCATGGCAGCCTTCGGCCACCACG 1000
        1010      1020      1030      1040
CCTACCGCATGCAGGCGGCTGACGTGCTCTATGACTGCCT 1040
GCCCCTGTACCACTCGGCAGGAAACATCATCGGCGTGGGG 1080
CAGTGTCTCATCTATGGGCTGACAGTCGTCCTCCGCAAGA 1120
AATTCTCGGCCAGCCGCTTCTGGGACGACTGCATCAAGTA 1160
CAACTGCACGGTGGTTCAGTACATCGGGGAGATCTGCCGC 1200
```

FIG. 44A 1210 1220 1230 1240

TACCTGCTGAAGCAGCCGGTGCGCGAGGCGGAGAGGCGAC 1240
ACCGCGTGCGCCTGGCGGTGGGGAACGGGCTGCGTCCTGC 1280
CATCTGGGAGGAGTTCACGGAGCGCTTCGGCGTACGCCAA 1320
ATCGGGGAGTTCTACGGCGCCACCGAGTGCAACTGCAGCA 1360
TTGCCAACATGGACGGCAAGGTCGGCTCCTGTGGTTTCAA 1400

1410 1420 1430 1440

CAGCCGCATCCTGCCCCACGTGTACCCCATCCGGCTGGTG 1440
AAGGTCAATGAGGACACAATGGAGCTGCTGCGGGATGCCC 1480
AGGGCCTCTGCATCCCCTGCCAGGCCGGGGAGCCTGGCCT 1520
CCTTGTGGGTCAGATCAACCAACAGGACCCGCTGCGCCGC 1560
TTCGATGGCTATGTCAGCGAGAGCGCCACCAGCAAGAAGA 1600

1610 1620 1630 1640

TCGCCCACAGCGTCTTCAGCAAGGGCGACAGCGCCTACCT 1640
CTCAGGTGACGTGCTAGTGATGGATGAGCTGGGCTACATG 1680
TACTTCCGGGACCGTAGCGGGGACACCTTCCGCTGGCGAG 1720
GGGAGAACGTCTCCACCACCGAGGTGGAGGGCGTGCTGAG 1760
CCGCCTGCTGGGCCAGACAGACGTGGCCGTCTATGGGGTG 1800

1810 1820 1830 1840

GCTGTTCCAGGAGTGGAGGGTAAGGCAGGGATGGCGGCCG 1840
TCGCAGACCCCCACAGCCTGCTGGACCCCAACGCGATATA 1880
CCAGGAGCTGCAGAAGGTGCTGGCACCCTATGCCCGGCCC 1920
ATCTTCCTGCGCCTCCTGCCCCAGGTGGACACCACAGGCA 1960
CCTTCAAGATCCAGAAGACGAGGCTGCAGCGAGAGGGCTT 2000

2010 2020 2030 2040

TGACCCACGCCAGACCTCAGACCGGCTCTTCTTCCTGGAC 2040
CTGAAGCAGGGCCACTACCTGCCCTTAAATGAGGCAGTCT 2080
ACACTCGCATCTGCTCGGGCGCCTTCGCCCTCTGAAGCTG 2120
TTCCTCTACTGGCCACAAACTCTGGGCCTGGTGGGAGAGG 2160
CCAGCTTGAGCCAGACAGCGCTGCCCAGGGGTGGCCGCCT 2200

FIG. 44B

```
     2610      2620      2630      2640
GGTCAGGCTGGTCTTGAACTCCTGACCTCAGGTGATCCGC 2640
TGGCCTCGGCCTCCCAGAGTGCTGGGATTATAGGCGTGAG 2680
CCTCTGGCCCGGCCTTTCCTTTTTCCTCTCCTCTCCTGCC 2720
GAGAGTGGAACACACGTGTCCTGGGAGCTGCATCTTGTGT 2760
AGGGTCCAGCTGCTTTTGGGGACTGCAGGAATCATCTCCC 2800
     2810      2820      2830      2840
CTGGGCCCTGGACTCGGACTGGGGCCTCCCCACCTCCCTC 2840
TCGGCTGTGCCTTACGGAGCCCCAATCCAGGCCTCCTGTG 2880
GCTGTTGGGTTCCAGATGCTGCAGCTCCATGTGACTTCCA 2920
AGCAGGCCCTCCGCCCTCCCTGCTGAATGGAGGAGCCGGG 2960
GGTCCCCCAGGCCAACTGGAAAATCTCCCAGGCTAGGCCA 3000
     3010      3020      3030      3040
ATTGCCTTTTGCACTTCCCCGTTCCTGTCACATTTCCCCA 3040
GCCCCACCTTCCCCTCCTGATGCCCTGAAAGCTTCCGGAA 3080
TTGACTGTGACCACTTGGATGTCACCACTGTCAGCCCCTG 3120
CCTTGATGTCCCCATTTAGCCATCTCCATGGAGCTCCTGC 3160
TGGAGGGCCCTGAACCCTGCACTGCGTGGCTGCCCAGCCA 3200
     3210      3220      3230      3240
GCTGCCTCCTGTCCTGGGAGGAGGCCTCCTGGGTGTCCTC 3240
ATCTGGTGTGTCTACTGGAGGGTCCCACAGGAGAGGCAGC 3280
AGAGGGGTCAGGGGAGGTCTCCTGCCGGGGGTTGGCCTCT 3320
CAAGCCTCAGGGGTTCTAGCCTGTTGAATATACCCCACCT 3360
GGTGGGTGGCCCCTCCGATGTCCCCACTGATGGCTCTGAC 3400
     3410      3420      3430      3440
ACCGTGTTGGTGGCGATGTCCCAGACAATCCCACCAGGAC 3440
GGCCCAGACATCCCTACTGGCTTCGCTGGTGGCTCATCTC 3480
GAACATCCACGCCAGCCTTTCTGGGGCCGGCCACCCAGGC 3520
CGCCTGTCCGTCTGTCCTCCCTCCAGCAGCACCCCCTGGC 3560
CCCTGGAGTGGTGGGGCCATGGCAAGAGACACCGTGGCGT 3600
     3610      3620      3630      3640
CTCATGTGAACTTTCCTGGGCACTGTGGTTTTATTTCCTA 3640
ATTGATTTAAGAAATAAACCTGAAGACCGTCTGGTGAAAA 3680
AAAAAAAAAAAAAA 3694
```

FIG. 44C

```
       2610      2620      2630      2640
GGTCAGGCTGGTCTTGAACTCCTGACCTCAGGTGATCCGC 2640
TGGCCTCGGCCTCCCAGAGTGCTGGGATTATAGGCGTGAG 2680
CCTCTGGCCCGGCCTTTCCTTTTTCCTCTCCTCTCCTGCC 2720
GAGAGTGGAACACACGTGTCCTGGGAGCTGCATCTTGTGT 2760
AGGGTCCAGCTGCTTTTGGGGACTGCAGGAATCATCTCCC 2800
       2810      2820      2830      2840
CTGGGCCCTGGACTCGGACTGGGGCCTCCCCACCTCCCTC 2840
TCGGCTGTGCCTTACGGAGCCCCAATCCAGGCCTCCTGTG 2880
GCTGTTGGGTTCCAGATGCTGCAGCTCCATGTGACTTCCA 2920
AGCAGGCCCTCCGCCCTCCCTGCTGAATGGAGGAGCCGGG 2960
GGTCCCCCAGGCCAACTGGAAAATCTCCCAGGCTAGGCCA 3000
       3010      3020      3030      3040
ATTGCCTTTTGCACTTCCCCGTTCCTGTCACATTTCCCCA 3040
GCCCCACCTTCCCCTCCTGATGCCCTGAAAGCTTCCGGAA 3080
TTGACTGTGACCACTTGGATGTCACCACTGTCAGCCCCTG 3120
CCTTGATGTCCCCATTTAGCCATCTCCATGGAGCTCCTGC 3160
TGGAGGGCCCTGAACCCTGCACTGCGTGGCTGCCCAGCCA 3200
       3210      3220      3230      3240
GCTGCCTCCTGTCCTGGGAGGAGGCCTCCTGGGTGTCCTC 3240
ATCTGGTGTGTCTACTGGAGGGTCCCACAGGAGAGGCAGC 3280
AGAGGGGTCAGGGGAGGTCTCCTGCCGGGGGTTGGCCTCT 3320
CAAGCCTCAGGGGTTCTAGCCTGTTGAATATACCCCACCT 3360
GGTGGGTGGCCCCTCCGATGTCCCCACTGATGGCTCTGAC 3400
       3410      3420      3430      3440
ACCGTGTTGGTGGCGATGTCCCAGACAATCCCACCAGGAC 3440
GGCCCAGACATCCCTACTGGCTTCGCTGGTGGCTCATCTC 3480
GAACATCCACGCCAGCCTTTCTGGGGCCGGCCACCCAGGC 3520
CGCCTGTCCGTCTGTCCTCCCTCCAGCAGCACCCCCTGGC 3560
CCCTGGAGTGGTGGGGCCATGGCAAGAGACACCGTGGCGT 3600
       3610      3620      3630      3640
CTCATGTGAACTTTCCTGGGCACTGTGGTTTTATTTCCTA 3640
ATTGATTTAAGAAATAAACCTGAAGACCGTCTGGTGAAAA 3680
AAAAAAAAAAAAAA 3694
```

FIG. 44D hsFATP1 full length protein

```
          10        20        30        40
MRAPGAGAASVVSLALLWLLGLPWTWSAAAALGVYVGSGG 40
WRFLRIVCKTARRDLFGLSVLIRVRLELRRHQRAGHTIPR 80
IFQAVVQRQPERLALVDAGTGECWTFAQLDAYSNAVANLF 120
RQLGFAPGDVVAIFLEGRPEFVGLWLGLAKAGMEAALLNV 160
NLRREPLAFCLGTSGAKALIFGGEMVAAVAEVSGHLGKSL 200
         210       220       230       240
IKFCSGDLGPEGILPDTHLLDPLLKEASTAPLAQIPSKGM 240
DDRLFYIYTSGTTGLPKAAIVVHSRYYRMAAFGHHAYRMQ 280
AADVLYDCLPLYHSAGNIIGVGQCLIYGLTVVLRKKFSAS 320
RFWDDCIKYNCTVVQYIGEICRYLLKQPVREAERRHRVRL 360
AVGNGLRPAIWEEFTERFGVRQIGEFYGATECNCSIANMD 400
         410       420       430       440
GKVGSCGFNSRILPHVYPIRLVKVNEDTMELLRDAQGLCI 440
PCQAGEPGLLVGQINQQDPLRRFDGYVSESATSKKIAHSV 480
FSKGDSAYLSGDVLVMDELGYMYFRDRSGDTFRWRGENVS 520
TTEVEGVLSRLLGQTDVAVYGVAVPGVEGKAGMAAVADPH 560
SLLDPNAIYQELQKVLAPYARPIFLRLLPQVDTTGTFKIQ 600
         610       620       630       640
KTRLQREGFDPRQTSDRLFFLDLKQGHYLPLNEAVYTRIC 640
SGAFAL 646
```

FIG. 45

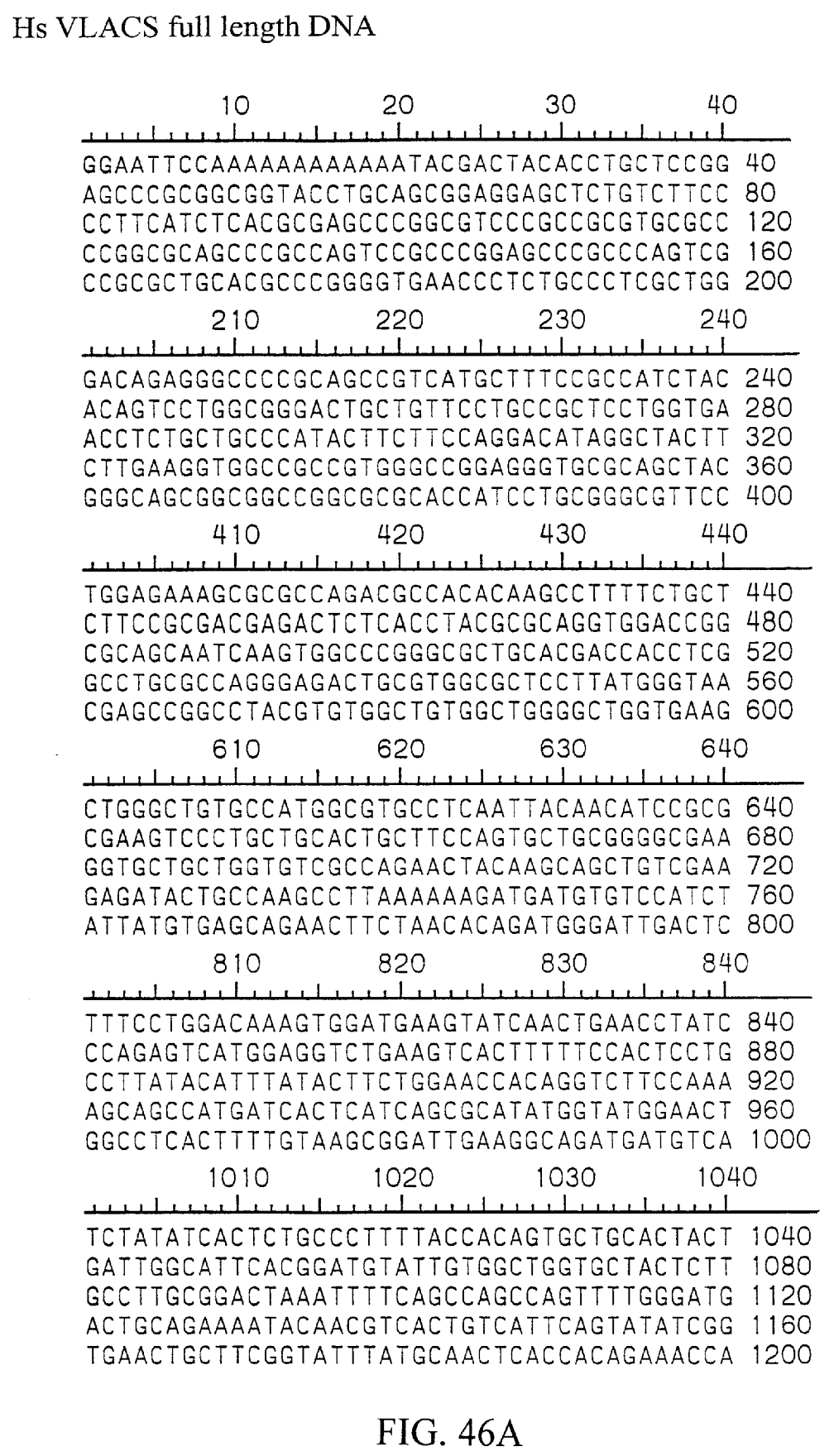

Hs VLACS full length DNA

```
         10        20        30        40
         |         |         |         |
GGAATTCCAAAAAAAAAAAATACGACTACACCTGCTCCGG  40
AGCCCGCGGCGGTACCTGCAGCGGAGGAGCTCTGTCTTCC  80
CCTTCATCTCACGCGAGCCCGGCGTCCCGCCGCGTGCGCC 120
CCGGCGCAGCCCGCCAGTCCGCCCGGAGCCCGCCCAGTCG 160
CCGCGCTGCACGCCCGGGGTGAACCCTCTGCCCTCGCTGG 200
        210       220       230       240
         |         |         |         |
GACAGAGGGCCCCGCAGCCGTCATGCTTTCCGCCATCTAC 240
ACAGTCCTGGCGGGACTGCTGTTCCTGCCGCTCCTGGTGA 280
ACCTCTGCTGCCCATACTTCTTCCAGGACATAGGCTACTT 320
CTTGAAGGTGGCCGCCGTGGGCCGGAGGGTGCGCAGCTAC 360
GGGCAGCGGCGGCCGGCGCGCACCATCCTGCGGGCGTTCC 400
        410       420       430       440
         |         |         |         |
TGGAGAAAGCGCGCCAGACGCCACACAAGCCTTTTCTGCT 440
CTTCCGCGACGAGACTCTCACCTACGCGCAGGTGGACCGG 480
CGCAGCAATCAAGTGGCCCGGGCGCTGCACGACCACCTCG 520
GCCTGCGCCAGGGAGACTGCGTGGCGCTCCTTATGGGTAA 560
CGAGCCGGCCTACGTGTGGCTGTGGCTGGGGCTGGTGAAG 600
        610       620       630       640
         |         |         |         |
CTGGGCTGTGCCATGGCGTGCCTCAATTACAACATCCGCG 640
CGAAGTCCCTGCTGCACTGCTTCCAGTGCTGCGGGGCGAA 680
GGTGCTGCTGGTGTCGCCAGAACTACAAGCAGCTGTCGAA 720
GAGATACTGCCAAGCCTTAAAAAAGATGATGTGTCCATCT 760
ATTATGTGAGCAGAACTTCTAACACAGATGGGATTGACTC 800
        810       820       830       840
         |         |         |         |
TTTCCTGGACAAAGTGGATGAAGTATCAACTGAACCTATC 840
CCAGAGTCATGGAGGTCTGAAGTCACTTTTTCCACTCCTG 880
CCTTATACATTTATACTTCTGGAACCACAGGTCTTCCAAA 920
AGCAGCCATGATCACTCATCAGCGCATATGGTATGGAACT 960
GGCCTCACTTTTGTAAGCGGATTGAAGGCAGATGATGTCA 1000
       1010      1020      1030      1040
         |         |         |         |
TCTATATCACTCTGCCCTTTTACCACAGTGCTGCACTACT 1040
GATTGGCATTCACGGATGTATTGTGGCTGGTGCTACTCTT 1080
GCCTTGCGGACTAAATTTTCAGCCAGCCAGTTTTGGGATG 1120
ACTGCAGAAAATACAACGTCACTGTCATTCAGTATATCGG 1160
TGAACTGCTTCGGTATTTATGCAACTCACCACAGAAACCA 1200
```

FIG. 46A

```
         1210       1220       1230       1240
AATGACCGTGATCATAAAGTGAGACTGGCACTGGGAAATG 1240
GCTTACGAGGAGATGTGTGGAGACAATTTGTCAAGAGATT 1280
TGGGGACATATGCATCTATGAGTTCTATGCTGCCACTGAA 1320
GGCAATATTGGATTTATGAATTATGCGAGAAAAGTTGGTG 1360
CTGTTGGAAGAGTAAACTACCTACAGAAAAAAATCATAAC 1400
         1410       1420       1430       1440
TTATGACCTGATTAAATATGATGTGGAGAAAGATGAACCT 1440
GTCCGAGATGAAAATGGATATTGCGTCAGAGTTCCCAAAG 1480
GTGAAGTTGGACTTCTGGTTTGCAAAATCACACAACTTAC 1520
ACCATTTAATGGCTATGCTGGAGCAAAGGCTCAGACAGAG 1560
AAGAAAAAACTGAGAGATGTCTTTAAGAAAGGAGACCTCT 1600
         1610       1620       1630       1640
ATTTCAACAGTGGAGATCTCTTAATGGTTGACCATGAAAA 1640
TTTCATCTATTTCCACGACAGAGTTGGAGATACATTCCGG 1680
TGGAAAGGGGAAAATGTGGCCACCACTGAAGTTGCTGATA 1720
CAGTTGGACTGGTTGATTTTGTCCAAGAAGTAAATGTTTA 1760
TGGAGTGCATGTGCCAGATCATGAGGGTCGCATTGGCATG 1800
         1810       1820       1830       1840
GCCTCCATCAAAATGAAAGAAAACCATGAATTTGATGGAA 1840
AGAAACTCTTTCAGCACATTGCTGATTACCTACCTAGTTA 1880
TGCAAGGCCCCGGTTTCTAAGAATACAGGACACCATTGAG 1920
ATCACTGGAACTTTTAAACACCGCAAAATGACCCTGGTGG 1960
AGGAGGGCTTTAACCCTGCTGTCATCAAAGATGCCTTGTA 2000
         2010       2020       2030       2040
TTTCTTGGATGACACAGCAAAAATGTATGTGCCTATGACT 2040
GAGGACATCTATAATGCCATAAGTGCTAAAACCCTGAAAC 2080
TCTGAATATTCCCAGGAGGATAACTCAACATTTCCAGAAA 2120
GAAACTGAATGGACAGCCACTTGATATAATCCAACTTTAA 2160
TTTGATTGAAGATTGTGAGGAAATTTTGTAGGAAATTTGC 2200
         2210       2220       2230       2240
ATACCCGTAAAGGGAGACTTTTTTAAATAACAGTTGAGTC 2240
TTTGCAAGTAAAAAGATTTAGAGATTATTATTTTTCAGTG 2280
TGCACCTACTGTTTGTATTTGCAAACTGAGCTTGTTGGAG 2320
GGAAGGCATTATTTTTTAAAATACTTAGTAAATTAAATGA 2360
AC 2362
```

FIG. 46B hs VLACS full length protein

```
         10        20        30        40
MLSAIYTVLAGLLFLPLLVNLCCPYFFQDIGYFLKVAAVG 40
RRVRSYGQRRPARTILRAFLEKARQTPHKPFLLFRDETLT 80
YAQVDRRSNQVARALHDHLGLRQGDCVALLMGNEPAYVWL 120
WLGLVKLGCAMACLNYNIRAKSLLHCFQCCGAKVLLVSPE 160
LQAAVEEILPSLKKDDVSIYYVSRTSNTDGIDSFLDKVDE 200
        210       220       230       240
VSTEPIPESWRSEVTFSTPALYIYTSGTTGLPKAAMITHQ 240
RIWYGTGLTFVSGLKADDVIYITLPFYHSAALLIGIHGCI 280
VAGATLALRTKFSASQFWDDCRKYNVTVIQYIGELLRYLC 320
NSPQKPNDRDHKVRLALGNGLRGDVWRQFVKRFGDICIYE 360
FYAATEGNIGFMNYARKVGAVGRVNYLQKKIITYDLIKYD 400
        410       420       430       440
VEKDEPVRDENGYCVRVPKGEVGLLVCKITQLTPFNGYAG 440
AKAQTEKKKLRDVFKKGDLYFNSGDLLMVDHENFIYFHDR 480
VGDTFRWKGENVATTEVADTVGLVDFVQEVNVYGVHVPDH 520
EGRIGMASIKMKENHEFDGKKLFQHIADYLPSYARPRFLR 560
IQDTIEITGTFKHRKMTLVEEGFNPAVIKDALYFLDDTAK 600
        610       620       630       640
MYVPMTEDIYNAISAKTLKL   620
```

FIG. 47 hsFATP3 partial DNA

```
          10        20        30        40
AAGTTCTCGGCTGGTCAGTTCTGGGAAGATTGCCAGCAGC 40
ACAGGGTGACGGTGTTCCAGTACATTGGGGAGCTGTGCCG 80
ATACCTTGTCAACCAGCCCCCGAGCAAGGCAGAACGTGGC 120
CATAAGGTCCGGCTGGCAGTGGGCAGCGGGCTGCGCCCAG 160
ATACCTGGGAGCGTTTTGTGCGGCGCTTCGGGCCCCTGCA 200
         210       220       230       240
GGTGCTGGAGACATATGGACTGACAGAGGGCAACGTGGCC 240
ACCATCAACTACACAGGACAGCGGGGCGCTGTGGGGCGTG 280
CTTCCTGGCTTTACAAGCATATCTTCCCCTTCTCCTTGAT 320
TCGCTATGATGTCACCACAGGAGAGCCAATTCGGGACCCC 360
CAGGGGCACTGTATGGCCACATCTCCAGGTGAGCCAGGGC 400
         410       420       430       440
TGCTGGTGGCCCCGGTAAGCCAGCAGTCCCCATTCCTGGG 440
CTATGCTGGCGGGCCAGAGCTGGCCCAGGGGAAGTTGCTA 480
AAGGATGTCTTCCGGCCTGGGGATGTTTTCTTCAACACTG 520
GGGACCTGCTGGTCTGCGATGACCAAGGTTTTCTCCGCTT 560
CCATGATCGTACTGGAGACACCTTCAGGTGGAAGGGGGAG 600
         610       620       630       640
AATGTGGCCACAACCGAGGTGGCAGAGGTCTTCGAGGCCC 640
TAGATTTTCTTCAGGAGGTGAACGTCTATGGAGTCACTGT 680
GCCAGGGCATGAAGGCAGGGCTGGAATGGCAGCCCTAGTT 720
CTGCGTCCCCCCCACGCTTTGGACCTTATGCAGCTCTACA 760
CCCACGTGTCTGAGAACTTGCCACCTTATGCCCGGCCCCG 800
         810       820       830       840
ATTCCTCAGGCTCCAGGAGTCTTTGGCCACCACAGAGACC 840
TTCAAACAGCAGAAAGTTCGGATGGCAAATGAGGGCTTCG 880
ACCCCAGCACCCTGTCTGACCCACTGTACGTTCTGGACCA 920
GGCTGTAGGTGCCTACCTGCCCCTCACAACTGCCCGGTAC 960
AGCGCCCTCCTGGCAGGAAACCTTCGAATCTGAGAACTTC 1000
        1010      1020      1030      1040
CACACCTGAGGCACCTGAGAGAGGAACTCTGTGGGGTGGG 1040
GGCCGTTGCAGGTGTACTGGGCTGTCAGGGATCTTTTCTA 1080
TACCAGAACTGCGGTCACTATTTTGTAATAAATGTGGCTG 1120
GAGCTGATCCAGCTGTCTCTGACAAAAAAAAAAAAAAAAA 1160
AAAGGGCGGCCGC 1173
```

FIG. 48 hsFATP3 partial protein

```
                  10         20         30         40
KFSAGQFWEDCQQHRVTVFQYIGELCRYLVNQPPSKAERG 40
HKVRLAVGSGLRPDTWERFVRRFGPLQVLETYGLTEGNVA 80
TINYTGQRGAVGRASWLYKHIFPFSLIRYDVTTGEPIRDP 120
QGHCMATSPGEPGLLVAPVSQQSPFLGYAGGPELAQGKLL 160
KDVFRPGDVFFNTGDLLVCDDQGFLRFHDRTGDTFRWKGE 200
                 210        220        230        240
NVATTEVAEVFEALDFLQEVNVYGVTVPGHEGRAGMAALV 240
LRPPHALDLMQLYTHVSENLPPYARPRFLRLQESLATTET 280
FKQQKVRMANEGFDPSTLSDPLYVLDQAVGAYLPLTTARY 320
SALLAGNLRI 330
```

FIG. 49 hsFATP4 full length

```
CGACCCACGCGTCCGGGCGGGCGGGGCCGGGCGGCGGGCG 40
GGGCTGGCGGGGCGGCCGGGCCATGCAGGGCGCAGAGCCG 80
GCTAAACCCTGCTGAGACCCGGCTCCGTGCGTCCAGGGGC 120
GGCTAATGCCCCTCACGCTGTCTACGCTGCTGCAACCGGG 160
CCGCATCTGGACGGGGCGCCGCGCGGCGGAGCCGACGCCG 200
GGCCACAATGCTGCTTGGAGCCTCTCTGGTGGGGGTGCTG 240
CTGTTCTCCAAGCTGGTGCTGAAACTGCCCTGGACCCAGG 280
TGGGATTCTCCCTGTTGTTCCTCTACTTGGGATCTGGCGG 320
CTGGCGCTTCATCCGGGTCTTCATCAAGACCATCAGGCGC 360
GATATCTTTGGCGGCCTGGTCCTCCTGAAGGTGAAGGCAA 400
AGGTGCGACAGTGCCTGCAGGAGCGGCGGACAGTGCCCAT 440
TTTGTTTGCCTCTACCGTTCGGCGCCACCCCGACAAGACG 480
GCCCTGATCTTCGAGGGCACAGATACCCACTGGACCTTCC 520
GCCAGCTGGATGAGTACTCAAGCAGTGTAGCCAACTTCCT 560
GCAGGCCCGGGGCCTGGCCTCGGGCGATGTGGCTGCCATC 600
TTCATGGAGAACCGCAATGAGTTCGTGGGCCTATGGCTGG 640
GCATGGCCAAGCTCGGTGTGGAGGCAGCCCTCATCAACAC 680
CAACCTGCGGCGGGATGCTCTGCTCCACTGCCTCACCACC 720
TCGCGCGCACGGGCCCTTGTCTTTGGCAGCGAAATGGCCT 760
CAGCCATCTGTGAGGTCCATGCCAGCCTGGACCCCTCGCT 800
CAGCCTCTTCTGCTCTGGCTCCTGGGAGCCCGGTGCGGTG 840
CCTCCAAGCACAGAACACCTGGACCCTCTGCTGAAAGATG 880
CTCCCAAGCACCTTCCCAGTTGCCCTGACAAGGGCTTCAC 920
AGATAAACTGTTCTACATCTACACATCCGGCACCACAGGG 960
CTGCCCAAGGCCGCCATCGTGGTGCACAGCAGGTATTACC 1000
GCATGGCTGCCCTGGTGTACTATGGATTCCGCATGCGGCC 1040
CAACGACATCGTCTATGACTGCCTCCCCCTCTACCACTCA 1080
GCAGGAAACATCGTGGGAATCGGCCAGTGCCTGCTGCATG 1120
GCATGACGGTGGTGATTCGGAAGAAGTTCTCAGCCTCCCG 1160
GTTCTGGGACGATTGTATCAAGTACAACTGCACGATTGTG 1200
```

FIG. 50A 1210 1220 1230 1240

CAGTACATTGGTGAACTGTGCCGCTACCTCCTGAACCAGC 1240
CACCGCGGGAGGCAGAAAACCAGCACCAGGTTCGCATGGC 1280
ACTAGGCAATGGCCTCCGGCAGTCCATCTGGACCAACTTT 1320
TCCAGCCGCTTCCACATACCCCAGGTGGCTGAGTTCTACG 1360
GGGCCACAGAGTGCAACTGTAGCCTGGGCAACTTCGACAG 1400

1410 1420 1430 1440

CCAGGTGGGGGCCTGTGGTTTCAATAGCCGCATCCTGTCC 1440
TTCGTGTACCCCATCCGGTTGGTACGTGTCAACGAGGACA 1480
CCATGGAGCTGATCCGGGGGCCCGACGGCGTCTGCATTCC 1520
CTGCCAGCCAGGTGAGCCGGGCCAGCTGGTGGGCCGCATC 1560
ATCCAGAAAGACCCCCTGCGCCGCTTCGATGGCTACCTCA 1600

1610 1620 1630 1640

ACCAGGGCGCCAACAACAAGAAGATTGCCAAGGATGTCTT 1640
CAAGAAGGGGGACCAGGCCTACCTTACTGGTGATGTGCTG 1680
GTGATGGACGAGCTGGGCTACCTGTACTTCCGAGACCGCA 1720
CTGGGGACACGTTCCGCTGGAAAGGTGAGAACGTGTCCAC 1760
CACCGAGGTGGAAGGCACACTCAGCCGCCTGCTGGACATG 1800

1810 1820 1830 1840

GCTGACGTGGCCGTGTATGGTGTCGAGGTGCCAGGAACCG 1840
AGGGCCGGGCCGGAATGGCTGCTGTGGCCAGCCCCACTGG 1880
CAACTGTGACCTGGAGCGCTTTGCTCAGGTCTTGGAGAAG 1920
GAACTGCCCCTGTATGCGCGCCCCATCTTCCTGCGCCTCC 1960
TGCCTGAGCTGCACAAAACAGGAACCTACAAGTTCCAGAA 2000

2010 2020 2030 2040

GACAGAGCTACGGAAGGAGGGCTTTGACCCGGCTATTGTG 2040
AAAGACCCGCTGTTCTATCTAGATGCCCAGAAGGGCCGCT 2080
ACGTCCCGCTGGACCAAGAGGCCTACAGCCGCATCCAGGC 2120
AGGCGAGGAGAAGCTGTGATTCCCCCCATCCCTCTGAGGG 2160
CCGGCGGATGCTGGATCCGGAGCCCCAGGTTCCGCCCCAG 2200

FIG. 50B 2210 2220 2230 2240

AGCGGTCCTGGACAAGGCCAGACCAAAGCAAGCAGGGCCT 2240
GGCACCTCCATCCTGAGGTGCTGCCCCTCCATCCAAAACT 2280
GCCAAGTGACTCATTGCCTTCCCAACCCTTCCAGAGGCTT 2320
TCTGTGAAAGTCTCATGTCCAAGTTCCGTCTTCTGGGCTG 2360
GGCAGGCCCTCTGGTTCCCAGGCTGAGACTGACGGGTTTT 2400

2410 2420 2430 2440

CTCAGGATGATGTCTTGGGTGAGGGTAGGGAGAGGACAAG 2440
GGGTCACCGAGCCCTTCCCAGAGAGCAGGGAGCTTATAAA 2480
TGGAACCAGAGCAGAAGTCCCCAGACTCAGGAAGTCAACA 2520
GAGTGGGCAGGGACAGTGGTAGCATCCATCTGGTGGCCAA 2560
AGAGAATCGTAGCCCCAGAGCTGCCCAAGTTCACTGGGCT 2600

2610 2620 2630 2640

CCACCCCCACCTCCAGGAGGGGAGGAGAGGACCTGACATC 2640
TGTAGGTGGCCCCTGATGCCCCATCTACAGCAGGAGGTCA 2680
GGACCACGCCCCTGGCCTCTCCCCACTCCCCCATCCTCCT 2720
CCCTGGGTGGCTGCCTGATTATCCCTCAGGCAGGGCCTCT 2760
CAGTCCTTGTGGGTCTGTGTCACCTCCATCTCAGTCTTGG 2800

2810 2820 2830 2840

CCTGGCTATGAGGGGAGGAGGAATGGGAGAGGGGGCTCAG 2840
GGGCCAATAAACTCTGCCTTGAGTCCTCCTAAAAAAAAAA 2880
AAAAAAAAAAAAAAAAAAAAAAAAAAA 2907

FIG. 50C hsFATP4 full length protein

```
         10         20         30         40
MLLGASLVGVLLFSKLVLKLPWTQVGFSLLFLYLGSGGWR 40
FIRVFIKTIRRDIFGGLVLLKVKAKVRQCLQERRTVPILF 80
ASTVRRHPDKTALIFEGTDTHWTFRQLDEYSSSVANFLQA 120
RGLASGDVAAIFMENRNEFVGLWLGMAKLGVEAALINTNL 160
RRDALLHCLTTSRARALVFGSEMASAICEVHASLDPSLSL 200
        210        220        230        240
FCSGSWEPGAVPPSTEHLDPLLKDAPKHLPSCPDKGFTDK 240
LFYIYTSGTTGLPKAAIVVHSRYYRMAALVYYGFRMRPND 280
IVYDCLPLYHSAGNIVGIGQCLLHGMTVVIRKKFSASRFW 320
DDCIKYNCTIVQYIGELCRYLLNQPPREAENQHQVRMALG 360
NGLRQSIWTNFSSRFHIPQVAEFYGATECNCSLGNFDSQV 400
        410        420        430        440
GACGFNSRILSFVYPIRLVRVNEDTMELIRGPDGVCIPCQ 440
PGEPGQLVGRIIQKDPLRRFDGYLNQGANNKKIAKDVFKK 480
GDQAYLTGDVLVMDELGYLYFRDRTGDTFRWKGENVSTTE 520
VEGTLSRLLDMADVAVYGVEVPGTEGRAGMAAVASPTGNC 560
DLERFAQVLEKELPLYARPIFLRLLPELHKTGTYKFQKTE 600
        610        620        630        640
LRKEGFDPAIVKDPLFYLDAQKGRYVPLDQEAYSRIQAGE 640
EKL 643
```

FIG. 51 hsFATP5(partial)

GTCGTTGGGATCCTCGGCTGCTTAGATCTCGGAGCCACCTGTGTTCT
GGCCCCCAAGTTCTCTACTTCCTGCTTCTGGGATGACTGTCGGCAGC
ATGGCGTGACAGTGATCCTGTATGTGGGCGAGCTCCTGCGATACTTG
TGTAACATTCCCCAGCAACCAGAGGACCGGACACATACAGTCCGCC
TGGCAATGGGCAATGGACTACGGGCTGATGTGTGGGGAGACCTTCC
AGCAGCGTTTCGGTCCTATTTCGGATCTNGGGAAGTCTTACGGGCTT
CCACAGAAGGGCAACATGGGGCTTTAGTTCAAATATTGTTGGGGGC
GCTGCGGGGCCCTGGGGGCAAAGATGGAGCTTGCCTCCTCCGAATG
CTGTCCCCCTTTGAGCTGGTGCAGTTCGACATGGAGGCGGCGGAGC
CTGTGAGGGACAATCAGGGCTTCTGCATCCCTGTAGGGCTAGGGGA
GCCGGGGCTGCTGTTGACCAAGGTGGTAAGCCAGCAACCCTTCGTG
GGCTACCGCGGCCCCCGAGAGCTGTCGGAACGGAAGCTGGTGCGCA
ACGTGCGGCAATCGGGCGACGTTTACTACAACACCGGGGACGTACT
GGCCATGGACCGCGAAGGCTTCCTCTACTTCCGCGACCGACTCGGG
GACACCTTCCGATGGAAGGGCGAGAACGTGTCCACGCACGAGGTGG
AGGGCGTGTTGTCGCAGGTGGACTTCTTGCAACAGGTTAACGTGTAT
GGCGTGTGCGTGCCAGGTTGTGAGGGTAAGGTGGGCATGGCTGCTG
TGGCATTAGCCCCCGGCCAGACTTTCGACGGGGAGAAGTTGTACCA
GCACGTTCGCGCTTGGCTCCCTGCCTACGCTACCCCCCATTTCATCC
GCATCCAGGACGCCATGGAGGTCACCAGCACGTTCAAACTGATGAA
GACCCGGTTGGTGCGTGAGGGCTTCAATGTGGGGATCGTGGTTGAC
CCTCTGTTTGTACTGGACAACCGGGCCCAGTCCTTCCGGCCCCTGAC
GGCAGAAATGTACCAGGCTGTGTGTGAGGGAACCTGGAGGCTCTGA
TCACCTGGCCAACCCACTGGGGTAGGGATCAAAGCCAGCCACCCCC
ACCCCAACACACTCGGTGTCCCTTTCATCCTGGGCCTGTGTGAATCC
CAGCCTGGCCATACCCTCAACCTCAGTGGGCTGGAAATGACAGTGG
GCCCTGTAGCAGTGGCAGAATAAACTCAGMTGYGTTCACAGAAA

FIG. 52 hsFATP5 partial protein

```
        10        20        30        40
VVGILGCLDLGATCVLAPKFSTSCFWDDCRQHGVTVILYV  40
GELLRYLCNIPQQPEDRTHTVRLAMGNGLRADVWGDLPAA  80
FRSYFGSXEVLRASTEGQHGALVQILLGALRGPGGKDGAC 120
LLRMLSPFELVQFDMEAAEPVRDNQGFCIPVGLGEPGLLL 160
TKVVSQQPFVGYRGPRELSERKLVRNVRCSGDVYYNTGDV 200
       210       220       230       240
LAMDREGFLYFRDRLGDTFRWKGENVSTHEVEGVLSQVDF 240
LQQVNVYGVCVPGCEGKVGMAAVALAPGQTFDGEKLYQHV 280
RAWLPAYATPHFIRIQDAMEVTSTFKLMKTRLVREGFNVG 320
IVVDPLFVLDNRAQSFRPLTAEMYQAVCEGTWRL       354
```

FIG. 53 hsFATP6 full length DNA 10 20 30 40

AACGGCAAGTAAGCGCAACGCAATTAATGTGAGTAGCTCA 40
CTCATTAGGCACCCCAGGCTTTACACTTTATGCTTCCGGG 80
CTCGTATGTTGTGTGGAATTGTGAGCGGATACCAATTTCA 120
CACAGGAACCAGCTATGACATGATTACGAATTTAATACGA 160
CTCACTATAGGGAATTTGGCCCTCGAGGCCAAGAATTCGG 200

210 220 230 240

CACGAGGGGTGCTGAGCCCCTGCGCGGTTTCTGGTGCGTA 240
GAGACTGTAAATCGCTGCGCTTCTCAGTCATCATCATCCC 280
AGCTTTTCCCGGCTCGAATTCAGCCTCCAACTCAAGCTCG 320
CGGGAAAGACTACCTGAGAGGAGAAAAGCTTCTGTCCCTG 360
GACCTTCTTCTGAGGGTGGAGTCGGAGGCTCCCTGCTTTC 400

410 420 430 440

CAGCCGCCCAGTGACCCAAGCTTAATCTTCAGCACCACTT 440
GGGGCGACCTTTTCGGTGCAAACCTACGATTCTGTTTCTC 480
AGGATTCCTCCCCATCCCGCTTCGCCCCGGAAAAGCTGAC 520
AAGAACTTCAGGTGTAAGCCCTGAGTAGTGAGGATCTGCG 560
GTCTCCGTGGAGAGCTGTGCCTGGAAGAGAAGGACGCTGG 600

610 620 630 640

TGGGGGCTGAGATCAGAGCTGTCTTCTGGCCCAGTTGCCC 640
CCATGCTTCTGTCATGGCTAACAGTTCTAGGGGCTGGAAT 680
GGTCGTCCTGCACTTCTTGCAG-AACTCCTGTTCCCTTAC 720
TTTTGGGATGACTTCTGGTTCGTGTTGAAGGTGGTGCTCA 760
TTATAATTCGGCTGAAGAAGTATGAAAAGAGAGGGGAGCT 800

810 820 830 840

GGTGACTGTGCTGGATAAATTCTTGAGTCATGCCAAAAGA 840
CAACCTCGGAAACCTTTCATCATCTATGAGGGAGACATCT 880
ACACCTATCAGGATGTAGACAAAAGGAGCAGCAGAGTGGC 920
CCATGTCTTCCTGAACCATTCCTCTCTGAAAAAGGGGGAC 960
ACGGTGGCTCTGCTGATGAGCAATGAGCCGGACTTCGTTC 1000

1010 1020 1030 1040

ACGTGTGGTTCGGCCTCGCCAAGCTGGGCTGCGTGGTGGC 1040
CTTTCTCAACACCAACATTCGCTCCAACTCCCTCCTGAAT 1080
TGCATCCGCGCCTGTGGGCCCAGAGCCCTAGTGGTGGGCG 1120
CAGATTTGCTTGGAACGGTAGAAGAAATCCTTCCAAGCCT 1160
CTCAGAAAATATCAGTGTTTGGGGGATGAAAGATTCTGTT 1200

FIG. 54A

```
        1210        1220        1230        1240
CCACAAGGTGTAATTTCACTCAAAGAAAAACTGAGCACCT 1240
CACCTGATGAGCCCGTGCCACGCAGCCACCATGTTGTCTC 1280
ACTCCTCAAGTCTACTTGTCTTTACATTTTTACCTCTGGA 1320
ACAACAGGTCTACCAAAAGCAGCTGTGATTAGTCAGCTGC 1360
AGGTTTTAAGGGGTTCTGCTGTCCTGTGGGCTTTTGGTTG 1400
        1410        1420        1430        1440
TACTGCTCATGACATTGTTTATATAACCCTTCCTCTGTAT 1440
CATAGTTCAGCAGCTATCCTGGGAATTTCTGGATGTGTTG 1480
AGTTGGGTGCCACTTGTGTGTTAAAGAAGAAATTTTCAGC 1520
AAGCCAGTTTTGGAGTGACTGCAAGAAGTATGATGTGACT 1560
GTGTTTCAGTATATTGGAGAACTTTGTCGCTACCTTTGCA 1600
        1610        1620        1630        1640
AACAATCTAAGAGAGAAGGAGAAAAGGATCATAAGGTGCG 1640
TTTGGCAATTGGAAATGGCATACGGAGTGATGTATGGAGA 1680
GAATTTTTAGACAGATTTGGAAATATAAAGGTGTGTGAAC 1720
TTTATGCAGCTACCGAATCAAGCATATCTTTCATGAACTA 1760
CACTGGGAGAATTGGAGCAATTGGGAGAACAAATTTGTTT 1800
        1810        1820        1830        1840
TACAAACTTCTTTCCACTTTTGACTTAATAAAGTATGACT 1840
TTCAGAAAGATGAACCCATGAGAAATGAGCAGGGTTGGTG 1880
TATTCATGTGAAAAAAAGGAGAACCTGGACTTCTCATTTCT 1920
CGAGTGAATGCAAAAAAATCCCTTCTTTGGCTATGCTGGGC 1960
CTTATAAGCACACAAAAGACAAATTGCTTTGTGATGTTTT 2000
        2010        2020        2030        2040
TAAGAAGGGAGATGTTTACCTTAATACTGGAGACTTAATA 2040
GTCCAGGATCAGGACAATTTCCTTTATTTTTGGGACCGTA 2080
CTGGAGACACTTTCAGATGGAAAGGAGAAAATGTCGCAAC 2120
CACTGAGGTTGCTGATGTTATTGGAATGTTGGATTTCATA 2160
CAGGAAGCAAACGTCTATGGTGTGGCTATATCAGGTTATG 2200
```

FIG. 54B

```
        2210      2220      2230      2240
AAGGAAGAGCAGGAATGGCTTCTATTATTTTAAAACCAAA 2240
TACATCTTTAGATTTGGAAAAAGTTTATGAACAAGTTGTA 2280
ACATTTCTACCAGCTTATGCTTGTCCACGATTTTTAAGAA 2320
TTCAGGAAAAAATGGAAGCAACAGGAACATTCAAACTATT 2360
GAAGCATCAGTTGGTGGAAGATGGATTTAATCCACTGAAA 2400
        2410      2420      2430      2440
ATTTCTGAACCACTTTACTTCATGGATAACTTGAAAAAGT 2440
CTTATGTTCTACTGACCAGGGAACTTTATGATCAAATAAT 2480
GTTAGGGGAAATAAAACTTTAAGATTTTTATATCTAGAAC 2520
TTTCATATGCTTTCTTAGGAAGAGTGAGAGGGGGGTATAT 2560
GATTCTTTATGAAATGGGGAAAGGGAGCTAACATTAATTA 2600
        2610      2620      2630      2640
TGCATGTACTATATTTCCTTAATATGAGAGATAATTTTTT 2640
AATTGCATAAGAATTTTAATTTCTTTTAATTGATATAAAC 2680
ATTAGTTGATTATTCTTTTTATCTATTTGGAGATTCAGTG 2720
CATAACTAAGTATTTTCCTTAATACTAAAGATTTTAAATA 2760
ATAAATAGTGGCTAGCGGTTTGGACAATCACTAAAAATGT 2800
        2810      2820      2830      2840
ACTTTCTAATAAGTAAAATTTCTAATTTTGAATAAAAGAT 2840
TAAATTTTACTGAAAAAAAAAAAAAAAAAAAAAAATTGGCG 2880
GCCGC 2885
```

FIG. 54C hsFATP6 full length protein

```
         10        20        30        40
MLLSWLTVLGAGMVVLHFLQKLLFPYFWDDFWFVLKVVLI  40
IIRLKKYEKRGELVTVLDKFLSHAKRQPRKPFIIYEGDIY  80
TYQDVDKRSSRVAHVFLNHSSLKKGDTVALLMSNEPDFVH 120
VWFGLAKLGCVVAFLNTNIRSNSLLNCIRACGPRALVVGA 160
DLLGTVEEILPSLSENISVWGMKDSVPQGVISLKEKLSTS 200
        210       220       230       240
PDEPVPRSHHVVSLLKSTCLYIFTSGTTGLPKAAVISQLQ 240
VLRGSAVLWAFGCTAHDIVYITLPLYHSSAAILGISGCVE 280
LGATCVLKKKFSASQFWSDCKKYDVTVFQYIGELCRYLCK 320
QSKREGEKDHKVRLAIGNGIRSDVWREFLDRFGNIKVCEL 360
YAATESSISFMNYTGRIGAIGRTNLFYKLLSTFDLIKYDF 400
        410       420       430       440
QKDEPMRNEQGWCIHVKKGEPGLLISRVNAKNPFFGYAGP 440
YKHTKDKLLCDVFKKGDVYLNTGDLIVQDQDNFLYFWDRT 480
GDTFRWKGENVATTEVADVIGMLDFIQEANVYGVAISGYE 520
GRAGMASIILKPNTSLDLEKVYEQVVTFLPAYACPRFLRI 560
QEKMEATGTFKLLKHQLVEDGFNPLKISEPLYFMDNLKKS 600
        610       620       630       640
YVLLTRELYDQIMLGEIKL 619
```

FIG. 55 mFATP1 full length DNA

```
       10        20        30        40
AAGTTCCCACTCCAGACTTCTGCGAGAACCCGTGAGGAAG 40
CAGCGAGAACCGGGGGTTTGCAAGCCAGAGAAGGATGCGG 80
ACTCCGGGAGCAGGAACAGCCTCTGTGGCCTCATTGGGGC 120
TGCTTTGGCTTCTGGGACTTCCGTGGACCTGGAGCGCGGC 160
GGCGGCGTTCGGTGTGTACGTGGGTAGCGGTGGCTGGCGA 200
      210       220       230       240
TTTCTGCGTATCGTCTGCAAGACGGCGAGGCGAGACCTCT 240
TTGGCCTCTCTGTTCTGATCCGCGTGCGGCTAGAGCTACG 280
ACGACACCGGCGAGCAGGAGACACGATCCCACGCATCTTC 320
CAGGCCGTGGCCCAGCGACAGCCGGAGCGCCTGGCGCTGG 360
TAGATGCGAGTAGCGGTATCTGCTGGACCTTCGCACAGCT 400
      410       420       430       440
AGACACCTACTCCAATGCTGTGGCCAATCTGTTCCTCCAG 440
CTGGGCTTTGCGCCAGGCGATGTGGTGGCTGTGTTCCTGG 480
AAGGCCGGCCCGAGTTCGTGGGACTGTGGCTGGGCCTGGC 520
CAAGGCCGGTGTAGTGGCTGCGCTTCTCAATGTCAACCTG 560
AGGCGGGAGCCCCTTGCCTTCTGCTTGGGCACATCAGCTG 600
      610       620       630       640
CCAAGGCCCTCATTTATGGCGGGGAGATGGCAGCGGCGGT 640
GGCGGAGGTGAGTGAGCAGCTGGGGAAGAGCCTGCTCAAG 680
TTCTGCTCTGGAGATCTGGGGCCTGAGAGCGTCCTGCCTG 720
ACACGCAGCTTCTGGACCCCATGCTTGCTGAGGCGCCCAC 760
CACACCCCTGGCACAGGCCCCAGGCAAGGGCATGGATGAT 800
      810       820       830       840
CGGCTATTTTACATCTATACTTCTGGGACCACCGGACTTC 840
CTAAGGCGGCCATTGTGGTGCACAGCAGGTACTACCGCAT 880
CGCAGCCTTCGGCCACCATTCCTACAGCATGCGGGCCAAC 920
GATGTGCTCTATGACTGCCTACCTCTCTACCACTCAGCAG 960
GGAACATCATGGGCGTGGGACAGTGTATCATCTACGGGTT 1000
      1010      1020      1030      1040
AACGGTGGTACTGCGCAAGAAGTTCTCCGCCAGCCGCTTC 1040
TGGGACGACTGTGTCAAATATAATTGCACGGTAGTGCAGT 1080
ACATCGGTGAAATATGCCGCTACCTGCTAAGGCAGCCGGT 1120
TCGCGATGTAGAGCGGCGGCACCGCGTGCGCCTGGCCGTG 1160
GGTAACGGACTGCGGCCAGCCATCTGGGAGGAGTTCACGC 1200
```

FIG. 56A 1210 1220 1230 1240

```
AGGGTTTCGGTGTGCGACAGATTGGCGAGTTCTACGGCGC 1240
CACCGAATGCAACTGCAGCATTGCCAACATGGACGGCAAG 1280
GTCGGCTCCTGCGGCTTCAACAGCCGTATCCTCACGCATG 1320
TGTACCCCATCCGTCTGGTCAAGGTCAACGAGGACACGAT 1360
GGAGCCACTGAGGGACTCCCAAGGCCTCTGCATCCCGTGC 1400
```

1410 1420 1430 1440

```
CAGCCCGGGGAACCTGGGCTTCTCGTGGGCCAGATCAACC 1440
AGCAAGACCCTCTGCGGCGCTTCGATGGCTATGTTAGTGA 1480
CAGCGCCACCAACAAGAAGATTGCCCACAGCGTGTTCCGA 1520
AAGGGGGACAGCGCCTACCTTTCAGGTGACGTGCTAGTGA 1560
TGGACGAGCTGGGGTACATGTACTTCCGTGACCGCAGCGG 1600
```

1610 1620 1630 1640

```
GGATACCTTCCGATGGCGCGGCGAGAACGTATCCACCACG 1640
GAGGTGGAAGCCGTGCTGAGCCGCCTGTTGGGCCAGACGG 1680
ACGTGGCTGTGTATGGAGTGGCTGTGCCAGGAGTGGAGGG 1720
GAAAAGCGGCATGGCGGCCATTGCAGACCCCCACAACCAG 1760
CTGGACCCTAACTCAATGTACCAGGAATTGCAGAAGGTTC 1800
```

1810 1820 1830 1840

```
TTGCATCCTATGCCCAGCCCATCTTCCTGCGTCTTCTGCC 1840
CCAAGTGGATACAACAGGCACCTTCAAGATCCAGAAGACC 1880
CGACTACAGCGTGAAGGCTTTGACCCCCGCCAGACCTCAG 1920
ACCGGCTCTTCTTTCTAGACCTGAAACAGGGACGCTACCT 1960
ACCCCTGGATGAGAGAGTCCATGCCCGCATCTGCGCAGGC 2000
```

2010 2020 2030 2040

```
GACTTCTCACTCTGAGCCTGGTGAGTGGGATGGCCCTGGA 2040
CTTGTGAGACCAGGGAGCCGGACACCCCTGTTCAGGTGTT 2080
TCTCCTGCCTGGCCACGTGGCCAGCAGCACCTGTGGGTGC 2120
AGGAAACTGGAACCTGAGTGGCCGGGTGTCCCTTTCCTAC 2160
AACCCACCATGCACACATCTAGCCTCTGCCTTGGTCTTTT 2200
```

FIG. 56B

Figure 56C:
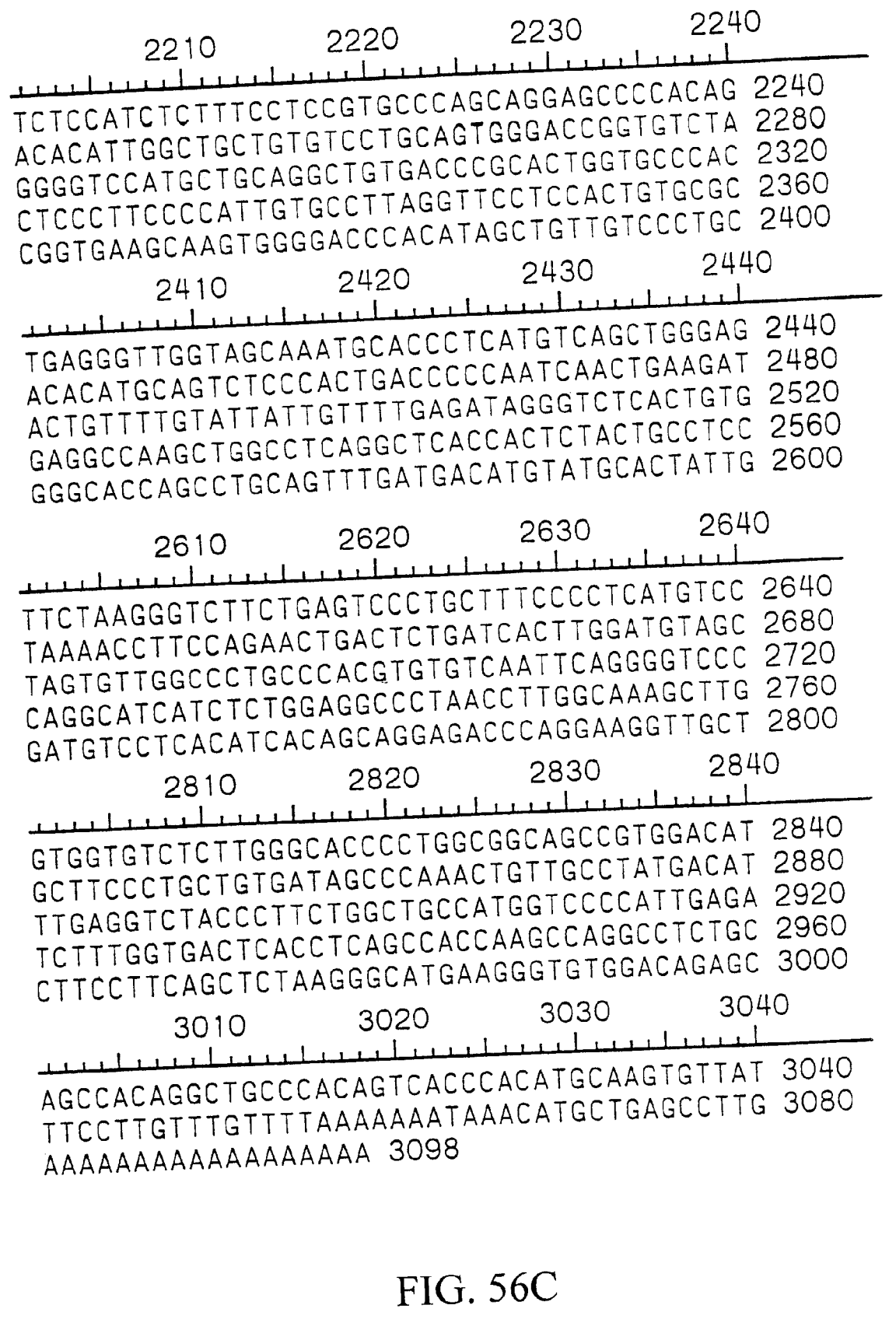

```
TCTCCATCTCTTTCCTCCGTGCCCAGCAGGAGCCCCACAG 2240
ACACATTGGCTGCTGTGTCCTGCAGTGGGACCGGTGTCTA 2280
GGGGTCCATGCTGCAGGCTGTGACCCGCACTGGTGCCCAC 2320
CTCCCTTCCCCATTGTGCCTTAGGTTCCTCCACTGTGCGC 2360
CGGTGAAGCAAGTGGGGACCCACATAGCTGTTGTCCCTGC 2400
TGAGGGTTGGTAGCAAATGCACCCTCATGTCAGCTGGGAG 2440
ACACATGCAGTCTCCCACTGACCCCCAATCAACTGAAGAT 2480
ACTGTTTTGTATTATTGTTTTGAGATAGGGTCTCACTGTG 2520
GAGGCCAAGCTGGCCTCAGGCTCACCACTCTACTGCCTCC 2560
GGGCACCAGCCTGCAGTTTGATGACATGTATGCACTATTG 2600
TTCTAAGGGTCTTCTGAGTCCCTGCTTTCCCCTCATGTCC 2640
TAAAACCTTCCAGAACTGACTCTGATCACTTGGATGTAGC 2680
TAGTGTTGGCCCTGCCCACGTGTGTCAATTCAGGGGTCCC 2720
CAGGCATCATCTCTGGAGGCCCTAACCTTGGCAAAGCTTG 2760
GATGTCCTCACATCACAGCAGGAGACCCAGGAAGGTTGCT 2800
GTGGTGTCTCTTGGGCACCCCTGGCGGCAGCCGTGGACAT 2840
GCTTCCCTGCTGTGATAGCCCAAACTGTTGCCTATGACAT 2880
TTGAGGTCTACCCTTCTGGCTGCCATGGTCCCCATTGAGA 2920
TCTTTGGTGACTCACCTCAGCCACCAAGCCAGGCCTCTGC 2960
CTTCCTTCAGCTCTAAGGGCATGAAGGGTGTGGACAGAGC 3000
AGCCACAGGCTGCCCACAGTCACCCACATGCAAGTGTTAT 3040
TTCCTTGTTTGTTTTAAAAAAATAAACATGCTGAGCCTTG 3080
AAAAAAAAAAAAAAAAAA 3098
```

FIG. 56C mFATP1 full length protein

```
                10        20        30        40
MRTPGAGTASVASLGLLWLLGLPWTWSAAAAFGVYVGSGG 40
WRFLRIVCKTARRDLFGLSVLIRVRLELRRHRRAGDTIPR 80
IFQAVAQRQPERLALVDASSGICWTFAQLDTYSNAVANLF 120
LQLGFAPGDVVAVFLEGRPEFVGLWLGLAKAGVVAALLNV 160
NLRREPLAFCLGTSAAKALIYGGEMAAAVAEVSEQLGKSL 200
               210       220       230       240
LKFCSGDLGPESVLPDTQLLDPMLAEAPTTPLAQAPGKGM 240
DDRLFYIYTSGTTGLPKAAIVVHSRYYRIAAFGHHSYSMR 280
ANDVLYDCLPLYHSAGNIMGVGQCIIYGLTVVLRKKFSAS 320
RFWDDCVKYNCTVVQYIGEICRYLLRQPVRDVERRHRVRL 360
AVGNGLRPAIWEEFTQGFGVRQIGEFYGATECNCSIANMD 400
               410       420       430       440
GKVGSCGFNSRILTHVYPIRLVKVNEDTMEPLRDSQGLCI 440
PCQPGEPGLLVGQINQQDPLRRFDGYVSDSATNKKIAHSV 480
FRKGDSAYLSGDVLVMDELGYMYFRDRSGDTFRWRGENVS 520
TTEVEAVLSRLLGQTDVAVYGVAVPGVEGKSGMAAIADPH 560
NQLDPNSMYQELQKVLASYAQPIFLRLLPQVDTTGTFKIQ 600
               610       620       630       640
KTRLQREGFDPRQTSDRLFFLDLKQGRYLPLDERVHARIC 640
AGDFSL 646
```

FIG. 57 mVLACS (FATP2) full length DNA

```
        10        20        30        40
GACACAGTACTGCCGATGTTGGACAGAGGATCGCTTAACA 40
GAACGAAATCTCAAAACAAATTAACAGGACCCGGTTGCTT 80
GATTTCCCAAATCAGAAAAGGCTCGAAATGTCTAGAGGGG 120
CTGACTGATGCAGCGGTGACCCGGACTGGAGACAGTTGGA 160
CGCGATCATCTCTGGTGCTTTTGTTCAACCTTGAAACCTT 200
       210       220       230       240
CGCCACAGGAGACTTGCCTGAGCAGAGAAGCAAACGTGGA 240
GAAACAAAGAGAGATCTAGCGAAAAGCCTCTGGGACCAAG 280
GAGGGGAGGTGGGACTCTGGGTTGGCGGTGGCACCTGCTG 320
CCGGCTATTAATAATAGGGTCGCGATGCGTTTATAAGGTG 360
TTTGATTAAACAAAGACTCTATGAGAGAAGAATAACTAGC 400
       410       420       430       440
AACAGCCCCACGTCTGAGTCGTCGCCTCCGACCTTTTTCA 440
ACGTGGGTTCTTTGGGCCGAGCGTCGTTTGCCGAGAACTA 480
GATCTCACCTGACCCCAGACGCTGAAAACAAGCGCTGTGG 520
CATCCTGGGCCACCCAAGCTGACAAGGGCGCGCCCCCTGA 560
GCACACGAGGTGCCCCACGAGGGGGAGGGACCCACAGCCG 600
       610       620       630       640
TCCCGCCCGCACCGCGGTGTCCGCTGCGGGCACCTGCAGC 640
CGAGCCGCCACCCGCAGTCGCAGCGCGTCCGGCGGCCGAA 680
CCCGGTCGTCAGCTCGTCAGCACCTGCTCTGCTTCTCTCC 720
CGCCCGCCGCCGCGCTGCACGCCTCGAGCGCTCCCTCGGC 760
CCCGGCGGGGACCGGGGACCCCGCAGCCACCGCCATGCTG 800
       810       820       830       840
CCTGTGCTCTACACCGGCCTGGCGGGGCTGCTGCTGCTGC 840
CTCTGCTGCTCACCTGCTGCTGCCCCTACCTCCTCCAGGA 880
CGTGCGGTTCTTCCTGCAACTGGCCAACATGGCCCGGCAG 920
GTGCGCAGCTACCGGCAGCGGCGACCCGTGCGCACCATCC 960
TGCATGTCTTCTTGGAGCAAGCGCGCAAGACCCCGCACAA 1000
      1010      1020      1030      1040
GCCCTTCCTGCTGTTTCGCGACGAGACGCTTACCTACGCC 1040
CAGGTAGACCGGCGCAGCAACCAAGTAGCGCGAGCGCTGC 1080
ATGATCACCTGGGCCTGCGGCAGGGGGATTGCGTGGCCCT 1120
CTTCATGGGCAATGAGCCGGCCTACGTGTGGCTCTGGCTG 1160
GGACTGCTCAAACTGGGCTGTCCCATGGCGTGCCTCAACT 1200
```

FIG. 58A 1210 1220 1230 1240

ACAACATCCGTGCCAAGTCTCTGCTACACTGCTTTCAGTG 1240
CTGCGGGGCGAAGGTGCTGCTGGCCTCCCCAGAGCTACAC 1280
GAAGCTGTCGAGGAGGTTCTTCCAACCCTGAAAAAGGAGG 1320
GCGTGTCCGTCTTCTACGTAAGCAGAACTTCTAACACTAA 1360
TGGCGTGGACACAGTACTGGACAAAGTAGACGGGGTGTCG 1400

1410 1420 1430 1440

GCGGACCCCATCCCGGAGTCGTGGAGGTCTGAAGTCACGT 1440
TCACCACACCCGCAGTCTACATATATACTTCGGGCACCAC 1480
AGGTCTTCCAAAGGCTGCAACCATTAATCACCATCGCCTC 1520
TGGTATGGGACCAGCCTTGCCCTGAGGTCCGGAATTAAGG 1560
CTCATGACGTCATCTACACCACCATGCCCCTGTACCACAG 1600

1610 1620 1630 1640

CGCGGCGCTCATGATTGGCCTCCACGGATGCATTGTGGTT 1640
GGGGCTACATTTGCTTTGCGGAGCAAATTTTCAGCCAGCC 1680
AGTTTTGGGACGACTGCAGGAAATACAACGCCACTGTCAT 1720
TCAGTACATCGGTGAACTGCTTCGGTACCTCTGCAACACG 1760
CCCCAGAAACCAAATGACCGGGACCACAAAGTGAAAATAG 1800

1810 1820 1830 1840

CACTAGGAAATGGCTTACGAGGAGATGTGTGGAGAGAGTT 1840
CATCAAGAGATTTGGGGACATTCACATTTATGAGTTCTAC 1880
GCTTCCACTGAAGGCAACATTGGATTTATGAACTATCCAA 1920
GAAAAATCGGAGCTGTTGGAAGAGAAAATTACCTACAAAA 1960
AAAAGTTGTAAGGCACGAGCTGATCAAGTATGACGTGGAG 2000

2010 2020 2030 2040

AAGGATGAGCCTGTCCGTGATGCAAATGGATATTGCATCA 2040
AAGTCCCCAAAGGAGAGGTTGGACTCTTGATTTGCAAAAT 2080
CACAGAGCTCACACCATTTTTTGGCTATGCTGGAGGAAAG 2120
ACCCAGACAGAGAAGAAAAAGCTCAGAGATGTTTTTAAGA 2160
AAGGAGACGTCTACTTCAACAGTGGCGATCTCCTGATGAT 2200

FIG. 58B

```
      2210      2220      2230      2240
CGACCGTGAAAATTTCATCTATTTTCACGACAGAGTTGGA 2240
GACACCTTCCGGTGGAAAGGAGAGAATGTAGCTACCACGG 2280
AAGTCGCTGACATTGTGGGACTGGTAGATTTTGTTGAAGA 2320
AGTGAATGTTTACGGTGTGCCCGTGCCAGGTCATGAAGGT 2360
CGCATCGGGATGGCCTCGATCAAGATGAAAGAAAACTACG 2400
      2410      2420      2430      2440
AGTTCAATGGAAAGAAACTCTTTCAGCACATCTCGGAGTA 2440
CCTGCCCAGTTACTCGAGGCCTCGGTTCCTGAGAATACAA 2480
GATACCATTGAGATCACCGGGACTTTTAAACACCGCAAAG 2520
TGACCCTGATGGAAGAGGGCTTTAACCCCTCAGTCATCAA 2560
AGATACCTTGTATTTCATGGATGACACAGAAAAAACATAC 2600

      2610      2620      2630      2640
GTGCCCATGACTGAGGACATTTATAATGCCATAATTGATA 2640
AGACTCTGAAGCTCTGAATGTTGCCTGGCTCCTAACACTT 2680
CCAGAAAGAAACACAATAGGCCTAGCATAGCCCCTTCACA 2720
TGTGTAATCCAACTTTAACTTGATTAAAGGTTATAGGTGT 2760
GATTTTTCCTAGGAAATTATTCATTTAAAGGACAATTGTT 2800
      2810      2820      2830      2840
TGTTTGTTTGTTTGTTTTTTATTAATTACACCAGAACGTT 2840
TGCAAGTAAAAAGATTTAAAGTCACTTATTTTTCAATGTG 2880
CACCTGCCATTTGTCCTTGCAAACTTAGCTTCTTGGAGAG 2920
AGGGCCTTATTTTTTTAAAGACATAATAAACTATGTAAAC 2960
ACT 2963
```

FIG. 58C mVLACS (FATP2) full length protein

```
          10         20         30         40
MLPVLYTGLAGLLLLPLLLTCCCPYLLQDVRFFLQLANMA 40
RQVRSYRQRRPVRTILHVFLEQARKTPHKPFLLFRDETLT 80
YAQVDRRSNQVARALHDHLGLRQGDCVALFMGNEPAYVWL 120
WLGLLKLGCPMACLNYNIRAKSLLHCFQCCGAKVLLASPE 160
LHEAVEEVLPTLKKEGVSVFYVSRTSNTNGVDTVLDKVDG 200
         210        220        230        240
VSADPIPESWRSEVTFTTPAVYIYTSGTTGLPKAATINHH 240
RLWYGTSLALRSGIKAHDVIYTTMPLYHSAALMIGLHGCI 280
VVGATFALRSKFSASQFWDDCRKYNATVIQYIGELLRYLC 320
NTPQKPNDRDHKVKIALGNGLRGDVWREFIKRFGDIHIYE 360
FYASTEGNIGFMNYPRKIGAVGRENYLQKKVVRHELIKYD 400
         410        420        430        440
VEKDEPVRDANGYCIKVPKGEVGLLICKITELTPFFGYAG 440
GKTQTEKKKLRDVFKKGDVYFNSGDLLMIDRENFIYFHDR 480
VGDTFRWKGENVATTEVADIVGLVDFVEEVNVYGVPVPGH 520
EGRIGMASIKMKENYEFNGKKLFQHISEYLPSYSRPRFLR 560
IQDTIEITGTFKHRKVTLMEEGFNPSVIKDTLYFMDDTEK 600
         610        620        630        640
TYVPMTEDIYNAIIDKTLKL 620
```

FIG. 59 mFATP4 partial DNA

```
GATCAGCTCTTCTATATCTACACGTCGGGCACCACGGGGC 40
TACCCAAAGCTGCCATTGTGGTGCACAGCAGGTATTACCG 80
AATGGCTGCCCTGGTGTACTATGGATTCCGCATGCGGCCT 120
GATGACATTGTCTATGACTGCCTCCCCCTCTACCACTCAG 160
CAGGAAACATTGTGGGGATTGGCCAGTGCGTACTCCACGG 200
CATGACTGTGGTGATCCGGAAGAAGTTTTCAGCCTCCCGG 240
TTCTGGGATGACTGTATCAAGTACAACTGCACAATTGTAC 280
AGTACATTGGTGAGCTTTGCCGCTACCTCCTGAACCAGCC 320
ACCCCGTGAGGCTGAGTCTCGGCACAAGGTGCGCATGGCA 360
CTGGGCAACGGTCTCCGGCAGTCCATCTGGACCGACTTCT 400
CCAGCCGTTTCCACATTCCCAAGGTGGCCGAGTTCTACGG 440
GGCCACCGAGTGCAACTGTAGCTTGGGCAACTTTGACAGC 480
CAGGTGGGGGCCTGTGGCTTCAATAGCCGCATCCTGTCCT 520
TTGTGTACCCCATCCGCTTGGTACGAGTCAATGAGGATAC 560
CATGGAACTGATCCGGGGACCCGATGGCGTCTGCATTCCC 600
TGTCAACCAGGCCAGCCAGGCCAGCTGGTGGGTCGCATCA 640
TCCAGCAGGACCCCCTACGCCGTTTTGATGGCTACCTCAA 680
CCAGGGTGCCAACAACAAGAAGATTGCTAGTGATGTCTTC 720
AAGAAAGGGGACCAAGCCTACCTCACTGGTGACGTGCTGG 760
TGATGGATGAGCTGGGCTACCTGTACTTCCGAGACCGCAC 800
AGGGGACACGTTCCGCTGGAAAGGGGAGAATGTGTCTACC 840
ACTGAAGTGGAGGGCACACTCAGCCGCCTGCTTCAGATGG 880
CAGATGTGGCTGTTTATGGTGTTGAGGTGCCAGGAGCTGA 920
GGGCCGAGCAGGAATGGCTGCTGTGGCAAGCCCCACTAGC 960
AACTGTGACCTGGAGAGCTTTGCACAGACCTTGAAAAAGG 1000
AGCTGCCCCTGTACGCCCGCCCCATCTTCCTCCGCTTCTT 1040
GCCTGAGCTGCACAAAACAGGAACCTTCAAGTTCCAGAAG 1080
ACAGAGTTGCGGAAGGAGGGCTTTGACCCGTCTGTTGTGA 1120
AAGACCCACTCTTCTATTTGGATGCCCGGACAGGCTGCTA 1160
TGTTGCACTGGACCAAGAGGCCTATACCCGCATCCAGGCA 1200
```

FIG. 60A

```
        1210       1220       1230       1240
GGCGAGGAGAAGCTGTGATTTCCCCCACATCCCTCTGAGG 1240
GCCAGAGGATGCTGGATTCAGAGCCCCAGCTTCCACTCCA 1280
GAAGGGGTCTGGGCAAGGCCAGACCAAAGCTAGCAGGGCC 1320
CGCACCTTCACCCTAGGTGCTGATCCCCCT 1350
```

FIG. 60B mFATP4 partial DNA

```
          10         20         30         40
DQLFYIYTSGTTGLPKAAIVVHSRYYRMAALVYYGFRMRP 40
DDIVYDCLPLYHSAGNIVGIGQCVLHGMTVVIRKKFSASR 80
FWDDCIKYNCTIVQYIGELCRYLLNQPPREAESRHKVRMA 120
LGNGLRQSIWTDFSSRFHIPKVAEFYGATECNCSLGNFDS 160
QVGACGFNSRILSFVYPIRLVRVNEDTMELIRGPDGVCIP 200
         210        220        230        240
CQPGQPGQLVGRIIQQDPLRRFDGYLNQGANNKKIASDVF 240
KKGDQAYLTGDVLVMDELGYLYFRDRTGDTFRWKGENVST 280
TEVEGTLSRLLQMADVAVYGVEVPGAEGRAGMAAVASPTS 320
NCDLESFAQTLKKELPLYARPIFLRFLPELHKTGTFKFQK 360
TELRKEGFDPSVVKDPLFYLDARTGCYVALDQEAYTRIQA 400
         410        420        430        440
GEEKL 405
```

FIG. 61 mmFATP1 full length DNA

```
ATGCGGGCTCCTGGAGCAGGAACAGCCTCTGTGGCCTCAC 40
TGGCGCTGCTTTGGTTTCTGGGACTTCCGTGGACCTGGAG 80
CGCGGCGGCGGCGTTCTGTGTGTACGTGGGTGGCGGCGGC 120
TGGCGCTTTCTGCGTATCGTCTGCAAGACGGCGAGGCGAG 160
ACCTCTTTGGCCTCTCTGTTCTGATTCGTGTTCGGCTAGA 200
GCTGCGACGACACCGGCGAGCAGGAGACACGATCCCGTGC 240
ATCTTCCAGGCTGTGGCCCGGCGACAACCAGAGCGCCTGG 280
CACTGGTGGACGCCAGTAGTGGTATATGCTGGACCTTCGC 320
ACAGCTGGACACCTACTCCAATGCTGTAGCCAACCTGTTC 360
CGCCAGCTGGGCTTTGCACCAGGCGATGTGGTGGCTGTGT 400
TCCTGGAGGGCCGGCCGGAGTTCGTGGGACTGTGGCTGGG 440
CCTGGCCAAGGCCGGTGTGGTGGCTGCTCTTCTCAATGTC 480
AACCTGAGGCGGGAGCCCCTGGCCTTCTGCCTGGGCACAT 520
CAGCTGCCAAGGCCCTCATTTATGGCGGGGAGATGGCAGC 560
GGCGGTGGCGGAGGTGAGCGAGCAGCTGGGGAAGAGCCTC 600
CTCAAGTTCTGCTCTGGAGATCTGGGGCCTGAGAGCATCC 640
TGCCTGACACGCAGCTCCTGGACCCCATGCTTGCTGAGGC 680
GCCCACCACACCCCTGGCACAAGCCCCAGGCAAGGGCATG 720
GATGATCGGCTGTTTTACATCTATACTTCTGGGACCACCG 760
GGCTTCCTAAGGCTGCCATTGTGGTGCACAGCAGGTACTA 800
CCGCATTGCTGCCTTTGGCCACCATTCCTACAGCATGCGT 840
GCCGCCGATGTGCTCTATGACTGCCTGCCACTCTACCACT 880
CTGCAGGGAACATCATGGGTGTGGGGCAGTGCGTCATCTA 920
CGGGTTGACGGTGGTACTGCGCAAGAAGTTCTCCGCCAGC 960
CGCTTCTGGGATGACTGTGTCAAGTACAATTGCACGGTAG 1000
TGGATGACATAGGTGAAATCTGCCGCTACCTGCTGAGGCA 1040
GCCGGTTCGCGACGTGGAGCAGCGACACCGCGTGCGCCTG 1080
GCCGTGGGTAATGGGCTGCGGCCAGCCATCTGGGAGGAGT 1120
TCACGCAGCGCTTCGGTGTGCCACAGATCGGCGAGTTCTA 1160
CGGCGCTACCGAGTGCAACTGCAGCATTGCCAACATGGAC 1200
```

FIG. 62A

```
       1210       1220       1230       1240
GGCAAGGTCGGCTCCTGCGGCTTCAACAGCCGTATCCTCA 1240
CGCATGTGTACCCCATCCGTCTGGTCAAGGTCAATGAGGA 1280
CACGATGGAGCCACTGCGGGACTCCGAGGGCCTCTGCATC 1320
CCGTGCCAGCCCGGGGAACCCGGCCTTCTCGTGGGCCAGA 1360
TCAACCAGCAGGACCCTCTGCGGCGTTTCGATGGTTATGT 1400
       1410       1420       1430       1440
TAGTGACAGTGCCACCAACAAGAAGATTGCCCACAGCGTT 1440
TTCCGAAAGGGCGATAGCGCCTACCTCTCAGGTGACGTGC 1480
TAGTGATGGACGAGCTGGGCTACATGTATTTCCGTGACCG 1520
CAGCGGGGACACCTTCCGCTGGCGCGGGGAGAACGTGTCC 1560
ACCACGGAGGTGGAAGCCGTGCTGAGCCGCCTACTGGGCC 1600
       1610       1620       1630       1640
AGACGGACGTGGCTGTGTATGGGGTGGCTGTGCCAGGAGT 1640
GGAGGGGAAAGCTGGCATGGCAGCCATCGCAGATCCCCAC 1680
AGCCAGTTGGACCCTAACTCAATGTACCAGGAATTACAGA 1720
AGGTTCTTGCATCCTATGCTCGGCCCATCTTCCTGCGTCT 1760
TCTGCCCCAGGTGGATACCACAGGCACCTTCAAGATCCAG 1800
       1810       1820       1830       1840
AAGACCCGGCTGCAGCGTGAAGGCTTTGACCCCCGTCAGA 1840
CCTCAGACAGGCTCTTCTTTCTAGACCTGAAGTCCGGCAC 1880
GAGGTATCTACCCCTGGATGAGAGAGTCCATGCCCGCATT 1920
TGCGCAGGCGACTTCTCACTCTGAGCCTGGAGAGTGGGCT 1960
GGGCCTGGACTCCTGAGACCTGGGAGCCTGACACCCCTCT 2000
       2010       2020       2030       2040
TCGGGTGCTTCTCCTGCCTGGCCACATGGACAGCAGCACC 2040
TGTGAGAGTAGGAAAATGGAACCTGAGTGGCTGGGACCCC 2080
TCTCCTACTTCCCACTATGCATCCATTTTGCCTCTGCCTT 2120
GATCTTTTTCTCCATCTCTTTTCTCCCTACCCAGCAGGAG 2160
CCCCACAAACACATGTTGGCTGCTGTGTCCTGCAGTTGGA 2200
```

FIG. 62B 2210 2220 2230 2240

CCAGTGTCCAGGGGTACAGGCTTCAGGCTGTGACCCACAC 2240
TGGTACCCACCTCCCTTTCCTATTTTGCCTTAGGTTCATC 2280
CACGGTTCCCCTGTGGAGCAAGTGGGGGCCCACATAGCTG 2320
CTGTCCCTGCTGAGGGTTGGTAGCAATCACACCCTCATGT 2360
CAGCTGGGAGACACGCGCAGTCTCCCACTGACCCCCAATC 2400

2410 2420 2430 2440

AACTGAAAATATTGTTTTGACTACTTTTTGTTTTTTTGTT 2440
TTTTTGTTTTTTTTTTTTTTCGAGACAGAGTTTCTCTGTA 2480
TAGCCCTGGCTGTCCTGGAACTCACTTTGTAGACCAGGCT 2520
GGCCTCGAACTCAAAAATCCTCCTGACTCTGCCTCTGCTT 2560
CCCAAGTGCTGGGATTAAAGACGTGCGCCACCACCGCCTG 2600

2610 2620 2630 2640

GCTGTTTTGTATTTTTGTTTTGTTTTGACGATAGGGTCTC 2640
ACTGTGGAGGCCAAGCTGGCCTCAGACTCCCCACCCCATT 2680
GCCTCTGGGCACCATTCTATATTCTCAGACTGATGACAAT 2720
GCACTAGTGTCCCTAGGAGTCTTGAGTCTGCACTTTCCCC 2760
TCATAGCCTCAAGCTTCCAGAACTGACTCTGATCACTTGG 2800

2810 2820 2830 2840

ATGTGGCTAGTGTTGGCTCTACCCACATGTGTCAATTCAG 2840
GGGTCCCCAGGCATAGTCTCTGGAAGCCCTCACCCGGAAA 2880
AAGCTTGGAGAGACCCAGGAAGGTTGTTGTGTTCTCTTGG 2920
GCACCCCCTGGTGGCAGTCCTGGGCATGCTTCCGCACTGT 2960
ACTGGTGCATATAGCCCAGACCTATGACATTTGAGGTCTA 3000

3010 3020 3030 3040

CCCTTCTGGCTCCTGTGGTCCCCATTGAGATCCTTGGTGA 3040
CTCACCTCAGTCACCAAGCAGAGCCTCTGCCTGCCTTCAT 3080
CTTCAAGGTCATGAAGGATGTGGACAGAGCAGCTACAGGC 3120
TGCCAGCAGTCAACCACATGAGAGTGTTACTTCCTTGTTG 3160
GTTTTTAAAAAATAAATGTGCTGAGCCTCGAAAAAAAAAA 3200

3210 3220 3230 3240

AAAAAAAAAAAAAAAAA 3217

FIG. 62C mmFATP1 full length protein

```
         10        20        30        40
MRAPGAGTASVASLALLWFLGLPWTWSAAAAFCVYVGGGG 40
WRFLRIVCKTARRDLFGLSVLIRVRLELRRHRRAGDTIPC 80
IFQAVARRQPERLALVDASSGICWTFAQLDTYSNAVANLF 120
RQLGFAPGDVVAVFLEGRPEFVGLWLGLAKAGVVAALLNV 160
NLRREPLAFCLGTSAAKALIYGGEMAAAVAEVSEQLGKSL 200
        210       220       230       240
LKFCSGDLGPESILPDTQLLDPMLAEAPTTPLAQAPGKGM 240
DDRLFYIYTSGTTGLPKAAIVVHSRYYRIAAFGHHSYSMR 280
AADVLYDCLPLYHSAGNIMGVGQCVIYGLTVVLRKKFSAS 320
RFWDDCVKYNCTVVDDIGEICRYLLRQPVRDVEQRHRVRL 360
AVGNGLRPAIWEEFTQRFGVPQIGEFYGATECNCSIANMD 400
        410       420       430       440
GKVGSCGFNSRILTHVYPIRLVKVNEDTMEPLRDSEGLCI 440
PCQPGEPGLLVGQINQQDPLRRFDGYVSDSATNKKIAHSV 480
FRKGDSAYLSGDVLVMDELGYMYFRDRSGDTFRWRGENVS 520
TTEVEAVLSRLLGQTDVAVYGVAVPGVEGKAGMAAIADPH 560
SQLDPNSMYQELQKVLASYARPIFLRLLPQVDTTGTFKIQ 600
        610       620       630       640
KTRLQREGFDPRQTSDRLFFLDLKSGTRYLPLDERVHARI 640
CAGDFSL 647
```

FIG. 63 mmFATP2 full length DNA

```
GGGCGGAGGCCGAGCCCAGTCGCCAGCTCCTGCTCTGCTC 40
CTCTCCCGCCTGCCGCCGCGCTGCACGCCTCGAGCACTCC 80
CTCGGCCCCGGCGGGGACCGGGGACCCCGCAGCTACCGCC 120
ATGCTGCCAGTGCTCTACACCGGCCTGGCGGGGCTGCTGC 160
TGCTGCCTCTGCTGCTCACCTGCTGCTGCCCCTACCTCCT 200
CCAAGATGTGCGGTACTTCCTGCGGCTGGCCAACATGGCC 240
CGGCGGGTGCGCAGCTACCGGCAGCGGCGACCCGTGCGTA 280
CCATCCTGCGGGCCTTCCTGGAACAAGCGCGCAAGACCCC 320
ACACAAGCCCTTCCTGCTGTTCCGAGACGAGACGCTCACC 360
TACGCCCAGGTGGACCGGCGCAGCAACCAAGTGGCGCGGG 400
CGCTGCACGATCAACTGGGCCTACGACAGGGGGATTGCGT 440
AGCCCTCTTCATGGGCAATGAGCCGGCCTACGTGTGGATC 480
TGGCTGGGACTGCTCAAACTGGGCTGTCCCATGGCGTGCC 520
TCAACTACAACATTCGTGCCAAGTCTCTGCTGCACTGCTT 560
TCAATGCTGCGGGGCGAAGGTGCTGCTGGCCTCCCCAGAT 600
CTACAAGAAGCTGTGGAGGAGGTTCTTCCAACCCTGAAAA 640
AGGATGCCGTGTCCGTCTTTTACGTAAGCAGAACTTCTAA 680
CACAAATGGTGTGGACACAATACTGGACAAAGTAGACGGA 720
GTGTCGGCGGAACCCACCCCGGAGTCGTGGAGGTCTGAAG 760
TCACTTTTACCACGCCAGCAGTATACATTTATACTTCGGG 800
AACCACAGGTCTTCCAAAAAGCGGAACCATCAATCATCAT 840
CGCCTAAGGTATGGGACAAGCCTTGCTATGTCGAGTGGGA 880
ATCACGGCCAAGGATGTCATCTATACCAACAATGCCCCTG 920
TTCCAACAGTGCAACGCTCAAGATCGGCCTTCACGGATGC 960
ATCCTGGGTTGGGGCTACTTTAACCTTGGCGGGGCAAATT 1000
CTCAAGCAAGCCAATTTTGGGAACGACTGGCAGGAAATAC 1040
AACGTCAACGGTCATTCAGTACATTGGTGAACTGCTTCGG 1080
TACCTGTGCAACACACCGCAGAAACCAAATGACCGGGACC 1120
ACAAAGTGAAAAAAGCCCTGGGAAATGGCTTACGAGGAGA 1160
TGTGTGGAGAGAGTTCATCAAGAGATTTGGGGACATCCAC 1200
```

FIG. 64A

Figure 64B:
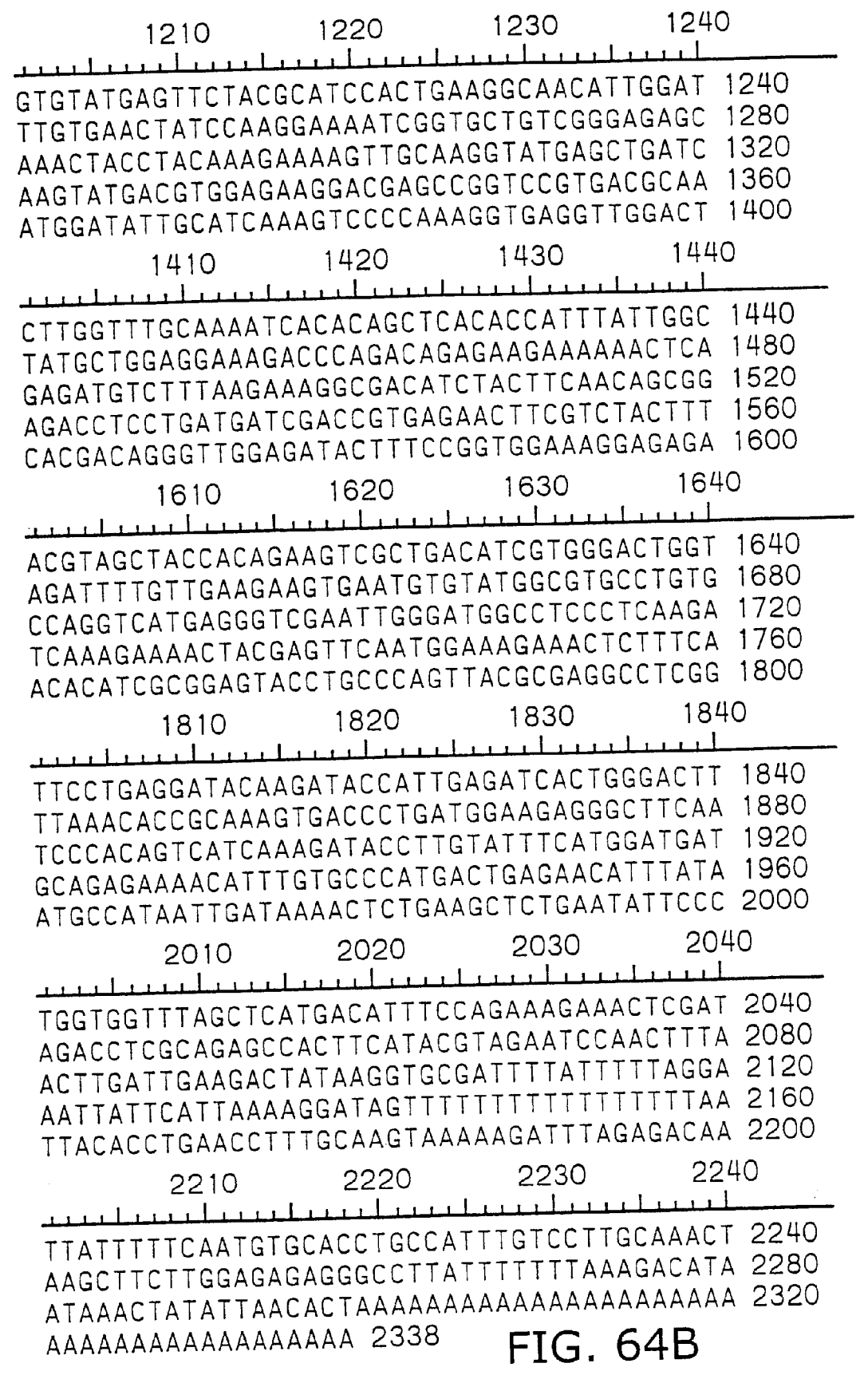

```
GTGTATGAGTTCTACGCATCCACTGAAGGCAACATTGGAT 1240
TTGTGAACTATCCAAGGAAAATCGGTGCTGTCGGGAGAGC 1280
AAACTACCTACAAAGAAAAGTTGCAAGGTATGAGCTGATC 1320
AAGTATGACGTGGAGAAGGACGAGCCGGTCCGTGACGCAA 1360
ATGGATATTGCATCAAAGTCCCCAAAGGTGAGGTTGGACT 1400
CTTGGTTTGCAAAATCACACAGCTCACACCATTTATTGGC 1440
TATGCTGGAGGAAAGACCCAGACAGAGAAGAAAAAACTCA 1480
GAGATGTCTTTAAGAAAGGCGACATCTACTTCAACAGCGG 1520
AGACCTCCTGATGATCGACCGTGAGAACTTCGTCTACTTT 1560
CACGACAGGGTTGGAGATACTTTCCGGTGGAAAGGAGAGA 1600
ACGTAGCTACCACAGAAGTCGCTGACATCGTGGGACTGGT 1640
AGATTTTGTTGAAGAAGTGAATGTGTATGGCGTGCCTGTG 1680
CCAGGTCATGAGGGTCGAATTGGGATGGCCTCCCTCAAGA 1720
TCAAAGAAAACTACGAGTTCAATGGAAAGAAACTCTTTCA 1760
ACACATCGCGGAGTACCTGCCCAGTTACGCGAGGCCTCGG 1800
TTCCTGAGGATACAAGATACCATTGAGATCACTGGGACTT 1840
TTAAACACCGCAAAGTGACCCTGATGGAAGAGGGCTTCAA 1880
TCCCACAGTCATCAAAGATACCTTGTATTTCATGGATGAT 1920
GCAGAGAAAACATTTGTGCCCATGACTGAGAACATTTATA 1960
ATGCCATAATTGATAAAACTCTGAAGCTCTGAATATTCCC 2000
TGGTGGTTTAGCTCATGACATTTCCAGAAAGAAACTCGAT 2040
AGACCTCGCAGAGCCACTTCATACGTAGAATCCAACTTTA 2080
ACTTGATTGAAGACTATAAGGTGCGATTTTATTTTTAGGA 2120
AATTATTCATTAAAAGGATAGTTTTTTTTTTTTTTTTTAA 2160
TTACACCTGAACCTTTGCAAGTAAAAAGATTTAGAGACAA 2200
TTATTTTTCAATGTGCACCTGCCATTTGTCCTTGCAAACT 2240
AAGCTTCTTGGAGAGAGGGCCTTATTTTTTTAAAGACATA 2280
ATAAACTATATTAACACTAAAAAAAAAAAAAAAAAAAAAA 2320
AAAAAAAAAAAAAAAAAA 2338
```

FIG. 64B mmFATP2 full length protein

```
         10        20        30        40
MLPVLYTGLAGLLLLPLLLTCCCPYLLQDVRYFLRLANMA 40
RRVRSYRQRRPVRTILRAFLEQARKTPHKPFLLFRDETLT 80
YAQVDRRSNQVARALHDQLGLRQGDCVALFMGNEPAYVWI 120
WLGLLKLGCPMACLNYNIRAKSLLHCFQCCGAKVLLASPD 160
LQEAVEEVLPTLKKDAVSVFYVSRTSNTNGVDTILDKVDG 200
        210       220       230       240
VSAEPTPESWRSEVTFTTPAVYIYTSGTTGLPKSGTINHH 240
RLRYGTSLAMSSGNHGQGCHLYQQCPCSNSATLKIGLHGC 280
ILGWGYFNLGGANSQASQFWERLAGNTTSTVIQYIGELLR 320
YLCNTPQKPNDRDHKVKKALGNGLRGDVWREFIKRFGDIH 360
VYEFYASTEGNIGFVNYPRKIGAVGRANYLQRKVARYELI 400
        410       420       430       440
KYDVEKDEPVRDANGYCIKVPKGEVGLLVCKITQLTPFIG 440
YAGGKTQTEKKKLRDVFKKGDIYFNSGDLLMIDRENFVYF 480
HDRVGDTFRWKGENVATTEVADIVGLVDFVEEVNVYGVPV 520
PGHEGRIGMASLKIKENYEFNGKKLFQHIAEYLPSYARPR 560
FLRIQDTIEITGTFKHRKVTLMEEGFNPTVIKDTLYFMDD 600
        610       620       630       640
AEKTFVPMTENIYNAIIDKTLKL 623
```

FIG. 65 mmFATP3 partial DNA

```
GAAAGCTCTGAGAGCGGGTGCAGTCTGGCCTGGCGTCTCG 40
CGTACCTGGCCCGGGAGCAGCCGACACACACCTTCCTCAT 80
CCACGGCGCGCAGCGCTTTAGCTACGCGGAGGCTGAGCGC 120
GAGAGCAACCGGATTGCTCGCGCCTTTCTGCGCGCACGGG 160
GCTGGACCGGGGGCCGCCGAGGCTCGGGCAGGGGCAGCAC 200
TGAGGAAGGCGCACGCGTGGCGCCTCCGGCTGGAGATGCG 240
GCTGCTAGAGGGACGACCGCGCCCCCTCTGGCACCCGGGG 280
CGACCGTGGCGCTGCTCCTCCCAGCGGGCCCGGATTTCCT 320
TTGGATTTGGTTCGGACTGGCCAAAGCTGGCCTGCGCACG 360
GCCTTTGTGCCCACCGCTTTACGCCGAGGACCCCTGCTGC 400
ACTGCCTCCGCAGCTGCGGTGCGAGTGCGCTCGTGCTGGC 440
CACAGAGTTCCTGGAGTCCCTGGAGCCGGACCTGCCGGCC 480
TTGAGAGCCATGGGGCTCCACCTATGGGCGACGGGCCCTG 520
AAACTAATGTAGCTGGAATCAGCAATTTGCTATCGGAAGC 560
AGCAGACCAAGTGGATGAGCCAGTGCCGGGGTACCTCTCT 600
GCCCCCCAGAACATAATGGACACCTGCCTGTACATCTTCA 640
CCTCTGGCACTACTGGCCTGCCCAAGGCTGCTCGAATCAG 680
TCATCTGAAGGTTCTACAGTGCCAGGGATTCTACCATCTG 720
TGTGGAGTCCACCAGGAGGACGTGATCTACCTCGCACTCC 760
CACTGTACCACATGTCTGGCTCCCTTCTGGGCATTGTGGG 800
CTGCTTGGGCATTGGGGCCACCGTGGTGCTGAAACCCAAG 840
TTCTCAGCTAGCCAGTTCTGGGACGATTGCCAGAAACACA 880
GGGTGACAGTGTTCCAGTACATTGGGGAGTTGTGCCGATA 920
CCTCGTCAACCAGCCCCCGAGCAAGGCAGAGTTTGACCAT 960
AAGGTGCGCTTGGCAGTGGGCAGTGGGTTGCGCCCAGACA 1000
CCTGGGAGCGTTTCCTGCGGCGATTTGGACCTCTGCAGAT 1040
ACTGGAGACGTATGGCATGACAGAGGGCAACGTAGCTACG 1080
TTCAATTACACAGGACGGCAGGGTGCAGTGGGGCGAGCTT 1120
CCTGGCTTTACAAGCACATCTTCCCCTTCTCCTTGATTCG 1160
ATACGATGTCATGACAGGGGAGCCTATTCGGAATGCCCAG 1200
```

FIG. 66A

```
      1210       1220       1230       1240
GGGCACTGCATGACCACATCTCCAGGTGAGCCAGGCCTAC 1240
TGGTGGCCCCAGTGAGCCAGCAGTCCCCCTTCCTGGGCTA 1280
TGCTGGGGCTCCGGAGCTGGCCAAGGACAAGCTGCTGAAG 1320
GATGTCTTCTGGTCTGGGGACGTTTTCTTCAATACTGGGG 1360
ACCTCTTGGTCTGTGATGAGCAAGGCTTTCTTCACTTCCA 1400
      1410       1420       1430       1440
CGATCGTACTGGAGACACCATCAGGTGGAAGGGAGAGAAT 1440
GTGGCCACAACTGAAGTGGCTGAGGTCTTGGAGACCCTGG 1480
ACTTCCTTCAGGAGGTGAACATCTATGGAGTCACGGTGCC 1520
AGGGCACGAAGGCAGGGCAGGCATGGCGGCCTTGGCTCTG 1560
CGGCCCCCGCAGGCTCTGAACCTGGTGCAGCTCTACAGCC 1600
      1610       1620       1630       1640
ATGTTTCTGAGAACTTGCCACCGTATGCCCGACCTCGGTT 1640
TCTCAGGCTCCAGGAATCTTTGGCCACTACTGAGACCTTC 1680
AAACAGCAGAAGGTTAGGATGGCCAATGAGGGCTTTGACC 1720
CCAGTGTACTGTCTGACCCACTCTATGTTCTGGACCAAGA 1760
TATAGGGGCCTACCTGCCCCTCACACCTGCCCGGTACAGT 1800
      1810       1820       1830       1840
GCCCTCCTGTCTGGAGACCTTCGAATCTGAAACCTTCCAC 1840
TTGAGGGAGGGGCTCGGAGGGTACAGGCCACCATGGCTGC 1880
ACCAGGGAGGGTTTTCGGGTATCTTTTGTATATGGAGTCA 1920
TTATTTTGTAATAAACAGCTGGAGCTTAAAAAAAAAAAAA 1960
AAAAAAAAAAAAAAAAAAAAAAAAAAAAAAAAAAAAAA 1998
```

FIG. 66B mmFATP3 partial protein

```
         10         20         30         40
ESSESGCSLAWRLAYLAREQPTHTFLIHGAQRFSYAEAER 40
ESNRIARAFLRARGWTGGRRGSGRGSTEEGARVAPPAGDA 80
AARGTTAPPLAPGATVALLLPAGPDFLWIWFGLAKAGLRT 120
AFVPTALRRGPLLHCLRSCGASALVLATEFLESLEPDLPA 160
LRAMGLHLWATGPETNVAGISNLLSEAADQVDEPVPGYLS 200
        210        220        230        240
APQNIMDTCLYIFTSGTTGLPKAARISHLKVLQCQGFYHL 240
CGVHQEDVIYLALPLYHMSGSLLGIVGCLGIGATVVLKPK 280
FSASQFWDDCQKHRVTVFQYIGELCRYLVNQPPSKAEFDH 320
KVRLAVGSGLRPDTWERFLRRFGPLQILETYGMTEGNVAT 360
FNYTGRQGAVGRASWLYKHIFPFSLIRYDVMTGEPIRNAQ 400
        410        420        430        440
GHCMTTSPGEPGLLVAPVSQQSPFLGYAGAPELAKDKLLK 440
DVFWSGDVFFNTGDLLVCDEQGFLHFHDRTGDTIRWKGEN 480
VATTEVAEVLETLDFLQEVNIYGVTVPGHEGRAGMAALAL 520
RPPQALNLVQLYSHVSENLPPYARPRFLRLQESLATTETF 560
KQQKVRMANEGFDPSVLSDPLYVLDQDIGAYLPLTPARYS 600
        610        620        630        640
ALLSGDLRI 609
```

FIG. 67 mmFATP4 full length DNA

```
        10         20         30         40
ATGCTGCTTGGAGCCTCTCTGGTGGGGGCGCTACTGTTCT 40
CCAAGCTAGTGCTGAAGCTGCCCTGGACCCAGGTGGGATT 80
CTCCCTGTTGCTCCTGTACTTGGGGTCTGGTGGCTGGCGT 120
TTCATCCGGGTCTTCATCAAGACGGTCAGGAGAGATATCT 160
TTGGTGGCATGGTGCTCCTGAAGGTGAAGACCAAGGTGCG 200
       210        220        230        240
ACGGTACCTTCAGGAGCGGAAGACGGTGCCCCTGCTGTTT 240
GCTTCAATGGTACAGCGCCACCCGGACAAGACAGCCCTGA 280
TTTTCGAGGGCACAGACACTCACTGGACCTTCCGCCAGCT 320
GGATGAGTACTCCAGTAGTGTGGCCAACTTCCTGCAGGCC 360
CGGGGCCTGGCCTCAGGCAATGTAGTTGCCCTCTTTATGG 400
       410        420        430        440
AAAACCGCAATGAGTTTGTGGGTCTGTGGCTAGGCATGGC 440
CAAGCTGGGCGTGGAGGCGGCTCTCATCAACACCAACCTT 480
AGGCGGGATGCCCTGCGCCACTGTCTTGACACCTCAAAGG 520
CACGAGCTCTCATCTTTGGCAGTGAGATGGCCTCAGCTAT 560
CTGTGAGATCCATGCTAGCCTGGAGCCCACACTCAGCCTC 600
       610        620        630        640
TTCTGCTCTGGATCCTGGGAGCCCAGCACAGTGCCCGTCA 640
GCACAGAGCATCTGGACCCTCTTCTGGAAGATGCCCCGAA 680
GCACCTGCCCAGTCACCCAGACAAGGGTTTTACAGATAAG 720
CTCTTCTACATCTACACATCGGGCACCACGGGGCTACCCA 760
AAGCTGCCATTGTGGTGCACAGCAGGTATTATCGTATGGC 800
       810        820        830        840
TTCCCTGGTGTACTATGGATTCCGCATGCGGCCTGATGAC 840
ATTGTCTATGACTGCCTCCCCCTCTACCACTCAAGCAGGA 880
AACATCGTGGGGATTGGCAGTGCTTACTCCACGGCATGAC 920
TGTGGTGATCCGGAAGAAGTTCTCAGCCTCCCGGTTCTGG 960
GATGATTGTATCAAGTACAACTGCACAGTGGTACAGTACA 1000
      1010       1020       1030       1040
TTGGCGAGCTCTGCCGCTACCTCCTGAACCAGCCACCCCG 1040
TGAGGCTGAGTCTCGGCACAAGGTGCGCATGGCACTGGGC 1080
AACGGTCTCCGGCAGTCCATCTGGACCGACTTCTCCAGCC 1120
GTTTCCACATCCCCCAGGTGGCTGAGTTCTATGGGGCCAC 1160
TGAATGCAACTGTAGCCTGGGCAACTTTGACAGCCGGGTG 1200
```

FIG. 68A

```
    1210      1220      1230      1240
GGGGCCTGTGGCTTCAATAGCCGCATCCTGTCCTTTGTGT 1240
ACCCTATCCGTTTGGTACGTGTCAATGAGGATACCATGGA 1280
ACTGATCCGGGGACCCGATGGAGTCTGCATTCCCTGTCAA 1320
CCAGGTCAGCCAGGCCAGCTGGTGGGTCGCATCATCCAGC 1360
AGGACCCTCTGCGCCGTTTCGACGGGTACCTCAACCAGGG 1400
    1410      1420      1430      1440
TGCCAACAACAAGAAGATTGCTAATGATGTCTTCAAGAAG 1440
GGGGACCAAGCCTACCTCACTGGTGACGTCCTGGTGATGG 1480
ATGAGCTGGGTTACCTGTACTTCCGAGATCGCACTGGGGA 1520
CACGTTCCGCTGGAAAGGGGAGAATGTATCTACCACTGAG 1560
GTGGAGGGCACACTCAGCCGCCTGCTTCATATGGCAGATG 1600
    1610      1620      1630      1640
TGGCAGTTTATGGTGTTGAGGTGCCAGGAACTGAAGGCCG 1640
AGCAGGAATGGCTGCCGTTGCAAGTCCCATCAGCAACTGT 1680
GACCTGGAGAGCTTTGCACAGACCTTGAAAAAGGAGCTGC 1720
CTCTGTATGCCCGCCCCATCTTCCTGCGCTTCTTGCCTGA 1760
GCTGCACAAGACAGGGACCTTCAAGTTCCAGAAGACAGAG 1800
    1810      1820      1830      1840
TTGCGGAAGGAGGGCTTTGACCCATCTGTTGTGAAAGACC 1840
CGCTGTTCTATCTGGATGCTCGGAAGGGCTGCTACGTTGC 1880
ACTGGACCAGGAGGCCTATACCCGCATCCAGGCAGGCGAG 1920
GAGAAGCTGTGATTTCCCCCTACATCCCTCTGAGGGCCAG 1960
AAGATGCTGGATTCAGAGCCCTAGCGTCCACCCCAGAGGG 2000
```

FIG. 68B

```
        2010      2020      2030      2040
TCCTGGGCAATGCCAGACCAAAGCTAGCAGGGCCCGCACC 2040
TCCGCCCCTAGGTGCTGATCTCCCCTCTCCCAAACTGCCA 2080
AGTGACTCACTGCCGCTTCCCCGACCCTCCAGAGGCTTTC 2120
TGTGAAAGTCTCATCCAAGCTGTGTCTTCTGGTCCAGGCG 2160
TGGCCCCTGGCCCCAGGGTTTCTGATAGGCTCCTTTAGGA 2200
        2210      2220      2230      2240
TGGTATCTTGGGTCCAGCGGGCCAGGGTGTGGGAGAGGAG 2240
TCACTAAGATCCCTCCAATCAGAAGGGAGCTTACAAAGGA 2280
ACCAAGGCAAAGCCTGTAGACTCAGGAAGCTAAGTGGCCA 2320
GAGACTATAGTGGCCAGTCATCCCATGTCCACAGAGGATC 2360
TTGGTCCAGAGCTGCCAAAGTGTCACCTCTCCCTGCCTGC 2400
        2410      2420      2430      2440
ACCTCTGGGGAAAAGAGGACAGCATGTGGCCACTGGGCAC 2440
CTGTCTCAAGAAGTCAGGATCACACACTCAGTCCTTGTTT 2480
CTCCAGGTTCCCTTGTTCTTGTCTCGGGGAGGGAGGGACG 2520
AGTGTCCTGTCTGTCCTTCCTGCCTGTCTGTGAGTCTGTG 2560
TTGCTTCTCCATCTGTCCTAGCCTGAGTGTGGGTGGAACA 2600
        2610      2620      2630      2640
GGCATGAGGAGAGTGTGGCTCAGGGGCCAATAAACTCTGC 2640
CTTGACTCCTCTTAAAAAAAAAAAAAAAAAAAAAAAAAAA 2680
AAAAAAAAAAAAAAAAAAAAAAAAAAAAAA 2710
```

FIG. 68C mmFATP4 full length protein

```
          10         20         30         40
          |          |          |          |
MLLGASLVGALLFSKLVLKLPWTQVGFSLLLLYLGSGGWR      40
FIRVFIKTVRRDIFGGMVLLKVKTKVRRYLQERKTVPLLF      80
ASMVQRHPDKTALIFEGTDTHWTFRQLDEYSSSVANFLQA     120
RGLASGNVVALFMENRNEFVGLWLGMAKLGVEAALINTNL     160
RRDALRHCLDTSKARALIFGSEMASAICEIHASLEPTLSL     200
         210        220        230        240
          |          |          |          |
FCSGSWEPSTVPVSTEHLDPLLEDAPKHLPSHPDKGFTDK     240
LFYIYTSGTTGLPKAAIVVHSRYYRMASLVYYGFRMRPDD     280
IVYDCLPLYHSSRKHRGDWQCLLHGMTVVIRKKFSASRFW     320
DDCIKYNCTVVQYIGELCRYLLNQPPREAESRHKVRMALG     360
NGLRQSIWTDFSSRFHIPQVAEFYGATECNCSLGNFDSRV     400
         410        420        430        440
          |          |          |          |
GACGFNSRILSFVYPIRLVRVNEDTMELIRGPDGVCIPCQ     440
PGQPGQLVGRIIQQDPLRRFDGYLNQGANNKKIANDVFKK     480
GDQAYLTGDVLVMDELGYLYFRDRTGDTFRWKGENVSTTE     520
VEGTLSRLLHMADVAVYGVEVPGTEGRAGMAAVASPISNC     560
DLESFAQTLKKELPLYARPIFLRFLPELHKTGTFKFQKTE     600
         610        620        630        640
          |          |          |          |
LRKEGFDPSVVKDPLFYLDARKGCYVALDQEAYTRIQAGE     640
EKL     643
```

FIG. 69 mmFATP5 full length DNA

```
         10        20        30        40
CACTCATCAGAGCTAAGAGAGACTACACGCTCTCATCTAC 40
TTCAGAAAGAGCCAATGCCATGGGTATTTGGAAGAAACTA 80
ACCTTACTGCTGTTGCTGCTTCTGCTGGTTGGCCTGGGGC 120
AGCCCCCATGGCCAGCAGCTATGGCTCTGGCCCTGCGTTG 160
GTTCCTGGGAGACCCCACATGCCTTGTGCTGCTTGGCTTG 200
        210       220       230       240
GCATTGCTGGGCAGACCCTGGATCAGCTCCTGGATGCCCC 240
ACTGGCTGAGCCTGGTAGGAGCAGCTCTTACCTTATTCCT 280
ATTGCCTCTACAGCCACCCCCAGGGCTACGCTGGCTGCAT 320
AAAGATGTGGCTTTCACCTTCAAGATGCTTTTCTATGGCC 360
TAAAGTTCAGGCGACGCCTTAACAAACATCCTCCAGAGAC 400
        410       420       430       440
CTTTGTGGATGCTTTAGAGCGGCAAGCACTGGCATGGCCT 440
GACCGGGTGGCCTTGGTGTGTACTGGGTCTGAGGGCTCCT 480
CAATCACAAATAGCCAGCTGGATGCCAGGTCCTGTCAGGC 520
AGCATGGGTCCTGAAAGCAAAGCTGAAGGATGCCGTAATC 560
CAGAACACAAGAGATGCTGCTGCTATCTTAGTTCTCCCGT 600
        610       620       630       640
CCAAGACCATTTCTGCTTTGAGTGTGTTTCTGGGGTTGGC 640
CAAGTTGGGCTGCCCTGTGGCCTGGATCAATCCACACAGC 680
CGAGGGATGCCCTTGCTACACTCTGTACGGAGCTCTGGGG 720
CCAGTGTGCTGATTGTGGATCCAGACCTCCAGGAGAACCT 760
GGAAGAAGTCCTTCCCAAGCTGCTAGCTGAGAACATTCAC 800
        810       820       830       840
TGCTTCTACCTTGGCCACAGCTCACCCACCCCGGGAGTAG 840
AGGCTCTGGGAGCTTCCCTGGATGCTGCACCTTCTGACCC 880
AGTACCTGCCAGCCTTCGAGCTACGATTAAGTGGAAATCT 920
CCTGCCATATTCATCTTTACTTCAGGGACCACTGGACTCC 960
CAAAGCCAGCCATCTTATCACATGAGCGGGTCATACAAGT 1000
       1010      1020      1030      1040
GAGCAACGTGCTGTCCTTCTGTGGATGCAGAGCTGATGAT 1040
GTGGTCTATGACGTCCTACCTCTGTACCATACGATAGGGC 1080
TTGTCCTTGGATTCCTTGGCTGCTTACAAGTTGGAGCCAC 1120
CTGTGTCCTGGCCCCCAAGTTCTCTGCCTCCCGATTCTGG 1160
GCTGAGTGCCGGCAGCATGGCGTAACAGTGATCTTGTATG 1200
```

FIG. 70A 1210 1220 1230 1240

TGGGTGAAATCCTGCGGTACTTGTGTAACGTCCCTGAGCA 1240
ACCAGAAGACAAGATACATACAGTGCGCTTGGCCATGGGA 1280
ACTGGACTTCGGGCAAATGTGTGGAAAAACTTCCAGCAAC 1320
GCTTTGGTCCCATTCGGATCTGGGAATTCTACGGATCCAC 1360
AGAGGGCAATGTGGGCTTAATGAACTATGTGGGCCACTGC 1400

1410 1420 1430 1440

GGGGCTGTGGGAAGGACCAGCTGCATCCTTCGAATGCTGA 1440
CTCCCTTTGAGCTTGTACAGTTCGACATAGAGACAGCAGA 1480
GCCTCTGAGGGACAAACAGGGTTTTTGCATTCCTGTGGAG 1520
CCAGGAAAGCCAGGACTTCTTTTGACCAAGGTTCGAAAGA 1560
ACCAACCCTTCCTGGGCTACCGTGGTTCCCAGGCCGAGTC 1600

1610 1620 1630 1640

CAATCGGAAACTTGTTGCGAATGTACGACGCGTAGGAGAC 1640
CTGTACTTCAACACTGGGGACGTGCTGACCTTGGACCAGG 1680
AAGGCTTCTTCTACTTTCAAGACCGCCTTGGTGACACCTT 1720
CCGGTGGAAGGGCGAAAACGTATCTACTGGAGAGGTGGAG 1760
TGTGTTTTGTCTAGCCTAGACTTCCTAGAGGAAGTCAATG 1800

1810 1820 1830 1840

TCTATGGTGTGCCTGTGCCAGGGTGTGAGGGTAAGGTTGG 1840
CATGGCTGCTGTGAAACTGGCTCCTGGGAAGACTTTTGAT 1880
GGGCAGAAGCTATACCAGCATGTCCGCTCCTGGCTCCCTG 1920
CCTATGCCACACCTCATTTCATCCGTATCCAGGATTCCCT 1960
GGAGATCACAAACACCTACAAGCTGGTAAAGTCACGGCTG 2000

2010 2020 2030 2040

GTGCGTGAGGGTTTTGATGTGGGGATCATTGCTGACCCCC 2040
TCTACATACTGGACAACAAGGCCCAGACCTTCCGGAGTCT 2080
GATGCCAGATGTGTACCAGGCTGTGTGTGAAGGAACCTGG 2120
AATCTCTGACCACCTAGCCAACTGGAAGGCAATCCAAAAG 2160
TGTAGAGATTGACACTAGTCAGCTTCACAAAGTTGTCCGG 2200

2210 2220 2230 2240

GTTCCAGATGCCCATGGCCCAGTAGTACTTAGAGAATAAA 2240
CTTGAATGTGTATACAAAAAAAAAAAAAAAAAAAAAAA 2277

FIG. 70B mmFATP5 full length protein

```
         10        20        30        40
MGIWKKLTLLLLLLLLVGLGQPPWPAAMALALRWFLGDPT  40
CLVLLGLALLGRPWISSWMPHWLSLVGAALTLFLLPLQPP  80
PGLRWLHKDVAFTFKMLFYGLKFRRRLNKHPPETFVDALE 120
RQALAWPDRVALVCTGSEGSSITNSQLDARSCQAAWVLKA 160
KLKDAVIQNTRDAAAILVLPSKTISALSVFLGLAKLGCPV 200
        210       220       230       240
AWINPHSRGMPLLHSVRSSGASVLIVDPDLQENLEEVLPK 240
LLAENIHCFYLGHSSPTPGVEALGASLDAAPSDPVPASLR 280
ATIKWKSPAIFIFTSGTTGLPKPAILSHERVIQVSNVLSF 320
CGCRADDVVYDVLPLYHTIGLVLGFLGCLQVGATCVLAPK 360
FSASRFWAECRQHGVTVILYVGEILRYLCNVPEQPEDKIH 400
        410       420       430       440
TVRLAMGTGLRANVWKNFQQRFGPIRIWEFYGSTEGNVGL 440
MNYVGHCGAVGRTSCILRMLTPFELVQFDIETAEPLRDKQ 480
GFCIPVEPGKPGLLLTKVRKNQPFLGYRGSQAESNRKLVA 520
NVRRVGDLYFNTGDVLTLDQEGFFYFQDRLGDTFRWKGEN 560
VSTGEVECVLSSLDFLEEVNVYGVPVPGCEGKVGMAAVKL 600
        610       620       630       640
APGKTFDGQKLYQHVRSWLPAYATPHFIRIQDSLEITNTY 640
KLVKSRLVREGFDVGIIADPLYILDNKAQTFRSLMPDVYQ 680
AVCEGTWNL 689
```

FIG. 71 dmFATP partial DNA

```
         10        20        30        40
GCTCTCTGGGCCTATATCAAGCTGCTGAGGTACACGAAGC 40
GCCATGAGCGGCTCAACTACACGGTGGCGGACGTCTTCGA 80
ACGAAATGTTCAGGCCCATCCGGACAAGGTGGCTGTGGTC 120
AGTGAGACGCAACGCTGGACCTTCCGTCAGGTGAACGAGC 160
ATGCGAACAAGGTGGCCAATGTGCTGCAGGCTCAGGGCTA 200
        210       220       230       240
CAAAAAGGGCGATGTGGTGGCCCTGTTGCTGGAGAACCGC 240
GCCGAGTACGTGGCCACCTGGCTGGGTCTCTCCAAGATCG 280
GTGTGATCACACCGCTGATCAACACGAATCTGCGCGGTCC 320
CTCCCTGCTGCACAGCATCACGGTGGCCCATTGCTCGGCT 360
CTCATTTACGGCGAGGACTTCCTGGAAGCTGTCACCGACG 400
        410       420       430       440
TGGCCAAGGATCTGCCAGCGAACCTCACACTCTTCCAGTT 440
CAACAACGAGAACAACAACAGCGAGACGGAAAAGAACATA 480
CCGCAGGCCAAGAATCTGAACGCGCTGCTGACCACGGCCA 520
GCTATGAGAAGCCTAACAAGACGCAGGTTAACCACCACGA 560
CAAGCTGGTCTACATCTACACCTCCGGCACCACAGGATTG 600
        610       620       630       640
CCAAAGGCTGCGGTTATCTCTCACTCCCGTTATCTGTTTA 640
TCGCTGCTGGCATCCACTACACCATGGGTTTCCAGGAGGA 680
GGACATCTTCTACACGCCCTTGCCTTTGTACCACACCGCT 720
GGTGGCATTATGTGCATGGGTCAGTCGGTGCTCTTTGGCT 760
CCACGGTCTCCATTCGCAAGAAGTTCTCGGCATCCAACTA 800
        810       820       830       840
TTTCGCCGACTGCGCCAAGTATAATGCAACTATTGGTCAG 840
TATATCGGTGAGATGGCTCGCTACATTCTAGCTACGAAAC 880
CCTCGGAATACGACCAGAAACACCGAGTGCGTCTGGTCTT 920
TGGAAACGGACTGCGACCGCAGATTTGGCCACAGTTTGTG 960
CAGCGCTTCAACATTGCCAAGGTTGGCGAGTTCTACGGCG 1000
       1010      1020      1030      1040
CCACCGAGGGTAATGCGAACATCATGAATCATGACAACAC 1040
GGTGGGCGCCATCGGCTTTGTGTCGCGCATCCTGCCCAAG 1080
ATCTACCCAATCTCGATCATTCGCGCCGATCCGGACACCG 1120
GAGAGCCCATTAGAGATAGGAATGGCCTATGCCAACTGTG 1160
CGCTCCCAACGAGCCAGGCGTATTCATCGGCAAGATCGTC 1200
```

FIG. 72A 1210 1220 1230 1240

AAAGGAAATCCTTCTCGCGAATTCCTCGGATACGTCGATG 1240
AAAAGGCCTCCGCGAAGAAGATTGTTAAGGATGTGTTCAA 1280
GCATGGCGATATGGCTTTCATCTCCGGAGATCTGCTGGTT 1320
GCCGACGAGAAGGGTTATCTGTACTTCAAGGATCGCACCG 1360
GTGACACCTTCCGCTGGAAGGGCGAGAATGTTTCCACCAG 1400

1410 1420 1430 1440

CGAGGTGGAGGCGCAAGTCAGCAATGTGGCCGGTTACAAG 1440
GATACCGTCGTTTACGGCGTAACCATTCCGCACACCGAGG 1480
GAAGGGCCGGCATGGCCGCCATCTATGATCCGGAGCGAGA 1520
ATTGGACCTCGACGTCTTCGCCGCTAGCTTGGCCAAGGTG 1560
CTGCCCGCGTACGCTCGTCCCCAGATCATTCGATTGCTCA 1600

1610 1620 1630 1640

CCAAGGTGGACCTGACTGGAACCTTTAAGCTGCGCAAGGT 1640
AGACCTGCAGAAGGAGGGCTACGATCCGAACGCGATCAAG 1680
GACGCGCTGTACTACCAGACTTCCAAGGGTCGGTACGAGC 1720
TGCTCACGCCCCAGGTTTACGACCAGGTGCAGCGCAACGA 1760
AATCCGCTTCTAAGAGCTGCAATAGAGTTGTGTCTGAACC 1800

1810 1820 1830 1840

TTGCCTTTTGCCCAATATGCTGTTAATTAGTTTGTAAGGC 1840
TAAGTGTAGTAGAGGAAAATCGGGGGAAATCGGCAGCAAA 1880
GATCATTCAGCCTAGGAGAGATGCATCCGAAGCACATTTC 1920
CATGTCAACAATGCACTTTTGTATATCGTAAGCATATATA 1960
TATCGTATATCGTAAACGTAGTTGTATCTGCATTTGTGTA 2000

2010 2020 2030 2040

GATGATAGCCTCCTATACGCATTTCAATTGTTTTTAGCGT 2040
GCTAAAGAACCTTGTTAAATGCAATTTCAGCTATTGTTTA 2080
GTCAGTTTTAGTGGCATTTACACTTCCATTCTCGTTGCGT 2120
TTCGTTTTTGCCTGTACATATGAGAAGCTCTGATGTTTTT 2160
GTATCAAATAAAGTTTTTTCCTTCACCACGGACCACGTGA 2200

2210 2220 2230 2240

AAAAAAAAAAAAAAAAAAAAA 2221

FIG. 72B dm FATP partial protein

```
           10        20        30        40
ALWAYIKLLRYTKRHERLNYTVADVFERNVQAHPDKVAVV 40
SETQRWTFRQVNEHANKVANVLQAQGYKKGDVVALLLENR 80
AEYVATWLGLSKIGVITPLINTNLRGPSLLHSITVAHCSA 120
LIYGEDFLEAVTDVAKDLPANLTLFQFNNENNNSETEKNI 160
PQAKNLNALLTTASYEKPNKTQVNHHDKLVYIYTSGTTGL 200
          210       220       230       240
PKAAVISHSRYLFIAAGIHYTMGFQEEDIFYTPLPLYHTA 240
GGIMCMGQSVLFGSTVSIRKKFSASNYFADCAKYNATIGQ 280
YIGEMARYILATKPSEYDQKHRVRLVFGNGLRPQIWPQFV 320
QRFNIAKVGEFYGATEGNANIMNHDNTVGAIGFVSRILPK 360
IYPISIIRADPDTGEPIRDRNGLCQLCAPNEPGVFIGKIV 400
          410       420       430       440
KGNPSREFLGYVDEKASAKKIVKDVFKHGDMAFISGDLLV 440
ADEKGYLYFKDRTGDTFRWKGENVSTSEVEAQVSNVAGYK 480
DTVVYGVTIPHTEGRAGMAAIYDPERELDLDVFAASLAKV 520
LPAYARPQIIRLLTKVDLTGTFKLRKVDLQKEGYDPNAIK 560
DALYYQTSKGRYELLTPQVYDQVQRNEIRF 590
```

FIG. 73 drFATP partial DNA

```
         10        20        30        40
AGTGTAGATACCACAGGAACGTTTAAAATCCAGAAGACCA 40
GACTGCAAAGGGAAGGATACGATCCACGGCTCACAACTGA 80
CCAGATCTACTTCCTAAACTCCAGAGCAGGGCGTTACGAG 120
CTTGTCAACGAGGAGCTGTACAATGCATTTGAACAAGGGC 160
AGGATTTCCCTTT 173
```

FIG. 74 drFATP partial protein

```
         10        20        30        40
SVDTTGTFKIQKTRLQREGYDPRLTTDQIYFLNSRAGRYE 40
LVNEELYNAFEQGQDFP 57
```

FIG. 75 ceFATPa coding only DNA

```
         10        20        30        40
ATGAAGCTGGAGGAGCTTGTGACAGTTATGCTTCTCACAG 40
TGGCTGTCATTGCTCAGAATCTTCCGATTGGAGTAATATT 80
GGCTGGAGTTCTTATTTTATACATCACAGTGGTTCATGGA 120
GATTTCATTTATAGAAGTTATCTTACGTTGAATAGGGATT 160
TAACAGGATTGGCTCTAATTATTGAAGTCAAAATCGACCT 200
        210       220       230       240
ATGGTGGAGGTTGCATCAGAATAAAGGAATCCATGAACTG 240
TTTTTGGATATTGTGAAAAAGAATCCAAATAAGCCGGCGA 280
TGATTGACATCGAGACGAATACAACAGAAACATACGCAGA 320
GTTCAATGCACATTGTAATAGATATGCCAATTATTTCCAG 360
GGTCTTGGCTATCGATCCGGAGACGTTGTCGCCTTGTACA 400
        410       420       430       440
TGGAGAACTCGGTCGAGTTTGTGGCCGCGTGGATGGGACT 440
CGCAAAAAATCGGAGTTGTAACGGCTTGGATCAACTCGAAT 480
TTGAAAAGAGAGCAACTTGTTCATTGTATCACTGCGAGCA 520
AGACAAAGGCGATTATCACAAGTGTAACACTTCAGAATAT 560
TATGCTTGATGCTATCGATCAGAAGCTGTTTGATGTTGAG 600
        610       620       630       640
GGAATTGAGGTTTACTCTGTCGGAGAGCCCAAGAAGAATT 640
CTGGATTCAAGAATCTCAAGAAGAAGTTGGATGCTCAAAT 680
TACTACGGAACCAAAGACCCTTGACATAGTAGATTTTAAA 720
AGTATTCTTTGCTTCATCTATACAAGTGGTACTACTGGAA 760
TGCCAAAAGCCGCTGTCATGAAGCACTTCAGATATTACTC 800
        810       820       830       840
GATTGCCGTTGGAGCCGCAAAATCATTCGGAATCCGCCCT 840
TCTGATCGTATGTACGTCTCGATGCCAATTTATCACACTG 880
CAGCTGGAATTCTTGGAGTTGGGCAAGCTCTGTTGGGTGG 920
ATCATCGTGTGTCATTAGAAAAAAATTCTCGGCTAGCAAC 960
TTTTGGAGGGATTGTGTAAAGTATGATTGTACAGTTTCAC 1000
       1010      1020      1030      1040
AATACATTGGAGAGATTTGTCGGTACTTGTTGGCTCAGCC 1040
AGTTGTGGAAGAGGAATCCAGGCATAGAATGAGATTGTTG 1080
GTTGGAAACGGACTCCGTGCTGAAATCTGGCAACCATTTG 1120
TAGATCGATTCCGTGTCAGAATTGGAGAACTTTATGGTTC 1160
AACTGAAGGAACTTCATCTCTCGTGAACATTGACGGACAT 1200
```

FIG. 76A 1210 1220 1230 1240

GTCGGAGCTTGCGGATTCTTGCCAATATCCCCATTAACAA 1240
AGAAAATGCATCCGGTTCGATTAATTAAGGTTGATGATGT 1280
CACTGGAGAAGCAATCCGAACTTCCGATGGACTTTGCATT 1320
GCATGTAATCCAGGAGAGTCTGGAGCAATGGTGTCGACGA 1360
TCAGAAAAAATAATCCATTATTGCAATTCGAGGGATATCT 1400

1410 1420 1430 1440

GAATAAGAAGGAAACGAATAAAAAGATTATCAGAGATGTC 1440
TTCGCAAAGGGAGATAGTTGCTTTTTGACTGGAGATCTTC 1480
TTCATTGGGATCGTCTTGGTTATGTATATTTCAAGGATCG 1520
TACTGGAGATACTTTCCGTTGGAAGGGAGAGAATGTGTCG 1560
ACTACTGAAGTCGAGGCAATTCTTCATCCAATTACTGGAT 1600

1610 1620 1630 1640

TGTCTGATGCAACTGTTTATGGTGTAGAGGTTCCTCAAAG 1640
AGAGGGAAGAGTTGGAATGGCGTCAGTTGTTCGAGTTGTA 1680
TCGCATGAGGAAGATGAAACTCAATTTGTTCATAGAGTTG 1720
GAGCAAGACTTGCCTCTTCGCTTACCAGCTACGCGATTCC 1760
TCAGTTTATGCGAATTTGTCAGGATGTTGAGAAAACAGGT 1800

1810 1820 1830 1840

ACATTCAAACTTGTGAAGACGAATCTACAACGATTAGGTA 1840
TCATGGATGCTCCTTCAGATTCAATTTACATCTACAATTC 1880
TGAAAATCGCAATTTTGTGCCGTTCGACAATGATTTGAGG 1920
TGCAAGGTCTCACTGGGAAGTTATCCATTTTAA 1953

FIG. 76B ceFATPa coding only protein

```
        10        20        30        40
MKLEELVTVMLLTVAVIAQNLPIGVILAGVLILYITVVHG 40
DFIYRSYLTLNRDLTGLALIIEVKIDLWWRLHQNKGIHEL 80
FLDIVKKNPNKPAMIDIETNTTETYAEFNAHCNRYANYFQ 120
GLGYRSGDVVALYMENSVEFVAAWMGLAKIGVVTAWINSN 160
LKREQLVHCITASKTKAIITSVTLQNIMLDAIDQKLFDVE 200
        210       220       230       240
GIEVYSVGEPKKNSGFKNLKKKLDAQITTEPKTLDIVDFK 240
SILCFIYTSGTTGMPKAAVMKHFRYYSIAVGAAKSFGIRP 280
SDRMYVSMPIYHTAAGILGVGQALLGGSSCVIRKKFSASN 320
FWRDCVKYDCTVSQYIGEICRYLLAQPVVEEESRHRMRLL 360
VGNGLRAEIWQPFVDRFRVRIGELYGSTEGTSSLVNIDGH 400
        410       420       430       440
VGACGFLPISPLTKKMHPVRLIKVDDVTGEAIRTSDGLCI 440
ACNPGESGAMVSTIRKNNPLLQFEGYLNKKETNKKIIRDV 480
FAKGDSCFLTGDLLHWDRLGYVYFKDRTGDTFRWKGENVS 520
TTEVEAILHPITGLSDATVYGVEVPQREGRVGMASVVRVV 560
SHEEDETQFVHRVGARLASSLTSYAIPQFMRICQDVEKTG 600
        610       620       630       640
TFKLVKTNLQRLGIMDAPSDSIYIYNSENRNFVPFDNDLR 640
CKVSLGSYPF 650
```

FIG. 77 ceFATPb coding only DNA

```
        10        20        30        40
ATGAGGGAAATGCCGGACAGTCCCAAGTTTGCGTTAGTCA 40
CGTTTGTTGTGTATGCAGTGGTTTTGTACAATGTCAACAG 80
CGTTTTCTGGAAATTTGTATTCATCGGATATGTTGTATTT 120
AGGCTGCTTCGCACTGATTTTGGAAGAAGAGCACTTGCCA 160
CGTTACCTAGAGATTTTGCGGGACTGAAGCTCTTAATATC 200
       210       220       230       240
GGTTAAGTCGACAATTCGTGGCTTGTTCAAGAAAGATCGC 240
CCAATTCATGAAATCTTTTTGAATCAGGTGAAACAGCATC 280
CAAACAAAGTGGCGATTATTGAAATTGAAAGTGGTAGGCA 320
GTTGACGTATCAAGAATTGAATGCGTTAGCTAATCAGTAT 360
GCTAACCTTTACGTGAGTGAAGGTTACAAAATGGGCGACG 400
       410       420       430       440
TTGTCGCTTTGTTTATGGAAAATAGCATCGACTTCTTTGC 440
AATTTGGCTGGGACTTTCCAAGATTGGAGTCGTGTCGGCG 480
TTCATCAACTCAAACTTGAAGTTGGAGCCATTGGCACATT 520
CGATTAATGTTTCGAAGTGCAAATCATGCATTACCAATAT 560
CAATCTGTTGCCGATGTTCAAAGCCGCTCGTGAAAAGAAT 600
       610       620       630       640
CTGATCAGTGACGAGATCCACGTGTTTCTGGCTGGAACTC 640
AGGTTGATGGACGTCATAGAAGTCTTCAGCAAGATCTCCA 680
TCTTTTCTCTGAGGATGAACCTCCAGTTATAGACGGACTC 720
AATTTTAGAAGCGTTCTGTGTTATATTTACACTTCCGGTA 760
CTACCGGAAATCCAAAGCCAGCCGTCATTAAACACTTCCG 800
       810       820       830       840
TTACTTCTGGATTGCGATGGGAGCAGGAAAAGCATTTGGA 840
ATTAATAAGTCAGACGTTGTGTACATTACGATGCCAATGT 880
ATCACTCTGCCGCCGGTATCATGGGTATTGGATCATTAAT 920
TGCATTCGGGTCGACCGCTGTTATTAGGAAAAAGTTTTCG 960
GCAAGCAACTTCTGGAAAGATTGCGTCAAGTACAACGTCA 1000
      1010      1020      1030      1040
CAGCGACACAGTACATTGGAGAAATCTGCAGGTATCTTCT 1040
GGCAGCGAATCCATGTCCTGAAGAGAAACAACACAACGTG 1080
CGATTGATGTGGGGAAATGGTTTGAGAGGACAAATTTGGA 1120
AAGAGTTTGTAGGAAGATTTGGAATTAAGAAAATTGGAGA 1160
GTTGTACGGCTCAACAGAAGGAAACTCCAATATTGTTAAC 1200
```

FIG. 78A 1210 1220 1230 1240

GTGGATAACCATGTTGGAGCTTGTGGATTCATGCCAATTT 1240
ATCCCCATATTGGATCCCTCTACCCAGTTCGACTTATTAA 1280
GGTTGATAGAGCCACTGGAGAGCTTGAACGTGATAAGAAC 1320
GGACTCTGTGTGCCGTGTGTGCCTGGTGAAACTGGGGAAA 1360
TGGTTGGCGTTATCAAGGAGAAAGATATTCTTCTAAAGTT 1400

1410 1420 1430 1440

CGAAGGATATGTCAGCGAAGGGGATACTGCAAAGAAAATC 1440
TACAGAGATGTGTTCAAGCATGGAGATAAGGTGTTTGCAA 1480
GTGGAGATATTCTTCATTGGGATGATCTTGGATACTTGTA 1520
CTTTGTGGACCGTTGTGGAGACACTTTCCGTTGGAAAGGG 1560
GAGAACGTGTCAACTACTGAAGTTGAGGGAATTCTTCAGC 1600

1610 1620 1630 1640

CTGTGATGGATGTGGAAGATGCAACTGTTTATGGAGTCAC 1640
TGTCGGTAAAATGGAGGGGCGTGCCGGAATGGCTGGTATT 1680
GTCGTCAAGGATGGAACGGATGTTGAGAAATTCATCGCCG 1720
ATATTACTTCTCGACTGACCGAAAATCTGGCGTCTTACGC 1760
AATCCCTGTTTTCATTCGGCTGTGCAAGGAAGTTGATCGA 1800

1810 1820 1830 1840

ACCGGAACCTTCAAACTCAAGAAGACTGATCTTCAAAAAC 1840
AAGGTTACGACCTGGTTGCTTGTAAAGGAGACCCAATTTA 1880
CTACTGGTCAGCTGCAGAAAAATCCTACAAACCACTGACT 1920
GACAAAATGCAACAGGATATTGACACTGGTGTTTATGATC 1960
GCATTTAA 1968

FIG. 78B ceFATPb coding only protein

```
          10         20         30         40
MREMPDSPKFALVTFVVYAVVLYNVNSVFWKFVFIGYVVF 40
RLLRTDFGRRALATLPRDFAGLKLLISVKSTIRGLFKKDR 80
PIHEIFLNQVKQHPNKVAIIEIESGRQLTYQELNALANQY 120
ANLYVSEGYKMGDVVALFMENSIDFFAIWLGLSKIGVVSA 160
FINSNLKLEPLAHSINVSKCKSCITNINLLPMFKAAREKN 200
         210        220        230        240
LISDEIHVFLAGTQVDGRHRSLQQDLHLFSEDEPPVIDGL 240
NFRSVLCYIYTSGTTGNPKPAVIKHFRYFWIAMGAGKAFG 280
INKSDVVYITMPMYHSAAGIMGIGSLIAFGSTAVIRKKFS 320
ASNFWKDCVKYNVTATQYIGEICRYLLAANPCPEEKQHNV 360
RLMWGNGLRGQIWKEFVGRFGIKKIGELYGSTEGNSNIVN 400
         410        420        430        440
VDNHVGACGFMPIYPHIGSLYPVRLIKVDRATGELERDKN 440
GLCVPCVPGETGEMVGVIKEKDILLKFEGYVSEGDTAKKI 480
YRDVFKHGDKVFASGDILHWDDLGYLYFVDRCGDTFRWKG 520
ENVSTTEVEGILQPVMDVEDATVYGVTVGKMEGRAGMAGI 560
VVKDGTDVEKFIADITSRLTENLASYAIPVFIRLCKEVDR 600
         610        620        630        640
TGTFKLKKTDLQKQGYDLVACKGDPIYYWSAAEKSYKPLT 640
DKMQQDIDTGVYDRI  655
```

FIG. 79 chFATP coding only DNA

```
         10        20        30        40
ATGGCGTGTATGCATCAGGCTCAGCTATACAATGATCTAG 40
AGGAATTGCTAACTGGTCCATCAGTACCCATCGTTGCTGG 80
AGCTGCTGGAGCTGCAGCTCTCACTGCCTACATTAACGCC 120
AAATACCACATAGCCCATGATCTCAAGACCCTCGGTGGTG 160
GATTGACACAATCGTCCGAAGCGATTGATTTCATAAACCG 200
        210       220       230       240
CCGCGTCGCACAAAAGCGCGTCCTCACGCACCACATCTTC 240
CAGGAGCAGGTCCAAAAACAATCAAATCATCCCTTTCTTA 280
TCTTTGAGGGCAAGACATGGTCTTACAAGGAGTTCTCTGA 320
GGCATACACGAGGGTCGCGAACTGGCTGATTGATGAGCTG 360
GACGTACAAGTAGGGGAGATGGTCGCAATTGATGGCGGAA 400
        410       420       430       440
ATAGTGCAGAGCACCTGATGCTTTGGCTTGCACTTGATGC 440
AATCGGTGCGGCTACGAGTTTTTTGAACTGGAACCTGACA 480
GGGGCAGGGTTAATTCATTGCATAAAGCTATGCGAATGTC 520
GATTCGTTATCGCAGACATCGATATTAAAGCGAACATTGA 560
ACCGTGCCGTGGCGAACTGGAGGAGACGGGCATCAACATT 600
        610       620       630       640
CACTACTATGACCCATCCTTCATCTCATCGCTACCGAATA 640
ACACGCCAATTCCCGACAGCCGCACTGAGAACATTGAATT 680
AGATTCAGTACGAGGACTGATATACACATCTGGAACCACT 720
GGTCTACCTAAAGGCGTGTTTATAAGCACTGGCCGCGAGC 760
TTAGGACTGACTGGTCGATTTCAAAGTATCTAAATCTCAA 800
        810       820       830       840
GCCCACGGATCGAATGTATACATGTATGCCGCTCTACCAT 840
GCCGCTGCACACAGCCTCTGTACAGCATCAGTTATTCATG 880
GTGGAGGTACCGTGGTATTGAGCAGGAAATTCTCACACAA 920
GAAGTTCTGGCCTGAAGTTGTGGCTTCGGAAGCAAATATC 960
ATTCAGTACGTTGGTGAATTAGGTCGATATCTCCTGAATG 1000
       1010      1020      1030      1040
GTCCAAAGAGTCCTTACGACAGGGCCCATAAAGTCCAGAT 1040
GGCGTGGGGCAATGGCATGCGTCCAGACGTGTGGGAAGCG 1080
TTTCGTGAACGCTTCAACATACCAATTATTCATGAGCTCT 1120
ATGCCGCAACCGATGGGCTCGGGTCAATGACCAATCGTAA 1160
CGCGGGCCCTTTTACAGCAAACTGTATTGCGCTGCGAGGG 1200
```

FIG. 80A

```
     1210      1220      1230      1240
CTGATCTGGCACTGGAAATTTCGAAATCAGGAAGTGCTGG 1240
TCAAGATGGATCTCGATACTGATGAGATCATGAGAGATCG 1280
CAATGGGTTTGCGATACGATGCGCTGTCAATGAACCTGGA 1320
CAGATGCTTTTTCGGCTGACACCCGAAACTCTGGCTGGTG 1360
CACCAAGCTACTACAACAACGAAACGGCCACACAGAGCAG 1400
     1410      1420      1430      1440
GCGGATTACAGATGTGTTTCAAAAGGGTGACCTGTGGTTC 1440
AAGTCCGGTGACATGCTACGGCAAGACGCCGAAGGCCGCG 1480
TCTACTTTGTCGATCGACTAGGCGATACGTTCCGCTGGAA 1520
ATCCGAAAACGTTTCTACCAATGAAGTCGCGGACGTGATG 1560
GGCACATTTCCTCAGATTGCTGAAACGAATGTATACGGTG 1600
     1610      1620      1630      1640
TCCTTGTGCCGGGTAACGATGGTCGAGTGCGCAGCCTCAA 1640
TTGTCATGGCAGACGGCGTGACAGAGTCGACATTCGCTTC 1680
GCTGCCCTTGCAAAGCACGCCCGAGATCGGTTACCGGGTT 1720
ATGCTGTACCACTGTTTCTGAGGGTAACTCCAGCACTTGA 1760
ATATACGGGCACATTAAAGATTCAGAAAGGACGCCTCAAG 1800
     1810      1820      1830      1840
CAGGAAGGTATAGACCCAGATAAGATTTCCGGCGAAGATA 1840
AGTTATACTGGCTGCCGCCTGGTAGCGATATATATTTACC 1880
ATTTGGAAAGATGGAGTGGCAGGGAATTGTAGATAAGCGT 1920
ATACGGCTGTGA 1932
```

FIG. 80B chFATP coding only protein

```
         10        20        30        40
MACMHQAQLYNDLEELLTGPSVPIVAGAAGAAALTAYINA 40
KYHIAHDLKTLGGGLTQSSEAIDFINRRVAQKRVLTHHIF 80
QEQVQKQSNHPFLIFEGKTWSYKEFSEAYTRVANWLIDEL 120
DVQVGEMVAIDGGNSAEHLMLWLALDAIGAATSFLNWNLT 160
GAGLIHCIKLCECRFVIADIDIKANIEPCRGELEETGINI 200
        210       220       230       240
HYYDPSFISSLPNNTPIPDSRTENIELDSVRGLIYTSGTT 240
GLPKGVFISTGRELRTDWSISKYLNLKPTDRMYTCMPLYH 280
AAAHSLCTASVIHGGGTVVLSRKFSHKKFWPEVVASEANI 320
IQYVGELGRYLLNGPKSPYDRAHKVQMAWGNGMRPDVWEA 360
FRERFNIPIIHELYAATDGLGSMTNRNAGPFTANCIALRG 400
        410       420       430       440
LIWHWKFRNQEVLVKMDLDTDEIMRDRNGFAIRCAVNEPG 440
QMLFRLTPETLAGAPSYYNNETATQSRRITDVFQKGDLWF 480
KSGDMLRQDAEGRVYFVDRLGDTFRWKSENVSTNEVADVM 520
GTFPQIAETNVYGVLVPGNDGRVRSLNCHGRRRDRVDIRF 560
AALAKHARDRLPGYAVPLFLRVTPALEYTGTLKIQKGRLK 600
        610       620       630       640
QEGIDPDKISGEDKLYWLPPGSDIYLPFGKMEWQGIVDKR 640
IRL 643
```

FIG. 81 aspergillus partial DNA

```
        10        20        30        40
GCAAAGGCCGACGCGTGGCTGCGGACGGGTAACGTGATCA 40
GGGCGGACAACGAAGGGCGACTCTTCTTCCACGACCGGAT 80
CGGAGACACGTTCCGATGGAAGGGAGAGACNGTCAGCACA 120
CAAGAGGTCAGTTTGGTGCTCGGACGACACGACTCAATCA 160
AGGAGGCCAACGTGTACGGCGTGACGGTGCCGAACCACGA 200
       210       220       230       240
CGGGCGGGCCGGCTGCGCTGCGCTCACGCTATCAGACGCT 240
CTGGCGACTGAAAAGAAGCTGGGCGATGAGCTGCTAAAGG 280
GATTGGCTACTCACTCGTCGACTTCGCTTCCCAAGTTTGC 320
GGTGCCGCAGTTCCTACGGGTGGTGCGCGGCGAGATGCAG 360
TCAACGGGCACCAACAAGCAACAGAAGCACGACCTGAGGG 400
       410       420       430       440
TGCAGGGTGTAGAGCCGGGCAAGGTGGGCGTAGACGAGGT 440
GTACTGGTTGCGGGGAGGGACATATGTACCATTCGGAACA 480
GAGGATTGGGATGGGTTGAAGAAGGGTCTTGTGAAGTTGT 520
GA 522
```

FIG. 82 aspergillus partial protein

```
        10        20        30        40
AKADAWLRTGNVIRADNEGRLFFHDRIGDTFRWKGETVST 40
QEVSLVLGRHDSIKEANVYGVTVPNHDGRAGCAALTLSDA 80
LATEKKLGDELLKGLATHSSTSLPKFAVPQFLRVVRGEMQ 120
STGTNKQQKHDLRVQGVEPGKVGVDEVYWLRGGTYVPFGT 160
EDWDGLKKGLVKL 173
```

FIG. 83 mgFATP partial DNA

```
         10        20        30        40
GCAAAGGCCGACGCGTGGCTGCGGACGGGTAACGTGATCA 40
GGGCGGACAACGAAGGGCGACTCTTCTTCCACGACCGGAT 80
CGGAGACACGTTCCGATGGAAGGGAGAGACNGTCAGCACA 120
CAAGAGGTCAGTTTGGTGCTCGGACGACACGACTCAATCA 160
AGGAGGCCAACGTGTACGGCGTGACGGTGCCGAACCACGA 200
        210       220       230       240
CGGGCGGGCCGGCTGCGCTGCGCTCACGCTATCAGACGCT 240
CTGGCGACTGAAAAGAAGCTGGGCGATGAGCTGCTAAAGG 280
GATTGGCTACTCACTCGTCGACTTCGCTTCCCAAGTTTGC 320
GGTGCCGCAGTTCCTACGGGTGGTGCGCGGCGAGATGCAG 360
TCAACGGGCACCAACAAGCAACAGAAGCACGACCTGAGGG 400
        410       420       430       440
TGCAGGGTGTAGAGCCGGGCAAGGTGGGCGTAGACGAGGT 440
GTACTGGTTGCGGGGAGGGACATATGTACCATTCGGAACA 480
GAGGATTGGGATGGGTTGAAGAAGGGTCTTGTGAAGTTGT 520
GA 522
```

FIG. 84 mgFATP partial protein

```
         10        20        30        40
AKADAWLRTGNVIRADNEGRLFFHDRIGDTFRWKGETVST 40
QEVSLVLGRHDSIKEANVYGVTVPNHDGRAGCAALTLSDA 80
LATEKKLGDELLKGLATHSSTSLPKFAVPQFLRVVRGEMQ 120
STGTNKQQKHDLRVQGVEPGKVGVDEVYWLRGGTYVPFGT 160
EDWDGLKKGLVKL 173
```

FIG. 85 scFATP coding only DNA

```
ATGTCTCCCATACAGGTTGTTGTCTTTGCCTTGTCAAGGA 40
TTTTCCTGCTATTATTCAGACTTATCAAGCTAATTATAAC 80
CCCTATCCAGAAATCACTGGGTTATCTATTTGGTAATTAT 120
TTTGATGAATTAGACCGTAAATATAGATACAAGGAGGATT 160
GGTATATTATTCCTTACTTTTTGAAAAGCGTGTTTTGTTA 200

TATCATTGATGTGAGAAGACATAGGTTTCAAAACTGGTAC 240
TTATTTATTAAACAGGTCCAACAAAATGGTGACCATTTAG 280
CGATTAGTTACACCCGTCCCATGGCCGAAAAGGGAGAATT 320
TCAACTCGAAACCTTTACGTATATTGAAACTTATAACATA 360
GTGTTGAGATTGTCTCATATTTTGCATTTTGATTATAACG 400

TTCAGGCCGGTGACTACGTGGCAATCGATTGTACTAATAA 440
ACCTCTTTTCGTATTTTTATGGCTTTCTTTGTGGAACATT 480
GGGGCTATTCCAGCTTTTTTAAACTATAATACTAAAGGCA 520
CTCCGCTGGTTCACTCCCTAAAGATTTCCAATATTACGCA 560
GGTATTTATTGACCCTGATGCCAGTAATCCGATCAGAGAA 600

TCGGAAGAAGAAATCAAAAACGCACTTCCTGATGTTAAAT 640
TAAACTATCTTGAAGAACAAGACTTAATGCATGAACTTTT 680
AAATTCGCAATCACCGGAATTCTTACAACAAGACAACGTT 720
AGGACACCACTAGGCTTGACCGATTTTAAACCCTCTATGT 760
TAATTTATACATCTGGAACCACTGGTTTGCCTAAATCCGC 800

TATTATGTCTTGGAGAAAATCCTCCGTAGGTTGTCAAGTT 840
TTTGGTCATGTTTTACATATGACTAATGAAAGCACTGTGT 880
TCACAGCCATGCCATTGTTCCATTCAACTGCTGCCTTATT 920
AGGTGCGTGCGCCATTCTATCTCACGGTGGTTGCCTTGCG 960
TTATCGCATAAATTTTCTGCCAGTACATTTTGGAAGCAAG 1000

TTTATTTAACAGGAGCCACGCACATCCAATATGTCGGAGA 1040
AGTCTGTAGATACCTGTTACATACGCCAATTTCTAAGTAT 1080
GAAAAGATGCATAAGGTGAAGGTTGCTTATGGTAACGGGC 1120
TGAGACCTGACATCTGGCAGGACTTCAGGAAGAGGTTCAA 1160
CATAGAAGTTATTGGTGAATTCTATGCCGCAACTGAAGCT 1200
```

FIG. 86A

```
       1210        1220        1230        1240
CCTTTTGCTACAACTACCTTCCAGAAAGGTGACTTTGGAA 1240
TTGGCGCATGTAGGAACTATGGTACTATAATTCAATGGTT 1280
TTTGTCATTCCAACAAACATTGGTAAGGATGGACCCAAAT 1320
GACGATTCCGTTATATATAGAAATTCCAAGGGTTTCTGCG 1360
AAGTGGCCCCTGTTGGCGAACCAGGAGAAATGTTAATGAG 1400
       1410        1420        1430        1440
AATCTTTTTCCCTAAAAAACCAGAAACATCTTTTCAAGGT 1440
TATCTTGGTAATGCCAAGGAAACAAAGTCCAAAGTTGTGA 1480
GGGATGTCTTCAGACGTGGCGATGCTTGGTATAGATGTGG 1520
AGATTTATTAAAAGCGGACGAATATGGATTATGGTATTTC 1560
CTTGATAGAATGGGTGATACTTTCAGATGGAAATCTGAAA 1600
       1610        1620        1630        1640
ATGTTTCCACTACTGAAGTAGAAGATCAGTTGACGGCCAG 1640
TAACAAAGAACAATATGCACAAGTTCTAGTTGTTGGTATT 1680
AAAGTACCTAAATATGAAGGTAGAGCTGGTTTTGCAGTTA 1720
TTAAACTAACTGACAACTCTCTTGACATCACTGCAAAGAC 1760
CAAATTATTAAATGATTCCTTGAGCCGGTTAAATCTACCG 1800
       1810        1820        1830        1840
TCTTATGCTATGCCCCTATTTGTTAAATTTGTTGATGAAA 1840
TTAAAATGACAGATAACCTCATAAAATTTTGA 1872
```

FIG. 86B scFATP coding only protein

```
         10         20         30         40
MSPIQVVVFALSRIFLLLFRLIKLIITPIQKSLGYLFGNY 40
FDELDRKYRYKEDWYIIPYFLKSVFCYIIDVRRHRFQNWY 80
LFIKQVQQNGDHLAISYTRPMAEKGEFQLETFTYIETYNI 120
VLRLSHILHFDYNVQAGDYVAIDCTNKPLFVFLWLSLWNI 160
GAIPAFLNYNTKGTPLVHSLKISNITQVFIDPDASNPIRE 200
        210        220        230        240
SEEEIKNALPDVKLNYLEEQDLMHELLNSQSPEFLQQDNV 240
RTPLGLTDFKPSMLIYTSGTTGLPKSAIMSWRKSSVGCQV 280
FGHVLHMTNESTVFTAMPLFHSTAALLGACAILSHGGCLA 320
LSHKFSASTFWKQVYLTGATHIQYVGEVCRYLLHTPISKY 360
EKMHKVKVAYGNGLRPDIWQDFRKRFNIEVIGEFYAATEA 400
        410        420        430        440
PFATTTFQKGDFGIGACRNYGTIIQWFLSFQQTLVRMDPN 440
DDSVIYRNSKGFCEVAPVGEPGEMLMRIFFPKKPETSFQG 480
YLGNAKETKSKVVRDVFRRGDAWYRCGDLLKADEYGLWYF 520
LDRMGDTFRWKSENVSTTEVEDQLTASNKEQYAQVLVVGI 560
KVPKYEGRAGFAVIKLTDNSLDITAKTKLLNDSLSRLNLP 600
        610        620        630        640
SYAMPLFVKFVDEIKMTDNLIKF  623
```

FIG. 87 mtFATP coding only DNA

```
         10        20        30        40
GTGTCCGATTACTACGGCGGCGCACACACAACGGTCAGGC 40
TGATCGACCTGGCAACTCGGATGCCGCGAGTGTTGGCGGA 80
CACGCCGGTGATTGTGCGTGGGGCAATGACCGGGCTGCTG 120
GCCCGGCCGAATTCCAAGGCGTCGATCGGCACGGTGTTCC 160
AGGACCGGGCCGCTCGCTACGGTGACCGAGTCTTCCTGAA 200
        210       220       230       240
ATTCGGCGATCAGCAGCTGACCTACCGCGACGCTAACGCC 240
ACCGCCAACCGGTACGCCGCGGTGTTGGCCGCCCGCGGCG 280
TCGGCCCCGGCGACGTCGTTGGCATCATGTTGCGTAACTC 320
ACCCAGCACAGTCTTGGCGATGCTGGCCACGGTCAAGTGC 360
GGCGCTATCGCCGGCATGCTCAACTACCACCAGCGCGGCG 400
        410       420       430       440
AGGTGTTGGCGCACAGCCTGGGTCTGCTGGACGCGAAGGT 440
ACTGATCGCAGAGTCCGACTTGGTCAGCGCCGTCGCCGAA 480
TGCGGCGCCTCGCGCGGCCGGGTAGCGGGCGACGTGCTGA 520
CCGTCGAGGACGTGGAGCGATTCGCCACAACGGCGCCCGC 560
CACCAACCCGGCGTCGGCGTCGGCGGTGCAAGCCAAAGAC 600
        610       620       630       640
ACCGCGTTCTACATCTTCACCTCGGGCACCACCGGATTTC 640
CCAAGGCCAGTGTCATGACGCATCATCGGTGGCTGCGGGC 680
GCTGGCCGTCTTCGGAGGGATGGGGCTGCGGCTGAAGGGT 720
TCCGACACGCTCTACAGCTGCCTGCCGCTGTACCACAACA 760
ACGCGTTAACGGTCGCGGTGTCGTCGGTGATCAATTCTGG 800
        810       820       830       840
GGCGACCCTGGCGCTGGGTAAGTCGTTTTCGGCGTCGCGG 840
TTCTGGGATGAGGTGATTGCCAACCGGGCGACGGCGTTCG 880
TCTACATCGGCGAAATCTGCCGTTATCTGCTCAACCAGCC 920
GGCCAAGCCGACCGACCGTGCCCACCAGGTGCGGGTGATC 960
TGCGGTAACGGGCTGCGGCCGGAGATCTGGGATGAGTTCA 1000
       1010      1020      1030      1040
CCACCCGCTTCGGGGTCGCGCGGGTGTGCGAGTTCTACGC 1040
CGCCAGCGAAGGCAACTCGGCCTTTATCAACATCTTCAAC 1080
GTGCCCAGGACCGCCGGGGTATCGCCGATGCCGCTTGCCT 1120
TTGTGGAATACGACCTGGACACCGGCGATCCGCTGCGGGA 1160
TGCGAGCGGGCGAGTGCGTCGGGTACCCGACGGTGAACCC 1200
```

FIG. 88A

```
           1210      1220      1230      1240
   ┴┴┴┴┴┴┴┴┴┴┴┴┴┴┴┴┴┴┴┴┴┴┴┴┴┴┴┴┴┴┴┴┴┴┴┴┴┴┴┴
   GGCCTGTTGCTTAGCCGGGTCAACCGGCTGCAGCCGTTCG 1240
   ACGGCTACACCGACCCGGTTGCCAGCGAAAAGAAGTTGGT 1280
   GCGCAACGCTTTTCGAGATGGCGACTGTTGGTTCAACACC 1320
   GGTGACGTGATGAGCCCGCAGGGCATGGGCCATGCCGCCT 1360
   TCGTCGATCGGCTGGGCGACACCTTCCGCTGGAAGGGCGA 1400
           1410      1420      1430      1440
   ┴┴┴┴┴┴┴┴┴┴┴┴┴┴┴┴┴┴┴┴┴┴┴┴┴┴┴┴┴┴┴┴┴┴┴┴┴┴┴┴
   GAATGTCGCCACCACTCAGGTCGAAGCGGCACTGGCCTCC 1440
   GACCAGACCGTCGAGGAGTGCACGGTCTACGGCGTCCAGA 1480
   TTCCGCGCACCGGCGGGCGCGCCGGAATGGCCGCGATCAC 1520
   ACTGCGCGCTGGCGCCGAATTCGACGGCCAGGCGCTGGCC 1560
   CGAACGGTTTACGGTCACTTGCCCGGCTATGCACTTCCGC 1600
           1610      1620      1630      1640
   ┴┴┴┴┴┴┴┴┴┴┴┴┴┴┴┴┴┴┴┴┴┴┴┴┴┴┴┴┴┴┴┴┴┴┴┴┴┴┴┴
   TCTTTGTTCGGGTAGTGGGGTCGCTGGCGCACACCACGAC 1640
   GTTCAAGAGTCGCAAGGTGGAGTTGCGCAACCAGGCCTAT 1680
   GGCGCCGACATCGAGGATCCGCTGTACGTACTGGCCGGCC 1720
   CGGACGAAGGATATGTGCCGTACTACGCCGAATACCCTGA 1760
   GGAGGTTTCGCTCGGAAGGCGACCGCAGGGCTAG 1794
```

FIG. 88B mtFATP coding only protein

```
           10        20        30        40
   ┴┴┴┴┴┴┴┴┴┴┴┴┴┴┴┴┴┴┴┴┴┴┴┴┴┴┴┴┴┴┴┴┴┴┴┴┴┴┴┴
   MSDYYGGAHTTVRLIDLATRMPRVLADTPVIVRGAMTGLL 40
   ARPNSKASIGTVFQDRAARYGDRVFLKFGDQQLTYRDANA 80
   TANRYAAVLAARGVGPGDVVGIMLRNSPSTVLAMLATVKC 120
   GAIAGMLNYHQRGEVLAHSLGLLDAKVLIAESDLVSAVAE 160
   CGASRGRVAGDVLTVEDVERFATTAPATNPASASAVQAKD 200
           210       220       230       240
   ┴┴┴┴┴┴┴┴┴┴┴┴┴┴┴┴┴┴┴┴┴┴┴┴┴┴┴┴┴┴┴┴┴┴┴┴┴┴┴┴
   TAFYIFTSGTTGFPKASVMTHHRWLRALAVFGGMGLRLKG 240
   SDTLYSCLPLYHNNALTVAVSSVINSGATLALGKSFSASR 280
   FWDEVIANRATAFVYIGEICRYLLNQPAKPTDRAHQVRVI 320
   CGNGLRPEIWDEFTTRFGVARVCEFYAASEGNSAFINIFN 360
   VPRTAGVSPMPLAFVEYDLDTGDPLRDASGRVRRVPDGEP 400
           410       420       430       440
   ┴┴┴┴┴┴┴┴┴┴┴┴┴┴┴┴┴┴┴┴┴┴┴┴┴┴┴┴┴┴┴┴┴┴┴┴┴┴┴┴
   GLLLSRVNRLQPFDGYTDPVASEKKLVRNAFRDGDCWFNT 440
   GDVMSPQGMGHAAFVDRLGDTFRWKGENVATTQVEAALAS 480
   DQTVEECTVYGVQIPRTGGRAGMAAITLRAGAEFDGQALA 520
   RTVYGHLPGYALPLFVRVVGSLAHTTTFKSRKVELRNQAY 560
   GADIEDPLYVLAGPDEGYVPYYAEYPEEVSLGRRPQG 597
```

FIG. 89 hsFATP3

| | | | | | | | | | | |
|---|---|---|---|---|---|---|---|---|---|---|
| 1 | cga | ccc | acg | cgt | ccg | ggg | atg | ttt | gcg | agc |
| 1 | | | | | | | M | F | A | S |
| 31 | ggc | tgg | aac | cag | acg | gtg | ccg | ata | gag | gaa |
| 5 | G | W | N | Q | T | V | P | I | E | E |
| 61 | gcg | ggc | tcc | atg | gct | gcc | ctc | ctg | ctg | ctg |
| 15 | A | G | S | M | A | A | L | L | L | L |
| 91 | ccc | ctg | ctg | ctg | ttg | cta | ccg | ctg | ctg | ctg |
| 25 | P | L | L | L | L | L | P | L | L | L |
| 121 | ctg | ctg | aag | cta | cac | ctc | tgg | ccg | cag | ttg |
| 35 | L | L | K | L | H | L | W | P | Q | L |
| 151 | cgc | tgg | ctt | ccg | gcg | gac | ttg | gcc | ttt | gcg |
| 45 | R | W | L | P | A | D | L | A | F | A |
| 181 | gtg | cga | gct | ctg | tgc | tgc | aaa | agg | gct | ctt |
| 55 | V | R | A | L | C | C | K | R | A | L |
| 211 | cga | gct | cgc | gcc | ctg | gcc | gcg | gct | gcc | gcc |
| 65 | R | A | R | A | L | A | A | A | A | A |
| 241 | gac | ccg | gaa | ggt | ccc | gag | ggg | ggc | tgc | agc |
| 75 | D | P | E | G | P | E | G | G | C | S |

FIG. 94A 271 ctg gcc tgg cgc ctc gcg gaa ctg gcc cag
85 L A W R L A E L A Q 301 cag cgc gcc gcg cac acc ttt ctc att cac
95 Q R A A H T F L I H 331 ggc tcg cgg cgc ttt agc tac tca gag gcg
105 G S R R F S Y S E A 361 gag cgc gag agt aac agg gct gca cgc gcc
115 E R E S N R A A R A 391 ttc cta cgt gcg cta ggc tgg gac tgg gga
125 F L R A L G W D W G

FIG. 94B 421 ccc gac ggc ggc gac agc ggc gag ggg agc
135 P D G G D S G E G S 451 gct gga gaa ggc gag cgg gca gcg ccg gga
145 A G E G E R A A P G 481 gcc gga gat gca gcg gcc gga agc ggc gcg
155 A G D A A A G S G A 521 gag ttt gcc gga ggg gac ggt gcc gcc aga
165 E F A G G D G A A R 541 ggt gga gga gag ccc gcc gcc cct ctg tca
175 G G G E P A A P L S 571 cct gga gca act gtg gcg ctg ctc ctc ccc
185 P G A T V A L L L P 601 gct ggc cca gag ttt ctg tgg ctc tgg ttc
195 A G P E F L W L W F

FIG. 94C

```
631   ggg ctg gcc aag gcc ggc ctg cgc act gcc
205    G   L   A   K   A   G   L   R   T   A

661   ttt gtg ccc acc gcc ctg cgc cgg ggc ccc
215    F   V   P   T   A   L   R   R   G   P

691   ctg ctg cac tgc ctc cgc agc tgc ggc gcg
225    L   L   H   C   L   R   S   C   G   A

721   cgc gcg ctg gtg ctg gcg cca gag ttt ctg
235    R   A   L   V   L   A   P   E   F   L

751   gag tcc ctg gag ccg gac ctg ccc gcc ctg
245    E   S   L   E   P   D   L   P   A   L

781   aga gcc atg ggg ctc cac ctg tgg gct gca
255    R   A   M   G   L   H   L   W   A   A

811   ggc cca gga acc cac cct gct gga att agc
265    G   P   G   T   H   P   A   G   I   S

841   gat ttg ctg gct gaa gtg tcc gct gaa gtg
275    D   L   L   A   E   V   S   A   E   V
```

FIG. 94D

| | | | | | | | | | | |
|---|---|---|---|---|---|---|---|---|---|---|
| 871 | gat | ggg | cca | gtg | cca | gga | tac | ctc | tct | tcc |
| 285 | D | G | P | V | P | G | Y | L | S | S |
| 901 | ccc | cag | agc | ata | aca | gac | acg | tgc | ctg | tac |
| 295 | P | Q | S | I | T | D | T | C | L | Y |
| 931 | atc | ttc | acc | tct | ggc | acc | acg | ggc | ctc | ccc |
| 305 | I | F | T | S | G | T | T | G | L | P |
| 961 | aag | gct | gct | cgg | atc | agt | cat | ctg | aag | atc |
| 315 | K | A | A | R | I | S | H | L | K | I |
| 991 | ctg | caa | tgc | cag | ggc | ttc | tat | cag | ctg | tgt |
| 325 | L | Q | C | Q | G | F | Y | Q | L | C |
| 1021 | ggt | gtc | cac | cag | gaa | gat | gtg | atc | tac | ctc |
| 335 | G | V | H | Q | E | D | V | I | Y | L |

FIG. 94E

| | | | | | | | | | | |
|---|---|---|---|---|---|---|---|---|---|---|
| 1051 | gcc | ctc | cca | ctc | tac | cac | atg | tcc | ggt | tcc |
| 345 | A | L | P | L | Y | H | M | S | G | S |
| 1081 | ctg | ctg | ggc | atc | gtg | ggc | tgc | atg | ggc | att |
| 355 | L | L | G | I | V | G | C | M | G | I |
| 1111 | ggg | gcc | aca | gtg | gtg | ctg | aaa | tcc | aag | ttc |
| 365 | G | A | T | V | V | L | K | S | K | F |
| 1141 | tcg | gct | ggt | cag | ttc | tgg | gaa | gat | tgc | cag |
| 375 | S | A | G | Q | F | W | E | D | C | Q |
| 1171 | cag | cac | agg | gtg | acg | gtg | ttc | cag | tac | att |
| 385 | Q | H | R | V | T | V | F | Q | Y | I |
| 1201 | ggg | gag | ctg | tgc | cga | tac | ctt | gtc | aac | cag |
| 395 | G | E | L | C | R | Y | L | V | N | Q |
| 1231 | ccc | ccg | agc | aag | gca | gaa | cgt | ggc | cat | aag |
| 405 | P | P | S | K | A | E | R | G | H | K |
| 1261 | gtc | cgg | ctg | gca | gtg | ggc | agc | ggg | ctg | cgc |
| 415 | V | R | L | A | V | G | S | G | L | R |

FIG. 94F

| | | | | | | | | | | |
|---|---|---|---|---|---|---|---|---|---|---|
| 1291 | cca | gat | acc | tgg | gag | cgt | ttt | gtg | cgg | cgc |
| 425 | P | D | T | W | E | R | F | V | R | R |
| 1321 | ttc | ggg | ccc | ctg | cag | gtg | ctg | gag | aca | tat |
| 435 | F | G | P | L | Q | V | L | E | T | Y |
| 1351 | gga | ctg | aca | gag | ggc | aac | gtg | gcc | acc | atc |
| 445 | G | L | T | E | G | N | V | A | T | I |
| 1381 | aac | tac | aca | gga | cag | cgg | ggc | gct | gtg | ggg |
| 455 | N | Y | T | G | Q | R | G | A | V | G |
| 1411 | cgt | gct | tcc | tgg | ctt | tac | aag | cat | atc | ttc |
| 465 | R | A | S | W | L | Y | K | H | I | F |
| 1441 | ccc | ttc | tcc | ttg | att | cgc | tat | gat | gtc | acc |
| 475 | P | F | S | L | I | R | Y | D | V | T |
| 1471 | aca | gga | gag | cca | att | cgg | gac | ccc | cag | ggg |
| 485 | T | G | E | P | I | R | D | P | Q | G |
| 1501 | cac | tgt | atg | gcc | aca | tct | cca | ggt | gag | cca |
| 495 | H | C | M | A | T | S | P | G | E | P |
| 1531 | ggg | ctg | ctg | gtg | gcc | ccg | gta | agc | cag | cag |
| 505 | G | L | L | V | A | P | V | S | Q | Q |

FIG. 94G

| | | | | | | | | | | |
|---|---|---|---|---|---|---|---|---|---|---|
| 1561 | tcc | cca | ttc | ctg | ggc | tat | gct | ggc | ggg | cca |
| 515 | S | P | F | L | G | Y | A | G | G | P |
| 1591 | gag | ctg | gcc | cag | ggg | aag | ttg | cta | aag | gat |
| 525 | E | L | A | Q | G | K | L | L | K | D |
| 1621 | gtc | ttc | cgg | cct | ggg | gat | gtt | ttc | ttc | aac |
| 535 | V | F | R | P | G | D | V | F | F | N |
| 1651 | act | ggg | gac | ctg | ctg | gtc | tgc | gat | gac | caa |
| 545 | T | G | D | L | L | V | C | D | D | Q |
| 1681 | ggt | ttt | ctc | cgc | ttc | cat | gat | cgt | act | gga |
| 555 | G | F | L | R | F | H | D | R | T | G |
| 1711 | gac | acc | ttc | agg | tgg | aag | ggg | gag | aat | gtg |
| 565 | D | T | F | R | W | K | G | E | N | V |
| 1741 | gcc | aca | acc | gag | gtg | gca | gag | gtc | ttc | gag |
| 575 | A | T | T | E | V | A | E | V | F | E |

FIG. 94H

| | | | | | | | | | | |
|---|---|---|---|---|---|---|---|---|---|---|
| 1741 | gcc | aca | acc | gag | gtg | gca | gag | gtc | ttc | gag |
| 575 | A | T | T | E | V | A | E | V | F | E |
| 1771 | gcc | cta | gat | ttt | ctt | cag | gag | gtg | aac | gtc |
| 585 | A | L | D | F | L | Q | E | V | N | V |
| 1801 | tat | gga | gtc | act | gtg | cca | ggg | cat | gaa | ggc |
| 595 | Y | G | V | T | V | P | G | H | E | G |
| 1831 | agg | gct | gga | atg | gca | gcc | cta | gtt | ctg | cgt |
| 605 | R | A | G | M | A | A | L | V | L | R |
| 1861 | ccc | ccc | cac | gct | ttg | gac | ctt | atg | cag | ctc |
| 615 | P | P | H | A | L | D | L | M | Q | L |
| 1891 | tac | acc | cac | gtg | tct | gag | aac | ttg | cca | cct |
| 625 | Y | T | H | V | S | E | N | L | P | P |
| 1921 | tat | gcc | cgg | ccc | cga | ttc | ctc | agg | ctc | cag |
| 635 | Y | A | R | P | R | F | L | R | L | Q |

FIG. 94I

| | | | | | | | | | | |
|---|---|---|---|---|---|---|---|---|---|---|
| 1951 | gag | tct | ttg | gcc | acc | aca | gag | acc | ttc | aaa |
| 645 | E | S | L | A | T | T | E | T | F | K |
| 1981 | cag | cag | aaa | gtt | cgg | atg | gca | aat | gag | ggc |
| 655 | Q | Q | K | V | R | M | A | N | E | G |
| 2011 | ttc | gac | ccc | agc | acc | ctg | tct | gac | cca | ctg |
| 665 | F | D | P | S | T | L | S | D | P | L |
| 2041 | tac | gtt | ctg | gac | cag | gct | gta | ggt | gcc | tac |
| 675 | Y | V | L | D | Q | A | V | G | A | Y |
| 2071 | ctg | ccc | ctc | aca | act | gcc | cgg | tac | agc | gcc |
| 685 | L | P | L | T | T | A | R | Y | S | A |
| 2101 | ctc | ctg | gca | gga | aac | ctt | cga | atc | tga | gaa |
| 695 | L | L | A | G | N | L | R | I | * | |
| 2131 | ctt | cca | cac | ctg | agg | cac | ctg | aga | gag | gaa |
| 2161 | ctc | tgt | | | | | | | | |

FIG. 94J

SEQUENCE LISTING

```
<160> NUMBER OF SEQ ID NOS: 105

<210> SEQ ID NO 1
<211> LENGTH: 340
<212> TYPE: PRT
<213> ORGANISM: Mus musculus

<400> SEQUENCE: 1

Phe Ile Phe Thr Ser Gly Thr Thr Gly Leu Pro Lys Pro Ala Ile Leu
 1               5                  10                  15

Ser His Glu Arg Val Ile Gln Val Ser Asn Val Leu Ser Phe Cys Gly
            20                  25                  30

Cys Arg Ala Asp Asp Val Val Tyr Asp Val Leu Pro Leu Tyr His Thr
        35                  40                  45

Ile Gly Leu Val Leu Gly Phe Leu Gly Cys Leu Gln Val Gly Ala Thr
    50                  55                  60

Cys Val Leu Ala Pro Lys Phe Ser Ala Ser Arg Phe Trp Ala Glu Cys
65                  70                  75                  80

Arg Gln His Gly Val Thr Val Ile Gln Tyr Ile Gly Glu Ile Cys Arg
                85                  90                  95

Tyr Leu Leu Arg Gln Pro Val Arg Asp Val Glu Gln Arg His Arg Val
            100                 105                 110

Arg Leu Ala Val Gly Asn Gly Leu Arg Pro Ala Ile Trp Glu Glu Phe
        115                 120                 125

Thr Gln Arg Phe Gly Val Pro Gln Ile Gly Glu Phe Tyr Gly Ala Thr
    130                 135                 140

Glu Cys Asn Cys Ser Ile Ala Asn Met Asp Gly Lys Val Gly Ser Cys
145                 150                 155                 160

Gly Phe Asn Ser Arg Ile Leu Thr His Val Tyr Pro Ile Arg Leu Val
                165                 170                 175

Lys Val Asn Glu Asp Thr Met Glu Pro Leu Arg Asp Ser Glu Gly Leu
            180                 185                 190

Cys Ile Pro Cys Gln Pro Gly Glu Pro Gly Leu Leu Val Gly Gln Ile
        195                 200                 205

Asn Gln Gln Asp Pro Leu Arg Arg Phe Asp Gly Tyr Val Ser Asp Ser
    210                 215                 220
```

-continued

```
Ala Thr Asn Lys Lys Ile Ala His Ser Val Phe Arg Lys Gly Asp Ser
225                 230                 235                 240

Ala Tyr Leu Ser Gly Asp Val Leu Val Met Asp Glu Leu Gly Tyr Met
                245                 250                 255

Tyr Phe Arg Asp Arg Ser Gly Asp Thr Phe Arg Trp Arg Gly Glu Asn
            260                 265                 270

Val Ser Thr Thr Glu Val Glu Ala Val Leu Ser Arg Leu Leu Gly Gln
        275                 280                 285

Thr Asp Val Ala Val Tyr Gly Val Ala Val Pro Gly Val Glu Gly Lys
    290                 295                 300

Ala Gly Met Ala Ala Ile Ala Asp Pro His Ser Gln Leu Asp Pro Asn
305                 310                 315                 320

Ser Met Tyr Gln Glu Leu Gln Lys Val Leu Ala Ser Tyr Ala Arg Pro
                325                 330                 335

Ile Phe Leu Arg
            340


<210> SEQ ID NO 2
<211> LENGTH: 339
<212> TYPE: PRT
<213> ORGANISM: Mus musculus

<400> SEQUENCE: 2

Tyr Ile Tyr Thr Ser Gly Thr Thr Gly Asn Pro Lys Pro Ala Val Ile
 1               5                  10                  15

Lys His Phe Arg Tyr Phe Trp Ile Ala Met Gly Ala Gly Lys Ala Phe
            20                  25                  30

Gly Ile Asn Lys Ser Asp Val Val Tyr Ile Thr Met Pro Met Tyr His
        35                  40                  45

Ser Ala Ala Gly Ile Met Gly Ile Gly Ser Leu Ile Ala Phe Gly Ser
    50                  55                  60

Thr Ala Val Ile Arg Lys Lys Phe Ser Ala Ser Asn Phe Trp Lys Asp
65                  70                  75                  80

Cys Val Lys Tyr Asn Val Thr Ala Thr Leu Tyr Val Gly Glu Ile Leu
                85                  90                  95

Arg Tyr Leu Cys Asn Val Pro Glu Gln Pro Glu Asp Lys Ile His Thr
            100                 105                 110

Val Arg Leu Ala Met Gly Thr Gly Leu Arg Ala Asn Val Trp Lys Asn
        115                 120                 125

Phe Gln Gln Arg Phe Gly Pro Ile Arg Ile Trp Glu Phe Tyr Gly Ser
    130                 135                 140

Thr Glu Gly Asn Val Gly Leu Met Asn Tyr Val Gly His Cys Gly Ala
145                 150                 155                 160

Val Gly Arg Thr Ser Cys Ile Leu Arg Met Leu Thr Pro Phe Glu Leu
                165                 170                 175

Val Gln Phe Asp Ile Glu Thr Ala Glu Pro Leu Arg Asp Lys Gln Gly
            180                 185                 190

Phe Cys Ile Pro Val Glu Pro Gly Lys Pro Gly Leu Leu Leu Thr Lys
        195                 200                 205

Val Arg Lys Asn Gln Pro Phe Leu Gly Tyr Arg Gly Ser Gln Ala Glu
    210                 215                 220

Ser Asn Arg Lys Leu Val Ala Asn Val Arg Arg Val Gly Asp Leu Tyr
225                 230                 235                 240

Phe Asn Thr Gly Asp Val Leu Thr Leu Asp Gln Glu Gly Phe Phe Tyr
                245                 250                 255
```

-continued

```
Phe Gln Asp Arg Leu Gly Asp Thr Phe Arg Trp Lys Gly Glu Asn Val
            260                 265                 270

Ser Thr Gly Glu Val Glu Cys Val Leu Ser Ser Leu Asp Phe Leu Glu
        275                 280                 285

Glu Val Asn Val Tyr Gly Val Pro Val Pro Gly Cys Glu Gly Lys Val
    290                 295                 300

Gly Met Ala Ala Val Lys Leu Ala Pro Gly Lys Thr Phe Asp Gly Lys
305                 310                 315                 320

Lys Tyr Gln His Val Arg Ser Trp Leu Pro Ala Tyr Ala Thr Pro His
                325                 330                 335

Phe Ile Arg


<210> SEQ ID NO 3
<211> LENGTH: 345
<212> TYPE: PRT
<213> ORGANISM: Caenorhabditis elegans

<400> SEQUENCE: 3

Ile Tyr Thr Ser Gly Thr Thr Gly Leu Pro Lys Ser Ala Ile Met Ser
 1               5                  10                  15

Trp Arg Lys Ser Ser Val Gly Cys Gln Val Phe Gly His Val Leu His
            20                  25                  30

Met Thr Asn Glu Ser Thr Val Phe Thr Ala Met Pro Leu Phe His Ser
        35                  40                  45

Thr Ala Ala Leu Leu Gly Ala Cys Ala Ile Leu Ser His Gly Gly Cys
    50                  55                  60

Leu Ala Leu Ser His Lys Phe Ser Ala Ser Thr Phe Trp Lys Gln Val
65                  70                  75                  80

Tyr Leu Thr Gly Ala Thr His Ile Gln Tyr Ile Gly Glu Ile Cys Arg
                85                  90                  95

Tyr Leu Leu Ala Ala Asn Pro Cys Pro Glu Glu Lys Gln His Asn Val
            100                 105                 110

Arg Leu Met Trp Gly Asn Gly Leu Arg Gly Gln Ile Trp Lys Glu Phe
        115                 120                 125

Val Gly Arg Phe Gly Ile Lys Lys Ile Gly Glu Leu Tyr Gly Ser Thr
    130                 135                 140

Glu Gly Asn Ser Asn Ile Val Asn Val Asp Asn His Val Gly Ala Cys
145                 150                 155                 160

Gly Phe Met Pro Ile Tyr Pro His Ile Gly Ser Leu Tyr Pro Val Arg
                165                 170                 175

Leu Ile Lys Val Asp Arg Ala Thr Gly Glu Leu Glu Arg Asp Lys Asn
            180                 185                 190

Gly Leu Cys Val Pro Cys Val Pro Gly Glu Thr Gly Glu Met Val Gly
        195                 200                 205

Val Ile Lys Glu Lys Asp Ile Leu Leu Lys Phe Glu Gly Tyr Val Ser
    210                 215                 220

Glu Gly Asp Thr Ala Lys Lys Ile Tyr Arg Asp Val Phe Lys His Gly
225                 230                 235                 240

Asp Lys Val Phe Ala Ser Gly Asp Ile Leu His Trp Asp Asp Leu Gly
                245                 250                 255

Tyr Leu Tyr Phe Val Asp Arg Cys Gly Asp Thr Phe Arg Trp Lys Gly
            260                 265                 270

Glu Asn Val Ser Thr Thr Glu Val Glu Gly Ile Leu Gln Pro Val Met
        275                 280                 285
```

-continued

```
Asp Val Glu Asp Ala Thr Val Tyr Gly Val Thr Val Gly Lys Met Glu
    290                 295                 300

Gly Arg Ala Gly Met Ala Gly Ile Val Val Lys Asp Gly Thr Asp Val
305                 310                 315                 320

Glu Lys Phe Ile Ala Asp Ile Thr Ser Arg Leu Thr Glu Asn Leu Ala
                325                 330                 335

Ser Tyr Ala Ile Pro Val Phe Ile Arg
            340                 345


<210> SEQ ID NO 4
<211> LENGTH: 356
<212> TYPE: PRT
<213> ORGANISM: Saccharomyces cerevisiae

<400> SEQUENCE: 4

Tyr Ile Tyr Thr Ser Gly Thr Thr Gly Leu Pro Lys Ala Ala Ile Val
 1               5                  10                  15

Val His Ser Arg Tyr Tyr Arg Ile Ala Ala Phe Gly His His Ser Tyr
            20                  25                  30

Ser Met Arg Ala Ala Asp Val Leu Tyr Asp Cys Leu Pro Leu Tyr His
        35                  40                  45

Ser Ala Gly Asn Ile Met Gly Val Gly Gln Cys Val Ile Tyr Gly Leu
    50                  55                  60

Thr Val Val Leu Arg Lys Lys Phe Ser Ala Ser Arg Phe Trp Asp Asp
65                  70                  75                  80

Cys Val Lys Tyr Asn Cys Thr Val Val Gln Tyr Val Gly Glu Val Cys
                85                  90                  95

Arg Tyr Leu Leu His Thr Pro Ile Ser Lys Tyr Glu Lys Met His Lys
            100                 105                 110

Val Lys Val Ala Tyr Gly Asn Gly Leu Arg Pro Asp Ile Trp Gln Asp
        115                 120                 125

Phe Arg Lys Arg Phe Asn Ile Glu Val Ile Gly Glu Phe Tyr Ala Ala
    130                 135                 140

Thr Glu Ala Pro Phe Ala Thr Thr Thr Phe Gln Lys Gly Asp Phe Gly
145                 150                 155                 160

Ile Gly Ala Cys Arg Asn Tyr Gly Thr Ile Ile Gln Trp Phe Leu Ser
                165                 170                 175

Phe Gln Gln Thr Leu Val Arg Met Asp Pro Asn Asp Asp Ser Val Ile
            180                 185                 190

Tyr Arg Asn Ser Lys Gly Phe Cys Glu Val Ala Pro Val Gly Glu Pro
        195                 200                 205

Gly Glu Met Leu Met Arg Ile Phe Phe Pro Lys Lys Pro Glu Thr Ser
    210                 215                 220

Phe Gln Gly Tyr Leu Gly Asn Ala Lys Glu Thr Lys Ser Lys Val Val
225                 230                 235                 240

Arg Asp Val Phe Arg Arg Gly Asp Ala Trp Tyr Arg Cys Gly Asp Leu
                245                 250                 255

Leu Lys Ala Asp Glu Tyr Gly Leu Trp Tyr Phe Leu Asp Arg Met Gly
            260                 265                 270

Asp Thr Phe Arg Trp Lys Ser Glu Asn Val Ser Thr Thr Glu Val Glu
        275                 280                 285

Asp Gln Leu Thr Ala Ser Asn Lys Glu Gln Tyr Ala Gln Val Leu Val
    290                 295                 300

Val Gly Ile Lys Val Pro Lys Tyr Glu Gly Arg Ala Gly Phe Ala Val
```

-continued

```
305                 310                 315                 320

Ile Lys Leu Thr Asp Asn Ser Leu Asp Ile Thr Ala Lys Thr Lys Leu
                325                 330                 335

Leu Asn Asp Ser Leu Ser Arg Leu Asn Leu Pro Ser Tyr Ala Met Pro
            340                 345                 350

Leu Phe Val Lys
        355


<210> SEQ ID NO 5
<211> LENGTH: 334
<212> TYPE: PRT
<213> ORGANISM: Mycobacterium tuberculosis

<400> SEQUENCE: 5

Tyr Ile Phe Thr Ser Gly Thr Thr Gly Phe Pro Lys Ala Ser Val Met
 1               5                  10                  15

Thr His His Arg Trp Leu Arg Ala Leu Ala Val Phe Gly Gly Met Gly
            20                  25                  30

Leu Arg Leu Lys Gly Ser Asp Thr Leu Tyr Ser Cys Leu Pro Leu Tyr
        35                  40                  45

His Asn Asn Ala Leu Thr Val Ala Val Ser Ser Val Ile Asn Ser Gly
    50                  55                  60

Ala Thr Leu Ala Leu Gly Lys Ser Phe Ser Ala Ser Arg Phe Trp Asp
65                  70                  75                  80

Glu Val Ile Ala Asn Arg Ala Thr Ala Phe Val Tyr Ile Gly Glu Ile
                85                  90                  95

Cys Arg Tyr Leu Leu Asn Gln Pro Ala Lys Pro Thr Asp Arg Ala His
            100                 105                 110

Gln Val Arg Val Ile Cys Gly Asn Gly Leu Arg Pro Glu Ile Trp Asp
        115                 120                 125

Glu Phe Thr Thr Arg Phe Gly Val Ala Arg Val Cys Glu Phe Tyr Ala
    130                 135                 140

Ala Ser Glu Gly Asn Ser Ala Phe Ile Asn Ile Phe Asn Val Pro Arg
145                 150                 155                 160

Thr Ala Gly Val Ser Pro Met Pro Leu Ala Phe Val Glu Tyr Asp Leu
                165                 170                 175

Asp Thr Gly Asp Pro Leu Arg Asp Ala Ser Gly Arg Val Arg Arg Val
            180                 185                 190

Pro Asp Gly Glu Pro Gly Leu Leu Leu Ser Arg Val Asn Arg Leu Gln
        195                 200                 205

Pro Phe Asp Gly Tyr Thr Asp Pro Val Ala Ser Glu Lys Lys Leu Val
    210                 215                 220

Arg Asn Ala Phe Arg Asp Gly Asp Cys Trp Phe Asn Thr Gly Asp Val
225                 230                 235                 240

Met Ser Pro Gln Gly Met Gly His Ala Ala Phe Val Asp Arg Leu Gly
                245                 250                 255

Asp Thr Phe Arg Trp Lys Gly Glu Asn Val Ala Thr Thr Gln Val Glu
            260                 265                 270

Ala Ala Leu Ala Ser Asp Gln Thr Val Glu Glu Cys Thr Val Tyr Gly
        275                 280                 285

Val Gln Ile Pro Arg Thr Gly Gly Arg Ala Gly Met Ala Ala Ile Thr
    290                 295                 300

Leu Arg Ala Gly Ala Glu Phe Asp Gly Gln Ala Leu Ala Arg Thr Val
305                 310                 315                 320
```

-continued

Tyr Gly His Leu Pro Gly Tyr Ala Leu Pro Leu Phe Val Arg
325 330

<210> SEQ ID NO 6
<211> LENGTH: 2087
<212> TYPE: DNA
<213> ORGANISM: Mus musculus

<400> SEQUENCE: 6
acgactcact atagggagag agctatgacg tcgcatgcac gcgtaagctt gggcccctcg 60
agggatcctc tagagcggcc gccgaccccg aaagctctga gagcgggtgc agtctggcct 120
ggcgtctcgc gtacctggcc cgggagcagc cgacacacac cttcctcatc cacggcgcgc 180
agcgctttag ctacgcggag gctgagcgcg agagcaaccg gattgctcgc gcctttctgc 240
gcgcacgggg ctggaccggg ggccgccgag gctcgggcag gggcagcact gaggaaggcg 300
cacgcgtggc gcctccggct ggagatgcgg ctgctagagg gacgaccgcg ccccctctgg 360
cacccggggc gaccgtggcg ctgctcctcc cagcgggccc ggatttcctt tggatttggt 420
tcggactggc caaagctggc ctgcgcacgg cctttgtgcc caccgcttta cgccgaggac 480
ccctgctgca ctgcctccgc agctgcggtg cgagtgcgct cgtgctggcc acagagttcc 540
tggagtccct ggagccggac ctgccggcct tgagagccat ggggctccac ctatgggcga 600
cgggccctga aactaatgta gctggaatca gcaatttgct atcggaagca gcagaccaag 660
tggatgagcc agtgccgggg tacctctctg ccccccagaa cataatggac acctgcctgt 720
acatcttcac ctctggcact actggcctgc ccaaggctgc tcgaatcagt catctgaagg 780
ttctacagtg ccagggattc taccatctgt gtggagtcca ccaggaggac gtgatctacc 840
tcgcactccc actgtaccac atgtctggct cccttctggg cattgtgggc tgcttgggca 900
ttggggccac cgtggtgctg aaacccaagt tctcagctag ccagttctgg gacgattgcc 960
agaaacacag ggtgacagtg ttccagtaca ttggggagtt gtgccgatac ctcgtcaacc 1020
agcccccgag caaggcagag tttgaccata aggtgcgctt ggcagtgggc agtgggttgc 1080
gcccagacac ctgggagcgt ttcctgcggc gatttggacc tctgcagata ctggagacgt 1140
atggcatgac agagggcaac gtagctacgt tcaattacac aggacggcag ggtgcagtgg 1200
ggcgagcttc ctggctttac aagcacatct tccccttctc cttgattcga tacgatgtca 1260
tgacagggga gcctattcgg aatgcccagg ggcactgcat gaccacatct ccaggtgagc 1320
caggcctact ggtggcccca gtgagccagc agtccccctt cctgggctat gctggggctc 1380
cggagctggc caaggacaag ctgctgaagg atgtcttctg gtctggggac gttttcttca 1440
atactgggga cctcttggtc tgtgatgagc aaggctttct tcacttccac gatcgtactg 1500
gagacaccat caggtggaag ggagagaatg tggccacaac tgaagtggct gaggtcttgg 1560
agaccctgga cttccttcag gaggtgaaca tctatggagt cacggtgcca gggcacgaag 1620
gcagggcagg catggcggcc ttggctctgc ggcccccgca ggctctgaac ctggtgcagc 1680
tctacagcca tgtttctgag aacttgccac cgtatgcccg acctcggttt ctcaggctcc 1740
aggaatcttt ggccactact gagaccttca aacagcagaa ggttaggatg gccaatgagg 1800
gctttgaccc cagtgtactg tctgacccac tctatgttct ggaccaagat ataggggcct 1860
acctgcccct cacacctgcc cggtacagtg ccctcctgtc tggagacctt cgaatctgaa 1920
accttccact tgagggaggg gctcggaggg tacaggccac catggctgca ccagggaggg 1980
ttttcgggta tcttttgtat atggagtcat tatttttgtaa taaacagctg gagcttaaaa 2040

-continued

```
aaaaaaaaaa aaaaaaaaaa aaaaaaaaaa aaaaaaaaaa aaaaaaa                2087


<210> SEQ ID NO 7
<211> LENGTH: 613
<212> TYPE: PRT
<213> ORGANISM: Mus musculus

<400> SEQUENCE: 7

Ala Ala Asp Pro Glu Ser Ser Glu Ser Gly Cys Ser Leu Ala Trp Arg
 1               5                  10                  15

Leu Ala Tyr Leu Ala Arg Glu Gln Pro Thr His Thr Phe Leu Ile His
            20                  25                  30

Gly Ala Gln Arg Phe Ser Tyr Ala Glu Ala Glu Arg Glu Ser Asn Arg
        35                  40                  45

Ile Ala Arg Ala Phe Leu Arg Ala Arg Gly Trp Thr Gly Gly Arg Arg
    50                  55                  60

Gly Ser Gly Arg Gly Ser Thr Glu Glu Gly Ala Arg Val Ala Pro Pro
65                  70                  75                  80

Ala Gly Asp Ala Ala Ala Arg Gly Thr Thr Ala Pro Pro Leu Ala Pro
                85                  90                  95

Gly Ala Thr Val Ala Leu Leu Leu Pro Ala Gly Pro Asp Phe Leu Trp
            100                 105                 110

Ile Trp Phe Gly Leu Ala Lys Ala Gly Leu Arg Thr Ala Phe Val Pro
        115                 120                 125

Thr Ala Leu Arg Arg Gly Pro Leu Leu His Cys Leu Arg Ser Cys Gly
    130                 135                 140

Ala Ser Ala Leu Val Leu Ala Thr Glu Phe Leu Glu Ser Leu Glu Pro
145                 150                 155                 160

Asp Leu Pro Ala Leu Arg Ala Met Gly Leu His Leu Trp Ala Thr Gly
                165                 170                 175

Pro Glu Thr Asn Val Ala Gly Ile Ser Asn Leu Leu Ser Glu Ala Ala
            180                 185                 190

Asp Gln Val Asp Glu Pro Val Pro Gly Tyr Leu Ser Ala Pro Gln Asn
        195                 200                 205

Ile Met Asp Thr Cys Leu Tyr Ile Phe Thr Ser Gly Thr Thr Gly Leu
    210                 215                 220

Pro Lys Ala Ala Arg Ile Ser His Leu Lys Val Leu Gln Cys Gln Gly
225                 230                 235                 240

Phe Tyr His Leu Cys Gly Val His Gln Glu Asp Val Ile Tyr Leu Ala
                245                 250                 255

Leu Pro Leu Tyr His Met Ser Gly Ser Leu Leu Gly Ile Val Gly Cys
            260                 265                 270

Leu Gly Ile Gly Ala Thr Val Val Leu Lys Pro Lys Phe Ser Ala Ser
        275                 280                 285

Gln Phe Trp Asp Asp Cys Gln Lys His Arg Val Thr Val Phe Gln Tyr
    290                 295                 300

Ile Gly Glu Leu Cys Arg Tyr Leu Val Asn Gln Pro Pro Ser Lys Ala
305                 310                 315                 320

Glu Phe Asp His Lys Val Arg Leu Ala Val Gly Ser Gly Leu Arg Pro
                325                 330                 335

Asp Thr Trp Glu Arg Phe Leu Arg Arg Phe Gly Pro Leu Gln Ile Leu
            340                 345                 350

Glu Thr Tyr Gly Met Thr Glu Gly Asn Val Ala Thr Phe Asn Tyr Thr
        355                 360                 365
```

-continued

```
Gly Arg Gln Gly Ala Val Gly Arg Ala Ser Trp Leu Tyr Lys His Ile
    370                 375                 380

Phe Pro Phe Ser Leu Ile Arg Tyr Asp Val Met Thr Gly Glu Pro Ile
385                 390                 395                 400

Arg Asn Ala Gln Gly His Cys Met Thr Thr Ser Pro Gly Glu Pro Gly
                405                 410                 415

Leu Leu Val Ala Pro Val Ser Gln Gln Ser Pro Phe Leu Gly Tyr Ala
            420                 425                 430

Gly Ala Pro Glu Leu Ala Lys Asp Lys Leu Leu Lys Asp Val Phe Trp
        435                 440                 445

Ser Gly Asp Val Phe Phe Asn Thr Gly Asp Leu Leu Val Cys Asp Glu
    450                 455                 460

Gln Gly Phe Leu His Phe His Asp Arg Thr Gly Asp Thr Ile Arg Trp
465                 470                 475                 480

Lys Gly Glu Asn Val Ala Thr Thr Glu Val Ala Glu Val Leu Glu Thr
                485                 490                 495

Leu Asp Phe Leu Gln Glu Val Asn Ile Tyr Gly Val Thr Val Pro Gly
            500                 505                 510

His Glu Gly Arg Ala Gly Met Ala Ala Leu Ala Leu Arg Pro Pro Gln
        515                 520                 525

Ala Leu Asn Leu Val Gln Leu Tyr Ser His Val Ser Glu Asn Leu Pro
    530                 535                 540

Pro Tyr Ala Arg Pro Arg Phe Leu Arg Leu Gln Glu Ser Leu Ala Thr
545                 550                 555                 560

Thr Glu Thr Phe Lys Gln Gln Lys Val Arg Met Ala Asn Glu Gly Phe
                565                 570                 575

Asp Pro Ser Val Leu Ser Asp Pro Leu Tyr Val Leu Asp Gln Asp Ile
            580                 585                 590

Gly Ala Tyr Leu Pro Leu Thr Pro Ala Arg Tyr Ser Ala Leu Leu Ser
        595                 600                 605

Gly Asp Leu Arg Ile
    610
```

<210> SEQ ID NO 8
<211> LENGTH: 2301
<212> TYPE: DNA
<213> ORGANISM: Mus musculus

<400> SEQUENCE: 8

```
cccacgcgtc cgcccacgcg tccggcatgg ccaagctggg cgtggaggcg gctctcatca     60

acaccaacct taggcgggat gccctgcgcc actgtcttga cacctcaaag gcacgagctc    120

tcatctttgg cagtgagatg gcctcagcta tctgtgagat ccatgctagc ctggagccca    180

cactcagcct cttctgctct ggatcctggg agcccagcac agtgcccgtc agcacagagc    240

atctggaccc tcttctggaa gatgccccga agcacctgcc cagtcaccca gacaagggtt    300

ttacagataa gctcttctac atctacacat cgggcaccac ggggctaccc aaagctgcca    360

ttgtggtgca cagcaggtat tatcgtatgg cttccctggt gtactatgga ttccgcatgc    420

ggcctgatga cattgtctat gactgcctcc ccctctacca ctcaagcagg aaacatcgtg    480

gggattggca gtgcttactc cacggcatga ctgtggtgat ccggaagaag ttctcagcct    540

cccggttctg ggatgattgt atcaagtaca actgcacagt ggtacagtac attggcgagc    600

tctgccgcta cctcctgaac cagccacccc gtgaggctga gtctcggcac aaggtgcgca    660

tggcactggg caacggtctc cggcagtcca tctggaccga cttctccagc cgtttccaca    720
```

-continued

```
tcccccaggt ggctgagttc tatggggcca ctgaatgcaa ctgtagcctg ggcaactttg    780
acagccgggt gggggcctgt ggcttcaata gccgcatcct gtcctttgtg taccctatcc    840
gtttggtacg tgtcaatgag gataccatgg aactgatccg gggacccgat ggagtctgca    900
ttccctgtca accaggtcag ccaggccagc tggtgggtcg catcatccag caggaccctc    960
tgcgccgttt cgacgggtac ctcaaccagg gtgccaacaa caagaagatt gctaatgatg   1020
tcttcaagaa gggggaccaa gcctacctca ctggtgacgt cctggtgatg gatgagctgg   1080
gttacctgta cttccgagat cgcactgggg acacgttccg ctggaaaggg gagaatgtat   1140
ctaccactga ggtggagggc acactcagcc gcctgcttca tatggcagat gtggcagttt   1200
atggtgttga ggtgccagga actgaaggcc gagcaggaat ggctgccgtt gcaagtccca   1260
tcagcaactg tgacctggag agctttgcac agaccttgaa aaaggagctg cctctgtatg   1320
cccgccccat cttcctgcgc ttcttgcctg agctgcacaa gacagggacc ttcaagttcc   1380
agaagacaga gttgcggaag gagggctttg acccatctgt tgtgaaagac ccgctgttct   1440
atctggatgc tcggaagggc tgctacgttg cactggacca ggaggcctat acccgcatcc   1500
aggcaggcga ggagaagctg tgatttcccc ctacatccct ctgagggcca gaagatgctg   1560
gattcagagc cctagcgtcc accccagagg gtcctgggca atgccagacc aaagctagca   1620
gggcccgcac ctccgcccct aggtgctgat ctcccctctc ccaaactgcc aagtgactca   1680
ctgccgcttc cccgaccctc cagaggcttt ctgtgaaagt ctcatccaag ctgtgtcttc   1740
tggtccaggc gtggcccctg gccccagggt ttctgatagg ctcctttagg atggtatctt   1800
gggtccagcg ggccagggtg tgggagagga gtcactaaga tccctccaat cagaagggag   1860
cttacaaagg aaccaaggca aagcctgtag actcaggaag ctaagtggcc agagactata   1920
gtggccagtc atcccatgtc cacagaggat cttggtccag agctgccaaa gtgtcacctc   1980
tccctgcctg cacctctggg gaaaagagga cagcatgtgg ccactgggca cctgtctcaa   2040
gaagtcagga tcacacactc agtccttgtt tctccaggtt cccttgttct tgtctcgggg   2100
agggagggac gagtgtcctg tctgtccttc ctgcctgtct gtgagtctgt gttgcttctc   2160
catctgtcct agcctgagtg tgggtggaac aggcatgagg agagtgtggc tcaggggcca   2220
ataaactctg ccttgactcc tcttaaaaaa aaaaaaaaaa aaaaaaaaaa aaaaaaaaaa   2280
aaaaaaaaaa aaaaaaaaaa a                                             2301
```

```
<210> SEQ ID NO 9
<211> LENGTH: 506
<212> TYPE: PRT
<213> ORGANISM: Mus musculus

<400> SEQUENCE: 9

His Ala Ser Ala His Ala Ser Gly Met Ala Lys Leu Gly Val Glu Ala
 1               5                  10                  15

Ala Leu Ile Asn Thr Asn Leu Arg Arg Asp Ala Leu Arg His Cys Leu
            20                  25                  30

Asp Thr Ser Lys Ala Arg Ala Leu Ile Phe Gly Ser Glu Met Ala Ser
        35                  40                  45

Ala Ile Cys Glu Ile His Ala Ser Leu Glu Pro Thr Leu Ser Leu Phe
    50                  55                  60

Cys Ser Gly Ser Trp Glu Pro Ser Thr Val Pro Val Ser Thr Glu His
65                  70                  75                  80

Leu Asp Pro Leu Leu Glu Asp Ala Pro Lys His Leu Pro Ser His Pro
```

-continued

```
                85                  90                  95

Asp Lys Gly Phe Thr Asp Lys Leu Phe Tyr Ile Tyr Thr Ser Gly Thr
            100                 105                 110

Thr Gly Leu Pro Lys Ala Ala Ile Val Val His Ser Arg Tyr Tyr Arg
        115                 120                 125

Met Ala Ser Leu Val Tyr Tyr Gly Phe Arg Met Arg Pro Asp Asp Ile
    130                 135                 140

Val Tyr Asp Cys Leu Pro Leu Tyr His Ser Ser Arg Lys His Arg Gly
145                 150                 155                 160

Asp Trp Gln Cys Leu Leu His Gly Met Thr Val Val Ile Arg Lys Lys
                165                 170                 175

Phe Ser Ala Ser Arg Phe Trp Asp Asp Cys Ile Lys Tyr Asn Cys Thr
            180                 185                 190

Val Val Gln Tyr Ile Gly Glu Leu Cys Arg Tyr Leu Leu Asn Gln Pro
        195                 200                 205

Pro Arg Glu Ala Glu Ser Arg His Lys Val Arg Met Ala Leu Gly Asn
    210                 215                 220

Gly Leu Arg Gln Ser Ile Trp Thr Asp Phe Ser Ser Arg Phe His Ile
225                 230                 235                 240

Pro Gln Val Ala Glu Phe Tyr Gly Ala Thr Glu Cys Asn Cys Ser Leu
                245                 250                 255

Gly Asn Phe Asp Ser Arg Val Gly Ala Cys Gly Phe Asn Ser Arg Ile
            260                 265                 270

Leu Ser Phe Val Tyr Pro Ile Arg Leu Val Arg Val Asn Glu Asp Thr
        275                 280                 285

Met Glu Leu Ile Arg Gly Pro Asp Gly Val Cys Ile Pro Cys Gln Pro
    290                 295                 300

Gly Gln Pro Gly Gln Leu Val Gly Arg Ile Ile Gln Gln Asp Pro Leu
305                 310                 315                 320

Arg Arg Phe Asp Gly Tyr Leu Asn Gln Gly Ala Asn Asn Lys Lys Ile
                325                 330                 335

Ala Asn Asp Val Phe Lys Lys Gly Asp Gln Ala Tyr Leu Thr Gly Asp
            340                 345                 350

Val Leu Val Met Asp Glu Leu Gly Tyr Leu Tyr Phe Arg Asp Arg Thr
        355                 360                 365

Gly Asp Thr Phe Arg Trp Lys Gly Glu Asn Val Ser Thr Thr Glu Val
    370                 375                 380

Glu Gly Thr Leu Ser Arg Leu Leu His Met Ala Asp Val Ala Val Tyr
385                 390                 395                 400

Gly Val Glu Val Pro Gly Thr Glu Gly Arg Ala Gly Met Ala Ala Val
                405                 410                 415

Ala Ser Pro Ile Ser Asn Cys Asp Leu Glu Ser Phe Ala Gln Thr Leu
            420                 425                 430

Lys Lys Glu Leu Pro Leu Tyr Ala Arg Pro Ile Phe Leu Arg Phe Leu
        435                 440                 445

Pro Glu Leu His Lys Thr Gly Thr Phe Lys Phe Gln Lys Thr Glu Leu
    450                 455                 460

Arg Lys Glu Gly Phe Asp Pro Ser Val Val Lys Asp Pro Leu Phe Tyr
465                 470                 475                 480

Leu Asp Ala Arg Lys Gly Cys Tyr Val Ala Leu Asp Gln Glu Ala Tyr
                485                 490                 495

Thr Arg Ile Gln Ala Gly Glu Glu Lys Leu
            500                 505
```

-continued

<210> SEQ ID NO 10
<211> LENGTH: 2277
<212> TYPE: DNA
<213> ORGANISM: Mus musculus

<400> SEQUENCE: 10

```
cactcatcag agctaagaga gactacacgc tctcatctac ttcagaaaga gccaatgcca      60
tgggtatttg gaagaaacta accttactgc tgttgctgct tctgctggtt ggcctggggc     120
agcccccatg gccagcagct atggctctgg ccctgcgttg gttcctggga gaccccacat     180
gccttgtgct gcttggcttg gcattgctgg gcagaccctg gatcagctcc tggatgcccc     240
actggctgag cctggtagga gcagctctta ccttattcct attgcctcta cagccacccc     300
cagggctacg ctggctgcat aaagatgtgg ctttcacctt caagatgctt ttctatggcc     360
taaagttcag gcgacgcctt aacaaacatc ctccagagac ctttgtggat gctttagagc     420
ggcaagcact ggcatggcct gaccgggtgg ccttggtgtg tactgggtct gagggctcct     480
caatcacaaa tagccagctg gatgccaggt cctgtcaggc agcatgggtc ctgaaagcaa     540
agctgaagga tgccgtaatc cagaacacaa gagatgctgc tgctatctta gttctcccgt     600
ccaagaccat ttctgctttg agtgtgtttc tggggttggc caagttgggc tgccctgtgg     660
cctggatcaa tccacacagc cgagggatgc ccttgctaca ctctgtacgg agctctgggg     720
ccagtgtgct gattgtggat ccagacctcc aggagaacct ggaagaagtc cttcccaagc     780
tgctagctga gaacattcac tgcttctacc ttggccacag ctcacccacc ccgggagtag     840
aggctctggg agcttccctg gatgctgcac cttctgaccc agtacctgcc agccttcgag     900
ctacgattaa gtggaaatct cctgccatat tcatctttac ttcagggacc actggactcc     960
caaagccagc catcttatca catgagcggg tcatacaagt gagcaacgtg ctgtccttct    1020
gtggatgcag agctgatgat gtggtctatg acgtcctacc tctgtaccat acgatagggc    1080
ttgtccttgg attccttggc tgcttacaag ttggagccac ctgtgtcctg gcccccaagt    1140
tctctgcctc ccgattctgg gctgagtgcc ggcagcatgg cgtaacagtg atcttgtatg    1200
tgggtgaaat cctgcggtac ttgtgtaacg tccctgagca accagaagac aagatacata    1260
cagtgcgctt ggccatggga actggacttc gggcaaatgt gtggaaaaac ttccagcaac    1320
gctttggtcc cattcggatc tgggaattct acggatccac agagggcaat gtgggcttaa    1380
tgaactatgt gggccactgc ggggctgtgg gaaggaccag ctgcatcctt cgaatgctga    1440
ctccctttga gcttgtacag ttcgacatag agacagcaga gcctctgagg gacaaacagg    1500
gtttttgcat tcctgtggag ccaggaaagc caggacttct tttgaccaag gttcgaaaga    1560
accaaccctt cctgggctac cgtggttccc aggccgagtc caatcggaaa cttgttgcga    1620
atgtacgacg cgtaggagac ctgtacttca acactgggga cgtgctgacc ttggaccagg    1680
aaggcttctt ctactttcaa gaccgccttg gtgacacctt ccggtggaag ggcgaaaacg    1740
tatctactgg agaggtggag tgtgttttgt ctagcctaga cttcctagag gaagtcaatg    1800
tctatggtgt gcctgtgcca gggtgtgagg gtaaggttgg catggctgct gtgaaactgg    1860
ctcctgggaa gacttttgat gggcagaagc tataccagca tgtccgctcc tggctccctg    1920
cctatgccac acctcatttc atccgtatcc aggattccct ggagatcaca aacacctaca    1980
agctggtaaa gtcacggctg gtgcgtgagg gttttgatgt ggggatcatt gctgaccccc    2040
tctacatact ggacaacaag gcccagacct tccggagtct gatgccagat gtgtaccagg    2100
```

-continued

```
ctgtgtgtga aggaacctgg aatctctgac cacctagcca actggaaggc aatccaaaag   2160

tgtagagatt gacactagtc agcttcacaa agttgtccgg gttccagatg cccatggccc   2220

agtagtactt agagaataaa cttgaatgtg tatacaaaaa aaaaaaaaaa aaaaaaa      2277
```

<210> SEQ ID NO 11
<211> LENGTH: 662
<212> TYPE: PRT
<213> ORGANISM: Mus musculus

<400> SEQUENCE: 11

```
Met Ala Leu Ala Leu Arg Trp Phe Leu Gly Asp Pro Thr Cys Leu Val
 1               5                  10                  15

Leu Leu Gly Leu Ala Leu Leu Gly Arg Pro Trp Ile Ser Ser Trp Met
            20                  25                  30

Pro His Trp Leu Ser Leu Val Gly Ala Ala Leu Thr Leu Phe Leu Leu
        35                  40                  45

Pro Leu Gln Pro Pro Pro Gly Leu Arg Trp Leu His Lys Asp Val Ala
    50                  55                  60

Phe Thr Phe Lys Met Leu Phe Tyr Gly Leu Lys Phe Arg Arg Arg Leu
65                  70                  75                  80

Asn Lys His Pro Pro Glu Thr Phe Val Asp Ala Leu Glu Arg Gln Ala
                85                  90                  95

Leu Ala Trp Pro Asp Arg Val Ala Leu Val Cys Thr Gly Ser Glu Gly
            100                 105                 110

Ser Ser Ile Thr Asn Ser Gln Leu Asp Ala Arg Ser Cys Gln Ala Ala
        115                 120                 125

Trp Val Leu Lys Ala Lys Leu Lys Asp Ala Val Ile Gln Asn Thr Arg
    130                 135                 140

Asp Ala Ala Ala Ile Leu Val Leu Pro Ser Lys Thr Ile Ser Ala Leu
145                 150                 155                 160

Ser Val Phe Leu Gly Leu Ala Lys Leu Gly Cys Pro Val Ala Trp Ile
                165                 170                 175

Asn Pro His Ser Arg Gly Met Pro Leu Leu His Ser Val Arg Ser Ser
            180                 185                 190

Gly Ala Ser Val Leu Ile Val Asp Pro Asp Leu Gln Glu Asn Leu Glu
        195                 200                 205

Glu Val Leu Pro Lys Leu Leu Ala Glu Asn Ile His Cys Phe Tyr Leu
    210                 215                 220

Gly His Ser Ser Pro Thr Pro Gly Val Glu Ala Leu Gly Ala Ser Leu
225                 230                 235                 240

Asp Ala Ala Pro Ser Asp Pro Val Pro Ala Ser Leu Arg Ala Thr Ile
                245                 250                 255

Lys Trp Lys Ser Pro Ala Ile Phe Ile Phe Thr Ser Gly Thr Thr Gly
            260                 265                 270

Leu Pro Lys Pro Ala Ile Leu Ser His Glu Arg Val Ile Gln Val Ser
        275                 280                 285

Asn Val Leu Ser Phe Cys Gly Cys Arg Ala Asp Asp Val Val Tyr Asp
    290                 295                 300

Val Leu Pro Leu Tyr His Thr Ile Gly Leu Val Leu Gly Phe Leu Gly
305                 310                 315                 320

Cys Leu Gln Val Gly Ala Thr Cys Val Leu Ala Pro Lys Phe Ser Ala
                325                 330                 335

Ser Arg Phe Trp Ala Glu Cys Arg Gln His Gly Val Thr Val Ile Leu
            340                 345                 350
```

-continued

```
Tyr Val Gly Glu Ile Leu Arg Tyr Leu Cys Asn Val Pro Glu Gln Pro
        355                 360                 365

Glu Asp Lys Ile His Thr Val Arg Leu Ala Met Gly Thr Gly Leu Arg
    370                 375                 380

Ala Asn Val Trp Lys Asn Phe Gln Gln Arg Phe Gly Pro Ile Arg Ile
385                 390                 395                 400

Trp Glu Phe Tyr Gly Ser Thr Glu Gly Asn Val Gly Leu Met Asn Tyr
                405                 410                 415

Val Gly His Cys Gly Ala Val Gly Arg Thr Ser Cys Ile Leu Arg Met
            420                 425                 430

Leu Thr Pro Phe Glu Leu Val Gln Phe Asp Ile Glu Thr Ala Glu Pro
        435                 440                 445

Leu Arg Asp Lys Gln Gly Phe Cys Ile Pro Val Glu Pro Gly Lys Pro
    450                 455                 460

Gly Leu Leu Leu Thr Lys Val Arg Lys Asn Gln Pro Phe Leu Gly Tyr
465                 470                 475                 480

Arg Gly Ser Gln Ala Glu Ser Asn Arg Lys Leu Val Ala Asn Val Arg
                485                 490                 495

Arg Val Gly Asp Leu Tyr Phe Asn Thr Gly Asp Val Leu Thr Leu Asp
            500                 505                 510

Gln Glu Gly Phe Phe Tyr Phe Gln Asp Arg Leu Gly Asp Thr Phe Arg
        515                 520                 525

Trp Lys Gly Glu Asn Val Ser Thr Gly Glu Val Glu Cys Val Leu Ser
    530                 535                 540

Ser Leu Asp Phe Leu Glu Glu Val Asn Val Tyr Gly Val Pro Val Pro
545                 550                 555                 560

Gly Cys Glu Gly Lys Val Gly Met Ala Ala Val Lys Leu Ala Pro Gly
                565                 570                 575

Lys Thr Phe Asp Gly Gln Lys Leu Tyr Gln His Val Arg Ser Trp Leu
            580                 585                 590

Pro Ala Tyr Ala Thr Pro His Phe Ile Arg Ile Gln Asp Ser Leu Glu
        595                 600                 605

Ile Thr Asn Thr Tyr Lys Leu Val Lys Ser Arg Leu Val Arg Glu Gly
    610                 615                 620

Phe Asp Val Gly Ile Ile Ala Asp Pro Leu Tyr Ile Leu Asp Asn Lys
625                 630                 635                 640

Ala Gln Thr Phe Arg Ser Leu Met Pro Asp Val Tyr Gln Ala Val Cys
                645                 650                 655

Glu Gly Thr Trp Asn Leu
            660


<210> SEQ ID NO 12
<211> LENGTH: 1622
<212> TYPE: DNA
<213> ORGANISM: Homo sapiens
<220> FEATURE:
<221> NAME/KEY: misc_feature
<222> LOCATION: (1)...(1622)
<223> OTHER INFORMATION: n = A,T,C or G

<400> SEQUENCE: 12

atgggattga ctctttcctg gacaaagtgg atgaagtatc aactgaacct atcccagagt     60

catggaggtc tgaagtcact tttccactc ctgccttata catttatact tctggaacca    120

caggtcttcc aaaagcagcc atgatcactc atcagcgcat atggtatgga actggcctca    180
```

-continued

```
cttttgtaag cggattgaag gcagatgatg tcatctatat cactctgccc ttttaccaca    240
gtgctgcact actgattggc attcacggat gtattgtggc tggtgctact cttgccttgc    300
ggactaaatt ttcagccagc cagttttggg atgactgcag aaaatacaac gtcactgtca    360
ttcagtatat cggtgaactg cttcggtatt tatgcaactc accacagaaa ccaaatgacc    420
gtgatcataa agtgagactg gcactgggaa atggcttacg aggagatgtg tggagacaat    480
ttgtcaagag atttggggac atatgcatct atgagttcta tgctgccact gaaggcaata    540
ttggatttat gaattatgcg agaaaagttg gtgctgttgg aagagtaaac tacctacaga    600
aaaaaatcat aacttatgac ctgattaaat atgatgtgga gaaagatgaa cctgtccgtg    660
atgaaaatgg atattgcgtc agagttccca aaggtgaagt tggacttctg gtttgcaaaa    720
tcacacaact tacaccattt aatggctatg ctggagcaaa ggctcagaca gagaagaaaa    780
aactgagaga tgtctttaag aaaggagacc tctatttcaa cagtggagat ctcttaatgg    840
ttgaccatga aaatttcatc tatttccacg acagagttgg agatacattc cggtggaaag    900
gggaaaatgt ggccaccact gaagttgctg atatagttgg actggttgat ttttttccaa    960
ggaagtaaaa tgtttatggg agtgcatggg ccaagatnat ggaggttcga attggcatgg   1020
cnttccnttc aaaatggaaa gaaaaccatg gaatttgatg gaaagaaatt ttttcagnac   1080
attgctgata accnacctag ttatgcaagg ccccggtttt ntaagaanac aggacaccat   1140
tgagatcact ggaattttta aacaccgcaa aatgaccttt ggtggaggag ggctttaacc   1200
cngctgtcat caaagatgcc ttgtattttc ttggatgaca cagcaaaaat gtatgtgcct   1260
atgactgagg acatntataa tgccataagt gntaaaaccc tgaaattntg aatattccca   1320
ggaggataat tcaacatttc cagaaagaaa ctgaatggac agccacttga tataatccaa   1380
ctttaatttg attgaagatt gtgaggaaat tttgtaggaa atttgcatac ccgtaaaggg   1440
agactttttt aaataacagt tgagtctttg caagtaaaaa gatttagaga ttattatttt   1500
tcagtgtgca cctactgttt gtatttgcaa actgagcttg ttggagggaa ggcattattt   1560
tttaaaatac ttagtaaatt aaagaacacc aacatgtgaa aaaaaaaaaa aaaaaaaaaa   1620
aa                                                                  1622
```

<210> SEQ ID NO 13
<211> LENGTH: 286
<212> TYPE: PRT
<213> ORGANISM: Homo sapiens

<400> SEQUENCE: 13

```
Tyr Ile Tyr Thr Ser Gly Thr Thr Gly Leu Pro Lys Ala Ala Met Ile
 1               5                  10                  15

Thr His Gln Arg Ile Trp Tyr Gly Thr Gly Leu Thr Phe Val Ser Gly
            20                  25                  30

Leu Lys Ala Asp Asp Val Ile Tyr Ile Thr Leu Pro Phe Tyr His Ser
        35                  40                  45

Ala Ala Leu Leu Ile Gly Ile His Gly Cys Ile Val Ala Gly Ala Thr
    50                  55                  60

Leu Ala Leu Arg Thr Lys Phe Ser Ala Ser Gln Phe Trp Asp Asp Cys
65                  70                  75                  80

Arg Lys Tyr Asn Val Thr Val Ile Gln Tyr Ile Gly Glu Leu Leu Arg
                85                  90                  95

Tyr Leu Cys Asn Ser Pro Gln Lys Pro Asn Asp Arg Asp His Lys Val
            100                 105                 110
```

-continued

```
Arg Leu Ala Leu Gly Asn Gly Leu Arg Gly Asp Val Trp Arg Gln Phe
        115                 120                 125

Val Lys Arg Phe Gly Asp Ile Cys Ile Tyr Glu Phe Tyr Ala Ala Thr
    130                 135                 140

Glu Gly Asn Ile Gly Phe Met Asn Tyr Ala Arg Lys Val Gly Ala Val
145                 150                 155                 160

Gly Arg Val Asn Tyr Leu Gln Lys Lys Ile Ile Thr Tyr Asp Leu Ile
                165                 170                 175

Lys Tyr Asp Val Glu Lys Asp Glu Pro Val Arg Asp Glu Asn Gly Tyr
            180                 185                 190

Cys Val Arg Val Pro Lys Gly Glu Val Gly Leu Leu Val Cys Lys Ile
        195                 200                 205

Thr Gln Leu Thr Pro Phe Asn Gly Tyr Ala Gly Ala Lys Ala Gln Thr
    210                 215                 220

Glu Lys Lys Lys Leu Arg Asp Val Phe Lys Lys Gly Asp Leu Tyr Phe
225                 230                 235                 240

Asn Ser Gly Asp Leu Leu Met Val Asp His Glu Asn Phe Ile Tyr Phe
                245                 250                 255

His Asp Arg Val Gly Asp Thr Phe Arg Trp Lys Gly Glu Asn Val Ala
            260                 265                 270

Thr Thr Glu Val Ala Asp Ile Val Gly Leu Val Asp Phe Phe
        275                 280                 285


<210> SEQ ID NO 14
<211> LENGTH: 753
<212> TYPE: DNA
<213> ORGANISM: Homo sapiens

<400> SEQUENCE: 14

caattcggga cccccagggg cactgtatgg ccacatctcc aggtgagcca ggggaagttg     60

ctaaaggatg tcttccggcc tggggatgtt ttcttcaaca ctggggacct gctggtctgc    120

gatgaccaag gttttctccg cttccatgat cgtactggag acaccttcag gtggaaaggg    180

gagaatgtgg ccacaaccga ggtggcagag gtcttcgagg ccctagattt tcttcaggag    240

gtgaacgtct atggagtcac tgtgccaggg catgaaggca gggctggaat ggcagcccta    300

gttctgcgtc ccccccacgc tttggacctt atgcagctct acacccacgt gtctgagaac    360

ttgccacctt atgcccggcc ccgattcctc aggctccagg agtctttggc caccacagag    420

accttcaaac agcagaaagt tcggatggca aatgagggct tcgaccccag caccctgtct    480

gacccactgt acgttctgga ccaggctgta ggtgcctacc tgcccctcac aactgcccgg    540

tacagcgccc tcctggcagg aaaccttcga atctgagaac ttccacacct gaggcacctg    600

agagaggaac tctgtggggt gggggccgtt gcaggtgtac tgggctgtca gggatctttt    660

ctataccaga actgcggtca ctattttgta ataaatgtgg ctggagctga tccagctgtc    720

tctgacctac aaaaaaaaaa aaaaaaaaaa aaa                                 753


<210> SEQ ID NO 15
<211> LENGTH: 191
<212> TYPE: PRT
<213> ORGANISM: Homo sapiens

<400> SEQUENCE: 15

Gln Phe Gly Thr Pro Arg Gly Thr Val Trp Pro His Leu Gln Val Ser
 1               5                  10                  15

Gln Gly Lys Leu Leu Lys Asp Val Phe Arg Pro Gly Asp Val Phe Phe
```

-continued

```
            20                  25                  30

Asn Thr Gly Asp Leu Leu Val Cys Asp Asp Gln Gly Phe Leu Arg Phe
        35                  40                  45

His Asp Arg Thr Gly Asp Thr Phe Arg Trp Lys Gly Glu Asn Val Ala
    50                  55                  60

Thr Thr Glu Val Ala Glu Val Phe Glu Ala Leu Asp Phe Leu Gln Glu
65                  70                  75                  80

Val Asn Val Tyr Gly Val Thr Val Pro Gly His Glu Gly Arg Ala Gly
                85                  90                  95

Met Ala Ala Leu Val Leu Arg Pro Pro His Ala Leu Asp Leu Met Gln
            100                 105                 110

Leu Tyr Thr His Val Ser Glu Asn Leu Pro Pro Tyr Ala Arg Pro Arg
        115                 120                 125

Phe Leu Arg Leu Gln Glu Ser Leu Ala Thr Thr Glu Thr Phe Lys Gln
    130                 135                 140

Gln Lys Val Arg Met Ala Asn Glu Gly Phe Asp Pro Ser Thr Leu Ser
145                 150                 155                 160

Asp Pro Leu Tyr Val Leu Asp Gln Ala Val Gly Ala Tyr Leu Pro Leu
                165                 170                 175

Thr Thr Ala Arg Tyr Ser Ala Leu Leu Ala Gly Asn Leu Arg Ile
            180                 185                 190
```

<210> SEQ ID NO 16
<211> LENGTH: 734
<212> TYPE: DNA
<213> ORGANISM: Homo sapiens
<220> FEATURE:
<221> NAME/KEY: misc_feature
<222> LOCATION: (1)...(734)
<223> OTHER INFORMATION: n = A,T,C or G

<400> SEQUENCE: 16

```
tcaagtacaa ctgcacgatt gtcatancat tggtgaactg tgccgntacc tcctgaacca     60

gccaccgcgg gaggcagaaa accagcacca ggttcgcatg gcactaggca atggcctccg    120

gcagtccatc tggaccaact tttccagccg cttccacata ccccaggtgg ctgagttyta    180

cggggccaca gagtgcaact gtagcctggg caacttcgac agccaggtgg gggcctgtgg    240

tttcaatagc cgcatcctgt ccttcgtgta ccccatccgg ttggtacgtg tcaacgagga    300

caccatggag ctgatccggg ggcccgacgg cgtctgcatt ccctgccagc caggtgagcc    360

gggccagctg gtgggccgca tcatccagaa agaccccctg cgccgcttcg atggctacct    420

caaccagggc gccaacaaca agaagattgc caaggatgtc ttcaagaagg gggaccaggc    480

ctaccttact ggtgatgtgc tggtgatgga cgagctgggc tacctgtact tccgagaccg    540

cactggggac acgttccgct ggaaaggtga gaacgtgtcc accaccgagg tggaaggcac    600

actcagccgc ctgctggaca tggctgacgt ggccgtgtat ggtgtcgagg tgccaggaac    660

cgagggccgg gccggaatgg ctgctgtggc cagccccact ggcaactgtg acctgggagc    720

gctttgctca ggtc                                                      734
```

<210> SEQ ID NO 17
<211> LENGTH: 213
<212> TYPE: PRT
<213> ORGANISM: Homo sapiens

<400> SEQUENCE: 17

```
Ile Gly Glu Leu Cys Arg Tyr Leu Leu Asn Gln Pro Pro Arg Glu Ala
```

-continued

```
1               5                   10                  15

Glu Asn Gln His Gln Val Arg Met Ala Leu Gly Asn Gly Leu Arg Gln
            20                  25                  30

Ser Ile Trp Thr Asn Phe Ser Ser Arg Phe His Ile Pro Gln Val Ala
        35                  40                  45

Glu Phe Tyr Gly Ala Thr Glu Cys Asn Cys Ser Leu Gly Asn Phe Asp
    50                  55                  60

Ser Gln Val Gly Ala Cys Gly Phe Asn Ser Arg Ile Leu Ser Phe Val
65                  70                  75                  80

Tyr Pro Ile Arg Leu Val Arg Val Asn Glu Asp Thr Met Glu Leu Ile
                85                  90                  95

Arg Gly Pro Asp Gly Val Cys Ile Pro Cys Gln Pro Gly Glu Pro Gly
            100                 105                 110

Gln Leu Val Gly Arg Ile Ile Gln Lys Asp Pro Leu Arg Arg Phe Asp
        115                 120                 125

Gly Tyr Leu Asn Gln Gly Ala Asn Asn Lys Lys Ile Ala Lys Asp Val
    130                 135                 140

Phe Lys Lys Gly Asp Gln Ala Tyr Leu Thr Gly Asp Val Leu Val Met
145                 150                 155                 160

Asp Glu Leu Gly Tyr Leu Tyr Phe Arg Asp Arg Thr Gly Asp Thr Phe
                165                 170                 175

Arg Trp Lys Gly Glu Asn Val Ser Thr Thr Glu Val Glu Gly Thr Leu
            180                 185                 190

Ser Arg Leu Leu Asp Met Ala Asp Val Ala Val Tyr Gly Val Glu Val
        195                 200                 205

Pro Gly Thr Glu Gly
    210
```

<210> SEQ ID NO 18
<211> LENGTH: 1278
<212> TYPE: DNA
<213> ORGANISM: Homo sapiens
<220> FEATURE:
<221> NAME/KEY: misc_feature
<222> LOCATION: (1)...(1278)
<223> OTHER INFORMATION: n = A,T,C or G

<400> SEQUENCE: 18

```
cntgcctctt gtaccacgtg atgggacttt gtcgttggga tcctcggctg cttagatctc     60

ggagccacct gtgttctggc ccccaagttc tctacttcct gcttctggga tgactgtcgg    120

cagcatggcg tgacagtgat cctgtatgtg ggcgagctcc tgcgntactt gtgtaacatt    180

ccccagcaac cagaggaccg gacacataca gtccgcctgg caatgggcaa tggactacgg    240

gctgatgtgt ggggagacct tccagcagcg tttcggtcct atttcggatc tngggaagtc    300

ttacgggcty ccacagaagg gcaacatggg gctttagttc aactattgtt gggggcgctg    360

cggggscctg grggcaaaga tggagcttgc ctcctccgaa tgctgtcccc ctttgagctg    420

gtgcagttcg acatggaggc ggcggagcct gtgagggaca atcagggctt ctgcatccct    480

gtagggctag gggagccggg gctgctgttg accaaggtgg taagccagca acccttcgtg    540

ggctaccgcg gcccccgaga gctgtcggaa cggaagctgg tgcgcaacgt gcggcaatcg    600

ggcgacgttt actacaacac cggggacgta ctggccatgg accgcgaagg cttcctctac    660

ttccgcgacc gactcgggga caccttccga tggaagggcg agaacgtgtc cacgcacgag    720

gtggagggcg tgttgtcgca ggtggacttc ttgcaacagg ttaacgtgta tggcgtgtgc    780
```

-continued

```
gtgccaggtt gtgagggtaa ggtgggcatg gctgctgtgg cattagcccc cggccagact    840

ttcgacgggg agaagttgta ccagcacgtt cgcgcttggc tccctgccta cgctaccccc    900

catttcatcc gcatccagga cgccatggag gtcaccagca cgttcaaact gatgaagacc    960

cggttggtgc gtgagggctt caatgtgggg atcgtggttg accctctgtt tgtactggac   1020

aaccgggccc agtccttccg gcccctgacg gcagaaatgt accaggctgt gtgtgaggga   1080

acctggaggc tctgatcacc tggccaaccc actggggtag ggatcaaagc cagccacccc   1140

caccccaaca cactcggtgt ccctttcatc ctgggcctgt gtgaatccca gcctggccat   1200

accctcaacc tcagtgggct ggaaatgaca gtgggccctg tagcagtggc agaataaact   1260

cagmtgygtt cacagaaa                                                 1278
```

<210> SEQ ID NO 19
<211> LENGTH: 199
<212> TYPE: PRT
<213> ORGANISM: Homo sapiens

<400> SEQUENCE: 19

```
Glu Gly Gln His Gly Ala Leu Val Gln Leu Leu Leu Gly Ala Leu Arg
 1               5                  10                  15

Gly Pro Gly Gly Lys Asp Gly Ala Cys Leu Leu Arg Met Leu Ser Pro
            20                  25                  30

Phe Glu Leu Val Gln Phe Asp Met Glu Ala Ala Glu Pro Val Arg Asp
        35                  40                  45

Asn Gln Gly Phe Cys Ile Pro Val Gly Leu Gly Glu Pro Gly Leu Leu
    50                  55                  60

Leu Thr Lys Val Val Ser Gln Gln Pro Phe Val Gly Tyr Arg Gly Pro
65                  70                  75                  80

Arg Glu Leu Ser Glu Arg Lys Leu Val Arg Asn Val Arg Gln Ser Gly
                85                  90                  95

Asp Val Tyr Tyr Asn Thr Gly Asp Val Leu Ala Met Asp Arg Glu Gly
            100                 105                 110

Phe Leu Tyr Phe Arg Asp Arg Leu Gly Asp Thr Phe Arg Trp Lys Gly
        115                 120                 125

Glu Asn Val Ser Thr His Glu Val Glu Gly Val Leu Ser Gln Val Asp
    130                 135                 140

Phe Leu Gln Gln Val Asn Val Tyr Gly Val Cys Val Pro Gly Cys Glu
145                 150                 155                 160

Gly Lys Val Gly Met Ala Ala Val Ala Leu Ala Pro Gly Gln Thr Phe
                165                 170                 175

Asp Gly Glu Lys Leu Tyr Gln His Val Arg Ala Trp Leu Pro Ala Tyr
            180                 185                 190

Ala Thr Pro His Phe Ile Arg
        195
```

<210> SEQ ID NO 20
<211> LENGTH: 1361
<212> TYPE: DNA
<213> ORGANISM: Homo sapiens

<400> SEQUENCE: 20

```
cgcttgtgtg ttaaagaaga aattttcagc aagccagttt tggagtgact gcaagaagta     60

tgatgtgact gtgtttcagt atattggaga actttgtcgc tacctttgca aacaatctaa    120

gagagaagga gaaaaggatc ataaggtgcg tttggcaatt ggaaatggca tacggagtga    180
```

-continued

```
tgtatggaga gaatttttag acagatttgg aaatataaag gtgtgtgaac tttatgcagc    240

taccgaatca agcatatctt tcatgaacta cactgggaga attggagcaa ttgggagaac    300

aaatttgttt tacaaacttc tttccacttt tgacttaata aagtatgact ttcagaaaga    360

tgaacccatg agaaatgagc agggttgggt attcatgaga aaaaggagac ctggacttct    420

catttctcga gtgaatgcaa aaaatccctt ctttggctat gctgggcctt ataagcacac    480

aaaagacaaa ttgctttgtg atgtttttaa gaagggagat gtttacctta atactggaga    540

cttaatagtc caggatcagg acaatttcct ttatttttgg gaccgtactg gagacacttt    600

cagatggaaa ggagaaaatg tcgcaaccac tgaggttgct gatgttattg gaatgttgga    660

tttcatacag gaagcaaacg tctatggtgt ggctatatca ggttatgaag gaagagcagg    720

aatggcttct attattttaa aaccaaatac atctttagat ttggaaaaag tttatgaaca    780

agttgtaaca tttctaccag cttatgcttg tccacgattt ttaagaattc aggaaaaaat    840

ggaagcaaca ggaacattca aactattgaa gcatcagttg gtggaagatg gatttaatcc    900

actgaaaatt tctgaaccac tttacttcat ggataacttg aaaaagtctt atgttctact    960

gaccagggaa ctttatgatc aaataatgtt aggggaaata aaactttaag atttttatat   1020

ctagaacttt catatgcttt cttaggaaga gtgagagggg ggtatatgat tctttatgaa   1080

atggggaaag ggagctaaca ttaattatgc atgtactata tttccttaat atgagagata   1140

attttttaat tgcataagaa ttttaatttc ttttaattga tataaacaga gttgattatt   1200

ctttttatct atttggagat tcagtgcata actaagtatt ttccttaata ctaaagattt   1260

taaataataa atagtggcta gcggtttgga caatcactaa aaatgtactt tctaataagt   1320

aaaatttcta attttgaata aaagattaaa ttttactgaa a                        1361
```

```
<210> SEQ ID NO 21
<211> LENGTH: 335
<212> TYPE: PRT
<213> ORGANISM: Homo sapiens

<400> SEQUENCE: 21

Ala Cys Val Leu Lys Lys Lys Phe Ser Ala Ser Gln Phe Trp Ser Asp
 1               5                  10                  15

Cys Lys Lys Tyr Asp Val Thr Val Phe Gln Tyr Ile Gly Glu Leu Cys
            20                  25                  30

Arg Tyr Leu Cys Lys Gln Ser Lys Arg Glu Gly Glu Lys Asp His Lys
        35                  40                  45

Val Arg Leu Ala Ile Gly Asn Gly Ile Arg Ser Asp Val Trp Arg Glu
    50                  55                  60

Phe Leu Asp Arg Phe Gly Asn Ile Lys Val Cys Glu Leu Tyr Ala Ala
65                  70                  75                  80

Thr Glu Ser Ser Ile Ser Phe Met Asn Tyr Thr Gly Arg Ile Gly Ala
                85                  90                  95

Ile Gly Arg Thr Asn Leu Phe Tyr Lys Leu Leu Ser Thr Phe Asp Leu
            100                 105                 110

Ile Lys Tyr Asp Phe Gln Lys Asp Glu Pro Met Arg Asn Glu Gln Gly
        115                 120                 125

Trp Val Phe Met Arg Lys Arg Arg Pro Gly Leu Leu Ile Ser Arg Val
    130                 135                 140

Asn Ala Lys Asn Pro Phe Phe Gly Tyr Ala Gly Pro Tyr Lys His Thr
145                 150                 155                 160

Lys Asp Lys Leu Leu Cys Asp Val Phe Lys Lys Gly Asp Val Tyr Leu
```

-continued

```
                165                 170                 175

Asn Thr Gly Asp Leu Ile Val Gln Asp Gln Asp Asn Phe Leu Tyr Phe
            180                 185                 190

Trp Asp Arg Thr Gly Asp Thr Phe Arg Trp Lys Gly Glu Asn Val Ala
        195                 200                 205

Thr Thr Glu Val Ala Asp Val Ile Gly Met Leu Asp Phe Ile Gln Glu
    210                 215                 220

Ala Asn Val Tyr Gly Val Ala Ile Ser Gly Tyr Glu Gly Arg Ala Gly
225                 230                 235                 240

Met Ala Ser Ile Ile Leu Lys Pro Asn Thr Ser Leu Asp Leu Glu Lys
                245                 250                 255

Val Tyr Glu Gln Val Val Thr Phe Leu Pro Ala Tyr Ala Cys Pro Arg
            260                 265                 270

Phe Leu Arg Ile Gln Glu Lys Met Glu Ala Thr Gly Thr Phe Lys Leu
        275                 280                 285

Leu Lys His Gln Leu Val Glu Asp Gly Phe Asn Pro Leu Lys Ile Ser
    290                 295                 300

Glu Pro Leu Tyr Phe Met Asp Asn Leu Lys Lys Ser Tyr Val Leu Leu
305                 310                 315                 320

Thr Arg Glu Leu Tyr Asp Gln Ile Met Leu Gly Glu Ile Lys Leu
                325                 330                 335


<210> SEQ ID NO 22
<211> LENGTH: 2007
<212> TYPE: DNA
<213> ORGANISM: Mycobacterium tuberculosis

<400> SEQUENCE: 22

tagtcgataa cgtcaaggac gctctgcggg cctgcgcacc ttcctgaggt tggtcgacaa     60

ccaattcgac atttcgcaaa cgaatcgagg gcttacgtgt ccgattacta cggcggcgca    120

cacacaacgg tcaggctgat cgacctggca actcggatgc cgcgagtgtt ggcggacacg    180

ccggtgattg tgcgtggggc aatgaccggg ctgctggccc ggccgaattc caaggcgtcg    240

atcggcacgg tgttccagga ccgggccgct cgctacggtg accgagtctt cctgaaattc    300

ggcgatcagc agctgaccta ccgcgacgct aacgccaccg ccaaccggta cgccgcggtg    360

ttggccgccc gcggcgtcgg ccccggcgac gtcgttggca tcatgttgcg taactcaccc    420

agcacagtct tggcgatgct ggccacggtc aagtgcggcg ctatcgccgg catgctcaac    480

taccaccagc gcggcgaggt gttggcgcac agcctgggtc tgctggacgc gaaggtactg    540

atcgcagagt ccgacttggt cagcgccgtc gccgaatgcg gcgcctcgcg cggccgggta    600

gcgggcgacg tgctgaccgt cgaggacgtg gagcgattcg ccacaacggc gcccgccacc    660

aacccggcgt cggcgtcggc ggtgcaagcc aaagacaccg cgttctacat cttcacctcg    720

ggcaccaccg gatttcccaa ggccagtgtc atgacgcatc atcggtggct gcgggcgctg    780

gccgtcttcg gagggatggg gctgcggctg aagggttccg acacgctcta cagctgcctg    840

ccgctgtacc acaacaacgc gttaacggtc gcggtgtcgt cggtgatcaa ttctggggcg    900

accctggcgc tgggtaagtc gttttcggcg tcgcggttct gggatgaggt gattgccaac    960

cgggcgacgg cgttcgtcta catcggcgaa atctgccgtt atctgctcaa ccagccggcc   1020

aagccgaccg accgtgccca ccaggtgcgg gtgatctgcg gtaacgggct gcggccggag   1080

atctgggatg agttcaccac ccgcttcggg gtcgcgcggg tgtgcgagtt ctacgccgcc   1140

agcgaaggca actcggcctt tatcaacatc ttcaacgtgc ccaggaccgc cggggtatcg   1200
```

-continued ccgatgccgc ttgcctttgt ggaatacgac ctggacaccg gcgatccgct gcgggatgcg 1260
agcgggcgag tgcgtcgggt acccgacggt gaacccggcc tgttgcttag ccgggtcaac 1320
cggctgcagc cgttcgacgg ctacaccgac ccggttgcca gcgaaaagaa gttggtgcgc 1380
aacgcttttc gagatggcga ctgttggttc aacaccggtg acgtgatgag cccgcagggc 1440
atgggccatg ccgccttcgt cgatcggctg ggcgacacct tccgctggaa gggcgagaat 1500
gtcgccacca ctcaggtcga agcggcactg gcctccgacc agaccgtcga ggagtgcacg 1560
gtctacggcg tccagattcc gcgcaccggc gggcgcgccg gaatggccgc gatcacactg 1620
cgcgctggcg ccgaattcga cggccaggcg ctggcccgaa cggtttacgg tcacttgccc 1680
ggctatgcac ttccgctctt tgttcgggta gtggggtcgc tggcgcacac cacgacgttc 1740
aagagtcgca aggtggagtt gcgcaaccag gcctatggcg ccgacatcga ggatccgctg 1800
tacgtactgg ccggcccgga cgaaggatat gtgccgtact acgccgaata ccctgaggag 1860
gtttcgctcg gaaggcgacc gcagggctag cggattccgg gcgcagtctc gatacccgca 1920
ctggacgctc gacggtaacc aggcactatg gatgcgtgcg ttcaacaccg ccggcctcag 1980
ccggtcgttc aacaccgccg gcgttag 2007

<210> SEQ ID NO 23
<211> LENGTH: 597
<212> TYPE: PRT
<213> ORGANISM: Mycobacterium tuberculosis

<400> SEQUENCE: 23

Met Ser Asp Tyr Tyr Gly Gly Ala His Thr Thr Val Arg Leu Ile Asp
1 5 10 15

Leu Ala Thr Arg Met Pro Arg Val Leu Ala Asp Thr Pro Val Ile Val
20 25 30

Arg Gly Ala Met Thr Gly Leu Leu Ala Arg Pro Asn Ser Lys Ala Ser
35 40 45

Ile Gly Thr Val Phe Gln Asp Arg Ala Ala Arg Tyr Gly Asp Arg Val
50 55 60

Phe Leu Lys Phe Gly Asp Gln Gln Leu Thr Tyr Arg Asp Ala Asn Ala
65 70 75 80

Thr Ala Asn Arg Tyr Ala Ala Val Leu Ala Ala Arg Gly Val Gly Pro
85 90 95

Gly Asp Val Val Gly Ile Met Leu Arg Asn Ser Pro Ser Thr Val Leu
100 105 110

Ala Met Leu Ala Thr Val Lys Cys Gly Ala Ile Ala Gly Met Leu Asn
115 120 125

Tyr His Gln Arg Gly Glu Val Leu Ala His Ser Leu Gly Leu Leu Asp
130 135 140

Ala Lys Val Leu Ile Ala Glu Ser Asp Leu Val Ser Ala Val Ala Glu
145 150 155 160

Cys Gly Ala Ser Arg Gly Arg Val Ala Gly Asp Val Leu Thr Val Glu
165 170 175

Asp Val Glu Arg Phe Ala Thr Thr Ala Pro Ala Thr Asn Pro Ala Ser
180 185 190

Ala Ser Ala Val Gln Ala Lys Asp Thr Ala Phe Tyr Ile Phe Thr Ser
195 200 205

Gly Thr Thr Gly Phe Pro Lys Ala Ser Val Met Thr His His Arg Trp
210 215 220

-continued

```
Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
        355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Arg Val Pro Asp Gly Glu Pro
385                 390                 395                 400

Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
        435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
                485                 490                 495

Thr Gly Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
            580                 585                 590

Arg Arg Pro Gln Gly
        595
```

<210> SEQ ID NO 24
<211> LENGTH: 3704
<212> TYPE: DNA
<213> ORGANISM: Homo sapiens
<220> FEATURE:
<221> NAME/KEY: CDS -continued

```
<222> LOCATION: (175)...(2112)

<400> SEQUENCE: 24

tcgacccacg gcgtccggga ccccaaagca gaagcccgca cagtaggcac agcgcaccca      60

agaagggtcc aggagtctgc agaaacagaa aggtccccgg cctcagcctc ctagtccctg     120

cctgcctcct gcctgagctt ctgggagact gaaggcacgg cttgcagctt cagg atg       177
                                                            Met
                                                             1

cgg gct ccg ggt gcg ggc gcg gcc tcg gtg gtc tcg ctg gcg ctg ttg       225
Arg Ala Pro Gly Ala Gly Ala Ala Ser Val Val Ser Leu Ala Leu Leu
            5                  10                  15

tgg ctg ctg ggg ctg ccg tgg acc tgg agc gcg gca gcg gcg ctc ggc       273
Trp Leu Leu Gly Leu Pro Trp Thr Trp Ser Ala Ala Ala Ala Leu Gly
        20                  25                  30

gtg tac gtg ggc agc ggc ggc tgg cgc ttc ctg cgc atc gtc tgc aag       321
Val Tyr Val Gly Ser Gly Gly Trp Arg Phe Leu Arg Ile Val Cys Lys
    35                  40                  45

acc gcg agg cga gac ctc ttc ggt ctc tct gtg ctg atc cgc gtg cgc       369
Thr Ala Arg Arg Asp Leu Phe Gly Leu Ser Val Leu Ile Arg Val Arg
 50                  55                  60                  65

ctg gag ctg cgg cgg cac cag cgt gcc ggc cac acc atc ccg cgc atc       417
Leu Glu Leu Arg Arg His Gln Arg Ala Gly His Thr Ile Pro Arg Ile
                 70                  75                  80

ttt cag gcg gta gtg cag cga cag ccc gag cgc ctg gcg ctg gtg gat       465
Phe Gln Ala Val Val Gln Arg Gln Pro Glu Arg Leu Ala Leu Val Asp
            85                  90                  95

gcc ggg acc ggc gag tgc tgg acc ttt gcg cag ctg gac gcc tac tcc       513
Ala Gly Thr Gly Glu Cys Trp Thr Phe Ala Gln Leu Asp Ala Tyr Ser
        100                 105                 110

aat gcg gta gcc aac ctc ttc cgc cag ctg ggc ttc gcg ccg ggc gac       561
Asn Ala Val Ala Asn Leu Phe Arg Gln Leu Gly Phe Ala Pro Gly Asp
    115                 120                 125

gtg gtg gcc atc ttc ctg gag ggc cgg ccg gag ttc gtg ggg ctg tgg       609
Val Val Ala Ile Phe Leu Glu Gly Arg Pro Glu Phe Val Gly Leu Trp
130                 135                 140                 145

ctg ggc ctg gcc aag gcg ggc atg gag gcc gcg ctg ctc aac gtg aac       657
Leu Gly Leu Ala Lys Ala Gly Met Glu Ala Ala Leu Leu Asn Val Asn
                150                 155                 160

ctg cgg cgc gag ccc ctg gcc ttc tgc ctg ggc acc tcg ggc gct aag       705
Leu Arg Arg Glu Pro Leu Ala Phe Cys Leu Gly Thr Ser Gly Ala Lys
            165                 170                 175

gcc ctg atc ttt gga gga gaa atg gtg gcg gcg gtg gcc gaa gtg agc       753
Ala Leu Ile Phe Gly Gly Glu Met Val Ala Ala Val Ala Glu Val Ser
        180                 185                 190

ggg cat ctg ggg aaa agt ttg atc aag ttc tgc tct gga gac ttg ggg       801
Gly His Leu Gly Lys Ser Leu Ile Lys Phe Cys Ser Gly Asp Leu Gly
    195                 200                 205

ccc gag ggc atc ttg ccg gac acc cac ctc ctg gac ccg ctg ctg aag       849
Pro Glu Gly Ile Leu Pro Asp Thr His Leu Leu Asp Pro Leu Leu Lys
210                 215                 220                 225

gag gcc tct act gcc ccc ttg gca cag atc ccc agc aag ggc atg gac       897
Glu Ala Ser Thr Ala Pro Leu Ala Gln Ile Pro Ser Lys Gly Met Asp
                230                 235                 240

gat cgt ctt ttc tac atc tac acg tcg ggg acc acc ggg ctg ccc aag       945
Asp Arg Leu Phe Tyr Ile Tyr Thr Ser Gly Thr Thr Gly Leu Pro Lys
            245                 250                 255

gct gcc att gtc gtg cac agc agg tac tac cgc atg gca gcc ttc ggc       993
Ala Ala Ile Val Val His Ser Arg Tyr Tyr Arg Met Ala Ala Phe Gly
        260                 265                 270
```

-continued

```
cac cac gcc tac cgc atg cag gcg gct gac gtg ctc tat gac tgc ctg     1041
His His Ala Tyr Arg Met Gln Ala Ala Asp Val Leu Tyr Asp Cys Leu
    275                 280                 285

ccc ctg tac cac tcg gca gga aac atc atc ggc gtg ggg cag tgt ctc     1089
Pro Leu Tyr His Ser Ala Gly Asn Ile Ile Gly Val Gly Gln Cys Leu
290                 295                 300                 305

atc tat ggg ctg aca gtc gtc ctc cgc aag aaa ttc tcg gcc agc cgc     1137
Ile Tyr Gly Leu Thr Val Val Leu Arg Lys Lys Phe Ser Ala Ser Arg
                310                 315                 320

ttc tgg gac gac tgc atc aag tac aac tgc acg gtg gtt cag tac atc     1185
Phe Trp Asp Asp Cys Ile Lys Tyr Asn Cys Thr Val Val Gln Tyr Ile
            325                 330                 335

ggg gag atc tgc cgc tac ctg ctg aag cag ccg gtg cgc gag gcg gag     1233
Gly Glu Ile Cys Arg Tyr Leu Leu Lys Gln Pro Val Arg Glu Ala Glu
        340                 345                 350

agg cga cac cgc gtg cgc ctg gcg gtg ggg aac ggg ctg cgt cct gcc     1281
Arg Arg His Arg Val Arg Leu Ala Val Gly Asn Gly Leu Arg Pro Ala
    355                 360                 365

atc tgg gag gag ttc acg gag cgc ttc ggc gta cgc caa atc ggg gag     1329
Ile Trp Glu Glu Phe Thr Glu Arg Phe Gly Val Arg Gln Ile Gly Glu
370                 375                 380                 385

ttc tac ggc gcc acc gag tgc aac tgc agc att gcc aac atg gac ggc     1377
Phe Tyr Gly Ala Thr Glu Cys Asn Cys Ser Ile Ala Asn Met Asp Gly
                390                 395                 400

aag gtc ggc tcc tgt ggt ttc aac agc cgc atc ctg ccc cac gtg tac     1425
Lys Val Gly Ser Cys Gly Phe Asn Ser Arg Ile Leu Pro His Val Tyr
            405                 410                 415

ccc atc cgg ctg gtg aag gtc aat gag gac aca atg gag ctg ctg cgg     1473
Pro Ile Arg Leu Val Lys Val Asn Glu Asp Thr Met Glu Leu Leu Arg
        420                 425                 430

gat gcc cag ggc ctc tgc atc ccc tgc cag gcc ggg gag cct ggc ctc     1521
Asp Ala Gln Gly Leu Cys Ile Pro Cys Gln Ala Gly Glu Pro Gly Leu
    435                 440                 445

ctt gtg ggt cag atc aac caa cag gac ccg ctg cgc cgc ttc gat ggc     1569
Leu Val Gly Gln Ile Asn Gln Gln Asp Pro Leu Arg Arg Phe Asp Gly
450                 455                 460                 465

tat gtc agc gag agc gcc acc agc aag aag atc gcc cac agc gtc ttc     1617
Tyr Val Ser Glu Ser Ala Thr Ser Lys Lys Ile Ala His Ser Val Phe
                470                 475                 480

agc aag ggc gac agc gcc tac ctc tca ggt gac gtg cta gtg atg gat     1665
Ser Lys Gly Asp Ser Ala Tyr Leu Ser Gly Asp Val Leu Val Met Asp
            485                 490                 495

gag ctg ggc tac atg tac ttc cgg gac cgt agc ggg gac acc ttc cgc     1713
Glu Leu Gly Tyr Met Tyr Phe Arg Asp Arg Ser Gly Asp Thr Phe Arg
        500                 505                 510

tgg cga ggg gag aac gtc tcc acc acc gag gtg gag ggc gtg ctg agc     1761
Trp Arg Gly Glu Asn Val Ser Thr Thr Glu Val Glu Gly Val Leu Ser
    515                 520                 525

cgc ctg ctg ggc cag aca gac gtg gcc gtc tat ggg gtg gct gtt cca     1809
Arg Leu Leu Gly Gln Thr Asp Val Ala Val Tyr Gly Val Ala Val Pro
530                 535                 540                 545

gga gtg gag ggt aag gca ggg atg gcg gcc gtc gca gac ccc cac agc     1857
Gly Val Glu Gly Lys Ala Gly Met Ala Ala Val Ala Asp Pro His Ser
                550                 555                 560

ctg ctg gac ccc aac gcg ata tac cag gag ctg cag aag gtg ctg gca     1905
Leu Leu Asp Pro Asn Ala Ile Tyr Gln Glu Leu Gln Lys Val Leu Ala
            565                 570                 575

ccc tat gcc cgg ccc atc ttc ctg cgc ctc ctg ccc cag gtg gac acc     1953
Pro Tyr Ala Arg Pro Ile Phe Leu Arg Leu Leu Pro Gln Val Asp Thr
```

-continued

```
        580                 585                 590

aca ggc acc ttc aag atc cag aag acg agg ctg cag cga gag ggc ttt     2001
Thr Gly Thr Phe Lys Ile Gln Lys Thr Arg Leu Gln Arg Glu Gly Phe
    595                 600                 605

gac cca cgc cag acc tca gac cgg ctc ttc ttc ctg gac ctg aag cag     2049
Asp Pro Arg Gln Thr Ser Asp Arg Leu Phe Phe Leu Asp Leu Lys Gln
610                 615                 620                 625

ggc cac tac ctg ccc tta aat gag gca gtc tac act cgc atc tgc tcg     2097
Gly His Tyr Leu Pro Leu Asn Glu Ala Val Tyr Thr Arg Ile Cys Ser
                630                 635                 640

ggc gcc ttc gcc ctc tgaagctgtt cctctactgg ccacaaactc tgggcctggt     2152
Gly Ala Phe Ala Leu
            645

gggagaggcc agcttgagcc agacagcgct gcccaggggt ggccgcctag tacacaccca   2212

cctggccgag ctgtacctgg cacggcccat cctggactga gaaactggaa cctcagagga   2272

acccgtgcct ctctgctgcc ttggtgcccc tgtgtctgcc tcctctccct gcttttcagc   2332

ctctgtctcc ttccatccct gtccctgtct ggccttaact cttccctctc tttcttttct   2392

ttctttcttt cttttttttt aagatagagt ctcactctgc tgcccgggct agagtgcagt   2452

ggtgggatct cggctcactg caacctctgc ctcctggggt tcaagtgatc ctcccacctc   2512

agcctcctga gtagctggga ttacaggcac ccgccaccac gtccagctaa tttttatatt   2572

tttagtagag acggggtttc accatgttgg tcaggctggt cttgaactcc tgacctcagg   2632

tgatccgctg gcctcggcct cccagagtgc tgggattata ggcgtgagcc tctggcccgg   2692

cctttccttt ttcctctcct ctcctgccga gagtggaaca cacgtgtcct gggagctgca   2752

tcttgtgtag ggtccagctg cttttgggga ctgcaggaat catctcccct gggccctgga   2812

ctcggactgg ggcctcccca cctccctctc ggctgtgcct tacggagccc caatccaggc   2872

ctcctgtggc tgttgggttc cagatgctgc agctccatgt gacttccaag caggccctcc   2932

gccctccctg ctgaatggag gagccggggg tcccccaggc caactggaaa atctcccagg   2992

ctaggccaat tgccttttgc acttccccgt tcctgtcaca tttccccagc cccaccttcc   3052

cctcctgatg ccctgaaagc ttccggaatt gactgtgacc acttggatgt caccactgtc   3112

agcccctgcc ttgatgtccc catttagcca tctccatgga gctcctgctg gagggccctg   3172

aaccctgcac tgcgtggctg cccagccagc tgcctcctgt cctgggagga ggcctcctgg   3232

gtgtcctcat ctggtgtgtc tactggaggg tcccacagga gaggcagcag aggggtcagg   3292

ggaggtctcc tgccggggggt tggcctctca agcctcaggg gttctagcct gttgaatata   3352

ccccacctgg tgggtggccc ctccgatgtc cccactgatg gctctgacac cgtgttggtg   3412

gcgatgtccc agacaatccc accaggacgg cccagacatc cctactggct tcgctggtgg   3472

ctcatctcga acatccacgc cagcctttct ggggccggcc acccaggccg cctgtccgtc   3532

tgtcctccct ccagcagcac cccctggccc ctggagtggt ggggccatgg caagagacac   3592

cgtggcgtct catgtgaact ttcctgggca ctgtggtttt atttcctaat tgatttaaga   3652

aataaacctg aagaccgtct ggtgaaaaaa aaaaaaaaaa aagggcggcc gc           3704
```

<210> SEQ ID NO 25
<211> LENGTH: 646
<212> TYPE: PRT
<213> ORGANISM: Homo sapiens

<400> SEQUENCE: 25

Met Arg Ala Pro Gly Ala Gly Ala Ala Ser Val Val Ser Leu Ala Leu

-continued

```
1               5                  10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80

Ile Phe Gln Ala Val Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Ala Val Ala Glu Val
            180                 185                 190

Ser Gly His Leu Gly Lys Ser Leu Ile Lys Phe Cys Ser Gly Asp Leu
        195                 200                 205

Gly Pro Glu Gly Ile Leu Pro Asp Thr His Leu Leu Asp Pro Leu Leu
    210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
        275                 280                 285

Leu Pro Leu Tyr His Ser Ala Gly Asn Ile Ile Gly Val Gly Gln Cys
    290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430
```

-continued

```
Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly His Tyr Leu Pro Leu Asn Glu Ala Val Tyr Thr Arg Ile Cys
625                 630                 635                 640

Ser Gly Ala Phe Ala Leu
                645


<210> SEQ ID NO 26
<211> LENGTH: 2917
<212> TYPE: DNA
<213> ORGANISM: Homo sapiens
<220> FEATURE:
<221> NAME/KEY: CDS
<222> LOCATION: (208)...(2136)

<400> SEQUENCE: 26

cgacccacgc gtccgggcgg gcggggccgg gcggcgggcg gggctggcgg ggcggccggg      60

ccatgcaggg cgcagagccg gctaaaccct gctgagaccc ggctccgtgc gtccaggggc     120

ggctaatgcc cctcacgctg tctacgctgc tgcaaccggg ccgcatctgg acggggcgcc     180

gcgcggcgga gccgacgccg ggccaca atg ctg ctt gga gcc tct ctg gtg ggg     234
                              Met Leu Leu Gly Ala Ser Leu Val Gly
                               1               5

gtg ctg ctg ttc tcc aag ctg gtg ctg aaa ctg ccc tgg acc cag gtg       282
Val Leu Leu Phe Ser Lys Leu Val Leu Lys Leu Pro Trp Thr Gln Val
 10                  15                  20                  25

gga ttc tcc ctg ttg ttc ctc tac ttg gga tct ggc ggc tgg cgc ttc       330
Gly Phe Ser Leu Leu Phe Leu Tyr Leu Gly Ser Gly Gly Trp Arg Phe
                 30                  35                  40

atc cgg gtc ttc atc aag acc atc agg cgc gat atc ttt ggc ggc ctg       378
Ile Arg Val Phe Ile Lys Thr Ile Arg Arg Asp Ile Phe Gly Gly Leu
             45                  50                  55

gtc ctc ctg aag gtg aag gca aag gtg cga cag tgc ctg cag gag cgg       426
Val Leu Leu Lys Val Lys Ala Lys Val Arg Gln Cys Leu Gln Glu Arg
         60                  65                  70
```

```
cgg aca gtg ccc att ttg ttt gcc tct acc gtt cgg cgc cac ccc gac      474
Arg Thr Val Pro Ile Leu Phe Ala Ser Thr Val Arg Arg His Pro Asp
     75                  80                  85

aag acg gcc ctg atc ttc gag ggc aca gat acc cac tgg acc ttc cgc      522
Lys Thr Ala Leu Ile Phe Glu Gly Thr Asp Thr His Trp Thr Phe Arg
 90                  95                 100                 105

cag ctg gat gag tac tca agc agt gta gcc aac ttc ctg cag gcc cgg      570
Gln Leu Asp Glu Tyr Ser Ser Ser Val Ala Asn Phe Leu Gln Ala Arg
                110                 115                 120

ggc ctg gcc tcg ggc gat gtg gct gcc atc ttc atg gag aac cgc aat      618
Gly Leu Ala Ser Gly Asp Val Ala Ala Ile Phe Met Glu Asn Arg Asn
            125                 130                 135

gag ttc gtg ggc cta tgg ctg ggc atg gcc aag ctc ggt gtg gag gca      666
Glu Phe Val Gly Leu Trp Leu Gly Met Ala Lys Leu Gly Val Glu Ala
        140                 145                 150

gcc ctc atc aac acc aac ctg cgg cgg gat gct ctg ctc cac tgc ctc      714
Ala Leu Ile Asn Thr Asn Leu Arg Arg Asp Ala Leu Leu His Cys Leu
    155                 160                 165

acc acc tcg cgc gca cgg gcc ctt gtc ttt ggc agc gaa atg gcc tca      762
Thr Thr Ser Arg Ala Arg Ala Leu Val Phe Gly Ser Glu Met Ala Ser
170                 175                 180                 185

gcc atc tgt gag gtc cat gcc agc ctg gac ccc tcg ctc agc ctc ttc      810
Ala Ile Cys Glu Val His Ala Ser Leu Asp Pro Ser Leu Ser Leu Phe
                190                 195                 200

tgc tct ggc tcc tgg gag ccc ggt gcg gtg cct cca agc aca gaa cac      858
Cys Ser Gly Ser Trp Glu Pro Gly Ala Val Pro Pro Ser Thr Glu His
            205                 210                 215

ctg gac cct ctg ctg aaa gat gct ccc aag cac ctt ccc agt tgc cct      906
Leu Asp Pro Leu Leu Lys Asp Ala Pro Lys His Leu Pro Ser Cys Pro
        220                 225                 230

gac aag ggc ttc aca gat aaa ctg ttc tac atc tac aca tcc ggc acc      954
Asp Lys Gly Phe Thr Asp Lys Leu Phe Tyr Ile Tyr Thr Ser Gly Thr
    235                 240                 245

aca ggg ctg ccc aag gcc gcc atc gtg gtg cac agc agg tat tac cgc     1002
Thr Gly Leu Pro Lys Ala Ala Ile Val Val His Ser Arg Tyr Tyr Arg
250                 255                 260                 265

atg gct gcc ctg gtg tac tat gga ttc cgc atg cgg ccc aac gac atc     1050
Met Ala Ala Leu Val Tyr Tyr Gly Phe Arg Met Arg Pro Asn Asp Ile
                270                 275                 280

gtc tat gac tgc ctc ccc ctc tac cac tca gca gga aac atc gtg gga     1098
Val Tyr Asp Cys Leu Pro Leu Tyr His Ser Ala Gly Asn Ile Val Gly
            285                 290                 295

atc ggc cag tgc ctg ctg cat ggc atg acg gtg gtg att cgg aag aag     1146
Ile Gly Gln Cys Leu Leu His Gly Met Thr Val Val Ile Arg Lys Lys
        300                 305                 310

ttc tca gcc tcc cgg ttc tgg gac gat tgt atc aag tac aac tgc acg     1194
Phe Ser Ala Ser Arg Phe Trp Asp Asp Cys Ile Lys Tyr Asn Cys Thr
    315                 320                 325

att gtg cag tac att ggt gaa ctg tgc cgc tac ctc ctg aac cag cca     1242
Ile Val Gln Tyr Ile Gly Glu Leu Cys Arg Tyr Leu Leu Asn Gln Pro
330                 335                 340                 345

ccg cgg gag gca gaa aac cag cac cag gtt cgc atg gca cta ggc aat     1290
Pro Arg Glu Ala Glu Asn Gln His Gln Val Arg Met Ala Leu Gly Asn
                350                 355                 360

ggc ctc cgg cag tcc atc tgg acc aac ttt tcc agc cgc ttc cac ata     1338
Gly Leu Arg Gln Ser Ile Trp Thr Asn Phe Ser Ser Arg Phe His Ile
            365                 370                 375

ccc cag gtg gct gag ttc tac ggg gcc aca gag tgc aac tgt agc ctg     1386
Pro Gln Val Ala Glu Phe Tyr Gly Ala Thr Glu Cys Asn Cys Ser Leu
```

-continued

```
        380                 385                 390

ggc aac ttc gac agc cag gtg ggg gcc tgt ggt ttc aat agc cgc atc     1434
Gly Asn Phe Asp Ser Gln Val Gly Ala Cys Gly Phe Asn Ser Arg Ile
    395                 400                 405

ctg tcc ttc gtg tac ccc atc cgg ttg gta cgt gtc aac gag gac acc     1482
Leu Ser Phe Val Tyr Pro Ile Arg Leu Val Arg Val Asn Glu Asp Thr
410                 415                 420                 425

atg gag ctg atc cgg ggg ccc gac ggc gtc tgc att ccc tgc cag cca     1530
Met Glu Leu Ile Arg Gly Pro Asp Gly Val Cys Ile Pro Cys Gln Pro
                430                 435                 440

ggt gag ccg ggc cag ctg gtg ggc cgc atc atc cag aaa gac ccc ctg     1578
Gly Glu Pro Gly Gln Leu Val Gly Arg Ile Ile Gln Lys Asp Pro Leu
            445                 450                 455

cgc cgc ttc gat ggc tac ctc aac cag ggc gcc aac aac aag aag att     1626
Arg Arg Phe Asp Gly Tyr Leu Asn Gln Gly Ala Asn Asn Lys Lys Ile
        460                 465                 470

gcc aag gat gtc ttc aag aag ggg gac cag gcc tac ctt act ggt gat     1674
Ala Lys Asp Val Phe Lys Lys Gly Asp Gln Ala Tyr Leu Thr Gly Asp
    475                 480                 485

gtg ctg gtg atg gac gag ctg ggc tac ctg tac ttc cga gac cgc act     1722
Val Leu Val Met Asp Glu Leu Gly Tyr Leu Tyr Phe Arg Asp Arg Thr
490                 495                 500                 505

ggg gac acg ttc cgc tgg aaa ggt gag aac gtg tcc acc acc gag gtg     1770
Gly Asp Thr Phe Arg Trp Lys Gly Glu Asn Val Ser Thr Thr Glu Val
                510                 515                 520

gaa ggc aca ctc agc cgc ctg ctg gac atg gct gac gtg gcc gtg tat     1818
Glu Gly Thr Leu Ser Arg Leu Leu Asp Met Ala Asp Val Ala Val Tyr
            525                 530                 535

ggt gtc gag gtg cca gga acc gag ggc cgg gcc gga atg gct gct gtg     1866
Gly Val Glu Val Pro Gly Thr Glu Gly Arg Ala Gly Met Ala Ala Val
        540                 545                 550

gcc agc ccc act ggc aac tgt gac ctg gag cgc ttt gct cag gtc ttg     1914
Ala Ser Pro Thr Gly Asn Cys Asp Leu Glu Arg Phe Ala Gln Val Leu
    555                 560                 565

gag aag gaa ctg ccc ctg tat gcg cgc ccc atc ttc ctg cgc ctc ctg     1962
Glu Lys Glu Leu Pro Leu Tyr Ala Arg Pro Ile Phe Leu Arg Leu Leu
570                 575                 580                 585

cct gag ctg cac aaa aca gga acc tac aag ttc cag aag aca gag cta     2010
Pro Glu Leu His Lys Thr Gly Thr Tyr Lys Phe Gln Lys Thr Glu Leu
                590                 595                 600

cgg aag gag ggc ttt gac ccg gct att gtg aaa gac ccg ctg ttc tat     2058
Arg Lys Glu Gly Phe Asp Pro Ala Ile Val Lys Asp Pro Leu Phe Tyr
            605                 610                 615

cta gat gcc cag aag ggc cgc tac gtc ccg ctg gac caa gag gcc tac     2106
Leu Asp Ala Gln Lys Gly Arg Tyr Val Pro Leu Asp Gln Glu Ala Tyr
        620                 625                 630

agc cgc atc cag gca ggc gag gag aag ctg tgattccccc catccctctg       2156
Ser Arg Ile Gln Ala Gly Glu Glu Lys Leu
    635                 640

agggccggcg gatgctggat ccggagcccc aggttccgcc ccagagcggt cctggacaag   2216

gccagaccaa agcaagcagg gcctggcacc tccatcctga ggtgctgccc ctccatccaa   2276

aactgccaag tgactcattg ccttcccaac ccttccagag gctttctgtg aaagtctcat   2336

gtccaagttc cgtcttctgg gctgggcagg ccctctggtt cccaggctga gactgacggg   2396

ttttctcagg atgatgtctt gggtgagggt agggagagga caaggggtca ccgagccctt   2456

cccagagagc agggagctta taaatggaac cagagcagaa gtccccagac tcaggaagtc   2516

aacagagtgg gcagggacag tggtagcatc catctggtgg ccaaagagaa tcgtagcccc   2576
```

-continued

```
agagctgccc aagttcactg ggctccaccc ccacctccag gaggggagga gaggacctga   2636

catctgtagg tggcccctga tgccccatct acagcaggag gtcaggacca cgcccctggc   2696

ctctccccac tcccccatcc tcctccctgg gtggctgcct gattatccct caggcagggc   2756

ctctcagtcc ttgtgggtct gtgtcacctc catctcagtc ttggcctggc tatgagggga   2816

ggaggaatgg gagagggggc tcaggggcca ataaactctg ccttgagtcc tcctaaaaaa   2876

aaaaaaaaaa aaaaaaaaaa aaaaaaaaaa agggcggccg c                       2917
```

<210> SEQ ID NO 27
<211> LENGTH: 643
<212> TYPE: PRT
<213> ORGANISM: Homo sapiens

<400> SEQUENCE: 27

```
Met Leu Leu Gly Ala Ser Leu Val Gly Val Leu Leu Phe Ser Lys Leu
 1               5                  10                  15

Val Leu Lys Leu Pro Trp Thr Gln Val Gly Phe Ser Leu Leu Phe Leu
            20                  25                  30

Tyr Leu Gly Ser Gly Gly Trp Arg Phe Ile Arg Val Phe Ile Lys Thr
        35                  40                  45

Ile Arg Arg Asp Ile Phe Gly Gly Leu Val Leu Leu Lys Val Lys Ala
    50                  55                  60

Lys Val Arg Gln Cys Leu Gln Glu Arg Arg Thr Val Pro Ile Leu Phe
65                  70                  75                  80

Ala Ser Thr Val Arg Arg His Pro Asp Lys Thr Ala Leu Ile Phe Glu
                85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asp Val
        115                 120                 125

Ala Ala Ile Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Leu His Cys Leu Thr Thr Ser Arg Ala Arg Ala
                165                 170                 175

Leu Val Phe Gly Ser Glu Met Ala Ser Ala Ile Cys Glu Val His Ala
            180                 185                 190

Ser Leu Asp Pro Ser Leu Ser Leu Phe Cys Ser Gly Ser Trp Glu Pro
        195                 200                 205

Gly Ala Val Pro Pro Ser Thr Glu His Leu Asp Pro Leu Leu Lys Asp
    210                 215                 220

Ala Pro Lys His Leu Pro Ser Cys Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ala Leu Val Tyr Tyr
            260                 265                 270

Gly Phe Arg Met Arg Pro Asn Asp Ile Val Tyr Asp Cys Leu Pro Leu
        275                 280                 285

Tyr His Ser Ala Gly Asn Ile Val Gly Ile Gly Gln Cys Leu Leu His
    290                 295                 300

Gly Met Thr Val Val Ile Arg Lys Lys Phe Ser Ala Ser Arg Phe Trp
```

-continued

```
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Asn Gln
            340                 345                 350

His Gln Val Arg Met Ala Leu Gly Asn Gly Leu Arg Gln Ser Ile Trp
        355                 360                 365

Thr Asn Phe Ser Ser Arg Phe His Ile Pro Gln Val Ala Glu Phe Tyr
    370                 375                 380

Gly Ala Thr Glu Cys Asn Cys Ser Leu Gly Asn Phe Asp Ser Gln Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Glu Pro Gly Gln Leu Val
        435                 440                 445

Gly Arg Ile Ile Gln Lys Asp Pro Leu Arg Arg Phe Asp Gly Tyr Leu
    450                 455                 460

Asn Gln Gly Ala Asn Asn Lys Lys Ile Ala Lys Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
        515                 520                 525

Leu Asp Met Ala Asp Val Ala Val Tyr Gly Val Glu Val Pro Gly Thr
    530                 535                 540

Glu Gly Arg Ala Gly Met Ala Ala Val Ala Ser Pro Thr Gly Asn Cys
545                 550                 555                 560

Asp Leu Glu Arg Phe Ala Gln Val Leu Glu Lys Glu Leu Pro Leu Tyr
                565                 570                 575

Ala Arg Pro Ile Phe Leu Arg Leu Leu Pro Glu Leu His Lys Thr Gly
            580                 585                 590

Thr Tyr Lys Phe Gln Lys Thr Glu Leu Arg Lys Glu Gly Phe Asp Pro
        595                 600                 605

Ala Ile Val Lys Asp Pro Leu Phe Tyr Leu Asp Ala Gln Lys Gly Arg
    610                 615                 620

Tyr Val Pro Leu Asp Gln Glu Ala Tyr Ser Arg Ile Gln Ala Gly Glu
625                 630                 635                 640

Glu Lys Leu
```

<210> SEQ ID NO 28
<211> LENGTH: 1941
<212> TYPE: DNA
<213> ORGANISM: Homo sapiens

<400> SEQUENCE: 28

```
atgcgggctc cgggtgcggg cgcggcctcg gtggtctcgc tggcgctgtt gtggctgctg      60

gggctgccgt ggacctggag cgcggcagcg gcgctcggcg tgtacgtggg cagcggcggc     120

tggcgcttcc tgcgcatcgt ctgcaagacc gcgaggcgag acctcttcgg tctctctgtg     180

ctgatccgcg tgcgcctgga gctgcggcgg caccagcgtg ccggccacac catcccgcgc     240
```

-continued

```
atctttcagg cggtagtgca gcgacagccc gagcgcctgg cgctggtgga tgccgggacc    300
ggcgagtgct ggacctttgc gcagctggac gcctactcca atgcggtagc caacctcttc    360
cgccagctgg gcttcgcgcc gggcgacgtg gtggccatct tcctggaggg ccggccggag    420
ttcgtggggc tgtggctggg cctggccaag gcgggcatgg aggccgcgct gctcaacgtg    480
aacctgcggc gcgagcccct ggccttctgc ctgggcacct cgggcgctaa ggccctgatc    540
tttggaggag aaatggtggc ggcggtggcc gaagtgagcg ggcatctggg gaaaagtttg    600
atcaagttct gctctggaga cttggggccc gagggcatct tgccggacac ccacctcctg    660
gacccgctgc tgaaggaggc ctctactgcc cccttggcac agatccccag caagggcatg    720
gacgatcgtc ttttctacat ctacacgtcg gggaccaccg ggctgcccaa ggctgccatt    780
gtcgtgcaca gcaggtacta ccgcatggca gccttcggcc accacgccta ccgcatgcag    840
gcggctgacg tgctctatga ctgcctgccc ctgtaccact cggcaggaaa catcatcggc    900
gtggggcagt gtctcatcta tgggctgaca gtcgtcctcc gcaagaaatt ctcggccagc    960
cgcttctggg acgactgcat caagtacaac tgcacggtgg ttcagtacat cggggagatc   1020
tgccgctacc tgctgaagca gccggtgcgc gaggcggaga ggcgacaccg cgtgcgcctg   1080
gcggtgggga acgggctgcg tcctgccatc tgggaggagt tcacggagcg cttcggcgta   1140
cgccaaatcg gggagttcta cggcgccacc gagtgcaact gcagcattgc caacatggac   1200
ggcaaggtcg gctcctgtgg tttcaacagc cgcatcctgc cccacgtgta ccccatccgg   1260
ctggtgaagg tcaatgagga cacaatggag ctgctgcggg atgcccaggg cctctgcatc   1320
ccctgccagg ccggggagcc tggcctcctt gtgggtcaga tcaaccaaca ggacccgctg   1380
cgccgcttcg atggctatgt cagcgagagc gccaccagca agaagatcgc ccacagcgtc   1440
ttcagcaagg gcgacagcgc ctacctctca ggtgacgtgc tagtgatgga tgagctgggc   1500
tacatgtact tccgggaccg tagcggggac accttccgct ggcgagggga gaacgtctcc   1560
accaccgagg tggagggcgt gctgagccgc ctgctgggcc agacagacgt ggccgtctat   1620
ggggtggctg ttccaggagt ggagggtaag gcagggatgg cggccgtcgc agacccccac   1680
agcctgctgg accccaacgc gatataccag gagctgcaga aggtgctggc accctatgcc   1740
cggcccatct tcctgcgcct cctgccccag gtggacacca caggcacctt caagatccag   1800
aagacgaggc tgcagcgaga gggctttgac ccacgccaga cctcagaccg gctcttcttc   1860
ctggacctga agcagggcca ctacctgccc ttaaatgagg cagtctacac tcgcatctgc   1920
tcgggcgcct tcgccctctg a                                             1941
```

<210> SEQ ID NO 29
<211> LENGTH: 1938
<212> TYPE: DNA
<213> ORGANISM: Mus musculus

<400> SEQUENCE: 29

```
atgcgggctc ctggagcagg aacagcctct gtggcctcac tggcgctgct ttggtttctg     60
ggacttccgt ggacctggag cgcggcggcg gcgttctgtg tgtacgtggg tggcggcggc    120
tggcgctttc tgcgtatcgt ctgcaagacg gcgaggcgag acctctttgg cctctctgtt    180
ctgattcgtg ttcggctaga gctgcgacga caccggcgag caggagacac gatcccgtgc    240
atcttccagg ctgtggcccg gcgacaacca gagcgcctgg cactggtgga cgccagtagt    300
ggtatatgct ggaccttcgc acagctggac acctactcca atgctgtagc caacctgttc    360
```

-continued

```
cgccagctgg gctttgcacc aggcgatgtg gtggctgtgt tcctggaggg ccggccggag    420

ttcgtgggac tgtggctggg cctggccaag gccggtgtgg tggctgctct tctcaatgtc    480

aacctgaggc gggagcccct ggccttctgc ctgggcacat cagctgccaa ggccctcatt    540

tatggcgggg agatggcagc ggcggtggcg gaggtgagcg agcagctggg gaagagcctc    600

ctcaagttct gctctggaga tctggggcct gagagcatcc tgcctgacac gcagctcctg    660

gaccccatgc ttgctgaggc gcccaccaca cccctggcac aagccccagg caagggcatg    720

gatgatcggc tgttttacat ctatacttct gggaccaccg ggcttcctaa ggctgccatt    780

gtggtgcaca gcaggtacta ccgcattgct gcctttggcc accattccta cagcatgcgt    840

gccgccgatg tgctctatga ctgcctgcca ctctaccact ctgcagggaa catcatgggt    900

gtggggcagt gcgtcatcta cgggttgacg gtggtactgc gcaagaagtt ctccgccagc    960

cgcttctggg atgactgtgt caagtacaat tgcacggtag tgcagtacat aggtgaaatc   1020

tgccgctacc tgctgaggca gccggttcgc gacgtggagc agcgacaccg cgtgcgcctg   1080

gccgtgggta atgggctgcg gccagccatc tgggaggagt tcacgcagcg cttcggtgtg   1140

ccacagatcg gcgagttcta cggcgctacc gagtgcaact gcagcattgc caacatggac   1200

ggcaaggtcg gctcctgcgg cttcaacagc cgtatcctca cgcatgtgta ccccatccgt   1260

ctggtcaagg tcaatgagga cacgatggag ccactgcggg actccgaggg cctctgcatc   1320

ccgtgccagc ccggggaacc cggccttctc gtgggccaga tcaaccagca ggaccctctg   1380

cggcgtttcg atggttatgt tagtgacagt gccaccaaca agaagattgc ccacagcgtt   1440

ttccgaaagg gcgatagcgc ctacctctca ggtgacgtgc tagtgatgga cgagctgggc   1500

tacatgtatt tccgtgaccg cagcggggac accttccgct ggcgcgggga gaacgtgtcc   1560

accacggagg tggaagccgt gctgagccgc ctactgggcc agacggacgt ggctgtgtat   1620

ggggtggctg tgccaggagt ggaggggaaa gctggcatgg cagccatcgc agatccccac   1680

agccagttgg accctaactc aatgtaccag gaattacaga aggttcttgc atcctatgct   1740

cggcccatct tcctgcgtct tctgccccag gtggatacca caggcacctt caagatccag   1800

aagacccggc tgcagcgtga aggctttgac ccccgtcaga cctcagacag gctcttcttt   1860

ctagacctga agcagggacg ctatgtaccc ctggatgaga gagtccatgc ccgcatttgt   1920

gcaggcgact tctcactc                                                 1938
```

<210> SEQ ID NO 30
<211> LENGTH: 1896
<212> TYPE: DNA
<213> ORGANISM: Homo sapiens

<400> SEQUENCE: 30

```
ctgttctcca agctggtgct gaaactgccc tggacccagg tgggattctc cctgttgttc     60

ctctacttgg gatctggcgg ctggcgcttc atccgggtct tcatcaagac catcaggcgc    120

gatatctttg gcggcctggt cctcctgaag gtgaaggcaa aggtgcgaca gtgcctgcag    180

gagcggcgga cagtgcccat tttgtttgcc tctaccgttc ggcgccaccc cgacaagacg    240

gccctgatct tcgagggcac agatacccac tggaccttcc gccagctgga tgagtactca    300

agcagtgtag ccaacttcct gcaggcccgg ggcctggcct cgggcgatgt ggctgccatc    360

ttcatggaga accgcaatga gttcgtgggc ctatggctgg gcatggccaa gctcggtgtg    420

gaggcagccc tcatcaacac caacctgcgg cgggatgctc tgctccactg cctcaccacc    480

tcgcgcgcac gggcccttgt ctttggcagc gaaatggcct cagccatctg tgaggtccat    540
```

-continued

```
gccagcctgg accccctcgct cagcctcttc tgctctggct cctgggagcc cggtgcggtg    600
cctccaagca cagaacacct ggaccctctg ctgaaagatg ctcccaagca ccttcccagt    660
tgccctgaca agggcttcac agataaactg ttctacatct acacatccgg caccacaggg    720
ctgcccaagg ccgccatcgt ggtgcacagc aggtattacc gcatggctgc cctggtgtac    780
tatggattcc gcatgcggcc caacgacatc gtctatgact gcctccccct ctaccactca    840
gcaggaaaca tcgtgggaat cggccagtgc ctgctgcatg gcatgacggt ggtgattcgg    900
aagaagttct cagcctcccg gttctgggac gattgtatca agtacaactg cacgattgtg    960
cagtacattg gtgaactgtg ccgctacctc ctgaaccagc caccgcggga ggcagaaaac   1020
cagcaccagg ttcgcatggc actaggcaat ggcctccggc agtccatctg gaccaacttt   1080
tccagccgct tccacatacc ccaggtggct gagttctacg gggccacaga gtgcaactgt   1140
agcctgggca acttcgacag ccaggtgggg gcctgtggtt tcaatagccg catcctgtcc   1200
ttcgtgtacc ccatccggtt ggtacgtgtc aacgaggaca ccatggagct gatccggggg   1260
cccgacggcg tctgcattcc ctgccagcca ggtgagccgg gccagctggt gggccgcatc   1320
atccagaaag accccctgcg ccgcttcgat ggctacctca accagggcgc caacaacaag   1380
aagattgcca aggatgtctt caagaagggg gaccaggcct accttactgg tgatgtgctg   1440
gtgatggacg agctgggcta cctgtacttc cgagaccgca ctggggacac gttccgctgg   1500
aaaggtgaga acgtgtccac caccgaggtg gaaggcacac tcagccgcct gctggacatg   1560
gctgacgtgg ccgtgtatgg tgtcgaggtg ccaggaaccg agggccgggc cggaatggct   1620
gctgtggcca gccccactgg caactgtgac ctggagcgct ttgctcaggt cttggagaag   1680
gaactgcccc tgtatgcgcg ccccatcttc ctgcgcctcc tgcctgagct gcacaaaaca   1740
ggaacctaca agttccagaa gacagagcta cggaaggagg gctttgaccc ggctattgtg   1800
aaagacccgc tgttctatct agatgcccag aagggccgct acgtcccgct ggaccaagag   1860
gcctacagcc gcatccaggc aggcgaggag aagctg                              1896
```

```
<210> SEQ ID NO 31
<211> LENGTH: 1896
<212> TYPE: DNA
<213> ORGANISM: Mus musculus

<400> SEQUENCE: 31
```

```
cttgggtcca agctagtgct gaagctgccc tggacccagg tgggattctc cctgttgctc     60
ctgtacttgg ggtctggtgg ctggcgtttc atccgggtct tcatcaagac ggtcaggaga    120
gatatctttg gtggcatggt gctcctgaag gtgaagacca aggtgcgacg gtaccttcag    180
gagcggaaga cggtgcccct gctgtttgct tcaatggtac agcgccaccc ggacaagaca    240
gccctgattt tcgagggcac agacactcac tggaccttcc gccagctgga tgagtactcc    300
agtagtgtgg ccaacttcct gcaggcccgg ggcctggcct caggcaatgt agttgccctc    360
tttatggaaa accgcaatga gtttgtgggt ctgtggctag gcatggccaa gctgggcgtg    420
gaggcggctc tcatcaacac caaccttagg cgggatgccc tgcgccactg tcttgacacc    480
tcaaaggcac gagctctcat ctttggcagt gagatggcct cagctatctg tgagatccat    540
gctagcctgg agcccacact cagcctcttc tgctctggat cctgggagcc cagcacagtg    600
cccgtcagca cagagcatct ggaccctctt ctggaagatg ccccgaagca cctgcccagt    660
cacccagaca agggttttac agataagctc ttctacatct acacatcggg caccacgggg    720
```

-continued

```
ctacccaaag ctgccattgt ggtgcacagc aggtattatc gtatggcttc cctggtgtac    780

tatggattcc gcatgcggcc tgatgacatt gtctatgact gcctcccccct ctaccactca    840

agcaggaaac atcgtgggga ttggcagtgc ttactccacg gcatgactgt ggtgatccgg    900

aagaagttct cagcctcccg gttctgggat gattgtatca agtacaactg cacagtggta    960

cagtacattg gcgagctctg ccgctacctc ctgaaccagc caccccgtga ggctgagtct   1020

cggcacaagg tgcgcatggc actgggcaac ggtctccggc agtccatctg gaccgacttc   1080

tccagccgtt tccacatccc ccaggtggct gagttctatg ggccactga atgcaactgt   1140

agcctgggca actttgacag ccgggtgggg gcctgtggct tcaatagccg catcctgtcc   1200

tttgtgtacc ctatccgttt ggtacgtgtc aatgaggata ccatggaact gatccgggga   1260

cccgatggag tctgcattcc ctgtcaacca ggtcagccag gccagctggt gggtcgcatc   1320

atccagcagg accctctgcg ccgtttcgac gggtacctca accagggtgc caacaacaag   1380

aagattgcta atgatgtctt caagaagggg gaccaagcct acctcactgg tgacgtcctg   1440

gtgatggatg agctgggtta cctgtacttc cgagatcgca ctggggacac gttccgctgg   1500

aaaggggaga atgtatctac cactgaggtg gagggcacac tcagccgcct gcttcatatg   1560

gcagatgtgg cagtttatgg tgttgaggtg ccaggaactg aaggccgagc aggaatggct   1620

gccgttgcaa gtcccatcag caactgtgac ctggagagct ttgcacagac cttgaaaaag   1680

gagctgcctc tgtatgcccg ccccatcttc ctgcgcttct tgcctgagct gcacaagaca   1740

gggaccttca agttccagaa gacagagttg cggaaggagg gctttgaccc atctgttgtg   1800

aaagacccgc tgttctatct ggatgctcgg aagggctgct acgttgcact ggaccaggag   1860

gcctataccc gcatccaggc aggcgaggag aagctg                             1896
```

```
<210> SEQ ID NO 32
<211> LENGTH: 646
<212> TYPE: PRT
<213> ORGANISM: Homo sapiens

<400> SEQUENCE: 32

Met Arg Ala Pro Gly Ala Gly Ala Ala Ser Val Val Ser Leu Ala Leu
 1               5                  10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80

Ile Phe Gln Ala Val Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
```

-continued

```
                165                 170                 175

Lys Ala Leu Ile Phe Gly Gly Glu Met Val Ala Ala Val Ala Glu Val
            180                 185                 190

Ser Gly His Leu Gly Lys Ser Leu Ile Lys Phe Cys Ser Gly Asp Leu
        195                 200                 205

Gly Pro Glu Gly Ile Leu Pro Asp Thr His Leu Leu Asp Pro Leu Leu
    210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
        275                 280                 285

Leu Pro Leu Tyr His Ser Ala Gly Asn Ile Ile Gly Val Gly Gln Cys
    290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590
```

-continued

```
Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly His Tyr Leu Pro Leu Asn Glu Ala Val Tyr Thr Arg Ile Cys
625                 630                 635                 640

Ser Gly Ala Phe Ala Leu
                645


<210> SEQ ID NO 33
<211> LENGTH: 646
<212> TYPE: PRT
<213> ORGANISM: Mus musculus

<400> SEQUENCE: 33

Met Arg Ala Pro Gly Ala Gly Thr Ala Ser Val Ala Ser Leu Ala Leu
 1               5                  10                  15

Leu Trp Phe Leu Gly Leu Pro Trp Thr Trp Ser Ala Ala Ala Ala Phe
            20                  25                  30

Cys Val Tyr Val Gly Gly Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Arg Arg Ala Gly Asp Thr Ile Pro Cys
65                  70                  75                  80

Ile Phe Gln Ala Val Ala Arg Arg Gln Pro Glu Arg Leu Ala Leu Val
                85                  90                  95

Asp Ala Ser Ser Gly Ile Cys Trp Thr Phe Ala Gln Leu Asp Thr Tyr
            100                 105                 110

Ser Asn Ala Val Ala Asn Leu Phe Arg Gln Leu Gly Phe Ala Pro Gly
        115                 120                 125

Asp Val Val Ala Val Phe Leu Glu Gly Arg Pro Glu Phe Val Gly Leu
    130                 135                 140

Trp Leu Gly Leu Ala Lys Ala Gly Val Val Ala Ala Leu Leu Asn Val
145                 150                 155                 160

Asn Leu Arg Arg Glu Pro Leu Ala Phe Cys Leu Gly Thr Ser Ala Ala
                165                 170                 175

Lys Ala Leu Ile Tyr Gly Gly Glu Met Ala Ala Ala Val Ala Glu Val
            180                 185                 190

Ser Glu Gln Leu Gly Lys Ser Leu Leu Lys Phe Cys Ser Gly Asp Leu
        195                 200                 205

Gly Pro Glu Ser Ile Leu Pro Asp Thr Gln Leu Leu Asp Pro Met Leu
    210                 215                 220

Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Ile Ala Ala Phe
            260                 265                 270

Gly His His Ser Tyr Ser Met Arg Ala Ala Asp Val Leu Tyr Asp Cys
        275                 280                 285

Leu Pro Leu Tyr His Ser Ala Gly Asn Ile Met Gly Val Gly Gln Cys
    290                 295                 300

Val Ile Tyr Gly Leu Thr Val Val Leu Arg Lys Lys Phe Ser Ala Ser
```

-continued

```
305                 310                 315                 320

Arg Phe Trp Asp Asp Cys Val Lys Tyr Asn Cys Thr Val Val Gln Tyr
                325                 330                 335

Ile Gly Glu Ile Cys Arg Tyr Leu Leu Arg Gln Pro Val Arg Asp Val
            340                 345                 350

Glu Gln Arg His Arg Val Arg Leu Ala Val Gly Asn Gly Leu Arg Pro
        355                 360                 365

Ala Ile Trp Glu Glu Phe Thr Gln Arg Phe Gly Val Pro Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
                405                 410                 415

Tyr Pro Ile Arg Leu Val Lys Val Asn Glu Asp Thr Met Glu Pro Leu
            420                 425                 430

Arg Asp Ser Glu Gly Leu Cys Ile Pro Cys Gln Pro Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Ala Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Ile Ala Asp Pro His
545                 550                 555                 560

Ser Gln Leu Asp Pro Asn Ser Met Tyr Gln Glu Leu Gln Lys Val Leu
                565                 570                 575

Ala Ser Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly Arg Tyr Val Pro Leu Asp Glu Arg Val His Ala Arg Ile Cys
625                 630                 635                 640

Ala Gly Asp Phe Ser Leu
                645


<210> SEQ ID NO 34
<211> LENGTH: 632
<212> TYPE: PRT
<213> ORGANISM: Homo sapiens

<400> SEQUENCE: 34

Leu Phe Ser Lys Leu Val Leu Lys Leu Pro Trp Thr Gln Val Gly Phe
 1               5                  10                  15

Ser Leu Leu Phe Leu Tyr Leu Gly Ser Gly Gly Trp Arg Phe Ile Arg
            20                  25                  30
```

-continued

```
Val Phe Ile Lys Thr Ile Arg Arg Asp Ile Phe Gly Gly Leu Val Leu
        35                  40                  45

Leu Lys Val Lys Ala Lys Val Arg Gln Cys Leu Gln Glu Arg Arg Thr
    50                  55                  60

Val Pro Ile Leu Phe Ala Ser Thr Val Arg Arg His Pro Asp Lys Thr
65                  70                  75                  80

Ala Leu Ile Phe Glu Gly Thr Asp Thr His Trp Thr Phe Arg Gln Leu
                85                  90                  95

Asp Glu Tyr Ser Ser Ser Val Ala Asn Phe Leu Gln Ala Arg Gly Leu
            100                 105                 110

Ala Ser Gly Asp Val Ala Ala Ile Phe Met Glu Asn Arg Asn Glu Phe
        115                 120                 125

Val Gly Leu Trp Leu Gly Met Ala Lys Leu Gly Val Glu Ala Ala Leu
    130                 135                 140

Ile Asn Thr Asn Leu Arg Arg Asp Ala Leu Leu His Cys Leu Thr Thr
145                 150                 155                 160

Ser Arg Ala Arg Ala Leu Val Phe Gly Ser Glu Met Ala Ser Ala Ile
                165                 170                 175

Cys Glu Val His Ala Ser Leu Asp Pro Ser Leu Ser Leu Phe Cys Ser
            180                 185                 190

Gly Ser Trp Glu Pro Gly Ala Val Pro Pro Ser Thr Glu His Leu Asp
        195                 200                 205

Pro Leu Leu Lys Asp Ala Pro Lys His Leu Pro Ser Cys Pro Asp Lys
    210                 215                 220

Gly Phe Thr Asp Lys Leu Phe Tyr Ile Tyr Thr Ser Gly Thr Thr Gly
225                 230                 235                 240

Leu Pro Lys Ala Ala Ile Val Val His Ser Arg Tyr Tyr Arg Met Ala
                245                 250                 255

Ala Leu Val Tyr Tyr Gly Phe Arg Met Arg Pro Asn Asp Ile Val Tyr
            260                 265                 270

Asp Cys Leu Pro Leu Tyr His Ser Ala Gly Asn Ile Val Gly Ile Gly
        275                 280                 285

Gln Cys Leu Leu His Gly Met Thr Val Val Ile Arg Lys Lys Phe Ser
    290                 295                 300

Ala Ser Arg Phe Trp Asp Asp Cys Ile Lys Tyr Asn Cys Thr Ile Val
305                 310                 315                 320

Gln Tyr Ile Gly Glu Leu Cys Arg Tyr Leu Leu Asn Gln Pro Pro Arg
                325                 330                 335

Glu Ala Glu Asn Gln His Gln Val Arg Met Ala Leu Gly Asn Gly Leu
            340                 345                 350

Arg Gln Ser Ile Trp Thr Asn Phe Ser Ser Arg Phe His Ile Pro Gln
        355                 360                 365

Val Ala Glu Phe Tyr Gly Ala Thr Glu Cys Asn Cys Ser Leu Gly Asn
    370                 375                 380

Phe Asp Ser Gln Val Gly Ala Cys Gly Phe Asn Ser Arg Ile Leu Ser
385                 390                 395                 400

Phe Val Tyr Pro Ile Arg Leu Val Arg Val Asn Glu Asp Thr Met Glu
                405                 410                 415

Leu Ile Arg Gly Pro Asp Gly Val Cys Ile Pro Cys Gln Pro Gly Glu
            420                 425                 430

Pro Gly Gln Leu Val Gly Arg Ile Ile Gln Lys Asp Pro Leu Arg Arg
        435                 440                 445

Phe Asp Gly Tyr Leu Asn Gln Gly Ala Asn Asn Lys Lys Ile Ala Lys
```

-continued

```
    450                 455                 460

Asp Val Phe Lys Lys Gly Asp Gln Ala Tyr Leu Thr Gly Asp Val Leu
465                 470                 475                 480

Val Met Asp Glu Leu Gly Tyr Leu Tyr Phe Arg Asp Arg Thr Gly Asp
                485                 490                 495

Thr Phe Arg Trp Lys Gly Glu Asn Val Ser Thr Thr Glu Val Glu Gly
            500                 505                 510

Thr Leu Ser Arg Leu Leu Asp Met Ala Asp Val Ala Val Tyr Gly Val
        515                 520                 525

Glu Val Pro Gly Thr Glu Gly Arg Ala Gly Met Ala Ala Val Ala Ser
    530                 535                 540

Pro Thr Gly Asn Cys Asp Leu Glu Arg Phe Ala Gln Val Leu Glu Lys
545                 550                 555                 560

Glu Leu Pro Leu Tyr Ala Arg Pro Ile Phe Leu Arg Leu Leu Pro Glu
                565                 570                 575

Leu His Lys Thr Gly Thr Tyr Lys Phe Gln Lys Thr Glu Leu Arg Lys
            580                 585                 590

Glu Gly Phe Asp Pro Ala Ile Val Lys Asp Pro Leu Phe Tyr Leu Asp
        595                 600                 605

Ala Gln Lys Gly Arg Tyr Val Pro Leu Asp Gln Glu Ala Tyr Ser Arg
    610                 615                 620

Ile Gln Ala Gly Glu Glu Lys Leu
625                 630


<210> SEQ ID NO 35
<211> LENGTH: 632
<212> TYPE: PRT
<213> ORGANISM: Mus musculus

<400> SEQUENCE: 35

Leu Gly Ser Lys Leu Val Leu Lys Leu Pro Trp Thr Gln Val Gly Phe
 1               5                  10                  15

Ser Leu Leu Leu Leu Tyr Leu Gly Ser Gly Gly Trp Arg Phe Ile Arg
            20                  25                  30

Val Phe Ile Lys Thr Val Arg Arg Asp Ile Phe Gly Gly Met Val Leu
        35                  40                  45

Leu Lys Val Lys Thr Lys Val Arg Arg Tyr Leu Gln Glu Arg Lys Thr
    50                  55                  60

Val Pro Leu Leu Phe Ala Ser Met Val Gln Arg His Pro Asp Lys Thr
65                  70                  75                  80

Ala Leu Ile Phe Glu Gly Thr Asp Thr His Trp Thr Phe Arg Gln Leu
                85                  90                  95

Asp Glu Tyr Ser Ser Ser Val Ala Asn Phe Leu Gln Ala Arg Gly Leu
            100                 105                 110

Ala Ser Gly Asn Val Val Ala Leu Phe Met Glu Asn Arg Asn Glu Phe
        115                 120                 125

Val Gly Leu Trp Leu Gly Met Ala Lys Leu Gly Val Glu Ala Ala Leu
    130                 135                 140

Ile Asn Thr Asn Leu Arg Arg Asp Ala Leu Arg His Cys Leu Asp Thr
145                 150                 155                 160

Ser Lys Ala Arg Ala Leu Ile Phe Gly Ser Glu Met Ala Ser Ala Ile
                165                 170                 175

Cys Glu Ile His Ala Ser Leu Glu Pro Thr Leu Ser Leu Phe Cys Ser
            180                 185                 190
```

-continued

```
Gly Ser Trp Glu Pro Ser Thr Val Pro Val Ser Thr Glu His Leu Asp
        195                 200                 205

Pro Leu Leu Glu Asp Ala Pro Lys His Leu Pro Ser His Pro Asp Lys
    210                 215                 220

Gly Phe Thr Asp Lys Leu Phe Tyr Ile Tyr Thr Ser Gly Thr Thr Gly
225                 230                 235                 240

Leu Pro Lys Ala Ala Ile Val Val His Ser Arg Tyr Tyr Arg Met Ala
                245                 250                 255

Ser Leu Val Tyr Tyr Gly Phe Arg Met Arg Pro Asp Asp Ile Val Tyr
            260                 265                 270

Asp Cys Leu Pro Leu Tyr His Ser Ser Arg Lys His Arg Gly Asp Trp
        275                 280                 285

Gln Cys Leu Leu His Gly Met Thr Val Val Ile Arg Lys Lys Phe Ser
    290                 295                 300

Ala Ser Arg Phe Trp Asp Asp Cys Ile Lys Tyr Asn Cys Thr Val Val
305                 310                 315                 320

Gln Tyr Ile Gly Glu Leu Cys Arg Tyr Leu Leu Asn Gln Pro Pro Arg
                325                 330                 335

Glu Ala Glu Ser Arg His Lys Val Arg Met Ala Leu Gly Asn Gly Leu
            340                 345                 350

Arg Gln Ser Ile Trp Thr Asp Phe Ser Ser Arg Phe His Ile Pro Gln
        355                 360                 365

Val Ala Glu Phe Tyr Gly Ala Thr Glu Cys Asn Cys Ser Leu Gly Asn
    370                 375                 380

Phe Asp Ser Arg Val Gly Ala Cys Gly Phe Asn Ser Arg Ile Leu Ser
385                 390                 395                 400

Phe Val Tyr Pro Ile Arg Leu Val Arg Val Asn Glu Asp Thr Met Glu
                405                 410                 415

Leu Ile Arg Gly Pro Asp Gly Val Cys Ile Pro Cys Gln Pro Gly Gln
            420                 425                 430

Pro Gly Gln Leu Val Gly Arg Ile Ile Gln Gln Asp Pro Leu Arg Arg
        435                 440                 445

Phe Asp Gly Tyr Leu Asn Gln Gly Ala Asn Asn Lys Lys Ile Ala Asn
    450                 455                 460

Asp Val Phe Lys Lys Gly Asp Gln Ala Tyr Leu Thr Gly Asp Val Leu
465                 470                 475                 480

Val Met Asp Glu Leu Gly Tyr Leu Tyr Phe Arg Asp Arg Thr Gly Asp
                485                 490                 495

Thr Phe Arg Trp Lys Gly Glu Asn Val Ser Thr Thr Glu Val Glu Gly
            500                 505                 510

Thr Leu Ser Arg Leu Leu His Met Ala Asp Val Ala Val Tyr Gly Val
        515                 520                 525

Glu Val Pro Gly Thr Glu Gly Arg Ala Gly Met Ala Ala Val Ala Ser
    530                 535                 540

Pro Ile Ser Asn Cys Asp Leu Glu Ser Phe Ala Gln Thr Leu Lys Lys
545                 550                 555                 560

Glu Leu Pro Leu Tyr Ala Arg Pro Ile Phe Leu Arg Phe Leu Pro Glu
                565                 570                 575

Leu His Lys Thr Gly Thr Phe Lys Phe Gln Lys Thr Glu Leu Arg Lys
            580                 585                 590

Glu Gly Phe Asp Pro Ser Val Val Lys Asp Pro Leu Phe Tyr Leu Asp
        595                 600                 605

Ala Arg Lys Gly Cys Tyr Val Ala Leu Asp Gln Glu Ala Tyr Thr Arg
```

-continued 610 615 620

Ile Gln Ala Gly Glu Glu Lys Leu
625 630

<210> SEQ ID NO 36
<211> LENGTH: 2885
<212> TYPE: DNA
<213> ORGANISM: Homo sapiens

<400> SEQUENCE: 36
aacggcaagt aagcgcaacg caattaatgt gagtagctca ctcattaggc accccaggct 60
ttacacttta tgcttccggg ctcgtatgtt gtgtggaatt gtgagcggat accaatttca 120
cacaggaacc agctatgaca tgattacgaa tttaatacga ctcactatag ggaatttggc 180
cctcgaggcc aagaattcgg cacgaggggt gctgagcccc tgcgcggttt ctggtgcgta 240
gagactgtaa atcgctgcgc ttctcagtca tcatcatccc agcttttccc ggctcgaatt 300
cagcctccaa ctcaagctcg cgggaaagac tacctgagag gagaaaagct tctgtccctg 360
gaccttcttc tgagggtgga gtcggaggct ccctgctttc cagccgccca gtgacccaag 420
cttaatcttc agcaccactt ggggcgacct tttcggtgca aacctacgat tctgtttctc 480
aggattcctc cccatcccgc ttcgccccgg aaaagctgac aagaacttca ggtgtaagcc 540
ctgagtagtg aggatctgcg gtctccgtgg agagctgtgc ctggaagaga aggacgctgg 600
tgggggctga gatcagagct gtcttctggc ccagttgccc ccatgcttct gtcatggcta 660
acagttctag gggctggaat ggtcgtcctg cacttcttgc agaaactcct gttcccttac 720
ttttgggatg acttctggtt cgtgttgaag gtggtgctca ttataattcg gctgaagaag 780
tatgaaaaga gaggggagct ggtgactgtg ctggataaat tcttgagtca tgccaaaaga 840
caacctcgga aacctttcat catctatgag ggagacatct acacctatca ggatgtagac 900
aaaaggagca gcagagtggc ccatgtcttc ctgaaccatt cctctctgaa aaagggggac 960
acggtggctc tgctgatgag caatgagccg gacttcgttc acgtgtggtt cggcctcgcc 1020
aagctgggct gcgtggtggc ctttctcaac accaacattc gctccaactc cctcctgaat 1080
tgcatccgcg cctgtgggcc cagagcccta gtggtgggcg cagatttgct tggaacggta 1140
gaagaaatcc ttccaagcct ctcagaaaat atcagtgttt gggggatgaa agattctgtt 1200
ccacaaggtg taatttcact caaagaaaaa ctgagcacct cacctgatga gcccgtgcca 1260
cgcagccacc atgttgtctc actcctcaag tctacttgtc tttacatttt tacctctgga 1320
acaacaggtc taccaaaagc agctgtgatt agtcagctgc aggttttaag ggggttctgct 1380 gtcctgtggg cttttggttg tactgctcat gacattgttt atataaccct tcctctgtat 1440
catagttcag cagctatcct gggaatttct ggatgtgttg agttgggtgc cacttgtgtg 1500
ttaaagaaga aattttcagc aagccagttt tggagtgact gcaagaagta tgatgtgact 1560
gtgtttcagt atattggaga actttgtcgc tacctttgca aacaatctaa gagagaagga 1620
gaaaaggatc ataaggtgcg tttggcaatt ggaaatggca tacggagtga tgtatggaga 1680
gaatttttag acagatttgg aaatataaag gtgtgtgaac tttatgcagc taccgaatca 1740
agcatatctt tcatgaacta cactgggaga attggagcaa ttgggagaac aaatttgttt 1800
tacaaacttc tttccacttt tgacttaata aagtatgact ttcagaaaga tgaacccatg 1860
agaaatgagc agggttggtg tattcatgtg aaaaaaggag aacctggact tctcatttct 1920
cgagtgaatg caaaaaatcc cttctttggc tatgctgggc cttataagca cacaaaagac 1980

-continued

```
aaattgcttt gtgatgtttt taagaaggga gatgtttacc ttaatactgg agacttaata   2040

gtccaggatc aggacaattt cctttatttt tgggaccgta ctggagacac tttcagatgg   2100

aaaggagaaa atgtcgcaac cactgaggtt gctgatgtta ttggaatgtt ggatttcata   2160

caggaagcaa acgtctatgg tgtggctata tcaggttatg aaggaagagc aggaatggct   2220

tctattattt taaaaccaaa tacatcttta gatttggaaa aagtttatga acaagttgta   2280

acatttctac cagcttatgc ttgtccacga tttttaagaa ttcaggaaaa aatggaagca   2340

acaggaacat tcaaactatt gaagcatcag ttggtggaag atggatttaa tccactgaaa   2400

atttctgaac cactttactt catggataac ttgaaaaagt cttatgttct actgaccagg   2460

gaactttatg atcaaataat gttaggggaa ataaaacttt aagattttta tatctagaac   2520

tttcatatgc tttcttagga agagtgagag gggggtatat gattctttat gaaatgggga   2580

aagggagcta acattaatta tgcatgtact atatttcctt aatatgagag ataatttttt   2640

aattgcataa gaattttaat ttcttttaat tgatataaac attagttgat tattcttttt   2700

atctatttgg agattcagtg cataactaag tattttcctt aatactaaag attttaaata   2760

ataaatagtg gctagcggtt tggacaatca ctaaaaatgt actttctaat aagtaaaatt   2820

tctaattttg aataaaagat taaattttac tgaaaaaaaa aaaaaaaaaa aaaattggcg   2880

gccgc                                                               2885
```

```
<210> SEQ ID NO 37
<211> LENGTH: 619
<212> TYPE: PRT
<213> ORGANISM: Homo sapiens

<400> SEQUENCE: 37

Met Leu Leu Ser Trp Leu Thr Val Leu Gly Ala Gly Met Val Val Leu
 1               5                  10                  15

His Phe Leu Gln Lys Leu Leu Phe Pro Tyr Phe Trp Asp Asp Phe Trp
            20                  25                  30

Phe Val Leu Lys Val Val Leu Ile Ile Ile Arg Leu Lys Lys Tyr Glu
        35                  40                  45

Lys Arg Gly Glu Leu Val Thr Val Leu Asp Lys Phe Leu Ser His Ala
    50                  55                  60

Lys Arg Gln Pro Arg Lys Pro Phe Ile Ile Tyr Glu Gly Asp Ile Tyr
65                  70                  75                  80

Thr Tyr Gln Asp Val Asp Lys Arg Ser Ser Arg Val Ala His Val Phe
                85                  90                  95

Leu Asn His Ser Ser Leu Lys Lys Gly Asp Thr Val Ala Leu Leu Met
            100                 105                 110

Ser Asn Glu Pro Asp Phe Val His Val Trp Phe Gly Leu Ala Lys Leu
        115                 120                 125

Gly Cys Val Val Ala Phe Leu Asn Thr Asn Ile Arg Ser Asn Ser Leu
    130                 135                 140

Leu Asn Cys Ile Arg Ala Cys Gly Pro Arg Ala Leu Val Val Gly Ala
145                 150                 155                 160

Asp Leu Leu Gly Thr Val Glu Glu Ile Leu Pro Ser Leu Ser Glu Asn
                165                 170                 175

Ile Ser Val Trp Gly Met Lys Asp Ser Val Pro Gln Gly Val Ile Ser
            180                 185                 190

Leu Lys Glu Lys Leu Ser Thr Ser Pro Asp Glu Pro Val Pro Arg Ser
        195                 200                 205
```

-continued

```
His His Val Val Ser Leu Leu Lys Ser Thr Cys Leu Tyr Ile Phe Thr
    210                 215                 220

Ser Gly Thr Thr Gly Leu Pro Lys Ala Ala Val Ile Ser Gln Leu Gln
225                 230                 235                 240

Val Leu Arg Gly Ser Ala Val Leu Trp Ala Phe Gly Cys Thr Ala His
                245                 250                 255

Asp Ile Val Tyr Ile Thr Leu Pro Leu Tyr His Ser Ser Ala Ala Ile
            260                 265                 270

Leu Gly Ile Ser Gly Cys Val Glu Leu Gly Ala Thr Cys Val Leu Lys
        275                 280                 285

Lys Lys Phe Ser Ala Ser Gln Phe Trp Ser Asp Cys Lys Lys Tyr Asp
    290                 295                 300

Val Thr Val Phe Gln Tyr Ile Gly Glu Leu Cys Arg Tyr Leu Cys Lys
305                 310                 315                 320

Gln Ser Lys Arg Glu Gly Glu Lys Asp His Lys Val Arg Leu Ala Ile
                325                 330                 335

Gly Asn Gly Ile Arg Ser Asp Val Trp Arg Glu Phe Leu Asp Arg Phe
            340                 345                 350

Gly Asn Ile Lys Val Cys Glu Leu Tyr Ala Ala Thr Glu Ser Ser Ile
        355                 360                 365

Ser Phe Met Asn Tyr Thr Gly Arg Ile Gly Ala Ile Gly Arg Thr Asn
    370                 375                 380

Leu Phe Tyr Lys Leu Leu Ser Thr Phe Asp Leu Ile Lys Tyr Asp Phe
385                 390                 395                 400

Gln Lys Asp Glu Pro Met Arg Asn Glu Gln Gly Trp Cys Ile His Val
                405                 410                 415

Lys Lys Gly Glu Pro Gly Leu Leu Ile Ser Arg Val Asn Ala Lys Asn
            420                 425                 430

Pro Phe Phe Gly Tyr Ala Gly Pro Tyr Lys His Thr Lys Asp Lys Leu
        435                 440                 445

Leu Cys Asp Val Phe Lys Lys Gly Asp Val Tyr Leu Asn Thr Gly Asp
    450                 455                 460

Leu Ile Val Gln Asp Gln Asp Asn Phe Leu Tyr Phe Trp Asp Arg Thr
465                 470                 475                 480

Gly Asp Thr Phe Arg Trp Lys Gly Glu Asn Val Ala Thr Thr Glu Val
                485                 490                 495

Ala Asp Val Ile Gly Met Leu Asp Phe Ile Gln Glu Ala Asn Val Tyr
            500                 505                 510

Gly Val Ala Ile Ser Gly Tyr Glu Gly Arg Ala Gly Met Ala Ser Ile
        515                 520                 525

Ile Leu Lys Pro Asn Thr Ser Leu Asp Leu Glu Lys Val Tyr Glu Gln
    530                 535                 540

Val Val Thr Phe Leu Pro Ala Tyr Ala Cys Pro Arg Phe Leu Arg Ile
545                 550                 555                 560

Gln Glu Lys Met Glu Ala Thr Gly Thr Phe Lys Leu Leu Lys His Gln
                565                 570                 575

Leu Val Glu Asp Gly Phe Asn Pro Leu Lys Ile Ser Glu Pro Leu Tyr
            580                 585                 590

Phe Met Asp Asn Leu Lys Lys Ser Tyr Val Leu Leu Thr Arg Glu Leu
        595                 600                 605

Tyr Asp Gln Ile Met Leu Gly Glu Ile Lys Leu
    610                 615
```

-continued

<210> SEQ ID NO 38
<211> LENGTH: 646
<212> TYPE: PRT
<213> ORGANISM: Homo sapiens

<400> SEQUENCE: 38

```
Met Arg Ala Pro Gly Ala Gly Ala Ala Ser Val Val Ser Leu Ala Leu
 1               5                  10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80

Ile Phe Gln Ala Val Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Ala Val Ala Glu Val
            180                 185                 190

Ser Gly His Leu Gly Lys Ser Leu Ile Lys Phe Cys Ser Gly Asp Leu
        195                 200                 205

Gly Pro Glu Gly Ile Leu Pro Asp Thr His Leu Leu Asp Pro Leu Leu
    210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
        275                 280                 285

Leu Pro Leu Tyr His Ser Ala Gly Asn Ile Ile Gly Val Gly Gln Cys
    290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
    370                 375                 380
```

-continued

```
Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly His Tyr Leu Pro Leu Asn Glu Ala Val Tyr Thr Arg Ile Cys
625                 630                 635                 640

Ser Gly Ala Phe Ala Leu
                645
```

<210> SEQ ID NO 39
<211> LENGTH: 632
<212> TYPE: PRT
<213> ORGANISM: Homo sapiens

<400> SEQUENCE: 39

```
Leu Phe Ser Lys Leu Val Leu Lys Leu Pro Trp Thr Gln Val Gly Phe
 1               5                  10                  15

Ser Leu Leu Phe Leu Tyr Leu Gly Ser Gly Gly Trp Arg Phe Ile Arg
            20                  25                  30

Val Phe Ile Lys Thr Ile Arg Arg Asp Ile Phe Gly Gly Leu Val Leu
        35                  40                  45

Leu Lys Val Lys Ala Lys Val Arg Gln Cys Leu Gln Glu Arg Arg Thr
    50                  55                  60

Val Pro Ile Leu Phe Ala Ser Thr Val Arg Arg His Pro Asp Lys Thr
65                  70                  75                  80

Ala Leu Ile Phe Glu Gly Thr Asp Thr His Trp Thr Phe Arg Gln Leu
                85                  90                  95

Asp Glu Tyr Ser Ser Ser Val Ala Asn Phe Leu Gln Ala Arg Gly Leu
            100                 105                 110
```

-continued

```
Ala Ser Gly Asp Val Ala Ala Ile Phe Met Glu Asn Arg Asn Glu Phe
        115                 120                 125

Val Gly Leu Trp Leu Gly Met Ala Lys Leu Gly Val Glu Ala Ala Leu
    130                 135                 140

Ile Asn Thr Asn Leu Arg Arg Asp Ala Leu Leu His Cys Leu Thr Thr
145                 150                 155                 160

Ser Arg Ala Arg Ala Leu Val Phe Gly Ser Glu Met Ala Ser Ala Ile
                165                 170                 175

Cys Glu Val His Ala Ser Leu Asp Pro Ser Leu Ser Leu Phe Cys Ser
            180                 185                 190

Gly Ser Trp Glu Pro Gly Ala Val Pro Pro Ser Thr Glu His Leu Asp
        195                 200                 205

Pro Leu Leu Lys Asp Ala Pro Lys His Leu Pro Ser Cys Pro Asp Lys
    210                 215                 220

Gly Phe Thr Asp Lys Leu Phe Tyr Ile Tyr Thr Ser Gly Thr Thr Gly
225                 230                 235                 240

Leu Pro Lys Ala Ala Ile Val Val His Ser Arg Tyr Tyr Arg Met Ala
                245                 250                 255

Ala Leu Val Tyr Tyr Gly Phe Arg Met Arg Pro Asn Asp Ile Val Tyr
            260                 265                 270

Asp Cys Leu Pro Leu Tyr His Ser Ala Gly Asn Ile Val Gly Ile Gly
        275                 280                 285

Gln Cys Leu Leu His Gly Met Thr Val Val Ile Arg Lys Lys Phe Ser
    290                 295                 300

Ala Ser Arg Phe Trp Asp Asp Cys Ile Lys Tyr Asn Cys Thr Ile Val
305                 310                 315                 320

Gln Tyr Ile Gly Glu Leu Cys Arg Tyr Leu Leu Asn Gln Pro Pro Arg
                325                 330                 335

Glu Ala Glu Asn Gln His Gln Val Arg Met Ala Leu Gly Asn Gly Leu
            340                 345                 350

Arg Gln Ser Ile Trp Thr Asn Phe Ser Ser Arg Phe His Ile Pro Gln
        355                 360                 365

Val Ala Glu Phe Tyr Gly Ala Thr Glu Cys Asn Cys Ser Leu Gly Asn
    370                 375                 380

Phe Asp Ser Gln Val Gly Ala Cys Gly Phe Asn Ser Arg Ile Leu Ser
385                 390                 395                 400

Phe Val Tyr Pro Ile Arg Leu Val Arg Val Asn Glu Asp Thr Met Glu
                405                 410                 415

Leu Ile Arg Gly Pro Asp Gly Val Cys Ile Pro Cys Gln Pro Gly Glu
            420                 425                 430

Pro Gly Gln Leu Val Gly Arg Ile Ile Gln Lys Asp Pro Leu Arg Arg
        435                 440                 445

Phe Asp Gly Tyr Leu Asn Gln Gly Ala Asn Asn Lys Lys Ile Ala Lys
    450                 455                 460

Asp Val Phe Lys Lys Gly Asp Gln Ala Tyr Leu Thr Gly Asp Val Leu
465                 470                 475                 480

Val Met Asp Glu Leu Gly Tyr Leu Tyr Phe Arg Asp Arg Thr Gly Asp
                485                 490                 495

Thr Phe Arg Trp Lys Gly Glu Asn Val Ser Thr Thr Glu Val Glu Gly
            500                 505                 510

Thr Leu Ser Arg Leu Leu Asp Met Ala Asp Val Ala Val Tyr Gly Val
        515                 520                 525
```

-continued

```
Glu Val Pro Gly Thr Glu Gly Arg Ala Gly Met Ala Ala Val Ala Ser
    530                 535                 540

Pro Thr Gly Asn Cys Asp Leu Glu Arg Phe Ala Gln Val Leu Glu Lys
545                 550                 555                 560

Glu Leu Pro Leu Tyr Ala Arg Pro Ile Phe Leu Arg Leu Leu Pro Glu
                565                 570                 575

Leu His Lys Thr Gly Thr Tyr Lys Phe Gln Lys Thr Glu Leu Arg Lys
            580                 585                 590

Glu Gly Phe Asp Pro Ala Ile Val Lys Asp Pro Leu Phe Tyr Leu Asp
        595                 600                 605

Ala Gln Lys Gly Arg Tyr Val Pro Leu Asp Gln Glu Ala Tyr Ser Arg
    610                 615                 620

Ile Gln Ala Gly Glu Glu Lys Leu
625                 630


<210> SEQ ID NO 40
<211> LENGTH: 619
<212> TYPE: PRT
<213> ORGANISM: Homo sapiens

<400> SEQUENCE: 40

Met Leu Leu Ser Trp Leu Thr Val Leu Gly Ala Gly Met Val Val Leu
 1               5                  10                  15

His Phe Leu Gln Lys Leu Leu Phe Pro Tyr Phe Trp Asp Asp Phe Trp
            20                  25                  30

Phe Val Leu Lys Val Val Leu Ile Ile Ile Arg Leu Lys Lys Tyr Glu
        35                  40                  45

Lys Arg Gly Glu Leu Val Thr Val Leu Asp Lys Phe Leu Ser His Ala
    50                  55                  60

Lys Arg Gln Pro Arg Lys Pro Phe Ile Ile Tyr Glu Gly Asp Ile Tyr
65                  70                  75                  80

Thr Tyr Gln Asp Val Asp Lys Arg Ser Ser Arg Val Ala His Val Phe
                85                  90                  95

Leu Asn His Ser Ser Leu Lys Lys Gly Asp Thr Val Ala Leu Leu Met
            100                 105                 110

Ser Asn Glu Pro Asp Phe Val His Val Trp Phe Gly Leu Ala Lys Leu
        115                 120                 125

Gly Cys Val Val Ala Phe Leu Asn Thr Asn Ile Arg Ser Asn Ser Leu
    130                 135                 140

Leu Asn Cys Ile Arg Ala Cys Gly Pro Arg Ala Leu Val Val Gly Ala
145                 150                 155                 160

Asp Leu Leu Gly Thr Val Glu Glu Ile Leu Pro Ser Leu Ser Glu Asn
                165                 170                 175

Ile Ser Val Trp Gly Met Lys Asp Ser Val Pro Gln Gly Val Ile Ser
            180                 185                 190

Leu Lys Glu Lys Leu Ser Thr Ser Pro Asp Glu Pro Val Pro Arg Ser
        195                 200                 205

His His Val Val Ser Leu Leu Lys Ser Thr Cys Leu Tyr Ile Phe Thr
    210                 215                 220

Ser Gly Thr Thr Gly Leu Pro Lys Ala Ala Val Ile Ser Gln Leu Gln
225                 230                 235                 240

Val Leu Arg Gly Ser Ala Val Leu Trp Ala Phe Gly Cys Thr Ala His
                245                 250                 255

Asp Ile Val Tyr Ile Thr Leu Pro Leu Tyr His Ser Ser Ala Ala Ile
            260                 265                 270
```

Leu Gly Ile Ser Gly Cys Val Glu Leu Gly Ala Thr Cys Val Leu Lys
275 280 285

Lys Lys Phe Ser Ala Ser Gln Phe Trp Ser Asp Cys Lys Lys Tyr Asp
290 295 300

Val Thr Val Phe Gln Tyr Ile Gly Glu Leu Cys Arg Tyr Leu Cys Lys
305 310 315 320

Gln Ser Lys Arg Glu Gly Glu Lys Asp His Lys Val Arg Leu Ala Ile
325 330 335

Gly Asn Gly Ile Arg Ser Asp Val Trp Arg Glu Phe Leu Asp Arg Phe
340 345 350

Gly Asn Ile Lys Val Cys Glu Leu Tyr Ala Ala Thr Glu Ser Ser Ile
355 360 365

Ser Phe Met Asn Tyr Thr Gly Arg Ile Gly Ala Ile Gly Arg Thr Asn
370 375 380

Leu Phe Tyr Lys Leu Leu Ser Thr Phe Asp Leu Ile Lys Tyr Asp Phe
385 390 395 400

Gln Lys Asp Glu Pro Met Arg Asn Glu Gln Gly Trp Cys Ile His Val
405 410 415

Lys Lys Gly Glu Pro Gly Leu Leu Ile Ser Arg Val Asn Ala Lys Asn
420 425 430

Pro Phe Phe Gly Tyr Ala Gly Pro Tyr Lys His Thr Lys Asp Lys Leu
435 440 445

Leu Cys Asp Val Phe Lys Lys Gly Asp Val Tyr Leu Asn Thr Gly Asp
450 455 460

Leu Ile Val Gln Asp Gln Asp Asn Phe Leu Tyr Phe Trp Asp Arg Thr
465 470 475 480

Gly Asp Thr Phe Arg Trp Lys Gly Glu Asn Val Ala Thr Thr Glu Val
485 490 495

Ala Asp Val Ile Gly Met Leu Asp Phe Ile Gln Glu Ala Asn Val Tyr
500 505 510

Gly Val Ala Ile Ser Gly Tyr Glu Gly Arg Ala Gly Met Ala Ser Ile
515 520 525

Ile Leu Lys Pro Asn Thr Ser Leu Asp Leu Glu Lys Val Tyr Glu Gln
530 535 540

Val Val Thr Phe Leu Pro Ala Tyr Ala Cys Pro Arg Phe Leu Arg Ile
545 550 555 560

Gln Glu Lys Met Glu Ala Thr Gly Thr Phe Lys Leu Leu Lys His Gln
565 570 575

Leu Val Glu Asp Gly Phe Asn Pro Leu Lys Ile Ser Glu Pro Leu Tyr
580 585 590

Phe Met Asp Asn Leu Lys Lys Ser Tyr Val Leu Leu Thr Arg Glu Leu
595 600 605

Tyr Asp Gln Ile Met Leu Gly Glu Ile Lys Leu
610 615

<210> SEQ ID NO 41
<211> LENGTH: 643
<212> TYPE: PRT
<213> ORGANISM: Homo sapiens

<400> SEQUENCE: 41

Met Leu Leu Gly Ala Ser Leu Val Gly Val Leu Leu Phe Ser Lys Leu
1 5 10 15

Val Leu Lys Leu Pro Trp Thr Gln Val Gly Phe Ser Leu Leu Phe Leu

-continued

```
            20                  25                  30

Tyr Leu Gly Ser Gly Gly Trp Arg Phe Ile Arg Val Phe Ile Lys Thr
        35                  40                  45

Ile Arg Arg Asp Ile Phe Gly Gly Leu Val Leu Leu Lys Val Lys Ala
    50                  55                  60

Lys Val Arg Gln Cys Leu Gln Glu Arg Arg Thr Val Pro Ile Leu Phe
65                  70                  75                  80

Ala Ser Thr Val Arg Arg His Pro Asp Lys Thr Ala Leu Ile Phe Glu
                85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asp Val
        115                 120                 125

Ala Ala Ile Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Leu His Cys Leu Thr Thr Ser Arg Ala Arg Ala
                165                 170                 175

Leu Val Phe Gly Ser Glu Met Ala Ser Ala Ile Cys Glu Val His Ala
            180                 185                 190

Ser Leu Asp Pro Ser Leu Ser Leu Phe Cys Ser Gly Ser Trp Glu Pro
        195                 200                 205

Gly Ala Val Pro Pro Ser Thr Glu His Leu Asp Pro Leu Leu Lys Asp
    210                 215                 220

Ala Pro Lys His Leu Pro Ser Cys Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ala Leu Val Tyr Tyr
            260                 265                 270

Gly Phe Arg Met Arg Pro Asn Asp Ile Val Tyr Asp Cys Leu Pro Leu
        275                 280                 285

Tyr His Ser Ala Gly Asn Ile Val Gly Ile Gly Gln Cys Leu Leu His
    290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Asn Gln
            340                 345                 350

His Gln Val Arg Met Ala Leu Gly Asn Gly Leu Arg Gln Ser Ile Trp
        355                 360                 365

Thr Asn Phe Ser Ser Arg Phe His Ile Pro Gln Val Ala Glu Phe Tyr
    370                 375                 380

Gly Ala Thr Glu Cys Asn Cys Ser Leu Gly Asn Phe Asp Ser Gln Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Glu Pro Gly Gln Leu Val
        435                 440                 445
```

-continued

Gly Arg Ile Ile Gln Lys Asp Pro Leu Arg Arg Phe Asp Gly Tyr Leu
    450                 455                 460

Asn Gln Gly Ala Asn Asn Lys Lys Ile Ala Lys Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
        515                 520                 525

Leu Asp Met Ala Asp Val Ala Val Tyr Gly Val Glu Val Pro Gly Thr
    530                 535                 540

Glu Gly Arg Ala Gly Met Ala Ala Val Ala Ser Pro Thr Gly Asn Cys
545                 550                 555                 560

Asp Leu Glu Arg Phe Ala Gln Val Leu Glu Lys Glu Leu Pro Leu Tyr
                565                 570                 575

Ala Arg Pro Ile Phe Leu Arg Leu Leu Pro Glu Leu His Lys Thr Gly
            580                 585                 590

Thr Tyr Lys Phe Gln Lys Thr Glu Leu Arg Lys Glu Gly Phe Asp Pro
        595                 600                 605

Ala Ile Val Lys Asp Pro Leu Phe Tyr Leu Asp Ala Gln Lys Gly Arg
    610                 615                 620

Tyr Val Pro Leu Asp Gln Glu Ala Tyr Ser Arg Ile Gln Ala Gly Glu
625                 630                 635                 640

Glu Lys Leu

<210> SEQ ID NO 42
<211> LENGTH: 643
<212> TYPE: PRT
<213> ORGANISM: Mus musculus
<220> FEATURE:
<221> NAME/KEY: VARIANT
<222> LOCATION: (1)...(643)
<223> OTHER INFORMATION: Xaa = Any Amino Acid

<400> SEQUENCE: 42

Met Leu Leu Gly Ala Ser Leu Val Gly Val Leu Leu Phe Ser Lys Leu
 1               5                  10                  15

Val Leu Lys Leu Pro Trp Thr Gln Val Gly Phe Ser Leu Leu Xaa Leu
            20                  25                  30

Tyr Leu Gly Ser Gly Gly Trp Arg Phe Ile Arg Val Phe Ile Lys Thr
        35                  40                  45

Val Arg Arg Asp Ile Phe Gly Gly Met Val Leu Leu Lys Val Lys Thr
    50                  55                  60

Lys Val Arg Arg Tyr Leu Gln Glu Arg Lys Thr Val Pro Leu Leu Phe
65                  70                  75                  80

Ala Ser Met Val Gln Arg His Pro Asp Lys Thr Ala Leu Ile Phe Glu
                85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asn Val
        115                 120                 125

Val Ala Leu Phe Met Glu Asn Arg Asn Glu Phe Val Gly Leu Trp Xaa
    130                 135                 140

Gly Met Ala Lys Leu Gly Val Glu Ala Ala Leu Ile Asn Thr Asn Leu

-continued

```
145                 150                 155                 160

Arg Arg Asp Ala Leu Arg His Cys Leu Asp Thr Ser Lys Ala Arg Ala
                165                 170                 175

Leu Ile Phe Gly Ser Glu Met Ala Ser Ala Ile Cys Glu Ile His Ala
            180                 185                 190

Ser Leu Gly Pro Thr Leu Ser Leu Phe Cys Ser Gly Ser Trp Glu Pro
        195                 200                 205

Ser Thr Val Pro Val Ser Thr Glu His Leu Asp Pro Leu Leu Glu Asp
    210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ser Leu Val Tyr Tyr
            260                 265                 270

Gly Phe Arg Met Arg Pro Asp Asp Ile Val Tyr Asp Cys Leu Pro Leu
        275                 280                 285

Tyr His Ser Ser Arg Lys His Arg Gly Asp Trp Gln Cys Leu Leu His
    290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Ser Arg
            340                 345                 350

His Lys Val Arg Met Ala Leu Gly Asn Gly Leu Arg Gln Ser Ile Trp
        355                 360                 365

Thr Asp Phe Ser Ser Arg Phe His Ile Pro Gln Val Ala Glu Phe Tyr
    370                 375                 380

Gly Ala Thr Glu Cys Asn Cys Ser Leu Gly Asn Phe Asp Ser Arg Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Gln Pro Gly Gln Leu Val
        435                 440                 445

Gly Arg Ile Ile Gln Lys Asp Pro Leu Arg Arg Phe Asp Gly Tyr Leu
    450                 455                 460

Asn Gln Gly Ala Asn Asn Lys Lys Ile Ala Asn Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
        515                 520                 525

Leu His Met Ala Asp Val Ala Val Tyr Gly Val Glu Val Pro Gly Thr
    530                 535                 540

Glu Gly Arg Ala Gly Met Ala Ala Val Ala Ser Pro Ile Ser Asn Cys
545                 550                 555                 560

Asp Leu Glu Ser Phe Ala Gln Thr Leu Lys Lys Glu Leu Pro Leu Tyr
                565                 570                 575
```

-continued

```
Ala Arg Pro Ile Phe Leu Arg Phe Leu Pro Glu Leu His Lys Thr Gly
            580                 585                 590

Thr Phe Lys Phe Gln Lys Thr Glu Leu Arg Lys Glu Gly Phe Asp Pro
        595                 600                 605

Ser Val Val Lys Asp Pro Leu Phe Tyr Leu Asp Ala Arg Lys Gly Cys
    610                 615                 620

Tyr Val Ala Leu Asp Gln Glu Ala Tyr Thr Arg Ile Gln Ala Gly Glu
625                 630                 635                 640

Glu Lys Leu


<210> SEQ ID NO 43
<211> LENGTH: 646
<212> TYPE: PRT
<213> ORGANISM: Homo sapiens

<400> SEQUENCE: 43

Met Arg Ala Pro Gly Ala Gly Ala Ala Ser Val Val Ser Leu Ala Leu
 1               5                  10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80

Ile Phe Gln Ala Val Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Ala Val Ala Glu Val
            180                 185                 190

Ser Gly His Leu Gly Lys Ser Leu Ile Lys Phe Cys Ser Gly Asp Leu
        195                 200                 205

Gly Pro Glu Gly Ile Leu Pro Asp Thr His Leu Leu Asp Pro Leu Leu
    210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
        275                 280                 285

Leu Pro Leu Tyr His Ser Ala Gly Asn Ile Ile Gly Val Gly Gln Cys
    290                 295                 300
```

-continued

```
Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly His Tyr Leu Pro Leu Asn Glu Ala Val Tyr Thr Arg Ile Cys
625                 630                 635                 640

Ser Gly Ala Phe Ala Leu
                645


<210> SEQ ID NO 44
<211> LENGTH: 2710
<212> TYPE: DNA
<213> ORGANISM: Mus musculus

<400> SEQUENCE: 44

atgctgcttg gagcctctct ggtgggggcg ctacttgggt ccaagctagt gctgaagctg      60

ccctggaccc aggtgggatt ctccctgttg ctcctgtact tggggtctgg tggctggcgt     120
```

-continued

```
ttcatccggg tcttcatcaa gacggtcagg agagatatct ttggtggcat ggtgctcctg    180
aaggtgaaga ccaaggtgcg acggtacctt caggagcgga agacggtgcc cctgctgttt    240
gcttcaatgg tacagcgcca cccggacaag acagccctga ttttcgaggg cacagacact    300
cactggacct tccgccagct ggatgagtac tccagtagtg tggccaactt cctgcaggcc    360
cggggcctgg cctcaggcaa tgtagttgcc ctctttatgg aaaaccgcaa tgagtttgtg    420
ggtctgtggc taggcatggc caagctgggc gtggaggcgg ctctcatcaa caccaacctt    480
aggcgggatg ccctgcgcca ctgtcttgac acctcaaagg cacgagctct catctttggc    540
agtgagatgg cctcagctat ctgtgagatc catgctagcc tggagcccac actcagcctc    600
ttctgctctg gatcctggga gcccagcaca gtgcccgtca gcacagagca tctggaccct    660
cttctggaag atgccccgaa gcacctgccc agtcacccag acaagggttt tacagataag    720
ctcttctaca tctacacatc gggcaccacg gggctaccca aagctgccat tgtggtgcac    780
agcaggtatt atcgtatggc ttccctggtg tactatggat tccgcatgcg gcctgatgac    840
attgtctatg actgcctccc cctctaccac tcaagcagga aacatcgtgg ggattggcag    900
tgcttactcc acggcatgac tgtggtgatc cggaagaagt tctcagcctc ccggttctgg    960
gatgattgta tcaagtacaa ctgcacagtg gtacagtaca ttggcgagct ctgccgctac   1020
ctcctgaacc agccaccccg tgaggctgag tctcggcaca aggtgcgcat ggcactgggc   1080
aacggtctcc ggcagtccat ctggaccgac ttctccagcc gtttccacat cccccaggtg   1140
gctgagttct atggggccac tgaatgcaac tgtagcctgg gcaactttga cagccgggtg   1200
ggggcctgtg gcttcaatag ccgcatcctg tcctttgtgt accctatccg tttggtacgt   1260
gtcaatgagg ataccatgga actgatccgg ggacccgatg gagtctgcat tccctgtcaa   1320
ccaggtcagc caggccagct ggtgggtcgc atcatccagc aggaccctct gcgccgtttc   1380
gacgggtacc tcaaccaggg tgccaacaac aagaagattg ctaatgatgt cttcaagaag   1440
ggggaccaag cctacctcac tggtgacgtc ctggtgatgg atgagctggg ttacctgtac   1500
ttccgagatc gcactgggga cacgttccgc tggaaagggg agaatgtatc taccactgag   1560
gtggagggca cactcagccg cctgcttcat atggcagatg tggcagttta tggtgttgag   1620
gtgccaggaa ctgaaggccg agcaggaatg gctgccgttg caagtcccat cagcaactgt   1680
gacctggaga gctttgcaca gaccttgaaa aaggagctgc ctctgtatgc ccgccccatc   1740
ttcctgcgct tcttgcctga gctgcacaag acagggacct tcaagttcca gaagacagag   1800
ttgcggaagg agggctttga cccatctgtt gtgaaagacc cgctgttcta tctggatgct   1860
cggaagggct gctacgttgc actggaccag gaggcctata cccgcatcca ggcaggcgag   1920
gagaagctgt gatttccccc tacatccctc tgagggccag aagatgctgg attcagagcc   1980
ctagcgtcca ccccagaggg tcctgggcaa tgccagacca aagctagcag ggcccgcacc   2040
tccgccccta ggtgctgatc tcccctctcc caaactgcca agtgactcac tgccgcttcc   2100
ccgaccctcc agaggctttc tgtgaaagtc tcatccaagc tgtgtcttct ggtccaggcg   2160
tggcccctgg ccccagggtt tctgataggc tcctttagga tggtatcttg ggtccagcgg   2220
gccagggtgt gggagaggag tcactaagat ccctccaatc agaagggagc ttacaaagga   2280
accaaggcaa agcctgtaga ctcaggaagc taagtggcca gagactatag tggccagtca   2340
tcccatgtcc acagaggatc ttggtccaga gctgccaaag tgtcacctct ccctgcctgc   2400
acctctgggg aaaagaggac agcatgtggc cactgggcac ctgtctcaag aagtcaggat   2460
cacacactca gtccttgttt ctccaggttc ccttgttctt gtctcgggga gggagggacg   2520
```

-continued

```
agtgtcctgt ctgtccttcc tgcctgtctg tgagtctgtg ttgcttctcc atctgtccta   2580

gcctgagtgt gggtggaaca ggcatgagga gagtgtggct caggggccaa taaactctgc   2640

cttgactcct cttaaaaaaa aaaaaaaaaa aaaaaaaaaa aaaaaaaaaa aaaaaaaaaa   2700

aaaaaaaaaa                                                          2710


<210> SEQ ID NO 45
<211> LENGTH: 643
<212> TYPE: PRT
<213> ORGANISM: Mus musculus

<400> SEQUENCE: 45

Met Leu Leu Gly Ala Ser Leu Val Gly Ala Leu Leu Phe Ser Lys Leu
 1               5                  10                  15

Val Leu Lys Leu Pro Trp Thr Gln Val Gly Phe Ser Leu Leu Leu Leu
            20                  25                  30

Tyr Leu Gly Ser Gly Gly Trp Arg Phe Ile Arg Val Phe Ile Lys Thr
        35                  40                  45

Val Arg Arg Asp Ile Phe Gly Gly Met Val Leu Leu Lys Val Lys Thr
    50                  55                  60

Lys Val Arg Arg Tyr Leu Gln Glu Arg Lys Thr Val Pro Leu Leu Phe
65                  70                  75                  80

Ala Ser Met Val Gln Arg His Pro Asp Lys Thr Ala Leu Ile Phe Glu
                85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asn Val
        115                 120                 125

Val Ala Leu Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Arg His Cys Leu Asp Thr Ser Lys Ala Arg Ala
                165                 170                 175

Leu Ile Phe Gly Ser Glu Met Ala Ser Ala Ile Cys Glu Ile His Ala
            180                 185                 190

Ser Leu Glu Pro Thr Leu Ser Leu Phe Cys Ser Gly Ser Trp Glu Pro
        195                 200                 205

Ser Thr Val Pro Val Ser Thr Glu His Leu Asp Pro Leu Leu Glu Asp
    210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ser Leu Val Tyr Tyr
            260                 265                 270

Gly Phe Arg Met Arg Pro Asp Asp Ile Val Tyr Asp Cys Leu Pro Leu
        275                 280                 285

Tyr His Ser Ser Arg Lys His Arg Gly Asp Trp Gln Cys Leu Leu His
    290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Val Val Gln Tyr Ile Gly Glu
                325                 330                 335
```

-continued

```
Leu Cys Arg Tyr Leu Leu Asn Gln Pro Pro Arg Glu Ala Glu Ser Arg
            340                 345                 350

His Lys Val Arg Met Ala Leu Gly Asn Gly Leu Arg Gln Ser Ile Trp
        355                 360                 365

Thr Asp Phe Ser Ser Arg Phe His Ile Pro Gln Val Ala Glu Phe Tyr
    370                 375                 380

Gly Ala Thr Glu Cys Asn Cys Ser Leu Gly Asn Phe Asp Ser Arg Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Gln Pro Gly Gln Leu Val
        435                 440                 445

Gly Arg Ile Ile Gln Gln Asp Pro Leu Arg Arg Phe Asp Gly Tyr Leu
    450                 455                 460

Asn Gln Gly Ala Asn Asn Lys Lys Ile Ala Asn Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
        515                 520                 525

Leu His Met Ala Asp Val Ala Val Tyr Gly Val Glu Val Pro Gly Thr
    530                 535                 540

Glu Gly Arg Ala Gly Met Ala Ala Val Ala Ser Pro Ile Ser Asn Cys
545                 550                 555                 560

Asp Leu Glu Ser Phe Ala Gln Thr Leu Lys Lys Glu Leu Pro Leu Tyr
                565                 570                 575

Ala Arg Pro Ile Phe Leu Arg Phe Leu Pro Glu Leu His Lys Thr Gly
            580                 585                 590

Thr Phe Lys Phe Gln Lys Thr Glu Leu Arg Lys Glu Gly Phe Asp Pro
        595                 600                 605

Ser Val Val Lys Asp Pro Leu Phe Tyr Leu Asp Ala Arg Lys Gly Cys
    610                 615                 620

Tyr Val Ala Leu Asp Gln Glu Ala Tyr Thr Arg Ile Gln Ala Gly Glu
625                 630                 635                 640

Glu Lys Leu
```

<210> SEQ ID NO 46
<211> LENGTH: 3694
<212> TYPE: DNA
<213> ORGANISM: Homo sapiens

<400> SEQUENCE: 46

```
tcgacccacg gcgtccggga ccccaaagca gaagcccgca cagtaggcac agcgcaccca      60

agaagggtcc aggagtctgc agaaacagaa aggtccccgg cctcagcctc ctagtccctg     120

cctgcctcct gcctgagctt ctgggagact gaaggcacgg cttgcagctt caggatgcgg     180

gctccgggtg cgggcgcggc ctcggtggtc tcgctggcgc tgttgtggct gctggggctg     240

ccgtggacct ggagcgcggc agcggcgctc ggcgtgtacg tgggcagcgg cggctggcgc     300

ttcctgcgca tcgtctgcaa gaccgcgagg cgagacctct tcggtctctc tgtgctgatc     360
```

-continued

```
cgcgtgcgcc tggagctgcg gcggcaccag cgtgccggcc acaccatccc gcgcatcttt    420
caggcggtag tgcagcgaca gcccgagcgc ctggcgctgg tggatgccgg gaccggcgag    480
tgctggacct ttgcgcagct ggacgcctac tccaatgcgg tagccaacct cttccgccag    540
ctgggcttcg cgccgggcga cgtggtggcc atcttcctgg agggccggcc ggagttcgtg    600
gggctgtggc tgggcctggc caaggcgggc atggaggccg cgctgctcaa cgtgaacctg    660
cggcgcgagc ccctggcctt ctgcctgggc acctcgggcg ctaaggccct gatctttgga    720
ggagaaatgg tggcggcggt ggccgaagtg agcgggcatc tggggaaaag tttgatcaag    780
ttctgctctg gagacttggg gcccgagggc atcttgccgg acacccacct cctggacccg    840
ctgctgaagg aggcctctac tgcccccttg gcacagatcc ccagcaaggg catggacgat    900
cgtcttttct acatctacac gtcggggacc accgggctgc ccaaggctgc cattgtcgtg    960
cacagcaggt actaccgcat ggcagccttc ggccaccacg cctaccgcat gcaggcggct   1020
gacgtgctct atgactgcct gcccctgtac cactcggcag gaaacatcat cggcgtgggg   1080
cagtgtctca tctatgggct gacagtcgtc ctccgcaaga aattctcggc cagccgcttc   1140
tgggacgact gcatcaagta caactgcacg gtggttcagt acatcgggga gatctgccgc   1200
tacctgctga agcagccggt gcgcgaggcg gagaggcgac accgcgtgcg cctggcggtg   1260
gggaacgggc tgcgtcctgc catctgggag gagttcacgg agcgcttcgg cgtacgccaa   1320
atcggggagt tctacggcgc caccgagtgc aactgcagca ttgccaacat ggacggcaag   1380
gtcggctcct gtggtttcaa cagccgcatc ctgccccacg tgtaccccat ccggctggtg   1440
aaggtcaatg aggacacaat ggagctgctg cgggatgccc agggcctctg catcccctgc   1500
caggccgggg agcctggcct ccttgtgggt cagatcaacc aacaggaccc gctgcgccgc   1560
ttcgatggct atgtcagcga gagcgccacc agcaagaaga tcgcccacag cgtcttcagc   1620
aagggcgaca gcgcctacct ctcaggtgac gtgctagtga tggatgagct gggctacatg   1680
tacttccggg accgtagcgg ggacaccttc cgctggcgag gggagaacgt ctccaccacc   1740
gaggtggagg gcgtgctgag ccgcctgctg ggccagacag acgtggccgt ctatggggtg   1800
gctgttccag gagtggaggg taaggcaggg atggcggccg tcgcagaccc ccacagcctg   1860
ctggacccca acgcgatata ccaggagctg cagaaggtgc tggcacccta tgcccggccc   1920
atcttcctgc gcctcctgcc ccaggtggac accacaggca ccttcaagat ccagaagacg   1980
aggctgcagc gagagggctt tgacccacgc cagacctcag accggctctt cttcctggac   2040
ctgaagcagg gccactacct gcccttaaat gaggcagtct acactcgcat ctgctcgggc   2100
gccttcgccc tctgaagctg ttcctctact ggccacaaac tctgggcctg gtgggagagg   2160
ccagcttgag ccagacagcg ctgcccaggg gtggccgcct agtacacacc cacctggccg   2220
agctgtacct ggcacggccc atcctggact gagaaactgg aacctcagag gaacccgtgc   2280
ctctctgctg ccttggtgcc cctgtgtctg cctcctctcc ctgcttttca gcctctgtct   2340
ccttccatcc ctgtccctgt ctggccttaa ctcttccctc tctttctttt ctttctttct   2400
ttcttttttt ttaagataga gtctcactct gctgcccggg ctagagtgca gtggtgggat   2460
ctcggctcac tgcaacctct gcctcctggg gttcaagtga tcctcccacc tcagcctcct   2520
gagtagctgg gattacaggc acccgccacc acgtccagct aatttttata tttttagtag   2580
agacggggtt tcaccatgtt ggtcaggctg gtcttgaact cctgacctca ggtgatccgc   2640
tggcctcggc ctcccagagt gctgggatta taggcgtgag cctctggccc ggcctttcct   2700
```

-continued

```
ttttcctctc ctctcctgcc gagagtggaa cacacgtgtc ctgggagctg catcttgtgt   2760

agggtccagc tgcttttggg gactgcagga atcatctccc ctgggccctg gactcggact   2820

ggggcctccc cacctccctc tcggctgtgc cttacggagc cccaatccag gcctcctgtg   2880

gctgttgggt tccagatgct gcagctccat gtgacttcca agcaggccct ccgccctccc   2940

tgctgaatgg aggagccggg ggtcccccag gccaactgga aaatctccca ggctaggcca   3000

attgcctttt gcacttcccc gttcctgtca catttcccca gccccacctt cccctcctga   3060

tgccctgaaa gcttccggaa ttgactgtga ccacttggat gtcaccactg tcagcccctg   3120

ccttgatgtc cccatttagc catctccatg gagctcctgc tggagggccc tgaaccctgc   3180

actgcgtggc tgcccagcca gctgcctcct gtcctgggag gaggcctcct gggtgtcctc   3240

atctggtgtg tctactggag ggtcccacag gagaggcagc agaggggtca ggggaggtct   3300

cctgccgggg gttggcctct caagcctcag ggttctagc ctgttgaata taccccacct   3360

ggtgggtggc ccctccgatg tccccactga tggctctgac accgtgttgg tggcgatgtc   3420

ccagacaatc ccaccaggac ggcccagaca tccctactgg cttcgctggt ggctcatctc   3480

gaacatccac gccagccttt ctggggccgg ccacccaggc cgcctgtccg tctgtcctcc   3540

ctccagcagc accccctggc ccctggagtg gtggggccat ggcaagagac accgtggcgt   3600

ctcatgtgaa ctttcctggg cactgtggtt ttatttccta attgatttaa gaaataaacc   3660

tgaagaccgt ctggtgaaaa aaaaaaaaaa aaaa                               3694
```

<210> SEQ ID NO 47
<211> LENGTH: 646
<212> TYPE: PRT
<213> ORGANISM: Homo sapiens

<400> SEQUENCE: 47

```
Met Arg Ala Pro Gly Ala Gly Ala Ala Ser Val Val Ser Leu Ala Leu
 1               5                  10                  15

Leu Trp Leu Leu Gly Leu Pro Trp Thr Trp Ser Ala Ala Ala Ala Leu
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Gln Arg Ala Gly His Thr Ile Pro Arg
65                  70                  75                  80

Ile Phe Gln Ala Val Val Gln Arg Gln Pro Glu Arg Leu Ala Leu Val
                85                  90                  95

Asp Ala Gly Thr Gly Glu Cys Trp Thr Phe Ala Gln Leu Asp Ala Tyr
            100                 105                 110

Ser Asn Ala Val Ala Asn Leu Phe Arg Gln Leu Gly Phe Ala Pro Gly
        115                 120                 125

Asp Val Val Ala Ile Phe Leu Glu Gly Arg Pro Glu Phe Val Gly Leu
    130                 135                 140

Trp Leu Gly Leu Ala Lys Ala Gly Met Glu Ala Ala Leu Leu Asn Val
145                 150                 155                 160

Asn Leu Arg Arg Glu Pro Leu Ala Phe Cys Leu Gly Thr Ser Gly Ala
                165                 170                 175

Lys Ala Leu Ile Phe Gly Gly Glu Met Val Ala Ala Val Ala Glu Val
            180                 185                 190

Ser Gly His Leu Gly Lys Ser Leu Ile Lys Phe Cys Ser Gly Asp Leu
```

-continued

```
        195                 200                 205

Gly Pro Glu Gly Ile Leu Pro Asp Thr His Leu Leu Asp Pro Leu Leu
    210                 215                 220

Lys Glu Ala Ser Thr Ala Pro Leu Ala Gln Ile Pro Ser Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Met Ala Ala Phe
            260                 265                 270

Gly His His Ala Tyr Arg Met Gln Ala Ala Asp Val Leu Tyr Asp Cys
        275                 280                 285

Leu Pro Leu Tyr His Ser Ala Gly Asn Ile Ile Gly Val Gly Gln Cys
    290                 295                 300

Leu Ile Tyr Gly Leu Thr Val Val Leu Arg Lys Lys Phe Ser Ala Ser
305                 310                 315                 320

Arg Phe Trp Asp Asp Cys Ile Lys Tyr Asn Cys Thr Val Val Gln Tyr
                325                 330                 335

Ile Gly Glu Ile Cys Arg Tyr Leu Leu Lys Gln Pro Val Arg Glu Ala
            340                 345                 350

Glu Arg Arg His Arg Val Arg Leu Ala Val Gly Asn Gly Leu Arg Pro
        355                 360                 365

Ala Ile Trp Glu Glu Phe Thr Glu Arg Phe Gly Val Arg Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Pro His Val
                405                 410                 415

Tyr Pro Ile Arg Leu Val Lys Val Asn Glu Asp Thr Met Glu Leu Leu
            420                 425                 430

Arg Asp Ala Gln Gly Leu Cys Ile Pro Cys Gln Ala Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Glu Ser Ala Thr Ser Lys Lys Ile Ala His Ser Val
465                 470                 475                 480

Phe Ser Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Gly Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Val Ala Asp Pro His
545                 550                 555                 560

Ser Leu Leu Asp Pro Asn Ala Ile Tyr Gln Glu Leu Gln Lys Val Leu
                565                 570                 575

Ala Pro Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620
```

-continued

```
Gln Gly His Tyr Leu Pro Leu Asn Glu Ala Val Tyr Thr Arg Ile Cys
625                 630                 635                 640

Ser Gly Ala Phe Ala Leu
                645


<210> SEQ ID NO 48
<211> LENGTH: 2362
<212> TYPE: DNA
<213> ORGANISM: Homo sapiens

<400> SEQUENCE: 48

ggaattccaa aaaaaaaaaa tacgactaca cctgctccgg agcccgcggc ggtacctgca     60

gcggaggagc tctgtcttcc ccttcatctc acgcgagccc ggcgtcccgc cgcgtgcgcc    120

ccggcgcagc ccgccagtcc gcccggagcc cgcccagtcg ccgcgctgca cgcccggggt    180

gaaccctctg ccctcgctgg gacagagggc cccgcagccg tcatgctttc cgccatctac    240

acagtcctgg cgggactgct gttcctgccg ctcctggtga acctctgctg cccatacttc    300

ttccaggaca taggctactt cttgaaggtg gccgccgtgg gccggagggt gcgcagctac    360

gggcagcggc ggccggcgcg caccatcctg cgggcgttcc tggagaaagc gcgccagacg    420

ccacacaagc cttttctgct cttccgcgac gagactctca cctacgcgca ggtggaccgg    480

cgcagcaatc aagtggcccg ggcgctgcac gaccacctcg gcctgcgcca gggagactgc    540

gtggcgctcc ttatgggtaa cgagccggcc tacgtgtggc tgtggctggg gctggtgaag    600

ctgggctgtg ccatggcgtg cctcaattac aacatccgcg cgaagtccct gctgcactgc    660

ttccagtgct gcggggcgaa ggtgctgctg gtgtcgccag aactacaagc agctgtcgaa    720

gagatactgc caagccttaa aaaagatgat gtgtccatct attatgtgag cagaacttct    780

aacacagatg ggattgactc tttcctggac aaagtggatg aagtatcaac tgaacctatc    840

ccagagtcat ggaggtctga agtcactttt tccactcctg ccttatacat ttatacttct    900

ggaaccacag gtcttccaaa agcagccatg atcactcatc agcgcatatg gtatggaact    960

ggcctcactt ttgtaagcgg attgaaggca gatgatgtca tctatatcac tctgcccttt   1020

taccacagtg ctgcactact gattggcatt cacggatgta ttgtggctgg tgctactctt   1080

gccttgcgga ctaaattttc agccagccag ttttgggatg actgcagaaa atacaacgtc   1140

actgtcattc agtatatcgg tgaactgctt cggtatttat gcaactcacc acagaaacca   1200

aatgaccgtg atcataaagt gagactggca ctgggaaatg gcttacgagg agatgtgtgg   1260

agacaatttg tcaagagatt tggggacata tgcatctatg agttctatgc tgccactgaa   1320

ggcaatattg gatttatgaa ttatgcgaga aaagttggtg ctgttggaag agtaaactac   1380

ctacagaaaa aaatcataac ttatgacctg attaaatatg atgtggagaa agatgaacct   1440

gtccgagatg aaaatggata ttgcgtcaga gttcccaaag gtgaagttgg acttctggtt   1500

tgcaaaatca cacaacttac accatttaat ggctatgctg gagcaaaggc tcagacagag   1560

aagaaaaaac tgagagatgt ctttaagaaa ggagacctct atttcaacag tggagatctc   1620

ttaatggttg accatgaaaa tttcatctat ttccacgaca gagttggaga tacattccgg   1680

tggaaagggg aaaatgtggc caccactgaa gttgctgata cagttggact ggttgatttt   1740

gtccaagaag taaatgttta tggagtgcat gtgccagatc atgagggtcg cattggcatg   1800

gcctccatca aaatgaaaga aaaccatgaa tttgatggaa agaaactctt tcagcacatt   1860

gctgattacc tacctagtta tgcaaggccc cggtttctaa gaatacagga caccattgag   1920
```

-continued

```
atcactggaa cttttaaaca ccgcaaaatg accctggtgg aggagggctt taaccctgct   1980

gtcatcaaag atgccttgta tttcttggat gacacagcaa aaatgtatgt gcctatgact   2040

gaggacatct ataatgccat aagtgctaaa accctgaaac tctgaatatt cccaggagga   2100

taactcaaca tttccagaaa gaaactgaat ggacagccac ttgatataat ccaactttaa   2160

tttgattgaa gattgtgagg aaattttgta ggaaatttgc atacccgtaa agggagactt   2220

ttttaaataa cagttgagtc tttgcaagta aaaagattta gagattatta tttttcagtg   2280

tgcacctact gtttgtattt gcaaactgag cttgttggag ggaaggcatt atttttttaaa   2340

atacttagta aattaaatga ac                                            2362
```

<210> SEQ ID NO 49
<211> LENGTH: 620
<212> TYPE: PRT
<213> ORGANISM: Homo sapiens

<400> SEQUENCE: 49

```
Met Leu Ser Ala Ile Tyr Thr Val Leu Ala Gly Leu Leu Phe Leu Pro
 1               5                  10                  15

Leu Leu Val Asn Leu Cys Cys Pro Tyr Phe Phe Gln Asp Ile Gly Tyr
            20                  25                  30

Phe Leu Lys Val Ala Ala Val Gly Arg Arg Val Arg Ser Tyr Gly Gln
        35                  40                  45

Arg Arg Pro Ala Arg Thr Ile Leu Arg Ala Phe Leu Glu Lys Ala Arg
    50                  55                  60

Gln Thr Pro His Lys Pro Phe Leu Leu Phe Arg Asp Glu Thr Leu Thr
65                  70                  75                  80

Tyr Ala Gln Val Asp Arg Arg Ser Asn Gln Val Ala Arg Ala Leu His
                85                  90                  95

Asp His Leu Gly Leu Arg Gln Gly Asp Cys Val Ala Leu Leu Met Gly
            100                 105                 110

Asn Glu Pro Ala Tyr Val Trp Leu Trp Leu Gly Leu Val Lys Leu Gly
        115                 120                 125

Cys Ala Met Ala Cys Leu Asn Tyr Asn Ile Arg Ala Lys Ser Leu Leu
    130                 135                 140

His Cys Phe Gln Cys Cys Gly Ala Lys Val Leu Leu Val Ser Pro Glu
145                 150                 155                 160

Leu Gln Ala Ala Val Glu Glu Ile Leu Pro Ser Leu Lys Lys Asp Asp
                165                 170                 175

Val Ser Ile Tyr Tyr Val Ser Arg Thr Ser Asn Thr Asp Gly Ile Asp
            180                 185                 190

Ser Phe Leu Asp Lys Val Asp Glu Val Ser Thr Glu Pro Ile Pro Glu
        195                 200                 205

Ser Trp Arg Ser Glu Val Thr Phe Ser Thr Pro Ala Leu Tyr Ile Tyr
    210                 215                 220

Thr Ser Gly Thr Thr Gly Leu Pro Lys Ala Ala Met Ile Thr His Gln
225                 230                 235                 240

Arg Ile Trp Tyr Gly Thr Gly Leu Thr Phe Val Ser Gly Leu Lys Ala
                245                 250                 255

Asp Asp Val Ile Tyr Ile Thr Leu Pro Phe Tyr His Ser Ala Ala Leu
            260                 265                 270

Leu Ile Gly Ile His Gly Cys Ile Val Ala Gly Ala Thr Leu Ala Leu
        275                 280                 285

Arg Thr Lys Phe Ser Ala Ser Gln Phe Trp Asp Asp Cys Arg Lys Tyr
```

-continued

```
    290                 295                 300

Asn Val Thr Val Ile Gln Tyr Ile Gly Glu Leu Leu Arg Tyr Leu Cys
305                 310                 315                 320

Asn Ser Pro Gln Lys Pro Asn Asp Arg Asp His Lys Val Arg Leu Ala
                325                 330                 335

Leu Gly Asn Gly Leu Arg Gly Asp Val Trp Arg Gln Phe Val Lys Arg
            340                 345                 350

Phe Gly Asp Ile Cys Ile Tyr Glu Phe Tyr Ala Ala Thr Glu Gly Asn
        355                 360                 365

Ile Gly Phe Met Asn Tyr Ala Arg Lys Val Gly Ala Val Gly Arg Val
    370                 375                 380

Asn Tyr Leu Gln Lys Lys Ile Ile Thr Tyr Asp Leu Ile Lys Tyr Asp
385                 390                 395                 400

Val Glu Lys Asp Glu Pro Val Arg Asp Glu Asn Gly Tyr Cys Val Arg
                405                 410                 415

Val Pro Lys Gly Glu Val Gly Leu Leu Val Cys Lys Ile Thr Gln Leu
            420                 425                 430

Thr Pro Phe Asn Gly Tyr Ala Gly Ala Lys Ala Gln Thr Glu Lys Lys
        435                 440                 445

Lys Leu Arg Asp Val Phe Lys Lys Gly Asp Leu Tyr Phe Asn Ser Gly
    450                 455                 460

Asp Leu Leu Met Val Asp His Glu Asn Phe Ile Tyr Phe His Asp Arg
465                 470                 475                 480

Val Gly Asp Thr Phe Arg Trp Lys Gly Glu Asn Val Ala Thr Thr Glu
                485                 490                 495

Val Ala Asp Thr Val Gly Leu Val Asp Phe Val Gln Glu Val Asn Val
            500                 505                 510

Tyr Gly Val His Val Pro Asp His Glu Gly Arg Ile Gly Met Ala Ser
        515                 520                 525

Ile Lys Met Lys Glu Asn His Glu Phe Asp Gly Lys Lys Leu Phe Gln
    530                 535                 540

His Ile Ala Asp Tyr Leu Pro Ser Tyr Ala Arg Pro Arg Phe Leu Arg
545                 550                 555                 560

Ile Gln Asp Thr Ile Glu Ile Thr Gly Thr Phe Lys His Arg Lys Met
                565                 570                 575

Thr Leu Val Glu Glu Gly Phe Asn Pro Ala Val Ile Lys Asp Ala Leu
            580                 585                 590

Tyr Phe Leu Asp Asp Thr Ala Lys Met Tyr Val Pro Met Thr Glu Asp
        595                 600                 605

Ile Tyr Asn Ala Ile Ser Ala Lys Thr Leu Lys Leu
    610                 615                 620
```

<210> SEQ ID NO 50
<211> LENGTH: 1173
<212> TYPE: DNA
<213> ORGANISM: Homo sapiens

<400> SEQUENCE: 50

```
aagttctcgg ctggtcagtt ctgggaagat tgccagcagc acagggtgac ggtgttccag      60

tacattgggg agctgtgccg ataccttgtc aaccagcccc cgagcaaggc agaacgtggc     120

cataaggtcc ggctggcagt gggcagcggg ctgcgcccag atacctggga gcgttttgtg     180

cggcgcttcg ggcccctgca ggtgctggag acatatggac tgacagaggg caacgtggcc     240

accatcaact acacaggaca gcggggcgct gtggggcgtg cttcctggct ttacaagcat     300
```

-continued

```
atcttcccct tctccttgat tcgctatgat gtcaccacag gagagccaat tcgggacccc    360

caggggcact gtatggccac atctccaggt gagccagggc tgctggtggc cccggtaagc    420

cagcagtccc cattcctggg ctatgctggc gggccagagc tggcccaggg gaagttgcta    480

aaggatgtct tccggcctgg ggatgttttc ttcaacactg ggacctgct ggtctgcgat     540

gaccaaggtt ttctccgctt ccatgatcgt actggagaca ccttcaggtg gaagggggag    600

aatgtggcca caaccgaggt ggcagaggtc ttcgaggccc tagattttct tcaggaggtg    660

aacgtctatg gagtcactgt gccagggcat gaaggcaggg ctggaatggc agccctagtt    720

ctgcgtcccc cccacgcttt ggaccttatg cagctctaca cccacgtgtc tgagaacttg    780

ccaccttatg cccggccccg attcctcagg ctccaggagt ctttggccac cacagagacc    840

ttcaaacagc agaaagttcg gatggcaaat gagggcttcg accccagcac cctgtctgac    900

ccactgtacg ttctggacca ggctgtaggt gcctacctgc ccctcacaac tgcccggtac    960

agcgccctcc tggcaggaaa ccttcgaatc tgagaacttc cacacctgag gcacctgaga   1020

gaggaactct gtggggtggg ggccgttgca ggtgtactgg gctgtcaggg atcttttcta   1080

taccagaact gcggtcacta ttttgtaata aatgtggctg gagctgatcc agctgtctct   1140

gacaaaaaaa aaaaaaaaaa aaagggcggc cgc                                1173
```

<210> SEQ ID NO 51
<211> LENGTH: 330
<212> TYPE: PRT
<213> ORGANISM: Homo sapiens

<400> SEQUENCE: 51

```
Lys Phe Ser Ala Gly Gln Phe Trp Glu Asp Cys Gln Gln His Arg Val
 1               5                  10                  15

Thr Val Phe Gln Tyr Ile Gly Glu Leu Cys Arg Tyr Leu Val Asn Gln
            20                  25                  30

Pro Pro Ser Lys Ala Glu Arg Gly His Lys Val Arg Leu Ala Val Gly
        35                  40                  45

Ser Gly Leu Arg Pro Asp Thr Trp Glu Arg Phe Val Arg Arg Phe Gly
    50                  55                  60

Pro Leu Gln Val Leu Glu Thr Tyr Gly Leu Thr Glu Gly Asn Val Ala
65                  70                  75                  80

Thr Ile Asn Tyr Thr Gly Gln Arg Gly Ala Val Gly Arg Ala Ser Trp
                85                  90                  95

Leu Tyr Lys His Ile Phe Pro Phe Ser Leu Ile Arg Tyr Asp Val Thr
            100                 105                 110

Thr Gly Glu Pro Ile Arg Asp Pro Gln Gly His Cys Met Ala Thr Ser
        115                 120                 125

Pro Gly Glu Pro Gly Leu Leu Val Ala Pro Val Ser Gln Gln Ser Pro
    130                 135                 140

Phe Leu Gly Tyr Ala Gly Gly Pro Glu Leu Ala Gln Gly Lys Leu Leu
145                 150                 155                 160

Lys Asp Val Phe Arg Pro Gly Asp Val Phe Phe Asn Thr Gly Asp Leu
                165                 170                 175

Leu Val Cys Asp Asp Gln Gly Phe Leu Arg Phe His Asp Arg Thr Gly
            180                 185                 190

Asp Thr Phe Arg Trp Lys Gly Glu Asn Val Ala Thr Thr Glu Val Ala
        195                 200                 205

Glu Val Phe Glu Ala Leu Asp Phe Leu Gln Glu Val Asn Val Tyr Gly
```

-continued

```
    210                 215                 220

Val Thr Val Pro Gly His Glu Gly Arg Ala Gly Met Ala Ala Leu Val
225                 230                 235                 240

Leu Arg Pro Pro His Ala Leu Asp Leu Met Gln Leu Tyr Thr His Val
                245                 250                 255

Ser Glu Asn Leu Pro Pro Tyr Ala Arg Pro Arg Phe Leu Arg Leu Gln
            260                 265                 270

Glu Ser Leu Ala Thr Thr Glu Thr Phe Lys Gln Gln Lys Val Arg Met
        275                 280                 285

Ala Asn Glu Gly Phe Asp Pro Ser Thr Leu Ser Asp Pro Leu Tyr Val
    290                 295                 300

Leu Asp Gln Ala Val Gly Ala Tyr Leu Pro Leu Thr Thr Ala Arg Tyr
305                 310                 315                 320

Ser Ala Leu Leu Ala Gly Asn Leu Arg Ile
                325                 330


<210> SEQ ID NO 52
<211> LENGTH: 2907
<212> TYPE: DNA
<213> ORGANISM: Homo sapiens

<400> SEQUENCE: 52

cgacccacgc gtccgggcgg gcggggccgg gcggcgggcg gggctggcgg ggcggccggg     60

ccatgcaggg cgcagagccg gctaaaccct gctgagaccc ggctccgtgc gtccaggggc    120

ggctaatgcc cctcacgctg tctacgctgc tgcaaccggg ccgcatctgg acggggcgcc    180

gcgcggcgga gccgacgccg ggccacaatg ctgcttggag cctctctggt gggggtgctg    240

ctgttctcca agctggtgct gaaactgccc tggacccagg tgggattctc cctgttgttc    300

ctctacttgg gatctggcgg ctggcgcttc atccgggtct tcatcaagac catcaggcgc    360

gatatctttg gcggcctggt cctcctgaag gtgaaggcaa aggtgcgaca gtgcctgcag    420

gagcggcgga cagtgcccat tttgtttgcc tctaccgttc ggcgccaccc cgacaagacg    480

gccctgatct tcgagggcac agatacccac tggaccttcc gccagctgga tgagtactca    540

agcagtgtag ccaacttcct gcaggcccgg ggcctggcct cgggcgatgt ggctgccatc    600

ttcatggaga accgcaatga gttcgtgggc ctatggctgg gcatggccaa gctcggtgtg    660

gaggcagccc tcatcaacac caacctgcgg cgggatgctc tgctccactg cctcaccacc    720

tcgcgcgcac gggcccttgt ctttggcagc gaaatggcct cagccatctg tgaggtccat    780

gccagcctgg acccctcgct cagcctcttc tgctctggct cctgggagcc cggtgcggtg    840

cctccaagca cagaacacct ggaccctctg ctgaaagatg ctcccaagca ccttcccagt    900

tgccctgaca agggcttcac agataaactg ttctacatct acacatccgg caccacaggg    960

ctgcccaagg ccgccatcgt ggtgcacagc aggtattacc gcatggctgc cctggtgtac   1020

tatggattcc gcatgcggcc caacgacatc gtctatgact gcctccccct ctaccactca   1080

gcaggaaaca tcgtgggaat cggccagtgc ctgctgcatg gcatgacggt ggtgattcgg   1140

aagaagttct cagcctcccg gttctgggac gattgtatca agtacaactg cacgattgtg   1200

cagtacattg gtgaactgtg ccgctacctc ctgaaccagc caccgcggga ggcagaaaac   1260

cagcaccagg ttcgcatggc actaggcaat ggcctccggc agtccatctg gaccaacttt   1320

tccagccgct tccacatacc ccaggtggct gagttctacg gggccacaga gtgcaactgt   1380

agcctgggca acttcgacag ccaggtgggg gcctgtggtt tcaatagccg catcctgtcc   1440
```

-continued

```
ttcgtgtacc ccatccggtt ggtacgtgtc aacgaggaca ccatggagct gatccggggg   1500

cccgacggcg tctgcattcc ctgccagcca ggtgagccgg gccagctggt gggccgcatc   1560

atccagaaag accccctgcg ccgcttcgat ggctacctca accagggcgc caacaacaag   1620

aagattgcca aggatgtctt caagaagggg gaccaggcct accttactgg tgatgtgctg   1680

gtgatggacg agctgggcta cctgtacttc cgagaccgca ctggggacac gttccgctgg   1740

aaaggtgaga acgtgtccac caccgaggtg gaaggcacac tcagccgcct gctggacatg   1800

gctgacgtgg ccgtgtatgg tgtcgaggtg ccaggaaccg agggccgggc cggaatggct   1860

gctgtggcca gccccactgg caactgtgac ctggagcgct ttgctcaggt cttggagaag   1920

gaactgcccc tgtatgcgcg ccccatcttc ctgcgcctcc tgcctgagct gcacaaaaca   1980

ggaacctaca agttccagaa gacagagcta cggaaggagg gctttgaccc ggctattgtg   2040

aaagacccgc tgttctatct agatgcccag aagggccgct acgtcccgct ggaccaagag   2100

gcctacagcc gcatccaggc aggcgaggag aagctgtgat tccccccatc cctctgaggg   2160

ccggcggatg ctggatccgg agccccaggt tccgccccag agcggtcctg gacaaggcca   2220

gaccaaagca agcagggcct ggcacctcca tcctgaggtg ctgcccctcc atccaaaact   2280

gccaagtgac tcattgcctt cccaaccctt ccagaggctt tctgtgaaag tctcatgtcc   2340

aagttccgtc ttctgggctg ggcaggccct ctggttccca ggctgagact gacgggtttt   2400

ctcaggatga tgtcttgggt gagggtaggg agaggacaag ggtcaccga gcccttccca   2460

gagagcaggg agcttataaa tggaaccaga gcagaagtcc ccagactcag gaagtcaaca   2520

gagtgggcag ggacagtggt agcatccatc tggtggccaa agagaatcgt agccccagag   2580

ctgcccaagt tcactgggct ccacccccac ctccaggagg ggaggagagg acctgacatc   2640

tgtaggtggc ccctgatgcc ccatctacag caggaggtca ggaccacgcc cctggcctct   2700

ccccactccc ccatcctcct ccctgggtgg ctgcctgatt atccctcagg cagggcctct   2760

cagtccttgt gggtctgtgt cacctccatc tcagtcttgg cctggctatg aggggaggag   2820

gaatgggaga gggggctcag gggccaataa actctgcctt gagtcctcct aaaaaaaaaa   2880

aaaaaaaaaa aaaaaaaaaa aaaaaaa                                       2907
```

```
<210> SEQ ID NO 53
<211> LENGTH: 643
<212> TYPE: PRT
<213> ORGANISM: Homo sapiens

<400> SEQUENCE: 53

Met Leu Leu Gly Ala Ser Leu Val Gly Val Leu Leu Phe Ser Lys Leu
 1               5                  10                  15

Val Leu Lys Leu Pro Trp Thr Gln Val Gly Phe Ser Leu Leu Phe Leu
            20                  25                  30

Tyr Leu Gly Ser Gly Gly Trp Arg Phe Ile Arg Val Phe Ile Lys Thr
        35                  40                  45

Ile Arg Arg Asp Ile Phe Gly Gly Leu Val Leu Leu Lys Val Lys Ala
    50                  55                  60

Lys Val Arg Gln Cys Leu Gln Glu Arg Arg Thr Val Pro Ile Leu Phe
65                  70                  75                  80

Ala Ser Thr Val Arg Arg His Pro Asp Lys Thr Ala Leu Ile Phe Glu
                85                  90                  95

Gly Thr Asp Thr His Trp Thr Phe Arg Gln Leu Asp Glu Tyr Ser Ser
            100                 105                 110
```

-continued

```
Ser Val Ala Asn Phe Leu Gln Ala Arg Gly Leu Ala Ser Gly Asp Val
        115                 120                 125

Ala Ala Ile Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Leu His Cys Leu Thr Thr Ser Arg Ala Arg Ala
                165                 170                 175

Leu Val Phe Gly Ser Glu Met Ala Ser Ala Ile Cys Glu Val His Ala
            180                 185                 190

Ser Leu Asp Pro Ser Leu Ser Leu Phe Cys Ser Gly Ser Trp Glu Pro
        195                 200                 205

Gly Ala Val Pro Pro Ser Thr Glu His Leu Asp Pro Leu Leu Lys Asp
    210                 215                 220

Ala Pro Lys His Leu Pro Ser Cys Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255

Ile Val Val His Ser Arg Tyr Tyr Arg Met Ala Ala Leu Val Tyr Tyr
            260                 265                 270

Gly Phe Arg Met Arg Pro Asn Asp Ile Val Tyr Asp Cys Leu Pro Leu
        275                 280                 285

Tyr His Ser Ala Gly Asn Ile Val Gly Ile Gly Gln Cys Leu Leu His
    290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Ile Val Gln Tyr Ile Gly Glu
                325                 330                 335

Leu Cys Arg Tyr Leu Leu Asn Gln Pro Pro Arg Glu Ala Glu Asn Gln
            340                 345                 350

His Gln Val Arg Met Ala Leu Gly Asn Gly Leu Arg Gln Ser Ile Trp
        355                 360                 365

Thr Asn Phe Ser Ser Arg Phe His Ile Pro Gln Val Ala Glu Phe Tyr
    370                 375                 380

Gly Ala Thr Glu Cys Asn Cys Ser Leu Gly Asn Phe Asp Ser Gln Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Glu Pro Gly Gln Leu Val
        435                 440                 445

Gly Arg Ile Ile Gln Lys Asp Pro Leu Arg Arg Phe Asp Gly Tyr Leu
    450                 455                 460

Asn Gln Gly Ala Asn Asn Lys Lys Ile Ala Lys Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
        515                 520                 525

Leu Asp Met Ala Asp Val Ala Val Tyr Gly Val Glu Val Pro Gly Thr
```

-continued

```
    530                 535                 540

Glu Gly Arg Ala Gly Met Ala Ala Val Ala Ser Pro Thr Gly Asn Cys
545                 550                 555                 560

Asp Leu Glu Arg Phe Ala Gln Val Leu Glu Lys Glu Leu Pro Leu Tyr
                565                 570                 575

Ala Arg Pro Ile Phe Leu Arg Leu Leu Pro Glu Leu His Lys Thr Gly
            580                 585                 590

Thr Tyr Lys Phe Gln Lys Thr Glu Leu Arg Lys Glu Gly Phe Asp Pro
        595                 600                 605

Ala Ile Val Lys Asp Pro Leu Phe Tyr Leu Asp Ala Gln Lys Gly Arg
    610                 615                 620

Tyr Val Pro Leu Asp Gln Glu Ala Tyr Ser Arg Ile Gln Ala Gly Glu
625                 630                 635                 640

Glu Lys Leu


<210> SEQ ID NO 54
<211> LENGTH: 1248
<212> TYPE: DNA
<213> ORGANISM: Homo sapiens
<220> FEATURE:
<221> NAME/KEY: misc_feature
<222> LOCATION: (1)...(1248)
<223> OTHER INFORMATION: n = A,T,C or G

<400> SEQUENCE: 54

gtcgttggga tcctcggctg cttagatctc ggagccacct gtgttctggc ccccaagttc     60

tctacttcct gcttctggga tgactgtcgg cagcatggcg tgacagtgat cctgtatgtg    120

ggcgagctcc tgcgatactt gtgtaacatt ccccagcaac cagaggaccg gacacataca    180

gtccgcctgg caatgggcaa tggactacgg gctgatgtgt ggggagacct tccagcagcg    240

tttcggtcct atttcggatc tngggaagtc ttacgggctt ccacagaagg gcaacatggg    300

gctttagttc aaatattgtt gggggcgctg cggggccctg ggggcaaaga tggagcttgc    360

ctcctccgaa tgctgtcccc ctttgagctg gtgcagttcg acatggaggc ggcggagcct    420

gtgagggaca atcagggctt ctgcatccct gtagggctag gggagccggg gctgctgttg    480

accaaggtgg taagccagca acccttcgtg ggctaccgcg gcccccgaga gctgtcggaa    540

cggaagctgg tgcgcaacgt gcggcaatcg ggcgacgttt actacaacac cggggacgta    600

ctggccatgg accgcgaagg cttcctctac ttccgcgacc gactcgggga caccttccga    660

tggaagggcg agaacgtgtc cacgcacgag gtggagggcg tgttgtcgca ggtggacttc    720

ttgcaacagg ttaacgtgta tggcgtgtgc gtgccaggtt gtgagggtaa ggtgggcatg    780

gctgctgtgg cattagcccc cggccagact ttcgacgggg agaagttgta ccagcacgtt    840

cgcgcttggc tccctgccta cgctaccccc catttcatcc gcatccagga cgccatggag    900

gtcaccagca cgttcaaact gatgaagacc cggttggtgc gtgagggctt caatgtgggg    960

atcgtggttg accctctgtt tgtactggac aaccgggccc agtccttccg gcccctgacg   1020

gcagaaatgt accaggctgt gtgtgaggga acctggaggc tctgatcacc tggccaaccc   1080

actggggtag ggatcaaagc cagccacccc caccccaaca cactcggtgt ccctttcatc   1140

ctgggcctgt gtgaatccca gcctggccat accctcaacc tcagtgggct ggaaatgaca   1200

gtgggccctg tagcagtggc agaataaact cagmtgygtt cacagaaa                1248


<210> SEQ ID NO 55
<211> LENGTH: 354
```

-continued

<212> TYPE: PRT
<213> ORGANISM: Homo sapiens
<220> FEATURE:
<221> NAME/KEY: VARIANT
<222> LOCATION: (1)...(354)
<223> OTHER INFORMATION: Xaa = Any Amino Acid

<400> SEQUENCE: 55

Val Val Gly Ile Leu Gly Cys Leu Asp Leu Gly Ala Thr Cys Val Leu
1 5 10 15

Ala Pro Lys Phe Ser Thr Ser Cys Phe Trp Asp Asp Cys Arg Gln His
20 25 30

Gly Val Thr Val Ile Leu Tyr Val Gly Glu Leu Leu Arg Tyr Leu Cys
35 40 45

Asn Ile Pro Gln Gln Pro Glu Asp Arg Thr His Thr Val Arg Leu Ala
50 55 60

Met Gly Asn Gly Leu Arg Ala Asp Val Trp Gly Asp Leu Pro Ala Ala
65 70 75 80

Phe Arg Ser Tyr Phe Gly Ser Xaa Glu Val Leu Arg Ala Ser Thr Glu
85 90 95

Gly Gln His Gly Ala Leu Val Gln Ile Leu Leu Gly Ala Leu Arg Gly
100 105 110

Pro Gly Gly Lys Asp Gly Ala Cys Leu Leu Arg Met Leu Ser Pro Phe
115 120 125

Glu Leu Val Gln Phe Asp Met Glu Ala Ala Glu Pro Val Arg Asp Asn
130 135 140

Gln Gly Phe Cys Ile Pro Val Gly Leu Gly Glu Pro Gly Leu Leu Leu
145 150 155 160

Thr Lys Val Val Ser Gln Gln Pro Phe Val Gly Tyr Arg Gly Pro Arg
165 170 175

Glu Leu Ser Glu Arg Lys Leu Val Arg Asn Val Arg Gln Ser Gly Asp
180 185 190

Val Tyr Tyr Asn Thr Gly Asp Val Leu Ala Met Asp Arg Glu Gly Phe
195 200 205

Leu Tyr Phe Arg Asp Arg Leu Gly Asp Thr Phe Arg Trp Lys Gly Glu
210 215 220

Asn Val Ser Thr His Glu Val Glu Gly Val Leu Ser Gln Val Asp Phe
225 230 235 240

Leu Gln Gln Val Asn Val Tyr Gly Val Cys Val Pro Gly Cys Glu Gly
245 250 255

Lys Val Gly Met Ala Ala Val Ala Leu Ala Pro Gly Gln Thr Phe Asp
260 265 270

Gly Glu Lys Leu Tyr Gln His Val Arg Ala Trp Leu Pro Ala Tyr Ala
275 280 285

Thr Pro His Phe Ile Arg Ile Gln Asp Ala Met Glu Val Thr Ser Thr
290 295 300

Phe Lys Leu Met Lys Thr Arg Leu Val Arg Glu Gly Phe Asn Val Gly
305 310 315 320

Ile Val Val Asp Pro Leu Phe Val Leu Asp Asn Arg Ala Gln Ser Phe
325 330 335

Arg Pro Leu Thr Ala Glu Met Tyr Gln Ala Val Cys Glu Gly Thr Trp
340 345 350

Arg Leu

<210> SEQ ID NO 56

-continued

<211> LENGTH: 2885
<212> TYPE: DNA
<213> ORGANISM: Homo sapiens

<400> SEQUENCE: 56
aacggcaagt aagcgcaacg caattaatgt gagtagctca ctcattaggc accccaggct 60
ttacacttta tgcttccggg ctcgtatgtt gtgtggaatt gtgagcggat accaatttca 120
cacaggaacc agctatgaca tgattacgaa tttaatacga ctcactatag ggaatttggc 180
cctcgaggcc aagaattcgg cacgaggggt gctgagcccc tgcgcggttt ctggtgcgta 240
gagactgtaa atcgctgcgc ttctcagtca tcatcatccc agcttttccc ggctcgaatt 300
cagcctccaa ctcaagctcg cgggaaagac tacctgagag gagaaaagct tctgtccctg 360
gaccttcttc tgagggtgga gtcggaggct ccctgctttc cagccgccca gtgacccaag 420
cttaatcttc agcaccactt ggggcgacct tttcggtgca aacctacgat tctgtttctc 480
aggattcctc cccatcccgc ttcgccccgg aaaagctgac aagaacttca ggtgtaagcc 540
ctgagtagtg aggatctgcg gtctccgtgg agagctgtgc ctggaagaga aggacgctgg 600
tgggggctga gatcagagct gtcttctggc ccagttgccc ccatgcttct gtcatggcta 660
acagttctag ggctggaat ggtcgtcctg cacttcttgc agaaactcct gttcccttac 720
ttttgggatg acttctggtt cgtgttgaag gtggtgctca ttataattcg gctgaagaag 780
tatgaaaaga gaggggagct ggtgactgtg ctggataaat tcttgagtca tgccaaaaga 840
caacctcgga aacctttcat catctatgag ggagacatct acacctatca ggatgtagac 900
aaaaggagca gcagagtggc ccatgtcttc ctgaaccatt cctctctgaa aaagggggac 960
acggtggctc tgctgatgag caatgagccg gacttcgttc acgtgtggtt cggcctcgcc 1020
aagctgggct gcgtggtggc ctttctcaac accaacattc gctccaactc cctcctgaat 1080
tgcatccgcg cctgtgggcc cagagcccta gtggtgggcg cagatttgct tggaacggta 1140
gaagaaatcc ttccaagcct ctcagaaaat atcagtgttt gggggatgaa agattctgtt 1200
ccacaaggtg taatttcact caaagaaaaa ctgagcacct cacctgatga gcccgtgcca 1260
cgcagccacc atgttgtctc actcctcaag tctacttgtc tttacatttt tacctctgga 1320
acaacaggtc taccaaaagc agctgtgatt agtcagctgc aggttttaag gggttctgct 1380
gtcctgtggg cttttggttg tactgctcat gacattgttt atataaccct tcctctgtat 1440
catagttcag cagctatcct gggaatttct ggatgtgttg agttgggtgc cacttgtgtg 1500
ttaaagaaga aattttcagc aagccagttt tggagtgact gcaagaagta tgatgtgact 1560
gtgtttcagt atattggaga actttgtcgc tacctttgca aacaatctaa gagagaagga 1620
gaaaaggatc ataaggtgcg tttggcaatt ggaaatggca tacggagtga tgtatggaga 1680
gaatttttag acagatttgg aaatataaag gtgtgtgaac tttatgcagc taccgaatca 1740
agcatatctt tcatgaacta cactgggaga attggagcaa ttgggagaac aaatttgttt 1800
tacaaacttc tttccacttt tgacttaata aagtatgact ttcagaaaga tgaacccatg 1860
agaaatgagc agggttggtg tattcatgtg aaaaaaggag aacctggact tctcatttct 1920
cgagtgaatg caaaaaatcc cttctttggc tatgctgggc cttataagca cacaaaagac 1980
aaattgcttt gtgatgtttt taagaaggga gatgtttacc ttaatactgg agacttaata 2040
gtccaggatc aggacaattt cctttatttt tgggaccgta ctggagacac tttcagatgg 2100
aaaggagaaa atgtcgcaac cactgaggtt gctgatgtta ttggaatgtt ggatttcata 2160
caggaagcaa acgtctatgg tgtggctata tcaggttatg aaggaagagc aggaatggct 2220

-continued

```
tctattattt taaaaccaaa tacatcttta gatttggaaa aagtttatga acaagttgta   2280

acatttctac cagcttatgc ttgtccacga tttttaagaa ttcaggaaaa aatggaagca   2340

acaggaacat tcaaactatt gaagcatcag ttggtggaag atggatttaa tccactgaaa   2400

atttctgaac cactttactt catggataac ttgaaaaagt cttatgttct actgaccagg   2460

gaactttatg atcaaataat gttaggggaa ataaaacttt aagattttta tatctagaac   2520

tttcatatgc tttcttagga agagtgagag gggggtatat gattctttat gaaatgggga   2580

aagggagcta acattaatta tgcatgtact atatttcctt aatatgagag ataatttttt   2640

aattgcataa gaattttaat ttcttttaat tgatataaac attagttgat tattcttttt   2700

atctatttgg agattcagtg cataactaag tattttcctt aatactaaag atttaaaata   2760

ataaatagtg gctagcggtt tggacaatca ctaaaaatgt actttctaat aagtaaaatt   2820

tctaattttg aataaaagat taaattttac tgaaaaaaaa aaaaaaaaaa aaaattggcg   2880

gccgc                                                               2885


<210> SEQ ID NO 57
<211> LENGTH: 619
<212> TYPE: PRT
<213> ORGANISM: Homo sapiens

<400> SEQUENCE: 57

Met Leu Leu Ser Trp Leu Thr Val Leu Gly Ala Gly Met Val Val Leu
 1               5                  10                  15

His Phe Leu Gln Lys Leu Leu Phe Pro Tyr Phe Trp Asp Asp Phe Trp
            20                  25                  30

Phe Val Leu Lys Val Val Leu Ile Ile Ile Arg Leu Lys Lys Tyr Glu
        35                  40                  45

Lys Arg Gly Glu Leu Val Thr Val Leu Asp Lys Phe Leu Ser His Ala
    50                  55                  60

Lys Arg Gln Pro Arg Lys Pro Phe Ile Ile Tyr Glu Gly Asp Ile Tyr
65                  70                  75                  80

Thr Tyr Gln Asp Val Asp Lys Arg Ser Ser Arg Val Ala His Val Phe
                85                  90                  95

Leu Asn His Ser Ser Leu Lys Lys Gly Asp Thr Val Ala Leu Leu Met
            100                 105                 110

Ser Asn Glu Pro Asp Phe Val His Val Trp Phe Gly Leu Ala Lys Leu
        115                 120                 125

Gly Cys Val Val Ala Phe Leu Asn Thr Asn Ile Arg Ser Asn Ser Leu
    130                 135                 140

Leu Asn Cys Ile Arg Ala Cys Gly Pro Arg Ala Leu Val Val Gly Ala
145                 150                 155                 160

Asp Leu Leu Gly Thr Val Glu Glu Ile Leu Pro Ser Leu Ser Glu Asn
                165                 170                 175

Ile Ser Val Trp Gly Met Lys Asp Ser Val Pro Gln Gly Val Ile Ser
            180                 185                 190

Leu Lys Glu Lys Leu Ser Thr Ser Pro Asp Glu Pro Val Pro Arg Ser
        195                 200                 205

His His Val Val Ser Leu Leu Lys Ser Thr Cys Leu Tyr Ile Phe Thr
    210                 215                 220

Ser Gly Thr Thr Gly Leu Pro Lys Ala Ala Val Ile Ser Gln Leu Gln
225                 230                 235                 240

Val Leu Arg Gly Ser Ala Val Leu Trp Ala Phe Gly Cys Thr Ala His
```

-continued

```
                245                 250                 255

Asp Ile Val Tyr Ile Thr Leu Pro Leu Tyr His Ser Ser Ala Ala Ile
            260                 265                 270

Leu Gly Ile Ser Gly Cys Val Glu Leu Gly Ala Thr Cys Val Leu Lys
        275                 280                 285

Lys Lys Phe Ser Ala Ser Gln Phe Trp Ser Asp Cys Lys Lys Tyr Asp
    290                 295                 300

Val Thr Val Phe Gln Tyr Ile Gly Glu Leu Cys Arg Tyr Leu Cys Lys
305                 310                 315                 320

Gln Ser Lys Arg Glu Gly Glu Lys Asp His Lys Val Arg Leu Ala Ile
                325                 330                 335

Gly Asn Gly Ile Arg Ser Asp Val Trp Arg Glu Phe Leu Asp Arg Phe
            340                 345                 350

Gly Asn Ile Lys Val Cys Glu Leu Tyr Ala Ala Thr Glu Ser Ser Ile
        355                 360                 365

Ser Phe Met Asn Tyr Thr Gly Arg Ile Gly Ala Ile Gly Arg Thr Asn
    370                 375                 380

Leu Phe Tyr Lys Leu Leu Ser Thr Phe Asp Leu Ile Lys Tyr Asp Phe
385                 390                 395                 400

Gln Lys Asp Glu Pro Met Arg Asn Glu Gln Gly Trp Cys Ile His Val
                405                 410                 415

Lys Lys Gly Glu Pro Gly Leu Leu Ile Ser Arg Val Asn Ala Lys Asn
            420                 425                 430

Pro Phe Phe Gly Tyr Ala Gly Pro Tyr Lys His Thr Lys Asp Lys Leu
        435                 440                 445

Leu Cys Asp Val Phe Lys Lys Gly Asp Val Tyr Leu Asn Thr Gly Asp
    450                 455                 460

Leu Ile Val Gln Asp Gln Asp Asn Phe Leu Tyr Phe Trp Asp Arg Thr
465                 470                 475                 480

Gly Asp Thr Phe Arg Trp Lys Gly Glu Asn Val Ala Thr Thr Glu Val
                485                 490                 495

Ala Asp Val Ile Gly Met Leu Asp Phe Ile Gln Glu Ala Asn Val Tyr
            500                 505                 510

Gly Val Ala Ile Ser Gly Tyr Glu Gly Arg Ala Gly Met Ala Ser Ile
        515                 520                 525

Ile Leu Lys Pro Asn Thr Ser Leu Asp Leu Glu Lys Val Tyr Glu Gln
    530                 535                 540

Val Val Thr Phe Leu Pro Ala Tyr Ala Cys Pro Arg Phe Leu Arg Ile
545                 550                 555                 560

Gln Glu Lys Met Glu Ala Thr Gly Thr Phe Lys Leu Leu Lys His Gln
                565                 570                 575

Leu Val Glu Asp Gly Phe Asn Pro Leu Lys Ile Ser Glu Pro Leu Tyr
            580                 585                 590

Phe Met Asp Asn Leu Lys Lys Ser Tyr Val Leu Leu Thr Arg Glu Leu
        595                 600                 605

Tyr Asp Gln Ile Met Leu Gly Glu Ile Lys Leu
    610                 615
```

<210> SEQ ID NO 58
<211> LENGTH: 3098
<212> TYPE: DNA
<213> ORGANISM: Rattus norvegicus

<400> SEQUENCE: 58

-continued

```
aagttcccac tccagacttc tgcgagaacc cgtgaggaag cagcgagaac cgggggtttg     60
caagccagag aaggatgcgg actccgggag caggaacagc ctctgtggcc tcattggggc    120
tgctttggct tctgggactt ccgtggacct ggagcgcggc ggcggcgttc ggtgtgtacg    180
tgggtagcgg tggctggcga tttctgcgta tcgtctgcaa gacggcgagg cgagacctct    240
ttggcctctc tgttctgatc cgcgtgcggc tagagctacg acgacaccgg cgagcaggag    300
acacgatccc acgcatcttc caggccgtgg cccagcgaca gccggagcgc ctggcgctgg    360
tagatgcgag tagcggtatc tgctggacct tcgcacagct agacacctac tccaatgctg    420
tggccaatct gttcctccag ctgggctttg cgccaggcga tgtggtggct gtgttcctgg    480
aaggccggcc cgagttcgtg ggactgtggc tgggcctggc caaggccggt gtagtggctg    540
cgcttctcaa tgtcaacctg aggcgggagc cccttgcctt ctgcttgggc acatcagctg    600
ccaaggccct catttatggc ggggagatgg cagcggcggt ggcggaggtg agtgagcagc    660
tggggaagag cctgctcaag ttctgctctg gagatctggg gcctgagagc gtcctgcctg    720
acacgcagct tctggacccc atgcttgctg aggcgcccac cacacccctg gcacaggccc    780
caggcaaggg catggatgat cggctatttt acatctatac ttctgggacc accggacttc    840
ctaaggcggc cattgtggtg cacagcaggt actaccgcat cgcagccttc ggccaccatt    900
cctacagcat gcgggccaac gatgtgctct atgactgcct acctctctac cactcagcag    960
ggaacatcat gggcgtggga cagtgtatca tctacgggtt aacggtggta ctgcgcaaga   1020
agttctccgc cagccgcttc tgggacgact gtgtcaaata taattgcacg gtagtgcagt   1080
acatcggtga aatatgccgc tacctgctaa ggcagccggt tcgcgatgta gagcggcggc   1140
accgcgtgcg cctggccgtg ggtaacggac tgcggccagc catctgggag gagttcacgc   1200
agggtttcgg tgtgcgacag attggcgagt tctacggcgc caccgaatgc aactgcagca   1260
ttgccaacat ggacggcaag gtcggctcct gcggcttcaa cagccgtatc ctcacgcatg   1320
tgtaccccat ccgtctggtc aaggtcaacg aggacacgat ggagccactg agggactccc   1380
aaggcctctg catcccgtgc cagcccgggg aacctgggct tctcgtgggc cagatcaacc   1440
agcaagaccc tctgcggcgc ttcgatggct atgttagtga cagcgccacc aacaagaaga   1500
ttgcccacag cgtgttccga aagggggaca gcgcctacct ttcaggtgac gtgctagtga   1560
tggacgagct ggggtacatg tacttccgtg accgcagcgg ggataccttc cgatggcgcg   1620
gcgagaacgt atccaccacg gaggtggaag ccgtgctgag ccgcctgttg ggccagacgg   1680
acgtggctgt gtatggagtg gctgtgccag gagtggaggg gaaaagcggc atggcggcca   1740
ttgcagaccc ccacaaccag ctggacccta actcaatgta ccaggaattg cagaaggttc   1800
ttgcatccta tgcccagccc atcttcctgc gtcttctgcc ccaagtggat acaacaggca   1860
ccttcaagat ccagaagacc cgactacagc gtgaaggctt tgacccccgc cagacctcag   1920
accggctctt ctttctagac ctgaaacagg gacgctacct accccctggat gagagagtcc   1980
atgcccgcat ctgcgcaggc gacttctcac tctgagcctg gtgagtggga tggccctgga   2040
cttgtgagac cagggagccg gacaccccctg ttcaggtgtt tctcctgcct ggccacgtgg   2100
ccagcagcac ctgtgggtgc aggaaactgg aacctgagtg gccgggtgtc cctttcctac   2160
aacccaccat gcacacatct agcctctgcc ttggtctttt tctccatctc tttcctccgt   2220
gcccagcagg agccccacag acacattggc tgctgtgtcc tgcagtggga ccggtgtcta   2280
ggggtccatg ctgcaggctg tgacccgcac tggtgcccac ctcccttccc cattgtgcct   2340
taggttcctc cactgtgcgc cggtgaagca agtggggacc cacatagctg ttgtccctgc   2400
```

-continued

```
tgagggttgg tagcaaatgc accctcatgt cagctgggag acacatgcag tctcccactg   2460

acccccaatc aactgaagat actgttttgt attattgttt tgagataggg tctcactgtg   2520

gaggccaagc tggcctcagg ctcaccactc tactgcctcc gggcaccagc ctgcagtttg   2580

atgacatgta tgcactattg ttctaagggt cttctgagtc cctgctttcc cctcatgtcc   2640

taaaaccttc cagaactgac tctgatcact tggatgtagc tagtgttggc cctgcccacg   2700

tgtgtcaatt caggggtccc caggcatcat ctctggaggc cctaaccttg gcaaagcttg   2760

gatgtcctca catcacagca ggagacccag gaaggttgct gtggtgtctc ttgggcaccc   2820

ctggcggcag ccgtggacat gcttccctgc tgtgatagcc caaactgttg cctatgacat   2880

ttgaggtcta cccttctggc tgccatggtc cccattgaga tctttggtga ctcacctcag   2940

ccaccaagcc aggcctctgc cttccttcag ctctaagggc atgaagggtg tggacagagc   3000

agccacaggc tgcccacagt cacccacatg caagtgttat ttccttgttt gttttaaaaa   3060

aataaacatg ctgagccttg aaaaaaaaaa aaaaaaa                            3098


<210> SEQ ID NO 59
<211> LENGTH: 646
<212> TYPE: PRT
<213> ORGANISM: Rattus norvegicus

<400> SEQUENCE: 59

Met Arg Thr Pro Gly Ala Gly Thr Ala Ser Val Ala Ser Leu Gly Leu
 1               5                  10                  15

Leu Trp Leu Leu Gly Leu Pro Trp Thr Trp Ser Ala Ala Ala Ala Phe
            20                  25                  30

Gly Val Tyr Val Gly Ser Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Arg Arg Ala Gly Asp Thr Ile Pro Arg
65                  70                  75                  80

Ile Phe Gln Ala Val Ala Gln Arg Gln Pro Glu Arg Leu Ala Leu Val
                85                  90                  95

Asp Ala Ser Ser Gly Ile Cys Trp Thr Phe Ala Gln Leu Asp Thr Tyr
            100                 105                 110

Ser Asn Ala Val Ala Asn Leu Phe Leu Gln Leu Gly Phe Ala Pro Gly
        115                 120                 125

Asp Val Val Ala Val Phe Leu Glu Gly Arg Pro Glu Phe Val Gly Leu
    130                 135                 140

Trp Leu Gly Leu Ala Lys Ala Gly Val Val Ala Ala Leu Leu Asn Val
145                 150                 155                 160

Asn Leu Arg Arg Glu Pro Leu Ala Phe Cys Leu Gly Thr Ser Ala Ala
                165                 170                 175

Lys Ala Leu Ile Tyr Gly Gly Glu Met Ala Ala Ala Val Ala Glu Val
            180                 185                 190

Ser Glu Gln Leu Gly Lys Ser Leu Leu Lys Phe Cys Ser Gly Asp Leu
        195                 200                 205

Gly Pro Glu Ser Val Leu Pro Asp Thr Gln Leu Leu Asp Pro Met Leu
    210                 215                 220

Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
```

-continued

```
                245                 250                 255

Lys Ala Ala Ile Val Val His Ser Arg Tyr Tyr Arg Ile Ala Ala Phe
            260                 265                 270

Gly His His Ser Tyr Ser Met Arg Ala Asn Asp Val Leu Tyr Asp Cys
        275                 280                 285

Leu Pro Leu Tyr His Ser Ala Gly Asn Ile Met Gly Val Gly Gln Cys
    290                 295                 300

Ile Ile Tyr Gly Leu Thr Val Val Leu Arg Lys Lys Phe Ser Ala Ser
305                 310                 315                 320

Arg Phe Trp Asp Asp Cys Val Lys Tyr Asn Cys Thr Val Val Gln Tyr
                325                 330                 335

Ile Gly Glu Ile Cys Arg Tyr Leu Leu Arg Gln Pro Val Arg Asp Val
            340                 345                 350

Glu Arg Arg His Arg Val Arg Leu Ala Val Gly Asn Gly Leu Arg Pro
        355                 360                 365

Ala Ile Trp Glu Glu Phe Thr Gln Gly Phe Gly Val Arg Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
                405                 410                 415

Tyr Pro Ile Arg Leu Val Lys Val Asn Glu Asp Thr Met Glu Pro Leu
            420                 425                 430

Arg Asp Ser Gln Gly Leu Cys Ile Pro Cys Gln Pro Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Ala Val Leu
        515                 520                 525

Ser Arg Leu Leu Gly Gln Thr Asp Val Ala Val Tyr Gly Val Ala Val
    530                 535                 540

Pro Gly Val Glu Gly Lys Ser Gly Met Ala Ala Ile Ala Asp Pro His
545                 550                 555                 560

Asn Gln Leu Asp Pro Asn Ser Met Tyr Gln Glu Leu Gln Lys Val Leu
                565                 570                 575

Ala Ser Tyr Ala Gln Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly Arg Tyr Leu Pro Leu Asp Glu Arg Val His Ala Arg Ile Cys
625                 630                 635                 640

Ala Gly Asp Phe Ser Leu
                645

<210> SEQ ID NO 60
```

-continued

<211> LENGTH: 2963
<212> TYPE: DNA
<213> ORGANISM: Rattus norvegicus

<400> SEQUENCE: 60
gacacagtac tgccgatgtt ggacagagga tcgcttaaca gaacgaaatc tcaaaacaaa 60
ttaacaggac ccggttgctt gatttcccaa atcagaaaag gctcgaaatg tctagagggg 120
ctgactgatg cagcggtgac ccggactgga gacagttgga cgcgatcatc tctggtgctt 180
ttgttcaacc ttgaaacctt cgccacagga gacttgcctg agcagagaag caaacgtgga 240
gaaacaaaga gagatctagc gaaaagcctc tgggaccaag gaggggaggt gggactctgg 300
gttggcggtg gcacctgctg ccggctatta ataataggt cgcgatgcgt ttataaggtg 360
tttgattaaa caaagactct atgagagaag aataactagc aacagcccca cgtctgagtc 420
gtcgcctccg accttttca acgtgggttc tttgggccga gcgtcgtttg ccgagaacta 480
gatctcacct gaccccagac gctgaaaaca agcgctgtgg catcctgggc cacccaagct 540
gacaagggcg cgccccctga gcacacgagg tgccccacga gggggaggga cccacagccg 600
tcccgcccgc accgcggtgt ccgctgcggg cacctgcagc cgagccgcca cccgcagtcg 660
cagcgcgtcc ggcggccgaa cccggtcgtc agctcgtcag cacctgctct gcttctctcc 720
cgcccgccgc cgcgctgcac gcctcgagcg ctccctcggc cccggcgggg accggggacc 780
ccgcagccac cgccatgctg cctgtgctct acaccggcct ggcggggctg ctgctgctgc 840
ctctgctgct cacctgctgc tgcccctacc tcctccagga cgtgcggttc ttcctgcaac 900
tggccaacat ggcccggcag gtgcgcagct accggcagcg gcgacccgtg cgcaccatcc 960
tgcatgtctt cttggagcaa gcgcgcaaga ccccgcacaa gcccttcctg ctgtttcgcg 1020
acgagacgct tacctacgcc caggtagacc ggcgcagcaa ccaagtagcg cgagcgctgc 1080
atgatcacct gggcctgcgg caggggggatt gcgtggccct cttcatgggc aatgagccgg 1140
cctacgtgtg gctctggctg ggactgctca aactgggctg tcccatggcg tgcctcaact 1200
acaacatccg tgccaagtct ctgctacact gctttcagtg ctgcggggcg aaggtgctgc 1260
tggcctcccc agagctacac gaagctgtcg aggaggttct tccaaccctg aaaaaggagg 1320
gcgtgtccgt cttctacgta agcagaactt ctaacactaa tggcgtggac acagtactgg 1380
acaaagtaga cggggtgtcg gcggacccca tcccggagtc gtggaggtct gaagtcacgt 1440
tcaccacacc cgcagtctac atatatactt cgggcaccac aggtcttcca aaggctgcaa 1500
ccattaatca ccatcgcctc tggtatggga ccagccttgc cctgaggtcc ggaattaagg 1560
ctcatgacgt catctacacc accatgcccc tgtaccacag cgcggcgctc atgattggcc 1620
tccacggatg cattgtggtt ggggctacat ttgctttgcg gagcaaattt tcagccagcc 1680
agttttggga cgactgcagg aaatacaacg ccactgtcat tcagtacatc ggtgaactgc 1740
ttcggtacct ctgcaacacg ccccagaaac caaatgaccg ggaccacaaa gtgaaaatag 1800
cactaggaaa tggcttacga ggagatgtgt ggagagagtt catcaagaga tttggggaca 1860
ttcacattta tgagttctac gcttccactg aaggcaacat tggatttatg aactatccaa 1920
gaaaaatcgg agctgttgga agagaaaatt acctacaaaa aaaagttgta aggcacgagc 1980
tgatcaagta tgacgtggag aaggatgagc ctgtccgtga tgcaaatgga tattgcatca 2040
aagtccccaa aggagaggtt ggactcttga tttgcaaaat cacagagctc acaccatttt 2100
ttggctatgc tggaggaaag acccagacag agaagaaaaa gctcagagat gtttttaaga 2160
aaggagacgt ctacttcaac agtggcgatc tcctgatgat cgaccgtgaa aatttcatct 2220

-continued

```
attttcacga cagagttgga gacaccttcc ggtggaaagg agagaatgta gctaccacgg   2280

aagtcgctga cattgtggga ctggtagatt ttgttgaaga agtgaatgtt tacggtgtgc   2340

ccgtgccagg tcatgaaggt cgcatcggga tggcctcgat caagatgaaa gaaaactacg   2400

agttcaatgg aaagaaactc tttcagcaca tctcggagta cctgcccagt tactcgaggc   2460

ctcggttcct gagaatacaa gataccattg agatcaccgg gacttttaaa caccgcaaag   2520

tgaccctgat ggaagagggc tttaacccct cagtcatcaa agataccttg tatttcatgg   2580

atgacacaga aaaaacatac gtgcccatga ctgaggacat ttataatgcc ataattgata   2640

agactctgaa gctctgaatg ttgcctggct cctaacactt ccagaaagaa acacaatagg   2700

cctagcatag ccccttcaca tgtgtaatcc aactttaact tgattaaagg ttataggtgt   2760

gatttttcct aggaaattat tcatttaaag gacaattgtt tgtttgtttg tttgtttttt   2820

attaattaca ccagaacgtt tgcaagtaaa aagatttaaa gtcacttatt tttcaatgtg   2880

cacctgccat ttgtccttgc aaacttagct tcttggagag agggccttat ttttttaaag   2940

acataataaa ctatgtaaac act                                           2963


<210> SEQ ID NO 61
<211> LENGTH: 620
<212> TYPE: PRT
<213> ORGANISM: Rattus norvegicus

<400> SEQUENCE: 61

Met Leu Pro Val Leu Tyr Thr Gly Leu Ala Gly Leu Leu Leu Leu Pro
 1               5                  10                  15

Leu Leu Leu Thr Cys Cys Cys Pro Tyr Leu Leu Gln Asp Val Arg Phe
            20                  25                  30

Phe Leu Gln Leu Ala Asn Met Ala Arg Gln Val Arg Ser Tyr Arg Gln
        35                  40                  45

Arg Arg Pro Val Arg Thr Ile Leu His Val Phe Leu Glu Gln Ala Arg
    50                  55                  60

Lys Thr Pro His Lys Pro Phe Leu Leu Phe Arg Asp Glu Thr Leu Thr
65                  70                  75                  80

Tyr Ala Gln Val Asp Arg Arg Ser Asn Gln Val Ala Arg Ala Leu His
                85                  90                  95

Asp His Leu Gly Leu Arg Gln Gly Asp Cys Val Ala Leu Phe Met Gly
            100                 105                 110

Asn Glu Pro Ala Tyr Val Trp Leu Trp Leu Gly Leu Leu Lys Leu Gly
        115                 120                 125

Cys Pro Met Ala Cys Leu Asn Tyr Asn Ile Arg Ala Lys Ser Leu Leu
    130                 135                 140

His Cys Phe Gln Cys Cys Gly Ala Lys Val Leu Leu Ala Ser Pro Glu
145                 150                 155                 160

Leu His Glu Ala Val Glu Glu Val Leu Pro Thr Leu Lys Lys Glu Gly
                165                 170                 175

Val Ser Val Phe Tyr Val Ser Arg Thr Ser Asn Thr Asn Gly Val Asp
            180                 185                 190

Thr Val Leu Asp Lys Val Asp Gly Val Ser Ala Asp Pro Ile Pro Glu
        195                 200                 205

Ser Trp Arg Ser Glu Val Thr Phe Thr Thr Pro Ala Val Tyr Ile Tyr
    210                 215                 220

Thr Ser Gly Thr Thr Gly Leu Pro Lys Ala Ala Thr Ile Asn His His
225                 230                 235                 240
```

-continued

```
Arg Leu Trp Tyr Gly Thr Ser Leu Ala Leu Arg Ser Gly Ile Lys Ala
                245                 250                 255

His Asp Val Ile Tyr Thr Thr Met Pro Leu Tyr His Ser Ala Ala Leu
            260                 265                 270

Met Ile Gly Leu His Gly Cys Ile Val Val Gly Ala Thr Phe Ala Leu
        275                 280                 285

Arg Ser Lys Phe Ser Ala Ser Gln Phe Trp Asp Asp Cys Arg Lys Tyr
    290                 295                 300

Asn Ala Thr Val Ile Gln Tyr Ile Gly Glu Leu Leu Arg Tyr Leu Cys
305                 310                 315                 320

Asn Thr Pro Gln Lys Pro Asn Asp Arg Asp His Lys Val Lys Ile Ala
                325                 330                 335

Leu Gly Asn Gly Leu Arg Gly Asp Val Trp Arg Glu Phe Ile Lys Arg
            340                 345                 350

Phe Gly Asp Ile His Ile Tyr Glu Phe Tyr Ala Ser Thr Glu Gly Asn
        355                 360                 365

Ile Gly Phe Met Asn Tyr Pro Arg Lys Ile Gly Ala Val Gly Arg Glu
    370                 375                 380

Asn Tyr Leu Gln Lys Lys Val Val Arg His Glu Leu Ile Lys Tyr Asp
385                 390                 395                 400

Val Glu Lys Asp Glu Pro Val Arg Asp Ala Asn Gly Tyr Cys Ile Lys
                405                 410                 415

Val Pro Lys Gly Glu Val Gly Leu Leu Ile Cys Lys Ile Thr Glu Leu
            420                 425                 430

Thr Pro Phe Phe Gly Tyr Ala Gly Gly Lys Thr Gln Thr Glu Lys Lys
        435                 440                 445

Lys Leu Arg Asp Val Phe Lys Lys Gly Asp Val Tyr Phe Asn Ser Gly
    450                 455                 460

Asp Leu Leu Met Ile Asp Arg Glu Asn Phe Ile Tyr Phe His Asp Arg
465                 470                 475                 480

Val Gly Asp Thr Phe Arg Trp Lys Gly Glu Asn Val Ala Thr Thr Glu
                485                 490                 495

Val Ala Asp Ile Val Gly Leu Val Asp Phe Val Glu Glu Val Asn Val
            500                 505                 510

Tyr Gly Val Pro Val Pro Gly His Glu Gly Arg Ile Gly Met Ala Ser
        515                 520                 525

Ile Lys Met Lys Glu Asn Tyr Glu Phe Asn Gly Lys Lys Leu Phe Gln
    530                 535                 540

His Ile Ser Glu Tyr Leu Pro Ser Tyr Ser Arg Pro Arg Phe Leu Arg
545                 550                 555                 560

Ile Gln Asp Thr Ile Glu Ile Thr Gly Thr Phe Lys His Arg Lys Val
                565                 570                 575

Thr Leu Met Glu Glu Gly Phe Asn Pro Ser Val Ile Lys Asp Thr Leu
            580                 585                 590

Tyr Phe Met Asp Asp Thr Glu Lys Thr Tyr Val Pro Met Thr Glu Asp
        595                 600                 605

Ile Tyr Asn Ala Ile Ile Asp Lys Thr Leu Lys Leu
    610                 615                 620
```

<210> SEQ ID NO 62
<211> LENGTH: 1350
<212> TYPE: DNA
<213> ORGANISM: Rattus norvegicus -continued

<400> SEQUENCE: 62

```
gatcagctct tctatatcta cacgtcgggc accacggggc tacccaaagc tgccattgtg     60
gtgcacagca ggtattaccg aatggctgcc ctggtgtact atggattccg catgcggcct    120
gatgacattg tctatgactg cctccccctc taccactcag caggaaacat tgtggggatt    180
ggccagtgcg tactccacgg catgactgtg gtgatccgga agaagttttc agcctcccgg    240
ttctgggatg actgtatcaa gtacaactgc acaattgtac agtacattgg tgagctttgc    300
cgctacctcc tgaaccagcc accccgtgag gctgagtctc ggcacaaggt gcgcatggca    360
ctgggcaacg gtctccggca gtccatctgg accgacttct ccagccgttt ccacattccc    420
aaggtggccg agttctacgg ggccaccgag tgcaactgta gcttgggcaa ctttgacagc    480
caggtggggg cctgtggctt caatagccgc atcctgtcct ttgtgtaccc catccgcttg    540
gtacgagtca atgaggatac catggaactg atccggggac ccgatggcgt ctgcattccc    600
tgtcaaccag gccagccagg ccagctggtg ggtcgcatca tccagcagga ccccctacgc    660
cgttttgatg gctacctcaa ccagggtgcc aacaacaaga agattgctag tgatgtcttc    720
aagaaagggg accaagccta cctcactggt gacgtgctgg tgatggatga gctgggctac    780
ctgtacttcc gagaccgcac aggggacacg ttccgctgga aaggggagaa tgtgtctacc    840
actgaagtgg agggcacact cagccgcctg cttcagatgg cagatgtggc tgtttatggt    900
gttgaggtgc caggagctga gggccgagca ggaatggctg ctgtggcaag ccccactagc    960
aactgtgacc tggagagctt tgcacagacc ttgaaaaagg agctgcccct gtacgcccgc   1020
cccatcttcc tccgcttctt gcctgagctg cacaaaacag gaaccttcaa gttccagaag   1080
acagagttgc ggaaggaggg ctttgacccg tctgttgtga aagacccact cttctatttg   1140
gatgcccgga caggctgcta tgttgcactg gaccaagagg cctatacccg catccaggca   1200
ggcgaggaga agctgtgatt tcccccacat ccctctgagg gccagaggat gctggattca   1260
gagccccagc ttccactcca gaaggggtct gggcaaggcc agaccaaagc tagcagggcc   1320
cgcaccttca ccctaggtgc tgatccccct                                    1350
```

<210> SEQ ID NO 63
<211> LENGTH: 405
<212> TYPE: PRT
<213> ORGANISM: Rattus norvegicus

<400> SEQUENCE: 63

```
Asp Gln Leu Phe Tyr Ile Tyr Thr Ser Gly Thr Thr Gly Leu Pro Lys
 1               5                  10                  15

Ala Ala Ile Val Val His Ser Arg Tyr Tyr Arg Met Ala Ala Leu Val
            20                  25                  30

Tyr Tyr Gly Phe Arg Met Arg Pro Asp Asp Ile Val Tyr Asp Cys Leu
        35                  40                  45

Pro Leu Tyr His Ser Ala Gly Asn Ile Val Gly Ile Gly Gln Cys Val
    50                  55                  60

Leu His Gly Met Thr Val Val Ile Arg Lys Lys Phe Ser Ala Ser Arg
65                  70                  75                  80

Phe Trp Asp Asp Cys Ile Lys Tyr Asn Cys Thr Ile Val Gln Tyr Ile
                85                  90                  95

Gly Glu Leu Cys Arg Tyr Leu Leu Asn Gln Pro Pro Arg Glu Ala Glu
            100                 105                 110

Ser Arg His Lys Val Arg Met Ala Leu Gly Asn Gly Leu Arg Gln Ser
        115                 120                 125
```

-continued

```
Ile Trp Thr Asp Phe Ser Ser Arg Phe His Ile Pro Lys Val Ala Glu
    130                 135                 140

Phe Tyr Gly Ala Thr Glu Cys Asn Cys Ser Leu Gly Asn Phe Asp Ser
145                 150                 155                 160

Gln Val Gly Ala Cys Gly Phe Asn Ser Arg Ile Leu Ser Phe Val Tyr
                165                 170                 175

Pro Ile Arg Leu Val Arg Val Asn Glu Asp Thr Met Glu Leu Ile Arg
            180                 185                 190

Gly Pro Asp Gly Val Cys Ile Pro Cys Gln Pro Gly Gln Pro Gly Gln
        195                 200                 205

Leu Val Gly Arg Ile Ile Gln Gln Asp Pro Leu Arg Arg Phe Asp Gly
    210                 215                 220

Tyr Leu Asn Gln Gly Ala Asn Asn Lys Lys Ile Ala Ser Asp Val Phe
225                 230                 235                 240

Lys Lys Gly Asp Gln Ala Tyr Leu Thr Gly Asp Val Leu Val Met Asp
                245                 250                 255

Glu Leu Gly Tyr Leu Tyr Phe Arg Asp Arg Thr Gly Asp Thr Phe Arg
            260                 265                 270

Trp Lys Gly Glu Asn Val Ser Thr Thr Glu Val Glu Gly Thr Leu Ser
        275                 280                 285

Arg Leu Leu Gln Met Ala Asp Val Ala Val Tyr Gly Val Glu Val Pro
    290                 295                 300

Gly Ala Glu Gly Arg Ala Gly Met Ala Ala Val Ala Ser Pro Thr Ser
305                 310                 315                 320

Asn Cys Asp Leu Glu Ser Phe Ala Gln Thr Leu Lys Lys Glu Leu Pro
                325                 330                 335

Leu Tyr Ala Arg Pro Ile Phe Leu Arg Phe Leu Pro Glu Leu His Lys
            340                 345                 350

Thr Gly Thr Phe Lys Phe Gln Lys Thr Glu Leu Arg Lys Glu Gly Phe
        355                 360                 365

Asp Pro Ser Val Val Lys Asp Pro Leu Phe Tyr Leu Asp Ala Arg Thr
    370                 375                 380

Gly Cys Tyr Val Ala Leu Asp Gln Glu Ala Tyr Thr Arg Ile Gln Ala
385                 390                 395                 400

Gly Glu Glu Lys Leu
                405


<210> SEQ ID NO 64
<211> LENGTH: 3217
<212> TYPE: DNA
<213> ORGANISM: Mus musculus

<400> SEQUENCE: 64

atgcgggctc ctggagcagg aacagcctct gtggcctcac tggcgctgct ttggtttctg      60

ggacttccgt ggacctggag cgcggcggcg gcgttctgtg tgtacgtggg tggcggcggc     120

tggcgctttc tgcgtatcgt ctgcaagacg gcgaggcgag acctctttgg cctctctgtt     180

ctgattcgtg ttcggctaga gctgcgacga caccggcgag caggagacac gatcccgtgc     240

atcttccagg ctgtggcccg gcgacaacca gagcgcctgg cactggtgga cgccagtagt     300

ggtatatgct ggaccttcgc acagctggac acctactcca atgctgtagc caacctgttc     360

cgccagctgg gctttgcacc aggcgatgtg gtggctgtgt tcctggaggg ccggccggag     420

ttcgtgggac tgtggctggg cctggccaag gccggtgtgg tggctgctct tctcaatgtc     480
```

-continued

```
aacctgaggc gggagcccct ggccttctgc ctgggcacat cagctgccaa ggccctcatt    540
tatggcgggg agatggcagc ggcggtggcg gaggtgagcg agcagctggg gaagagcctc    600
ctcaagttct gctctggaga tctggggcct gagagcatcc tgcctgacac gcagctcctg    660
gaccccatgc ttgctgaggc gcccaccaca cccctggcac aagccccagg caagggcatg    720
gatgatcggc tgttttacat ctatacttct gggaccaccg ggcttcctaa ggctgccatt    780
gtggtgcaca gcaggtacta ccgcattgct gcctttggcc accattccta cagcatgcgt    840
gccgccgatg tgctctatga ctgcctgcca ctctaccact ctgcagggaa catcatgggt    900
gtggggcagt gcgtcatcta cgggttgacg gtggtactgc gcaagaagtt ctccgccagc    960
cgcttctggg atgactgtgt caagtacaat tgcacggtag tggatgacat aggtgaaatc   1020
tgccgctacc tgctgaggca gccggttcgc gacgtggagc agcgacaccg cgtgcgcctg   1080
gccgtgggta atgggctgcg gccagccatc tgggaggagt tcacgcagcg cttcggtgtg   1140
ccacagatcg gcgagttcta cggcgctacc gagtgcaact gcagcattgc caacatggac   1200
ggcaaggtcg gctcctgcgg cttcaacagc cgtatcctca cgcatgtgta ccccatccgt   1260
ctggtcaagg tcaatgagga cacgatggag ccactgcggg actccgaggg cctctgcatc   1320
ccgtgccagc ccggggaacc cggccttctc gtgggccaga tcaaccagca ggaccctctg   1380
cggcgtttcg atggttatgt tagtgacagt gccaccaaca agaagattgc ccacagcgtt   1440
ttccgaaagg gcgatagcgc ctacctctca ggtgacgtgc tagtgatgga cgagctgggc   1500
tacatgtatt tccgtgaccg cagcggggac accttccgct ggcgcgggga gaacgtgtcc   1560
accacggagg tggaagccgt gctgagccgc ctactgggcc agacggacgt ggctgtgtat   1620
ggggtggctg tgccaggagt ggaggggaaa gctggcatgg cagccatcgc agatccccac   1680
agccagttgg accctaactc aatgtaccag gaattacaga aggttcttgc atcctatgct   1740
cggcccatct tcctgcgtct tctgccccag gtggatacca caggcacctt caagatccag   1800
aagacccggc tgcagcgtga aggctttgac ccccgtcaga cctcagacag gctcttcttt   1860
ctagacctga agtccggcac gaggtatcta cccctggatg agagagtcca tgcccgcatt   1920
tgcgcaggcg acttctcact ctgagcctgg agagtgggct gggcctggac tcctgagacc   1980
tgggagcctg acacccctct tcgggtgctt ctcctgcctg gccacatgga cagcagcacc   2040
tgtgagagta ggaaaatgga acctgagtgg ctgggacccc tctcctactt cccactatgc   2100
atccattttg cctctgcctt gatctttttc tccatctctt ttctccctac ccagcaggag   2160
ccccacaaac acatgttggc tgctgtgtcc tgcagttgga ccagtgtcca ggggtacagg   2220
cttcaggctg tgacccacac tggtacccac ctccctttcc tattttgcct taggttcatc   2280
cacggttccc ctgtggagca agtgggggcc cacatagctg ctgtccctgc tgagggttgg   2340
tagcaatcac accctcatgt cagctgggag acacgcgcag tctcccactg acccccaatc   2400
aactgaaaat attgttttga ctacttttttg tttttttgtt tttttgtttt ttttttttt   2460
cgagacagag tttctctgta tagccctggc tgtcctggaa ctcactttgt agaccaggct   2520
ggcctcgaac tcaaaaatcc tcctgactct gcctctgctt cccaagtgct gggattaaag   2580
acgtgcgcca ccaccgcctg gctgttttgt atttttgttt tgttttgacg atagggtctc   2640
actgtggagg ccaagctggc ctcagactcc ccaccccatt gcctctgggc accattctat   2700
attctcagac tgatgacaat gcactagtgt ccctaggagt cttgagtctg cactttcccc   2760
tcatagcctc aagcttccag aactgactct gatcacttgg atgtggctag tgttggctct   2820
acccacatgt gtcaattcag gggtccccag gcatagtctc tggaagccct cacccggaaa   2880
```

-continued

```
aagcttggag agacccagga aggttgttgt gttctcttgg gcaccccctg gtggcagtcc   2940

tgggcatgct tccgcactgt actggtgcat atagcccaga cctatgacat ttgaggtcta   3000

cccttctggc tcctgtggtc cccattgaga tccttggtga ctcacctcag tcaccaagca   3060

gagcctctgc ctgccttcat cttcaaggtc atgaaggatg tggacagagc agctacaggc   3120

tgccagcagt caaccacatg agagtgttac ttccttgttg gtttttaaaa aataaatgtg   3180

ctgagcctcg aaaaaaaaaa aaaaaaaaaa aaaaaaa                            3217


<210> SEQ ID NO 65
<211> LENGTH: 646
<212> TYPE: PRT
<213> ORGANISM: Mus musculus

<400> SEQUENCE: 65

Met Arg Ala Pro Gly Ala Gly Thr Ala Ser Val Ala Ser Leu Ala Leu
 1               5                  10                  15

Leu Trp Phe Leu Gly Leu Pro Trp Thr Trp Ser Ala Ala Ala Ala Phe
            20                  25                  30

Cys Val Tyr Val Gly Gly Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Arg Arg Ala Gly Asp Thr Ile Pro Cys
65                  70                  75                  80

Ile Phe Gln Ala Val Ala Arg Arg Gln Pro Glu Arg Leu Ala Leu Val
                85                  90                  95

Asp Ala Ser Ser Gly Ile Cys Trp Thr Phe Ala Gln Leu Asp Thr Tyr
            100                 105                 110

Ser Asn Ala Val Ala Asn Leu Phe Arg Gln Leu Gly Phe Ala Pro Gly
        115                 120                 125

Asp Val Val Ala Val Phe Leu Glu Gly Arg Pro Glu Phe Val Gly Leu
    130                 135                 140

Trp Leu Gly Leu Ala Lys Ala Gly Val Val Ala Ala Leu Leu Asn Val
145                 150                 155                 160

Asn Leu Arg Arg Glu Pro Leu Ala Phe Cys Leu Gly Thr Ser Ala Ala
                165                 170                 175

Lys Ala Leu Ile Tyr Gly Gly Glu Met Ala Ala Ala Val Ala Glu Val
            180                 185                 190

Ser Glu Gln Leu Gly Lys Ser Leu Leu Lys Phe Cys Ser Gly Asp Leu
        195                 200                 205

Gly Pro Glu Ser Ile Leu Pro Asp Thr Gln Leu Leu Asp Pro Met Leu
    210                 215                 220

Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Ile Ala Ala Phe
            260                 265                 270

Gly His His Ser Tyr Ser Met Arg Ala Ala Asp Val Leu Tyr Asp Cys
        275                 280                 285

Leu Pro Leu Tyr His Ser Ala Gly Asn Ile Met Gly Val Gly Gln Cys
    290                 295                 300

Val Ile Tyr Gly Leu Thr Val Val Leu Arg Lys Lys Phe Ser Ala Ser
```

-continued

```
305                 310                 315                 320

Arg Phe Trp Asp Asp Cys Val Lys Tyr Asn Cys Thr Val Val Gln Tyr
                325                 330                 335

Ile Gly Glu Ile Cys Arg Tyr Leu Leu Arg Gln Pro Val Arg Asp Val
            340                 345                 350

Glu Gln Arg His Arg Val Arg Leu Ala Val Gly Asn Gly Leu Arg Pro
        355                 360                 365

Ala Ile Trp Glu Glu Phe Thr Gln Arg Phe Gly Val Pro Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
                405                 410                 415

Tyr Pro Ile Arg Leu Val Lys Val Asn Glu Asp Thr Met Glu Pro Leu
            420                 425                 430

Arg Asp Ser Glu Gly Leu Cys Ile Pro Cys Gln Pro Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Ala Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Ile Ala Asp Pro His
545                 550                 555                 560

Ser Gln Leu Asp Pro Asn Ser Met Tyr Gln Glu Leu Gln Lys Val Leu
                565                 570                 575

Ala Ser Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly Arg Tyr Val Pro Leu Asp Glu Arg Val His Ala Arg Ile Cys
625                 630                 635                 640

Ala Gly Asp Phe Ser Leu
                645


<210> SEQ ID NO 66
<211> LENGTH: 2338
<212> TYPE: DNA
<213> ORGANISM: Mus musculus

<400> SEQUENCE: 66

gggcggaggc cgagcccagt cgccagctcc tgctctgctc ctctcccgcc tgccgccgcg     60

ctgcacgcct cgagcactcc ctcggccccg gcggggaccg gggaccccgc agctaccgcc    120

atgctgccag tgctctacac cggcctggcg ggctgctgc tgctgcctct gctgctcacc    180
```

-continued

```
tgctgctgcc cctacctcct ccaagatgtg cggtacttcc tgcggctggc caacatggcc    240
cggcgggtgc gcagctaccg gcagcggcga cccgtgcgta ccatcctgcg ggccttcctg    300
gaacaagcgc gcaagacccc acacaagccc ttcctgctgt tccgagacga gacgctcacc    360
tacgcccagg tggaccggcg cagcaaccaa gtggcgcggg cgctgcacga tcaactgggc    420
ctacgacagg gggattgcgt agccctcttc atgggcaatg agccggccta cgtgtggatc    480
tggctgggac tgctcaaact gggctgtccc atggcgtgcc tcaactacaa cattcgtgcc    540
aagtctctgc tgcactgctt tcaatgctgc ggggcgaagg tgctgctggc ctccccagat    600
ctacaagaag ctgtggagga ggttcttcca accctgaaaa aggatgccgt gtccgtcttt    660
tacgtaagca gaacttctaa cacaaatggt gtggacacaa tactggacaa agtagacgga    720
gtgtcggcgg aacccacccc ggagtcgtgg aggtctgaag tcacttttac cacgccagca    780
gtatacattt atacttcggg aaccacaggt cttccaaaaa gcggaaccat caatcatcat    840
cgcctaaggt atgggacaag ccttgctatg tcgagtggga atcacggcca aggatgtcat    900
ctataccaac aatgcccctg ttccaacagt gcaacgctca agatcggcct tcacggatgc    960
atcctgggtt ggggctactt taaccttggc ggggcaaatt ctcaagcaag ccaattttgg   1020
gaacgactgg caggaaatac aacgtcaacg gtcattcagt acattggtga actgcttcgg   1080
tacctgtgca acacaccgca gaaaccaaat gaccgggacc acaaagtgaa aaaagccctg   1140
ggaaatggct tacgaggaga tgtgtggaga gagttcatca agagatttgg ggacatccac   1200
gtgtatgagt tctacgcatc cactgaaggc aacattggat ttgtgaacta tccaaggaaa   1260
atcggtgctg tcgggagagc aaactaccta caaagaaaag ttgcaaggta tgagctgatc   1320
aagtatgacg tggagaagga cgagccggtc cgtgacgcaa atggatattg catcaaagtc   1380
cccaaaggtg aggttggact cttggtttgc aaaatcacac agctcacacc atttattggc   1440
tatgctggag gaaagaccca gacagagaag aaaaaactca gagatgtctt taagaaaggc   1500
gacatctact tcaacagcgg agacctcctg atgatcgacc gtgagaactt cgtctacttt   1560
cacgacaggg ttggagatac tttccggtgg aaaggagaga acgtagctac cacagaagtc   1620
gctgacatcg tgggactggt agattttgtt gaagaagtga atgtgtatgg cgtgcctgtg   1680
ccaggtcatg agggtcgaat tgggatggcc tccctcaaga tcaaagaaaa ctacgagttc   1740
aatggaaaga aactctttca acacatcgcg gagtacctgc ccagttacgc gaggcctcgg   1800
ttcctgagga tacaagatac cattgagatc actgggactt ttaaacaccg caaagtgacc   1860
ctgatggaag agggcttcaa tcccacagtc atcaaagata ccttgtattt catggatgat   1920
gcagagaaaa catttgtgcc catgactgag aacatttata atgccataat tgataaaact   1980
ctgaagctct gaatattccc tggtggttta gctcatgaca tttccagaaa gaaactcgat   2040
agacctcgca gagccacttc atacgtagaa tccaacttta acttgattga agactataag   2100
gtgcgatttt atttttagga aattattcat taaaaggata gttttttttt ttttttttaa   2160
ttacacctga acctttgcaa gtaaaaagat ttagagacaa ttatttttca atgtgcacct   2220
gccatttgtc cttgcaaact aagcttcttg gagagagggc cttatttttt taaagacata   2280
ataaactata ttaacactaa aaaaaaaaaa aaaaaaaaaa aaaaaaaaaa aaaaaaaa     2338
```

<210> SEQ ID NO 67
<211> LENGTH: 623
<212> TYPE: PRT
<213> ORGANISM: Mus musculus

<400> SEQUENCE: 67

-continued

```
Met Leu Pro Val Leu Tyr Thr Gly Leu Ala Gly Leu Leu Leu Leu Pro
 1               5                  10                  15

Leu Leu Leu Thr Cys Cys Cys Pro Tyr Leu Leu Gln Asp Val Arg Tyr
            20                  25                  30

Phe Leu Arg Leu Ala Asn Met Ala Arg Arg Val Arg Ser Tyr Arg Gln
        35                  40                  45

Arg Arg Pro Val Arg Thr Ile Leu Arg Ala Phe Leu Glu Gln Ala Arg
    50                  55                  60

Lys Thr Pro His Lys Pro Phe Leu Leu Phe Arg Asp Glu Thr Leu Thr
65                  70                  75                  80

Tyr Ala Gln Val Asp Arg Arg Ser Asn Gln Val Ala Arg Ala Leu His
                85                  90                  95

Asp Gln Leu Gly Leu Arg Gln Gly Asp Cys Val Ala Leu Phe Met Gly
            100                 105                 110

Asn Glu Pro Ala Tyr Val Trp Ile Trp Leu Gly Leu Leu Lys Leu Gly
        115                 120                 125

Cys Pro Met Ala Cys Leu Asn Tyr Asn Ile Arg Ala Lys Ser Leu Leu
    130                 135                 140

His Cys Phe Gln Cys Cys Gly Ala Lys Val Leu Leu Ala Ser Pro Asp
145                 150                 155                 160

Leu Gln Glu Ala Val Glu Glu Val Leu Pro Thr Leu Lys Lys Asp Ala
                165                 170                 175

Val Ser Val Phe Tyr Val Ser Arg Thr Ser Asn Thr Asn Gly Val Asp
            180                 185                 190

Thr Ile Leu Asp Lys Val Asp Gly Val Ser Ala Glu Pro Thr Pro Glu
        195                 200                 205

Ser Trp Arg Ser Glu Val Thr Phe Thr Thr Pro Ala Val Tyr Ile Tyr
    210                 215                 220

Thr Ser Gly Thr Thr Gly Leu Pro Lys Ser Gly Thr Ile Asn His His
225                 230                 235                 240

Arg Leu Arg Tyr Gly Thr Ser Leu Ala Met Ser Ser Gly Asn His Gly
                245                 250                 255

Gln Gly Cys His Leu Tyr Gln Gln Cys Pro Cys Ser Asn Ser Ala Thr
            260                 265                 270

Leu Lys Ile Gly Leu His Gly Cys Ile Leu Gly Trp Gly Tyr Phe Asn
        275                 280                 285

Leu Gly Gly Ala Asn Ser Gln Ala Ser Gln Phe Trp Glu Arg Leu Ala
    290                 295                 300

Gly Asn Thr Thr Ser Thr Val Ile Gln Tyr Ile Gly Glu Leu Leu Arg
305                 310                 315                 320

Tyr Leu Cys Asn Thr Pro Gln Lys Pro Asn Asp Arg Asp His Lys Val
                325                 330                 335

Lys Lys Ala Leu Gly Asn Gly Leu Arg Gly Asp Val Trp Arg Glu Phe
            340                 345                 350

Ile Lys Arg Phe Gly Asp Ile His Val Tyr Glu Phe Tyr Ala Ser Thr
        355                 360                 365

Glu Gly Asn Ile Gly Phe Val Asn Tyr Pro Arg Lys Ile Gly Ala Val
    370                 375                 380

Gly Arg Ala Asn Tyr Leu Gln Arg Lys Val Ala Arg Tyr Glu Leu Ile
385                 390                 395                 400

Lys Tyr Asp Val Glu Lys Asp Glu Pro Val Arg Asp Ala Asn Gly Tyr
                405                 410                 415
```

-continued

```
Cys Ile Lys Val Pro Lys Gly Glu Val Gly Leu Leu Val Cys Lys Ile
            420                 425                 430

Thr Gln Leu Thr Pro Phe Ile Gly Tyr Ala Gly Gly Lys Thr Gln Thr
        435                 440                 445

Glu Lys Lys Lys Leu Arg Asp Val Phe Lys Lys Gly Asp Ile Tyr Phe
    450                 455                 460

Asn Ser Gly Asp Leu Leu Met Ile Asp Arg Glu Asn Phe Val Tyr Phe
465                 470                 475                 480

His Asp Arg Val Gly Asp Thr Phe Arg Trp Lys Gly Glu Asn Val Ala
                485                 490                 495

Thr Thr Glu Val Ala Asp Ile Val Gly Leu Val Asp Phe Val Glu Glu
            500                 505                 510

Val Asn Val Tyr Gly Val Pro Val Pro Gly His Glu Gly Arg Ile Gly
        515                 520                 525

Met Ala Ser Leu Lys Ile Lys Glu Asn Tyr Glu Phe Asn Gly Lys Lys
    530                 535                 540

Leu Phe Gln His Ile Ala Glu Tyr Leu Pro Ser Tyr Ala Arg Pro Arg
545                 550                 555                 560

Phe Leu Arg Ile Gln Asp Thr Ile Glu Ile Thr Gly Thr Phe Lys His
                565                 570                 575

Arg Lys Val Thr Leu Met Glu Glu Gly Phe Asn Pro Thr Val Ile Lys
            580                 585                 590

Asp Thr Leu Tyr Phe Met Asp Asp Ala Glu Lys Thr Phe Val Pro Met
        595                 600                 605

Thr Glu Asn Ile Tyr Asn Ala Ile Ile Asp Lys Thr Leu Lys Leu
    610                 615                 620
```

<210> SEQ ID NO 68
<211> LENGTH: 1998
<212> TYPE: DNA
<213> ORGANISM: Mus musculus

<400> SEQUENCE: 68

```
gaaagctctg agagcgggtg cagtctggcc tggcgtctcg cgtacctggc ccgggagcag     60

ccgacacaca ccttcctcat ccacggcgcg cagcgcttta gctacgcgga ggctgagcgc    120

gagagcaacc ggattgctcg cgcctttctg cgcgcacggg gctggaccgg gggccgccga    180

ggctcgggca ggggcagcac tgaggaaggc gcacgcgtgg cgcctccggc tggagatgcg    240

gctgctagag ggacgaccgc gccccctctg gcacccgggg cgaccgtggc gctgctcctc    300

ccagcgggcc cggatttcct ttggatttgg ttcggactgg ccaaagctgg cctgcgcacg    360

gcctttgtgc ccaccgcttt acgccgagga cccctgctgc actgcctccg cagctgcggt    420

gcgagtgcgc tcgtgctggc cacagagttc ctggagtccc tggagccgga cctgccggcc    480

ttgagagcca tggggctcca cctatgggcg acgggccctg aaactaatgt agctggaatc    540

agcaatttgc tatcggaagc agcagaccaa gtggatgagc cagtgccggg gtacctctct    600

gccccccaga acataatgga cacctgcctg tacatcttca cctctggcac tactggcctg    660

cccaaggctg ctcgaatcag tcatctgaag gttctacagt gccagggatt ctaccatctg    720

tgtggagtcc accaggagga cgtgatctac ctcgcactcc cactgtacca catgtctggc    780

tcccttctgg gcattgtggg ctgcttgggc attggggcca ccgtggtgct gaaacccaag    840

ttctcagcta gccagttctg ggacgattgc cagaaacaca gggtgacagt gttccagtac    900

attggggagt tgtgccgata cctcgtcaac cagcccccga gcaaggcaga gtttgaccat    960
```

-continued

```
aaggtgcgct tggcagtggg cagtgggttg cgcccagaca cctgggagcg tttcctgcgg   1020

cgatttggac ctctgcagat actggagacg tatggcatga cagagggcaa cgtagctacg   1080

ttcaattaca caggacggca gggtgcagtg gggcgagctt cctggcttta caagcacatc   1140

ttccccttct ccttgattcg atacgatgtc atgacagggg agcctattcg gaatgcccag   1200

gggcactgca tgaccacatc tccaggtgag ccaggcctac tggtggcccc agtgagccag   1260

cagtccccct tcctgggcta tgctggggct ccggagctgg ccaaggacaa gctgctgaag   1320

gatgtcttct ggtctgggga cgttttcttc aatactgggg acctcttggt ctgtgatgag   1380

caaggctttc ttcacttcca cgatcgtact ggagacacca tcaggtggaa gggagagaat   1440

gtggccacaa ctgaagtggc tgaggtcttg gagaccctgg acttccttca ggaggtgaac   1500

atctatggag tcacggtgcc agggcacgaa ggcagggcag gcatggcggc cttggctctg   1560

cggcccccgc aggctctgaa cctggtgcag ctctacagcc atgtttctga gaacttgcca   1620

ccgtatgccc gacctcggtt tctcaggctc caggaatctt tggccactac tgagaccttc   1680

aaacagcaga aggttaggat ggccaatgag ggctttgacc ccagtgtact gtctgaccca   1740

ctctatgttc tggaccaaga tataggggcc tacctgcccc tcacacctgc ccggtacagt   1800

gccctcctgt ctggagacct tcgaatctga aaccttccac ttgagggagg ggctcggagg   1860

gtacaggcca ccatggctgc accagggagg gttttcgggt atcttttgta tatggagtca   1920

ttattttgta ataaacagct ggagcttaaa aaaaaaaaaa aaaaaaaaaa aaaaaaaaaa   1980

aaaaaaaaaa aaaaaaaa                                                 1998


<210> SEQ ID NO 69
<211> LENGTH: 609
<212> TYPE: PRT
<213> ORGANISM: Mus musculus

<400> SEQUENCE: 69

Glu Ser Ser Glu Ser Gly Cys Ser Leu Ala Trp Arg Leu Ala Tyr Leu
 1               5                  10                  15

Ala Arg Glu Gln Pro Thr His Thr Phe Leu Ile His Gly Ala Gln Arg
            20                  25                  30

Phe Ser Tyr Ala Glu Ala Glu Arg Glu Ser Asn Arg Ile Ala Arg Ala
        35                  40                  45

Phe Leu Arg Ala Arg Gly Trp Thr Gly Gly Arg Arg Gly Ser Gly Arg
    50                  55                  60

Gly Ser Thr Glu Glu Gly Ala Arg Val Ala Pro Pro Ala Gly Asp Ala
65                  70                  75                  80

Ala Ala Arg Gly Thr Thr Ala Pro Pro Leu Ala Pro Gly Ala Thr Val
                85                  90                  95

Ala Leu Leu Leu Pro Ala Gly Pro Asp Phe Leu Trp Ile Trp Phe Gly
            100                 105                 110

Leu Ala Lys Ala Gly Leu Arg Thr Ala Phe Val Pro Thr Ala Leu Arg
        115                 120                 125

Arg Gly Pro Leu Leu His Cys Leu Arg Ser Cys Gly Ala Ser Ala Leu
    130                 135                 140

Val Leu Ala Thr Glu Phe Leu Glu Ser Leu Glu Pro Asp Leu Pro Ala
145                 150                 155                 160

Leu Arg Ala Met Gly Leu His Leu Trp Ala Thr Gly Pro Glu Thr Asn
                165                 170                 175

Val Ala Gly Ile Ser Asn Leu Leu Ser Glu Ala Ala Asp Gln Val Asp
            180                 185                 190
```

-continued

```
Glu Pro Val Pro Gly Tyr Leu Ser Ala Pro Gln Asn Ile Met Asp Thr
        195                 200                 205

Cys Leu Tyr Ile Phe Thr Ser Gly Thr Thr Gly Leu Pro Lys Ala Ala
    210                 215                 220

Arg Ile Ser His Leu Lys Val Leu Gln Cys Gln Gly Phe Tyr His Leu
225                 230                 235                 240

Cys Gly Val His Gln Glu Asp Val Ile Tyr Leu Ala Leu Pro Leu Tyr
                245                 250                 255

His Met Ser Gly Ser Leu Leu Gly Ile Val Gly Cys Leu Gly Ile Gly
            260                 265                 270

Ala Thr Val Val Leu Lys Pro Lys Phe Ser Ala Ser Gln Phe Trp Asp
        275                 280                 285

Asp Cys Gln Lys His Arg Val Thr Val Phe Gln Tyr Ile Gly Glu Leu
    290                 295                 300

Cys Arg Tyr Leu Val Asn Gln Pro Pro Ser Lys Ala Glu Phe Asp His
305                 310                 315                 320

Lys Val Arg Leu Ala Val Gly Ser Gly Leu Arg Pro Asp Thr Trp Glu
                325                 330                 335

Arg Phe Leu Arg Arg Phe Gly Pro Leu Gln Ile Leu Glu Thr Tyr Gly
            340                 345                 350

Met Thr Glu Gly Asn Val Ala Thr Phe Asn Tyr Thr Gly Arg Gln Gly
        355                 360                 365

Ala Val Gly Arg Ala Ser Trp Leu Tyr Lys His Ile Phe Pro Phe Ser
    370                 375                 380

Leu Ile Arg Tyr Asp Val Met Thr Gly Glu Pro Ile Arg Asn Ala Gln
385                 390                 395                 400

Gly His Cys Met Thr Thr Ser Pro Gly Glu Pro Gly Leu Leu Val Ala
                405                 410                 415

Pro Val Ser Gln Gln Ser Pro Phe Leu Gly Tyr Ala Gly Ala Pro Glu
            420                 425                 430

Leu Ala Lys Asp Lys Leu Leu Lys Asp Val Phe Trp Ser Gly Asp Val
        435                 440                 445

Phe Phe Asn Thr Gly Asp Leu Leu Val Cys Asp Glu Gln Gly Phe Leu
    450                 455                 460

His Phe His Asp Arg Thr Gly Asp Thr Ile Arg Trp Lys Gly Glu Asn
465                 470                 475                 480

Val Ala Thr Thr Glu Val Ala Glu Val Leu Glu Thr Leu Asp Phe Leu
                485                 490                 495

Gln Glu Val Asn Ile Tyr Gly Val Thr Val Pro Gly His Glu Gly Arg
            500                 505                 510

Ala Gly Met Ala Ala Leu Ala Leu Arg Pro Pro Gln Ala Leu Asn Leu
        515                 520                 525

Val Gln Leu Tyr Ser His Val Ser Glu Asn Leu Pro Pro Tyr Ala Arg
    530                 535                 540

Pro Arg Phe Leu Arg Leu Gln Glu Ser Leu Ala Thr Thr Glu Thr Phe
545                 550                 555                 560

Lys Gln Gln Lys Val Arg Met Ala Asn Glu Gly Phe Asp Pro Ser Val
                565                 570                 575

Leu Ser Asp Pro Leu Tyr Val Leu Asp Gln Asp Ile Gly Ala Tyr Leu
            580                 585                 590

Pro Leu Thr Pro Ala Arg Tyr Ser Ala Leu Leu Ser Gly Asp Leu Arg
        595                 600                 605
```

-continued

Ile

<210> SEQ ID NO 70
<211> LENGTH: 2710
<212> TYPE: DNA
<213> ORGANISM: Mus musculus

<400> SEQUENCE: 70
atgctgcttg gagcctctct ggtgggggcg ctactgttct ccaagctagt gctgaagctg 60
ccctggaccc aggtgggatt ctccctgttg ctcctgtact tggggtctgg tggctggcgt 120
ttcatccggg tcttcatcaa gacggtcagg agagatatct ttggtggcat ggtgctcctg 180
aaggtgaaga ccaaggtgcg acggtacctt caggagcgga agacggtgcc cctgctgttt 240
gcttcaatgg tacagcgcca cccggacaag acagccctga ttttcgaggg cacagacact 300
cactggacct tccgccagct ggatgagtac tccagtagtg tggccaactt cctgcaggcc 360
cggggcctgg cctcaggcaa tgtagttgcc ctctttatgg aaaaccgcaa tgagtttgtg 420
ggtctgtggc taggcatggc caagctgggc gtggaggcgg ctctcatcaa caccaacctt 480
aggcgggatg ccctgcgcca ctgtcttgac acctcaaagg cacgagctct catctttggc 540
agtgagatgg cctcagctat ctgtgagatc catgctagcc tggagcccac actcagcctc 600
ttctgctctg gatcctggga gcccagcaca gtgcccgtca gcacagagca tctggaccct 660
cttctggaag atgccccgaa gcacctgccc agtcacccag acaagggttt tacagataag 720
ctcttctaca tctacacatc gggcaccacg gggctaccca aagctgccat tgtggtgcac 780
agcaggtatt atcgtatggc ttccctggtg tactatggat tccgcatgcg gcctgatgac 840
attgtctatg actgcctccc cctctaccac tcaagcagga aacatcgtgg ggattggcag 900
tgcttactcc acggcatgac tgtggtgatc cggaagaagt tctcagcctc ccggttctgg 960
gatgattgta tcaagtacaa ctgcacagtg gtacagtaca ttggcgagct ctgccgctac 1020
ctcctgaacc agccaccccg tgaggctgag tctcggcaca aggtgcgcat ggcactgggc 1080
aacggtctcc ggcagtccat ctggaccgac ttctccagcc gtttccacat cccccaggtg 1140
gctgagttct atggggccac tgaatgcaac tgtagcctgg gcaactttga cagccgggtg 1200
ggggcctgtg gcttcaatag ccgcatcctg tcctttgtgt accctatccg tttggtacgt 1260
gtcaatgagg ataccatgga actgatccgg ggacccgatg gagtctgcat tccctgtcaa 1320
ccaggtcagc caggccagct ggtgggtcgc atcatccagc aggaccctct gcgccgtttc 1380
gacgggtacc tcaaccaggg tgccaacaac aagaagattg ctaatgatgt cttcaagaag 1440
ggggaccaag cctacctcac tggtgacgtc ctggtgatgg atgagctggg ttacctgtac 1500
ttccgagatc gcactgggga cacgttccgc tggaaagggg agaatgtatc taccactgag 1560
gtggagggca cactcagccg cctgcttcat atggcagatg tggcagttta tggtgttgag 1620
gtgccaggaa ctgaaggccg agcaggaatg gctgccgttg caagtcccat cagcaactgt 1680
gacctggaga gctttgcaca gaccttgaaa aaggagctgc ctctgtatgc ccgccccatc 1740
ttcctgcgct tcttgcctga gctgcacaag acagggacct tcaagttcca gaagacagag 1800
ttgcggaagg agggctttga cccatctgtt gtgaaagacc cgctgttcta tctggatgct 1860
cggaagggct gctacgttgc actggaccag gaggcctata cccgcatcca ggcaggcgag 1920
gagaagctgt gatttccccc tacatccctc tgagggccag aagatgctgg attcagagcc 1980
ctagcgtcca ccccagaggg tcctgggcaa tgccagacca aagctagcag ggcccgcacc 2040
tccgccccta ggtgctgatc tcccctctcc caaactgcca agtgactcac tgccgcttcc 2100

-continued

```
ccgaccctcc agaggctttc tgtgaaagtc tcatccaagc tgtgtcttct ggtccaggcg   2160

tggcccctgg ccccagggtt tctgataggc tcctttagga tggtatcttg ggtccagcgg   2220

gccagggtgt gggagaggag tcactaagat ccctccaatc agaagggagc ttacaaagga   2280

accaaggcaa agcctgtaga ctcaggaagc taagtggcca gagactatag tggccagtca   2340

tcccatgtcc acagaggatc ttggtccaga gctgccaaag tgtcacctct ccctgcctgc   2400

acctctgggg aaaagaggac agcatgtggc cactgggcac ctgtctcaag aagtcaggat   2460

cacacactca gtccttgttt ctccaggttc ccttgttctt gtctcgggga gggagggacg   2520

agtgtcctgt ctgtccttcc tgcctgtctg tgagtctgtg ttgcttctcc atctgtccta   2580

gcctgagtgt gggtggaaca ggcatgagga gagtgtggct caggggccaa taaactctgc   2640

cttgactcct cttaaaaaaa aaaaaaaaaa aaaaaaaaaa aaaaaaaaaa aaaaaaaaaa   2700

aaaaaaaaaa                                                          2710


<210> SEQ ID NO 71
<211> LENGTH: 643
<212> TYPE: PRT
<213> ORGANISM: Mus musculus

<400> SEQUENCE: 71

Met Leu Leu Gly Ala Ser Leu Val Gly Ala Leu Leu Gly Ser Lys Leu
 1               5                  10                  15

Val Leu Lys Leu Pro Trp Thr Gln Val Gly Phe Ser Leu Leu Leu Leu
            20                  25                  30

Tyr Leu Gly Ser Gly Gly Trp Arg Phe Ile Arg Val Phe Ile Lys Thr
        35                  40                  45

Val Arg Arg Asp Ile Phe Gly Gly Met Val Leu Leu Lys Val Lys Thr
    50                  55                  60

Lys Val Arg Arg Tyr Leu Gln Glu Arg Lys Thr Val Pro Leu Leu Phe
65                  70                  75                  80

Ala Ser Met Val Gln Arg His Pro Asp Lys Thr Ala Leu Ile Phe Glu
                85                  90                  95

Gly Thr Asp Thr His Trp Thr Phe Arg Gln Leu Asp Glu Tyr Ser Ser
            100                 105                 110

Ser Val Ala Asn Phe Leu Gln Ala Arg Gly Leu Ala Ser Gly Asn Val
        115                 120                 125

Val Ala Leu Phe Met Glu Asn Arg Asn Glu Phe Val Gly Leu Trp Leu
    130                 135                 140

Gly Met Ala Lys Leu Gly Val Glu Ala Ala Leu Ile Asn Thr Asn Leu
145                 150                 155                 160

Arg Arg Asp Ala Leu Arg His Cys Leu Asp Thr Ser Lys Ala Arg Ala
                165                 170                 175

Leu Ile Phe Gly Ser Glu Met Ala Ser Ala Ile Cys Glu Ile His Ala
            180                 185                 190

Ser Leu Glu Pro Thr Leu Ser Leu Phe Cys Ser Gly Ser Trp Glu Pro
        195                 200                 205

Ser Thr Val Pro Val Ser Thr Glu His Leu Asp Pro Leu Leu Glu Asp
    210                 215                 220

Ala Pro Lys His Leu Pro Ser His Pro Asp Lys Gly Phe Thr Asp Lys
225                 230                 235                 240

Leu Phe Tyr Ile Tyr Thr Ser Gly Thr Thr Gly Leu Pro Lys Ala Ala
                245                 250                 255
```

-continued

```
Ile Val Val His Ser Arg Tyr Tyr Arg Met Ala Ser Leu Val Tyr Tyr
            260                 265                 270

Gly Phe Arg Met Arg Pro Asp Asp Ile Val Tyr Asp Cys Leu Pro Leu
        275                 280                 285

Tyr His Ser Ser Arg Lys His Arg Gly Asp Trp Gln Cys Leu Leu His
    290                 295                 300

Gly Met Thr Val Val Ile Arg Lys Lys Phe Ser Ala Ser Arg Phe Trp
305                 310                 315                 320

Asp Asp Cys Ile Lys Tyr Asn Cys Thr Val Val Gln Tyr Ile Gly Glu
                325                 330                 335

Leu Cys Arg Tyr Leu Leu Asn Gln Pro Pro Arg Glu Ala Glu Ser Arg
            340                 345                 350

His Lys Val Arg Met Ala Leu Gly Asn Gly Leu Arg Gln Ser Ile Trp
        355                 360                 365

Thr Asp Phe Ser Ser Arg Phe His Ile Pro Gln Val Ala Glu Phe Tyr
    370                 375                 380

Gly Ala Thr Glu Cys Asn Cys Ser Leu Gly Asn Phe Asp Ser Arg Val
385                 390                 395                 400

Gly Ala Cys Gly Phe Asn Ser Arg Ile Leu Ser Phe Val Tyr Pro Ile
                405                 410                 415

Arg Leu Val Arg Val Asn Glu Asp Thr Met Glu Leu Ile Arg Gly Pro
            420                 425                 430

Asp Gly Val Cys Ile Pro Cys Gln Pro Gly Gln Pro Gly Gln Leu Val
        435                 440                 445

Gly Arg Ile Ile Gln Gln Asp Pro Leu Arg Arg Phe Asp Gly Tyr Leu
    450                 455                 460

Asn Gln Gly Ala Asn Asn Lys Lys Ile Ala Asn Asp Val Phe Lys Lys
465                 470                 475                 480

Gly Asp Gln Ala Tyr Leu Thr Gly Asp Val Leu Val Met Asp Glu Leu
                485                 490                 495

Gly Tyr Leu Tyr Phe Arg Asp Arg Thr Gly Asp Thr Phe Arg Trp Lys
            500                 505                 510

Gly Glu Asn Val Ser Thr Thr Glu Val Glu Gly Thr Leu Ser Arg Leu
        515                 520                 525

Leu His Met Ala Asp Val Ala Val Tyr Gly Val Glu Val Pro Gly Thr
    530                 535                 540

Glu Gly Arg Ala Gly Met Ala Ala Val Ala Ser Pro Ile Ser Asn Cys
545                 550                 555                 560

Asp Leu Glu Ser Phe Ala Gln Thr Leu Lys Lys Glu Leu Pro Leu Tyr
                565                 570                 575

Ala Arg Pro Ile Phe Leu Arg Phe Leu Pro Glu Leu His Lys Thr Gly
            580                 585                 590

Thr Phe Lys Phe Gln Lys Thr Glu Leu Arg Lys Glu Gly Phe Asp Pro
        595                 600                 605

Ser Val Val Lys Asp Pro Leu Phe Tyr Leu Asp Ala Arg Lys Gly Cys
    610                 615                 620

Tyr Val Ala Leu Asp Gln Glu Ala Tyr Thr Arg Ile Gln Ala Gly Glu
625                 630                 635                 640

Glu Lys Leu
```

<210> SEQ ID NO 72
<211> LENGTH: 2277
<212> TYPE: DNA
<213> ORGANISM: Mus musculus -continued

<400> SEQUENCE: 72

```
cactcatcag agctaagaga gactacacgc tctcatctac ttcagaaaga gccaatgcca      60
tgggtatttg gaagaaacta accttactgc tgttgctgct tctgctggtt ggcctggggc     120
agcccccatg gccagcagct atggctctgg ccctgcgttg gttcctggga gaccccacat     180
gccttgtgct gcttggcttg gcattgctgg gcagaccctg gatcagctcc tggatgcccc     240
actggctgag cctggtagga gcagctctta ccttattcct attgcctcta cagccacccc     300
cagggctacg ctggctgcat aaagatgtgg ctttcacctt caagatgctt ttctatggcc     360
taaagttcag gcgacgcctt aacaaacatc ctccagagac ctttgtggat gctttagagc     420
ggcaagcact ggcatggcct gaccgggtgg ccttggtgtg tactgggtct gagggctcct     480
caatcacaaa tagccagctg gatgccaggt cctgtcaggc agcatgggtc ctgaaagcaa     540
agctgaagga tgccgtaatc cagaacacaa gagatgctgc tgctatctta gttctcccgt     600
ccaagaccat ttctgctttg agtgtgtttc tggggttggc caagttgggc tgccctgtgg     660
cctggatcaa tccacacagc cgagggatgc ccttgctaca ctctgtacgg agctctgggg     720
ccagtgtgct gattgtggat ccagacctcc aggagaacct ggaagaagtc cttcccaagc     780
tgctagctga gaacattcac tgcttctacc ttggccacag ctcacccacc ccgggagtag     840
aggctctggg agcttccctg gatgctgcac cttctgaccc agtacctgcc agccttcgag     900
ctacgattaa gtggaaatct cctgccatat tcatctttac ttcagggacc actggactcc     960
caaagccagc catcttatca catgagcggg tcatacaagt gagcaacgtg ctgtccttct    1020
gtggatgcag agctgatgat gtggtctatg acgtcctacc tctgtaccat acgatagggc    1080
ttgtccttgg attccttggc tgcttacaag ttggagccac ctgtgtcctg gcccccaagt    1140
tctctgcctc ccgattctgg gctgagtgcc ggcagcatgg cgtaacagtg atcttgtatg    1200
tgggtgaaat cctgcggtac ttgtgtaacg tccctgagca accagaagac aagatacata    1260
cagtgcgctt ggccatggga actggacttc gggcaaatgt gtggaaaaac ttccagcaac    1320
gctttggtcc cattcggatc tgggaattct acggatccac agagggcaat gtgggcttaa    1380
tgaactatgt gggccactgc ggggctgtgg gaaggaccag ctgcatcctt cgaatgctga    1440
ctccctttga gcttgtacag ttcgacatag agacagcaga gcctctgagg gacaaacagg    1500
gtttttgcat tcctgtggag ccaggaaagc caggacttct tttgaccaag gttcgaaaga    1560
accaaccctt cctgggctac cgtggttccc aggccgagtc caatcggaaa cttgttgcga    1620
atgtacgacg cgtaggagac ctgtacttca acactgggga cgtgctgacc ttggaccagg    1680
aaggcttctt ctactttcaa gaccgccttg gtgacacctt ccggtggaag ggcgaaaacg    1740
tatctactgg agaggtggag tgtgttttgt ctagcctaga cttcctagag gaagtcaatg    1800
tctatggtgt gcctgtgcca gggtgtgagg gtaaggttgg catggctgct gtgaaactgg    1860
ctcctgggaa gacttttgat gggcagaagc tataccagca tgtccgctcc tggctccctg    1920
cctatgccac acctcatttc atccgtatcc aggattccct ggagatcaca aacacctaca    1980
agctggtaaa gtcacggctg gtgcgtgagg gttttgatgt ggggatcatt gctgaccccc    2040
tctacatact ggacaacaag gcccagacct tccggagtct gatgccagat gtgtaccagg    2100
ctgtgtgtga aggaacctgg aatctctgac cacctagcca actggaaggc aatccaaaag    2160
tgtagagatt gacactagtc agcttcacaa agttgtccgg gttccagatg cccatggccc    2220
agtagtactt agagaataaa cttgaatgtg tatacaaaaa aaaaaaaaaa aaaaaaa       2277
```

-continued

<210> SEQ ID NO 73
<211> LENGTH: 689
<212> TYPE: PRT
<213> ORGANISM: Mus musculus

<400> SEQUENCE: 73

```
Met Gly Ile Trp Lys Lys Leu Thr Leu Leu Leu Leu Leu Leu Leu Leu
 1               5                  10                  15

Val Gly Leu Gly Gln Pro Pro Trp Pro Ala Ala Met Ala Leu Ala Leu
            20                  25                  30

Arg Trp Phe Leu Gly Asp Pro Thr Cys Leu Val Leu Leu Gly Leu Ala
        35                  40                  45

Leu Leu Gly Arg Pro Trp Ile Ser Ser Trp Met Pro His Trp Leu Ser
    50                  55                  60

Leu Val Gly Ala Ala Leu Thr Leu Phe Leu Leu Pro Leu Gln Pro Pro
65                  70                  75                  80

Pro Gly Leu Arg Trp Leu His Lys Asp Val Ala Phe Thr Phe Lys Met
                85                  90                  95

Leu Phe Tyr Gly Leu Lys Phe Arg Arg Arg Leu Asn Lys His Pro Pro
            100                 105                 110

Glu Thr Phe Val Asp Ala Leu Glu Arg Gln Ala Leu Ala Trp Pro Asp
        115                 120                 125

Arg Val Ala Leu Val Cys Thr Gly Ser Glu Gly Ser Ser Ile Thr Asn
    130                 135                 140

Ser Gln Leu Asp Ala Arg Ser Cys Gln Ala Ala Trp Val Leu Lys Ala
145                 150                 155                 160

Lys Leu Lys Asp Ala Val Ile Gln Asn Thr Arg Asp Ala Ala Ala Ile
                165                 170                 175

Leu Val Leu Pro Ser Lys Thr Ile Ser Ala Leu Ser Val Phe Leu Gly
            180                 185                 190

Leu Ala Lys Leu Gly Cys Pro Val Ala Trp Ile Asn Pro His Ser Arg
        195                 200                 205

Gly Met Pro Leu Leu His Ser Val Arg Ser Ser Gly Ala Ser Val Leu
    210                 215                 220

Ile Val Asp Pro Asp Leu Gln Glu Asn Leu Glu Glu Val Leu Pro Lys
225                 230                 235                 240

Leu Leu Ala Glu Asn Ile His Cys Phe Tyr Leu Gly His Ser Ser Pro
                245                 250                 255

Thr Pro Gly Val Glu Ala Leu Gly Ala Ser Leu Asp Ala Ala Pro Ser
            260                 265                 270

Asp Pro Val Pro Ala Ser Leu Arg Ala Thr Ile Lys Trp Lys Ser Pro
        275                 280                 285

Ala Ile Phe Ile Phe Thr Ser Gly Thr Thr Gly Leu Pro Lys Pro Ala
    290                 295                 300

Ile Leu Ser His Glu Arg Val Ile Gln Val Ser Asn Val Leu Ser Phe
305                 310                 315                 320

Cys Gly Cys Arg Ala Asp Asp Val Val Tyr Asp Val Leu Pro Leu Tyr
                325                 330                 335

His Thr Ile Gly Leu Val Leu Gly Phe Leu Gly Cys Leu Gln Val Gly
            340                 345                 350

Ala Thr Cys Val Leu Ala Pro Lys Phe Ser Ala Ser Arg Phe Trp Ala
        355                 360                 365

Glu Cys Arg Gln His Gly Val Thr Val Ile Leu Tyr Val Gly Glu Ile
    370                 375                 380
```

-continued

```
Leu Arg Tyr Leu Cys Asn Val Pro Glu Gln Pro Glu Asp Lys Ile His
385                 390                 395                 400

Thr Val Arg Leu Ala Met Gly Thr Gly Leu Arg Ala Asn Val Trp Lys
                405                 410                 415

Asn Phe Gln Gln Arg Phe Gly Pro Ile Arg Ile Trp Glu Phe Tyr Gly
            420                 425                 430

Ser Thr Glu Gly Asn Val Gly Leu Met Asn Tyr Val Gly His Cys Gly
        435                 440                 445

Ala Val Gly Arg Thr Ser Cys Ile Leu Arg Met Leu Thr Pro Phe Glu
    450                 455                 460

Leu Val Gln Phe Asp Ile Glu Thr Ala Glu Pro Leu Arg Asp Lys Gln
465                 470                 475                 480

Gly Phe Cys Ile Pro Val Glu Pro Gly Lys Pro Gly Leu Leu Leu Thr
                485                 490                 495

Lys Val Arg Lys Asn Gln Pro Phe Leu Gly Tyr Arg Gly Ser Gln Ala
            500                 505                 510

Glu Ser Asn Arg Lys Leu Val Ala Asn Val Arg Arg Val Gly Asp Leu
        515                 520                 525

Tyr Phe Asn Thr Gly Asp Val Leu Thr Leu Asp Gln Glu Gly Phe Phe
    530                 535                 540

Tyr Phe Gln Asp Arg Leu Gly Asp Thr Phe Arg Trp Lys Gly Glu Asn
545                 550                 555                 560

Val Ser Thr Gly Glu Val Glu Cys Val Leu Ser Ser Leu Asp Phe Leu
                565                 570                 575

Glu Glu Val Asn Val Tyr Gly Val Pro Val Pro Gly Cys Glu Gly Lys
            580                 585                 590

Val Gly Met Ala Ala Val Lys Leu Ala Pro Gly Lys Thr Phe Asp Gly
        595                 600                 605

Gln Lys Leu Tyr Gln His Val Arg Ser Trp Leu Pro Ala Tyr Ala Thr
    610                 615                 620

Pro His Phe Ile Arg Ile Gln Asp Ser Leu Glu Ile Thr Asn Thr Tyr
625                 630                 635                 640

Lys Leu Val Lys Ser Arg Leu Val Arg Glu Gly Phe Asp Val Gly Ile
                645                 650                 655

Ile Ala Asp Pro Leu Tyr Ile Leu Asp Asn Lys Ala Gln Thr Phe Arg
            660                 665                 670

Ser Leu Met Pro Asp Val Tyr Gln Ala Val Cys Glu Gly Thr Trp Asn
        675                 680                 685

Leu


<210> SEQ ID NO 74
<211> LENGTH: 2221
<212> TYPE: DNA
<213> ORGANISM: Drosophila melanogaster

<400> SEQUENCE: 74

gctctctggg cctatatcaa gctgctgagg tacacgaagc gccatgagcg gctcaactac      60

acggtggcgg acgtcttcga acgaaatgtt caggcccatc cggacaaggt ggctgtggtc     120

agtgagacgc aacgctggac cttccgtcag gtgaacgagc atgcgaacaa ggtggccaat     180

gtgctgcagg ctcagggcta caaaaagggc gatgtggtgg ccctgttgct ggagaaccgc     240

gccgagtacg tggccacctg gctgggtctc tccaagatcg gtgtgatcac accgctgatc     300

aacacgaatc tgcgcggtcc ctccctgctg cacagcatca cggtggccca ttgctcggct     360
```

-continued

```
ctcatttacg gcgaggactt cctggaagct gtcaccgacg tggccaagga tctgccagcg    420

aacctcacac tcttccagtt caacaacgag aacaacaaca gcgagacgga aaagaacata    480

ccgcaggcca agaatctgaa cgcgctgctg accacggcca gctatgagaa gcctaacaag    540

acgcaggtta accaccacga caagctggtc tacatctaca cctccggcac cacaggattg    600

ccaaaggctg cggttatctc tcactcccgt tatctgttta tcgctgctgg catccactac    660

accatgggtt tccaggagga ggacatcttc tacacgccct tgcctttgta ccacaccgct    720

ggtggcatta tgtgcatggg tcagtcggtg ctctttggct ccacggtctc cattcgcaag    780

aagttctcgg catccaacta tttcgccgac tgcgccaagt ataatgcaac tattggtcag    840

tatatcggtg agatggctcg ctacattcta gctacgaaac cctcggaata cgaccagaaa    900

caccgagtgc gtctggtctt tggaaacgga ctgcgaccgc agatttggcc acagtttgtg    960

cagcgcttca acattgccaa ggttggcgag ttctacggcg ccaccgaggg taatgcgaac   1020

atcatgaatc atgacaacac ggtgggcgcc atcggctttg tgtcgcgcat cctgcccaag   1080

atctacccaa tctcgatcat tcgcgccgat ccggacaccg gagagcccat tagagatagg   1140

aatggcctat gccaactgtg cgctcccaac gagccaggcg tattcatcgg caagatcgtc   1200

aaaggaaatc cttctcgcga attcctcgga tacgtcgatg aaaaggcctc cgcgaagaag   1260

attgttaagg atgtgttcaa gcatggcgat atggctttca tctccggaga tctgctggtt   1320

gccgacgaga agggttatct gtacttcaag gatcgcaccg gtgacacctt ccgctggaag   1380

ggcgagaatg tttccaccag cgaggtggag gcgcaagtca gcaatgtggc cggttacaag   1440

gataccgtcg tttacggcgt aaccattccg cacaccgagg gaagggccgg catggccgcc   1500

atctatgatc cggagcgaga attggacctc gacgtcttcg ccgctagctt ggccaaggtg   1560

ctgcccgcgt acgctcgtcc ccagatcatt cgattgctca ccaaggtgga cctgactgga   1620

acctttaagc tgcgcaaggt agacctgcag aaggagggct acgatccgaa cgcgatcaag   1680

gacgcgctgt actaccagac ttccaagggt cggtacgagc tgctcacgcc ccaggtttac   1740

gaccaggtgc agcgcaacga aatccgcttc taagagctgc aatagagttg tgtctgaacc   1800

ttgccttttg cccaatatgc tgttaattag tttgtaaggc taagtgtagt agaggaaaat   1860

cgggggaaat cggcagcaaa gatcattcag cctaggagag atgcatccga agcacatttc   1920

catgtcaaca atgcactttt gtatatcgta agcatatata tatcgtatat cgtaaacgta   1980

gttgtatctg catttgtgta gatgatagcc tcctatacgc atttcaattg tttttagcgt   2040

gctaaagaac cttgttaaat gcaatttcag ctattgttta gtcagtttta gtggcattta   2100

cacttccatt ctcgttgcgt ttcgtttttg cctgtacata tgagaagctc tgatgttttt   2160

gtatcaaata aagtttttc cttcaccacg gaccacgtga aaaaaaaaaa aaaaaaaaaa    2220

a                                                                   2221
```

<210> SEQ ID NO 75
<211> LENGTH: 590
<212> TYPE: PRT
<213> ORGANISM: Drosophila melanogaster

<400> SEQUENCE: 75

```
Ala Leu Trp Ala Tyr Ile Lys Leu Leu Arg Tyr Thr Lys Arg His Glu
 1               5                  10                  15

Arg Leu Asn Tyr Thr Val Ala Asp Val Phe Glu Arg Asn Val Gln Ala
            20                  25                  30
```

-continued

```
His Pro Asp Lys Val Ala Val Val Ser Glu Thr Gln Arg Trp Thr Phe
        35                  40                  45

Arg Gln Val Asn Glu His Ala Asn Lys Val Ala Asn Val Leu Gln Ala
    50                  55                  60

Gln Gly Tyr Lys Lys Gly Asp Val Val Ala Leu Leu Leu Glu Asn Arg
65                  70                  75                  80

Ala Glu Tyr Val Ala Thr Trp Leu Gly Leu Ser Lys Ile Gly Val Ile
                85                  90                  95

Thr Pro Leu Ile Asn Thr Asn Leu Arg Gly Pro Ser Leu Leu His Ser
            100                 105                 110

Ile Thr Val Ala His Cys Ser Ala Leu Ile Tyr Gly Glu Asp Phe Leu
        115                 120                 125

Glu Ala Val Thr Asp Val Ala Lys Asp Leu Pro Ala Asn Leu Thr Leu
    130                 135                 140

Phe Gln Phe Asn Asn Glu Asn Asn Asn Ser Glu Thr Glu Lys Asn Ile
145                 150                 155                 160

Pro Gln Ala Lys Asn Leu Asn Ala Leu Leu Thr Thr Ala Ser Tyr Glu
                165                 170                 175

Lys Pro Asn Lys Thr Gln Val Asn His His Asp Lys Leu Val Tyr Ile
            180                 185                 190

Tyr Thr Ser Gly Thr Thr Gly Leu Pro Lys Ala Ala Val Ile Ser His
        195                 200                 205

Ser Arg Tyr Leu Phe Ile Ala Ala Gly Ile His Tyr Thr Met Gly Phe
    210                 215                 220

Gln Glu Glu Asp Ile Phe Tyr Thr Pro Leu Pro Leu Tyr His Thr Ala
225                 230                 235                 240

Gly Gly Ile Met Cys Met Gly Gln Ser Val Leu Phe Gly Ser Thr Val
                245                 250                 255

Ser Ile Arg Lys Lys Phe Ser Ala Ser Asn Tyr Phe Ala Asp Cys Ala
            260                 265                 270

Lys Tyr Asn Ala Thr Ile Gly Gln Tyr Ile Gly Glu Met Ala Arg Tyr
        275                 280                 285

Ile Leu Ala Thr Lys Pro Ser Glu Tyr Asp Gln Lys His Arg Val Arg
    290                 295                 300

Leu Val Phe Gly Asn Gly Leu Arg Pro Gln Ile Trp Pro Gln Phe Val
305                 310                 315                 320

Gln Arg Phe Asn Ile Ala Lys Val Gly Glu Phe Tyr Gly Ala Thr Glu
                325                 330                 335

Gly Asn Ala Asn Ile Met Asn His Asp Asn Thr Val Gly Ala Ile Gly
            340                 345                 350

Phe Val Ser Arg Ile Leu Pro Lys Ile Tyr Pro Ile Ser Ile Ile Arg
        355                 360                 365

Ala Asp Pro Asp Thr Gly Glu Pro Ile Arg Asp Arg Asn Gly Leu Cys
    370                 375                 380

Gln Leu Cys Ala Pro Asn Glu Pro Gly Val Phe Ile Gly Lys Ile Val
385                 390                 395                 400

Lys Gly Asn Pro Ser Arg Glu Phe Leu Gly Tyr Val Asp Glu Lys Ala
                405                 410                 415

Ser Ala Lys Lys Ile Val Lys Asp Val Phe Lys His Gly Asp Met Ala
            420                 425                 430

Phe Ile Ser Gly Asp Leu Leu Val Ala Asp Glu Lys Gly Tyr Leu Tyr
        435                 440                 445

Phe Lys Asp Arg Thr Gly Asp Thr Phe Arg Trp Lys Gly Glu Asn Val
```

-continued

```
    450                 455                 460

Ser Thr Ser Glu Val Glu Ala Gln Val Ser Asn Val Ala Gly Tyr Lys
465                 470                 475                 480

Asp Thr Val Val Tyr Gly Val Thr Ile Pro His Thr Glu Gly Arg Ala
                485                 490                 495

Gly Met Ala Ala Ile Tyr Asp Pro Glu Arg Glu Leu Asp Leu Asp Val
            500                 505                 510

Phe Ala Ala Ser Leu Ala Lys Val Leu Pro Ala Tyr Ala Arg Pro Gln
        515                 520                 525

Ile Ile Arg Leu Leu Thr Lys Val Asp Leu Thr Gly Thr Phe Lys Leu
    530                 535                 540

Arg Lys Val Asp Leu Gln Lys Glu Gly Tyr Asp Pro Asn Ala Ile Lys
545                 550                 555                 560

Asp Ala Leu Tyr Tyr Gln Thr Ser Lys Gly Arg Tyr Glu Leu Leu Thr
                565                 570                 575

Pro Gln Val Tyr Asp Gln Val Gln Arg Asn Glu Ile Arg Phe
            580                 585                 590


<210> SEQ ID NO 76
<211> LENGTH: 173
<212> TYPE: DNA
<213> ORGANISM: Danio rerio

<400> SEQUENCE: 76

agtgtagata ccacaggaac gtttaaaatc cagaagacca gactgcaaag ggaaggatac     60

gatccacggc tcacaactga ccagatctac ttcctaaact ccagagcagg gcgttacgag    120

cttgtcaacg aggagctgta caatgcattt gaacaagggc aggatttccc ttt           173


<210> SEQ ID NO 77
<211> LENGTH: 57
<212> TYPE: PRT
<213> ORGANISM: Danio rerio

<400> SEQUENCE: 77

Ser Val Asp Thr Thr Gly Thr Phe Lys Ile Gln Lys Thr Arg Leu Gln
 1               5                  10                  15

Arg Glu Gly Tyr Asp Pro Arg Leu Thr Thr Asp Gln Ile Tyr Phe Leu
            20                  25                  30

Asn Ser Arg Ala Gly Arg Tyr Glu Leu Val Asn Glu Glu Leu Tyr Asn
        35                  40                  45

Ala Phe Glu Gln Gly Gln Asp Phe Pro
    50                  55


<210> SEQ ID NO 78
<211> LENGTH: 1953
<212> TYPE: DNA
<213> ORGANISM: Caenorhabditis elegans

<400> SEQUENCE: 78

atgaagctgg aggagcttgt gacagttatg cttctcacag tggctgtcat tgctcagaat     60

cttccgattg gagtaatatt ggctggagtt cttattttat acatcacagt ggttcatgga    120

gatttcattt atagaagtta tcttacgttg aatagggatt taacaggatt ggctctaatt    180

attgaagtca aaatcgacct atggtggagg ttgcatcaga ataaaggaat ccatgaactg    240

tttttggata ttgtgaaaaa gaatccaaat aagccggcga tgattgacat cgagacgaat    300

acaacagaaa catacgcaga gttcaatgca cattgtaata gatatgccaa ttatttccag    360
```

-continued

```
ggtcttggct atcgatccgg agacgttgtc gccttgtaca tggagaactc ggtcgagttt    420
gtggccgcgt ggatgggact cgcaaaaatc ggagttgtaa cggcttggat caactcgaat    480
ttgaaaagag agcaacttgt tcattgtatc actgcgagca agacaaaggc gattatcaca    540
agtgtaacac ttcagaatat tatgcttgat gctatcgatc agaagctgtt tgatgttgag    600
ggaattgagg tttactctgt cggagagccc aagaagaatt ctggattcaa gaatctcaag    660
aagaagttgg atgctcaaat tactacggaa ccaaagaccc ttgacatagt agattttaaa    720
agtattcttt gcttcatcta tacaagtggt actactggaa tgccaaaagc cgctgtcatg    780
aagcacttca gatattactc gattgccgtt ggagccgcaa aatcattcgg aatccgccct    840
tctgatcgta tgtacgtctc gatgccaatt tatcacactg cagctggaat tcttggagtt    900
gggcaagctc tgttgggtgg atcatcgtgt gtcattagaa aaaaattctc ggctagcaac    960
ttttggaggg attgtgtaaa gtatgattgt acagtttcac aatacattgg agagatttgt   1020
cggtacttgt tggctcagcc agttgtggaa gaggaatcca ggcatagaat gagattgttg   1080
gttggaaacg gactccgtgc tgaaatctgg caaccatttg tagatcgatt ccgtgtcaga   1140
attggagaac tttatggttc aactgaagga acttcatctc tcgtgaacat tgacggacat   1200
gtcggagctt gcggattctt gccaatatcc ccattaacaa agaaaatgca tccggttcga   1260
ttaattaagg ttgatgatgt cactggagaa gcaatccgaa cttccgatgg actttgcatt   1320
gcatgtaatc caggagagtc tggagcaatg gtgtcgacga tcagaaaaaa taatccatta   1380
ttgcaattcg agggatatct gaataagaag gaaacgaata aaaagattat cagagatgtc   1440
ttcgcaaagg gagatagttg ctttttgact ggagatcttc ttcattggga tcgtcttggt   1500
tatgtatatt tcaaggatcg tactggagat actttccgtt ggaagggaga gaatgtgtcg   1560
actactgaag tcgaggcaat tcttcatcca attactggat tgtctgatgc aactgtttat   1620
ggtgtagagg ttcctcaaag agagggaaga gttggaatgg cgtcagttgt tcgagttgta   1680
tcgcatgagg aagatgaaac tcaatttgtt catagagttg gagcaagact tgcctcttcg   1740
cttaccagct acgcgattcc tcagtttatg cgaatttgtc aggatgttga gaaaacaggt   1800
acattcaaac ttgtgaagac gaatctacaa cgattaggta tcatggatgc tccttcagat   1860
tcaatttaca tctacaattc tgaaaatcgc aattttgtgc cgttcgacaa tgatttgagg   1920
tgcaaggtct cactgggaag ttatccattt taa                               1953
```

<210> SEQ ID NO 79
<211> LENGTH: 650
<212> TYPE: PRT
<213> ORGANISM: Caenorhabditis elegans

<400> SEQUENCE: 79

```
Met Lys Leu Glu Glu Leu Val Thr Val Met Leu Leu Thr Val Ala Val
 1               5                  10                  15

Ile Ala Gln Asn Leu Pro Ile Gly Val Ile Leu Ala Gly Val Leu Ile
            20                  25                  30

Leu Tyr Ile Thr Val Val His Gly Asp Phe Ile Tyr Arg Ser Tyr Leu
        35                  40                  45

Thr Leu Asn Arg Asp Leu Thr Gly Leu Ala Leu Ile Ile Glu Val Lys
    50                  55                  60

Ile Asp Leu Trp Trp Arg Leu His Gln Asn Lys Gly Ile His Glu Leu
65                  70                  75                  80

Phe Leu Asp Ile Val Lys Lys Asn Pro Asn Lys Pro Ala Met Ile Asp
```

-continued

```
                85                  90                  95

Ile Glu Thr Asn Thr Thr Glu Thr Tyr Ala Glu Phe Asn Ala His Cys
            100                 105                 110

Asn Arg Tyr Ala Asn Tyr Phe Gln Gly Leu Gly Tyr Arg Ser Gly Asp
        115                 120                 125

Val Val Ala Leu Tyr Met Glu Asn Ser Val Glu Phe Val Ala Ala Trp
    130                 135                 140

Met Gly Leu Ala Lys Ile Gly Val Val Thr Ala Trp Ile Asn Ser Asn
145                 150                 155                 160

Leu Lys Arg Glu Gln Leu Val His Cys Ile Thr Ala Ser Lys Thr Lys
                165                 170                 175

Ala Ile Ile Thr Ser Val Thr Leu Gln Asn Ile Met Leu Asp Ala Ile
            180                 185                 190

Asp Gln Lys Leu Phe Asp Val Glu Gly Ile Glu Val Tyr Ser Val Gly
        195                 200                 205

Glu Pro Lys Lys Asn Ser Gly Phe Lys Asn Leu Lys Lys Lys Leu Asp
    210                 215                 220

Ala Gln Ile Thr Thr Glu Pro Lys Thr Leu Asp Ile Val Asp Phe Lys
225                 230                 235                 240

Ser Ile Leu Cys Phe Ile Tyr Thr Ser Gly Thr Thr Gly Met Pro Lys
                245                 250                 255

Ala Ala Val Met Lys His Phe Arg Tyr Tyr Ser Ile Ala Val Gly Ala
            260                 265                 270

Ala Lys Ser Phe Gly Ile Arg Pro Ser Asp Arg Met Tyr Val Ser Met
        275                 280                 285

Pro Ile Tyr His Thr Ala Ala Gly Ile Leu Gly Val Gly Gln Ala Leu
    290                 295                 300

Leu Gly Gly Ser Ser Cys Val Ile Arg Lys Lys Phe Ser Ala Ser Asn
305                 310                 315                 320

Phe Trp Arg Asp Cys Val Lys Tyr Asp Cys Thr Val Ser Gln Tyr Ile
                325                 330                 335

Gly Glu Ile Cys Arg Tyr Leu Leu Ala Gln Pro Val Val Glu Glu Glu
            340                 345                 350

Ser Arg His Arg Met Arg Leu Leu Val Gly Asn Gly Leu Arg Ala Glu
        355                 360                 365

Ile Trp Gln Pro Phe Val Asp Arg Phe Arg Val Arg Ile Gly Glu Leu
    370                 375                 380

Tyr Gly Ser Thr Glu Gly Thr Ser Ser Leu Val Asn Ile Asp Gly His
385                 390                 395                 400

Val Gly Ala Cys Gly Phe Leu Pro Ile Ser Pro Leu Thr Lys Lys Met
                405                 410                 415

His Pro Val Arg Leu Ile Lys Val Asp Asp Val Thr Gly Glu Ala Ile
            420                 425                 430

Arg Thr Ser Asp Gly Leu Cys Ile Ala Cys Asn Pro Gly Glu Ser Gly
        435                 440                 445

Ala Met Val Ser Thr Ile Arg Lys Asn Asn Pro Leu Leu Gln Phe Glu
    450                 455                 460

Gly Tyr Leu Asn Lys Lys Glu Thr Asn Lys Lys Ile Ile Arg Asp Val
465                 470                 475                 480

Phe Ala Lys Gly Asp Ser Cys Phe Leu Thr Gly Asp Leu Leu His Trp
                485                 490                 495

Asp Arg Leu Gly Tyr Val Tyr Phe Lys Asp Arg Thr Gly Asp Thr Phe
            500                 505                 510
```

-continued

```
Arg Trp Lys Gly Glu Asn Val Ser Thr Thr Glu Val Glu Ala Ile Leu
        515                 520                 525

His Pro Ile Thr Gly Leu Ser Asp Ala Thr Val Tyr Gly Val Glu Val
    530                 535                 540

Pro Gln Arg Glu Gly Arg Val Gly Met Ala Ser Val Val Arg Val Val
545                 550                 555                 560

Ser His Glu Glu Asp Glu Thr Gln Phe Val His Arg Val Gly Ala Arg
                565                 570                 575

Leu Ala Ser Ser Leu Thr Ser Tyr Ala Ile Pro Gln Phe Met Arg Ile
            580                 585                 590

Cys Gln Asp Val Glu Lys Thr Gly Thr Phe Lys Leu Val Lys Thr Asn
        595                 600                 605

Leu Gln Arg Leu Gly Ile Met Asp Ala Pro Ser Asp Ser Ile Tyr Ile
    610                 615                 620

Tyr Asn Ser Glu Asn Arg Asn Phe Val Pro Phe Asp Asn Asp Leu Arg
625                 630                 635                 640

Cys Lys Val Ser Leu Gly Ser Tyr Pro Phe
                645                 650
```

<210> SEQ ID NO 80
<211> LENGTH: 1968
<212> TYPE: DNA
<213> ORGANISM: Caenorhabditis elegans

<400> SEQUENCE: 80

```
atgagggaaa tgccggacag tcccaagttt gcgttagtca cgtttgttgt gtatgcagtg     60

gttttgtaca atgtcaacag cgttttctgg aaatttgtat tcatcggata tgttgtattt    120

aggctgcttc gcactgattt tggaagaaga gcacttgcca cgttacctag agattttgcg    180

ggactgaagc tcttaatatc ggttaagtcg acaattcgtg gcttgttcaa gaaagatcgc    240

ccaattcatg aaatcttttt gaatcaggtg aaacagcatc caaacaaagt ggcgattatt    300

gaaattgaaa gtggtaggca gttgacgtat caagaattga atgcgttagc taatcagtat    360

gctaaccttt acgtgagtga aggttacaaa atgggcgacg ttgtcgcttt gtttatggaa    420

aatagcatcg acttctttgc aatttggctg ggactttcca agattggagt cgtgtcggcg    480

ttcatcaact caaacttgaa gttggagcca ttggcacatt cgattaatgt ttcgaagtgc    540

aaatcatgca ttaccaatat caatctgttg ccgatgttca aagccgctcg tgaaaagaat    600

ctgatcagtg acgagatcca cgtgtttctg gctggaactc aggttgatgg acgtcataga    660

agtcttcagc aagatctcca tcttttctct gaggatgaac ctccagttat agacggactc    720

aattttagaa gcgttctgtg ttatatttac acttccggta ctaccggaaa tccaaagcca    780

gccgtcatta aacacttccg ttacttctgg attgcgatgg gagcaggaaa agcatttgga    840

attaataagt cagacgttgt gtacattacg atgccaatgt atcactctgc cgccggtatc    900

atgggtattg gatcattaat tgcattcggg tcgaccgctg ttattaggaa aaagttttcg    960

gcaagcaact tctggaaaga ttgcgtcaag tacaacgtca cagcgacaca gtacattgga   1020

gaaatctgca ggtatcttct ggcagcgaat ccatgtcctg aagagaaaca acacaacgtg   1080

cgattgatgt ggggaaatgg tttgagagga caaatttgga aagagtttgt aggaagattt   1140

ggaattaaga aaattggaga gttgtacggc tcaacagaag gaaactccaa tattgttaac   1200

gtggataacc atgttggagc ttgtggattc atgccaattt atccccatat tggatccctc   1260

tacccagttc gacttattaa ggttgataga gccactggag agcttgaacg tgataagaac   1320
```

-continued

```
ggactctgtg tgccgtgtgt gcctggtgaa actggggaaa tggttggcgt tatcaaggag   1380

aaagatattc ttctaaagtt cgaaggatat gtcagcgaag gggatactgc aaagaaaatc   1440

tacagagatg tgttcaagca tggagataag gtgtttgcaa gtggagatat tcttcattgg   1500

gatgatcttg gatacttgta ctttgtggac cgttgtggag acactttccg ttggaaaggg   1560

gagaacgtgt caactactga agttgaggga attcttcagc ctgtgatgga tgtggaagat   1620

gcaactgttt atggagtcac tgtcggtaaa atggaggggc gtgccggaat ggctggtatt   1680

gtcgtcaagg atggaacgga tgttgagaaa ttcatcgccg atattacttc tcgactgacc   1740

gaaaatctgg cgtcttacgc aatccctgtt ttcattcggc tgtgcaagga agttgatcga   1800

accggaacct tcaaactcaa gaagactgat cttcaaaaac aaggttacga cctggttgct   1860

tgtaaaggag acccaattta ctactggtca gctgcagaaa aatcctacaa accactgact   1920

gacaaaatgc aacaggatat tgacactggt gtttatgatc gcatttaa               1968
```

```
<210> SEQ ID NO 81
<211> LENGTH: 655
<212> TYPE: PRT
<213> ORGANISM: Caenorhabditis elegans

<400> SEQUENCE: 81

Met Arg Glu Met Pro Asp Ser Pro Lys Phe Ala Leu Val Thr Phe Val
 1               5                  10                  15

Val Tyr Ala Val Val Leu Tyr Asn Val Asn Ser Val Phe Trp Lys Phe
            20                  25                  30

Val Phe Ile Gly Tyr Val Val Phe Arg Leu Leu Arg Thr Asp Phe Gly
        35                  40                  45

Arg Arg Ala Leu Ala Thr Leu Pro Arg Asp Phe Ala Gly Leu Lys Leu
    50                  55                  60

Leu Ile Ser Val Lys Ser Thr Ile Arg Gly Leu Phe Lys Lys Asp Arg
65                  70                  75                  80

Pro Ile His Glu Ile Phe Leu Asn Gln Val Lys Gln His Pro Asn Lys
                85                  90                  95

Val Ala Ile Ile Glu Ile Glu Ser Gly Arg Gln Leu Thr Tyr Gln Glu
            100                 105                 110

Leu Asn Ala Leu Ala Asn Gln Tyr Ala Asn Leu Tyr Val Ser Glu Gly
        115                 120                 125

Tyr Lys Met Gly Asp Val Val Ala Leu Phe Met Glu Asn Ser Ile Asp
    130                 135                 140

Phe Phe Ala Ile Trp Leu Gly Leu Ser Lys Ile Gly Val Val Ser Ala
145                 150                 155                 160

Phe Ile Asn Ser Asn Leu Lys Leu Glu Pro Leu Ala His Ser Ile Asn
                165                 170                 175

Val Ser Lys Cys Lys Ser Cys Ile Thr Asn Ile Asn Leu Leu Pro Met
            180                 185                 190

Phe Lys Ala Ala Arg Glu Lys Asn Leu Ile Ser Asp Glu Ile His Val
        195                 200                 205

Phe Leu Ala Gly Thr Gln Val Asp Gly Arg His Arg Ser Leu Gln Gln
    210                 215                 220

Asp Leu His Leu Phe Ser Glu Asp Glu Pro Pro Val Ile Asp Gly Leu
225                 230                 235                 240

Asn Phe Arg Ser Val Leu Cys Tyr Ile Tyr Thr Ser Gly Thr Thr Gly
                245                 250                 255
```

-continued

```
Asn Pro Lys Pro Ala Val Ile Lys His Phe Arg Tyr Phe Trp Ile Ala
            260                 265                 270

Met Gly Ala Gly Lys Ala Phe Gly Ile Asn Lys Ser Asp Val Val Tyr
        275                 280                 285

Ile Thr Met Pro Met Tyr His Ser Ala Ala Gly Ile Met Gly Ile Gly
    290                 295                 300

Ser Leu Ile Ala Phe Gly Ser Thr Ala Val Ile Arg Lys Lys Phe Ser
305                 310                 315                 320

Ala Ser Asn Phe Trp Lys Asp Cys Val Lys Tyr Asn Val Thr Ala Thr
                325                 330                 335

Gln Tyr Ile Gly Glu Ile Cys Arg Tyr Leu Leu Ala Ala Asn Pro Cys
            340                 345                 350

Pro Glu Glu Lys Gln His Asn Val Arg Leu Met Trp Gly Asn Gly Leu
        355                 360                 365

Arg Gly Gln Ile Trp Lys Glu Phe Val Gly Arg Phe Gly Ile Lys Lys
    370                 375                 380

Ile Gly Glu Leu Tyr Gly Ser Thr Glu Gly Asn Ser Asn Ile Val Asn
385                 390                 395                 400

Val Asp Asn His Val Gly Ala Cys Gly Phe Met Pro Ile Tyr Pro His
                405                 410                 415

Ile Gly Ser Leu Tyr Pro Val Arg Leu Ile Lys Val Asp Arg Ala Thr
            420                 425                 430

Gly Glu Leu Glu Arg Asp Lys Asn Gly Leu Cys Val Pro Cys Val Pro
        435                 440                 445

Gly Glu Thr Gly Glu Met Val Gly Val Ile Lys Glu Lys Asp Ile Leu
    450                 455                 460

Leu Lys Phe Glu Gly Tyr Val Ser Glu Gly Asp Thr Ala Lys Lys Ile
465                 470                 475                 480

Tyr Arg Asp Val Phe Lys His Gly Asp Lys Val Phe Ala Ser Gly Asp
                485                 490                 495

Ile Leu His Trp Asp Asp Leu Gly Tyr Leu Tyr Phe Val Asp Arg Cys
            500                 505                 510

Gly Asp Thr Phe Arg Trp Lys Gly Glu Asn Val Ser Thr Thr Glu Val
        515                 520                 525

Glu Gly Ile Leu Gln Pro Val Met Asp Val Glu Asp Ala Thr Val Tyr
    530                 535                 540

Gly Val Thr Val Gly Lys Met Glu Gly Arg Ala Gly Met Ala Gly Ile
545                 550                 555                 560

Val Val Lys Asp Gly Thr Asp Val Glu Lys Phe Ile Ala Asp Ile Thr
                565                 570                 575

Ser Arg Leu Thr Glu Asn Leu Ala Ser Tyr Ala Ile Pro Val Phe Ile
            580                 585                 590

Arg Leu Cys Lys Glu Val Asp Arg Thr Gly Thr Phe Lys Leu Lys Lys
        595                 600                 605

Thr Asp Leu Gln Lys Gln Gly Tyr Asp Leu Val Ala Cys Lys Gly Asp
    610                 615                 620

Pro Ile Tyr Tyr Trp Ser Ala Ala Glu Lys Ser Tyr Lys Pro Leu Thr
625                 630                 635                 640

Asp Lys Met Gln Gln Asp Ile Asp Thr Gly Val Tyr Asp Arg Ile
                645                 650                 655
```

<210> SEQ ID NO 82
<211> LENGTH: 1932
<212> TYPE: DNA

-continued

<213> ORGANISM: Cochliobolu heterostrophus

<400> SEQUENCE: 82
atggcgtgta tgcatcaggc tcagctatac aatgatctag aggaattgct aactggtcca 60
tcagtaccca tcgttgctgg agctgctgga gctgcagctc tcactgccta cattaacgcc 120
aaataccaca tagcccatga tctcaagacc ctcggtggtg gattgacaca atcgtccgaa 180
gcgattgatt tcataaaccg ccgcgtcgca caaaagcgcg tcctcacgca ccacatcttc 240
caggagcagg tccaaaaaca atcaaatcat ccctttctta tctttgaggg caagacatgg 300
tcttacaagg agttctctga ggcatacacg agggtcgcga actggctgat tgatgagctg 360
gacgtacaag taggggagat ggtcgcaatt gatggcggaa atagtgcaga gcacctgatg 420
ctttggcttg cacttgatgc aatcggtgcg gctacgagtt ttttgaactg gaacctgaca 480
ggggcagggt taattcattg cataaagcta tgcgaatgtc gattcgttat cgcagacatc 540
gatattaaag cgaacattga accgtgccgt ggcgaactgg aggagacggg catcaacatt 600
cactactatg acccatcctt catctcatcg ctaccgaata acacgccaat tcccgacagc 660
cgcactgaga acattgaatt agattcagta cgaggactga tatacacatc tggaaccact 720
ggtctaccta aaggcgtgtt tataagcact ggccgcgagc ttaggactga ctggtcgatt 780
tcaaagtatc taaatctcaa gcccacggat cgaatgtata catgtatgcc gctctaccat 840
gccgctgcac acagcctctg tacagcatca gttattcatg gtggaggtac cgtggtattg 900
agcaggaaat tctcacacaa gaagttctgg cctgaagttg tggcttcgga agcaaatatc 960
attcagtacg ttggtgaatt aggtcgatat ctcctgaatg gtccaaagag tccttacgac 1020
agggcccata aagtccagat ggcgtggggc aatggcatgc gtccagacgt gtgggaagcg 1080
tttcgtgaac gcttcaacat accaattatt catgagctct atgccgcaac cgatgggctc 1140
gggtcaatga ccaatcgtaa cgcgggccct tttacagcaa actgtattgc gctgcgaggg 1200
ctgatctggc actggaaatt tcgaaatcag gaagtgctgg tcaagatgga tctcgatact 1260
gatgagatca tgagagatcg caatgggttt gcgatacgat gcgctgtcaa tgaacctgga 1320
cagatgcttt ttcggctgac acccgaaact ctggctggtg caccaagcta ctacaacaac 1380
gaaacggcca cacagagcag gcggattaca gatgtgtttc aaaagggtga cctgtggttc 1440
aagtccggtg acatgctacg gcaagacgcc gaaggccgcg tctactttgt cgatcgacta 1500
ggcgatacgt tccgctggaa atccgaaaac gtttctacca atgaagtcgc ggacgtgatg 1560
ggcacatttc ctcagattgc tgaaacgaat gtatacggtg tccttgtgcc gggtaacgat 1620
ggtcgagtgc gcagcctcaa ttgtcatggc agacggcgtg acagagtcga cattcgcttc 1680
gctgcccttg caaagcacgc ccgagatcgg ttaccgggtt atgctgtacc actgtttctg 1740
agggtaactc cagcacttga atatacgggc acattaaaga ttcagaaagg acgcctcaag 1800
caggaaggta tagacccaga taagatttcc ggcgaagata agttatactg gctgccgcct 1860
ggtagcgata tatatttacc atttggaaag atggagtggc agggaattgt agataagcgt 1920
atacggctgt ga 1932

<210> SEQ ID NO 83
<211> LENGTH: 643
<212> TYPE: PRT
<213> ORGANISM: Cochliobolu heterostrophus

<400> SEQUENCE: 83

Met Ala Cys Met His Gln Ala Gln Leu Tyr Asn Asp Leu Glu Glu Leu

-continued

```
1               5                   10                  15

Leu Thr Gly Pro Ser Val Pro Ile Val Ala Gly Ala Ala Gly Ala Ala
            20                  25                  30

Ala Leu Thr Ala Tyr Ile Asn Ala Lys Tyr His Ile Ala His Asp Leu
        35                  40                  45

Lys Thr Leu Gly Gly Gly Leu Thr Gln Ser Ser Glu Ala Ile Asp Phe
    50                  55                  60

Ile Asn Arg Arg Val Ala Gln Lys Arg Val Leu Thr His His Ile Phe
65                  70                  75                  80

Gln Glu Gln Val Gln Lys Gln Ser Asn His Pro Phe Leu Ile Phe Glu
                85                  90                  95

Gly Lys Thr Trp Ser Tyr Lys Glu Phe Ser Glu Ala Tyr Thr Arg Val
            100                 105                 110

Ala Asn Trp Leu Ile Asp Glu Leu Asp Val Gln Val Gly Glu Met Val
        115                 120                 125

Ala Ile Asp Gly Gly Asn Ser Ala Glu His Leu Met Leu Trp Leu Ala
    130                 135                 140

Leu Asp Ala Ile Gly Ala Ala Thr Ser Phe Leu Asn Trp Asn Leu Thr
145                 150                 155                 160

Gly Ala Gly Leu Ile His Cys Ile Lys Leu Cys Glu Cys Arg Phe Val
                165                 170                 175

Ile Ala Asp Ile Asp Ile Lys Ala Asn Ile Glu Pro Cys Arg Gly Glu
            180                 185                 190

Leu Glu Glu Thr Gly Ile Asn Ile His Tyr Tyr Asp Pro Ser Phe Ile
        195                 200                 205

Ser Ser Leu Pro Asn Asn Thr Pro Ile Pro Asp Ser Arg Thr Glu Asn
    210                 215                 220

Ile Glu Leu Asp Ser Val Arg Gly Leu Ile Tyr Thr Ser Gly Thr Thr
225                 230                 235                 240

Gly Leu Pro Lys Gly Val Phe Ile Ser Thr Gly Arg Glu Leu Arg Thr
                245                 250                 255

Asp Trp Ser Ile Ser Lys Tyr Leu Asn Leu Lys Pro Thr Asp Arg Met
            260                 265                 270

Tyr Thr Cys Met Pro Leu Tyr His Ala Ala Ala His Ser Leu Cys Thr
        275                 280                 285

Ala Ser Val Ile His Gly Gly Gly Thr Val Val Leu Ser Arg Lys Phe
    290                 295                 300

Ser His Lys Lys Phe Trp Pro Glu Val Val Ala Ser Glu Ala Asn Ile
305                 310                 315                 320

Ile Gln Tyr Val Gly Glu Leu Gly Arg Tyr Leu Leu Asn Gly Pro Lys
                325                 330                 335

Ser Pro Tyr Asp Arg Ala His Lys Val Gln Met Ala Trp Gly Asn Gly
            340                 345                 350

Met Arg Pro Asp Val Trp Glu Ala Phe Arg Glu Arg Phe Asn Ile Pro
        355                 360                 365

Ile Ile His Glu Leu Tyr Ala Ala Thr Asp Gly Leu Gly Ser Met Thr
    370                 375                 380

Asn Arg Asn Ala Gly Pro Phe Thr Ala Asn Cys Ile Ala Leu Arg Gly
385                 390                 395                 400

Leu Ile Trp His Trp Lys Phe Arg Asn Gln Glu Val Leu Val Lys Met
                405                 410                 415

Asp Leu Asp Thr Asp Glu Ile Met Arg Asp Arg Asn Gly Phe Ala Ile
            420                 425                 430
```

-continued

Arg Cys Ala Val Asn Glu Pro Gly Gln Met Leu Phe Arg Leu Thr Pro
435 440 445

Glu Thr Leu Ala Gly Ala Pro Ser Tyr Tyr Asn Asn Glu Thr Ala Thr
450 455 460

Gln Ser Arg Arg Ile Thr Asp Val Phe Gln Lys Gly Asp Leu Trp Phe
465 470 475 480

Lys Ser Gly Asp Met Leu Arg Gln Asp Ala Glu Gly Arg Val Tyr Phe
485 490 495

Val Asp Arg Leu Gly Asp Thr Phe Arg Trp Lys Ser Glu Asn Val Ser
500 505 510

Thr Asn Glu Val Ala Asp Val Met Gly Thr Phe Pro Gln Ile Ala Glu
515 520 525

Thr Asn Val Tyr Gly Val Leu Val Pro Gly Asn Asp Gly Arg Val Arg
530 535 540

Ser Leu Asn Cys His Gly Arg Arg Arg Asp Arg Val Asp Ile Arg Phe
545 550 555 560

Ala Ala Leu Ala Lys His Ala Arg Asp Arg Leu Pro Gly Tyr Ala Val
565 570 575

Pro Leu Phe Leu Arg Val Thr Pro Ala Leu Glu Tyr Thr Gly Thr Leu
580 585 590

Lys Ile Gln Lys Gly Arg Leu Lys Gln Glu Gly Ile Asp Pro Asp Lys
595 600 605

Ile Ser Gly Glu Asp Lys Leu Tyr Trp Leu Pro Pro Gly Ser Asp Ile
610 615 620

Tyr Leu Pro Phe Gly Lys Met Glu Trp Gln Gly Ile Val Asp Lys Arg
625 630 635 640

Ile Arg Leu

<210> SEQ ID NO 84
<211> LENGTH: 597
<212> TYPE: DNA
<213> ORGANISM: Aspergillus nidulans

<400> SEQUENCE: 84
ctttaccatt catcagcttc attctgcatt tttagcttga cggcagccgg gtctacgctg 60
atcatcggcc gcaagttctc cgcgagaaac ttcataaagg aagcgcgcga gaacgacgcc 120
acggtcatcc agtacgtggg tgagaccttg cgatatctgc tcgccacccc cggtgaaacc 180
gatccagtta ctggcgaaga cctggacaaa aagcacaata ttcgagcagt atacggcaac 240
gggctacggc cggatatctg gaaccgcttc aaggagcgct tcaacgtgcc gacggttgcc 300
gaattttatg ctgcaaccga gagcccaggc ggaacatgga actattcaac aaatgacttc 360
actgccggag ccattgggca cactggcgtg cttagtggat ggcttcttgg acgcggcctt 420
actattgtcg aggtggacca ggaatcacag gaaccatggc gcgatcccca aaccgggttc 480
tgcaagccgg tcccgcgagg cgaagcaggc gagctcctgt atgccattga tccggccgac 540
ccgggcgaga ccttccaggg ctactaccgc aactccttta gagcacactg gcggccg 597

<210> SEQ ID NO 85
<211> LENGTH: 199
<212> TYPE: PRT
<213> ORGANISM: Aspergillus nidulans

<400> SEQUENCE: 85

Leu Tyr His Ser Ser Ala Ser Phe Cys Ile Phe Ser Leu Thr Ala Ala

-continued

```
 1               5                   10                  15

Gly Ser Thr Leu Ile Ile Gly Arg Lys Phe Ser Ala Arg Asn Phe Ile
            20                  25                  30

Lys Glu Ala Arg Glu Asn Asp Ala Thr Val Ile Gln Tyr Val Gly Glu
        35                  40                  45

Thr Leu Arg Tyr Leu Leu Ala Thr Pro Gly Glu Thr Asp Pro Val Thr
    50                  55                  60

Gly Glu Asp Leu Asp Lys Lys His Asn Ile Arg Ala Val Tyr Gly Asn
65                  70                  75                  80

Gly Leu Arg Pro Asp Ile Trp Asn Arg Phe Lys Glu Arg Phe Asn Val
                85                  90                  95

Pro Thr Val Ala Glu Phe Tyr Ala Ala Thr Glu Ser Pro Gly Gly Thr
            100                 105                 110

Trp Asn Tyr Ser Thr Asn Asp Phe Thr Ala Gly Ala Ile Gly His Thr
        115                 120                 125

Gly Val Leu Ser Gly Trp Leu Leu Gly Arg Gly Leu Thr Ile Val Glu
    130                 135                 140

Val Asp Gln Glu Ser Gln Glu Pro Trp Arg Asp Pro Gln Thr Gly Phe
145                 150                 155                 160

Cys Lys Pro Val Pro Arg Gly Glu Ala Gly Glu Leu Leu Tyr Ala Ile
                165                 170                 175

Asp Pro Ala Asp Pro Gly Glu Thr Phe Gln Gly Tyr Tyr Arg Asn Ser
            180                 185                 190

Phe Arg Ala His Trp Arg Pro
        195
```

```
<210> SEQ ID NO 86
<211> LENGTH: 522
<212> TYPE: DNA
<213> ORGANISM: Magnaporthe grisea
<220> FEATURE:
<221> NAME/KEY: misc_feature
<222> LOCATION: (1)...(522)
<223> OTHER INFORMATION: n = A,T,C or G

<400> SEQUENCE: 86

gcaaaggccg acgcgtggct gcggacgggt aacgtgatca gggcggacaa cgaagggcga     60

ctcttcttcc acgaccggat cggagacacg ttccgatgga agggagagac ngtcagcaca    120

caagaggtca gtttggtgct cggacgacac gactcaatca aggaggccaa cgtgtacggc    180

gtgacggtgc cgaaccacga cgggcgggcc ggctgcgctg cgctcacgct atcagacgct    240

ctggcgactg aaaagaagct gggcgatgag ctgctaaagg gattggctac tcactcgtcg    300

acttcgcttc ccaagtttgc ggtgccgcag ttcctacggg tggtgcgcgg cgagatgcag    360

tcaacgggca ccaacaagca acagaagcac gacctgaggg tgcagggtgt agagccgggc    420

aaggtgggcg tagacgaggt gtactggttg cggggaggga catatgtacc attcggaaca    480

gaggattggg atgggttgaa gaagggtctt gtgaagttgt ga                       522


<210> SEQ ID NO 87
<211> LENGTH: 173
<212> TYPE: PRT
<213> ORGANISM: Magnaporthe grisea

<400> SEQUENCE: 87

Ala Lys Ala Asp Ala Trp Leu Arg Thr Gly Asn Val Ile Arg Ala Asp
 1               5                   10                  15
```

-continued

```
Asn Glu Gly Arg Leu Phe Phe His Asp Arg Ile Gly Asp Thr Phe Arg
            20                  25                  30

Trp Lys Gly Glu Thr Val Ser Thr Gln Glu Val Ser Leu Val Leu Gly
        35                  40                  45

Arg His Asp Ser Ile Lys Glu Ala Asn Val Tyr Gly Val Thr Val Pro
    50                  55                  60

Asn His Asp Gly Arg Ala Gly Cys Ala Ala Leu Thr Leu Ser Asp Ala
65                  70                  75                  80

Leu Ala Thr Glu Lys Lys Leu Gly Asp Glu Leu Leu Lys Gly Leu Ala
                85                  90                  95

Thr His Ser Ser Thr Ser Leu Pro Lys Phe Ala Val Pro Gln Phe Leu
            100                 105                 110

Arg Val Val Arg Gly Glu Met Gln Ser Thr Gly Thr Asn Lys Gln Gln
        115                 120                 125

Lys His Asp Leu Arg Val Gln Gly Val Glu Pro Gly Lys Val Gly Val
    130                 135                 140

Asp Glu Val Tyr Trp Leu Arg Gly Gly Thr Tyr Val Pro Phe Gly Thr
145                 150                 155                 160

Glu Asp Trp Asp Gly Leu Lys Lys Gly Leu Val Lys Leu
                165                 170
```

<210> SEQ ID NO 88
<211> LENGTH: 1872
<212> TYPE: DNA
<213> ORGANISM: Saccharomyces cerevisiae

<400> SEQUENCE: 88

```
atgtctccca tacaggttgt tgtctttgcc ttgtcaagga ttttcctgct attattcaga     60

cttatcaagc taattataac ccctatccag aaatcactgg gttatctatt tggtaattat    120

tttgatgaat tagaccgtaa atatagatac aaggaggatt ggtatattat tccttacttt    180

ttgaaaagcg tgttttgtta tatcattgat gtgagaagac ataggtttca aaactggtac    240

ttatttatta aacaggtcca acaaaatggt gaccatttag cgattagtta cacccgtccc    300

atggccgaaa agggagaatt tcaactcgaa acctttacgt atattgaaac ttataacata    360

gtgttgagat tgtctcatat tttgcatttt gattataacg ttcaggccgg tgactacgtg    420

gcaatcgatt gtactaataa acctcttttc gtatttttat ggctttcttt gtggaacatt    480

ggggctattc cagctttttt aaactataat actaaaggca ctccgctggt tcactcccta    540

aagatttcca atattacgca ggtatttatt gaccctgatg ccagtaatcc gatcagagaa    600

tcggaagaag aaatcaaaaa cgcacttcct gatgttaaat taaactatct tgaagaacaa    660

gacttaatgc atgaactttt aaattcgcaa tcaccggaat tcttacaaca agacaacgtt    720

aggacaccac taggcttgac cgattttaaa ccctctatgt taatttatac atctggaacc    780

actggtttgc ctaaatccgc tattatgtct tggagaaaat cctccgtagg ttgtcaagtt    840

tttggtcatg ttttacatat gactaatgaa agcactgtgt tcacagccat gccattgttc    900

cattcaactg ctgccttatt aggtgcgtgc gccattctat ctcacggtgg ttgccttgcg    960

ttatcgcata aattttctgc cagtacattt tggaagcaag tttatttaac aggagccacg   1020

cacatccaat atgtcggaga agtctgtaga tacctgttac atacgccaat ttctaagtat   1080

gaaaagatgc ataaggtgaa ggttgcttat ggtaacgggc tgagacctga catctggcag   1140

gacttcagga agaggttcaa catagaagtt attggtgaat tctatgccgc aactgaagct   1200

ccttttgcta caactacctt ccagaaaggt gactttggaa ttggcgcatg taggaactat   1260
```

-continued

```
ggtactataa ttcaatggtt tttgtcattc caacaaacat tggtaaggat ggacccaaat   1320

gacgattccg ttatatatag aaattccaag ggtttctgcg aagtggcccc tgttggcgaa   1380

ccaggagaaa tgttaatgag aatctttttc cctaaaaaac cagaaacatc ttttcaaggt   1440

tatcttggta atgccaagga aacaaagtcc aaagttgtga gggatgtctt cagacgtggc   1500

gatgcttggt atagatgtgg agatttatta aaagcggacg aatatggatt atggtatttc   1560

cttgatagaa tgggtgatac tttcagatgg aaatctgaaa atgtttccac tactgaagta   1620

gaagatcagt tgacggccag taacaaagaa caatatgcac aagttctagt tgttggtatt   1680

aaagtaccta aatatgaagg tagagctggt tttgcagtta ttaaactaac tgacaactct   1740

cttgacatca ctgcaaagac caaattatta aatgattcct tgagccggtt aaatctaccg   1800

tcttatgcta tgcccctatt tgttaaattt gttgatgaaa ttaaaatgac agataacctc   1860

ataaaatttt ga                                                       1872
```

```
<210> SEQ ID NO 89
<211> LENGTH: 623
<212> TYPE: PRT
<213> ORGANISM: Saccharomyces cerevisiae

<400> SEQUENCE: 89

Met Ser Pro Ile Gln Val Val Val Phe Ala Leu Ser Arg Ile Phe Leu
 1               5                  10                  15

Leu Leu Phe Arg Leu Ile Lys Leu Ile Ile Thr Pro Ile Gln Lys Ser
            20                  25                  30

Leu Gly Tyr Leu Phe Gly Asn Tyr Phe Asp Glu Leu Asp Arg Lys Tyr
        35                  40                  45

Arg Tyr Lys Glu Asp Trp Tyr Ile Ile Pro Tyr Phe Leu Lys Ser Val
    50                  55                  60

Phe Cys Tyr Ile Ile Asp Val Arg Arg His Arg Phe Gln Asn Trp Tyr
65                  70                  75                  80

Leu Phe Ile Lys Gln Val Gln Gln Asn Gly Asp His Leu Ala Ile Ser
                85                  90                  95

Tyr Thr Arg Pro Met Ala Glu Lys Gly Glu Phe Gln Leu Glu Thr Phe
            100                 105                 110

Thr Tyr Ile Glu Thr Tyr Asn Ile Val Leu Arg Leu Ser His Ile Leu
        115                 120                 125

His Phe Asp Tyr Asn Val Gln Ala Gly Asp Tyr Val Ala Ile Asp Cys
    130                 135                 140

Thr Asn Lys Pro Leu Phe Val Phe Leu Trp Leu Ser Leu Trp Asn Ile
145                 150                 155                 160

Gly Ala Ile Pro Ala Phe Leu Asn Tyr Asn Thr Lys Gly Thr Pro Leu
                165                 170                 175

Val His Ser Leu Lys Ile Ser Asn Ile Thr Gln Val Phe Ile Asp Pro
            180                 185                 190

Asp Ala Ser Asn Pro Ile Arg Glu Ser Glu Glu Glu Ile Lys Asn Ala
        195                 200                 205

Leu Pro Asp Val Lys Leu Asn Tyr Leu Glu Glu Gln Asp Leu Met His
    210                 215                 220

Glu Leu Leu Asn Ser Gln Ser Pro Glu Phe Leu Gln Gln Asp Asn Val
225                 230                 235                 240

Arg Thr Pro Leu Gly Leu Thr Asp Phe Lys Pro Ser Met Leu Ile Tyr
                245                 250                 255
```

-continued

```
Thr Ser Gly Thr Thr Gly Leu Pro Lys Ser Ala Ile Met Ser Trp Arg
            260                 265                 270

Lys Ser Ser Val Gly Cys Gln Val Phe Gly His Val Leu His Met Thr
        275                 280                 285

Asn Glu Ser Thr Val Phe Thr Ala Met Pro Leu Phe His Ser Thr Ala
    290                 295                 300

Ala Leu Leu Gly Ala Cys Ala Ile Leu Ser His Gly Gly Cys Leu Ala
305                 310                 315                 320

Leu Ser His Lys Phe Ser Ala Ser Thr Phe Trp Lys Gln Val Tyr Leu
                325                 330                 335

Thr Gly Ala Thr His Ile Gln Tyr Val Gly Glu Val Cys Arg Tyr Leu
            340                 345                 350

Leu His Thr Pro Ile Ser Lys Tyr Glu Lys Met His Lys Val Lys Val
        355                 360                 365

Ala Tyr Gly Asn Gly Leu Arg Pro Asp Ile Trp Gln Asp Phe Arg Lys
    370                 375                 380

Arg Phe Asn Ile Glu Val Ile Gly Glu Phe Tyr Ala Ala Thr Glu Ala
385                 390                 395                 400

Pro Phe Ala Thr Thr Thr Phe Gln Lys Gly Asp Phe Gly Ile Gly Ala
                405                 410                 415

Cys Arg Asn Tyr Gly Thr Ile Ile Gln Trp Phe Leu Ser Phe Gln Gln
            420                 425                 430

Thr Leu Val Arg Met Asp Pro Asn Asp Asp Ser Val Ile Tyr Arg Asn
        435                 440                 445

Ser Lys Gly Phe Cys Glu Val Ala Pro Val Gly Glu Pro Gly Glu Met
    450                 455                 460

Leu Met Arg Ile Phe Phe Pro Lys Lys Pro Glu Thr Ser Phe Gln Gly
465                 470                 475                 480

Tyr Leu Gly Asn Ala Lys Glu Thr Lys Ser Lys Val Val Arg Asp Val
                485                 490                 495

Phe Arg Arg Gly Asp Ala Trp Tyr Arg Cys Gly Asp Leu Leu Lys Ala
            500                 505                 510

Asp Glu Tyr Gly Leu Trp Tyr Phe Leu Asp Arg Met Gly Asp Thr Phe
        515                 520                 525

Arg Trp Lys Ser Glu Asn Val Ser Thr Thr Glu Val Glu Asp Gln Leu
    530                 535                 540

Thr Ala Ser Asn Lys Glu Gln Tyr Ala Gln Val Leu Val Val Gly Ile
545                 550                 555                 560

Lys Val Pro Lys Tyr Glu Gly Arg Ala Gly Phe Ala Val Ile Lys Leu
                565                 570                 575

Thr Asp Asn Ser Leu Asp Ile Thr Ala Lys Thr Lys Leu Leu Asn Asp
            580                 585                 590

Ser Leu Ser Arg Leu Asn Leu Pro Ser Tyr Ala Met Pro Leu Phe Val
        595                 600                 605

Lys Phe Val Asp Glu Ile Lys Met Thr Asp Asn Leu Ile Lys Phe
    610                 615                 620
```

<210> SEQ ID NO 90
<211> LENGTH: 1794
<212> TYPE: DNA
<213> ORGANISM: Mycobacterium tuberculosis

<400> SEQUENCE: 90

```
gtgtccgatt actacggcgg cgcacacaca acggtcaggc tgatcgacct ggcaactcgg     60
```

-continued

```
atgccgcgag tgttggcgga cacgccggtg attgtgcgtg gggcaatgac cgggctgctg    120
gcccggccga attccaaggc gtcgatcggc acggtgttcc aggaccgggc cgctcgctac    180
ggtgaccgag tcttcctgaa attcggcgat cagcagctga cctaccgcga cgctaacgcc    240
accgccaacc ggtacgccgc ggtgttggcc gcccgcggcg tcggccccgg cgacgtcgtt    300
ggcatcatgt tgcgtaactc acccagcaca gtcttggcga tgctggccac ggtcaagtgc    360
ggcgctatcg ccggcatgct caactaccac cagcgcggcg aggtgttggc gcacagcctg    420
ggtctgctgg acgcgaaggt actgatcgca gagtccgact tggtcagcgc cgtcgccgaa    480
tgcggcgcct cgcgcggccg ggtagcgggc gacgtgctga ccgtcgagga cgtggagcga    540
ttcgccacaa cggcgcccgc caccaacccg gcgtcggcgt cggcggtgca agccaaagac    600
accgcgttct acatcttcac ctcgggcacc accggatttc ccaaggccag tgtcatgacg    660
catcatcggt ggctgcgggc gctggccgtc ttcggaggga tggggctgcg gctgaagggt    720
tccgacacgc tctacagctg cctgccgctg taccacaaca acgcgttaac ggtcgcggtg    780
tcgtcggtga tcaattctgg ggcgaccctg gcgctgggta agtcgttttc ggcgtcgcgg    840
ttctgggatg aggtgattgc caaccgggcg acggcgttcg tctacatcgg cgaaatctgc    900
cgttatctgc tcaaccagcc ggccaagccg accgaccgtg cccaccaggt gcgggtgatc    960
tgcggtaacg ggctgcggcc ggagatctgg gatgagttca ccacccgctt cggggtcgcg   1020
cgggtgtgcg agttctacgc cgccagcgaa ggcaactcgg cctttatcaa catcttcaac   1080
gtgcccagga ccgccggggt atcgccgatg ccgcttgcct ttgtggaata cgacctggac   1140
accggcgatc cgctgcggga tgcgagcggg cgagtgcgtc gggtacccga cggtgaaccc   1200
ggcctgttgc ttagccgggt caaccggctg cagccgttcg acggctacac cgacccggtt   1260
gccagcgaaa agaagttggt gcgcaacgct tttcgagatg gcgactgttg gttcaacacc   1320
ggtgacgtga tgagcccgca gggcatgggc catgccgcct tcgtcgatcg gctgggcgac   1380
accttccgct ggaagggcga gaatgtcgcc accactcagg tcgaagcggc actggcctcc   1440
gaccagaccg tcgaggagtg cacggtctac ggcgtccaga ttccgcgcac cggcgggcgc   1500
gccggaatgg ccgcgatcac actgcgcgct ggcgccgaat tcgacggcca ggcgctggcc   1560
cgaacggttt acggtcactt gcccggctat gcacttccgc tctttgttcg ggtagtgggg   1620
tcgctggcgc acaccacgac gttcaagagt cgcaaggtgg agttgcgcaa ccaggcctat   1680
ggcgccgaca tcgaggatcc gctgtacgta ctggccggcc cggacgaagg atatgtgccg   1740
tactacgccg aataccctga ggaggtttcg ctcggaaggc gaccgcaggg ctag         1794
```

<210> SEQ ID NO 91
<211> LENGTH: 597
<212> TYPE: PRT
<213> ORGANISM: Mycobacterium tuberculosis

<400> SEQUENCE: 91

```
Met Ser Asp Tyr Tyr Gly Gly Ala His Thr Thr Val Arg Leu Ile Asp
 1               5                  10                  15

Leu Ala Thr Arg Met Pro Arg Val Leu Ala Asp Thr Pro Val Ile Val
            20                  25                  30

Arg Gly Ala Met Thr Gly Leu Leu Ala Arg Pro Asn Ser Lys Ala Ser
        35                  40                  45

Ile Gly Thr Val Phe Gln Asp Arg Ala Ala Arg Tyr Gly Asp Arg Val
    50                  55                  60

Phe Leu Lys Phe Gly Asp Gln Gln Leu Thr Tyr Arg Asp Ala Asn Ala
```

-continued

```
65                  70                  75                  80

Thr Ala Asn Arg Tyr Ala Ala Val Leu Ala Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205

Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
        355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Arg Val Pro Asp Gly Glu Pro
385                 390                 395                 400

Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
        435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
                485                 490                 495
```

-continued

```
Thr Gly Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
            580                 585                 590

Arg Arg Pro Gln Gly
        595


<210> SEQ ID NO 92
<211> LENGTH: 646
<212> TYPE: PRT
<213> ORGANISM: Mus musculus

<400> SEQUENCE: 92

Met Arg Ala Pro Gly Ala Gly Thr Ala Ser Val Ala Ser Leu Ala Leu
 1               5                  10                  15

Leu Trp Phe Leu Gly Leu Pro Trp Thr Trp Ser Ala Ala Ala Ala Phe
            20                  25                  30

Cys Val Tyr Val Gly Gly Gly Gly Trp Arg Phe Leu Arg Ile Val Cys
        35                  40                  45

Lys Thr Ala Arg Arg Asp Leu Phe Gly Leu Ser Val Leu Ile Arg Val
    50                  55                  60

Arg Leu Glu Leu Arg Arg His Arg Arg Ala Gly Asp Thr Ile Pro Cys
65                  70                  75                  80

Ile Phe Gln Ala Val Ala Arg Arg Gln Pro Glu Arg Leu Ala Leu Val
                85                  90                  95

Asp Ala Ser Ser Gly Ile Cys Trp Thr Phe Ala Gln Leu Asp Thr Tyr
            100                 105                 110

Ser Asn Ala Val Ala Asn Leu Phe Arg Gln Leu Gly Phe Ala Pro Gly
        115                 120                 125

Asp Val Val Ala Val Phe Leu Glu Gly Arg Pro Glu Phe Val Gly Leu
    130                 135                 140

Trp Leu Gly Leu Ala Lys Ala Gly Val Val Ala Ala Leu Leu Asn Val
145                 150                 155                 160

Asn Leu Arg Arg Glu Pro Leu Ala Phe Cys Leu Gly Thr Ser Ala Ala
                165                 170                 175

Lys Ala Leu Ile Tyr Gly Gly Glu Met Ala Ala Ala Val Ala Glu Val
            180                 185                 190

Ser Glu Gln Leu Gly Lys Ser Leu Leu Lys Phe Cys Ser Gly Asp Leu
        195                 200                 205

Gly Pro Glu Ser Ile Leu Pro Asp Thr Gln Leu Leu Asp Pro Met Leu
    210                 215                 220

Ala Glu Ala Pro Thr Thr Pro Leu Ala Gln Ala Pro Gly Lys Gly Met
225                 230                 235                 240

Asp Asp Arg Leu Phe Tyr Ile Tyr Thr Ser Gly Thr Thr Gly Leu Pro
                245                 250                 255

Lys Ala Ala Ile Val Val His Ser Arg Tyr Tyr Arg Ile Ala Ala Phe
```

-continued

```
            260                 265                 270

Gly His His Ser Tyr Ser Met Arg Ala Ala Asp Val Leu Tyr Asp Cys
        275                 280                 285

Leu Pro Leu Tyr His Ser Ala Gly Asn Ile Met Gly Val Gly Gln Cys
    290                 295                 300

Val Ile Tyr Gly Leu Thr Val Val Leu Arg Lys Lys Phe Ser Ala Ser
305                 310                 315                 320

Arg Phe Trp Asp Asp Cys Val Lys Tyr Asn Cys Thr Val Val Gln Tyr
                325                 330                 335

Ile Gly Glu Ile Cys Arg Tyr Leu Leu Arg Gln Pro Val Arg Asp Val
            340                 345                 350

Glu Gln Arg His Arg Val Arg Leu Ala Val Gly Asn Gly Leu Arg Pro
        355                 360                 365

Ala Ile Trp Glu Glu Phe Thr Gln Arg Phe Gly Val Pro Gln Ile Gly
    370                 375                 380

Glu Phe Tyr Gly Ala Thr Glu Cys Asn Cys Ser Ile Ala Asn Met Asp
385                 390                 395                 400

Gly Lys Val Gly Ser Cys Gly Phe Asn Ser Arg Ile Leu Thr His Val
                405                 410                 415

Tyr Pro Ile Arg Leu Val Lys Val Asn Glu Asp Thr Met Glu Pro Leu
            420                 425                 430

Arg Asp Ser Glu Gly Leu Cys Ile Pro Cys Gln Pro Gly Glu Pro Gly
        435                 440                 445

Leu Leu Val Gly Gln Ile Asn Gln Gln Asp Pro Leu Arg Arg Phe Asp
    450                 455                 460

Gly Tyr Val Ser Asp Ser Ala Thr Asn Lys Lys Ile Ala His Ser Val
465                 470                 475                 480

Phe Arg Lys Gly Asp Ser Ala Tyr Leu Ser Gly Asp Val Leu Val Met
                485                 490                 495

Asp Glu Leu Gly Tyr Met Tyr Phe Arg Asp Arg Ser Gly Asp Thr Phe
            500                 505                 510

Arg Trp Arg Gly Glu Asn Val Ser Thr Thr Glu Val Glu Ala Val Leu
        515                 520                 525

Ser Arg Leu Leu Gly Gln Thr Asp Val Ala Val Tyr Gly Val Ala Val
    530                 535                 540

Pro Gly Val Glu Gly Lys Ala Gly Met Ala Ala Ile Ala Asp Pro His
545                 550                 555                 560

Ser Gln Leu Asp Pro Asn Ser Met Tyr Gln Glu Leu Gln Lys Val Leu
                565                 570                 575

Ala Ser Tyr Ala Arg Pro Ile Phe Leu Arg Leu Leu Pro Gln Val Asp
            580                 585                 590

Thr Thr Gly Thr Phe Lys Ile Gln Lys Thr Arg Leu Gln Arg Glu Gly
        595                 600                 605

Phe Asp Pro Arg Gln Thr Ser Asp Arg Leu Phe Phe Leu Asp Leu Lys
    610                 615                 620

Gln Gly Arg Tyr Leu Pro Leu Asp Glu Arg Val His Ala Arg Ile Cys
625                 630                 635                 640

Ala Gly Asp Phe Ser Leu
                645
```

<210> SEQ ID NO 93
<211> LENGTH: 620
<212> TYPE: PRT
<213> ORGANISM: Mus musculus -continued

```
<220> FEATURE:
<221> NAME/KEY: VARIANT
<222> LOCATION: (1)...(620)
<223> OTHER INFORMATION: Xaa = Any Amino Acid

<400> SEQUENCE: 93

Met Leu Pro Val Leu Tyr Thr Gly Leu Ala Gly Leu Leu Leu Leu Pro
 1               5                  10                  15

Leu Leu Leu Thr Cys Cys Cys Pro Tyr Leu Leu Gln Asp Val Arg Tyr
            20                  25                  30

Phe Leu Arg Leu Ala Asn Met Ala Arg Arg Val Arg Ser Tyr Arg Gln
        35                  40                  45

Arg Arg Pro Val Arg Thr Ile Leu Arg Ala Phe Leu Glu Gln Ala Arg
    50                  55                  60

Lys Thr Pro His Lys Pro Phe Leu Leu Phe Arg Asp Glu Thr Leu Thr
65                  70                  75                  80

Tyr Ala Gln Val Asp Arg Arg Ser Asn Gln Val Ala Arg Ala Leu His
                85                  90                  95

Asp Gln Leu Gly Leu Arg Gln Gly Asp Cys Val Ala Leu Phe Met Gly
            100                 105                 110

Asn Glu Pro Ala Tyr Val Trp Ile Trp Leu Gly Leu Leu Lys Leu Gly
        115                 120                 125

Cys Pro Met Ala Cys Leu Asn Tyr Asn Ile Arg Ala Lys Ser Leu Leu
    130                 135                 140

His Cys Phe Gln Cys Cys Gly Ala Lys Val Leu Leu Ala Ser Pro Asp
145                 150                 155                 160

Leu Gln Glu Ala Val Glu Glu Val Leu Pro Thr Leu Lys Lys Asp Ala
                165                 170                 175

Val Ser Val Phe Tyr Val Ser Arg Thr Ser Asn Thr Asn Gly Val Asp
            180                 185                 190

Thr Ile Leu Asp Lys Val Asp Gly Val Ser Ala Glu Pro Thr Pro Glu
        195                 200                 205

Ser Trp Arg Ser Glu Val Thr Phe Thr Thr Pro Ala Val Tyr Ile Tyr
    210                 215                 220

Thr Ser Gly Thr Thr Gly Leu Pro Lys Ala Ala Thr Ile Asn His His
225                 230                 235                 240

Arg Leu Arg Tyr Gly Thr Gly Leu Ala Met Ser Ser Gly Ile Thr Ala
                245                 250                 255

Gln Asp Val Ile Tyr Thr Thr Met Pro Leu Tyr His Ser Ala Ala Leu
            260                 265                 270

Met Ile Gly Leu His Gly Cys Ile Val Val Gly Ala Xaa Xaa Xaa Leu
        275                 280                 285

Cys Asp Lys Phe Ser Ala Ser Gln Phe Trp Asp Asp Cys Arg Lys Tyr
    290                 295                 300

Asn Val Thr Val Ile Gln Tyr Ile Gly Glu Leu Leu Arg Tyr Leu Cys
305                 310                 315                 320

Asn Thr Pro Gln Lys Pro Asn Asp Arg Asp His Lys Val Lys Lys Ala
                325                 330                 335

Leu Gly Asn Gly Leu Arg Gly Asp Val Trp Arg Glu Phe Ile Lys Arg
            340                 345                 350

Phe Gly Asp Ile His Val Tyr Glu Phe Tyr Ala Ser Thr Glu Gly Asn
        355                 360                 365

Ile Gly Phe Val Asn Tyr Pro Arg Lys Ile Gly Ala Val Gly Arg Ala
    370                 375                 380
```

-continued

```
Asn Tyr Leu Gln Arg Lys Val Ala Arg Tyr Glu Leu Ile Lys Tyr Asp
385                 390                 395                 400

Val Glu Lys Asp Glu Pro Val Arg Asp Ala Asn Gly Tyr Cys Ile Lys
                405                 410                 415

Val Pro Lys Gly Glu Val Gly Leu Leu Val Cys Lys Ile Thr Gln Leu
            420                 425                 430

Thr Pro Phe Ile Gly Tyr Ala Gly Gly Lys Thr Gln Thr Glu Lys Lys
        435                 440                 445

Lys Leu Arg Asp Val Phe Lys Lys Gly Asp Ile Tyr Phe Asn Ser Gly
    450                 455                 460

Asp Leu Leu Met Ile Asp Arg Glu Asn Phe Val Tyr Phe His Asp Arg
465                 470                 475                 480

Val Gly Asp Thr Phe Arg Trp Lys Gly Glu Asn Val Ala Thr Thr Glu
                485                 490                 495

Val Ala Asp Ile Val Gly Leu Val Asp Phe Val Glu Glu Val Asn Val
            500                 505                 510

Tyr Gly Val Pro Val Pro Gly His Glu Gly Arg Ile Gly Met Ala Ser
        515                 520                 525

Leu Lys Ile Lys Glu Asn Tyr Glu Phe Asn Gly Lys Lys Leu Phe Gln
    530                 535                 540

His Ile Ala Glu Tyr Leu Pro Ser Tyr Ala Arg Pro Arg Phe Leu Arg
545                 550                 555                 560

Ile Gln Asp Thr Ile Glu Ile Thr Gly Thr Phe Lys His Arg Lys Val
                565                 570                 575

Thr Leu Met Glu Glu Gly Phe Asn Pro Thr Val Ile Lys Asp Thr Leu
            580                 585                 590

Tyr Phe Met Asp Asp Ala Glu Lys Thr Phe Val Pro Met Thr Glu Asn
        595                 600                 605

Ile Tyr Asn Ala Ile Ile Asp Lys Thr Leu Lys Leu
    610                 615                 620


<210> SEQ ID NO 94
<211> LENGTH: 613
<212> TYPE: PRT
<213> ORGANISM: Mus musculus

<400> SEQUENCE: 94

Ala Ala Asp Pro Glu Ser Ser Glu Ser Gly Cys Ser Leu Ala Trp Arg
 1               5                  10                  15

Leu Ala Tyr Leu Ala Arg Glu Gln Pro Thr His Thr Phe Leu Ile His
            20                  25                  30

Gly Ala Gln Arg Phe Ser Tyr Ala Glu Ala Glu Arg Glu Ser Asn Arg
        35                  40                  45

Ile Ala Arg Ala Phe Leu Arg Ala Arg Gly Trp Thr Gly Gly Arg Arg
    50                  55                  60

Gly Ser Gly Arg Gly Ser Thr Glu Glu Gly Ala Arg Val Ala Pro Pro
65                  70                  75                  80

Ala Gly Asp Ala Ala Ala Arg Gly Thr Thr Ala Pro Pro Leu Ala Pro
                85                  90                  95

Gly Ala Thr Val Ala Leu Leu Leu Pro Ala Gly Pro Asp Phe Leu Trp
            100                 105                 110

Ile Trp Phe Gly Leu Ala Lys Ala Gly Leu Arg Thr Ala Phe Val Pro
        115                 120                 125

Thr Ala Leu Arg Arg Gly Pro Leu Leu His Cys Leu Arg Ser Cys Gly
    130                 135                 140
```

-continued

```
Ala Ser Ala Leu Val Leu Ala Thr Glu Phe Leu Glu Ser Leu Glu Pro
145                 150                 155                 160

Asp Leu Pro Ala Leu Arg Ala Met Gly Leu His Leu Trp Ala Thr Gly
                165                 170                 175

Pro Glu Thr Asn Val Ala Gly Ile Ser Asn Leu Leu Ser Glu Ala Ala
            180                 185                 190

Asp Gln Val Asp Glu Pro Val Pro Gly Tyr Leu Ser Ala Pro Gln Asn
        195                 200                 205

Ile Met Asp Thr Cys Leu Tyr Ile Phe Thr Ser Gly Thr Thr Gly Leu
    210                 215                 220

Pro Lys Ala Ala Arg Ile Ser His Leu Lys Val Leu Gln Cys Gln Gly
225                 230                 235                 240

Phe Tyr His Leu Cys Gly Val His Gln Glu Asp Val Ile Tyr Leu Ala
                245                 250                 255

Leu Pro Leu Tyr His Met Ser Gly Ser Leu Leu Gly Ile Val Gly Cys
            260                 265                 270

Leu Gly Ile Gly Ala Thr Val Val Leu Lys Pro Lys Phe Ser Ala Ser
        275                 280                 285

Gln Phe Trp Asp Asp Cys Gln Lys His Arg Val Thr Val Phe Gln Tyr
    290                 295                 300

Ile Gly Glu Leu Cys Arg Tyr Leu Val Asn Gln Pro Pro Ser Lys Ala
305                 310                 315                 320

Glu Phe Asp His Lys Val Arg Leu Ala Val Gly Ser Gly Leu Arg Pro
                325                 330                 335

Asp Thr Trp Glu Arg Phe Leu Arg Arg Phe Gly Pro Leu Gln Ile Leu
            340                 345                 350

Glu Thr Tyr Gly Met Thr Glu Gly Asn Val Ala Thr Phe Asn Tyr Thr
        355                 360                 365

Gly Arg Gln Gly Ala Val Gly Arg Ala Ser Trp Leu Tyr Lys His Ile
    370                 375                 380

Phe Pro Phe Ser Leu Ile Arg Tyr Asp Val Met Thr Gly Glu Pro Ile
385                 390                 395                 400

Arg Asn Ala Gln Gly His Cys Met Thr Thr Ser Pro Gly Glu Pro Gly
                405                 410                 415

Leu Leu Val Ala Pro Val Ser Gln Gln Ser Pro Phe Leu Gly Tyr Ala
            420                 425                 430

Gly Ala Pro Glu Leu Ala Lys Asp Lys Leu Leu Lys Asp Val Phe Trp
        435                 440                 445

Ser Gly Asp Val Phe Phe Asn Thr Gly Asp Leu Leu Val Cys Asp Glu
    450                 455                 460

Gln Gly Phe Leu His Phe His Asp Arg Thr Gly Asp Thr Ile Arg Trp
465                 470                 475                 480

Lys Gly Glu Asn Val Ala Thr Thr Glu Val Ala Glu Val Leu Glu Thr
                485                 490                 495

Leu Asp Phe Leu Gln Glu Val Asn Ile Tyr Gly Val Thr Val Pro Gly
            500                 505                 510

His Glu Gly Arg Ala Gly Met Ala Ala Leu Ala Leu Arg Pro Pro Gln
        515                 520                 525

Ala Leu Asn Leu Val Gln Leu Tyr Ser His Val Ser Glu Asn Leu Pro
    530                 535                 540

Pro Tyr Ala Arg Pro Arg Phe Leu Arg Leu Gln Glu Ser Leu Ala Thr
545                 550                 555                 560
```

-continued

```
Thr Glu Thr Phe Lys Gln Gln Lys Val Arg Met Ala Asn Glu Gly Phe
                565                 570                 575

Asp Pro Ser Val Leu Ser Asp Pro Leu Tyr Val Leu Asp Gln Asp Ile
            580                 585                 590

Gly Ala Tyr Leu Pro Leu Thr Pro Ala Arg Tyr Ser Ala Leu Leu Ser
        595                 600                 605

Gly Asp Leu Arg Ile
    610


<210> SEQ ID NO 95
<211> LENGTH: 506
<212> TYPE: PRT
<213> ORGANISM: Mus musculus

<400> SEQUENCE: 95

His Ala Ser Ala His Ala Ser Gly Met Ala Lys Leu Gly Val Glu Ala
 1               5                  10                  15

Ala Leu Ile Asn Thr Asn Leu Arg Arg Asp Ala Leu Arg His Cys Leu
            20                  25                  30

Asp Thr Ser Lys Ala Arg Ala Leu Ile Phe Gly Ser Glu Met Ala Ser
        35                  40                  45

Ala Ile Cys Glu Ile His Ala Ser Leu Glu Pro Thr Leu Ser Leu Phe
    50                  55                  60

Cys Ser Gly Ser Trp Glu Pro Ser Thr Val Pro Val Ser Thr Glu His
65                  70                  75                  80

Leu Asp Pro Leu Leu Glu Asp Ala Pro Lys His Leu Pro Ser His Pro
                85                  90                  95

Asp Lys Gly Phe Thr Asp Lys Leu Phe Tyr Ile Tyr Thr Ser Gly Thr
            100                 105                 110

Thr Gly Leu Pro Lys Ala Ala Ile Val Val His Ser Arg Tyr Tyr Arg
        115                 120                 125

Met Ala Ser Leu Val Tyr Tyr Gly Phe Arg Met Arg Pro Asp Asp Ile
    130                 135                 140

Val Tyr Asp Cys Leu Pro Leu Tyr His Ser Ser Arg Lys His Arg Gly
145                 150                 155                 160

Asp Trp Gln Cys Leu Leu His Gly Met Thr Val Val Ile Arg Lys Lys
                165                 170                 175

Phe Ser Ala Ser Arg Phe Trp Asp Asp Cys Ile Lys Tyr Asn Cys Thr
            180                 185                 190

Val Val Gln Tyr Ile Gly Glu Leu Cys Arg Tyr Leu Leu Asn Gln Pro
        195                 200                 205

Pro Arg Glu Ala Glu Ser Arg His Lys Val Arg Met Ala Leu Gly Asn
    210                 215                 220

Gly Leu Arg Gln Ser Ile Trp Thr Asp Phe Ser Ser Arg Phe His Ile
225                 230                 235                 240

Pro Gln Val Ala Glu Phe Tyr Gly Ala Thr Glu Cys Asn Cys Ser Leu
                245                 250                 255

Gly Asn Phe Asp Ser Arg Val Gly Ala Cys Gly Phe Asn Ser Arg Ile
            260                 265                 270

Leu Ser Phe Val Tyr Pro Ile Arg Leu Val Arg Val Asn Glu Asp Thr
        275                 280                 285

Met Glu Leu Ile Arg Gly Pro Asp Gly Val Cys Ile Pro Cys Gln Pro
    290                 295                 300

Gly Gln Pro Gly Gln Leu Val Gly Arg Ile Ile Gln Gln Asp Pro Leu
305                 310                 315                 320
```

-continued

```
Arg Arg Phe Asp Gly Tyr Leu Asn Gln Gly Ala Asn Asn Lys Lys Ile
            325                 330                 335

Ala Asn Asp Val Phe Lys Lys Gly Asp Gln Ala Tyr Leu Thr Gly Asp
            340                 345                 350

Val Leu Val Met Asp Glu Leu Gly Tyr Leu Tyr Phe Arg Asp Arg Thr
        355                 360                 365

Gly Asp Thr Phe Arg Trp Lys Gly Glu Asn Val Ser Thr Thr Glu Val
    370                 375                 380

Glu Gly Thr Leu Ser Arg Leu Leu His Met Ala Asp Val Ala Val Tyr
385                 390                 395                 400

Gly Val Glu Val Pro Gly Thr Glu Gly Arg Ala Gly Met Ala Ala Val
                405                 410                 415

Ala Ser Pro Ile Ser Asn Cys Asp Leu Glu Ser Phe Ala Gln Thr Leu
            420                 425                 430

Lys Lys Glu Leu Pro Leu Tyr Ala Arg Pro Ile Phe Leu Arg Phe Leu
        435                 440                 445

Pro Glu Leu His Lys Thr Gly Thr Phe Lys Phe Gln Lys Thr Glu Leu
    450                 455                 460

Arg Lys Glu Gly Phe Asp Pro Ser Val Val Lys Asp Pro Leu Phe Tyr
465                 470                 475                 480

Leu Asp Ala Arg Lys Gly Cys Tyr Val Ala Leu Asp Gln Glu Ala Tyr
                485                 490                 495

Thr Arg Ile Gln Ala Gly Glu Glu Lys Leu
            500                 505


<210> SEQ ID NO 96
<211> LENGTH: 662
<212> TYPE: PRT
<213> ORGANISM: Mus musculus

<400> SEQUENCE: 96

Met Ala Leu Ala Leu Arg Trp Phe Leu Gly Asp Pro Thr Cys Leu Val
 1               5                  10                  15

Leu Leu Gly Leu Ala Leu Leu Gly Arg Pro Trp Ile Ser Ser Trp Met
            20                  25                  30

Pro His Trp Leu Ser Leu Val Gly Ala Ala Leu Thr Leu Phe Leu Leu
        35                  40                  45

Pro Leu Gln Pro Pro Pro Gly Leu Arg Trp Leu His Lys Asp Val Ala
    50                  55                  60

Phe Thr Phe Lys Met Leu Phe Tyr Gly Leu Lys Phe Arg Arg Arg Leu
65                  70                  75                  80

Asn Lys His Pro Pro Glu Thr Phe Val Asp Ala Leu Glu Arg Gln Ala
                85                  90                  95

Leu Ala Trp Pro Asp Arg Val Ala Leu Val Cys Thr Gly Ser Glu Gly
            100                 105                 110

Ser Ser Ile Thr Asn Ser Gln Leu Asp Ala Arg Ser Cys Gln Ala Ala
        115                 120                 125

Trp Val Leu Lys Ala Lys Leu Lys Asp Ala Val Ile Gln Asn Thr Arg
    130                 135                 140

Asp Ala Ala Ala Ile Leu Val Leu Pro Ser Lys Thr Ile Ser Ala Leu
145                 150                 155                 160

Ser Val Phe Leu Gly Leu Ala Lys Leu Gly Cys Pro Val Ala Trp Ile
                165                 170                 175

Asn Pro His Ser Arg Gly Met Pro Leu Leu His Ser Val Arg Ser Ser
```

-continued

```
            180                 185                 190

Gly Ala Ser Val Leu Ile Val Asp Pro Asp Leu Gln Glu Asn Leu Glu
        195                 200                 205

Glu Val Leu Pro Lys Leu Leu Ala Glu Asn Ile His Cys Phe Tyr Leu
    210                 215                 220

Gly His Ser Ser Pro Thr Pro Gly Val Glu Ala Leu Gly Ala Ser Leu
225                 230                 235                 240

Asp Ala Ala Pro Ser Asp Pro Val Pro Ala Ser Leu Arg Ala Thr Ile
                245                 250                 255

Lys Trp Lys Ser Pro Ala Ile Phe Ile Phe Thr Ser Gly Thr Thr Gly
            260                 265                 270

Leu Pro Lys Pro Ala Ile Leu Ser His Glu Arg Val Ile Gln Val Ser
        275                 280                 285

Asn Val Leu Ser Phe Cys Gly Cys Arg Ala Asp Asp Val Val Tyr Asp
    290                 295                 300

Val Leu Pro Leu Tyr His Thr Ile Gly Leu Val Leu Gly Phe Leu Gly
305                 310                 315                 320

Cys Leu Gln Val Gly Ala Thr Cys Val Leu Ala Pro Lys Phe Ser Ala
                325                 330                 335

Ser Arg Phe Trp Ala Glu Cys Arg Gln His Gly Val Thr Val Ile Leu
            340                 345                 350

Tyr Val Gly Glu Ile Leu Arg Tyr Leu Cys Asn Val Pro Glu Gln Pro
        355                 360                 365

Glu Asp Lys Ile His Thr Val Arg Leu Ala Met Gly Thr Gly Leu Arg
    370                 375                 380

Ala Asn Val Trp Lys Asn Phe Gln Gln Arg Phe Gly Pro Ile Arg Ile
385                 390                 395                 400

Trp Glu Phe Tyr Gly Ser Thr Glu Gly Asn Val Gly Leu Met Asn Tyr
                405                 410                 415

Val Gly His Cys Gly Ala Val Gly Arg Thr Ser Cys Ile Leu Arg Met
            420                 425                 430

Leu Thr Pro Phe Glu Leu Val Gln Phe Asp Ile Glu Thr Ala Glu Pro
        435                 440                 445

Leu Arg Asp Lys Gln Gly Phe Cys Ile Pro Val Glu Pro Gly Lys Pro
    450                 455                 460

Gly Leu Leu Leu Thr Lys Val Arg Lys Asn Gln Pro Phe Leu Gly Tyr
465                 470                 475                 480

Arg Gly Ser Gln Ala Glu Ser Asn Arg Lys Leu Val Ala Asn Val Arg
                485                 490                 495

Arg Val Gly Asp Leu Tyr Phe Asn Thr Gly Asp Val Leu Thr Leu Asp
            500                 505                 510

Gln Glu Gly Phe Phe Tyr Phe Gln Asp Arg Leu Gly Asp Thr Phe Arg
        515                 520                 525

Trp Lys Gly Glu Asn Val Ser Thr Gly Glu Val Glu Cys Val Leu Ser
    530                 535                 540

Ser Leu Asp Phe Leu Glu Glu Val Asn Val Tyr Gly Val Pro Val Pro
545                 550                 555                 560

Gly Cys Glu Gly Lys Val Gly Met Ala Ala Val Lys Leu Ala Pro Gly
                565                 570                 575

Lys Thr Phe Asp Gly Gln Lys Leu Tyr Gln His Val Arg Ser Trp Leu
            580                 585                 590

Pro Ala Tyr Ala Thr Pro His Phe Ile Arg Ile Gln Asp Ser Leu Glu
        595                 600                 605
```

-continued

Ile Thr Asn Thr Tyr Lys Leu Val Lys Ser Arg Leu Val Arg Glu Gly
    610                 615                 620

Phe Asp Val Gly Ile Ile Ala Asp Pro Leu Tyr Ile Leu Asp Asn Lys
625                 630                 635                 640

Ala Gln Thr Phe Arg Ser Leu Met Pro Asp Val Tyr Gln Ala Val Cys
                645                 650                 655

Glu Gly Thr Trp Asn Leu
            660

<210> SEQ ID NO 97
<211> LENGTH: 650
<212> TYPE: PRT
<213> ORGANISM: Caenorhabditis elegans

<400> SEQUENCE: 97

Met Lys Leu Glu Glu Leu Val Thr Val Met Leu Leu Thr Val Ala Val
 1               5                  10                  15

Ile Ala Gln Asn Leu Pro Ile Gly Val Ile Leu Ala Gly Val Leu Ile
            20                  25                  30

Leu Tyr Ile Thr Val Val His Gly Asp Phe Ile Tyr Arg Ser Tyr Leu
        35                  40                  45

Thr Leu Asn Arg Asp Leu Thr Gly Leu Ala Leu Ile Ile Glu Val Lys
    50                  55                  60

Ile Asp Leu Trp Trp Arg Leu His Gln Asn Lys Gly Ile His Glu Leu
65                  70                  75                  80

Phe Leu Asp Ile Val Lys Lys Asn Pro Asn Lys Pro Ala Met Ile Asp
                85                  90                  95

Ile Glu Thr Asn Thr Thr Glu Thr Tyr Ala Glu Phe Asn Ala His Cys
            100                 105                 110

Asn Arg Tyr Ala Asn Tyr Phe Gln Gly Leu Gly Tyr Arg Ser Gly Asp
        115                 120                 125

Val Val Ala Leu Tyr Met Glu Asn Ser Val Glu Phe Val Ala Ala Trp
    130                 135                 140

Met Gly Leu Ala Lys Ile Gly Val Val Thr Ala Trp Ile Asn Ser Asn
145                 150                 155                 160

Leu Lys Arg Glu Gln Leu Val His Cys Ile Thr Ala Ser Lys Thr Lys
                165                 170                 175

Ala Ile Ile Thr Ser Val Thr Leu Gln Asn Ile Met Leu Asp Ala Ile
            180                 185                 190

Asp Gln Lys Leu Phe Asp Val Glu Gly Ile Glu Val Tyr Ser Val Gly
        195                 200                 205

Glu Pro Lys Lys Asn Ser Gly Phe Lys Asn Leu Lys Lys Lys Leu Asp
    210                 215                 220

Ala Gln Ile Thr Thr Glu Pro Lys Thr Leu Asp Ile Val Asp Phe Lys
225                 230                 235                 240

Ser Ile Leu Cys Phe Ile Tyr Thr Ser Gly Thr Thr Gly Met Pro Lys
                245                 250                 255

Ala Ala Val Met Lys His Phe Arg Tyr Tyr Ser Ile Ala Val Gly Ala
            260                 265                 270

Ala Lys Ser Phe Gly Ile Arg Pro Ser Asp Arg Met Tyr Val Ser Met
        275                 280                 285

Pro Ile Tyr His Thr Ala Ala Gly Ile Leu Gly Val Gly Gln Ala Leu
    290                 295                 300

Leu Gly Gly Ser Ser Cys Val Ile Arg Lys Lys Phe Ser Ala Ser Asn

-continued

```
305                 310                 315                 320

Phe Trp Arg Asp Cys Val Lys Tyr Asp Cys Thr Val Ser Gln Tyr Ile
                325                 330                 335

Gly Glu Ile Cys Arg Tyr Leu Leu Ala Gln Pro Val Val Glu Glu Glu
            340                 345                 350

Ser Arg His Arg Met Arg Leu Leu Val Gly Asn Gly Leu Arg Ala Glu
        355                 360                 365

Ile Trp Gln Pro Phe Val Asp Arg Phe Arg Val Arg Ile Gly Glu Leu
    370                 375                 380

Tyr Gly Ser Thr Glu Gly Thr Ser Ser Leu Val Asn Ile Asp Gly His
385                 390                 395                 400

Val Gly Ala Cys Gly Phe Leu Pro Ile Ser Pro Leu Thr Lys Lys Met
                405                 410                 415

His Pro Val Arg Leu Ile Lys Val Asp Asp Val Thr Gly Glu Ala Ile
            420                 425                 430

Arg Thr Ser Asp Gly Leu Cys Ile Ala Cys Asn Pro Gly Glu Ser Gly
        435                 440                 445

Ala Met Val Ser Thr Ile Arg Lys Asn Asn Pro Leu Leu Gln Phe Glu
    450                 455                 460

Gly Tyr Leu Asn Lys Lys Glu Thr Asn Lys Lys Ile Ile Arg Asp Val
465                 470                 475                 480

Phe Ala Lys Gly Asp Ser Cys Phe Leu Thr Gly Asp Leu Leu His Trp
                485                 490                 495

Asp Arg Leu Gly Tyr Val Tyr Phe Lys Asp Arg Thr Gly Asp Thr Phe
            500                 505                 510

Arg Trp Lys Gly Glu Asn Val Ser Thr Thr Glu Val Glu Ala Ile Leu
        515                 520                 525

His Pro Ile Thr Gly Leu Ser Asp Ala Thr Val Tyr Gly Val Glu Val
    530                 535                 540

Pro Gln Arg Glu Gly Arg Val Gly Met Ala Ser Val Val Arg Val Val
545                 550                 555                 560

Ser His Glu Glu Asp Glu Thr Gln Phe Val His Arg Val Gly Ala Arg
                565                 570                 575

Leu Ala Ser Ser Leu Thr Ser Tyr Ala Ile Pro Gln Phe Met Arg Ile
            580                 585                 590

Cys Gln Asp Val Glu Lys Thr Gly Thr Phe Lys Leu Val Lys Thr Asn
        595                 600                 605

Leu Gln Arg Leu Gly Ile Met Asp Ala Pro Ser Asp Ser Ile Tyr Ile
    610                 615                 620

Tyr Asn Ser Glu Asn Arg Asn Phe Val Pro Phe Asp Asn Asp Leu Arg
625                 630                 635                 640

Cys Lys Val Ser Leu Gly Ser Tyr Pro Phe
                645                 650


<210> SEQ ID NO 98
<211> LENGTH: 623
<212> TYPE: PRT
<213> ORGANISM: Saccharomyces cerevisiae

<400> SEQUENCE: 98

Met Ser Pro Ile Gln Val Val Val Phe Ala Leu Ser Arg Ile Phe Leu
 1              5                   10                  15

Leu Leu Phe Arg Leu Ile Lys Leu Ile Ile Thr Pro Ile Gln Lys Ser
            20                  25                  30
```

-continued

```
Leu Gly Tyr Leu Phe Gly Asn Tyr Phe Asp Glu Leu Asp Arg Lys Tyr
        35                  40                  45

Arg Tyr Lys Glu Asp Trp Tyr Ile Ile Pro Tyr Phe Leu Lys Ser Val
    50                  55                  60

Phe Cys Tyr Ile Ile Asp Val Arg Arg His Arg Phe Gln Asn Trp Tyr
65                  70                  75                  80

Leu Phe Ile Lys Gln Val Gln Gln Asn Gly Asp His Leu Ala Ile Ser
                85                  90                  95

Tyr Thr Arg Pro Met Ala Glu Lys Gly Glu Phe Gln Leu Glu Thr Phe
            100                 105                 110

Thr Tyr Ile Glu Thr Tyr Asn Ile Val Leu Arg Leu Ser His Ile Leu
        115                 120                 125

His Phe Asp Tyr Asn Val Gln Ala Gly Asp Tyr Val Ala Ile Asp Cys
    130                 135                 140

Thr Asn Lys Pro Leu Phe Val Phe Leu Trp Leu Ser Leu Trp Asn Ile
145                 150                 155                 160

Gly Ala Ile Pro Ala Phe Leu Asn Tyr Asn Thr Lys Gly Thr Pro Leu
                165                 170                 175

Val His Ser Leu Lys Ile Ser Asn Ile Thr Gln Val Phe Ile Asp Pro
            180                 185                 190

Asp Ala Ser Asn Pro Ile Arg Glu Ser Glu Glu Glu Ile Lys Asn Ala
        195                 200                 205

Leu Pro Asp Val Lys Leu Asn Tyr Leu Glu Glu Gln Asp Leu Met His
    210                 215                 220

Glu Leu Leu Asn Ser Gln Ser Pro Glu Phe Leu Gln Gln Asp Asn Val
225                 230                 235                 240

Arg Thr Pro Leu Gly Leu Thr Asp Phe Lys Pro Ser Met Leu Ile Tyr
                245                 250                 255

Thr Ser Gly Thr Thr Gly Leu Pro Lys Ser Ala Ile Met Ser Trp Arg
            260                 265                 270

Lys Ser Ser Val Gly Cys Gln Val Phe Gly His Val Leu His Met Thr
        275                 280                 285

Asn Glu Ser Thr Val Phe Thr Ala Met Pro Leu Phe His Ser Thr Ala
    290                 295                 300

Ala Leu Leu Gly Ala Cys Ala Ile Leu Ser His Gly Gly Cys Leu Ala
305                 310                 315                 320

Leu Ser His Lys Phe Ser Ala Ser Thr Phe Trp Lys Gln Val Tyr Leu
                325                 330                 335

Thr Gly Ala Thr His Ile Gln Tyr Val Gly Glu Val Cys Arg Tyr Leu
            340                 345                 350

Leu His Thr Pro Ile Ser Lys Tyr Glu Lys Met His Lys Val Lys Val
        355                 360                 365

Ala Tyr Gly Asn Gly Leu Arg Pro Asp Ile Trp Gln Asp Phe Arg Lys
    370                 375                 380

Arg Phe Asn Ile Glu Val Ile Gly Glu Phe Tyr Ala Ala Thr Glu Ala
385                 390                 395                 400

Pro Phe Ala Thr Thr Thr Phe Gln Lys Gly Asp Phe Gly Ile Gly Ala
                405                 410                 415

Cys Arg Asn Tyr Gly Thr Ile Ile Gln Trp Phe Leu Ser Phe Gln Gln
            420                 425                 430

Thr Leu Val Arg Met Asp Pro Asn Asp Asp Ser Val Ile Tyr Arg Asn
        435                 440                 445

Ser Lys Gly Phe Cys Glu Val Ala Pro Val Gly Glu Pro Gly Glu Met
```

-continued

```
    450                 455                 460

Leu Met Arg Ile Phe Phe Pro Lys Lys Pro Glu Thr Ser Phe Gln Gly
465                 470                 475                 480

Tyr Leu Gly Asn Ala Lys Glu Thr Lys Ser Lys Val Val Arg Asp Val
                485                 490                 495

Phe Arg Arg Gly Asp Ala Trp Tyr Arg Cys Gly Asp Leu Leu Lys Ala
            500                 505                 510

Asp Glu Tyr Gly Leu Trp Tyr Phe Leu Asp Arg Met Gly Asp Thr Phe
        515                 520                 525

Arg Trp Lys Ser Glu Asn Val Ser Thr Thr Glu Val Glu Asp Gln Leu
    530                 535                 540

Thr Ala Ser Asn Lys Glu Gln Tyr Ala Gln Val Leu Val Val Gly Ile
545                 550                 555                 560

Lys Val Pro Lys Tyr Glu Gly Arg Ala Gly Phe Ala Val Ile Lys Leu
                565                 570                 575

Thr Asp Asn Ser Leu Asp Ile Thr Ala Lys Thr Lys Leu Leu Asn Asp
            580                 585                 590

Ser Leu Ser Arg Leu Asn Leu Pro Ser Tyr Ala Met Pro Leu Phe Val
        595                 600                 605

Lys Phe Val Asp Glu Ile Lys Met Thr Asp Asn Leu Ile Lys Phe
    610                 615                 620


<210> SEQ ID NO 99
<211> LENGTH: 597
<212> TYPE: PRT
<213> ORGANISM: Mycobacterium tuberculosis

<400> SEQUENCE: 99

Met Ser Asp Tyr Tyr Gly Gly Ala His Thr Thr Val Arg Leu Ile Asp
 1               5                  10                  15

Leu Ala Thr Arg Met Pro Arg Val Leu Ala Asp Thr Pro Val Ile Val
            20                  25                  30

Arg Gly Ala Met Thr Gly Leu Leu Ala Arg Pro Asn Ser Lys Ala Ser
        35                  40                  45

Ile Gly Thr Val Phe Gln Asp Arg Ala Ala Arg Tyr Gly Asp Arg Val
    50                  55                  60

Phe Leu Lys Phe Gly Asp Gln Gln Leu Thr Tyr Arg Asp Ala Asn Ala
65                  70                  75                  80

Thr Ala Asn Arg Tyr Ala Ala Val Leu Ala Ala Arg Gly Val Gly Pro
                85                  90                  95

Gly Asp Val Val Gly Ile Met Leu Arg Asn Ser Pro Ser Thr Val Leu
            100                 105                 110

Ala Met Leu Ala Thr Val Lys Cys Gly Ala Ile Ala Gly Met Leu Asn
        115                 120                 125

Tyr His Gln Arg Gly Glu Val Leu Ala His Ser Leu Gly Leu Leu Asp
    130                 135                 140

Ala Lys Val Leu Ile Ala Glu Ser Asp Leu Val Ser Ala Val Ala Glu
145                 150                 155                 160

Cys Gly Ala Ser Arg Gly Arg Val Ala Gly Asp Val Leu Thr Val Glu
                165                 170                 175

Asp Val Glu Arg Phe Ala Thr Thr Ala Pro Ala Thr Asn Pro Ala Ser
            180                 185                 190

Ala Ser Ala Val Gln Ala Lys Asp Thr Ala Phe Tyr Ile Phe Thr Ser
        195                 200                 205
```

-continued

```
Gly Thr Thr Gly Phe Pro Lys Ala Ser Val Met Thr His His Arg Trp
    210                 215                 220

Leu Arg Ala Leu Ala Val Phe Gly Gly Met Gly Leu Arg Leu Lys Gly
225                 230                 235                 240

Ser Asp Thr Leu Tyr Ser Cys Leu Pro Leu Tyr His Asn Asn Ala Leu
                245                 250                 255

Thr Val Ala Val Ser Ser Val Ile Asn Ser Gly Ala Thr Leu Ala Leu
            260                 265                 270

Gly Lys Ser Phe Ser Ala Ser Arg Phe Trp Asp Glu Val Ile Ala Asn
        275                 280                 285

Arg Ala Thr Ala Phe Val Tyr Ile Gly Glu Ile Cys Arg Tyr Leu Leu
    290                 295                 300

Asn Gln Pro Ala Lys Pro Thr Asp Arg Ala His Gln Val Arg Val Ile
305                 310                 315                 320

Cys Gly Asn Gly Leu Arg Pro Glu Ile Trp Asp Glu Phe Thr Thr Arg
                325                 330                 335

Phe Gly Val Ala Arg Val Cys Glu Phe Tyr Ala Ala Ser Glu Gly Asn
            340                 345                 350

Ser Ala Phe Ile Asn Ile Phe Asn Val Pro Arg Thr Ala Gly Val Ser
        355                 360                 365

Pro Met Pro Leu Ala Phe Val Glu Tyr Asp Leu Asp Thr Gly Asp Pro
    370                 375                 380

Leu Arg Asp Ala Ser Gly Arg Val Arg Arg Val Pro Asp Gly Glu Pro
385                 390                 395                 400

Gly Leu Leu Leu Ser Arg Val Asn Arg Leu Gln Pro Phe Asp Gly Tyr
                405                 410                 415

Thr Asp Pro Val Ala Ser Glu Lys Lys Leu Val Arg Asn Ala Phe Arg
            420                 425                 430

Asp Gly Asp Cys Trp Phe Asn Thr Gly Asp Val Met Ser Pro Gln Gly
        435                 440                 445

Met Gly His Ala Ala Phe Val Asp Arg Leu Gly Asp Thr Phe Arg Trp
    450                 455                 460

Lys Gly Glu Asn Val Ala Thr Thr Gln Val Glu Ala Ala Leu Ala Ser
465                 470                 475                 480

Asp Gln Thr Val Glu Glu Cys Thr Val Tyr Gly Val Gln Ile Pro Arg
                485                 490                 495

Thr Gly Gly Arg Ala Gly Met Ala Ala Ile Thr Leu Arg Ala Gly Ala
            500                 505                 510

Glu Phe Asp Gly Gln Ala Leu Ala Arg Thr Val Tyr Gly His Leu Pro
        515                 520                 525

Gly Tyr Ala Leu Pro Leu Phe Val Arg Val Val Gly Ser Leu Ala His
    530                 535                 540

Thr Thr Thr Phe Lys Ser Arg Lys Val Glu Leu Arg Asn Gln Ala Tyr
545                 550                 555                 560

Gly Ala Asp Ile Glu Asp Pro Leu Tyr Val Leu Ala Gly Pro Asp Glu
                565                 570                 575

Gly Tyr Val Pro Tyr Tyr Ala Glu Tyr Pro Glu Glu Val Ser Leu Gly
            580                 585                 590

Arg Arg Pro Gln Gly
        595
```

<210> SEQ ID NO 100
<211> LENGTH: 304
<212> TYPE: PRT

-continued

<213> ORGANISM: concensus FATP signature sequence

<400> SEQUENCE: 100

```
Tyr Ile Tyr Thr Ser Gly Thr Thr Gly Leu Pro Lys Ala Ala Ile Ile
 1               5                  10                  15

Val His Ser Arg Tyr Tyr Arg Gly Ala Ala Leu His Ser Gly Arg Met
            20                  25                  30

Arg Pro Asp Val Val Tyr Asp Cys Leu Pro Leu Tyr His Ser Ala Ala
        35                  40                  45

Leu Ile Leu Gly Ile Gly Gln Cys Leu Leu His Gly Ala Thr Val Val
    50                  55                  60

Leu Arg Lys Lys Phe Ser Ala Ser Arg Phe Trp Asp Asp Cys Val Lys
65                  70                  75                  80

Tyr Asn Val Thr Val Ile Gln Tyr Ile Gly Glu Leu Cys Arg Tyr Leu
                85                  90                  95

Leu Asn Gln Pro Pro Arg Pro Ala Glu Arg Arg His Lys Val Arg Leu
            100                 105                 110

Ala Val Gly Asn Gly Leu Arg Pro Asp Ile Trp Glu Glu Phe Val Ser
        115                 120                 125

Arg Phe Gly Ile Pro Gln Ile Gly Glu Phe Tyr Gly Ala Thr Glu Gly
    130                 135                 140

Asn Cys Ser Leu Met Asn Tyr Asp Gly Lys Val Gly Ala Cys Gly Ser
145                 150                 155                 160

Arg Ile Leu Lys Lys Val Tyr Pro Ile Arg Leu Val Lys Val Asp Glu
                165                 170                 175

Asp Thr Gly Glu Pro Ile Arg Asp Ala Gln Gly Leu Cys Ile Pro Cys
            180                 185                 190

Gln Pro Gly Glu Pro Gly Leu Leu Val Gly Arg Ile Asn Gln Gln Asp
        195                 200                 205

Pro Phe Arg Gly Phe Gly Tyr Gly Ser Glu Gly Ala Thr Asn Lys Lys
    210                 215                 220

Ile Ala Arg Asp Val Phe Lys Lys Gly Asp Val Ala Phe Asn Thr Gly
225                 230                 235                 240

Asp Val Leu Val Met Asp Glu Leu Gly Tyr Leu Tyr Phe Arg Asp Arg
                245                 250                 255

Thr Gly Asp Thr Phe Arg Trp Lys Gly Glu Asn Val Ser Thr Thr Glu
            260                 265                 270

Val Glu Gly Val Leu Ser Arg Leu Asp Phe Val Ala Glu Val Asn Val
        275                 280                 285

Tyr Gly Val Thr Val Pro Gly His Glu Gly Arg Ala Gly Met Ala Ala
    290                 295                 300
```

<210> SEQ ID NO 101
<211> LENGTH: 2166
<212> TYPE: DNA
<213> ORGANISM: Homo sapiens
<220> FEATURE:
<221> NAME/KEY: CDS
<222> LOCATION: (19)...(2124)

<400> SEQUENCE: 101

```
cgacccacgc gtccgggg atg ttt gcg agc ggc tgg aac cag acg gtg ccg       51
                    Met Phe Ala Ser Gly Trp Asn Gln Thr Val Pro
                     1               5                  10

ata gag gaa gcg ggc tcc atg gct gcc ctc ctg ctg ctg ccc ctg ctg       99
Ile Glu Glu Ala Gly Ser Met Ala Ala Leu Leu Leu Leu Pro Leu Leu
            15                  20                  25
```

-continued

```
ctg ttg cta ccg ctg ctg ctg ctg ctg aag cta cac ctc tgg ccg cag      147
Leu Leu Leu Pro Leu Leu Leu Leu Leu Lys Leu His Leu Trp Pro Gln
        30                  35                  40

ttg cgc tgg ctt ccg gcg gac ttg gcc ttt gcg gtg cga gct ctg tgc      195
Leu Arg Trp Leu Pro Ala Asp Leu Ala Phe Ala Val Arg Ala Leu Cys
    45                  50                  55

tgc aaa agg gct ctt cga gct cgc gcc ctg gcc gcg gct gcc gcc gac      243
Cys Lys Arg Ala Leu Arg Ala Arg Ala Leu Ala Ala Ala Ala Ala Asp
 60                  65                  70                  75

ccg gaa ggt ccc gag ggg ggc tgc agc ctg gcc tgg cgc ctc gcg gaa      291
Pro Glu Gly Pro Glu Gly Gly Cys Ser Leu Ala Trp Arg Leu Ala Glu
                 80                  85                  90

ctg gcc cag cag cgc gcc gcg cac acc ttt ctc att cac ggc tcg cgg      339
Leu Ala Gln Gln Arg Ala Ala His Thr Phe Leu Ile His Gly Ser Arg
             95                 100                 105

cgc ttt agc tac tca gag gcg gag cgc gag agt aac agg gct gca cgc      387
Arg Phe Ser Tyr Ser Glu Ala Glu Arg Glu Ser Asn Arg Ala Ala Arg
        110                 115                 120

gcc ttc cta cgt gcg cta ggc tgg gac tgg gga ccc gac ggc ggc gac      435
Ala Phe Leu Arg Ala Leu Gly Trp Asp Trp Gly Pro Asp Gly Gly Asp
    125                 130                 135

agc ggc gag ggg agc gct gga gaa ggc gag cgg gca gcg ccg gga gcc      483
Ser Gly Glu Gly Ser Ala Gly Glu Gly Glu Arg Ala Ala Pro Gly Ala
140                 145                 150                 155

gga gat gca gcg gcc gga agc ggc gcg gag ttt gcc gga ggg gac ggt      531
Gly Asp Ala Ala Ala Gly Ser Gly Ala Glu Phe Ala Gly Gly Asp Gly
                160                 165                 170

gcc gcc aga ggt gga gga gag ccc gcc gcc cct ctg tca cct gga gca      579
Ala Ala Arg Gly Gly Gly Glu Pro Ala Ala Pro Leu Ser Pro Gly Ala
            175                 180                 185

act gtg gcg ctg ctc ctc ccc gct ggc cca gag ttt ctg tgg ctc tgg      627
Thr Val Ala Leu Leu Leu Pro Ala Gly Pro Glu Phe Leu Trp Leu Trp
        190                 195                 200

ttc ggg ctg gcc aag gcc ggc ctg cgc act gcc ttt gtg ccc acc gcc      675
Phe Gly Leu Ala Lys Ala Gly Leu Arg Thr Ala Phe Val Pro Thr Ala
    205                 210                 215

ctg cgc cgg ggc ccc ctg ctg cac tgc ctc cgc agc tgc ggc gcg cgc      723
Leu Arg Arg Gly Pro Leu Leu His Cys Leu Arg Ser Cys Gly Ala Arg
220                 225                 230                 235

gcg ctg gtg ctg gcg cca gag ttt ctg gag tcc ctg gag ccg gac ctg      771
Ala Leu Val Leu Ala Pro Glu Phe Leu Glu Ser Leu Glu Pro Asp Leu
                240                 245                 250

ccc gcc ctg aga gcc atg ggg ctc cac ctg tgg gct gca ggc cca gga      819
Pro Ala Leu Arg Ala Met Gly Leu His Leu Trp Ala Ala Gly Pro Gly
            255                 260                 265

acc cac cct gct gga att agc gat ttg ctg gct gaa gtg tcc gct gaa      867
Thr His Pro Ala Gly Ile Ser Asp Leu Leu Ala Glu Val Ser Ala Glu
        270                 275                 280

gtg gat ggg cca gtg cca gga tac ctc tct tcc ccc cag agc ata aca      915
Val Asp Gly Pro Val Pro Gly Tyr Leu Ser Ser Pro Gln Ser Ile Thr
    285                 290                 295

gac acg tgc ctg tac atc ttc acc tct ggc acc acg ggc ctc ccc aag      963
Asp Thr Cys Leu Tyr Ile Phe Thr Ser Gly Thr Thr Gly Leu Pro Lys
300                 305                 310                 315

gct gct cgg atc agt cat ctg aag atc ctg caa tgc cag ggc ttc tat     1011
Ala Ala Arg Ile Ser His Leu Lys Ile Leu Gln Cys Gln Gly Phe Tyr
                320                 325                 330

cag ctg tgt ggt gtc cac cag gaa gat gtg atc tac ctc gcc ctc cca     1059
Gln Leu Cys Gly Val His Gln Glu Asp Val Ile Tyr Leu Ala Leu Pro
```

-continued

```
            335                 340                 345

ctc tac cac atg tcc ggt tcc ctg ctg ggc atc gtg ggc tgc atg ggc      1107
Leu Tyr His Met Ser Gly Ser Leu Leu Gly Ile Val Gly Cys Met Gly
        350                 355                 360

att ggg gcc aca gtg gtg ctg aaa tcc aag ttc tcg gct ggt cag ttc      1155
Ile Gly Ala Thr Val Val Leu Lys Ser Lys Phe Ser Ala Gly Gln Phe
    365                 370                 375

tgg gaa gat tgc cag cag cac agg gtg acg gtg ttc cag tac att ggg      1203
Trp Glu Asp Cys Gln Gln His Arg Val Thr Val Phe Gln Tyr Ile Gly
380                 385                 390                 395

gag ctg tgc cga tac ctt gtc aac cag ccc ccg agc aag gca gaa cgt      1251
Glu Leu Cys Arg Tyr Leu Val Asn Gln Pro Pro Ser Lys Ala Glu Arg
                400                 405                 410

ggc cat aag gtc cgg ctg gca gtg ggc agc ggg ctg cgc cca gat acc      1299
Gly His Lys Val Arg Leu Ala Val Gly Ser Gly Leu Arg Pro Asp Thr
            415                 420                 425

tgg gag cgt ttt gtg cgg cgc ttc ggg ccc ctg cag gtg ctg gag aca      1347
Trp Glu Arg Phe Val Arg Arg Phe Gly Pro Leu Gln Val Leu Glu Thr
        430                 435                 440

tat gga ctg aca gag ggc aac gtg gcc acc atc aac tac aca gga cag      1395
Tyr Gly Leu Thr Glu Gly Asn Val Ala Thr Ile Asn Tyr Thr Gly Gln
    445                 450                 455

cgg ggc gct gtg ggg cgt gct tcc tgg ctt tac aag cat atc ttc ccc      1443
Arg Gly Ala Val Gly Arg Ala Ser Trp Leu Tyr Lys His Ile Phe Pro
460                 465                 470                 475

ttc tcc ttg att cgc tat gat gtc acc aca gga gag cca att cgg gac      1491
Phe Ser Leu Ile Arg Tyr Asp Val Thr Thr Gly Glu Pro Ile Arg Asp
                480                 485                 490

ccc cag ggg cac tgt atg gcc aca tct cca ggt gag cca ggg ctg ctg      1539
Pro Gln Gly His Cys Met Ala Thr Ser Pro Gly Glu Pro Gly Leu Leu
            495                 500                 505

gtg gcc ccg gta agc cag cag tcc cca ttc ctg ggc tat gct ggc ggg      1587
Val Ala Pro Val Ser Gln Gln Ser Pro Phe Leu Gly Tyr Ala Gly Gly
        510                 515                 520

cca gag ctg gcc cag ggg aag ttg cta aag gat gtc ttc cgg cct ggg      1635
Pro Glu Leu Ala Gln Gly Lys Leu Leu Lys Asp Val Phe Arg Pro Gly
    525                 530                 535

gat gtt ttc ttc aac act ggg gac ctg ctg gtc tgc gat gac caa ggt      1683
Asp Val Phe Phe Asn Thr Gly Asp Leu Leu Val Cys Asp Asp Gln Gly
540                 545                 550                 555

ttt ctc cgc ttc cat gat cgt act gga gac acc ttc agg tgg aag ggg      1731
Phe Leu Arg Phe His Asp Arg Thr Gly Asp Thr Phe Arg Trp Lys Gly
                560                 565                 570

gag aat gtg gcc aca acc gag gtg gca gag gtc ttc gag gcc cta gat      1779
Glu Asn Val Ala Thr Thr Glu Val Ala Glu Val Phe Glu Ala Leu Asp
            575                 580                 585

ttt ctt cag gag gtg aac gtc tat gga gtc act gtg cca ggg cat gaa      1827
Phe Leu Gln Glu Val Asn Val Tyr Gly Val Thr Val Pro Gly His Glu
        590                 595                 600

ggc agg gct gga atg gca gcc cta gtt ctg cgt ccc ccc cac gct ttg      1875
Gly Arg Ala Gly Met Ala Ala Leu Val Leu Arg Pro Pro His Ala Leu
    605                 610                 615

gac ctt atg cag ctc tac acc cac gtg tct gag aac ttg cca cct tat      1923
Asp Leu Met Gln Leu Tyr Thr His Val Ser Glu Asn Leu Pro Pro Tyr
620                 625                 630                 635

gcc cgg ccc cga ttc ctc agg ctc cag gag tct ttg gcc acc aca gag      1971
Ala Arg Pro Arg Phe Leu Arg Leu Gln Glu Ser Leu Ala Thr Thr Glu
                640                 645                 650

acc ttc aaa cag cag aaa gtt cgg atg gca aat gag ggc ttc gac ccc      2019
```

-continued

```
Thr Phe Lys Gln Gln Lys Val Arg Met Ala Asn Glu Gly Phe Asp Pro
            655                 660                 665

agc acc ctg tct gac cca ctg tac gtt ctg gac cag gct gta ggt gcc     2067
Ser Thr Leu Ser Asp Pro Leu Tyr Val Leu Asp Gln Ala Val Gly Ala
        670                 675                 680

tac ctg ccc ctc aca act gcc cgg tac agc gcc ctc ctg gca gga aac     2115
Tyr Leu Pro Leu Thr Thr Ala Arg Tyr Ser Ala Leu Leu Ala Gly Asn
    685                 690                 695

ctt cga atc tgagaacttc cacacctgag gcacctgaga gaggaactct             2164
Leu Arg Ile
700

gt                                                                  2166


<210> SEQ ID NO 102
<211> LENGTH: 702
<212> TYPE: PRT
<213> ORGANISM: Homo sapiens

<400> SEQUENCE: 102

Met Phe Ala Ser Gly Trp Asn Gln Thr Val Pro Ile Glu Glu Ala Gly
 1               5                  10                  15

Ser Met Ala Ala Leu Leu Leu Leu Pro Leu Leu Leu Leu Leu Pro Leu
            20                  25                  30

Leu Leu Leu Leu Lys Leu His Leu Trp Pro Gln Leu Arg Trp Leu Pro
        35                  40                  45

Ala Asp Leu Ala Phe Ala Val Arg Ala Leu Cys Cys Lys Arg Ala Leu
    50                  55                  60

Arg Ala Arg Ala Leu Ala Ala Ala Ala Ala Asp Pro Glu Gly Pro Glu
65                  70                  75                  80

Gly Gly Cys Ser Leu Ala Trp Arg Leu Ala Glu Leu Ala Gln Gln Arg
                85                  90                  95

Ala Ala His Thr Phe Leu Ile His Gly Ser Arg Arg Phe Ser Tyr Ser
            100                 105                 110

Glu Ala Glu Arg Glu Ser Asn Arg Ala Ala Arg Ala Phe Leu Arg Ala
        115                 120                 125

Leu Gly Trp Asp Trp Gly Pro Asp Gly Gly Asp Ser Gly Glu Gly Ser
    130                 135                 140

Ala Gly Glu Gly Glu Arg Ala Ala Pro Gly Ala Gly Asp Ala Ala Ala
145                 150                 155                 160

Gly Ser Gly Ala Glu Phe Ala Gly Gly Asp Gly Ala Ala Arg Gly Gly
                165                 170                 175

Gly Glu Pro Ala Ala Pro Leu Ser Pro Gly Ala Thr Val Ala Leu Leu
            180                 185                 190

Leu Pro Ala Gly Pro Glu Phe Leu Trp Leu Trp Phe Gly Leu Ala Lys
        195                 200                 205

Ala Gly Leu Arg Thr Ala Phe Val Pro Thr Ala Leu Arg Arg Gly Pro
    210                 215                 220

Leu Leu His Cys Leu Arg Ser Cys Gly Ala Arg Ala Leu Val Leu Ala
225                 230                 235                 240

Pro Glu Phe Leu Glu Ser Leu Glu Pro Asp Leu Pro Ala Leu Arg Ala
                245                 250                 255

Met Gly Leu His Leu Trp Ala Ala Gly Pro Gly Thr His Pro Ala Gly
            260                 265                 270

Ile Ser Asp Leu Leu Ala Glu Val Ser Ala Glu Val Asp Gly Pro Val
        275                 280                 285
```

-continued

```
Pro Gly Tyr Leu Ser Ser Pro Gln Ser Ile Thr Asp Thr Cys Leu Tyr
    290                 295                 300

Ile Phe Thr Ser Gly Thr Thr Gly Leu Pro Lys Ala Ala Arg Ile Ser
305                 310                 315                 320

His Leu Lys Ile Leu Gln Cys Gln Gly Phe Tyr Gln Leu Cys Gly Val
                325                 330                 335

His Gln Glu Asp Val Ile Tyr Leu Ala Leu Pro Leu Tyr His Met Ser
            340                 345                 350

Gly Ser Leu Leu Gly Ile Val Gly Cys Met Gly Ile Gly Ala Thr Val
        355                 360                 365

Val Leu Lys Ser Lys Phe Ser Ala Gly Gln Phe Trp Glu Asp Cys Gln
    370                 375                 380

Gln His Arg Val Thr Val Phe Gln Tyr Ile Gly Glu Leu Cys Arg Tyr
385                 390                 395                 400

Leu Val Asn Gln Pro Pro Ser Lys Ala Glu Arg Gly His Lys Val Arg
                405                 410                 415

Leu Ala Val Gly Ser Gly Leu Arg Pro Asp Thr Trp Glu Arg Phe Val
            420                 425                 430

Arg Arg Phe Gly Pro Leu Gln Val Leu Glu Thr Tyr Gly Leu Thr Glu
        435                 440                 445

Gly Asn Val Ala Thr Ile Asn Tyr Thr Gly Gln Arg Gly Ala Val Gly
    450                 455                 460

Arg Ala Ser Trp Leu Tyr Lys His Ile Phe Pro Phe Ser Leu Ile Arg
465                 470                 475                 480

Tyr Asp Val Thr Thr Gly Glu Pro Ile Arg Asp Pro Gln Gly His Cys
                485                 490                 495

Met Ala Thr Ser Pro Gly Glu Pro Gly Leu Leu Val Ala Pro Val Ser
            500                 505                 510

Gln Gln Ser Pro Phe Leu Gly Tyr Ala Gly Gly Pro Glu Leu Ala Gln
        515                 520                 525

Gly Lys Leu Leu Lys Asp Val Phe Arg Pro Gly Asp Val Phe Phe Asn
    530                 535                 540

Thr Gly Asp Leu Leu Val Cys Asp Asp Gln Gly Phe Leu Arg Phe His
545                 550                 555                 560

Asp Arg Thr Gly Asp Thr Phe Arg Trp Lys Gly Glu Asn Val Ala Thr
                565                 570                 575

Thr Glu Val Ala Glu Val Phe Glu Ala Leu Asp Phe Leu Gln Glu Val
            580                 585                 590

Asn Val Tyr Gly Val Thr Val Pro Gly His Glu Gly Arg Ala Gly Met
        595                 600                 605

Ala Ala Leu Val Leu Arg Pro Pro His Ala Leu Asp Leu Met Gln Leu
    610                 615                 620

Tyr Thr His Val Ser Glu Asn Leu Pro Pro Tyr Ala Arg Pro Arg Phe
625                 630                 635                 640

Leu Arg Leu Gln Glu Ser Leu Ala Thr Thr Glu Thr Phe Lys Gln Gln
                645                 650                 655

Lys Val Arg Met Ala Asn Glu Gly Phe Asp Pro Ser Thr Leu Ser Asp
            660                 665                 670

Pro Leu Tyr Val Leu Asp Gln Ala Val Gly Ala Tyr Leu Pro Leu Thr
        675                 680                 685

Thr Ala Arg Tyr Ser Ala Leu Leu Ala Gly Asn Leu Arg Ile
    690                 695                 700
```

-continued

```
<210> SEQ ID NO 103
<211> LENGTH: 19
<212> TYPE: DNA
<213> ORGANISM: Artificial Sequence
<220> FEATURE:
<223> OTHER INFORMATION: Oligonucleotide

<400> SEQUENCE: 103

cccccaccag agaggctcc                                                   19


<210> SEQ ID NO 104
<211> LENGTH: 19
<212> TYPE: DNA
<213> ORGANISM: Artificial Sequence
<220> FEATURE:
<223> OTHER INFORMATION: Oligonucleotide

<400> SEQUENCE: 104

ccacccccgg aaagcctgc                                                   19


<210> SEQ ID NO 105
<211> LENGTH: 19
<212> TYPE: DNA
<213> ORGANISM: Artificial Sequence
<220> FEATURE:
<223> OTHER INFORMATION: Oligonucleotide

<400> SEQUENCE: 105

ggagcctctc tggtggggg                                                   19
```

FATTY ACID TRANSPORT PROTEINS

RELATED APPLICATIONS

This application claims the benefit of U.S. Provisional Application No. 60/071,374 entitled "Identification of a Family of Fatty Acid Transporters Conserved From Mycobacterium to Man," by Andreas Stahl, David Hirsch and Harvey F. Lodish, filed on Jan. 15, 1998; U.S. Provisional Application No. 60/093,491 entitled "Fatty Acid Transport Proteins," by Andreas Stahl, David J. Hirsch, Harvey F. Lodish, Ruth E. Gimeno and Louis A. Tartaglia, filed on Jul. 20, 1998; and U.S. Provisional Application No. 60/110,941 entitled "Fatty Acid Transport Proteins," by Andreas Stahl, David J. Hirsch, Harvey F. Lodish, Ruth E. Gimeno and Louis A. Tartaglia, filed on Dec. 4, 1998. The teachings of each of these referenced applications are incorporated herein by reference in their entirety.

GOVERNMENT SUPPORT

The invention was supported, in whole or in part, by National Institutes of Health Grant DK 47618 and National Institutes of Health Grant 5 T32 CA 09541. The United States Government has certain rights in the invention.

BACKGROUND OF THE INVENTION

Long chain fatty acids (LCFAs) are an important source of energy for most organisms. They also function as blood hormones, regulating key metabolic functions such as hepatic glucose production. Although LCFAs can diffuse through the hydrophobic core of the plasma membrane into cells, this nonspecific transport cannot account for the high affinity and specific transport of LCFAs exhibited by cells such as cardiac muscle, hepatocytes, enterocytes, and adipocytes. The molecular mechanisms of LCFA transport remains largely unknown. Identifying these mechanisms can lead to pharmaceuticals that modulate fatty acid uptake by the intestine and by other organs, thereby alleviating certain medical conditions (e.g. obesity).

SUMMARY OF THE INVENTION

Described herein is a diverse family of fatty acid transport proteins (FATPs) which are evolutionarily conserved; these FATPs are plasma membrane proteins which mediate transport of LCFAs across the membranes and into cells. Members of the FATP family described herein are present in a wide variety of organisms, from mycobacteria to humans, and exhibit very different expression patterns in tissues among the organisms. FATP family members are expressed in prokaryotic and eukaryotic organisms and comprise characteristic amino acid domains or sequences which are highly conserved across family members. In addition, the function of the FATP gene family is conserved throughout evolution, as shown by the fact that the *Caenorhabditis* (*C*). *elegans* and mycobacterial FATPs described herein facilitate LCFA uptake when they are overexpressed in COS cells or *Escherichia* (*E.*) *coli,* respectively. FATPs are expressed in a wide variety of tissues, including all tissues which are important to fatty acid metabolism (uptake and processing).

In specific embodiments, FATPs of the present invention are from such diverse organisms as humans (*Homo* (*H.*) *sapiens*), mice, (*Mus* (*M.*) *musculus*), *F. rubripes, C. elegans, Drosophila* (*D.*) *melanogaster, Saccharomyces* (*S.*) *cerevisiae, Aspergillus nidulans, Cochliobolu heterostrophus, Magnaporthe grisea* and Mycobacterium (M.), such as *M. tuberculosis.* As described herein, four novel mouse FATPs, referred to as mmFATP2, mmFATP3, mmFATP4 and mmFATP5, and six human FATPs, referred to as hsFATP1, hsFATP2, hsFATP3, hsFATP4, hsFATP5 and hsFATP6, have been identified. All four novel murine FATPs (mmFATP2–5) and a previously identified murine FATP (renamed herein FATP1) have orthologs in humans (hsFATP1–5); the sixth human FATP (hsFATP6) does not as yet have a mouse ortholog. The expression patterns of these FATPs vary, as described in detail below.

The present invention relates to FATP family members from prokaryotes and eukaryotes, nucleic acids (DNA, RNA) encoding FATPs, and nucleic acids which are useful as probes or primers (e.g., for use in hybridization methods, amplification methods) for example, in methods of detecting FATP-encoding genes, producing FATPs, and purifying or isolating FATP-encoding DNA or RNA. Also the subject of this invention are antibodies (polyclonal or monoclonal) which bind an FATP or FATPs; methods of identifying additional FATP family members (for example, orthologs of those FATPs described herein by amino acid sequence) and variant alleles of known FATP genes; methods of identifying compounds which bind to an FATP, or modulate or alter (enhance or inhibit) FATP function; compounds which modulate or alter FATP function; methods of modulating or altering (enhancing or inhibiting) FATP function and, thus, LCFA uptake into tissues of a mammal (e.g. human) by administering a compound or molecule (a drug or agent) which increases or reduces FATP activity; and methods of targeting compounds to tissues by administering a complex of the compound to be targeted to tissues and a component which is bound by an FATP present on cells of the tissues to which the compound is to be targeted. For example, a complex of a drug to be delivered to the liver and a component which is bound by an FATP present on liver cells (e.g., FATP5) can be administered.

In one embodiment, the present invention relates to modulating or altering (enhancing or inhibiting/reducing) LCFA uptake in the small intestine and, thus, increasing or reducing the number of calories in the form of fats available to an individual. In another embodiment, the present invention relates to inhibiting or reducing LCFA uptake in the small intestine in order to reduce circulating fatty acid levels; that is, LCFA uptake in the small intestine is reduced and, therefore, circulating (blood) levels are not as high as they otherwise would be. FATP4 has been shown to be expressed in epithelial cells of the small intestine and particularly in the brush border layer of the small intestine. FATP2 has also been shown to be expressed at low levels in epithelial cells of the small intestine, particularly in the duodenum. In contrast, FATP1, FATP3, FATP5 and FATP6 were not detected in any of the intestinal tissues. Thus, also described herein are FATPs which are present in the epithelial cell layer of the small intestine where they mediate LCFA uptake. These FATPs, particularly FATP4 and also FATP2, are targets for methods and drugs which block their function or activity and are useful in treating obesity, diabetes and heart disease. The ability of these FATPs to mediate fat uptake can be modulated or altered (enhanced or inhibited), thus modulating fat uptake in the small intestine. This can be done, for example, by administering to an individual, such as a human or other animal, a drug which blocks interaction of LCFAs with FATP4 and/or FATP2 in the small intestine, thus inhibiting LCFA passage into the cells of the small intestine. As a result, fat absorption is reduced and, although the individual has consumed a certain quantity of fat, the LCFAs are not absorbed to the same extent they would have been in the absence of the compound administered.

Thus, one embodiment of this invention is a method of reducing LCFA uptake (absorption) in the small intestine and, as a result, reducing caloric uptake in the form of fat. A further embodiment is a compound (drug) useful in inhibiting or reducing fat absorption in the small intestine. In another embodiment, the invention is a method of reducing circulating fatty acid levels by administering to an individual a compound which blocks interactions of LCFAs with FATP4 and/or FATP2 in the small intestine, thus inhibiting LCFA passage into cells of the small intestine. As a result, fatty acids pass into the circulatory system at a diminished level and/or rate, and circulating fatty acid levels are lower than they would be in the absence of the compound administered. This method is particularly useful for therapy in individuals who are at risk for or have hyperlipidemia. That is, it can be used to prevent the occurrence of elevated levels of lipids in the blood or to treat an individual in whom blood lipid levels are elevated. Also the subject of this invention is a method of identifying compounds which alter FATP function (and thus, in the case of FATP2 and/or FATP4, alter LCFA uptake in the small intestine).

In another embodiment, the present invention relates to a method of modulating or altering (enhancing or inhibiting) the function of FATP6, which is expressed at high levels in the heart. A method of inhibiting FATP6 function is useful, for example, in individuals with heart disease, such as ischemia, since reducing LCFA uptake into heart muscle in an individual who has ischemic heart disease, which may be manifested by, for example, angina or heart attack, can reduce symptoms or reduce the extent of damage caused by the ischemia. In this embodiment, a drug which inhibits FATP6 function is administered to an individual who has had or is having a heart attack, to reduce LCFA uptake by the individual's heart and, as a result, reduce the damage caused by ischemia. In a further embodiment, this invention is a method of targeting a compound, such as a therapeutic drug or an imaging reagent, to heart tissue by administering to an individual (e.g., a human) a complex of the compound and a component (e.g., a LCFA or LCFA-like compound) which is bound by an FATP (e.g., FATP6) present in cells of heart tissue.

In a further embodiment, LCFA uptake by the liver is modulated or altered (enhanced or reduced), in an individual. For example, a drug which inhibits the function of an FATP present in liver (e.g., FATP5) is administered to an individual who is diabetic, in order to reduce LCFA uptake by liver cells and, thus reduce insulin resistance.

The present invention, thus, provides methods which are useful to alter, particularly reduce, LCFA uptake in individuals and, as a result, to alter (particularly reduce), availability of the LCFAs for further metabolism. In a specific embodiment, the present invention provides methods useful to reduce LCFA uptake and, thus, fatty acid metabolism in individuals, with the result that caloric availability from fats is reduced, and circulating fatty acid levels are lower than they otherwise would be. These methods are useful, for example, as a means of weight control in individuals, (e.g., humans) and as a means of preventing elevated serum lipid levels or reducing serum lipid levels in humans. FATPs expressed in the small intestine, such as FATP4, are useful targets to be blocked in treating obesity (e.g., chronic obesity) or to be enhanced in treating conditions in which enhanced LCFA uptake is desired (e.g., malabsorption syndrome or other wasting conditions).

The identification of this evolutionarily conserved fatty acid transporter family will allow a better understanding of the mechanisms whereby LCFAs traverse the lipid bilayer as well as yield insight into the control of energy homeostasis and its dysregulation in diseases such as diabetes and obesity.

BRIEF DESCRIPTION OF THE DRAWINGS

FIGS. 2A–2D: COS cells were cotransfected using the DEAE-dextran method with the mammalian expression vectors pCDNA-CD2 either alone (control; FIG. 2A) or in combination with one of the FATP-containing expression vectors (pCDNA-mmFATP1, FIG. 2B; pCDNA-mmFATP2, FIG. 2C; or pCMV-SPORT2-mmFATP5, FIG. 2D) as described in Materials and Methods for Example 2. COS cells were gated on forward scatter (FSC) and side scatter (SS), and the results shown represent>10,000 cells. Cells exhibiting>300 CD2 fluorescence units (vertical line) representing 15% of all cells were deemed CD2 positive.

FIG. 6 shows a comparison of the FATP signature sequences of mmFATP1 (SEQ ID NO:1), mmFATP5, (SEQ ID NO:2), ceFATPa (SEQ ID NO:3), scFATP (SEQ ID NO:4) and mtFATP (SEQ ID NO:5).

FIG. 7 shows the sequence identity among the FATP family members and VLACs, based on the 360 amino acid signature sequence of FATP from FIG. 1.

FIGS. 8A and 8B are the mmFATP3 DNA sequence (SEQ ID NO:6).

FIG. 9 is the mmFATP3 protein sequence (SEQ ID NO:7).

FIGS. 10A and 10B are the mmFATP4 DNA sequence (SEQ ID NO:8).

FIG. 11 is the mmFATP4 protein sequence (SEQ ID NO:9).

FIGS. 12A and 12B are the mmFATP5 DNA sequence (SEQ ID NO:10).

FIG. 13 is the mmFATP5 protein sequence (SEQ ID NO:11).

FIGS. 14A and 14B are the hsFATP2 DNA sequence (SEQ ID NO:12).

FIG. 15 is the hsFATP2 protein sequence (SEQ ID NO:13).

FIGS. 16A and 16B are the hsFATP3 DNA sequence (SEQ ID NO:14).

FIG. 17 is the hsFATP3 protein sequence (SEQ ID NO:15).

FIGS. 18A and 18B are the hsFATP4 DNA sequence (SEQ ID NO:16).

FIG. 19 is the hsFATP4 protein sequence (SEQ ID NO:17).

FIGS. 20A and 20B are the hsFATP5 DNA sequence (SEQ ID NO:18).

FIG. 21 is the hsFATP5 protein sequence (SEQ ID NO:19).

FIGS. 22A and 22B are the hsFATP6 DNA sequence (SEQ ID NO:20).

FIG. 23 is the hsFATP6 protein sequence (SEQ ID NO:21).

FIGS. 24A and 24B are the mtFATP DNA sequence (SEQ ID NO:22).

FIG. 25 is the mtFATP protein sequence (SEQ ID NO:23).

FIG. 26 shows the DNA sequence (SEQ ID NO:24) and predicted amino acid sequence (SEQ ID NO:25) of human FATP1.

FIG. 27 shows the DNA sequence (SEQ ID NO:26) and predicted amino acid sequence (SEQ ID NO:27) of human FATP4.

FIG. 28B is the amino acid composition of hsFATP1.

FIG. 29B is a listing of the amino acid composition of hsFATP4.

FIGS. 30A and 30B show a comparison of the nucleotide sequence of human FATP1 (SEQ ID NO:28) and the nucleotide sequence of mouse FATP1 (SEQ ID NO:29).

FIGS. 31A and 31B show a comparison of the nucleotide sequence of human FATP4 (SEQ ID NO:30) and the nucleotide sequence of mouse FATP4 (SEQ ID NO:31).

FIG. 32 shows a comparison of the amino acid sequence of human FATP1 (SEQ ID NO:32) and the amino acid sequence of mouse FATP1 (SEQ ID NO:33). Shaded amino acid residues match the concensus sequence exactly FIG. 33 shows a comparison at the amino acid level of human FATP4 (SEQ ID NO:34) and mouse FATP4 (SEQ ID NO:35). Shaded amino acid residues match the concensus sequence exactly.

FIG. 34 shows the nucleotide sequence (SEQ ID NO:36) and predicted amino acid sequence (SEQ ID NO:37) of hsFATP6.

FIG. 35B is a listing of the amino acid composition of hsFATP6.

FIG. 36 shows an alignment of the amino acid sequences of hsFATP1 (SEQ ID NO:38), hsFATP4 (SEQ ID NO:39) and hsFATP6 (SEQ ID NO:40). Shaded amino acid residues match the concensus sequence exactly.

FIG. 39 is an illustration of the amino acid sequences of human FATP4 (SEQ ID NO:41) and mouse FATP4 (SEQ ID NO:42) compared to human FATP1 (SEQ ID NO:43). Shown by underlining are the FATP consensus sequence (236–556 of hsFATP1) and the AMP-binding motif (246–254 of hsFATP1). The human FATPs were cloned by screening libraries with sequences from ESTs (expressed sequence tags). Mouse FATP4 was cloned by PCR using degenerate primers.

FIG. 43A is the nucleotide sequence of the gene encoding mouse FATP4 (SEQ ID NO:44).

FIG. 43B is the amino acid sequence of mouse FATP4 protein (SEQ ID NO:45).

FIGS. 44A, 44B, and 44C are the hsFATP1 DNA sequence (SEQ ID NO:46). Coding region: 175–2115 (1941 nt).

FIG. 45 is the hsFATP1 protein sequence (SEQ ID NO:47).

FIGS. 46A and 46B are the hsFATP2 DNA sequence (SEQ ID NO:48). Coding region: 223–2085 (1863 nt).

FIG. 47 is the hsFATP2 protein sequence (SEQ ID NO:49).

FIG. 48 is the partial DNA sequence of hsFATP3 (SEQ ID NO:50). Coding region: 1–993.

FIG. 49 is the partial protein sequence of hsFATP3 (SEQ ID NO:51).

FIGS. 50A, 50B, and 50C are the hsFATP4 DNA sequence (SEQ ID NO:52). Coding region: 208–2139 (1932 nt).

FIG. 51 is the hsFATP4 protein sequence (SEQ ID NO:53).

FIG. 52 is the hsFATP5 partial DNA sequence (SEQ ID NO:54). Coding region: 1–1062.

FIG. 53 is the hsFATP5 partial protein sequence (SEQ ID NO:55).

FIGS. 54A, 54B, and 54C are the hsFATP6 DNA sequence (SEQ ID NO:56). Coding region: 643–2502 (1860 nt).

FIG. 55 is the hsFATP6 protein sequence (SEQ ID NO:57).

FIGS. 56A, 56B, and 56C are the rnFATP1 DNA sequence (rn=*Rattus norvegicus;* (SEQ ID NO:58). Coding region: 75–2015 (1941 nt).

FIG. 57 is the rnFATP1 protein sequence (SEQ ID NO:59).

FIGS. 58A, 58B, and 58C are the rnFATP2 DNA sequence (SEQ ID NO:60). Coding region: 795–2657 (1863 nt).

FIG. 59 is the rnFATP2 protein sequence (SEQ ID NO:61).

FIGS. 60A and 60B are the rnFATP4 partial DNA sequence (SEQ ID NO:62). Coding region: 1–1218.

FIG. 61 is the rnFATP4 partial DNA sequence (SEQ ID NO:63).

FIGS. 62A, 62B, and 62C are the mmFATP1 DNA sequence (SEQ ID NO:64). Coding region: 1–1944.

FIG. 63 is the mmFATP1 protein sequence (SEQ ID NO:65).

FIGS. 64A and 64B are the mmFATP2 DNA sequence (SEQ ID NO:66). Coding region: 121–1992 (1872 nt).

FIG. 65 is the mmFATP2 protein sequence (SEQ ID NO:67).

FIGS. 66A and 66B are the mmFATP3 partial DNA sequence (SEQ ID NO:68). Coding region: 1–1830.

FIG. 67 is the mmFATP3 partial protein sequence (SEQ ID NO:69).

FIGS. 68A, 68B, and 68C are the mmFATP4 DNA sequence (SEQ ID NO:70). Coding region: 1–1932.

FIG. 69 is the mmFATP4 protein sequence (SEQ ID NO:71).

FIGS. 70A and 70B are the mmFATP5 DNA sequence (SEQ ID NO:72). Coding region: 60–2129.

FIG. 71 is the mmFATP5 protein sequence (SEQ ID NO:73).

FIGS. 72A and 72B are the dmFATP partial DNA sequence (dm=*Drosophila melanogaster;* SEQ ID NO:74). Coding region: 1–1773.

FIG. 73 is the dmFATP partial protein sequence (SEQ ID NO:75).

FIG. 74 is the drFATP partial DNA sequence (dr=*Danio rerio,* zebrafish; SEQ ID NO:76) Coding region: 1–173.

FIG. 75 is the drFATP partial protein sequence (SEQ ID NO:77).

FIGS. 76A and 76B are the ceFATPa DNA sequence (SEQ ID NO:78). Coding region: 1–1953.

FIG. 77 is the ceFATPa protein sequence (SEQ ID NO:79).

FIGS. 78A and 78B are the ceFATPb DNA sequence (SEQ ID NO:80). Coding region: 1–1968.

FIG. 79 is the ceFATPb protein sequence (SEQ ID NO:81).

FIGS. 80A and 80B are the chFATP DNA sequence (SEQ ID NO:82; ch=*Cochliobolu heterostrophus*). Coding region: 1–1932.

FIG. 81 is the chFATP protein sequence (SEQ ID NO:83).

FIG. 82 is the anFATP partial protein sequence (an=*Aspergillus nidulans;* SEQ ID NO:84). Coding region: 1–597.

FIG. 83 is the anFATP partial protein sequence (SEQ ID NO:85).

FIG. 84 is the mgFATP partial DNA sequence (mg=*Magnaporthe grisea,* rice blast; SEQ ID NO:86). Coding region: 1–522.

FIG. 85 is the mgFATP partial protein sequence (SEQ ID NO:87).

FIGS. 86A and 86B are the scFATP DNA sequence (SEQ ID NO:88). Coding region: 1–1872.

FIG. 87 is the scFATP protein sequence (SEQ ID NO:89).

FIGS. 88A and 88B are the mtFATP DNA sequence (SEQ ID NO:90).

FIG. 89 is the mtFATP protein sequence (SEQ ID NO:91). Coding region: 1–1794.

FIGS. 94A and 94B are a representation of the DNA sequence (SEQ ID NO:101) of the hsFATP 3 gene, and the amino acid sequence (SEQ ID NO: 102) of the hsFATP3 protein.

DETAILED DESCRIPTION OF THE INVENTION

Figure 90:
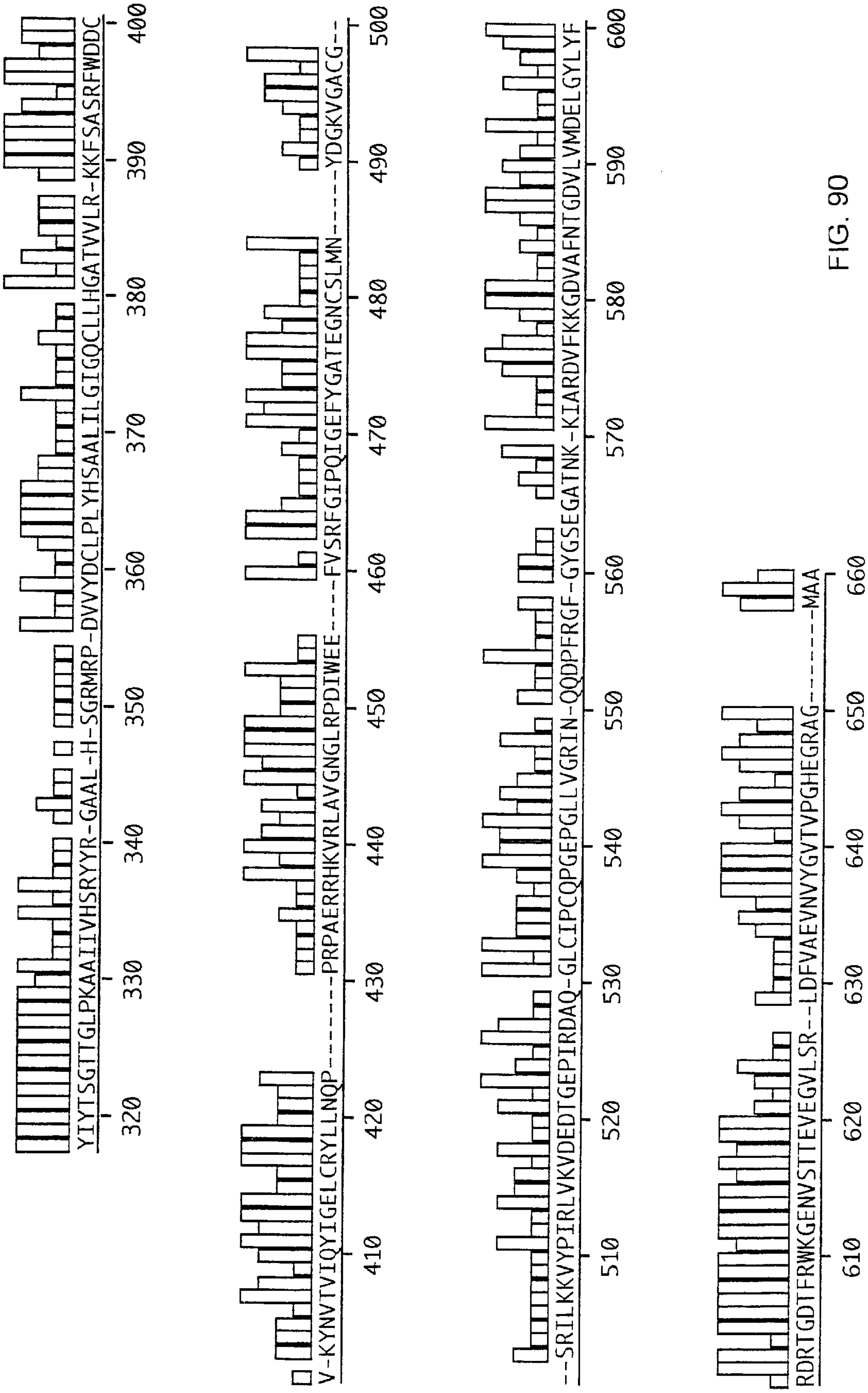
FIG. 90 is a concensus sequence of the FATP signature sequence (SEQ ID NO: 100), based on 23 independent sequences aligned in ClustalX. The height of the bar at each amino acid residue position indicates the degree of conservation at that position. Gaps have been inserted to maintain the strength of the alignment.
Figure 91:
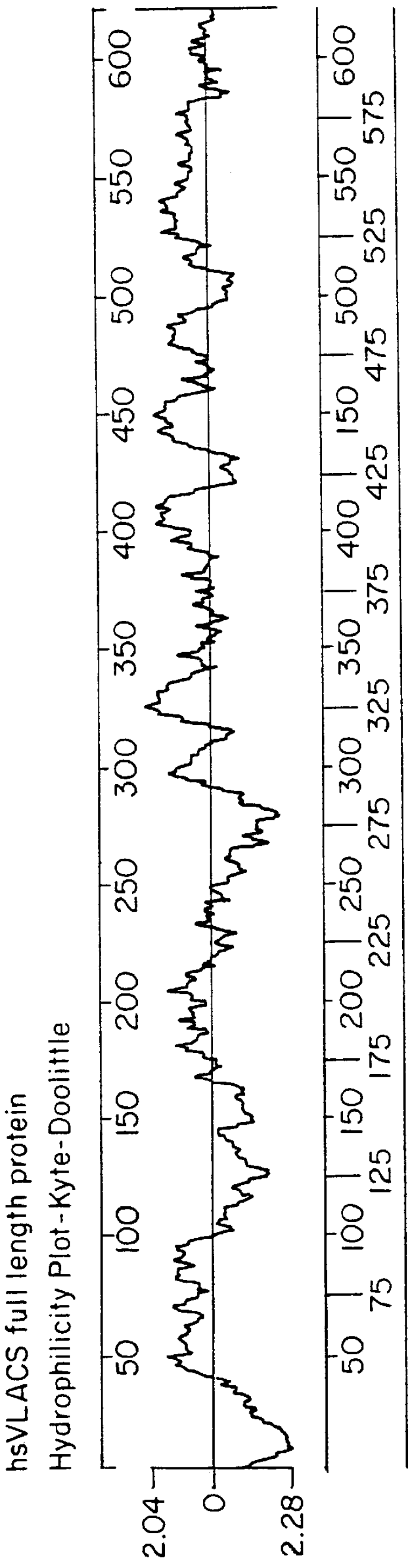
FIG. 91 is a hydrophilicity plot for hsFATP2, made using the Kyte-Doolittle method, averaging hydrophilicity values for 18 amino acid residues at a time.
Figure 92:
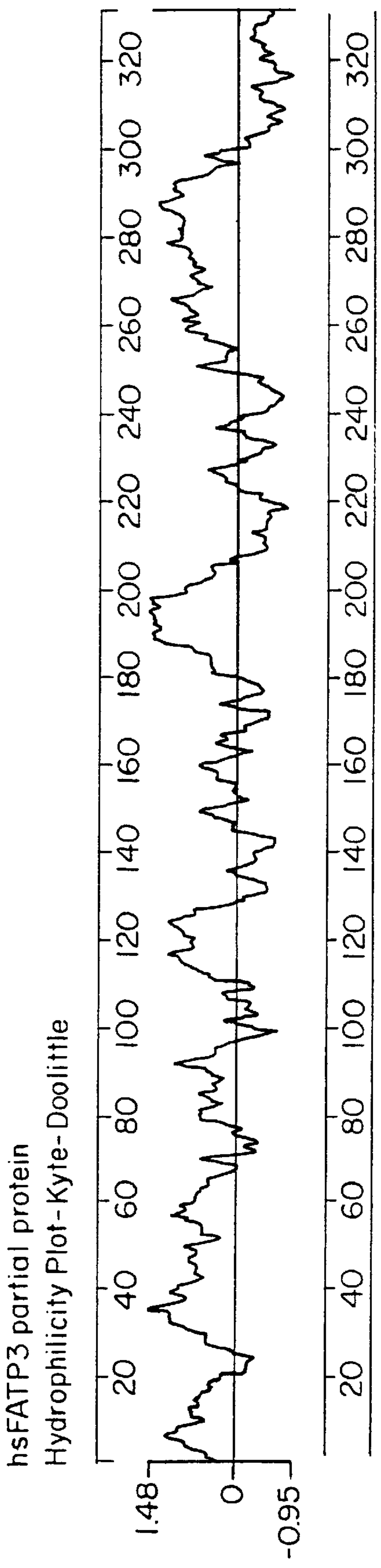
FIG. 92 is a hydrophilicity plot for the hsFATP3 partial protein, made using the Kyte-Doolittle method, averaging hydrophilicity values for 18 amino acid residues at a time.
Figure 93:
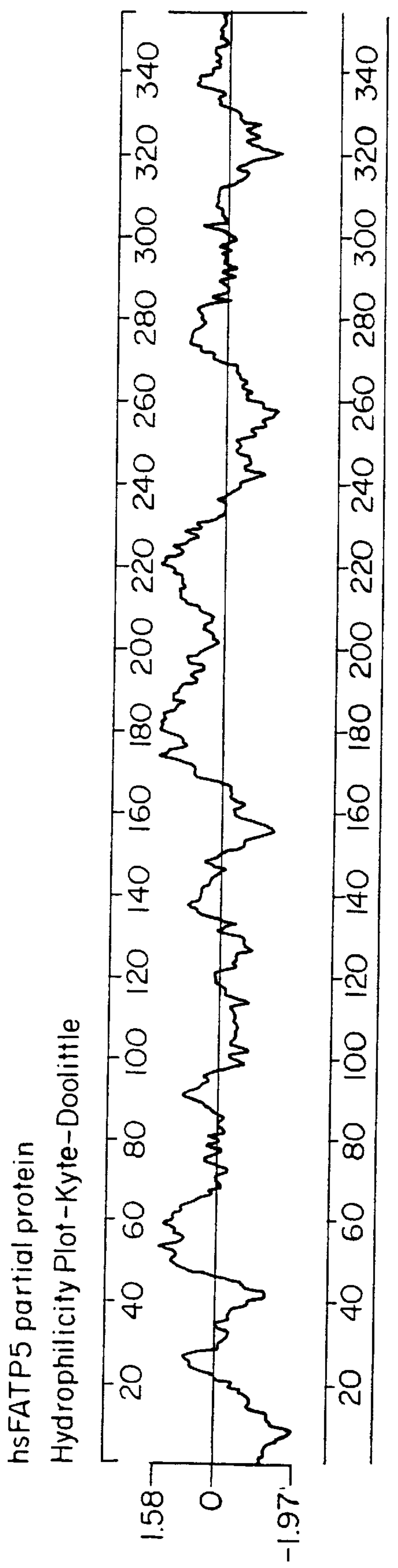
FIG. 93 is a hydrophilicity plot for the hsFATP5 partial protein, made using the Kyte-Doolittle method, averaging hydrophilicity values for 18 amino acid residues at a time.

As described herein, FATPs are a large evolutionarily conserved family of proteins that mediate the transport of LCFAs into cells. The family includes proteins which are conserved from mycobacteria to humans and exhibit very different expression patterns in tissues. Specific embodiments described include FATPs from mice, humans, nematodes, fungi and mycobacteria which have been shown to be functional LCFA transporters. The term "fatty acid transport proteins" ("FATPs") as used herein, refers to the proteins described herein as FATP1, FATP2, FATP3, FATP4, FATP5 and FATP6, which have been described in one or more species of mammals, as well as mtFATP, ceFATP, scFATP, anFATP, mgFATP, and chFATP, and other proteins sharing at least about 50% amino acid sequence similarity, preferably at least about 60% sequence similarity, more preferably at least about 70% sequence similarity, and still more preferably, at least about 80% sequence similarity, and most preferably, at least about 90% sequence similarity in the approximately 360 amino acid signature sequence. The approximaely 360 amino acid FATP signature sequence is shown in FIG. 1. The concensus sequence of the signature sequence is shown in FIG. 90. The nomenclature used herein to refer to FATPs includes a species-specific prefix (e.g., mm, *Mus musculus;* hs or h, *Homo sapiens* or human; mt *M. tuberculosis;* dm. *D. melanogaster;* ce, *C. elegans;* sc, *Saccharomyces cerevisiae*) and a number such that mammalian homologues in different species share the same number. For example, six human and five mouse FATP genes which are expressed in a variety of tissues are described herein and are referred to, respectively, as hsFATP1-hsFATP6 and mmFATP1-mmFATP5; for example, hsFATP4 and mmFATP4 are the human and mouse orthologs.

Expression patterns of human and mouse FATPs have been assessed and are described below. Briefly, results of these assessments show that FATP5 is a liver-specific gene. FATP2 is highly expressed in liver and kidney. Both of these proteins, as well as FATP4 and FATPs from nematodes and mycobacteria, have been shown to be functional LCFA transporters. Results have also shown that FATP4 mRNA is present at high levels in epithelial cells of two regions of the small intestine (the jejunum and ileum) and at lower, but significant, levels in a third region (the duodenum). They further showed that FATP2 mRNA is present in epithelial cells of the duodenum at a level similar to that of FATP4 mRNA levels, but is present at lower levels in the jejunum and ileum. FATP4 mRNA was absent from other cell types of the small intestine and no FATP4 mRNA could be detected in any cells of the colon. No signals above background could be detected for FATP 1, FATP3 and FATP5 in any of the intestinal tissues. Thus, FATP4 is the major FATP in the mouse small intestine, which supports a major role for FATP4 (along with FATP2 to a lesser extent) in absorption of free fatty acids. hsFATP4 was clearly expressed in the jejunum and ileum; expression was absent in the stomach. This, too, is consistent with a major role for FATP4 in absorption of fatty acids in the human gut. Analysis of FATP expression in human tissues, also described in detail below, showed that hsFATP6, which has no mouse ortholog as yet, is expressed at high levels in the heart and at low levels in the placenta, but is undetectable in the other tissues assessed (Example 9). This is consistent with a major role for FATP6 in absorption of fatty acids in the heart.

Long chain fatty acids (LCFAs) are an important energy source for pro- and eukaryotes and are involved in diverse cellular processes, such as membrane synthesis, intracellular signaling, protein modification, and transcriptional regulation. In developed Western countries, human dietary lipids are mainly di- and triglycerides and account for approximately 40% of caloric intake (Weisburger, J. H. (1997) *J. Am. Diet. Assoc.* 97:S16–S23). These lipids are broken down into fatty acids and glycerol by pancreatic lipases in the small intestine (Chapus, C., Rovery, M., Sarda, L & Verger, R. (1988) *Biochimie* 70:1223–34); LCFAs are then transported into brush border cells, where the majority is re-esterified and secreted into the lymphatic system as chylomicrons (Green, P. H. & Riley, J. W. (1981) *Aust. N. Z. J. Med.* 11:84–90). Fatty acids are liberated from lipoproteins by the enzyme lipoprotein lipase, which is bound to the luminal side of endothelial cells (Scow, R. O. & Blachette-Mackie, E. J. (1992) *Mol. Cell. Biochem* 116:181–191). "Free" fatty acids in the circulation are bound to serum albumin (Spector, A. A. (1984) *Clin. Physiol. Biochem* 2:123–134) and are rapidly incorporated by adipocytes, hepatocytes, and cardiac muscle cells. The latter derive 60–90% of their energy through the oxidation of LCFAs (Neely, J. F. Rovetto, M. J. & Oram, J. F. (1972) *Prog. Cardiovasc. Dis:* 15:289–329). Although saturable and specific uptake of LCFAs has been demonstrated for intestinal cells, hepatocytes, cardiac myocytes, and adipocytes, the molecular mechanisms of LCFA transport across the plasma membrane have remained controversial (Hui, T. Y. & Bernlohr, D. A. (1997) *Front. Biosci.* 15:d222-31–d231; Schaffer, J. E. & Lodish, H. F, (1995) *Trends Cardiovasc. Med.* 5:218–224). Described herein is a large family of highly homologous mammalian LCFA transporters which show wide expression, including in all tissues relevant to fatty acid metabolism. Further described are novel members of this family in other species, including mycobacterial and nematode FATPs which, like their mammalian counterparts, are functional fatty acid transporters.

The discovery of a diverse but highly homologous family of FATPs is reminiscent of the glucose transporter family. In a manner similar to the FATPs, the glucose transporters have very divergent patterns of tissue expression (McGowan, K. M., Long, S. D. & Pekala, P. H. (1995) *Pharmacol. Ther.* 66:465–505). The FATPs, like glucose transporters, may also differ in their substrate specificities, uptake kinetics, and hormonal regulation (Thorens, B. (1996) *Am. J. Physiol.* 270:G541–G553). Indeed, the levels of fatty acids in the blood, like those of glucose, can be regulated by insulin and are dysregulated in diseases such as noninsulin-dependent diabetes and obesity (Boden, G. (1997) *Diabetes* 46:3–10). The underlying mechanisms for the regulation of free fatty acid concentrations in the blood are not understood, but could be explained by hormonal modulation of FATPs.

Insulin-resistance is thought to be the major defect in non insulin-dependent diabetes mellitus (NIDDM) and is one of the earliest manifestations of NIDDM (McGarry (1992) Science 258:766–770). Free fatty acids (FFAs) may provide an explanation for why obesity is a risk factor for NIDDM. Plasma levels of FFAs are elevated in diabetic patients (Reaven et al. (1988) *Diabetes* 37:1020). Elevated plasma free fatty acids (FFAs) have been demonstrated to induce insulin-resistance in whole animals and humans (Boden (1998) *Front. Biosci.* 3:D169–D175). This insulin-resistance is likely mediated by effects of FFAs on a variety of issues. FFAs added to adipocytes in vitro induce insulin resistance in this cell type as evidenced by inhibition of insulin-induced glucose transport (Van Epps-Fung et al. (1997) *Endocrinology* 138:4338–4345). Rats fed a high fat diet developed skeletal muscle insulin resistance as evidenced by a decrease in insulin-induced glucose uptake by skeletal muscle (Han et al., (1997) *Diabetes* 46:1761–1767). In addition, elevated plasma FFAs increase insulin-suppressed endogenous glucose production in the liver (Boden (1998) *Front. Biosci.* 3:D169–D175), thus increasing hepatic glucose output. It has been postulated that the adverse effects of plasma free fatty acids are due to the FFAs being taken up into the cell, leading to an increase in intracellular long chain fatty acyl CoA; intracellular long chain acyl CoAs are thought to mediate the effects of FFAs inside the cell. Thus, fatty acid induced insulin-resistance may be prevented by blocking uptake of FFAs into select tissues, in particular liver (by blocking FATP2 and/or FATP5), adipocyte (by blocking FATP1), and skeletal muscle (by blocking FATP1). Blocking intestinal fat absorption (by blocking FATP4) is also expected to reduce plasma FFA levels and thus improve insulin resistance.

During the pathogenesis of NIDDM insulin-resistance can initially be counteracted by increasing insulin output by the pancreatic beta cell. Ultimately, this compensation fails, beta cell function decreases and overt diabetes results (McGarry (1992) *Science* 258: 766–770). Manipulating beta cell function is a second point where fatty acid transporter blockers may be beneficial for diabetes. While no FATP homolog has been identified so far that is expressed in the beta cell of the pancreas, the data described below suggest the existence of such a transporter and the sequence information included herein provides the means to identify such a transporter by degenerate PCR, using primers to regions conserved in all FATP family members or by low stringency hybridization. It has been demonstrated that exposure of pancreatic beta-cells to FFAs increases the basal rate of insulin secretion; this in turn leads to a decrease in the intracellular stores of insulin, resulting in decreased capacity for insulin secretion after chronic exposure (Bollheimer et al., (1998) *J. Clin. Invest.* 101:1094–1101). The effects of FFAs are again likely to be mediated by intracellular long chain fatty acyl CoA molecules (Liu et al., (1998) *J Clin. Invest.* 101:1870–1875). FFAs have also been demonstrated to increase beta cell apoptosis (Shimabukuro et al., (1998) *Proc. Nat. Acad. Sci.* USA 95:2498–2502), possibly contributing to the decrease in beta cell numbers in late stage NIDDM.

Another finding with potentially broad implications is the identification of a FATP homologue in *M. tuberculosis.* Tuberculosis causes more deaths worldwide than any other infectious agent and drug-resistant tuberculosis is re-emerging as a problem in industrialized nations (Bloom, B. R. & Small, P. M. (1998) *N. Engl. J Med.* 338:677–678). Mycobacterium tuberculosis has about 250 enzymes involved in fatty acid metabolism, compared with only about 50 in *E. coli.* It has been suggested that, living as a pathogen, the mycobacteria are largely lipolytic, rather than lipogenic, relying on the lipds within mammalian cells and the tubercle (Cole, S. T. et al., *Nature* 393:537–544 (1998)). The de novo synthesis of fatty acids in *Mycobacterium leprae* is insufficient to maintain growth (Wheeler, P. R., Bulmer, K & Ratledge, C. (1990) *J. Gene. Microbiol.* 136:211–217). Thus, it is reasonable to expect that inhibitors of mtFATP will serve as therapeutics for tuberculosis. FATPs expressed in mycobacteria can be targeted to reduce or prevent replication of mycobacteria (e.g., to reduce or prevent replication of *M. tuberculosis*) and, thus, reduce or prevent their adverse effects. For example, a FATP or FATPs expressed by *M. tuberculosis* can be targeted and inhibited, thus reducing or preventing growth of this pathogen (and tuberculosis in humans and other mammals). An inhibitor of an *M. tuberculosis* FATP can be identified, using methods described herein (e.g., expressing the FATP in an appropriate host cell, such as *E. coli* or COS cells; contacting the cells with an agent or drug to be assessed for its ability to inhibit the FATP and, as a result, mycobacterial growth, and assessing its effects on growth). A drug or agent identified in this manner can be further tested for its ability to inhibit a *M. tuberculosis* FATP and *M. tuberculosis* infection in an appropriate animal model or in humans. A method of inhibiting mycobacterial growth, particularly growth of *M. tuberculosis,* and compounds useful as drugs for doing so are also the subject of this invention.

An isolated polynucleotide encoding mtFATP, like other polynucleotides encoding FATPs of the FATP family, can be incorporated into vectors, nucleic acids of viruses, and other nucleic acid constructs that can be used in various types of host cells to produce mtFATP. This mtFATP can be used, as it appears on the surface of cells, or in various artificial membrane systems, to assess fatty acid transport function, to identify ligands and molecules that are modulators of fatty acid transport activity. Molecules found to be inhibitors of mtFATP function can be incorporated into pharmaceutical compositions to administer to a human for the treatment of tuberculosis.

Particular embodiments of the invention are polynucleotides encoding a FATP of *Cochliobolus* (Helminthosporium) *heterostrophus* or portions or variants thereof, the isolated or recombinantly produced FATP, methods for assessing whether an agent binds to the chFATP, and further methods for assessing the effect of an agent being tested for its ability to modulate fatty acid transport activity. *Cochliobolus heterostrophus* is an ascomycete that is the cause of southern corn leaf blight, an economically important threat to the corn crop in the United States. The related species *C. sativus* causes crown rot and common root rot in wheat and barley. One or more FATPs of *C. heterostrophus* can be targeted for the identification of an inhibitor of chFATP function, which can be then be used as an agent effective against infection of plants by *C. heterostrophus* and related organisms. Methods described herein that were applied in studying the expression of a FATP gene and the function of the FATP in its natural site of expression or in a host cell, can be used in the study of the chFATP gene and protein.

*Magnaporthe grisea* (rice blast) is an economically important fungal pathogen of rice. Further embodiments of the invention are nucleic acid molecules encoding a FATP of *Magnaporthe grisea,* portions thereof, or variants thereof, isolated mgFATP, nucleic acid constructs, and engineered cells expressing mgFATP. Other aspects of the invention are assays to identify an agent which binds to mgFATP and assays to identify an agent which modulates the function of mgFATP in cells in which mgFATP is expressed or in artificial membrane systems. Agents identified as inhibiting mgFATP activity can be developed into anti-fungal agents to be used to treat rice infected with rice blast.

*Caenorhabditis elegans* is a nematode related to plant pathogens and human parasites. An isolated polynucleotide which encodes ceFATP, like other polynucleotides encoding FATPs of the FATP family described herein, can be incorporated into nucleic acid vectors and other constructs that can be used in various types of cells to produce ceFATP. ceFATP as it occurs in cells or as it can be isolated or incorporated into various artificial or reconstructed membrane systems, can be used to assess fatty acid transport, and to identify ligands and agents that modulate fatty acid transport activity. Agents found by such assays to be inhibitors of ceFATP activity can be incorporated into compositions for the treatment of diseases caused by genetically related organisms with a FATP of similar sensitivity to the agents.

*Aspergillus nidulans* is one of a family of fungal species that can infect humans. Further embodiments of the invention of the family of polynucleotides encoding FATPs are polynucleotides encoding a FATP of *Aspergillus nidulans,* and vectors and host cells that can be constructed to comprise such polynucleotides. Further embodiments are a polypeptide encoded by such polynucleotides, portions thereof having one or more functions characteristic of a FATP, and various methods. The methods include those for identifying agents that bind to anFATP and those for assessing the effect of an agent being tested for its ability to modulate fatty acid transport activity. Those agents found to inhibit fatty acid transport function can be used in compositions as anti-fungal pharmaceuticals, or can be modified for greater effectiveness as a pharmaceutical.

One aspect of the invention relates to isolated nucleic acids that encode a FATP as described herein, such as those FATPs having an amino acid sequence in FIG. 45 (SEQ ID NO:47), FIG. 47 (SEQ ID NO:49), FIG. 49 (SEQ ID NO:51), FIG. 51 (SEQ ID NO:53), FIGS. 94A and 94B (SEQ ID NO:102), and FIG. 55 (SEQ ID NO:57) and nucleic acids closely related thereto as described herein.

Using the information provided herein, such as a nucleic acid sequence set forth in FIGS. 44A–44C (SEQ ID NO:46), FIGS. 46A and 46B (SEQ ID NO:48), FIG. 48 (SEQ ID NO:50), FIGS. 50A–50C (SEQ ID NO:52), FIGS. 94A and 94B (SEQ ID NO:101), and FIGS. 54A–54C (SEQ ID NO:56), a nucleic acid of the invention encoding a FATP polypeptide may be obtained using standard cloning and screening methods, such as those for cloning and sequencing cDNA library fragments, followed by obtaining a fall length clone. For example, to obtain a nucleic acid of the invention, a library of clones of cDNA of human or other mammalian DNA can be probed with a labeled oligonucleotide, such as a radiolabeled oligonucleotide, preferably about 17 nucleotides or longer, derived from a partial sequence. Clones carrying DNA identical to that of the probe can then be distinguished using stringent (also, "high stringency") hybridization conditions. By sequencing the individual clones thus identified with sequencing primers designed from the original sequence it is then possible to extend the sequence in both directions to determine the full length sequence. Suitable techniques are described, for example, in *Current Protocols in Molecular Biology* (F. M. Ausubel et al, eds), containing supplements through Supplement 42, 1998, John Wiley and Sons, Inc., especially chapters 5, 6 and 7.

Embodiments of the invention include isolated nucleic acid molecules comprising any of the following nucleotide sequences: 1.) a nucleotide sequence which encodes a protein comprising the amino acid sequence of hsFATP1 (SEQ ID NO:47), the amino acid sequence of hsFATP2 (SEQ ID NO:49), the amino acid sequence of hsFATP3 (SEQ ID NO:102), the amino acid sequence of hsFATP4 (SEQ ID NO: 53), the amino acid sequence of hsFATP5 (SEQ ID NO:55) or the amino acid sequence of hsFATP6 (SEQ ID NO:57); 2.) nucleotide sequences of hsFATP1, hsFATP2, hsFATP3, hsFATP4, hsFATP5, or hsFATP6 (SEQ ID NO:46, 48, 101, 52, 54, or 56, respectively); 3.) a nucleotide sequence which is complementary to the nucleotide sequence of hsFATP1 (SEQ ID NO:46), hsFATP2 (SEQ ID NO:48), hsFATP3 (SEQ ID NO:101), hsFATP4 (SEQ ID NO:52), hsFATP5 (SEQ ID NO:54) or hsFATP6 (SEQ ID NO:56); 4.) a nucleotide sequence which consists of the coding region of hsFATP1 (SEQ ID NO:46), the coding region of hsFATP2 (SEQ ID NO:48), the coding region of hsFATP3 (SEQ ID NO:101), the coding region of hsFATP4 (SEQ ID NO:52), the coding region of hsFATP5 (SEQ ID NO:54), or the coding region of hsFATP6 (SEQ ID NO:56).

The invention further relates to nucleic acids (nucleic acid molecules or polynucleotides) having nucleotide sequences identical over their entire length to those shown in the figures, for instance FIGS. 44A–44C (SEQ ID NO:46), FIGS. 46A and 46B (SEQ ID NO:48), FIG. 48 (SEQ ID NO:50), FIGS. 50A–50C (SEQ ID NO:52), FIGS. 94A and 94B (SEQ ID NO:101), and FIGS. 54A–54C (SEQ ID NO:56). It further relates to DNA, which due to the degeneracy of the genetic code, encodes a FATP encoded by one of the FATP-encoding DNAs, whose amino acid sequence is provided herein. Also provided by the invention are nucleic acids having the coding sequences for the mature polypeptides or fragments in reading frame with other coding sequences, such as those encoding a leader or secretory sequence, a pre-, or pro- or prepro- protein sequence. The nucleic acids of the invention encompass nucleic acids that include a single continuous region or discontinuous regions encoding the polypeptide, together with additional regions, that may also contain coding or non-coding sequences. The nucleic acids may also contain non-coding sequences, including, for example, but not limited to, non-coding 5' and 3' sequences, such as the transcribed, non-translated sequences, termination signals, ribosome binding sites, sequences that stabilize mRNA, introns, polyadenylation signals, and additional coding sequences which encode additional amino acids. For example, a marker sequence that facilitates purification of the fused polypeptide can be encoded. In certain embodiments of the invention, the marker sequence can be a hexa-histidine peptide, as provided in the pQE vector (Qiagen, Inc.) and described in Gentz et al., *Proc. Natl. Acad, Sci. USA* 86: 821–824 (1989), or an HA tag (Wilson et al., *Cell* 37:767 (1984)), or a sequence encoding glutathione S-trans ferase of *Schistosoma japonicum* (vectors available from Pharmacia; see Smith, D. B. and Johnson K. S., *Gene* 67:31 (1988) and Kaelin, W. G. et al., *Cell* 70:351 (1992)). Nucleic acids of the invention also include, but are not limited to, nucleic acids comprising a structural gene and its naturally associated sequences that control gene expression.

The invention further relates to variants, including naturally-occurring allelic variants, of those nucleic acids described specifically herein by DNA sequence, that encode variants of such polypeptides as those having the amino acid sequences shown in FIG. 45 (SEQ ID NO:47), FIG. 47 (SEQ ID NO:49), FIG. 49 (SEQ ID NO:51), FIG. 51 (SEQ ID NO:53) FIGS. 94A and 94B (SEQ ID NO:102), or FIG. 55 (SEQ ID NO:57). Such variants include nucleic acids encoding variants of the above-listed amino acid sequences, wherein those variants have several, such as 5 to 10, 1 to 5, or 3, 2 or 1 amino acids substituted, deleted, or added, in any combination. Variants include polynucleotides encoding polypeptides with at least 95% but less than 100% amino acid sequence identity to the polypeptides described herein by amino acid sequence. Variant polynucleotides hybridize, under low to high stringency conditions, to the alleles described herein by DNA sequence. In one embodiment, variants have silent substitutions, additions and deletions that do not alter the properties and activities of the FATP. Allelic variants of the polynucleotides encoding hsFATP1 (FIG. 45; SEQ ID NO:47), hsFATP2 (FIG. 47; SEQ ID NO:49), hsFATP3 (FIGS. 94A and 94B; SEQ ID NO:102), hsFATP4 (FIG. 51; SEQ ID NO:53), FIG. 53 (SEQ ID NO:35) and hsFATP6 (FIG. 55; SEQ ID NO:57) will be identified as mapping to chromosomal locations listed for the corresponding wild type genes in Table 2 in Example 1.

Orthologous genes are gene loci in different species that are sufficiently similar to each other in their nucleotide sequences to suggest that they originated from a common ancestral gene. Orthologous genes arise when a lineage splits into two species, rather than when a gene is duplicated within a genome. Proteins that are orthologs are encoded by genes of two different species, wherein the genes are said to be orthologous.

The invention further relates to polynucleotides encoding polypeptides which are orthologous to those polypeptides having a specific amino acid sequence described herein, such as the amino acid sequences shown in FIG. 45 (SEQ ID NO:47), FIG. 47 (SEQ ID NO:49), FIG. 49 (SEQ ID NO:51), FIG. 51 (SEQ ID NO:53), FIGS. 94A and 94B (SEQ ID NO:102), or FIG. 55 (SEQ ID NO:57). These polynucleotides, which can be called ortholog polynucleotides, encode orthologous polypeptides that can range in amino acid sequence identity to a reference amino acid sequence described herein, from about 65% to less than 100%, but preferably 70% to 80%, more preferably 80% to 90%, and still more preferably 90% to less than 100%.

Orthologous polypeptides can also be those polypeptides that range in amino acid sequence similarity to a reference amino acid sequence described herein from about 75% to 100%, within the signature sequence. The amino acid sequence similarity between the signature sequences of orthologous polypeptides is preferably 80%, more preferably 90%, and still more preferably, 95%. The ortholog polynucleotides encode polypeptides that have similar functional characteristics (e.g., fatty acid transport activity) and similar tissue distribution, as appropriate to the organism from which the ortholog polynucleotides can be isolated.

Ortholog polynucleotides can be isolated from (e.g., by cloning or nucleic acid amplification methods) a great number of species, as shown by the sample of FATPs from evolutionarily divergent species described herein (see, e.g., FIGS. 44A–C through FIG. 89). Ortholog polynucleotides corresponding to those in FIG. 45 (SEQ ID NO:47), FIG. 47 (SEQ ID NO:49), FIG. 49 (SEQ ID NO:51), FIG. 51 (SEQ ID NO:53), FIGS. 94A and 94B (SEQ ID NO:102) and FIG. 55 (SEQ ID NO:57) are those which can be isolated from mammals such as rat, dog, chimpanzee, monkey, baboon, pig, rabbit and guinea pig, for example.

Further variants that are fragments of the nucleic acids of the invention may be used to synthesize full-length nucleic acids of the invention, such as by use as primers in a polymerase chain reaction. As used herein, the term primer refers to a single-stranded oligonucleotide which acts as a point of initiation of template-directed DNA synthesis under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but must be sufficiently complementary to hybridize with a template. The term primer site refers to the area of the target DNA to which a primer hybridizes. The term primer pair refers to a set of primers including a 5' (upstream) primer that hybridizes with the 5' end of the DNA sequence to be amplified and a 3' (downstream) primer that hybridizes with the complement of the 3' end of the sequence to be amplified.

Further embodiments of the invention are nucleic acids that are at least 80% identical over their entire length to a nucleic acid described herein, for example a nucleic acid having the nucleotide sequence in FIGS. 44A–44C (SEQ ID NO:46), FIGS. 46A–46B (SEQ ID NO:48), FIG. 48 (SEQ ID NO:50), FIGS. 50A–50C (SEQ ID NO:52), FIGS. 94A and 94B (SEQ ID NO:101), and FIGS. 54A–54C (SEQ ID NO:56). Additional embodiments are nucleic acids, and the complements of such nucleic acids, having at least 90% nucleotide sequence identity to the above-described sequences, and nucleic acids having at least 95% nucleotide sequence identity. In preferred embodiments, DNA of the present invention has 97% nucleotide sequence identity, 98% nucleotide sequence identity, or at least 99% nucleotide sequence identity with the DNA whose sequences are presented herein.

Other embodiments of the invention are nucleic acids that are at least 80% identical in nucleotide sequence to a nucleic acid encoding a polypeptide having an amino acid sequence as set forth in FIG. 45 (SEQ ID NO:47), FIG. 47 (SEQ ID NO:49), FIG. 49 (SEQ ID NO:5 1), FIG. 51 (SEQ ID NO:53), FIGS. 94A and 94B (SEQ ID NO:102) or FIG. 55 (SEQ ID NO:57), or as such amino acid sequences are set forth elsewhere herein, and nucleic acids that are complementary to such nucleic acids. Specific embodiments are nucleic acids having at least 90% nucleotide sequence identity to a nucleic acid encoding a polypeptide having an amino acid sequence as described in the list above, nucleic acids having at least 95% sequence identity, and nucleic acids having at least 97% sequence identity.

The terms "complementary" or "complementarity" as used herein, refer to the natural binding of polynucleotides under permissive salt and temperature conditions by base-pairing. Complementarity between two single-stranded molecules may be "partial" in which only some of the nucleic acids bind, or it may be complete when total complementarity exists between the single-stranded molecules (that is, when A-T and G-C base pairing is 100% complete). The degree of complementarity between nucleic acid strands has significant effects on the efficiency and strength of hybridization between nucleic acid strands. This is of particular importance in amplification reactions, which depend on binding between nucleic acid strands.

The invention further includes nucleic acids that hybridize to the above-described nucleic acids, especially those nucleic acids that hybridize under stringent hybridization conditions. "Stringent hybridization conditions" or "high stringency conditions" generally occur within a range from about $T_m$ minus 5° C. (5° C. below the strand dissociation temperature or melting temperature ($T_m$) of the probe nucleic acid molecule) to about 20° C. to 25° C. below $T_m$. As will be understood by those of skill in the art, the stringency of hybridization may be altered in order to identify or detect molecules having identical or related polynucleotide sequences. An example of high stringency hybridization follows. Hybridization solution is (6×SSC/10 mM EDTA/0.5% SDS/5×Denhardt's solution/100 μg/ml sheared and denatured salmon sperm DNA). Hybridization is at 64–65° C. for 16 hours. The hybridized blot is washed two times with 2×SSC/0.5% SDS solution at room temperature for 15 minutes each, and two times with 0.2×SSC/0.5% SDS at 65° C., for one hour each. Further examples of high stringency conditions can be found on pages 2.10.1–2.10.16 (see particularly 2.10.8–11) and pages 6.3.1–6 in *Current Protocols in Molecular Biology* (Ausubel, F. M. et al., eds., containing supplements up through Supplement 42, 1998). Examples of high, medium, and low stringency conditions can be found on pages 36 and 37 of WO 98/40404, which are incorporated herein by reference.

The invention further relates to nucleic acids obtainable by screening an appropriate library with a probe having a nucleotide sequence such as that set forth in FIGS. 44A–44C (SEQ ID NO:46), FIGS. 46A–46B (SEQ ID NO:48), FIG. 48 (SEQ ID NO:50), FIGS. 50A–50C (SEQ ID NO:52), FIGS. 94A and 94B (SEQ ID NO:101) or FIGS. 54A–54C (SEQ ID NO:56), or a probe which is a sufficiently long fragment of any of the above; and isolating the nucleic acid. Such probes generally can comprise at least 15 nucleotides. Nucleic acids obtainable by such screenings may include RNAs, cDNAs and genomic DNA, for example, encoding FATPs of the FATP family described herein.

Further uses for the nucleic acid molecules of the invention, whether encoding a full-length FATP or whether comprising a contiguous portion of a nucleic acid molecule such as one given in SEQ ID NO:46, 48, 50, 52, 101, or 56, include use as markers for tissues in which the corresponding protein is preferentially expressed (to identify constitutively expressed proteins or proteins produced at a particular stage of tissue differentiation or stage of development of a disease state); as molecular weight markers on southern gels; as chromosome markers or tags (when labeled, for example with biotin, a radioactive label or a fluorescent label) to identify chromosomes or to map related gene positions; to compare with endogenous DNA sequences in a mammal to identify potential genetic disorders; as probes to hybridize and thus identify, related DNA sequences; as a source of information to derive PCR primers for genetic fingerprinting; as a probe to "subtract-out" known sequences in the process of discovering other novel nucleic acid molecules; for selecting and making oligomers for attachment to a "gene chip" or other support, to be used, for example, for examination of expression patterns; to raise anti-protein antibodies using DNA immunization techniques; and as an antigen to raise anti-DNA antibodies or to elicit another immune response.

Further methods to obtain nucleic acids encoding FATPs of the FATP family include PCR and variations thereof (e.g., "RACE" PCR and semi-specific PCR methods). Portions of the nucleic acids having a nucleotide sequence set forth in FIGS. 44A–44C (SEQ ID NO:46), FIGS. 46A–46B (SEQ ID NO:48), FIG. 48 (SEQ ID NO:50), FIGS. 50A–50C (SEQ ID NO:52), FIGS. 94A and 94B (SEQ ID NO:101) or FIGS. 54A–54C (SEQ ID NO:56), (especially "flanking sequences" on either side of a coding region) can be used as primers in methods using the polymerase chain reaction, to produce DNA from an appropriate template nucleic acid.

Once a fragment of the FATP gene is generated by PCR, it can be sequenced, and the sequence of the product can be compared to other DNA sequences, for example, by using the BLAST Network Service at the National Center for Biotechnology Information. The boundaries of the open reading frame can then be identified using semi-specific PCR or other suitable methods such as library screening. Once the 5' initiator methionine codon and the 3' stop codon have been identified, a PCR product encoding the full-length gene can be generated using genomic DNA as a template, with primers complementary to the extreme 5' and 3' ends of the gene or to their flanking sequences. The full-length genes can then be cloned into expression vectors for the production of functional proteins.

The invention also relates to isolated proteins or polypeptides such as those encoded by nucleic acids of the present invention. Isolated proteins can be purified from a natural source or can be made recombinantly. Proteins or polypeptides referred to herein as "isolated" are proteins or polypeptides that exist in a state different from the state in which they exist in cells in which they are normally expressed in an organism, and include proteins or polypeptides obtained by methods described herein, similar methods or other suitable methods, and also include essentially pure proteins or polypeptides, proteins or polypeptides produced by chemical synthesis or by combinations of biological and chemical methods, and recombinant proteins or polypeptides which are isolated. Thus, the term "isolated" as used herein, indicates that the polypeptide in question exists in a physical milieu distinct from that in which it occurs in nature. Thus, "isolated" includes existing in membrane fragments and vesicles membrane fractions, liposomes, lipid bilayers and other artificial membrane systems. An isolated FATP may be substantially isolated with respect to the complex cellular milieu in which it naturally occurs, and may even be purified essentially to homogeneity, for example as determined by PAGE or column chromatography (for example, HPLC), but may also have further cofactors or molecular stabilizers, such as detergents, added to the purified protein to enhance activity. In one embodiment, proteins or polypeptides are isolated to a state at least about 75% pure; more preferably at least about 85% pure, and still more preferably at least about 95% pure, as determined by Coomassie blue staining of proteins on SDS-polyacrylamide gels. Proteins or polypeptides referred to herein as "recombinant" are proteins or polypeptides produced by the expression of recombinant nucleic acids.

In a preferred embodiment, an isolated polypeptide comprising a FATP, a functional portion thereof, or a functional equivalent of the FATP, has at least one function characteristic of a FATP, for example, transport activity, binding function (e.g., a domain which binds to AMP), or antigenic function (e.g., binding of antibodies that also bind to a naturally-occurring FATP, as that function is found in an antigenic determinant). Functional equivalents can have activities that are quantitatively similar to, greater than, or less than, the reference protein. These proteins include, for example, naturally occurring FATPs that can be purified from tissues in which they are produced (including polymorphic or allelic variants), variants (e.g., mutants) of those proteins and/or portions thereof. Such variants include mutants differing by the addition, deletion or substitution of one or more amino acid residues, or modified polypeptides in which one or more residues are modified, and mutants comprising one or more modified residues. Portions or fragments of a FATP can range in size from four amino acid residues to the entire amino acid sequence minus one amino acid.

The isolated proteins of the invention preferably include mammalian fatty acid transport proteins of the FATP family of homologous proteins. In one embodiment, the extent of amino acid sequence similarity between a polypeptide having one of the amino acid sequences shown in FIG. 45 (SEQ ID NO:47), FIG. 47 (SEQ ID NO:49), FIG. 49 (SEQ ID NO:51), FIG. 51 (SEQ ID NO:53), FIGS. 94A and 94B (SEQ ID NO:102), or FIG. 55 (SEQ ID NO:57), and the respective functional equivalents of these polypeptides is at least about 88%. In other embodiments, the degree of amino acid sequence similarity between a FATP and its respective functional equivalent is at least about 91%, at least about 94%, or at least about 97%.

The polypeptides of the invention also include those FATPs encoded by polynucleotides which are orthologous to those polynucleotides, the sequences of which are described herein in whole or in part. FATPs which are orthologs to those described herein by amino acid sequence, in whole or in part, are, for example fatty acid transport proteins 1–6 of dog, rat chimpanzee, monkey, rabbit, guinea pig, baboon and pig, and are also embodiments of the invention.

To determine the percent identity or similarity of two amino acid sequences or of two nucleic acid sequences, the sequences are aligned for optimal comparison purposes (e.g., gaps can be introduced in one or both of a first and a second amino acid or nucleic acid sequence for optimal alignment, and non-homologous (dissimilar) sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein, amino acid or nucleic acid "identity" is equivalent to amino acid or nucleic acid "similarity"). The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but having sufficient similarity so as to perform one or more of the same functions performed by the polypeptides described herein by amino acid sequence. Similarity for a polypeptide is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent is found in Bowie et al., *Science* 247:1306–1310 (1990).

TABLE 1

| Conservative Amino Acid Substitutions | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

The comparison of sequences and determination of percent identity and similarity between two sequences can be accomplished using a mathematical algorithm. (*Computational Molecular Biology,* Lesk, A. M.,ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereaux, J., eds., M. Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NTWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (*CABIOS,* 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against databases to, for example, identify other family members or related sequences. Such searches can be performed using the NBLAST and XBLAST programs (version 2.0) of Altschul, et at. (*J. Mol. Biol.* 215:403–10 (1990)). BLAST nucleotide searches can be performed with the NBLAST program, score=100, word length=12 to obtain nucleotide sequences homologous to (with calculatably significant similarity to) the nucleic acid molecules of the invention. BLAST protein searches can be performed with the XBLAST program, score=50, word length=3 to obtain amino acid sequences homologous to the proteins of the invention. To obtain gapped alignments for comparison purposes, Gapped BLAST can be utilized as described in Altschul et al., (*Nucleic Acids Res.* 25(17) :3389–3402 (1997)). When utilizing BLAST and gapped BLAST programs, the default parameters of the respective programs (e.g., XBLAST and NBLAST) can be used. See http://www.ncbi.nlm.nih.gov.

Similarity for nucleotide and amino acid sequences can be defined in terms of the parameters set by the Advanced Blast search available from NCBI (the National Center for Biotechnology Information; see, for Advanced BLAST page, www.ncbi.nlm.nih.gov/cgi-bin/BLAST/nph-newblast?Jform=1). These default parameters, recommended for a query molecule of length greater than 85 amino acid residues or nucleotides have been set as follows: gap existence cost, 11, per residue gap cost, 1; lambda ratio, 0.85. Further explanation of version 2.0 of BLAST can be found on related website pages and in Altschul, S. F. et al., *Nucleic Acids Res.* 25:3389–3402 (1997).

The invention further relates to fusion proteins, comprising a FATP or functional portion thereof (as described above) as a first moiety, linked to second moiety not occurring in the FATP as found in nature. Thus, the second moiety can be an amino acid, peptide or polypeptide. The first moiety can be in an N-terminal location, C-terminal location or internal to the fusion protein. In one embodiment, the fusion protein comprises a FATP as the first moiety, and a second moiety comprising a linker sequence and an affinity ligand. Fusion proteins can be produced by a variety of methods. For example, a fusion protein can be produced by the insertion of a FATP gene or portion thereof into a suitable expression vector, such as Bluescript SK+/− (Stratagene), pGEX-4T-2 (Pharmacia), pET-24(+) (Novagen), or vectors of similar construction. The resulting construct can be introduced into a suitable host cell for expression. Upon expression, fusion protein can be purified from cells by means of a suitable affinity matrix (See e.g., *Current Protocols in Molecular Biology,* Ausubel, F. M. et al., eds., Vol. 2, pp. 16.4.1–16.7.8, containing supplements up through Supplement 42, 1998).

The invention also relates to enzymatically produced, synthetically produced, or recombinantly produced portions of a fatty acid transport protein. Portions of a FATP can be made which have fall or partial function on their own, or which when mixed together (though fully, partially, or nonfunctional alone), spontaneously assemble with one or more other polypeptides to reconstitute a functional protein having at least one function characteristic of a FATP.

Fragments of a FATP can be produced by direct peptide synthesis, for example those using solid-phase techniques (Roberge, J. Y. et al., *Science* 269:202–204 (1995); Merrifield, J., *J. Am. Chem. Soc.* 85:2149–2154 (1963)). Protein synthesis can be performed using manual techniques or by automation. Automated synthesis can be carried out using, for instance, an Applied Biosystems 431A Peptide Synthesizer (Perkin Elmer). Various fragments of a FATP can be synthesized separately and combined using chemical methods.

One aspect of the invention is a peptide or polypeptide having the amino acid sequence of a portion of a fatty acid transport protein which is hydrophilic rather than hydrophobic, and ordinarily can be detected as facing the outside of the cell membrane. Such a peptide or polypeptide can be thought of as being an extracellular domain of the FATP, or a mimetic of said extracellular domain. It is known, for example, that a portion of human FATP4 that includes a highly conserved motif is involved in AMP-CoA binding function (Stuhlsatz-Krouper, S. M. et al., *J. Biol. Chem.* 44:28642–28650 (1998)).

The term "mimetic" as used herein, refers to a molecule, the structure of which is developed from knowledge of the structure of the FATP of interest, or one or more portions thereof, and, as such, is able to effect some or all of the functions of a FATP.

Portions of an FATP can be prepared by enzymatic cleavage of the isolated protein, or can be made by chemical synthesis methods. Portions of a FATP can also be made by recombinant DNA methods in which restriction fragments, or fragments that may have undergone further enzymatic processing, or synthetically made DNAs are joined together to construct an altered FATP gene. The gene can be made such that it encodes one or more desired portions of a FATP. These portions of FATP can be entirely homologous to a known FATP, or can be altered in amino acid sequence relative to naturally occurring FATPs to enhance or introduce desired properties such as solubility, stability, or affinity to a ligand. A further feature of the gene can be a sequence encoding an N-terminal signal peptide directed to the plasma membrane.

Figure 28A:
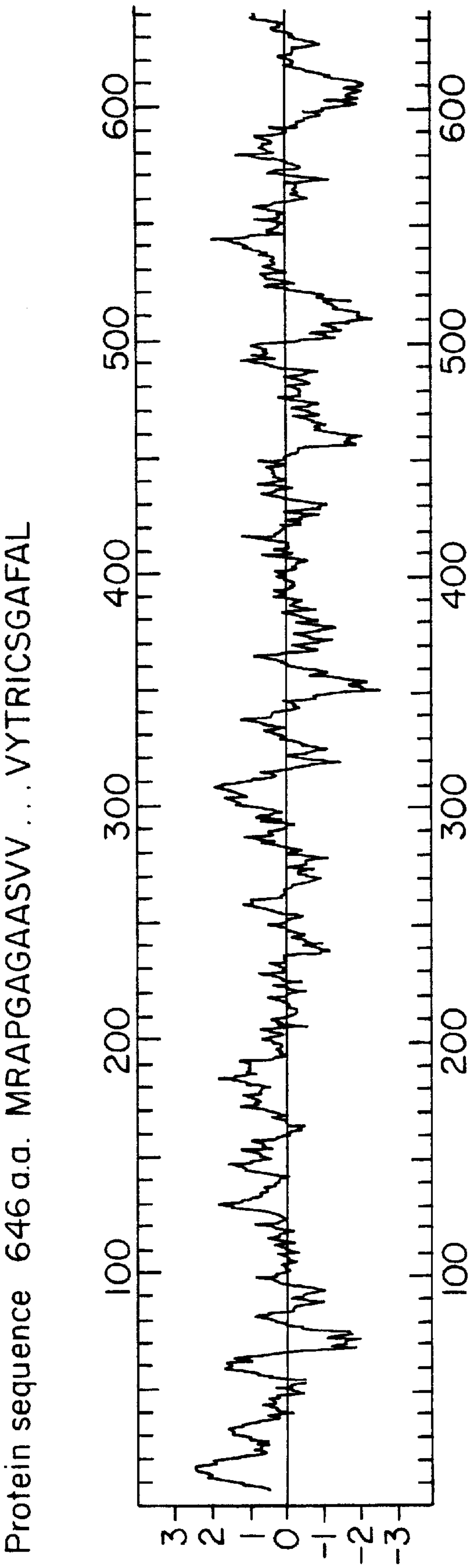
FIG. 28A is a hydrophobicity plot for hsFATP1, showing that it has multiple membrane-spanning domains.
Figure 28C:
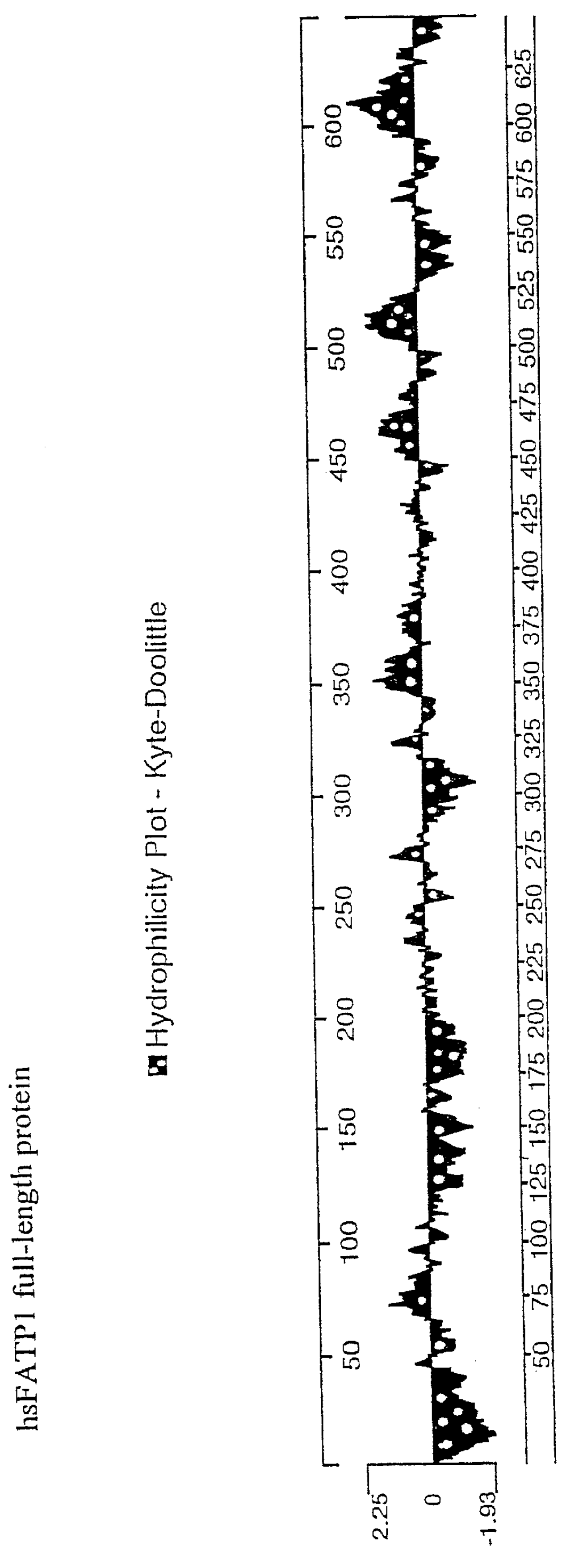
FIG. 28C is a hydrophilicity plot for hsFATP1, made using the Kyte-Doolittle method, averaging hydrophilicity values for 18 amino acid residues at a time.
Figure 29A:
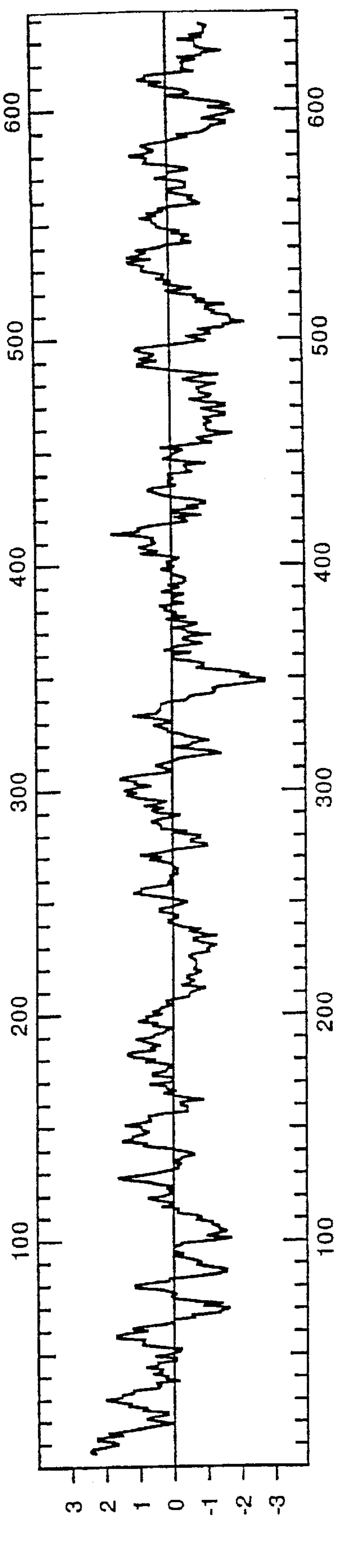
FIG. 29A is a hydrophobicity plot for hsFATP4, showing that it has multiple membrane-spanning domains.
Figure 29C:
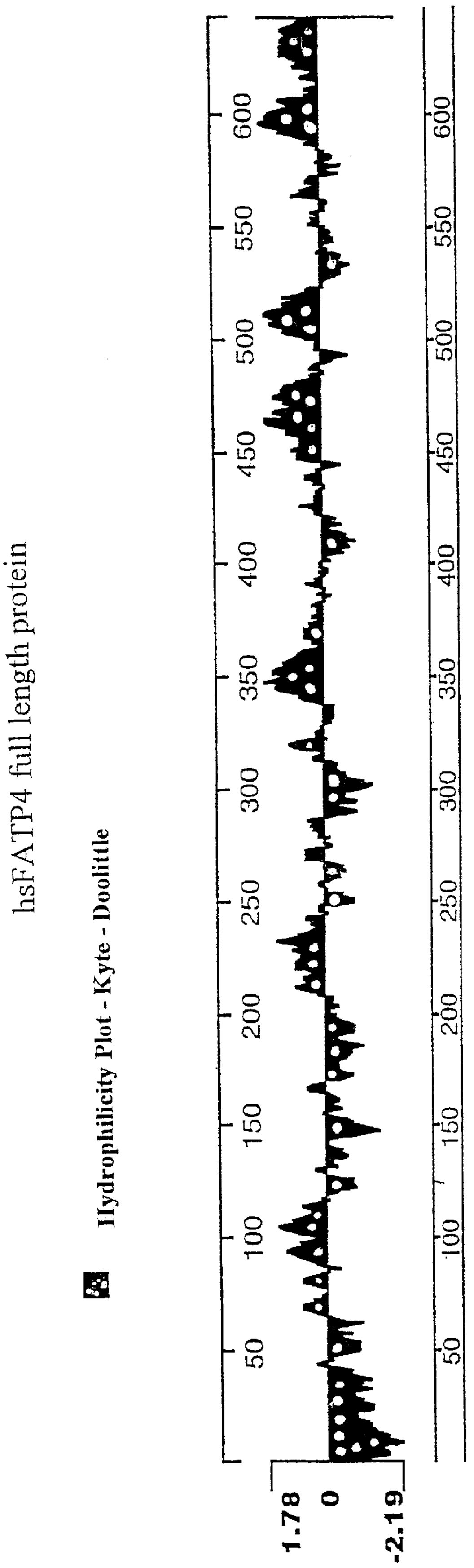
FIG. 29C is a hydrophilicity plot for hsFATP4, made using the Kyte-Doolittle method, averaging hydrophilicity values for 18 amino acid residues at a time.
Figure 35A:
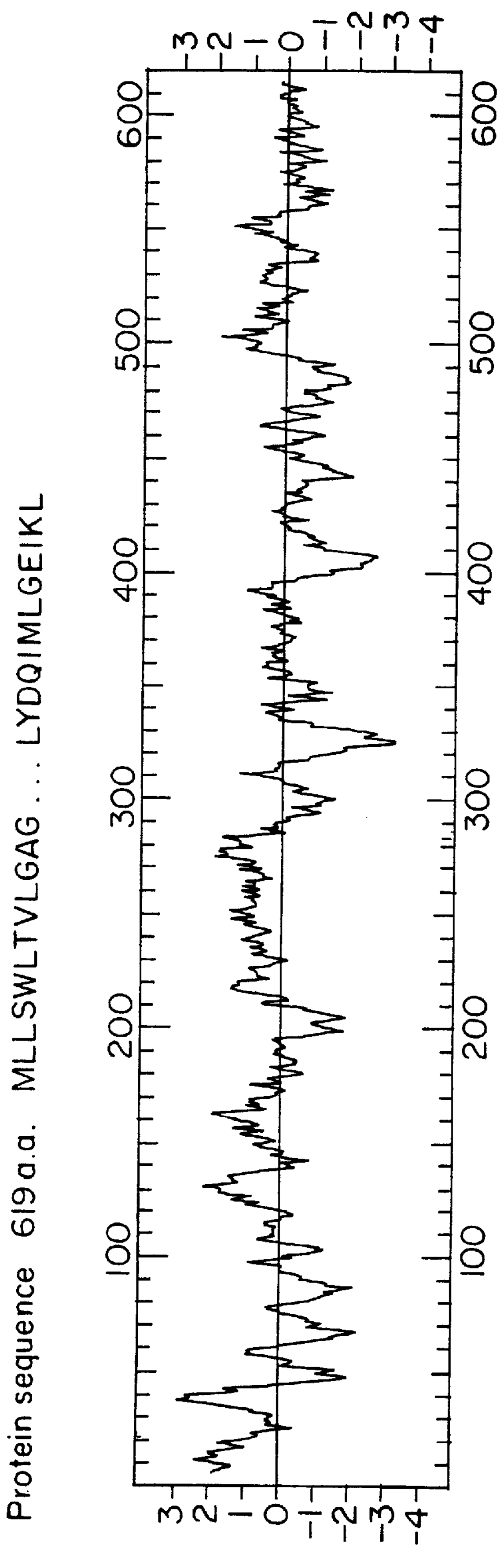
FIG. 35A is a hydrophobicity plot for hsFATP6, showing that it has multiple membrane-spanning domains.
Figure 35C:
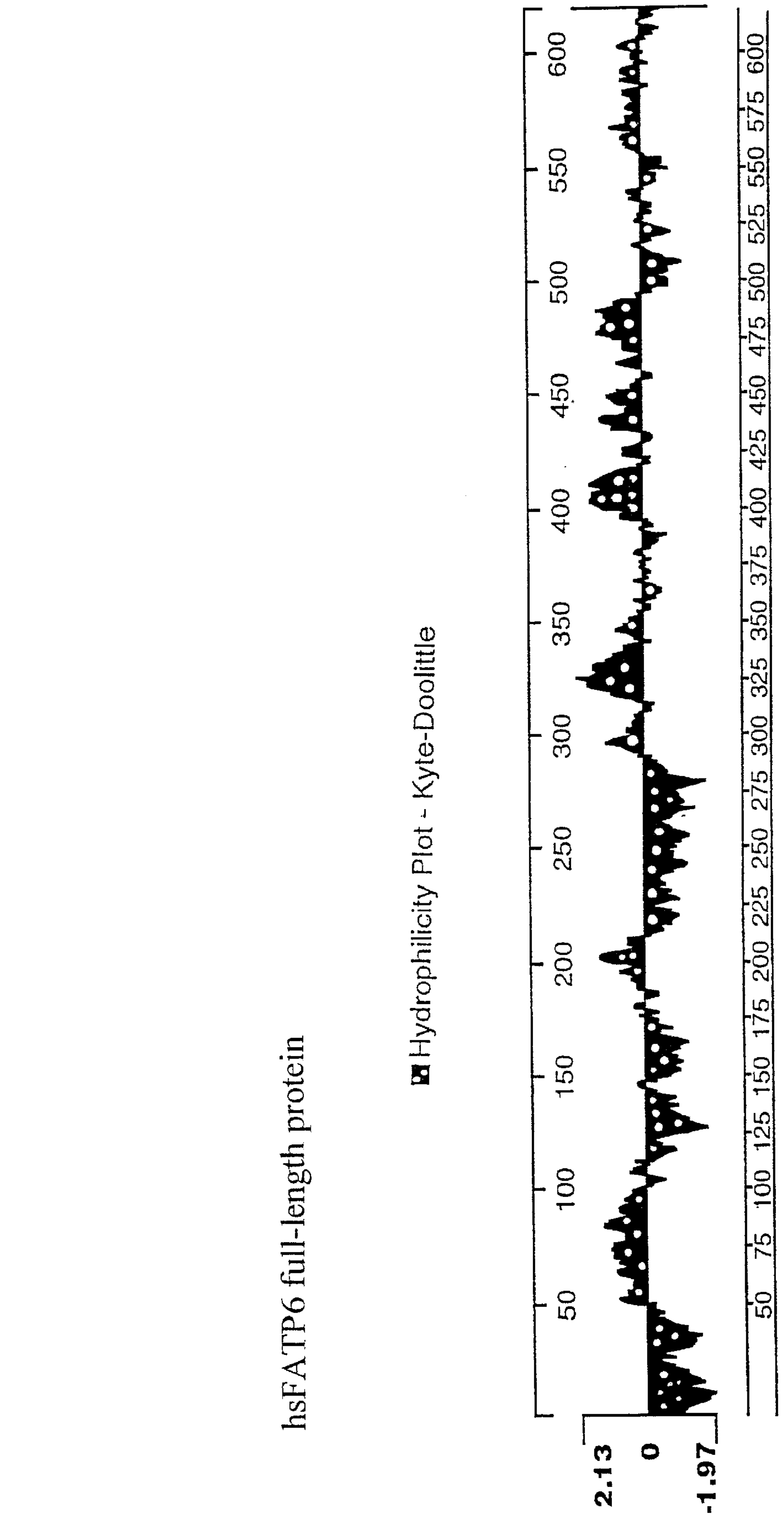
FIG. 35C is a hydrophilicity plot for hsFATP6, made using the Kyte-Doolittle method, averaging hydrophilicity values for 18 amino acid residues at a time.

An extracellular domain can be determined by a hydrophobicity plot, such as those shown in FIGS. 28A, 29A, and 35A, or by a hydrophilicity plot such as those shown in FIGS. 28C, 29C, 35C, 91, 92 and 93. A polypeptide or peptide comprising all or a portion of a FATP extracellular domain can be used in a pharmaceutical composition. When administered to a mammal by an appropriate route, the polypeptide or peptide can bind to fatty acids and compete with the native FATPs in the membrane of cells, thereby making fewer fatty acid molecules available as substrates for transport into cells, and reducing the amount of fatty acids taken up by, for example, the heart, in the case of FATP6.

Another aspect of the invention relates to a method of producing a fatty acid transport protein, variants or portions thereof, and to expression systems and host cells containing a vector appropriate for expression of a fatty acid transport protein.

Cells that express a FATP, a variant or a portion thereof, or an ortholog of a FATP described herein by amino acid sequence, can be made and maintained in culture, under conditions suitable for expression, to produce protein in the cells for cell-based assays, or to produce protein for isolation. These cells can be procaryotic or eucaryotic. Examples of procaryotic cells that can be used for expression include *Escherichia coli, Bacillus subtilis* and other bacteria. Examples of eucaryotic cells that can be used for expression include yeasts such as *Saccharomyces cerevisiae, Schizosaccharomyces pombe, Pichia pastoris* and other lower eucaryotic cells, and cells of higher eucaryotes such as those from insects and mammals, such as primary cells and cell lines such as CHO, HeLa, 3T3 and BHK cells, preferably COS cells and human kidney 293 cells, and more preferably Jurkat cells. (See, e.g., Ausubel, F. M. et al., eds. *Current Protocols in Molecular Biology,* Greene Publishing Associates and John Wiley & Sons, Inc., containing Supplements up through Supplement 42, 1998)).

In one embodiment, host cells that produce a recombinant FATP, or a portion thereof, a variant, or an ortholog of a FATP described herein by amino acid sequence, can be made as follows. A gene encoding a FATP, variant or a portion thereof can be inserted into a nucleic acid vector, e.g., a DNA vector, such as a plasmid, phage, cosmid, phagemid, virus, virus-derived vector (e.g., SV40, vaccinia, adenovirus, fowl pox virus, pseudorabies viruses, retroviruses) or other suitable replicon, which can be present in a single copy or multiple copies, or the gene can be integrated in a host cell chromosome. A suitable replicon or integrated gene can contain all or part of the coding sequence for a FATP or variant, operably linked to one or more expression control regions whereby the coding sequence is under the control of transcription signals and linked to appropriate translation signals to permit translation. The vector can be introduced into cells by a method appropriate to the type of host cells (e.g., transfection, electroporation, infection). For expression from the FATP gene, the host cells can be maintained under appropriate conditions (e.g., in the presence of inducer, normal growth conditions, etc.). Proteins or polypeptides thus produced can be recovered (e.g., from the cells, as in a membrane fraction, from the periplasmic space of bacteria, from culture medium) using suitable techniques. Appropriate membrane targeting signals may be incorporated into the expressed polypeptide. These signals may be endogenous to the polypeptide or they may be heterologous signals.

Polypeptides of the invention can be recovered and purified from cell cultures (or from their primary cell source) by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and high performance liquid chromatography. Known methods for refolding protein can be used to regenerate active conformation if the polypeptide is denatured during isolation or purification.

In a further aspect of the invention are methods for assessing the transport function of any of the fatty acid transport proteins or polypeptides described herein, including orthologs, and in variations of these, methods for identifying an inhibitor (or an enhancer) of such function and methods for assessing the transport function in the presence of a candidate inhibitor or a known inhibitor.

A variety of systems comprising living cells can be used for these methods. Cells to be used in fatty acid transport assays, and further in methods for identifying an inhibitor or enhancer of this function, express one or more FATPs. See Examples 3, 6, 9, 12 and 14 for data on tissue distribution of expression of FATPs, and Examples 10 and 11 describing recombinant cells expressing FATP. Cells for use in cell-based assays described herein can be drawn from a variety of sources, such as isolated primary cells of various organs and tissues wherein one or more FATPs are naturally expressed. In some cases, the cells can be from adult organs, and in some cases, from embryonic or fetal organs, such as heart, lung, liver, intestine, skeletal muscle, kidney and the like. Cells for this purpose can also include cells cultured as fragments of organs or in conditions simulating the cell type and/or tissue organization of organs, in which artificial materials may be used as substrates for cell growth. Other types of cells suitable for this purpose include cells of a cell strain or cell line (ordinarily comprising cells considered to be "transformed") transfected to express one or more FATPs.

A further embodiment of the invention is a method for detecting, in a sample of cells, a fatty acid transport protein, a portion or fragment thereof, a fusion protein comprising a FATP or a portion thereof, or an ortholog as described herein, wherein the cells can be, for instance, cells of a tissue, primary culture cells, or cells of a cell line, including cells into which nucleic acid has been introduced. The method comprises adding to the sample an agent that specifically binds to the protein, and detecting the agent specifically bound to the protein. Appropriate washing steps can be added to reduce nonspecific binding to the agent. The agent can be, for example, an antibody, a ligand or a substrate mimic. The agent can have incorporated into it, or have bound to it, covalently or by high affinity non-covalent interactions, for instance, a label that facilitates detection of the agent to which it is bound, wherein the label can be, but is not limited to, a phosphorescent label, a fluorescent label, a biotin or avidin label, or a radioactive label. The means of detection of a fatty acid transport protein can vary, as appropriate to the agent and label used. For example, for an antibody that binds to the fatty acid transport protein, the means of detection may call for binding a second antibody, which has been conjugated to an enzyme, to the antibody which binds the fatty acid transport protein, and detecting the presence of the second antibody by means of the enzymatic activity of the conjugated enzyme.

Similar principles can also be applied to a cell lysate or a more purified preparation of proteins from cells that may comprise a fatty acid transport protein of interest, for example in the methods of immunoprecipitation, inmmunoblotting, immunoaffinity methods, that in addition to detection of the particular FATP, can also be used in purification steps, and qualitative and quantitative immunoassays. See, for instance, chapters 11 through 14 in *Antibodies: A Laboratory Manual,* E. Harlow and D. Lane, eds., Cold Spring Harbor Laboratory, 1988.

Isolated fatty acid transport protein or, an antigenically similar portion thereof, especially a portion that is soluble, can be used in a method to select and identify molecules which bind specifically to the FATP. Fusion proteins comprising all of, or a portion of, the fatty acid transport protein linked to a second moiety not occurring in the FATP as found in nature, can be prepared for use in another embodiment of the method. Suitable fusion proteins for this purpose include those in which the second moiety comprises an affinity ligand (e.g., an enzyme, antigen, epitope). FATP fusion proteins can be produced by the insertion of a gene encoding the FATP or a variant thereof, or a suitable portion of such gene into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix.

In one embodiment, the fusion protein can be immobilized on a suitable affinity matrix under conditions sufficient to bind the affinity ligand portion of the fusion protein to the matrix, and is contacted with one or more candidate binding agents (e.g., a mixture of peptides) to be tested, under conditions suitable for binding of the binding agents to the FATP portion of the bound fusion protein. Next, the affinity matrix with bound fusion protein can be washed with a suitable wash buffer to remove unbound candidate binding agents and non-specifically bound candidate binding agents. Those agents which remain bound can be released by contacting the affinity matrix with fusion protein bound thereto with a suitable elution buffer. Wash buffer can be formulated to permit binding of the fusion protein to the affinity matrix, without significantly disrupting binding of specifically bound binding agents. In this aspect, elution buffer can be formulated to permit retention of the fusion protein by the affinity matrix, but can be formulated to interfere with binding of the candidate binding agents to the target portion of the fusion protein. For example, a change in the ionic strength or pH of the elution buffer can lead to release of specifically bound agent, or the elution buffer can comprise a release component or components designed to disrupt binding of specifically bound agent to the target portion of the fusion protein.

Immobilization can be performed prior to, simultaneous with, or after, contacting the fusion protein with candidate binding agent, as appropriate. Various permutations of the method are possible, depending upon factors such as the candidate molecules tested, the affinity matrix-ligand pair selected, and elution buffer formulation. For example, after the wash step, fusion protein with binding agent molecules bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with the candidate agent bound thereto. Bound agent molecules can then be released from the fusion protein or its cleavage product by an appropriate method, such as extraction.

One or more candidate binding agents can be tested simultaneously. Where a mixture of candidate binding agents is tested, those found to bind by the foregoing processes can be separated (as appropriate) and identified by suitable methods (e.g., PCR, sequencing, chromatography). Large libraries of candidate binding agents (e.g., peptides, RNA oligonucleotides) produced by combinatorial chemical synthesis or by other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rutter, W. J. et al. U.S. Pat. No. 5,010,175; Huebner, V. D. et al., U.S. Pat. No. 5,182,366; and Geysen, H. M., U.S. Pat. No. 4,833,092). Random sequence RNA libraries (see Ellington, A. D. et al., *Nature* 346:818–822 (1990); Bock, L. C. et al., *Nature* 355:584–566 (1992); and Szostak, J. W., *Trends in Biochem. Sci.* 17:89–93 (March, 1992)) can also be screened according to the present method to select RNA molecules which bind to a target FATP or FATP fusion protein. Where binding agents selected from a combinatorial library by the present method carry unique tags, identification of individual biomolecules by chromatographic methods is possible. Where binding agents do not carry tags, chromatographic separation, followed by mass spectrometry to ascertain structure, can be used to identify binding agents selected by the method, for example.

The invention also comprises a method for identifying an agent which inhibits interaction between a fatty acid transport protein (e.g., one comprising the amino acid sequence in SEQ ID NO:47, SEQ ID NO:49, SEQ ID NO:51, SEQ ID NO:53, SEQ ID NO:102, or SEQ ID NO:57), and a ligand of said protein. The FATP can be one described by amino acid sequence herein, a portion or fragment thereof, a variant thereof, or an ortholog thereof, or a FATP fusion protein. Here, a ligand can be, for instance, a substrate, or a substrate mimic, an antibody, or a compound, such as a peptide, that binds with specificity to a site on the protein. The method comprises combining, not limited to a particular order, the fatty acid protein, the ligand of the protein, and a candidate agent to be assessed for its ability to inhibit interaction between the protein and the ligand, under conditions appropriate for interaction between the protein and the ligand (e.g., pH, salt, temperature conditions conducive to appropriate conformation and molecular interactions); determining the extent to which the protein and ligand interact; and comparing (1) the extent of protein-ligand interaction in the presence of candidate agent with (2) the extent of protein-ligand interaction in the absence of candidate agent, wherein if (1) is less than (2), then the candidate agent is one which inhibits interaction between the protein and the ligand.

The method can be facilitated, for example, by using an experimental system which employs a solid support (column chromatography matrix, wall of a plate, microtiter wells, column pore glass, pins to be submerged in a solution, beads, etc.) to which the protein can be attached. Accordingly, in one embodiment, the protein can be fixed to a solid phase directly or indirectly, by a linker. The candidate agent to be tested is added under conditions conducive for interaction and binding to the protein. The ligand is added to the solid phase system under conditions appropriate for binding. Excess ligand is removed, as by a series of washes done under conditions that do not disrupt protein-ligand interactions. Detection of bound ligand can be facilitated by using a ligand that carries a label (e.g., fluorescent, chemiluminescent, radioactive). In a control experiment, protein and ligand are allowed to interact in the absence of any candidate agent, under conditions otherwise identical to those used for the "test" conditions where candidate inhibiting agent is present, and any washes used in the test conditions are also used in the control. The extent to which ligand binds to the protein in the presence of candidate agent is compared to the extent to which ligand binds to the protein in the absence of the candidate agent. If the extent to which interaction of the protein and the ligand occurs is less in the presence of the candidate agent than in the absence of the candidate agent, the candidate agent is an agent which inhibits interaction between the protein and the ligand of the protein.

In a further embodiment, an inhibitor (or an enhancer) of a fatty acid transport protein can be identified. The method comprises steps which are, or are variations of the following: contacting the cells with fatty acid, wherein the fatty acid can be labeled for convenience of detection; contacting a first aliquot of the cells with an agent being tested as an inhibitor (or enhancer) of fatty acid uptake while maintaining a second aliquot of cells under the same conditions but without contact with the agent; and measuring (e.g., quantitating) fatty acid in the first and second aliquots of cells; wherein a lesser quantity of fatty acid in the first aliquot compared to that in the second aliquot is indicative that the agent is an inhibitor of fatty acid uptake by a fatty acid transport protein. A greater quantity of fatty acid in the first aliquot compared to that in the second aliquot is indicative that the agent is an enhancer of fatty acid uptake by a fatty acid transport protein.

A particular embodiment of identifying an inhibitor or enhancer of fatty acid transport function employs the above steps, but also employs additional steps preceding those given above: introducing into cells of a cell strain or cell line ("host cells" for the intended introduction of, or after the introduction of, a vector) a vector comprising a fatty acid transport protein gene, wherein expression of the gene can be regulatable or constitutive, and providing conditions to the host cells under which expression of the gene can occur.

The terms "contacting" and "combining" as used herein in the context of bringing molecules into close proximity to each other, can be accomplished by conventional means. For example, when referring to molecules that are soluble, contacting is achieved by adding the molecules together in a solution. "Contacting" can also be adding an agent to a test system, such as a vessel containing cells in tissue culture.

The term "inhibitor" or "antagonist", as used herein, refers to an agent which blocks, diminishes, inhibits, hinders, limits, decreases, reduces, restricts or interferes with fatty acid transport into the cytoplasm of a cell, or alternatively and additionally, prevents or impedes the cellular effects associated with fatty acid transport. The term "enhancer" or "agonist", as used herein, refers to an agent which augments, enhances, or increases fatty acid transport into the cytoplasm of a cell. An antagonist will decrease fatty acid concentration, fatty acid metabolism and byproduct levels in the cell, leading to phenotypic and molecular changes.

In order to produce a "host cell" type suitable for fatty acid uptake assays and for assays derived therefrom for identifying inhibitors or enhancers thereof, a nucleic acid vector can be constructed to comprise a gene encoding a fatty acid transport protein, for example, human FATP1, FATP2, FATP3, FATP4, FATP5, FATP6, a mutant or variant thereof, an ortholog of the human proteins, such as mouse orthologs or orthologs found in other mammals, or a FATP family protein of origin in an organism other than a mammal. The gene of the vector can be regulatable, such as by the placement of the gene under the control of an inducible or repressible promoter in the vector (e.g., inducible or repressible by a change in growth conditions of the host cell harboring the vector, such as addition of inducer, binding or functional removal of repressor from the cell millieu, or change in temperature) such that expression of the FATP gene can be turned on or initiated by causing a change in growth conditions, thereby causing the protein encoded by the gene to be produced, in host cells comprising the vector, as a plasma membrane protein. Alternatively, the FATP gene can be constitutively expressed.

A vector comprising an FATP gene, such as a vector described herein, can be introduced into host cells by a means appropriate to the vector and to the host cell type. For example, commonly used methods such as electroporation, transfection, for instance, transfection using $CaCl_2$, and transduction (as for a virus or bacteriophage) can be used. Host cells can be, for example, mammalian cells such as primary culture cells or cells of cell lines such as COS cells, 293 cells or Jurkat cells. Host cells can also be, in some cases, cells derived from insects, cells of insect cell lines, bacterial cells, such as *E. coli,* or yeast cells, such as *S. cerevisiae.* It is preferred that the fatty acid transport protein whose function is to be assessed, with or without a candidate inhibitor or enhancer, be produced in host cells whose ancestor cells originated in a species related to the species of origin of the FATP gene encoding the fatty acid transport protein. For example, it is preferable that tests of function or of inhibition or enhancement of a mammalian FATP be carried out in host mammalian cells producing the FATP, rather than bacterial cells or yeast cells.

Host cells comprising a vector comprising a regulatable FATP gene can be treated so as to allow expression of the FATP gene and production of the encoded protein (e.g., by contacting the cells with an inducer compound that effects transcription from an inducible promoter operably linked to the FATP gene).

The test agent (e.g., an agonist or antagonist) is added to the cells to be used in a fatty acid transport assay, in the presence or absence of test agent, under conditions suitable for production and/or maintenance of the expressed FATP in a conformation appropriate for association of the FATP with test agent and substrate. For example, conditions under which an agent is assessed, such as media and temperature requirements, can, initially, be similar to those necessary for transport of typical fatty acid substrates across the plasma membrane. One of ordinary skill in the art will know how to vary experimental conditions depending upon the biochemical nature of the test agent. The test agent can be added to the cells in the presence of fatty acid, or in the absence of fatty acid substrate, with the fatty acid substrate being added following the addition of the test agent. The concentration at which the test agent can be evaluated can be varied, as appropriate, to test for an increased effect with increasing concentrations.

Test agents to be assessed for their effects on fatty acid transport can be any chemical (element, molecule, compound), made synthetically, made by recombinant techniques or isolated from a natural source. For example, test agents can be peptides, polypeptides, peptoids, sugars, hormones, or nucleic acid molecules, such as antisense nucleic acid molecules. In addition, test agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Test agents can also be natural or genetically engineered products isolated from lysates of cells, bacterial, animal or plant, or can be the cell lysates themselves. Presentation of test compounds to the test system can be in either an isolated form or as mixtures of compounds, especially in initial screening steps.

Thus, the invention relates to a method for identifying agents which alter fatty acid transport, the method comprising providing the test agent to the cell (wherein "cell" includes the plural, and can include cells of a cell strain, cell line or culture of primary cells or organ culture, for example), under conditions suitable for binding to its target, whether to the FATP itself or to another target on or in the cell, wherein the transformed cell comprises a FATP.

In greater detail, to test one or more agents or compounds (e.g., a mixture of compounds can conveniently be screened initially) for inhibition of the transport function of a fatty acid transport protein, the agent(s) can be contacted with the cells. The cells can be contacted with a labeled fatty acid. The fatty acid can be, for example, a known substrate of the fatty acid transport protein such as oleate or palmitate. The fatty acid can itself be labeled with a radioactive isotope, (e.g., $^{3}H$ or $^{14}C$) or can have a radioactively labeled adduct attached. In other variations, the fatty acid can have chemically attached to it a fluorescent label, or a substrate for an enzyme occurring within the cells, wherein the substrate yields a detectable product, such as a highly colored or fluorescent product. Addition of candidate inhibitors and labeled substrate to the cells comprising fatty acid transport protein can be in either order or can be simultaneous.

A second aliquot of cells, which can be called "control" cells (a "first" aliquot of cells can be called "test" cells), is treated, if necessary (as in the case of transformed "host" cells), so as to allow expression of the FATP gene, and is contacted with the labeled substrate of the fatty acid transport protein. The second aliquot of cells is not contacted with one or more agents to be tested for inhibition of the transport function of the protein produced in the cells, but is otherwise kept under the same culture conditions as the first aliquot of cells.

In a further step of a method to identify inhibitors of a fatty acid transport protein, the labeled fatty acid is measured in the first and second aliquots of cells. A preliminary step of this measurement process can be to separate the external medium from the cells so as to be able to distinguish the labeled fatty acid external to the cells from that which has been transported inside the cells. This can be accomplished, for instance, by removing the cells from their growth container, centrifuging the cell suspension, removing the supernatant and performing one or more wash steps to extensively dilute the remaining medium which may contain labeled fatty acid. Detection of the labeled fatty acid can be by a means appropriate to the label used. For example, for a radioactive label, detection can be by scintillation counting of appropriately prepared samples of cells (e.g., lysates or protein extracts); for a fluorescent label, by measuring fluorescence in the cells by appropriate instrumentation.

If a compound tested as a candidate inhibitor of transport function causes the test cells to have less labeled fatty acid detected in the cells than that detected in the control cells, then the compound is an inhibitor of the fatty acid transport protein. Procedures analogous to those above can be devised for identifying enhancers (agonists of FATPs) of fatty acid transport function wherein if the test cells contain more labeled fatty acid than that detected in the control cells, or if the fatty acid is taken up at a higher rate, then the compound being tested can be concluded to be an enhancer of the fatty acid transport protein.

Example 13 describes use of an assay of this type to identify an inhibitor of a FATP. In Example 13, an antisense oligonucleotide which specifically inhibits biosynthesis of mmFATP4 was demonstrated to inhibit fatty acid uptake into mouse enterocytes. Similarly, antisense oligonucleotides directed towards specifically inhibiting the biosynthesis of FATP6 in heart cells, FATP5 in liver cells, FATP3 in lung cells, and FATP2 in colon cells, can be demonstrated as examples of "test agents" that inhibit fatty acid transport.

Another assay to determine whether an agent is an inhibitor (or enhancer) of fatty acid transport employs animals, one or more of which are administered the agent, and one or more of which are maintained under similar conditions, but are not administered the agent. Both groups of animals are given fatty acids (e.g., orally, intravenously, by tube inserted into stomach or intestine), and the fatty acids taken up into a bodily fluid (e.g., serum) or into an organ or tissue of interest are measured from comparable samples taken from each group of animals. The fatty acids may carry a label (e.g., radioactive) to facilitate detection and quantitation of fatty acids taken up into the fluid or tissue being sampled.

This type of assay can be used alone or can be used in addition to in vitro assays of a candidate inhibitor or enhancer.

An agent determined to be an inhibitor (or enhancer) of FATP function, such as fatty acid binding and/or fatty acid uptake, can be administered to cells in culture, or in vivo, to a mammal (e.g. human) to inhibit (or enhance) FATP function. Such an agent may be one that acts directly on the FATP (for example, by binding) or can act on an intermediate in a biosynthetic pathway to produce FATP, such as transcription of the FATP gene, processing of the mRNA, or translation of the mRNA. An example of such an agent is antisense oligonucleotide.

Antisense methods similar to those illustrated in Example 13 can be used to determine the target FATP of a compound or agent that has an inhibitory or enhancing effect on fatty acid uptake. For example, antisense oligonucleotide directed to the inhibition of FATP4 biosynthesis can be added to lung cells or cell lines derived from lung cells. In addition, antisense oligonucleotides directed to the inhibition of other FATPs, except for FATP3, can also be added to the lung cells. The administration of antisense oligonucleotides in this manner ensures that the predominant FATP activity remaining in the cells comes from FATP3. After a period of incubation of the cells with the antisense oligonucleotides sufficient to deplete the plasma membrane of the FATPs whose biosynthesis has been inhibited, a test agent, preferably one that has been shown by some preliminary test to have an inhibitory or enhancing activity on fatty acid transport, can be added to the lung cells. If the test agent is now demonstrated, after treatment of the cells with antisense oligonucleotides, to have an inhibitory or enhancing activity on fatty acid transport in the lung cells, it can be concluded that the target of the test agent is FATP3, or a molecule involved in the biosynthesis or activity of FATP3.

In another type of cell-based assay for uptake of fatty acids, a change of intracellular pH resulting from the uptake of fatty acids can be followed by an indicator fluorophore. The fluorophore can be taken up by the cells in a preincubation step. Fatty acids can be added to the cell medium, and after some period of incubation to allow FATP-mediated uptake of fatty acids, the change in $\lambda_{max}$ of fluorescence can be measured, as an indicator of a change in intracellular pH, as the $\lambda_{max}$ of fluorescence of the fluorophore changes with the pH of its environment, thereby indicating uptake of fatty acids. One such fluorophore is BCECF (2', 7'-bis(2-carboxyethyl)-5(6)-carboxyfluorescein; Rink, T. J. et al., *J. Cell. Biol.* 95: 189 (1982)).

In assays similar to those described above, a candidate inhibitor or enhancer of fatty acid transport function can be added (or mock-added, for control cultures) to cultures of cells engineered to express a desired FATP to which fatty acid substrate is also added. Inhibition of fatty acid uptake is indicated by a lack of the drop in pH, indicating fatty acid uptake, that is seen in control cells. Enhancement of fatty acid uptake is indicated by a decrease in intracellular pH, as compared to control cells not receiving the candidate enhancer of fatty acid transport function.

Yeast cells can be used in a similar cell-based assay for the uptake of fatty acids mediated by a FATP, and such an assay can be adapted to a screening assay for the identification of agents that inhibit or enhance fatty acid uptake by an FATP. Yeast cells lacking an endogenous FATP activity (mutated, disrupted or deleted for FAT1; Faergeman, N. J. et al., *J. Biol. Chem.* 272(13):8531–8538 (1997); Watkins, P. A. et al., *J. Biol. Chem.* 273(29):18210–18219 (1998)) can be engineered to harbor a related gene of the family of FATP-encoding genes, such as a mammalian FATP (e.g., human FATP4).

Examples of expression vectors include pEG (Mitchell, D. A., et al., *Yeast* 9:715–723 (1993)) and pDAD1 and pDAD2, which contain a GAL1 promoter (Davis, L. I. and Fink, G. R., *Cell* 61:965–978 (1990)). A variety of promoters are suitable for expression. Available yeast vectors offer a choice of promoters. In one embodiment, the inducible GAL1 is used. In another embodiment, the constitutive ADH1 promoter (alcohol dehyrodrogenase; Bennetzen, J. L. and Hall, B. D., *J. Biol. Chem.* 257:3026–3031 (1982)) can be used to express an inserted gene on glucose-containing media. An example of a vector suitable for expression of a heterologous FATP gene in yeast is pQB169.

With the introduced FATP gene providing the only fatty acid transport protein function for the yeast cells, it is possible to study effect of the heterologous FATP on fatty acid transport into the yeast cells in isolation. Assays for the uptake of fatty acids into the yeast cells can be devised that are similar to those described above and/or those assays that have been illustrated in the Examples. Tests for candidate inhibitors or enhancers of the heterologous FATP can be done in cultures of yeast cells, wherein the yeast cells are incubated with fatty acid substrate and an agent to be tested as an inhibitor or enhancer of FATP function. FATP uptake after a period of time can be measured by analyzing the contents of the yeast cells for fatty acid substrate, as compared with control yeast cells incubated with the fatty acid, but not with the test agent. Yeast cells have the additional advantage, over mammalian cells in culture, for example, that yeast cells can be forced to rely upon fatty acids as their only source of carbon, if the growth medium supplied to the yeast cells is formulated to contain no other source of carbon. Thus, the effect of the heterologous FATP on fatty acid uptake and metabolism in the engineered yeast cells can be amplified. An agent that efficiently blocks transport function of the heterologous FATP could result in death of the yeast cells. Thus, in this case, inhibition of function of the heterologous FATP can result in loss of viability. A simple measure of viability is turbidity of the yeast suspension culture, which can be adapted to a high throughput screening assay for effects of various agents to be tested, using microtiter plates or similar devices for small-volume cultures of the engineered yeast cells.

Cell-free assays can also be used to measure the transport of fatty acids across a membrane, and therefor also to assess a test treatment or test agent for its effect on the rate or extent of fatty acid transport. An isolated FATP, for example in the presence of a detergent that preserves the native 3-dimensional structure of the FATP, or partially purified FATP, can be used in an artificial membrane system typically used to preserve the native conformation and activity of membrane proteins. Such systems include liposomes, artificial bilayers of phospholipids, isolated plasma membrane such as cell membrane fragments, cell membrane fractions, or cell membrane vesicles, and other systems in which the FATP can be properly oriented within the membrane to have transport activity. Assays for transport activity can be performed using methods analogous to those that can be used in cells engineered to predominantly express one FATP whose function is to be measured. A labeled (e.g., radioactively labeled) fatty acid substrate can be incubated with one side of a bilayer or in a suspension of liposomes constructed to integrate a properly oriented FATP. The accumulation of fatty acids with time can be measured, using appropriate means to detect the label (e.g., scintillation counting of medium on each side of the bilayer, or of the contents of liposomes isolated from the surrounding medium). Assays such as these can be adapted to use for the testing of agents which might interact with the FATP to produce an inhibitory or an enhancing effect on the rate or extent of fatty acid transport. That is, the above-described assay can be done in the presence or absence of the agent to be tested, and the results compared.

For examples of isolation of membrane proteins (ADP/ATP carrier and uncoupling protein), reconstitution into phospholipid vesicles, and assays of transport, see Klingenberg, M. et al., *Methods Enzymol.* 260:369–389 (1995). For an example of a membrane protein (phosphate carrier of *Saccharomyces cerevisiae*) that was purified and solubilized from *E. coli* inclusion bodies, see Schroer, A. et al., *J. Biol. Chem.* 273: 14269–14276 (1998). The Glut1 glucose transporter of rat has been expressed in yeast. A crude membrane fraction of the yeast was prepared and reconstituted with soybean phospholipids into liposomes. Glucose transport activity could be measured in the liposomes (Kasahara, T. and Kasahara, M., *J. Biol. Chem.* 273: 29113–29117 (1998)). Similar methods can be applied to the proteins and polypeptides of the invention.

Another embodiment of the invention is a method for inhibiting fatty acid uptake in a mammal (e.g., a human), comprising administering to the mammal a therapeutically effective amount of an inhibitor of the transport function of one or more of the fatty acid transport proteins, thereby decreasing fatty acid uptake by cells comprising the fatty acid protein(s). Where it is desirable to reduce the uptake of fatty acids, for example, in the treatment of chronic obesity or as a part of a program of weight control or hyperlipidemia control in a human, one or more inhibitors of one or more of the fatty acid transport proteins can be administered in an effective dose, and by an effective route, for example, orally, or by an indwelling device that can deliver doses to the small intestine. The inhibitor can be one identified by methods described herein, or can be one that is, for instance, structurally related to an inhibitor identified by methods described herein (e.g., having chemical adducts to better stabilize or solubilize the inhibitor). The invention further relates to compositions comprising inhibitors of fatty acid uptake in a mammal, which may further comprise pharmaceutical carriers suitable for administration to a subject mammal, such as sterile solubilizing or emulsifying agents.

A further embodiment of the present invention is a method of enhancing or increasing fatty acid uptake, such as enhancing or increasing LCFA uptake in the small intestine (e.g., to treat or prevent a malabsorption syndrome or other wasting condition) or in the liver (e.g., by an enhancer of FATP5 transport activity to treat acute liver failure) or in the kidney (e.g., by an enhancer of FATP2 transport activity to treat kidney failure). In this embodiment, a therapeutically effective amount of an enhancer of the transport function of one or more of the fatty acid transport proteins can be administered to a mammalian subject, with the result that fatty acid uptake in the small intestine is enhanced. In this embodiment, one or more enhancers of one or more of fatty acid transport proteins is administered in an effective dose and by a route (e.g., orally or by a device, such as an indwelling catheter or other device) which can deliver doses to the gut. The enhancer of FATP function (e.g., an enhancer of FATP4 function) can be identified by methods described herein or can be one that is structurally similar to an enhancer identified by methods described herein.

Aerobic reperfusion of ischemic myocardium is a common clinical event which can occur during such treatments as cardiac surgery, angioplasty, and thrombolytic therapy after a myocardial infarction. During reperfusion, a rapid recovery of myocardial energy production is essential for the complete recovery of contractile function. Not only the extent of recovery of myocardial energy metabolism but also the type of energy substrate used by the heart during reperfusion are important determinants of functional recovery. Circulating fatty acid levels increase following acute myocardial infarction or during cardiac surgery, such that during and following ischemia the heart muscle can be exposed to very high concentrations of fatty acids (Lopaschuk, G. D. and W. C. Stanley, *Science and Medicine* (November/December 1997)). High plasma fatty acid concentrations increase the severity of ischemic damage in a number of experimental models of cardiac ischemia and have been linked to depression of mechanical function during aerobic reperfusion of previously ischemic hearts. Further data show that modifying fatty acid utilization can be beneficial for heart function in ischemia and can be a useful approach for the treatment of angina. See, e.g., Desideri and Celegon, *Am. J. Cardiol.* 82(5A):50K–53K; Lopaschuk, *Am. J. Cardiol.* 82(5A):14K–17K. Plasma fatty acid concentrations can be reduced by administering to a human subject or other mammal an effective amount of an inhibitor of a FATP such as FATP2 or FATP4, thereby providing a way of reducing fatty acid utilization by the heart.

In a further embodiment of the invention, a therapeutically effective amount of an inhibitor of hsFATP6 can be administered to a human patient by a suitable route, to reduce the uptake of fatty acids by cardiac muscle. This treatment is desirable in patients who are diagnosed as having, or who are at risk of, abnormal accumulations of fatty acids in the heart or a detrimentally high rate of uptake of fatty acids into the heart, because of ischemic heart disease, or following ischemia or trauma to the heart.

The invention further relates to antibodies that bind to an isolated or recombinant fatty acid transport protein of the FATP family, including portions of antibodies, which can specifically recognize and bind to one or more FATPs. The antibodies and portions thereof of the invention include those which bind to one or more FATPs of mouse or other mammalian species. In a preferred embodiment, the antibodies specifically bind to a naturally occurring FATP of humans. The antibodies can be used in methods to detect or to purify a protein of the present invention or a portion thereof by various methods of inumunoaffinity chromatography, to inhibit the function of a protein in a method of therapy, or to selectively inactivate an active site, or to study other aspects of the structure of these proteins, for example.

The antibodies of the present invention can be polyclonal or monoclonal. The term antibody is intended to encompass both polyclonal and monoclonal antibodies. Antibodies of the present invention can be raised against an appropriate immunogen, including proteins or polypeptides of the present invention, such as an isolated or recombinant FATP1, FATP2, FATP3, FATP4, FATP5, FATP6, mtFATP, ceFATPa, ceFATPb, scFATP or portions thereof, or synthetic molecules, such as synthetic peptides (e.g., conjugated to a suitable carrier). Preferred embodiments are antibodies that bind to any of the following: hsFATP1, hsFATP2, hsFATP3, hsFATP4, hsFATP5 or hsFATP6. The immunogen can be a polypeptide comprising a portion of a FATP and having at least one function of a fatty acid transport protein, as described herein.

The term antibody is also intended to encompass single chain antibodies, chimeric, humanized or primatized (CDR-grafted) antibodies and the like, as well as chimeric or CDR-grafted single chain antibodies, comprising portions from more than one species. For example, the chimeric antibodies can comprise portions of proteins derived from two different species, joined together chemically by conventional techniques or prepared as a single contiguous protein using genetic engineering techniques (e.g., DNA encoding the protein portions of the chimeric antibody can be expressed to produce a contiguous protein chain. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., U.S. Pat. No. 5,585,089; and Queen et al., European Patent No. EP 0 451 216 B1. See also, Newman, R. et al., *BioTechnology,* 10:1455–1460 (1992), regarding primatized antibody, and Ladner et al., U.S. Pat. No. 4,946, 778 and Bird, R. E. et al., *Science,* 242:423–426 (1988) regarding single chain antibodies.)

Whole antibodies and biologically functional fragments thereof are also encompassed by the term antibody. Biologically functional antibody fragments which can be used include those fragments sufficient for binding of the antibody fragment to a FATP to occur, such as Fv, Fab, Fab' and $F(ab')_2$ fragments. Such fragments can be produced by enzymatic cleavage or by recombinant techniques. For instance, papain or pepsin cleavage can generate Fab or $F(ab')_2$ fragments, respectively. Antibodies can also be produced in a variety of truncated forms using antibody genes in which one or more stop codons have been introduced upstream of the natural stop site. For example, a chimeric gene encoding a $F(ab')_2$ heavy chain portion can be designed to include DNA sequences encoding the $CH_1$ domain and hinge region of the heavy chain.

Preparation of immunizing antigen (whole cells comprising FATP on the cell surface or purified FATP), and polyclonal and monoclonal antibody production can be performed using any suitable technique. A variety of methods have been described (See e.g., Kohler et al., *Nature,* 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); Chapter 11 In *Current Protocols In Molecular Biology,* Vol. 2 (containing supplements up through Supplement 42, 1998), Ausubel, F. M. et al., eds., (John Wiley & Sons: New York, N.Y.)). Generally, a hybridoma can be produced by fusing a suitable immortal cell line (e.g., a myeloma cell line such as SP2/0) with antibody producing cells. The antibody producing cells, preferably those obtained from the spleen or lymph nodes, can be obtained from animals immunized with the antigen of interest. Immunization of animals can be by introduction of whole cells comprising fatty acid transport protein on the cell surface. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies (including human antibodies) of the requisite specificity can used, including, for example, methods which select recombinant antibody from a library (e.g., Hoogenboom et al., WO 93/06213; Hoogenboom et al., U.S. Pat. No. 5,565, 332; WO 94/13804, published Jun. 23, 1994; and Dower, W. J. et al., U.S. Pat. No. 5,427,908), or which rely upon immunization of transgenic animals (e.g., mice) capable of producing a full repertoire of human antibodies (see e.g., Jakobovits et al., *Proc. Natl. Acad. Sci. USA,* 90: 2551–2555 (1993); Jakobovits et al., *Nature,* 362:255–258 (1993); Lonberg et al., U.S. Pat. No. 5,569,825; Lonberg et al., U.S. Pat. No. 5,545,806; Surani et al., U.S. Pat. No. 5,545,807; and Kucherlapati, R. et al., European Patent No. EP 0 463 151 B1).

Another aspect of the invention is a method for directing an agent to cardiac muscle. The differential expression of FATP6 in cardiac muscle but not in other tissue types allows for the specific targeting of drugs, diagnostic agents, tagging labels, histological stains or other substances specifically to cardiac muscle. A targeting vehicle can be used for the delivery of such a substance. Targeting vehicles which bind specifically to FATP6 can be linked to a substance to be delivered to the cells of cardiac muscle. The linkage can be, for instance, via one or more covalent bonds, or by high affinity non-covalent bonds. A targeting vehicle can be an antibody, for instance, or other compound (e.g., a fatty acid or fatty acid analog) which binds to FATP6 with high specificity.

Targeting vehicles specific to the heart-specific protein FATP6 have in vivo (e.g., therapeutic and diagnostic) applications. For example, an antibody which specifically binds to FATP6 can be conjugated to a drug to be targeted to the heart (e.g., a cardiac glycoside to treat congestive heart failure, or P-adrenergic agents, sodium channel blockers or calcium channel blockers to treat arrhythmias). A substance (e.g., a radioactive substance) which can be detected (e.g., a label) in viva can also be linked to a targeting vehicle which specifically binds to a heart-specific protein such as FATP6, and the conjugate can be used as a labeling agent to identify cardiac muscle cells.

Targeting vehicles specific to FATP6 find further applications in vitro. For example, an FATP6-specific targeting vehicle, such as an antibody (a polyclonal preparation or monoclonal) which specifically binds to FATP6, can be linked to a substance which can be used as a stain for a tissue sample (e.g., horseradish peroxidase) to provide a method for the identification of cardiac muscle in a sample, as can be used in embryology studies, for example.

In a similar manner, an agent can be directed to the liver of a mammal, as FATP5 is expressed in liver but not in other tissue types. A targeting vehicle which specifically binds to FATP5 can be conjugated to a drug for delivery of the drug to the liver, such as a drug to treat hepatitis, Wilson's disease, lipid storage diseases and liver cancer. As with targeting vehicles specific to FATP6, targeting vehicles specific to FATP5 can be used in studying tissue samples in vitro.

The invention also relates to compositions comprising a modulator of FATP function. The term "modulate" as used herein refers to the ability of a molecule to alter the function of another molecule. Thus, modulate could mean, for example, inhibit, antagonize, agonize, upregulate, downregulate, induce, or suppress. A modulator has the capability of altering function of its target. Such alteration can be accomplished at any stage of the transcription, translation, expression or function of the protein, so that, for example, modulation of a target gene can be accomplished by modulation of the DNA or RNA encoding the protein, and the protein itself.

Antagonists or agonists (inhibitors or enhancers) of the FATPs of the invention, antibodies that bind a FATP, or mimetics of a FATP can be employed in combination with a non-sterile or sterile carrier or carriers for use with cells, tissues or organisms, such as a pharmaceutical carrier suitable for administration to a mammalian subject. Such compositions comprise, for instance, a media additive or a therapeutically effective amount of an inhibitor or enhancer compound to be identified by an assay of the invention and a pharmaceutically acceptable carrier or excipient. Such carriers may include, but are not limited to, saline, buffered saline, dextrose, water, ethanol, surfactants, such as glycerol, excipients such as lactose and combinations thereof. The formulation can be chosen by one of ordinary skill in the art to suit the mode of administration. The chosen route of administration will be influenced by the predominant tissue or organ location of the FATP whose function is to be inhibited or enhanced. For example, for affecting the function of FATP4, a preferred administration can be oral or through a tube inserted into the stomach (e.g., direct stomach tube or nasopharyngeal tube), or through other means to accomplish delivery to the small intestine. The invention further relates to diagnostic and pharmaceutical packs and kits comprising one or more containers filled with one or more of the ingredients of the aforementioned compositions of the invention.

Compounds of the invention which are FATPs, FATP fusion proteins, FATP mimetics, FATP gene-specific antisense poly- or oligonucleotides, inhibitors or enhancers of a FATP may be employed alone or in conjunction with other compounds, such as therapeutic compounds. The pharmaceutical compositions may be administered in any effective, convenient manner, including administration by topical, oral, anal, vaginal, intravenous, intraperitoneal, intramuscular, subcutaneous, intranasal, transdermal or intradermal routes, among others. In therapy or as a prophylactic, the active agent may be administered to an individual as an injectable composition, for example as a sterile aqueous dispersion, preferably isotonic.

Alternatively, the composition may be formulated for topical application, for example, in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions.

In addition, the amount of the compound will vary depending on the size, age, body weight, general health, sex, and diet of the host, and the time of administration, the biological half-life of the compound, and the particular characteristics and symptoms of the disorder to be treated. Adjustment and manipulation of established dose ranges are well within the ability of those of skill in the art.

A further aspect of the invention is a method to identify a polymorphism, or the presence of an alternative or variant allele of a gene in the genome of an organism (of interest here, genes encoding FATPs). As used herein, polymorphism refers to the occurrence of two or more genetically determined alternative sequences or alleles in a population. A polymorphic locus may be as small as a base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified alleleic form, or the most frequently occurring form can be arbitrarily designated as the reference (usually, "wildtype") form, and other allelic forms are designated as alternative (sometimes, "mutant" or "variant"). Dipolid organisms may be homozygous or heterozygous for allelic forms.

An "allele" or "allelic sequence" is an alternative form of a gene which may result from at least one mutation in the nucleotide sequence. Alleles may result in altered mRNAs or polypeptides whose structure or function may or may not be altered. Any given gene may have none, one, or many allelic forms (polymorphism). Common mutational changes which give rise to alleles are generally ascribed to natural deletions, additions, or substitutions of nucleotides. Each of these types of changes may occur alone, or in combination with the others, one or more times in a given sequence.

Several different types of polymorphisms have been reported. A restriction fragment length polymorphism (RFLP) is a variation in DNA sequence that alters the length of a restriction fragment (Botstein et al., *Am. J. Hum. Genet.* 32:314–331 (1980)). The restriction fragment length polymorphism may create or delete a restriction site, thus changing the length of the restriction fragment. RFLPs have been widely used in human and animal genetic analyses (see WO 90/13668; WO 90/11369; Donis-Keller, *Cell* 51:319–337 (1987); Lander et al., *Genetics* 121:85–99 (1989)). When a heritable trait can be linked to a particular RFLP, the presence of the RFLP in an individual can be used to predict the likelihood that the individual will also exhibit the trait.

Other polymorphisms take the form of short tandem repeats (STRs) that include tandem di-, tri- and tetranucleotide repeated motifs. These tandem repeats are also referred to as variable number tandem repeat (VNTR) polymorphisms. VNTRs have been used in identity and paternity analysis (U.S. Pat. No. 5,075,217; Armour et al., *FEBS Lett.* 307:113–115 (1992); Horn et al., WO 91/14003; Jeffreys, EP 370,719), and in a large number of genetic mapping studies.

Other polymorphisms take the form of single nucleotide variations between individuals of the same species. Such polymorphisms are far more frequent than RFLPs, STRs (short tandem repeats) and VNTRs (variable number tandem repeats). Some single nucleotide polymorphisms occur in protein-coding sequences, in which case, one of the polymorphic forms may give rise to the expression of a defective or other variant protein arid, potentially, a genetic disease. Other single nucleotide polymorphisms occur in noncoding regions. Some of these polymorphisms may also result in defective protein expression (e.g., as a result of defective splicing). Other single nucleotide polymorphisms have no phenotypic effects.

Many of the methods described below require amplification of DNA from target samples and purification of the amplified products. This can be accomplished by PCR, for instance. See generally, *PCR Technology, Principles and Applications for DNA Amplification* (ed. H. A. Erlich), Freeman Press, New York, N.Y., 1992; *PCR Protocols: A Guide to Methods and Applications* (eds. Innis, et al.), Academic Press, San Diego, Calif., 1990; Mattila et al., *Nucleic Acids Res.* 19:4967 (1991); Eckert et al., *PCR Methods and Applications* 1:17 (1991); *PCR* (eds. McPherson et al., IRS Press, Oxford); and U.S. Pat. No. 4,683,202.

Other suitable amplification methods include the ligase chain reaction (LCR) (see Wu and Wallace, *Genomics* 4:560 (1989); Landegren et al., *Science* 241:1077 (1988)), transcription amplification (Kwoh et al., *Proc. Natl. Acad. Sci. USA* 86:1173 (1989), self-sustained sequence replication (Guatelli et al., *Proc. Natl. Acad. Sci. USA* 87:1874 (1990), and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

Another aspect of the invention is a method for detecting a variant allele of a human FATP gene, comprising preparing amplified, purified FATP DNA from a reference human and amplified, purified, FATP DNA from a "test" human to be compared to the reference as having a variant allele, using the same or comparable amplification procedures, and determining whether the reference DNA and test DNA differ in DNA sequence in the FATP gene, whether in a coding or a noncoding region, wherein, if the test DNA differs in sequence from the reference DNA, the test DNA comprises a variant allele of a human FATP gene. The following is a discussion of some of the methods by which it can be determined whether the reference FATP DNA and test FATP DNA differ in sequence.

Direct Sequencing. The direct analysis of the sequence of variant alleles of the present invention can be accomplished using either the dideoxy chain termination method or the Maxam and Gilbert method (see Sambrook et al., *Molecular Cloning: A Laboratory Manual,* 2nd ed., Cold Spring Harbor Press, New York 1989; Zyskind et al., *Recombinant DNA Laboratory Manual,* Acad. Press, 1988)).

Denaturing Gradient Gel Electrophoresis. Amplification products generated using the polymerase chain reaction can be analyzed by the use of denaturing gradient gel eletrophoresis. Different alleles can be identified based on the different sequence-dependent strand dissociation properties and electrophoretic migration of DNA in solution (chapter 7 in Erlich, ed. *PCR Technology, Principles and Applications for DNA Amplification,* W. H. Freeman and Co., New York, 1992).

Single-strand Conformation Polymorphism Analysis. Alleles of target sequences can be differentiated using single-strand conformation polymorphism analysis, which identifies base differences by alteration in electrophoretic migration of single stranded PCR products, as described in Orita et al., *Proc. Natl. Acad. Sci. USA* 86:2766–2770 (1989). Amplified PCR products can be generated as described above, and heated or otherwise denatured, to form single-stranded amplification products. Single-stranded nucleic acids may refold or form secondary structures which are partially dependent on the base sequence. The different electrophoretic mobilities of single-stranded amplification products can be related to base-sequence differences between alleles of target sequences.

Detection of Binding by Protein That Binds to Mismatches. Amplified DNA comprising the FATP gene or portion of the gene of interest from genomic DNA, for example, of a normal individual is prepared, using primers designed on the basis of the DNA sequences provided herein. Amplified DNA is also prepared, in a similar manner, from genomic DNA of an individual to be tested for bearing a distinguishable allele. The primers used in PCR carry different labels, for example, primer 1 with biotin, and primer 2 with $^{32}P$. Unused primers are separated form the PCR products, and the products are quantitated. The heteroduplexes are used in a mismatch detection assay using immobilized mismatch binding protein (MutS) bound to nitrocellulose. The presence of biotin-labeled DNA wherein mismatched regions are bound to the nitrocellulose via MutS protein, is detected by visualizing the binding of streptavidin to biotin. See WO 95/12689. MutS protein has also been used in the detection of point mutations in a gel-mobility-shift assay (Lishanski, A. et al., *Proc. Natl. Acad. Sci. USA* 91:2674–2678 (1994)).

Other methods, such as those described below, can be used to distinguish a FATP allele from a reference allele, once a particular allele has been characterized as to DNA sequence.

Allele-specific probes. The design and use of allele-specific probes for analyzing polymorphims is described by e.g., Saiki et al., *Nature* 324:163–166 (1986); Dattagupta, EP 235,726, Saiki, WO 89/11548. Allele-specific probes can be designed so that they hybridize to a segment of a target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15-mer at the 7 position; in a 16-mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

Allele-specific Primers. An allele-specific primer hybridizes to a site on target DNA overlapping a polymorphism, and only primes amplification of an allelic form to which the primer exhibits perfect complementarity. See Gibbs, *Nucleic Acid Res.* 17:2427–2448 (1989). This primer is used in conjunction with a second primer which hybridizes at a distal site. Amplification proceeds from the two primers, resulting in a detectable product which indicates the particular allelic form is present. A control is usually performed with a second pair of primers, one of which shows a single base mismatch at the polymorphic site and the other of which exhibits perfect complementarity to a distal site. The single-base mismatch prevents amplification and no detectable product is formed. The method works best when the mismatch is included in the 3'-most position of the oligonucleotide aligned with the polymorphism because this position is most destabilizing to elongation from the primer (see, e.g., WO 93/22456).

Gene Chips. Allelic variants can also be identified by hybridization to nucleic acids immobilized on solid supports (gene chips), as described, for example, in WO 95/11995 and U.S. Pat. No. 5,143,854, both of which are incorporated herein by reference. WO 95/11995 describes subarrays that are optimized for detection of a characterized variant allele. Such a subarray contains probes designed to be complementary to a second reference sequence, which is an allelic valiant of the first reference sequence.

The present method is illustrated by the following examples, which are not intended to be limiting in any way.

EXAMPLES

Materials and Methods

The following Materials and Methods were used in the work described in Examples 1–5.

Sequence Alignment of FATP Clones. The DNA sequence for mouse FATP1 was obtained from the National Center for Biotechnology Information nonredundant database. cDNAs for mmFATP2, 3, 4, and 5 were obtained by screening mouse expression libraries (purchased from GIBCO/BRL) with probes derived from the cloned expressed sequence tags (ESTS) (Research Genetics, Huntsville, Ala.). Full-length clones were obtained for mmFATP2 and 5 and partial sequences for mmFATP3 and 4. The sequences described herein have been deposited in the GenBank database (Accession Nos. FATP2, AF072760; FATP3, AF072759; FATP4, AF072758; FATP5, AF072757).

Neither FATP2 nor FATP5 contains an in-frame stop codon upstream of the putative initiator methionine; initiator methionines were assigned by homology with that in mmFATP1 and by the presence of a signal sequence immediately after it. The *Mycobacterium tuberculosis, Caenorhabditis elegans,* and *Saccharomyces cerevisiae* sequences were present in the dbEST database as part of the sequencing projects for these organisms. Sequences were aligned utilizing a ClustalX algorithm and the resulting alignment exported to SeqVu. Homologous amino acid substitutions are boxed in FIG. 1 and were determined using the Dayhoff 250 method with a 50% homology cutoff.

Cell Transfection and LCFA Uptake. COS cells were cotransfected using the DEAE-dextran method with the mammalian expression vector pCDNA 3.1 (Invitrogen) expressing the gene for CD2 (pCDNA-CD2) in combination with either a pCDNA 3.1 or pCMVSPORT2 (GIBCO/BRL) expression vector containing one of the murine or nematode FATP genes (pCDNA-mmFATP1, pCDNA-FATP2, pCMVSPORT-FATP5, pCDNA-ceFATPb). Two days after transfection, cells were assayed for CD2 expression with a phycoerythrin-coupled anti-CD2(PE-CD2) monoclonal antibody (PharMingen), and fatty acid uptake was assayed with a BODIPY-labeled fatty acid analogue (Molecular Probes). Briefly, cells were washed twice with PBS (phosphate buffered saline) and stained with PE-CD2 at 4° C. for 30 min in PBS containing 10% fetal calf serum. They were then washed three times with PBS/fetal calf serum for 5 min followed by an incubation for 2 min at 37° C. in fatty acid uptake solution, which contained 0.1 $\mu$M BODIPY-FA and 0.1% fatty acid-free BSA (bovine serum albumin) in PBS (Schaffer, J. E. & Lodish, H. F. (1994) *Cell* 79:427–436). After 2 min, the cells were washed four times with ice-cold PBS/0.1% BSA. The cells were then removed from the plates with PBS containing 5 mM EDTA and resuspended in PBS containing 10% fetal calf serum and 10 mM EDTA. PE-CD2 and BODIPY-FA fluorescence were measured using a FACScan (Becton Dickinson). COS cells were gated on forward scatter (FSC) and side scatter (SS). Cells exhibiting more than 300 CD2 fluorescence units (dsim) representing 15% of all cells were deemed CD2 positive and their BODIPY-FA fluorescence was quantitated.

*E. coli*-Based LCFA Uptake Assay. The full-length coding region of mtFATP and a control protein, the mammalian transcription factor TFE3, were subcloned into the inducible, prokaryotic expression vector pET (Novagen). Expression was induced with 1 mM isopropyl β-D-thiogalactoside (IPTG) for 1 hour, or cells were left uninduced. Cells were washed in PBS/0.1% BSA and resuspended in 1 ml PBS/0.1% BSA containing 0.1 $\mu$M [$^3$H] palmitate (NEN) at 37° C. Uptake was stopped after the indicated incubation time by transferring the cells onto filter paper using a cell harvester (Brandel, Bethesda, Md.). Filters were washed extensively with ice-cold PBS/0.1% BSA, and [$^3$H]palmitate was quantitated by scintillation counting.

Northern Blots. Northern blot analysis of murine FATP expression was done using poly(A) mRNA blots (Clontech). Probes of each of the FATPs were derived from the 3' untranslated regions of each gene and were <60% identical in sequence. Probes were labeled by random priming (Boehringer Mannheim) and hybridized at 65° C. Blots were extensively washed in 0.2% SSC/0.1% SDS at 65° C.

Figure 5:
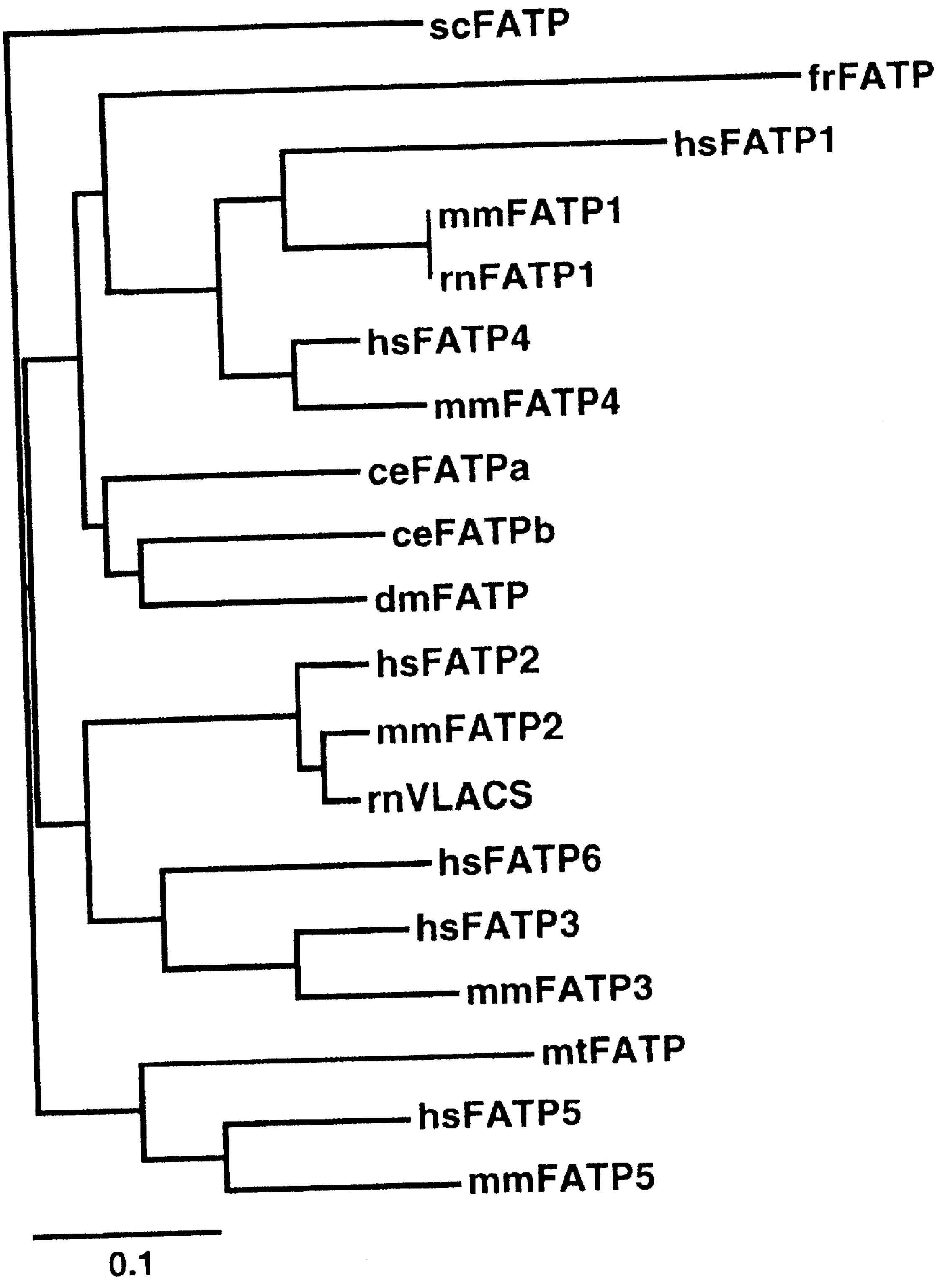
FIG. 5 is a phylogenetic tree produced by aligning complete and partial sequences for FATP genes from human, rat, mouse, puffer fish, *D. melanogaster, C. elegans, S. cerevisiae,* and *M. tuberculosis* using ClustalX and using these data to produce a phylogenetic tree using TreeView-PPC. The bar indicates the number of substitutions per residue, i.e., 0.1 corresponds to a distance of 10 substitutions per 100 residues.

Generation of Phylogenetic Trees. Complete and partial sequences for FATP genes from human, rat, mouse, puffer fish, *Drosophila melanogaster, C. elegans, S. cerevisiae,* and *M. tuberculosis* were aligned using ClustalX. A homologous region of 48 amino acids (residues 472–519 in mmFATP1) from all of the genes was used to determine phylogenetic relationship within ClustalX. Based on these data a phylogenetic tree was generated using Tree View PPC (FIG. 5).

Nomenclature. It is proposed that the FATP genes be given a species specific prefix (mm, *Mus musculus;* hs, *Homo sapiens;* mt, *M. tuberculosis;* dm, *D. melanogaster;* ce, *C. elegans,* sc, *S. cerevisiae*) and numbered such that mammalian homologues in different species share the same number but differ in their prefix. Since the two *C. elegans* genes cannot be paired with a specific human or mouse FATP, they have been designated ceFATPa and ceFATPb.

Example 1

Identification of Novel Mammalian FATPs

The National Center for Biotechnology Information EST database was screened, using the mouse FATP protein sequence (mmFATP1), to identify novel FATPs. This strategy led to the identification of more than 50 murine EST sequences which could be assembled into five distinct contiguous DNA sequences (contigs). One contig was identical to the previously cloned FATP, which has been renamed FATP1. Another, which has been renamed FATP2, is the murine homologue of a rat gene previously identified by others as a very long chain acyl-CoA synthase (Uchiyama, A., Aoyama, T., Kamijo, K., Uchida, Y., Kondo, N., Orii, T. & Hashimoto, T. (1996) *J. Biol. Chem.* 271:30360–30365). The other three contigs represented novel genes (FATP3, 4, and 5). Full-length clones for FATP2 and FATP5 and nearly complete sequences for FATP3 and 4 (FIG. 1) were obtained by screening cDNA libraries made from mouse day 10.5 embryos and adult liver. Also identified were human homologues for each of the murine genes in the EST database. A sixth human gene was also identified; whether this gene is also present in the mouse will require additional studies. Map positions are given in Tables 2 and 3.

The genetic loci for all of the human genes. with the exception of FATP5 which was already mapped as an unknown EST, were determined using the radiation hybrid panels. The map positions given below show the distance (in centiRays) from the closest framework marker. As a guideline, there are approximately 300 kb/cR.

TABLE 2

| Mapping Data for Human Genes | |
|---|---|
| hsFATP1 | Chromosome Chr19<br>places 13.35 cR from WI-6344 (lod > 3.0) |
| hsFATP2 | Chromosome Chr15<br>places 4.92 cR from D15S126 (lod > 3.0) |
| hsFATP3 | Chromosome Chr1<br>places 13.24 cR from WI-2862 (lod > 3.0) |
| hsFATP4 | Chromosome Chr9<br>places 7.80 cR from WI-9685 (lod > 3.0) |

TABLE 2-continued

| Mapping Data for Human Genes | |
|---|---|
| hsFATP5 | unknown EST previously mapped to near D19S418 |
| hsFATP6 | Chromosome Chr5<br>places 1.41 cR from WI-4907 (lod > 3.0) |

The mouse map is an internal backcross panel consisting of 188 mouse backcross DNA's plus 4 controls (B6, Spretus, F1, Water). The backcross was constructed by crossing B6 by Spretus animals and then crossing those F1's back to B6. Mapping is accomplished by taking advantage of recombinational events during meiosis, and the use of PCR primers to detect the differences (by size or re-annealing events) at any given locus between the B6 and Spretus allele.

For the purposes of mapping, a novel set of primers (gene of interest) is used to amplify from all 188 DNA's and then typed as being a B6 ("B") or a Spretus ("S"). This string of B's and S's is entered into the Map Manager program, which does a best fit calculation by comparing the string of 188 typings from the gene of interest to all loci already extant in the panel, for all 20 chromosomes. The gene of interest is then assigned to a particular area on a particular chromosome according to a number of parameters, including the minimalization of double cross-overs, and the highest LOD scores. Indicated in Table 3 are distances to the closest markers on either side of the FATP locus.

TABLE 3

| Mapping Data for Mouse Genes | |
|---|---|
| mmFATP1 | Chromosome 8<br>places 2.82 cM from D8Mit132 (lod 43.4) and<br>1.81 cM from D8Mit74 (lod 43.5) |
| mmFATP2 | Chromosome 2<br>places 1.29 cM from D2Mit258 (lod 47.9) and<br>1.75 cM from D2NDS3 (lod 44.9) |
| mmFATP3 | Chromosome 3<br>places 2.54 cM from D3Mit22 (lod 29.5) and<br>19.62 cM from D3Mit42 (lod 13.6) |
| mmFATP4 | Chromosome 2<br>places 13.78 cM from D2Mit1 (lod 22.9) and<br>3.85 cM from D2Mit65 (lod 41.9) |
| mmFATP5 | Chromosome 7<br>places 7.28 cM proximal of D7Mit21 (lod 28.3) |

Example 2

Assessment of Function

Figure 1A:
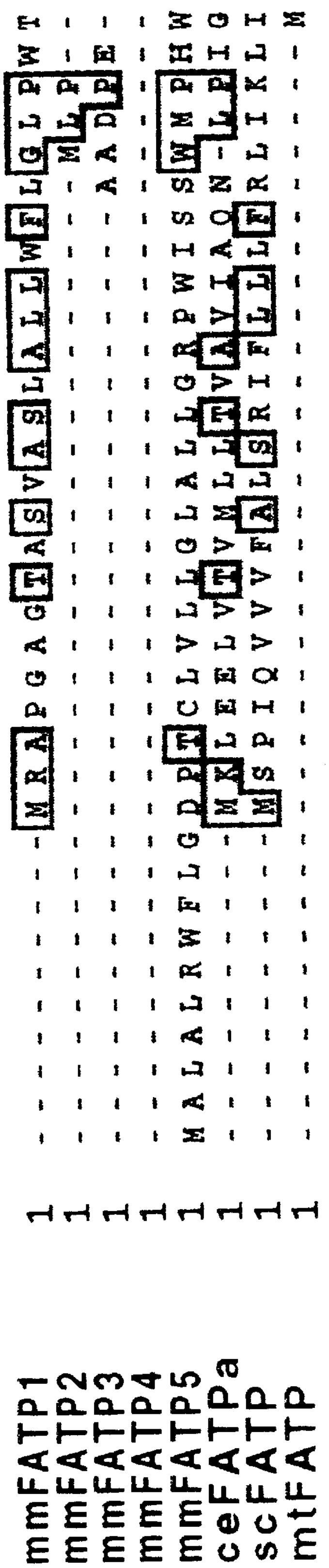
FIG. 1 shows the amino acid sequence alignment of FATPs: mmFATP1 (SEQ ID NO:92), mmFATP2 (SEQ ID NO:93), mmFATP3 (SEQ ID NO:94), mmFATP4 (SEQ ID NO:95), mmFATP5 (SEQ ID NO:96), ceFATPa (SEQ ID NO:97), scFATP (SEQ ID NO:98) and mtFATP (SEQ ID NO:99). The underlining (amino acid residues 204–212 of mtFATP) indicates an AMP binding motif which is found in many classes of proteins; the underlining at amino acid residues 204–507 of the mtFATP sequence indicates the FATP 360 amino acid signature sequence.
Figure 1B:
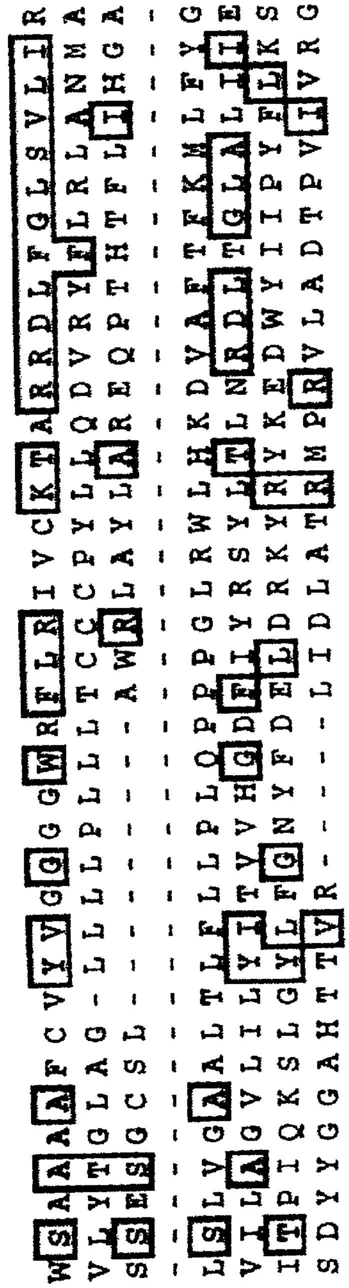
Figure 1C:
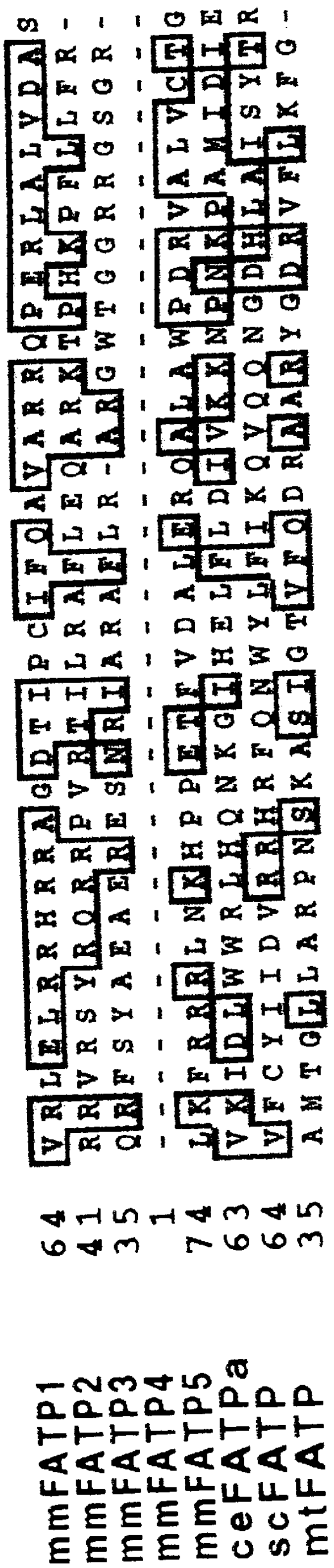
Figure 1D:
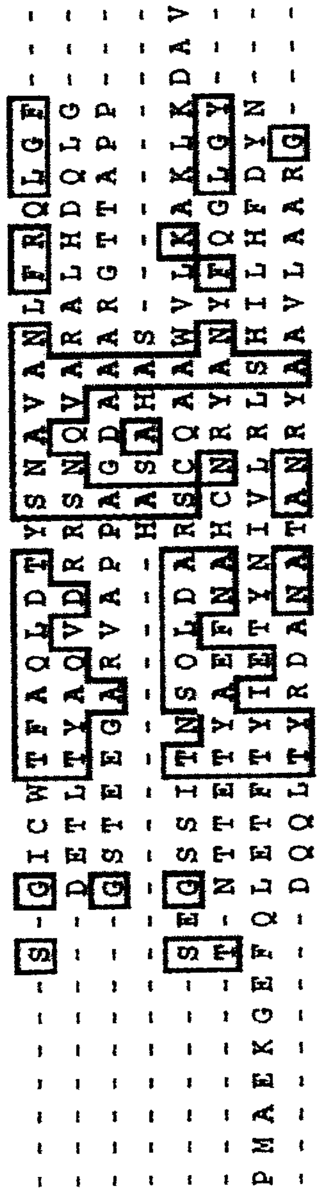
Figure 1E:
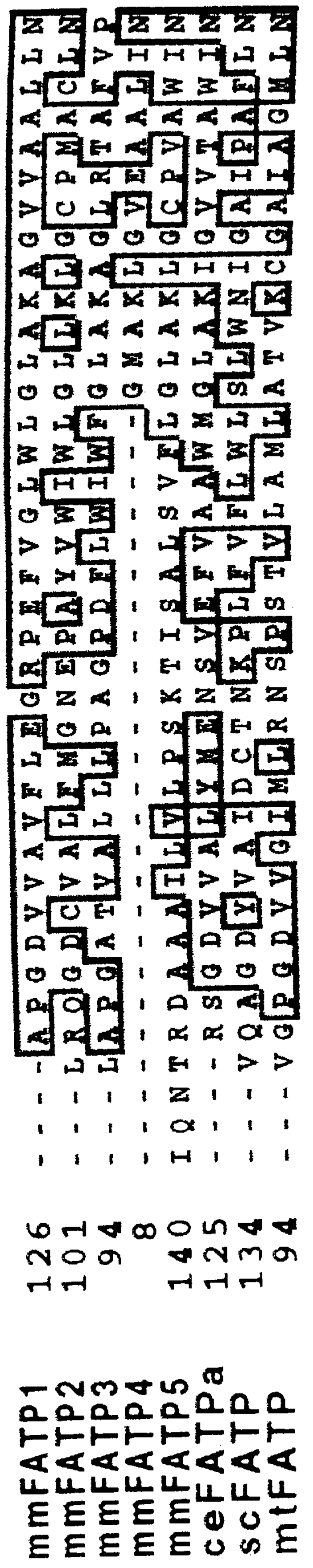
Figure 1F:
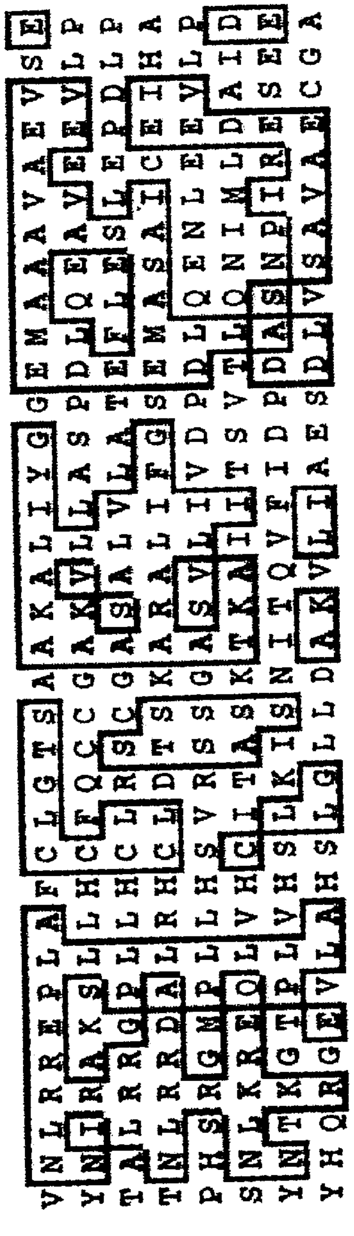
Figure 1I:
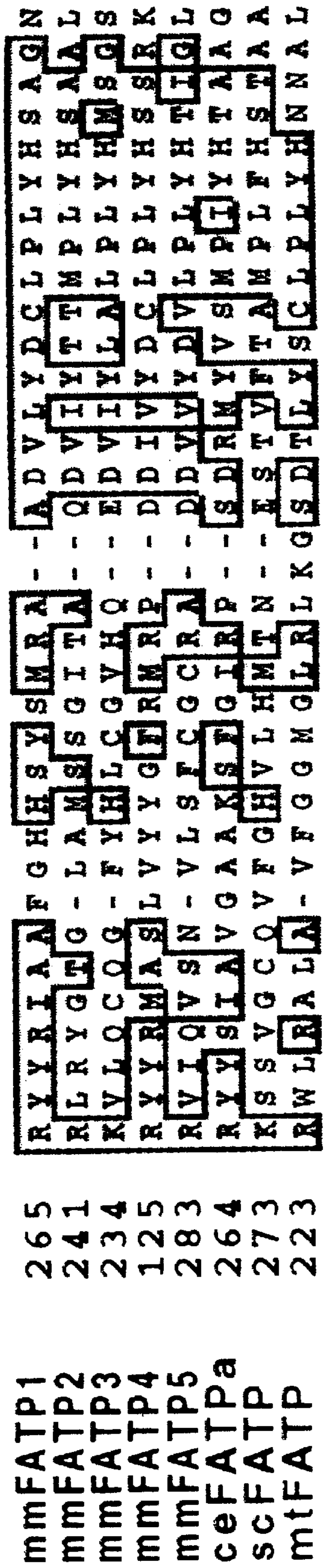
Figure 1J:
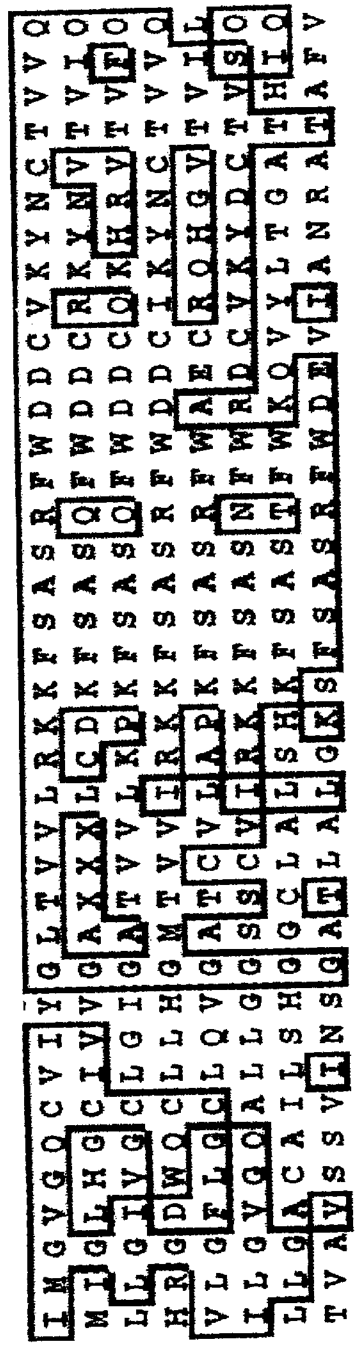
Figure 1M:
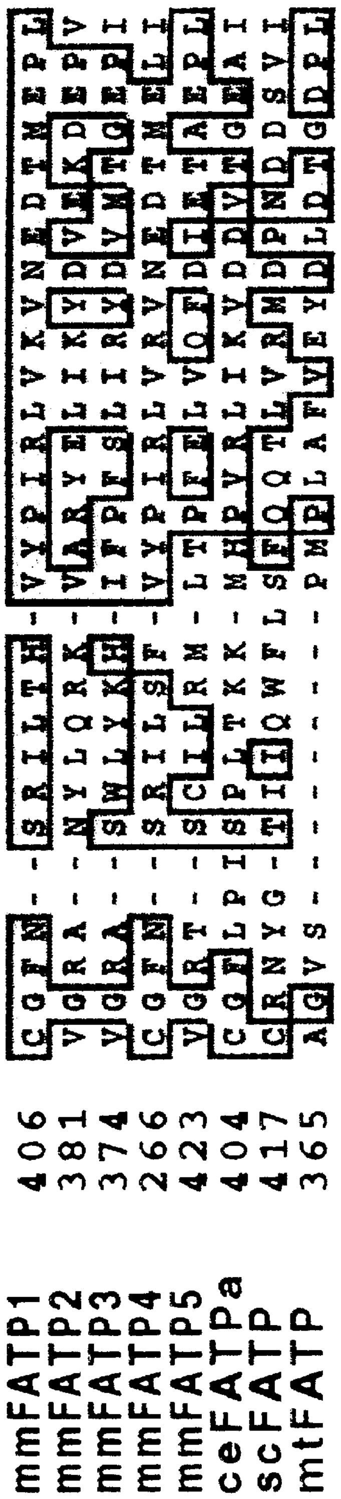
Figure 1N:
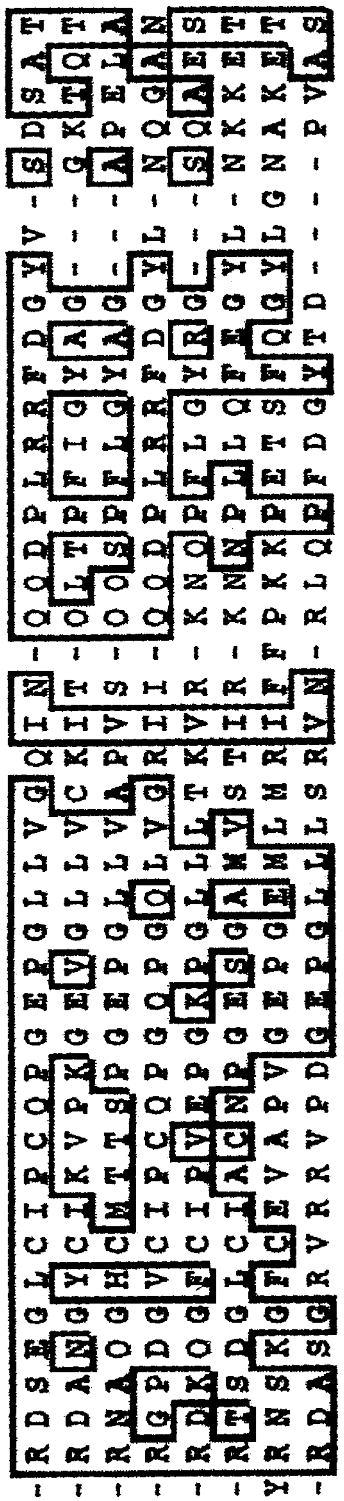
Figure 1O:
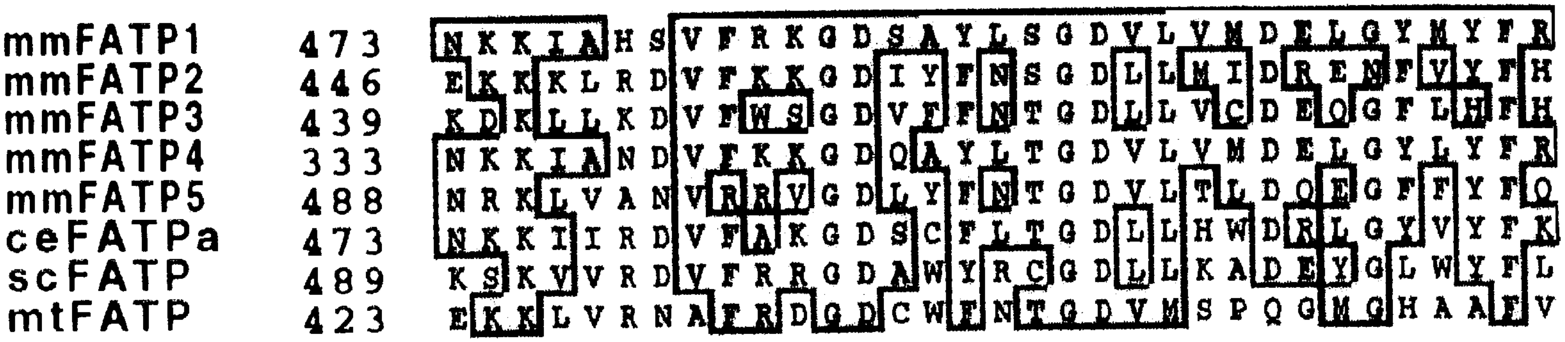
Figure 1P:
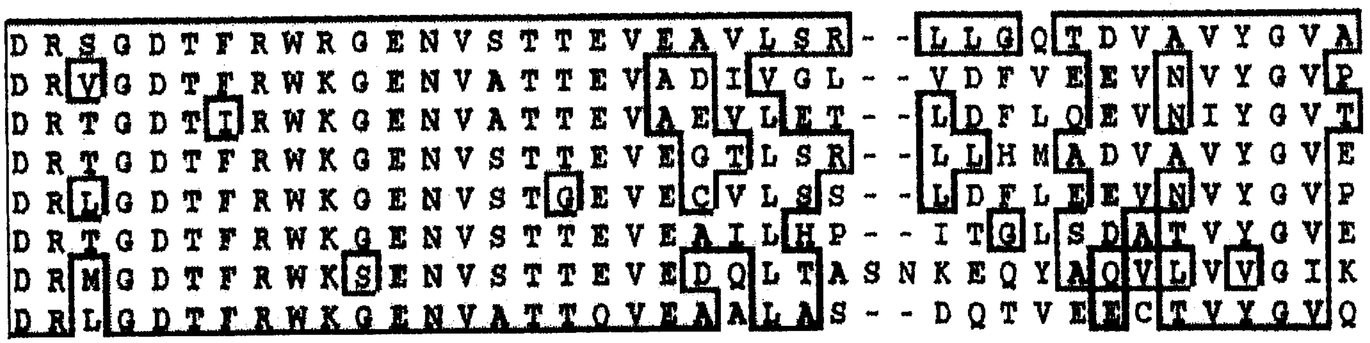
Figure 1Q:
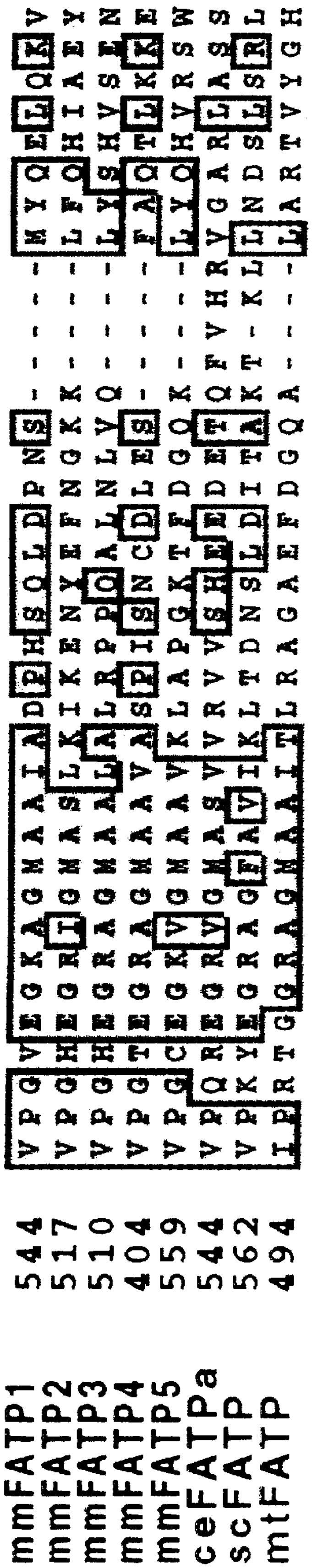
Figure 1R:
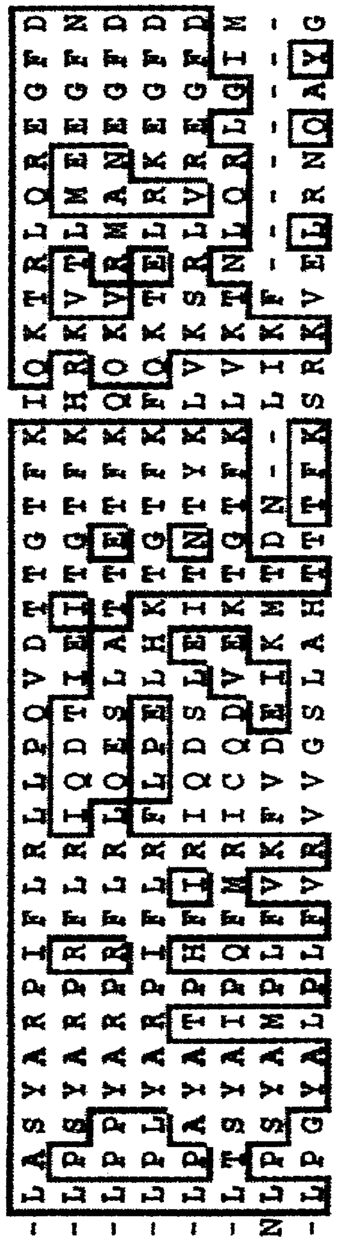
Figure 1S:
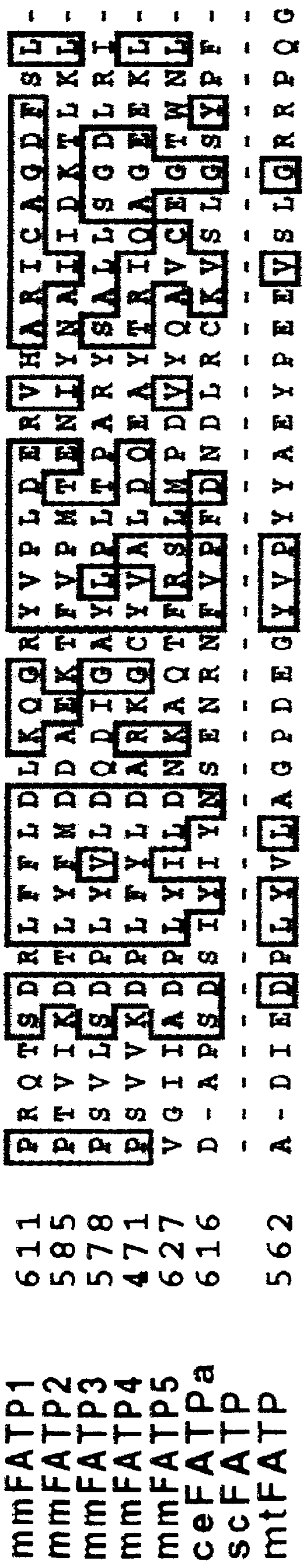
Figure 2A:
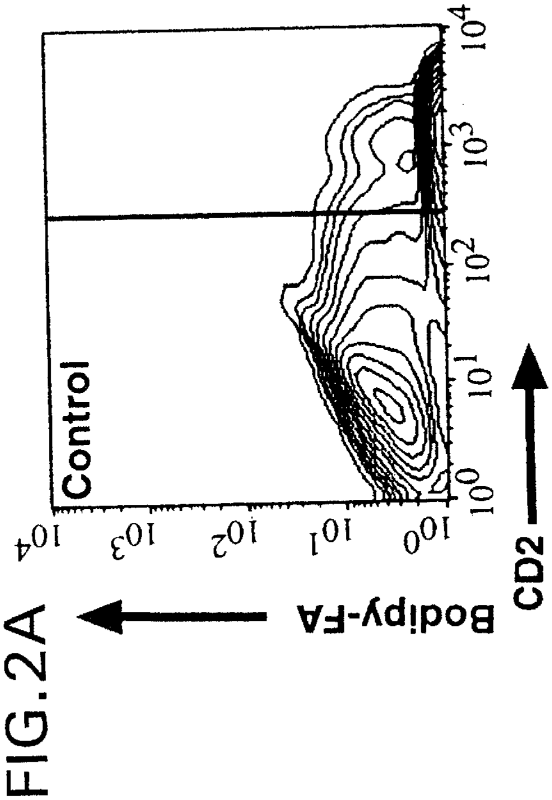
FIGS. 2A–2D show results of LCFA uptake assays.
Figure 2B:
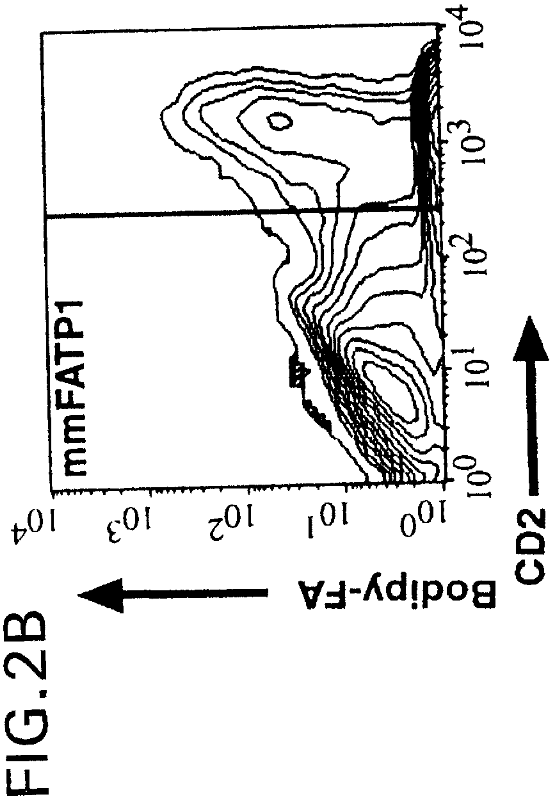
Figure 2C:
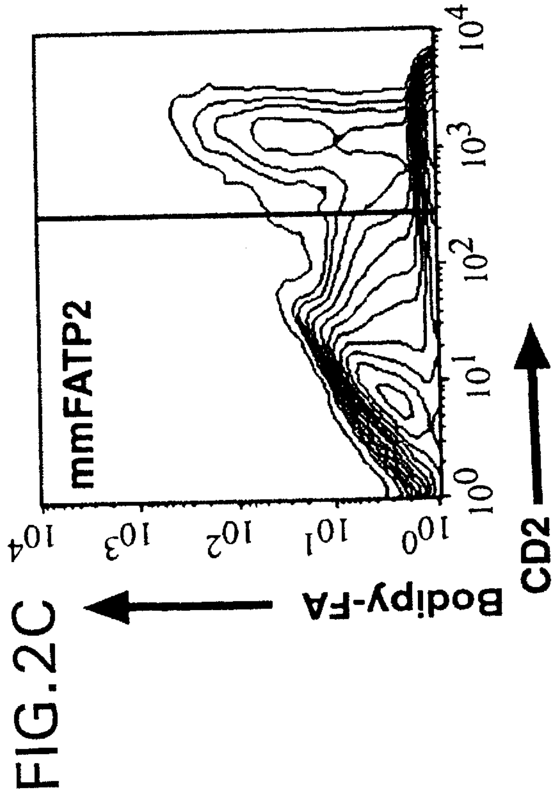
Figure 2D:
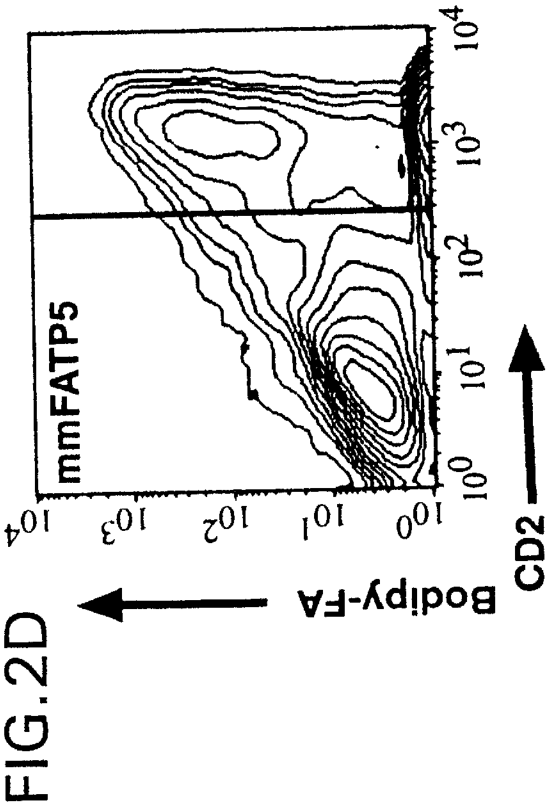

The ability of the newly identified mouse genes to function as fatty acid transporters was assessed using a fluorescence-activated cell sorting-based assay. COS cells were transiently cotransfected with expression vectors encoding the cell surface protein CD2 and either mmFATP 1, mmFATP2, or mmFATP5, respectively. Two days after transfection, COS cells were stained with an antibody to CD2 and then incubated with a BODIPY-labeled fatty acid [BODIPY-FA, (Schaffer, J. E. & Lodish, H. F. (1994) *Cell* 79:427–436)]. The cells were then washed extensively, lifted off the dish, and analyzed by fluorescence-activated cell sorting. As judged by the number of CD2-positive cells, the transfection efficiency was approximately 20–30%. Fatty acid uptake was quantitated in the transiently transfected COS cells by measuring the BODIPY-FA fluorescence of the CD2-positive cells. Expression of CD2 had no effect on fatty acid uptake as shown by the finding that COS cells expressing only the transfected CD2 cDNA (CD2-positive) had the same low level of BODIPY-FA uptake as did untransfected (CD2-negative) control cells (FIG. 2A, control). In COS cells cotransfected with CD2 and mmFATP1, mmFATP2, or mmFATP5, uptake of BODIPY-FA by the transfected (CD2-positive) cells was increased between 15- to 90-fold over control (CD2 cDNA only) cells (FIGS. 2A–2D).

Example 3

Expression Patterns of Murine FATPs

Expression patterns of members of the murine FATP gene family were characterized by Northern blot analysis; to avoid cross-hybridization, the probes used were from the 3' untranslated region of these genes, which are less than 60% identical in sequence. The expression pattern of FATP1 agrees with that previously found (Schaffer, J. E. & Lodish, H. F. (1994) *Cell* 79:427–436). Here, expression was seen primarily in heart and kidney. FATP2 is expressed almost exclusively in liver and kidney, which corresponds to the reported tissue distribution of the rat homologue [very long chain acyl-CoA (VLACS)] as assessed by Western blotting (Uchiyama, A., Aoyama, T., Kamijo, K., Uchida, Y., Kondo, N., Orii, T. & Hashimoto, T. (1996) *J. Biol. Chem.* 271:30360–30365). FATP3 is present in lung, liver, and testis. FATP5 is expressed only in liver and cannot be detected in other tissues even when the blot is overexposed. The human homologue of FATP5 is also liver specific and is not expressed in a wide array of other tissues tested, including fetal liver.

Example 4

FATPs are Evolutionarily Conserved

Figure 3:
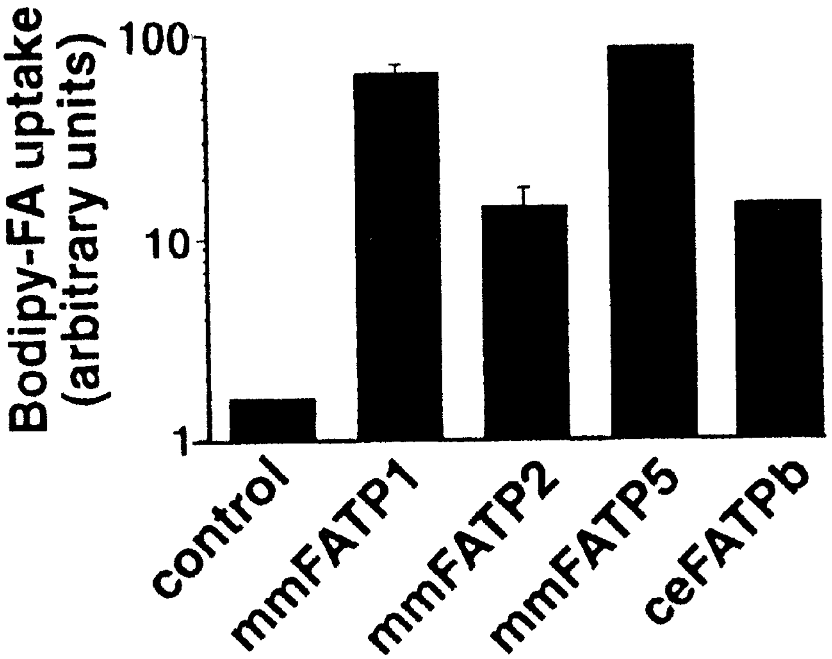
FIG. 3 is a graph of fluorescence of cells expressing a FATP gene. As in FIGS. 2A–2D, COS cells were cotransfected with pCDNA-CD2 either alone (control) or in combination with one of the FATP-containing expression vectors (pCDNA-mmFATP1, pCDNA-mmFATP2, pCMV-SPORT2-mmFATP5, or pCDNA-ceFATPb). The mean BODIPY-FA fluorescence of the CD2-positive cells is plotted; results shown represent the average of three experiments, each consisting of greater than 50,000 COS cells. Note that a logarithmic scale is used on the ordinate.
Figure 4:
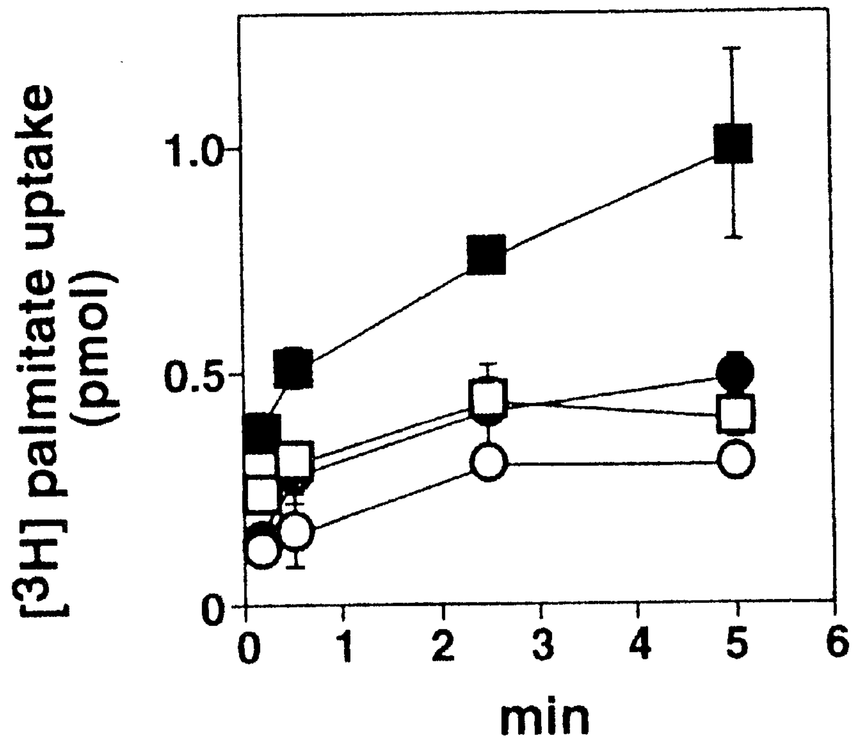
FIG. 4 is a graph of the uptake of palmitate with time. The full-length coding region of mtFATP (squares) or a control protein (TFE3; circles) was subcloned into the inducible, prokaryotic expression vector pET (Novagen). Expression from the resulting plasmid was induced (solid symbols) in transformed *E. coli* cells with 1 mM isopropyl-β-D-thiogalactoside (IPTG) for 1 hour, or cells were left uninduced (open symbols). Data points were done in triplicate and counts were normalized to the number of bacteria as determined by $OD_{600}$.

The EST database was searched, using sequences conserved among the five murine FATP genes, for FATP genes in other organisms. Two homologues were found in *C. elegans* and one in *M tuberculosis*. One of the *C. elegans* genes was cloned from a cDNA library and expressed in COS cells, as described for the murine FATPs. Overexpression of the nematode FATP resulted in a 15-fold increase of BODIPY-FA uptake compared with control cells (FIG. 3). The mycobacterial FATP gene was isolated from a phage library and assessed for its ability to facilitate fatty acid uptake. *E. coli* transformed with a prokaryotic, isopropyl β-D-thiogalactoside-inducible expression vector containing the mycobacterial FATP gene demonstrated a significant increase in the rate of [$^3$H]palmitate uptake after induction, compared with uninduced bacteria or *E. coli* transformed with a control protein (FIG. 4). Novel FATP genes were also identified in *F. rubripes* (puffer fish) and *D. melanogaster.*

Example 5

Phylogenetic Tree of FATPs

Faergeman et al. (Faergeman, N. J., DiRusso. C. C., Elberger, A., Knudsen, J. & Black, P. N. (1997) *J. Biol. Chem.* 272:8531–8538) identified three regions of very strong conservation between the scFATP and mmFATP1 genes. The sequences of the FATPS were compared over a 311-amino acid FATP "signature sequence" which includes these conserved regions corresponding to amino acids 246–557 in mmFATP1 (underlined in FIG. 1). When compared with National Center for Biotechnology Information nonredundant database, only one region of the "FATP signature sequence" shows significant homology to other proteins. This small stretch of amino acids (underlined in FIG. 1) is an AMP-binding motif found in a multitude of other proteins, such as acyl-CoA synthase, several CoA lipases, and gramicidin S synthetase component II (Schaffer, J. E. & Lodish, H. F. (1994) *Cell* 79:427–436). The relevance of this motif to fatty acid transport is unclear. Other highly conserved regions among the FATPs, including long stretches of amino acids >90% identical from mycobacteria to humans, are not found in any other class of proteins. A 48-amino acid segment of the FATP signature sequence was used to construct a phylogenetic tree (FIG. 5). Each of the human and mouse genes form their own branch; hsFATP6, which as yet has no murine homologue, is most closely related to hsFATP3 and mmFATP3. As expected, mVLACS is closer in sequence to mmFATP2 than to hsFATP2. The FATP genes of invertebrates i.e., *C. elegans* and *D. melanogaster,* are most closely related to each other. Surprisingly, the mycobacteral gene is more closely related to the human and mouse FATP5 genes than to the FATPs of any of the lower organisms. Whether this reflects coevolution of the mycobacterial and human genes awaits further study.

Materials and Methods

The following materials and methods were used in the work described in Examples 6–10.

Isolation of Full-length Human FATP1 and 4

Full-length clones encoding human FATP1 and human FATP4 were identified by searching databases for sequences similar to murine FATP1–5 coding regions using the BlastX algorithm (Altschul et al., *J. Mol. Biol.* 215: 403–410, 1990).

A concatamer of nucleotide sequences comprising the coding sequences of mmFATP1 (Genbank Accession U15976), mmFATP2, mmFATP3 (SEQ ID NO:6), mmFATP4 (SEQ ID NO:8) and mmFATP5 (SEQ ID NO:10) was used to search the Millennium database using the BLASTX algorithm. Sequences with a score >150 were evaluated for whether they represented known FATP coding sequences.

Human clones with similarity to the 5' end of murine FATP sequences were sequenced completely. Clones encoding full-length human FATP1 were obtained from a heart cDNA library constructed in the mammalian expression vector pMET7 (Tartaglia et al., *Cell,* 83: 1263–1271, 1995). Clones encoding full-length human FATP4 were obtained from a spleen cDNA library constructed in the mammalian expression vector pMET7.

Isolation of Full-length Human FATP6

Several clones encoding human FATP6 were identified by searching public databases as described above. Five clones were analyzed further by restriction digestion and DNA sequencing. One of these clones (Genbank Accession # AA412064) appeared to be full-length and its entire insert was sequenced.

DNA Sequence Analysis

Sequences were aligned with the DNAStar program using the Clustal method. Hydrophobicity plots were generated with DNA Strider using the Kyte Doolittle method.

In situ Hybridization

Tissues were collected from 8 week old C57/B16 mice. Tissues were fresh frozen, cut on a cryostat at 10 $\mu$m thickness and mounted on Superfrost Plus slides (VWR). Sections were air dried for 20 minutes and then incubated with ice cold 4% paraformaldehyde (PFA)/phosphate buffered saline (PBS) for 10 minutes. Slides were washed 2 times 5 minutes with PBS, incubated with 0.25% acetic anhydride/1 M triethanolamine for 10 minutes, washed with PBS for 5 minutes and dehydrated with 70%, 80%, 95% and 100% ethanol for 1 minute each. Sections were incubated with chloroform for 5 minutes. Hybridizations were performed with $^{35}$S-radiolabeled ($5\times10^7$ cpm/ml) cRNA probes generated from the 3' untranslated regions of mouse FATPs by PCR followed by in vitro transcription in the presence of 50% formamide, 10% dextran sulfate, 1×Denhardt's solution, 600 mM NaCl, 10 mM DTT, 0.25% SDS and 10 $\mu$g/ml tRNA for 18 hours at 55° C. After hybridization, slides were washed with 10 mM Tris-HCl pH 7.6, 500 mM NaCl, 1 mM EDTA (TNE) for 10 minutes, incubated in 40 $\mu$g/ml RNase A in TNE at 37° C. for 30 minutes, washed in TNE for 10 minutes, incubated once in 2×SSC at 60° C. for 1 hour, once in 0.2×SSC at 60° C. for 1 hour, once in 0.2×SSC at 65° C. for 1 hour and dehydrated with 50%, 70%, 80%, 90% and 100% ethanol. Localization of mRNA transcripts was detected by dipping slides in Kodak NBT-2 photoemulsion and exposing for 7 days at 4° C., followed by development with Kodak Dektol developer. Slides were counter stained with haematoxylon and eosin and photographed. Controls for the in situ hybridization experiments include the use of a sense probe which showed no signal above background in all cases.

Northern Blotting

Human mRNA blots were obtained from invitrogen or Clontech. PCR fragments from the 3' untranslated regions of human FATPs were used as probes. Blots were probed with $^{32}$P-labeled DNA probes using the Rapid-Hyb buffer (Amersham) according to the manufacturer's instructions.

Cell transfection and LCFA uptake. COS cells were cotransfected, using lipofectamine (GIBCO BRL) according to the manufacturer's instructions, with the mammalian expression vector pCDNA3.1 (Invitrogen) expressing the gene for CD2 in combination with a pMET7 expression vector (Tartaglia et al., *Cell,* 83:1263–1271, 1995) containing hsFATP1 (pMET7-hsFATP 1) or hsFATP4 (pMET7-hsFATP4) or pMET7 alone. Two days after transfection, cells were assayed for CD2 expression with a phycoerythrin-coupled anti-CD2 (PE-CD2) monoclonal antibody (PharMingen), and fatty acid uptake was assayed with a BODIPY-labeled fatty acid analog (Molecular Probes) as described above.

Example 6

Determination of Expression of mmFATPs mmFATP4, and to lesser extent mmFATP2, are expressed at high levels in the brush border layer of the small intestine.

Cell transfection and LCFA uptake. COS cells were cotransfected, using lipofectamine (GIBCO BRL) according to the manufacturer's instructions, with the mammalian expression vector pCDNA3.1 (Invitrogen) expressing the gene for CD2 in combination with a pMET7 expression vector (Tartaglia et al., *Cell,* 83:1263–1271, 1995) containing hsFATP1 (pMET7-hsFATP1) or hsFATP4 (pMET7-hsFATP4) or pMET7 alone. Two days after transfection, cells were assayed for CD2 expression with a phycoerythrin-coupled anti-CD2 (PE-CD2) monoclonal antibody (PharMingen), and fatty acid uptake was assayed with a BODIPY-labeled fatty acid analog (Molecular Probes) as described above.

Absorption of dietary fat requires transport of free fatty acids across the apical membrane of epithelial cells in the small intestine. Previous studies suggested that this transport is protein-mediated; however, the transport protein had not yet been identified. In situ hybridization was performed on each of the three regions of the small intestine—duodenum, jejunum and ileum—as well as the colon, using probes from the 3' untranslated regions of mmFATP1, mmFATP2, mmFATP3, mmFATP4 and mmFATP5, to determine whether any of the mouse FATPs are expressed in the small intestine. It was expected that a protein involved in fatty acid absorption would be expressed in the epithelial cells of the small intestine, but absent from the colon.

Expression of mmFATPs in the jejunum was identical to that in the ileum in all cases. High levels of mmFATP4 mRNA were present in the epithelial cells of the jejunum and ileum, and lower, but significant, amounts were detected in the epithelial cells of the duodenum. Significantly, FATP4 mRNA was absent from other cell types of the small intestine and no FATP4 mRNA could be detected in any of the cells of the colon. FATP2 mRNA was present in the epithelial cells of the duodenum at a level similar to that of FATP4, but was present at lower levels in the jejunum and ileum. No signals above background were detected for mmFATP1, mmFATP3 and mmFATP5 in any of the intestinal tissues. mmFATP3 and FATP5 were clearly detectable by in situ hybridization in adult liver and mmFATP1 could be detected in a variety of tissues on a whole embryo in situ, indicating that the FATP1, 3, and 5 probes were working.

mmFATP4 expression is predominant in the small intestine compared to the other organs of the mouse embryo. In the small intestine, FATP4 expression is limited to differentiated enterocytes, while no signal is detected in the connective tissue or the undifferentiated epithelial cells in the crypts. Differentiated enterocytes are known to be the cells that mediate the uptake of fatty acids. FATP4 is specifically and strongly expressed in the epithelial cells of adult murine duodenum and ileum but not colon. Other FATPs, such as FATP5, are not expressed in the small intestine. Thus, FATP4 is the major FATP in the mouse small intestine. Given its high level of expression, it is likely that FATP4, and to a lesser extent FATP2, play an important role in the absorption of fatty acids.

mmFATP2, and mmFATP5 are Expressed in Hepatocytes

Northern analysis of mmFATP2, mmFATP3, mmFATP4 and mmFATP5 showed expression in the liver. To determine whether these proteins are present in hepatocytes or other cells types present in liver homogenates, in situ hybridizations were performed. mmFATP2, and mmFATP5 mRNA was clearly present in hepatocytes, and was not concentrated in other cell types such as endothelial cells or macrophages. No signal above background was detected for mmFATP1 in any of the cell types in the liver, consistent with the results of the Northern blotting.

Example 7

Isolation and Sequence Analysis of Full-length Human FATP1 and Full-length Human FATP4

To identify human cDNA clones encoding FATP family members, Millennium databases were searched for sequences similar to murine FATP1–5 coding regions. Two clones were analyzed in detail; inspection of the entire DNA sequence of these two clones showed that they encode the human orthologs of mmFATP 1 and mm FATP4, respectively. These two clones were designated hsFATP1 and hsFATP4, and their DNA and predicted protein sequences are shown in FIGS. 44A–44C and 45, and 50A–50C and 51. hsFATP1 is predicted to encode a 646 amino acid, 71 kD protein with multiple membrane-spanning domains (FIG. 28A). HsFATP4 is predicted to encode a 643 amino acid, 72 kD protein with multiple membrane spanning domains (See FIG. 29A). A comparison of the DNA sequences of mouse and human FATP1 and mouse and human FATP4 (FIGS. 30A–30B and 31A–31B) shows that the mouse and human orthologs are 85% (FATP1) and 87% (FATP4) identical to each other within the coding sequences given in these figures. At the amino acid level, hsFATP1 and hsFATP4 are ~90% identical to their respective mouse orthologs within the coding region shown in these figures (FIGS. 32 and 33). The sequence identities between mouse and human FATP1 and FATP4 are considerably higher than the ones observed between different FATP family members within one species (~40%–60%) and are present in the N-terminal part of the protein, a region that is poorly conserved between different FATP family members. This high degree of sequence conservation clearly demonstrates that the newly identified human FATPs are orthologs of mouse FATP1 and FATP4 rather than novel FATP family members.

Table 4 is an identity/similarity matrix comparing the amino acid sequences of FATP1 and 4 from human and mouse. This shows that the gene whose sequence is shown in FIG. 43A is indeed human FATP4, since it is 91% identical with the murine FATP4 but only 62% identical with the closest related human FATP, which is FATP 1.

TABLE 4

Identity/Similarity Matrix

| | hsFATP4 | mmFATP4 | hsFATP1 | mmFATP1 |
|---|---|---|---|---|
| hsFATP4 | — | 93.2 | 72.3 | 72.0 |
| mmFATP4 | 91.0 | — | 71.2 | 71.1 |
| hsFATP1 | 61.9 | 61.0 | — | 92.4 |
| mmFATP1 | 60.7 | 59.6 | 89.5 | — |

Example 8

Isolation and Sequence Analysis of Full-length Human FATP6

A search of EST databases identified a set of overlapping human sequences that were similar to FATPs, but did not have a clear mouse ortholog. One of these EST clones was found to encode a full-length cDNA. The entire insert of this clone was sequenced and designated hsFATP6. The DNA and predicted protein sequences of hsFATP6 are shown in FIGS. 54A–54C and 55. HsFATP6 is predicted to encode a 619 amino acid, 70 kD protein with multiple membrane-spanning domains (FIG. 35A). A comparison of the amino acid sequences of hsFATP6 with other human FATPs shows about 37% identity to either hsFATP1 or hsFATP4 (FIG. 36). This degree of sequence identity is similar to what is observed between different mouse FATPs. The phylogenetic analysis described above clearly demonstrates that hsFATP6 is a member of the FATP family, but not an ortholog of any of the mouse FATPs. Comparisons were done with "ALIGN" (E. Myers and W. Miller, "Optimal Alignments in Linear Space," *CABIOS* 4:11–17 (1988) using standard settings.

Example 9

Tissue Distribution of Human FATPs

The tissue distribution of human FATPs was assessed by Northern blotting. Human FATP3 was expressed in a large variety of tissues. In contrast, human FATP5 was present at high levels in the liver, but was undetectable in all other tissues examined. Thus, both hsFATP3 and hsFATP5 recapitulate the expression pattern of their mouse orthologs (see above). HsFATP6 is a novel FATP with no mouse ortholog as yet. Northern blotting shows that hsFATP6 is expressed at high levels in the heart, but is undetectable in other tissues, including skeletal and smooth muscle. This tissue distribution suggests that human FATP6 performs an important role in energy metabolism in the heart; blocking FATP6-mediated fatty acid transport may therefore be beneficial for a number of heart diseases, e.g., ischemic heart disease.

To identify the major FATP expressed in the human small intestine, Northern blotting was performed on a blot containing mRNA from human stomach, jejunum, ileum, colon, rectum and lung. hsFATP5 and hsFATP6 were undetectable in any of these tissues. FATP5 is only expressed in liver and FATP6 only in heart, hsFATP2 was weakly expressed in the colon, and an even weaker signal was detectable in jejunum, ileum and lung lanes. hsFATP3 was expressed well in the lung, but was only weakly expressed in the other tissues tested. Importantly, no difference was seen in the expression of hsFATP3 between small intestine and stomach or colon, suggesting that the expression observed is not related to fatty acid absorption in the small intestine. hsFATP4 was clearly expressed in both jejunum and ileum; expression was significantly lower in the colon and was absent in the stomach. This expression pattern is consistent with a major role for FATP4 in absorption of fatty acids in the human gut.

Example 10

Expression of hsFATP1 and hsFATP4 Promotes Transport of Fatty Acids

Figure 37:
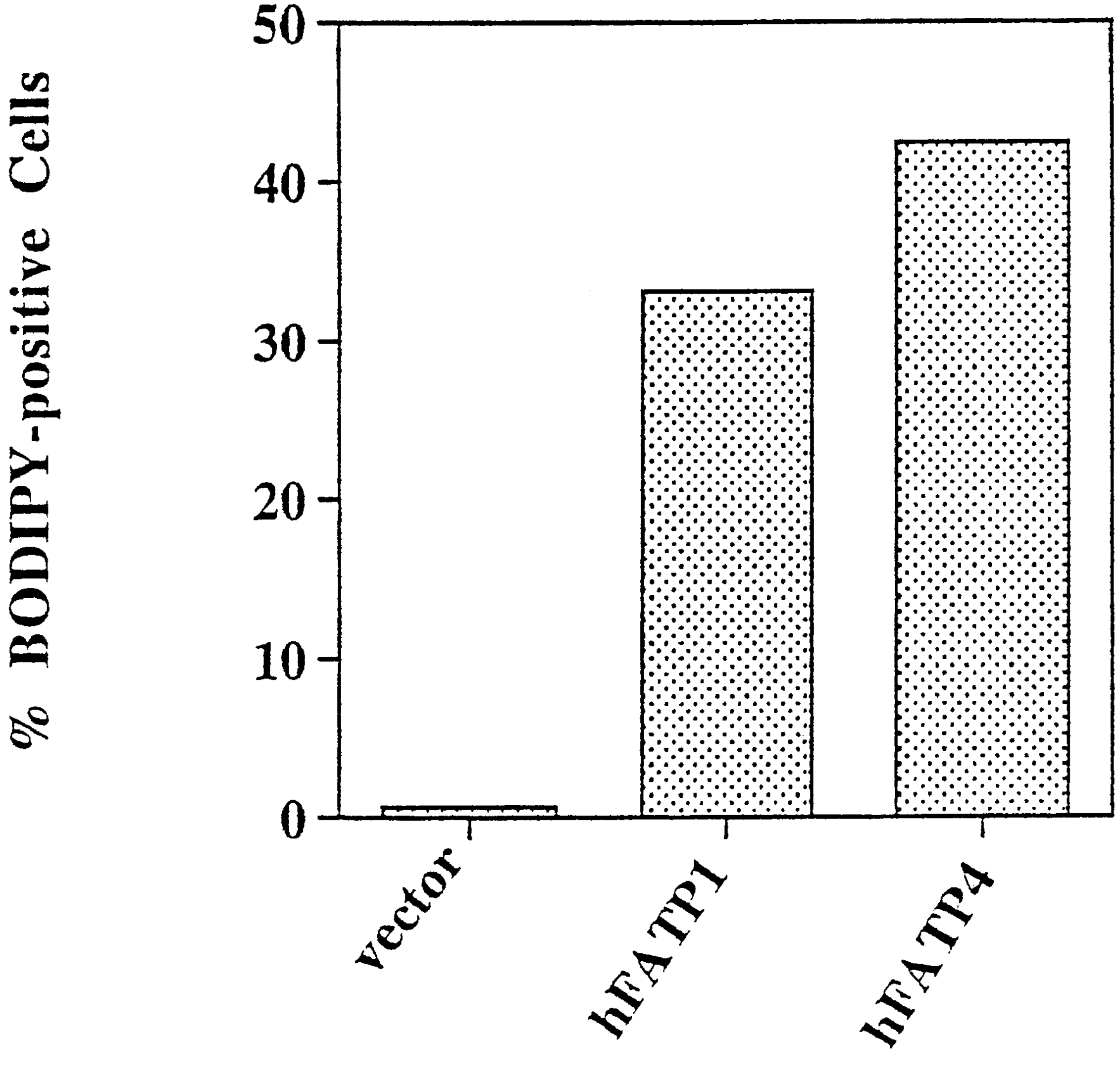
FIG. 37 shows results of assessment of fatty acid uptake by human FATP1 and human FATP4. The percent of CD2-positive cells exhibiting a BODIPY-fluorescence of more than 300 arbitrary units is plotted for the three different conditions tested.

COS cells were cotransfected using lipofectamine with the mammalian expression vector pCDNA-CD2 in combination with one of the FATP-containing expression vectors (pMET7-hsFATP1or pMET7-hsFATP4) or an insertless expression vector (pMET7, control) as described in Materials and Methods for Examples 6–10. COS cells were gated on forward scatter and side scatter. Cells exhibiting more than 400 CD2 fluorescence units representing ~30% of all cells were deemed CD2-positive. The percent of CD2-positive cells exhibiting a BODIPY-fluorescence of >300 is plotted for the three different vectors tested (FIG. 37).

Example 11

Stable Expression of Human FATP4 in 293 Cells

Stable cell lines were generated as follows. A DNA fragment containing the entire hsFATP4 coding sequence as well as 100 nucleotides of 5' and 50 nucleotides of 3' untranslated region was inserted into the vector pIRES-neo (Clontech) using standard cloning techniques. The resulting construct or a vector control (pIES-neo) was transfected into 293 cells using the lipofectamine method (Gibco BRL) according to the manufacturer's directions. Cells that had taken up the DNA were selected with 1 mg/ml G418 (Gibco BRL). Single colonies were picked 1 to 2 weeks after transfection and grown in medium containing 0.8 mg/ml G418. Colonies were screened for the ability to take up fatty acids by measuring uptake of a fluorescently labeled fatty acid (BODIPY-FA). About 40 colonies transfected with the pIRES-neo containing FATP4 and ~20 colonies transfected with pIRES-neo control were analyzed. All 20 of the vector control clones showed amounts of BODIFY-FA uptake similar to each other and to untransfected 293 cells. In contrast, among the 40 FATP4 transfected clones, 3 had a 5- to 10-fold increased BODIPY-FA uptake compared to any of the vector controls, and a large number (~20) showed an approximately two-fold increase in BODIPY-FA levels. This distribution is consistent with FATP4 conferring increased fatty acid uptake in these cells. One of the cell lines with the highest amount of BODIPY-FA uptake was selected to be used for measuring uptake of tritiated fatty acid.

Figure 38:
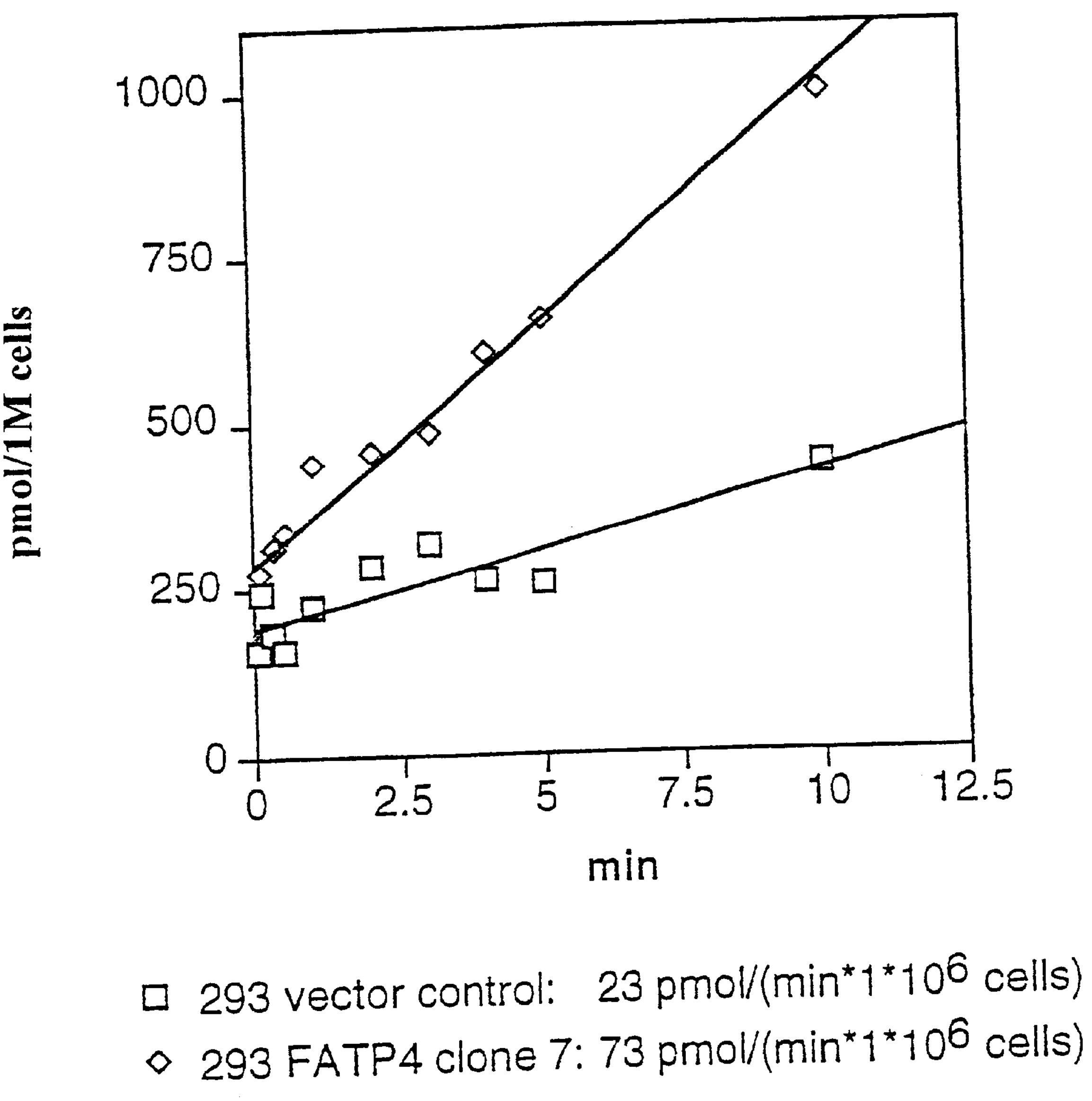
FIG. 38 is a graph showing uptake of tritiated oleate, with time, by 293 cells transfected with either (diamonds) a plasmid for expression of human FATP4 or (squares) a control plasmid.

The uptake of tritiated oleate over time by either FATP4 expressing or control cells was assayed over time. Expression of FATP4 increases the rate of fatty acid uptake by over 3-fold, demonstrating that FATP4 is, like the other FATPs, a functional fatty acid transporter (FIG. 38).

Example 12

Immuno-staining with FATP4-Specific Antiserum

A polyclonal antiserum against the C-terminus of mmFATP4 was raised using a GST-fusion protein having mmFATP4-specific amino acid sequence 552–643 (AVASP . . . GEEKL). In western blot experiments, the purified antibody reacted strongly with a synthetic peptide matching the C-terminus of mmFATP4, but not with a corresponding region of mmFATP2, mmFATP3, or mmFATP5. The mmFATP4 specific polyclonal antiserum detects, in western blot experiments with enterocyte lysates from 3 different mice, a ~70 kDa protein, which is in accordance with mmFATP4's predicted molecular weight of 72 kDa. The binding is specific for mmFATP4, since it can be completely abolished by preincubation of the antiserum with the GST-fusion peptide used to raise the antibody.

Immunofluorescence experiments were performed using the anti-mmFATP4 antiserum on fresh frozen sections of murine small intestine. The antibody binding demonstrates strong expression of mmFATP4 in enterocytes, confirming the results of the in situ hybridization experiments. At higher magnifications it is apparent that mmFATP4 is expressed at the apical side of the enterocyte, indicating that the transporter is present in the brush border membrane, which is known to mediate the uptake of fatty acids from the intestinal lumen.

Immuno-electron microscopy studies were performed on fresh frozen murine intestinal cells. The gold particles used, appearing as black specks on the electron micrographs, indicate the subcellular localization of mmFATP4 to be on the microvilli of the enterocyte. It can be seen from the electron micrographs that mmFATP4 is localized exclusively in membranes, preferentially the apical plasma membrane, confirming that it is indeed a membrane protein.

Example 13

Inhibition of Fatty Acid Uptake Specific to FATP4 Demonstrated in Isolated Mouse Enterocytes Phosphorothioate derivatives of the following oligonucleotides were synthesized:

```
FATP4-AS2     CCCCCACCAGAGAGGCTCC   (SEQ ID NO:103)

FATP4-AS2MM   CCACCCCCGGAAAGCCTGC   (SEQ ID NO:104)

FATP4-52      GGAGCCTCTCTGGTGGGGG   (SEQ ID NO:105)
```

FATP4 AS2 is the antisense oligo; it is designed to be complementary to the sequence extending from nucleotide 10 to nucleotide 28 of the mouse FATP4 coding sequence. FATP4-AS2MM is a control oligo; in the oligo every third nucleotide was changed creating mismatches; the overall nucleotide composition is identical to FATP4-AS2 (same number of G, A, T, C). FATP4-S2 is the sense control.

Figure 40:
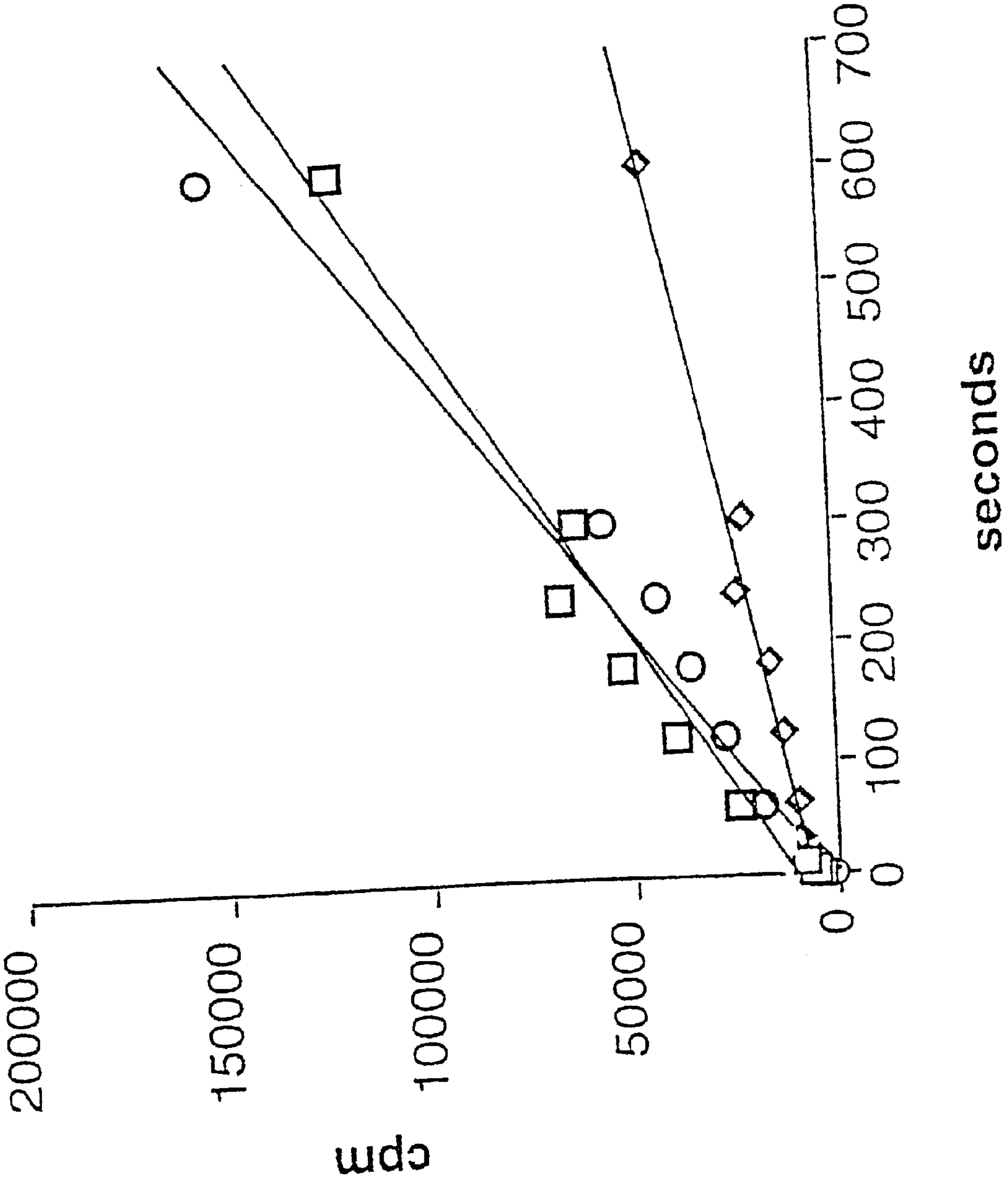
FIG. 40 is a graph showing the uptake, with time, of tritiated oleate by mouse enterocytes in the presence of no oligonucleotide (squares), sense oligonucleotide (circles) or antisense oligonucleotide (diamonds).

Enterocytes were isolated from the small intestine of mice and incubated for 48 h in tissue culture (FIG. 40) either without oligonucleotides (squares) or with 100 $\mu$M FATP4 specific sense (circles) or antisense (diamonds) oligonucleotides. The uptake over time of 25 $\mu$M oleate was then measured. While the FATP4 sense oligonucleotide did not significantly influence the uptake, the antisense oligonucleotide inhibited fatty acid uptake by ~50%.

Figure 41:
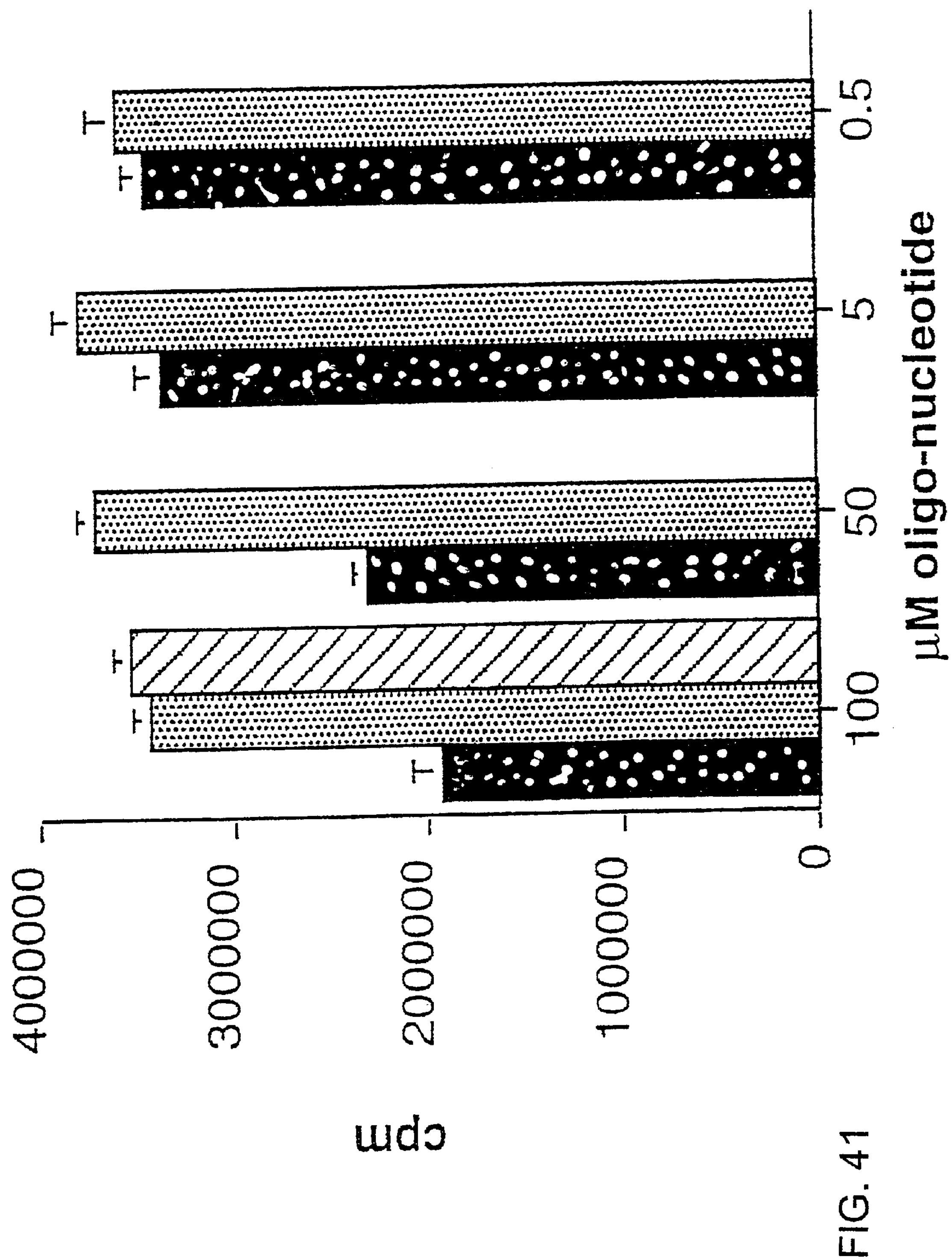
FIG. 41 is a bar graph showing uptake of tritiated oleate, by mouse enterocytes in the presence of various concentrations of antisense (solid bars), mismatch (stippled bars) or sense (lined bars) oligonucleotides.

The effect of either FATP4 sense, antisense or mismatch sequence oligonucleotides on the uptake of fatty acids was measured in enterocytes. Isolated enterocytes were incubated with increasing concentrations of FATP4 antisense oligonucleotides (solid bars in FIG. 41), or a mismatch control oligonucleotide with identical nucleotide composition (stippled bars), or with 100 $\mu$M of the FATP4 sense-oligonucleotide (lined bar). The medium for this incubation was Dulbecco's modified Eagle's medium with 4.5 g/L glucose, 1 mM sodium pyruvate, 0.01 mg/ml human transferrin and 10% fetal bovine serum. After 48 hours of incubation the uptake of oleate by enterocytes was measured over a 5 minute time interval. Measurements were done in quadruplicate. The uptake assay was done in Hank's buffered salt solution with 10 mM taurocholate. Only the enterocytes given FATP4 antisense oligonucleotide showed a concentration dependent decrease of fatty acid uptake, inhibiting it at a 100 $\mu$M concentration by ~50%. This effect was FATP4 specific, since only the antisense oligonucleotide which can bind to the FATP4 mRNA and block its translation inhibited uptake, but not a control oligonucleotide differing only in the sequence but not the nucleotide content, ruling out a toxic or otherwise nonspecific inhibitory effect of this oligonucleotide due to its chemical composition.

Figure 42:
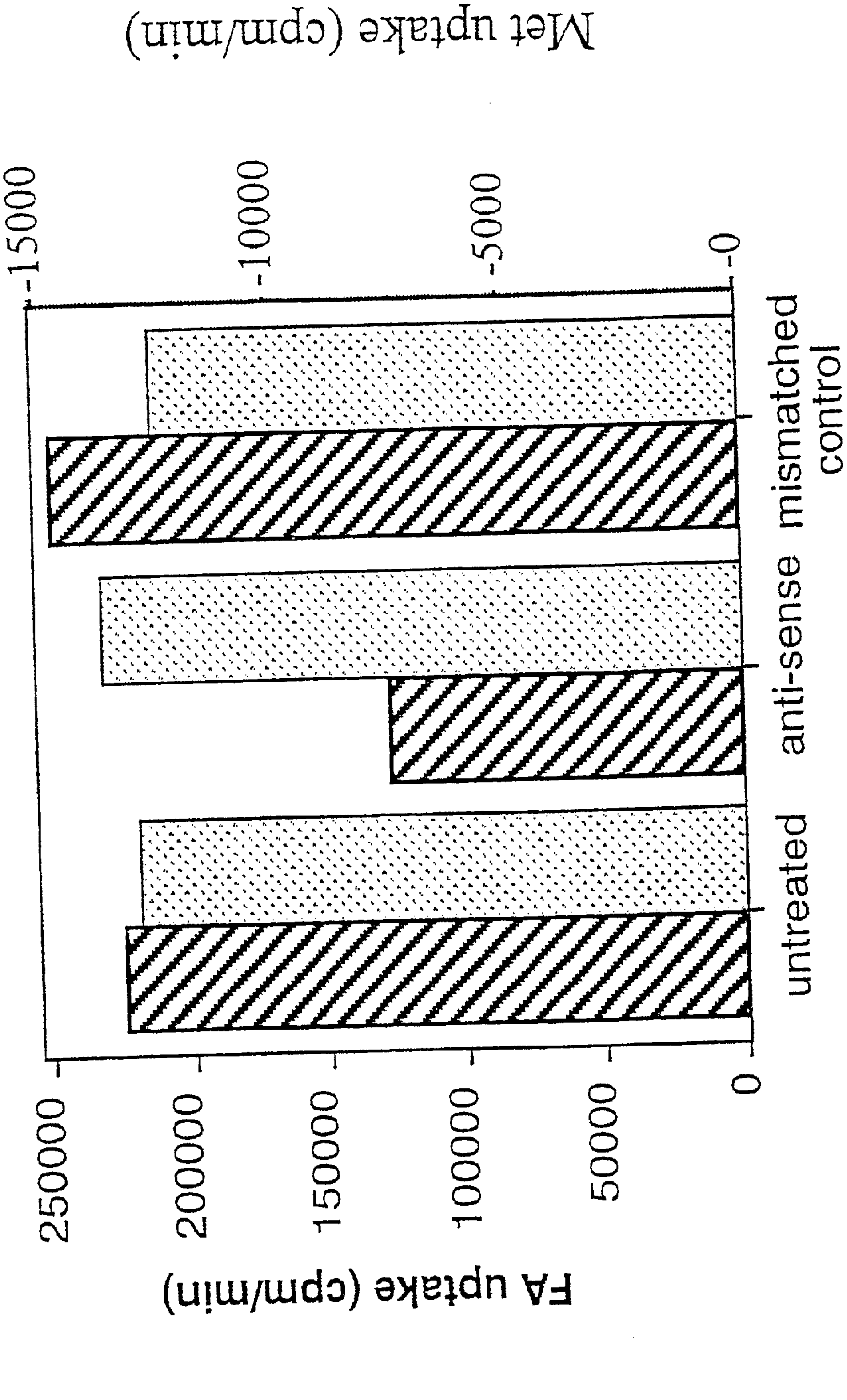
FIG. 42 is a bar graph showing uptake of tritiated oleate and uptake of $^{35}$S-labeled methionine by mouse enterocytes to which were added no oligonucleotide, the antisense oligonucleotide, or the mismatch oligonucleotide.

As a further control experiment, the uptake of oleate was measured along with the uptake of methionine in the same cultured enterocytes. Antisense oligonucleotide, mismatch sequence oligonucleotide, or no oligonucleotide was added to a concentration of 100 $\mu$M to cultures of enterocytes. After incubation for 43 hours, the uptake of both $^{3}$H-labeled oleate and $^{35}$S-labeled methionine was assayed. Results are shown in FIG. 42. Fatty acid uptake is at the left side of the paired bars; methionine uptake is on the right side of the paired bars. The fact that amino acid uptake was not influenced by the antisense oligonucleotide treatment further supports the conclusion that the antisense oligonucleotide causes a specific reduction in translation of FATP4-specific mRNA.

Example 14 mmFATP2 is Expressed in Proximal Renal Tubule Epithelium

Northern analysis showed that mmFATP1, FATP2, and mmFATP4 are present in the kidney. In situ hybridization (methods as for Example 6) was performed to determine which cell type(s) of the kidney these mRNAs are expressed in. mmFATP1 mRNA was present in virtually all cells throughout the kidney with no obvious preference for a particular cell type. In contrast, mmFATP2 was expressed only in the renal cortex. Within the cortex, expression of mmFATP2 was restricted to the epithelial cells of the proximal renal tubules. The primary function of proximal renal tubule cells is the reabsorption of filtered salts and nutrients (e.g., glucose), a process that requires mitochondrial oxidation and that can utilize fatty acids as energy substrates. Based on the localization of mmFATP2, it is possible that mmFATP2 is important for reabsorption in the kidney by allowing uptake of an energy source (fatty acids) from the blood into renal epithelial cells. Alternatively, if fatty acids need to be reabsorbed in the kidney, similarly to glucose, FATP2 could be involved in the reabsorption of fatty acids. Determination of the subcellular localization of FATP2 will distinguish between these two possibilities.

Table 5 summarizes data on expression of the mouse FATPs in various organs.

TABLE 5

| | Mouse FATP mRNA Expression | | | | |
|---|---|---|---|---|---|
| Mouse Probes | mFATP1 | mFATP2 | mFATP3 | mFATP4 | mFATP5 |
| E18.5 embryo expression | everywhere, brain = thymus > heart > brown fat, others | liver (hepatocytes) | — | Brain, small intestine, superior cervical ganglion (SCG), dorsal root ganglion (DRG), other regions have lower expression | Mouse Probes |
| Duodenum | — | villi (surface epithelium) | — | villi (surface epithelium) | — |
| Jejunum | — | villi (surface epithelium) | — | villi (surface epithelium) | — |
| Ileum | — | villi (surface epithelium) | — | villi (surface epithelium) | — |
| Colon | low expression in the crypt | very low level in the crypt | — | — | — |
| Kidney | cortex and medulla | proximal tubules | — | — | — |
| Liver | — | hepatocytes | hepatocytes | — | hepatocytes |
| Pancreas | exocrine secretory units or acinar cells; endocrine pancreas (islet) are negative | exocrine secretory units or acinar cells; endocrine pancreas (islet) are negative | — | — | — |
| Brain | Neuronal expression throughout the brain including hypothalamus | — | — | Neuronal expression throughout the brain including hypothalamus | — |
| Heart | myocytes | — | — | | |
| Testis | seminiferous tubules | — | seminiferous tubules | | |
| Lung | bronchiole | — | — | | |
| Adipose | adipocyte | adipocyte | — | | |

Example 15

Isolation of Full-length Human FATP3

Full-length clones encoding human FATP3 were identified by searching databases for sequences similar to the murine FATP1–5 coding regions using the BlastX algorithm (Altschul et al., *J. Mol. Biol.* 215: 403–410, 1990). Human clones with similarity to the 5' end of murine FATP sequences were sequenced completely. A clone encoding full-length human FATP3 was obtained from a human bone library constructed in the mammalian expression vector pMET7 (Tartaglia, L.A. et al., *Cell* 83: 1263–1271, 1995). To identify human cDNA clones encoding FATP family members, databases were searched for sequences similar to murine FATP1–5 coding regions. One clone was found to encode the human ortholog of mmFATP3 and was designated hsFATP3. The DNA and predicted protein sequences of hsFATP3 are shown in FIGS. 94A and 94B. hsFATP5 is predicted to encode a 703 amino acid 75.6 kD protein with multiple membrane-spanning domains. A comparison of the DNA sequences of mouse and human FATP3 shows that the mouse and human orthologs are 81% identical to each other within the coding region. At the amino acid level, hsFATP3 is ~86% identical to mm FATP3 within the coding region. The sequence identities between mouse and human FATP3 are considerably higher than those observed between different FATP family members within one species (~40%) and are present in the N-terminal part of the protein, a region that is poorly conserved between different FATP family members.

All references cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. An isolated polypeptide comprising the amino acid sequence of SEQ ID NO: 53.

2. An isolated polypeptide encoded by a nucleic acid that hybridizes to a nucleic acid consisting of the nucleotide sequence of SEQ ID NO:52 under stringency conditions of 6×SSC at 65° C., followed by two or more washes in 0.2×SSC/0.5% SDS at 65° C.

3. A fusion protein comprising a polypeptide consisting of the amino acid sequence of SEQ ID NO: 53.

4. The fusion protein of claim 3, wherein the fusion protein transports fatty acids across a cell membrane or an artificial cell membrane system.

5. An isolated polypeptide comprising the amino acid sequence of SEQ ID NO: 57.

6. An isolated polypeptide encoded by a nucleic acid that hybridizes to a nucleic acid consisting of the nucleotide sequence of SEQ ID NO:56 under stringency conditions of 6×SSC at 65° C., followed by two or more washes in 0.2×SSC/0.5% SDS at 65° C.

7. A fusion protein comprising a polypeptide consisting of the amino acid sequence in SEQ ID NO: 57.

8. The fusion protein of claim 7, wherein the fusion protein transports fatty acids across a cell membrane or an artificial cell membrane system.

9. An isolated polypeptide consisting of the amino acid sequence of SEQ ID NO: 53.

10. An isolated polypeptide comprising at least 360 contiguous amino acid residues of SEQ ID NO: 53.

11. An isolated polypeptide comprising an amino acid sequence having at least 30 contiguous amino acid residues of SEQ ID NO: 53, wherein the isolated polypeptide transports fatty acids across a cell membrane or an artificial cell membrane.

12. An isolated polypeptide consisting of the amino acid sequence of SEQ ID NO: 57.

13. An isolated polypeptide comprising at least 360 contiguous amino acid residues of SEQ ID NO: 57.

14. An isolated polypeptide comprising an amino acid sequence having at least 15 contiguous amino acid residues of SEQ ID NO: 57, wherein the isolated polypeptide transports fatty acids across a cell membrane or an artificial cell membrane.

* * * * *